(12) United States Patent
Miura et al.

(10) Patent No.: US 8,846,746 B2
(45) Date of Patent: Sep. 30, 2014

(54) PYRAZOLE COMPOUND AND PHARMACEUTICAL USE THEREOF

(75) Inventors: Tomoya Miura, Takatsuki (JP); Yosuke Ogoshi, Takatsuki (JP); Kazuhito Ueyama, Takatsuki (JP); Dai Motoda, Takatsuki (JP); Toshihiko Iwayama, Takatsuki (JP); Koichi Suzawa, Takatsuki (JP); Hironobu Nagamori, Takatsuki (JP); Hiroshi Ueno, Takatsuki (JP); Akihiko Takahashi, Takatsuki (JP); Kazuyuki Sugimoto, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 103 days.

(21) Appl. No.: 13/599,665

(22) Filed: Aug. 30, 2012

(65) Prior Publication Data

US 2013/0085132 A1 Apr. 4, 2013

Related U.S. Application Data

(60) Provisional application No. 61/573,433, filed on Sep. 6, 2011.

(30) Foreign Application Priority Data

Aug. 31, 2011 (JP) ................. 2011-188121

(51) Int. Cl.
| | | |
|---|---|---|
| *A01N 43/56* | (2006.01) | |
| *A61K 31/415* | (2006.01) | |
| *C07D 405/14* | (2006.01) | |
| *C07D 403/14* | (2006.01) | |
| *C07D 403/12* | (2006.01) | |
| *C07D 409/12* | (2006.01) | |
| *C07D 401/12* | (2006.01) | |
| *C07D 413/12* | (2006.01) | |
| *C07D 405/12* | (2006.01) | |

(52) U.S. Cl.
CPC ............ *C07D 403/12* (2013.01); *C07D 405/14* (2013.01); *C07D 403/14* (2013.01); *C07D 409/12* (2013.01); *C07D 401/12* (2013.01); *C07D 413/12* (2013.01); *C07D 405/12* (2013.01)
USPC ..................... 514/407; 514/228.8; 514/230.8; 514/254.05; 514/274; 514/326; 514/376; 514/392

(58) Field of Classification Search
CPC .. C07D 401/12; C07D 403/12; C07D 403/14; C07D 405/12; C07D 405/14; C07D 409/12; C07D 413/12
USPC ......... 514/212.08, 228.8, 230.8, 254.05, 274, 514/326, 376, 392, 407
See application file for complete search history.

(56) References Cited

U.S. PATENT DOCUMENTS

| | | |
|---|---|---|
| 5,624,941 A | 4/1997 | Barth et al. |
| 7,247,628 B2 | 7/2007 | Dow et al. |
| 7,446,121 B2 | 11/2008 | Pfefferkorn |
| 7,820,804 B2 | 10/2010 | Brummerhop et al. |
| 7,872,006 B2 | 1/2011 | Moritani et al. |
| 8,163,704 B2 * | 4/2012 | Bebernitz et al. ............... 514/23 |
| 2004/0122074 A1 | 6/2004 | Dow et al. |
| 2006/0111422 A1 | 5/2006 | Choi et al. |
| 2007/0117858 A1 | 5/2007 | Xia et al. |
| 2007/0197623 A1 | 8/2007 | Brummerhop et al. |
| 2007/0254935 A1 | 11/2007 | Dow et al. |
| 2009/0048256 A1 | 2/2009 | Moritani et al. |
| 2009/0170852 A1 | 7/2009 | Choi et al. |
| 2013/0040950 A1 | 2/2013 | Short et al. |
| 2013/0079306 A1 | 3/2013 | Uchida et al. |

FOREIGN PATENT DOCUMENTS

| | | |
|---|---|---|
| AU | 2005252329 A1 | 12/2005 |
| CA | 2098944 A1 | 12/1993 |
| CA | 2505887 A1 | 6/2004 |
| CA | 2570042 A1 | 12/2005 |
| CA | 2804225 A1 | 1/2012 |
| EP | 0576357 A1 | 12/1993 |
| EP | 0656354 A1 | 6/1995 |
| EP | 1572662 A1 | 9/2005 |
| EP | 1758914 A1 | 3/2007 |
| EP | 1819681 A1 | 8/2007 |
| EP | 1951678 A1 | 8/2008 |
| EP | 1966194 A2 | 9/2008 |
| EP | 2560966 A2 | 2/2013 |
| JP | 2006-514942 A | 5/2006 |

(Continued)

OTHER PUBLICATIONS

International Search Report for PCT/JP2012/072066, dated Oct. 2, 2012.

*Primary Examiner* — My-Chau T Tran
(74) *Attorney, Agent, or Firm* — Fitzpatrick, Cella, Harper & Scinto

(57) ABSTRACT

The present invention provides a pyrazole compound of the following general Formula [Ib] having SGLT1 inhibitory activity, or a pharmaceutically acceptable salt thereof, a pharmaceutical composition comprising the same, and its pharmaceutical use:

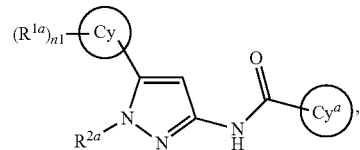

wherein each symbol is the same as defined in the description.

38 Claims, No Drawings

(56) References Cited

FOREIGN PATENT DOCUMENTS

| | | |
|---|---|---|
| JP | 2008-501745 A | 1/2008 |
| JP | 2008-024693 A | 2/2008 |
| JP | 2008-520642 A | 6/2008 |
| JP | 2008-285481 A | 11/2008 |
| JP | 2009-517388 A | 4/2009 |
| JP | 2010-222298 A | 10/2010 |
| NL | 1030487 A1 | 5/2006 |
| WO | WO 2004018491 A1 * | 3/2004 |
| WO | 2004/052864 A1 | 6/2004 |
| WO | 2005/121161 A1 | 12/2005 |
| WO | 2006/056845 A1 | 6/2006 |
| WO | 2007/034279 A2 | 3/2007 |
| WO | 2007/046550 A1 | 4/2007 |
| WO | 2007/061948 A2 | 5/2007 |
| WO | 2010/048149 A2 | 4/2010 |
| WO | 2011/126903 A2 | 10/2011 |
| WO | 2012/002527 A1 | 1/2012 |
| WO | 2012/080727 A2 | 6/2012 |
| WO | 2012/080729 A2 | 6/2012 |
| WO | WO 2013031922 A1 * | 3/2013 |

* cited by examiner

PYRAZOLE COMPOUND AND PHARMACEUTICAL USE THEREOF

TECHNICAL FIELD

The present invention relates to a pyrazole compound having SGLT1 inhibitory activity or a pharmaceutically acceptable salt thereof, a pharmaceutical composition comprising the same, and its pharmaceutical use.

BACKGROUND ART

It is known that SGLT1 (i.e., Sodium-Glucose Co-transporter 1) contributes to a great portion of absorption of glucose and galactose in the small intestine. It is reported that human SGLT1-deficiency in patients causes glucose-galactose malabsorption. Furthermore, it is confirmed that the expression of SGLT1 in the small intestine increases in diabetic patients and it is thought that increased sugar absorption in diabetic patients is caused by the high expression of SGLT1 in the small intestine.

From these knowledge, a SGLT1 inhibitor is expected to normalize the blood glucose level, since it blocks glucose absorption in the small intestine. Therefore, a SGLT1 inhibitor is considered to be effective against diabetes and diabetic complications associated with hyperglycemia, specifically retinopathy, nephropathy and neuropathy which are known as microangiopathy, and cerebrovascular disease, ischemic heart disease and membrum-inferius arteriosclerosis obliterans which are known as macroangiopathy. Moreover, it is thought to be effective against obesity by inhibiting the inflow of glucose into the body (non-patent literatures 1 and 2).

In addition, SGLT1 is expressed in cardiac muscle cells. It is known that GLUT1 and GLUT4 (Glucose Transporter Type 4) usually have a role in uptake of glucose to cardiac muscle cells and the contribution of SGLT1 is small. However, the expression of SGLT1 is induced in the cardiac muscles of mice into which was introduced mutated genes of PRKAG2 (gamma 2 subunit of AMPK (AMP-Activated Protein Kinase)) which is a responsible gene of familial hypertrophic cardiomyopathy (glycogen accumulation-type myocardosis), or mice which underwent myocardial ischemia treatment, and SGLT1 is reported to have contributed to the uptake of glucose to cardiac muscle cells in these pathologies. Glucose incorporated by SGLT1 is thought to be excessively accumulated or metabolized within cardiac muscle cells and impair the cells. It is reported in the former mouse model that accumulation of glycogen in the cardiac muscle is actually inhibited by the treatment of phlorizin which is a non-selective SGLT inhibitor.

From these knowledge, a SGLT1 inhibitor is thought to be effective against hypertrophic cardiomyopathy and ischemic heart disease by inhibiting uptake of excess glucose into cardiac muscle cells (non-patent literatures 3 and 4).

SGLT1 is stabilized by epidermal growth factor receptors (i.e., surface proteins on many kinds of cancer cells) in cancer cells. It is known that transporters of glucose, lactic acid, and amino acid, etc. are involved in nutrition supply to cancer cells, and especially, regarding the transportation of glucose, SGLT1 and GLUT1 supply glucose to cancer cells, continuously. When glucose is not supplied over a long period of time, cells are destroyed by autophagy.

From these knowledge, a SGLT1 inhibitor is thought to inhibit supply of glucose to cancer cells and show anticancer activity (non-patent literatures 5 and 6).

Since carbohydrate in diet is degraded to monosaccharide in the gastrointestinal tracts and is absorbed in the upper gastrointestinal tracts, not so many sugar would reach the lower gastrointestinal tracts. However, when drugs which delay and/or inhibit glucose absorption are administered, or a large amount of resistant polysaccharide are ingested, undigested sugar would be retained in the lower gastrointestinal tracts and the undigested sugar retained in the lower gastrointestinal tracts would cause osmotic diarrhea.

The amount of monosaccharide in the lower gastrointestinal tracts is increased by the inhibition of glucose absorption by a SGLT1 inhibitor. Therefore, it is believed that a SGLT1 inhibitor is effective against constipation.

NON-PATENT DOCUMENT

[Non-patent literature 1] Am J Physiol Gastrointest Liver Physiol. 2002; 282(2):G241-8
[Non-patent literature 2] Nature. 1991; 350(6316): 354-6
[Non-patent literature 3] J Mol Cell Cardiol. 2010; 49(4):683-92
[Non-patent literature 4] Cardiovasc Res. 2009; 84(1):111-8
[Non-patent literature 5] Cancer Cell. 2008, 13: 385-93
[Non-patent literature 6] Pharmacol Ther. 2009, 121: 29-40

SUMMARY OF INVENTION

Problems to be Solved by the Invention

An object of the present invention is to provide a pyrazole compound useful as a medicine which has SGLT1 inhibitory activity, or a pharmaceutically acceptable salt thereof, and a pharmaceutical composition comprising the same.

Means to Solve the Problems

The present invention is as follows.

Paragraph 1: A compound or a pharmaceutically acceptable salt thereof represented by the following general formula [I]:

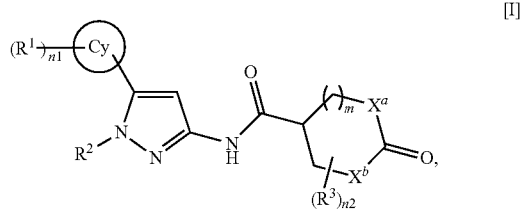

wherein
Ring Cy is
(1) $C_{6-10}$ aryl,
(2) $C_{3-8}$ cycloalkyl or
(3) $C_{3-8}$ cycloalkenyl,
n1 is 0, 1, 2, 3 or 4,
$R^1$ is
(1) a halogen atom,
(2) hydroxy,
(3) carboxy,
(4) a $C_{1-6}$ alkyl group,
(5) a $C_{1-6}$ alkoxy group,
(6) a $C_{3-6}$ cycloalkyl group,
(7) a halo $C_{1-6}$ alkyl group,
(8) a hydroxy $C_{1-6}$ alkyl group,
(9) a $C_{1-6}$ alkoxy $C_{1-6}$ alkyl group,

(10) a halo $C_{1-6}$ alkoxy group or
(11) a carboxy $C_{1-6}$ alkoxy group,
provided when n1 is 2, 3 or 4, $R^1$ each is the same or different,
$R^2$ is
(1) a $C_{1-8}$ alkyl group,
(2) a $C_{3-8}$ cycloalkyl $C_{1-6}$ alkyl group,
(3) a $C_{6-10}$ aryl $C_{1-6}$ alkyl group,
(4) a saturated heterocyclo $C_{1-6}$ alkyl group (the saturated heterocycle is of 5-membered to 6-membered saturated heterocycle having 1 to 2 heteroatoms selected from nitrogen, oxygen, and sulfur),
(5) a $C_{3-8}$ cycloalkyl group,
(6) a halo $C_{1-6}$ alkyl group,
(7) a $C_{1-6}$ alkoxy $C_{1-6}$ alkyl group,
(8) a halo $C_{3-8}$ cycloalkyl group,
(9) a $C_{6-10}$ aryl group (the $C_{6-10}$ aryl group is optionally substituted by 1 to 4 substituents selected from
    (a) a halogen atom,
    (b) a $C_{1-6}$ alkyl group,
    (c) a $C_{1-6}$ alkoxy group and
    (d) a carboxy $C_{1-6}$ alkoxy group), or
(10) a saturated heterocycle group (the saturated heterocycle is of 5-membered to 6-membered saturated heterocycle having 1 to 2 heteroatoms selected from nitrogen, oxygen, and sulfur, and is optionally substituted by 1 to 4 $C_{1-6}$ alkyl groups),
n2 is 0, 1, 2, 3 or 4,
m is 0, 1, 2, 3 or 4,
$R^3$ is
(1) a $C_{1-6}$ alkyl group or
(2) a hydroxy $C_{1-6}$ alkyl group,
provided when n2 is 2, 3 or 4, $R^3$ each is the same or different,
$X^a$ is
(1) a bond or
(2) N—$R^4$ (the $R^4$ is
    (a) a hydrogen atom or
    (b) a $C_{1-6}$ alkyl group), and
$X^b$ is
    (1) NH or
    (2) an oxygen atom,
    provided, when $X^a$ is N—$R^4$, $X^b$ is not an oxygen atom.

Paragraph 2: The compound or a pharmaceutically acceptable salt thereof according to paragraph 1, wherein $X^b$ is NH.

Paragraph 3: The compound or a pharmaceutically acceptable salt thereof according to paragraph 1 or 2, wherein the ring Cy is $C_{6-10}$ aryl.

Paragraph 4: The compound or a pharmaceutically acceptable salt thereof according to paragraph 3, wherein the ring Cy is phenyl.

Paragraph 5: The compound or a pharmaceutically acceptable salt thereof according to any one of paragraphs 1 to 4, wherein $R^1$ is
(1) a halogen atom,
(2) a $C_{1-6}$ alkyl group,
(3) a $C_{1-6}$ alkoxy group,
(4) a halo $C_{1-6}$ alkyl group,
(5) a $C_{1-6}$ alkoxy $C_{1-6}$ alkyl group or
(6) a halo $C_{1-6}$ alkoxy group,
provided when n1 is 2, 3 or 4, $R^1$ each is the same or different.

Paragraph 6: The compound or a pharmaceutically acceptable salt thereof according to any one of paragraphs 1 to 5, wherein $R^2$ is a $C_{6-10}$ aryl group (the $C_{6-10}$ aryl group is optionally substituted by 1 to 4 substituents selected from
(a) a halogen atom,
(b) a $C_{1-6}$ alkyl group,
(c) a $C_{1-6}$ alkoxy group and
(d) a carboxy $C_{1-6}$ alkoxy group).

Paragraph 7: The compound or a pharmaceutically acceptable salt thereof according to paragraph 6, wherein $R^2$ is a phenyl group (the phenyl group k is optionally substituted by 1 to 4 substituents selected from
(a) a halogen atom,
(b) a $C_{1-6}$ alkyl group,
(c) a $C_{1-6}$ alkoxy group and
(d) a carboxy $C_{1-6}$ alkoxy group).

Paragraph 8: A pharmaceutical composition which comprises a compound or a pharmaceutically acceptable salt thereof according to any one of paragraphs 1 to 7, and a pharmaceutically acceptable carrier.

Paragraph 9: A SGLT1 inhibitor which comprises a compound or a pharmaceutically acceptable salt thereof according to any one of paragraphs 1 to 7

Paragraph 10: An agent for treating or preventing diabetes which comprises a compound or a pharmaceutically acceptable salt thereof according to any one of paragraphs 1 to 7.

Paragraph 11: The agent for treating or preventing diabetes according to paragraph 10, wherein diabetes is type II diabetes mellitus.

Paragraph 12: A method for inhibiting of SGLT1 which comprises administrating to mammals a therapeutically effective amount of a compound or a pharmaceutically acceptable salt thereof according to any one of paragraphs 1 to 7

Paragraph 13: A method for treating or preventing diabetes which comprises administrating to mammals a therapeutically effective amount of a compound or a pharmaceutically acceptable salt thereof according to any one of paragraphs 1 to 7.

Paragraph 14: The method according to paragraph 13, wherein the diabetes is type II diabetes mellitus.

Paragraph 15: Use of a compound or a pharmaceutically acceptable salt thereof according to any one of paragraphs 1 to 7 for manufacturing a SGLT1 inhibitor.

Paragraph 16: The use of a compound or a pharmaceutically acceptable salt thereof according to any one of paragraphs 1 to 7, for manufacturing an agent for treating or preventing diabetes.

Paragraph 17: The use according to paragraph 16, wherein the diabetes is type II diabetes mellitus.

Paragraph 18: A kit for commerce comprising (a) a pharmaceutical composition which comprises a compound or a pharmaceutically acceptable salt thereof according to any one of paragraphs 1 to 7 as an active ingredient, and (b) a package insert about the pharmaceutical composition which indicates that the pharmaceutical composition can be used or should be used for treatment or prevention of type II diabetes mellitus.

Paragraph 19: A package for commerce comprising (a) a pharmaceutical composition which comprises a compound or a pharmaceutically acceptable salt thereof according to any one of paragraphs 1 to 7 as an active ingredient, and (b) a package insert about the pharmaceutical composition which indicates that the pharmaceutical composition can be used or should be used for treatment or prevention of type II diabetes mellitus.

Paragraph 20: A compound or a pharmaceutically acceptable salt thereof represented by the general formula [Ib]:

[Ib]

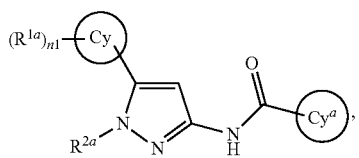

wherein
Ring Cy is
(1) $C_{6-10}$ aryl,
(2) $C_{3-8}$ cycloalkyl or
(3) $C_{3-8}$ cycloalkenyl,
n1 is 0, 1, 2, 3 or 4,
$R^{1a}$ is
(1) a halogen atom,
(2) hydroxy,
(3) carboxy,
(4) a $C_{1-6}$ alkyl group,
(5) a $C_{2-8}$ alkenyl group,
(6) a $C_{2-8}$ alkynyl group,
(7) a $C_{1-6}$ alkoxy group,
(8) a $C_{3-6}$ cycloalkyl group,
(9) a halo $C_{1-6}$ alkyl group,
(10) a hydroxy $C_{1-6}$ alkyl group,
(11) a $C_{1-6}$ alkoxy $C_{1-6}$ alkyl group,
(12) a halo $C_{1-6}$ alkoxy $C_{1-6}$ alkyl group,
(13) a $C_{1-6}$ alkylsulfonyl $C_{1-6}$ alkyl group,
(14) a halo $C_{1-6}$ alkylsulfonyl $C_{1-6}$ alkyl group,
(15) a halo $C_{1-6}$ alkylamino $C_{1-6}$ alkyl group,
(16) a $C_{3-6}$ cycloalkyl $C_{2-6}$ alkynyl group
(17) a halo $C_{1-6}$ alkoxy group,
(18) a carboxy $C_{1-6}$ alkoxy group,
(19) a $C_{1-6}$ alkylsulfanyl group,
(20) a $C_{1-6}$ alkylsulfonyl group,
(21) a halo $C_{1-6}$ alkylsulfonyl group,
(22) a $C_{1-8}$ alkylcarbonyl group,
(23) a $C_{1-6}$ alkyloxycarbonyl group,
(24) a group represented by the Formula:

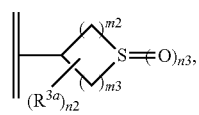

wherein
$R_5$ is
  (a) a hydrogen atom or
  (b) a $C_{1-6}$ alkyl group, and
$R_6$ is
  (a) a $C_{1-6}$ alkyl group or
  (b) a halo $C_{1-6}$ alkyl group,
(25) a saturated heterocyclo $C_{1-6}$ alkyl group (the saturated heterocycle is of 4-membered to 6-membered saturated heterocycle having 1 to 2 heteroatoms selected from nitrogen, oxygen, and sulfur) or
(26) a saturated heterocyclo oxy $C_{1-6}$ alkyl group (the saturated heterocycle is of 4-membered to 6-membered saturated heterocycle having 1 to 2 heteroatoms selected from nitrogen, oxygen, and sulfur),
provided when n1 is 2, 3 or 4, $R^{1a}$ each is the same or different, $R^{2a}$ is
(1) a $C_{1-8}$ alkyl group,
(2) a $C_{3-8}$ cycloalkyl $C_{1-6}$ alkyl group,
(3) a $C_{6-10}$ aryl $C_{1-6}$ alkyl group,
(4) a saturated heterocyclo $C_{1-6}$ alkyl group (the saturated heterocycle is of 4-membered to 6-membered saturated heterocycle having 1 to 2 heteroatoms selected from nitrogen, oxygen, and sulfur),
(5) a $C_{3-8}$ cycloalkyl group,
(6) a halo $C_{1-6}$ alkyl group,
(7) a $C_{1-6}$ alkoxy $C_{1-6}$ alkyl group,
(8) a halo $C_{3-8}$ cycloalkyl group,
(9) a $C_{6-10}$ aryl group (the $C_{6-10}$ aryl group is optionally substituted by 1 to 4 substituents selected from
    (a) a halogen atom,
    (b) hydroxy,
    (c) a $C_{1-6}$ alkyl group,
    (d) a $C_{2-8}$ alkenyl group,
    (e) a $C_{2-6}$ alkynyl group,
    (f) a $C_{1-6}$ alkoxy group,
    (g) a halo $C_{1-6}$ alkyl group,
    (h) a $C_{1-6}$ alkoxy $C_{1-6}$ alkyl group,
    (i) a halo $C_{1-6}$ alkoxy group,
    (j) a hydroxy $C_{1-6}$ alkoxy group,
    (k) a $C_{1-6}$ alkoxy $C_{1-6}$ alkoxy group,
    (l) a carboxy $C_{1-6}$ alkoxy group,
    (m) a $C_{6-10}$ aryl $C_{1-6}$ alkoxy group,
    (n) a $C_{1-6}$ alkylsulfanyl $C_{1-6}$ alkoxy group,
    (o) a $C_{1-6}$ alkylsulfonyl $C_{1-6}$ alkoxy group,
    (p) a $C_{6-10}$ aryl $C_{1-6}$ alkoxy $C_{1-6}$ alkoxy group,
    (q) a saturated heterocyclo $C_{1-6}$ alkoxy group (the saturated heterocycle is of 4-membered to 6-membered saturated heterocycle having 1 to 2 heteroatoms selected from nitrogen, oxygen, and sulfur, and is optionally substituted by 1 to 2 $C_{1-6}$ alkyl groups),
    (r) a saturated heterocyclo oxy group (the saturated heterocycle is a 4-membered to 6-membered saturated heterocycle having 1 to 2 heteroatoms selected from nitrogen, oxygen, and sulfur),
    (s) a $C_{3-8}$ cycloalkyloxy group,
    (t) a $C_{1-6}$ alkoxycarbonyloxy group and
    (u) a $C_{1-6}$ alkylsulfonyl group), or
(10) a saturated heterocycle group (the saturated heterocycle is of 4-membered to 6-membered saturated heterocycle having 1 to 2 heteroatoms selected from nitrogen, oxygen, and sulfur, and is optionally substituted by 1 to 4 $C_{1-6}$ alkyl groups), and
Ring $Cy^a$ is a group selected from
(1) a group represented by the Formula:

$$\left\lVert\begin{array}{c}\text{(R}^{3a})_{n2}\end{array}\right.\hspace{-0.5em}\left(\begin{array}{c}\,^{m2}\\\,_{m3}\end{array}\right)\!\!S(\!=\!O)_{n3},$$

wherein
m2 is 1, 2 or 3,
m3 is 1, 2 or 3,
n3 is 1 or 2, (2) a group represented by the Formula:

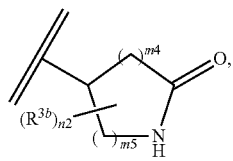

wherein
m4 is 0, 1, 2 or 3,
m5 is 0, 1 or 2,
provided sum of m4 and m5 is 1 or more,
(3) a group represented by the Formula:

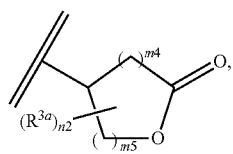

wherein
m4 is 0, 1, 2 or 3,
m5 is 0, 1 or 2,
provided sum of m4 and m5 is 1 or more,
(4) a group represented by the Formula:

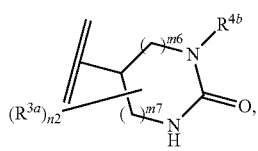

wherein
m6 is 0, 1 or 2,
m7 is 0, 1 or 2,
provided sum of m6 and m7 is 1 or more,
(5) a group represented by the Formula:

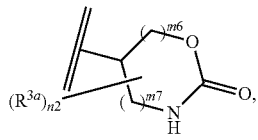

wherein
m6 is 0, 1 or 2,
m7 is 0, 1 or 2,
provided sum of m6 and m7 is 1 or more,
(6) a group represented by the Formula:

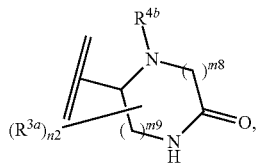

wherein
m8 is 1 or 2,
m9 is 1 or 2, and
(7) a group represented by the Formula:

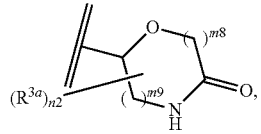

wherein
m8 is 1 or 2,
m9 is 1 or 2,
n2 is 0, 1, 2, 3 or 4,
$R^{3a}$ is
(1) hydroxy,
(2) a $C_{1-6}$ alkyl group or
(3) a hydroxy $C_{1-6}$ alkyl group,
provided when n2 is 2, 3 or 4, $R^{3a}$ each is the same or different,
$R^{3b}$ is
(1) hydroxy,
(2) a $C_{1-6}$ alkyl group (which optionally form a $C_{3-6}$ cycloalkyl group together with the carbon to which it is attached and the carbon adjacent thereto) or
(3) a hydroxy $C_{1-6}$ alkyl group, or
(4) when two $R^{3b}$ are attached to the same carbon, they optionally form a $C_{3-6}$ cycloalkyl group together with the carbon to which they are attached,
provided, when n2 is 2, 3 or 4, each $R^{3b}$ is the same or different, and
$R^{4b}$ is
(1) a hydrogen atom,
(2) a $C_{1-6}$ alkyl group,
(3) a carboxy $C_{1-6}$ alkyl group,
(4) a halo $C_{1-6}$ alkyl group or
(5) a $C_{1-6}$ alkoxy $C_{1-6}$ alkyl group.
Paragraph 21: The compound or a pharmaceutically acceptable salt thereof according to paragraph 20, wherein Ring $Cy^a$ is selected from
(1) a group represented by the Formula:

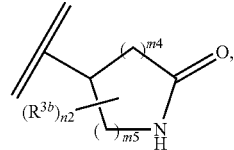

wherein
m4 is 0, 1, 2 or 3,
m5 is 0, 1 or 2,
provided sum of m4 and m5 is 1 or more,
(2) a group represented by the Formula:

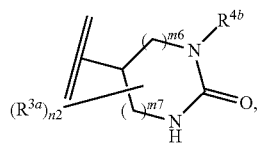

wherein
m6 is 0, 1 or 2,
m7 is 0, 1 or 2,
provided sum of m6 and m7 is 1 or more,
(3) a group represented by the Formula:

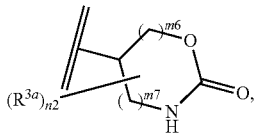

wherein
m6 is 0, 1 or 2,
m7 is 0, 1 or 2,
provided sum of m6 and m7 is 1 or more,
(4) a group represented by the Formula:

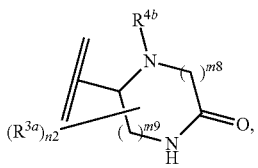

wherein
m8 is 1 or 2,
m9 is 1 or 2, and
(5) a group represented by the Formula:

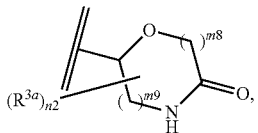

wherein
m8 is 1 or 2,
m9 is 1 or 2,
n2 is 0, 1, 2, 3 or 4,
$R^{3a}$ is
(1) hydroxy,
(2) a $C_{1-6}$ alkyl group or
(3) a hydroxy $C_{1-6}$ alkyl group,
provided when n2 is 2, 3 or 4, each $R^{3a}$ is the same or different,
$R^{3b}$ is
(1) hydroxy,
(2) a $C_{1-6}$ alkyl group (which optionally form a $C_{3-6}$ cycloalkyl group together with the carbon to which it is attached and the carbon adjacent thereto) or
(3) a hydroxy $C_{1-6}$ alkyl group, or
(4) when two $R^{3b}$ are attached to the same carbon, they optionally form a $C_{3-6}$ cycloalkyl group together with the carbon to which they are attached,
provided, when n2 is 2, 3 or 4, each $R^{3b}$ is the same or different, and
$R^{4b}$ is
(1) a hydrogen atom,
(2) a $C_{1-6}$ alkyl group,
(3) a carboxy $C_{1-6}$ alkyl group,
(4) a halo $C_{1-6}$ alkyl group or
(5) a $C_{1-6}$ alkoxy $C_{1-6}$ alkyl group.

Paragraph 22: The compound or a pharmaceutically acceptable salt thereof according to paragraph 20, wherein Ring $Cy^a$ is selected from
(1) a group represented by the Formula:

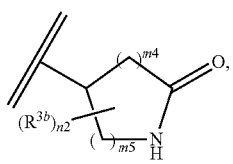

wherein,
m4 is 0, 1, 2 or 3,
m5 is 0, 1 or 2,
provided sum of m4 and m5 is 1 or more, and
(2) a group represented by the Formula:

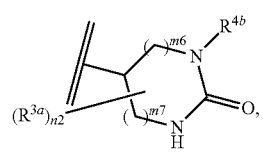

wherein
m6 is 0, 1 or 2,
m7 is 0, 1 or 2,
provided sum of m6 and m7 is 1 or more,
n2 is 0, 1, 2, 3 or 4,
$R^{3a}$ is
(1) hydroxy,
(2) a $C_{1-6}$ alkyl group or
(3) a hydroxy $C_{1-6}$ alkyl group,
provided, when n2 is 2, 3 or 4, each $R^{3a}$ is the same or different,
$R^{3b}$ is
(1) hydroxy,
(2) a $C_{1-6}$ alkyl group (which optionally form a $C_{3-6}$ cycloalkyl group together with the carbon to which it is attached and the carbon adjacent thereto) or
(3) a hydroxy $C_{1-6}$ alkyl group, or
(4) when two $R^{3b}$ are attached to the same carbon, they optionally form a $C_{3-6}$ cycloalkyl group together with the carbon to which they are attached,
provided, when n2 is 2, 3 or 4, each $R^{3b}$ is the same or different, and
$R^{4b}$ is
(1) a hydrogen atom,
(2) a $C_{1-6}$ alkyl group,
(3) a carboxy $C_{1-6}$ alkyl group,
(4) a halo $C_{1-6}$ alkyl group or
(5) a $C_{1-6}$ alkoxy $C_{1-6}$ alkyl group.

Paragraph 23: The compound or a pharmaceutically acceptable salt thereof according to paragraph 20, wherein Ring Cy$^a$ is selected from
(1) a group represented by the Formula:

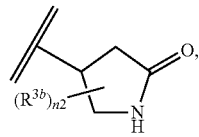

wherein
n2 is 0, 1, 2, 3 or 4, and
(2) a group represented by the Formula:

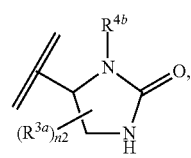

wherein
n2 is 0 or 1,
R$^{3a}$ is
(1) hydroxy,
(2) a C$_{1-6}$ alkyl group or
(3) a hydroxy C$_{1-6}$ alkyl group, and
R$^{3b}$ is
(1) hydroxy,
(2) a C$_{1-6}$ alkyl group (which optionally form a C$_{3-6}$ cycloalkyl group together with the carbon to which it is attached and the carbon adjacent thereto) or
(3) a hydroxy C$_{1-6}$ alkyl group, or
(4) when two R$^{3b}$ are attached to the same carbon, they optionally form a C$_{3-6}$ cycloalkyl group together with the carbon to which they are attached,
provided, when n2 is 2, 3 or 4, each R$^{3b}$ is the same or different, and
R$^{4b}$ is
(1) a hydrogen atom,
(2) a C$_{1-6}$ alkyl group,
(3) a carboxy C$_{1-6}$ alkyl group,
(4) a halo C$_{1-6}$ alkyl group or
(5) a C$_{1-6}$ alkoxy C$_{1-6}$ alkyl group.

Paragraph 24: The compound or a pharmaceutically acceptable salt thereof according to any one of paragraphs 20 to 23, wherein the ring Cy is C$_{6-10}$ aryl.

Paragraph 25: The compound or a pharmaceutically acceptable salt thereof according to paragraph 24, wherein the ring Cy is phenyl.

Paragraph 26: The compound or a pharmaceutically acceptable salt thereof according to any one of paragraphs 20 to 25 wherein R$^{1a}$ is
(1) a halogen atom,
(2) a C$_{1-6}$ alkyl group,
(3) a C$_{1-6}$ alkoxy group,
(4) a halo C$_{1-6}$ alkyl group,
(5) a C$_{1-6}$ alkoxy C$_{1-6}$ alkyl group,
(6) a halo C$_{1-6}$ alkoxy C$_{1-6}$ alkyl group or
(7) a halo C$_{1-6}$ alkoxy group,
provided when n1 is 2, 3, or 4, R$^{1a}$ each is the same or different.

Paragraph 27: The compound or a pharmaceutically acceptable salt thereof according to any one of paragraphs 20 to 26, wherein R$^{2a}$ is a C$_{6-10}$ aryl group (the C$_{6-10}$ aryl group is optionally substituted by 1 to 4 substituents selected from
(a) a halogen atom,
(b) a C$_{1-6}$ alkyl group,
(c) a C$_{1-6}$ alkoxy group and
(d) a carboxy C$_{1-6}$ alkoxy group).

Paragraph 28: The compound or a pharmaceutically acceptable salt thereof according to paragraph 27,
wherein R$^{2a}$ is a phenyl group (the phenyl group is optionally substituted by 1 to 4 substituents selected from
(a) a halogen atom,
(b) a C$_{1-6}$ alkyl group,
(c) a C$_{1-6}$ alkoxy group and
(d) a carboxy C$_{1-6}$ alkoxy group).

Paragraph 29: The compound or pharmaceutically acceptable salt thereof of paragraph 20, wherein the compound is selected from the following Formulae:

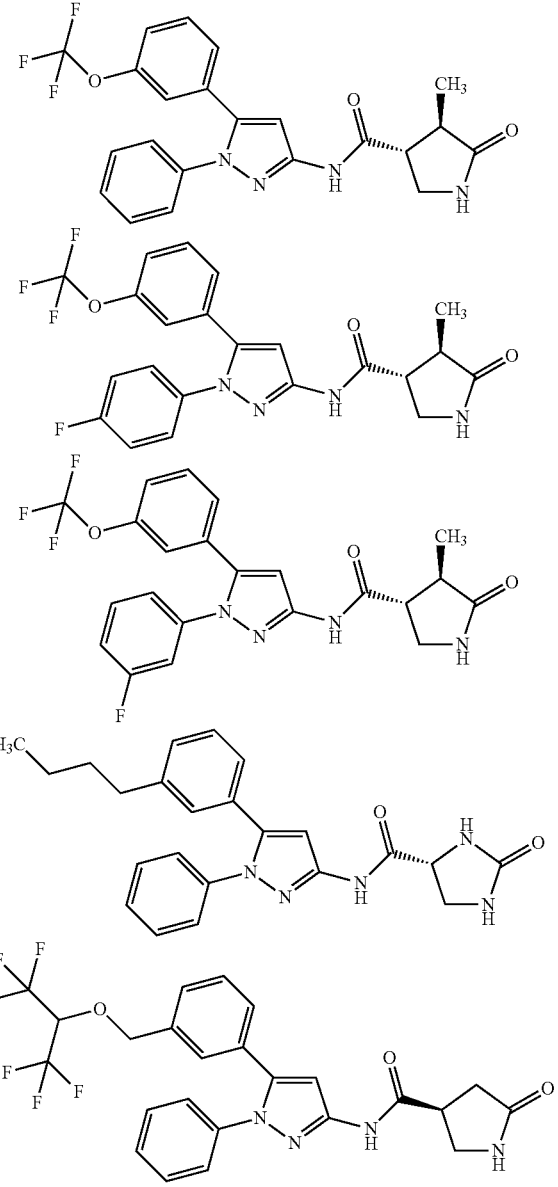

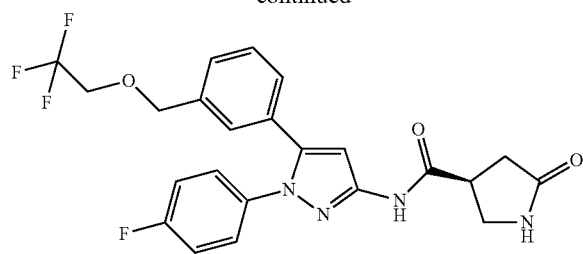
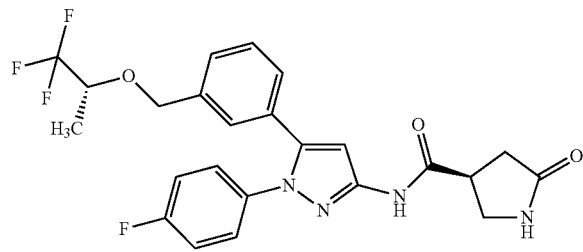
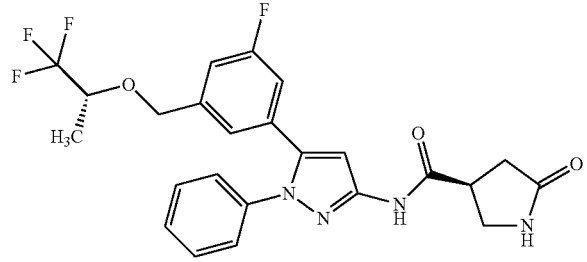
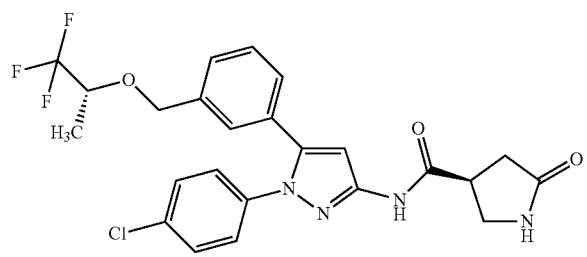
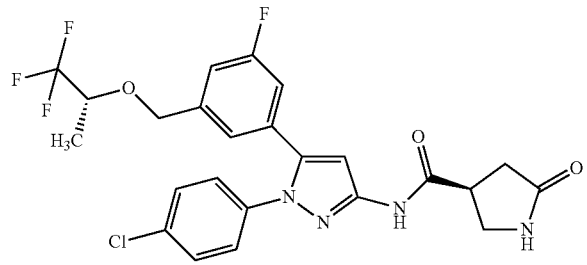
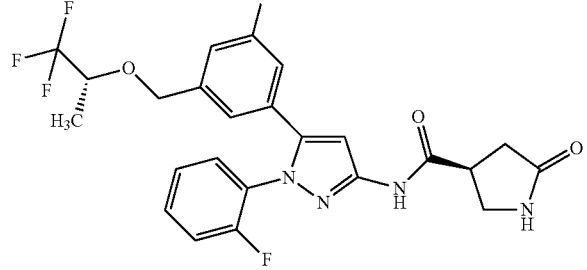
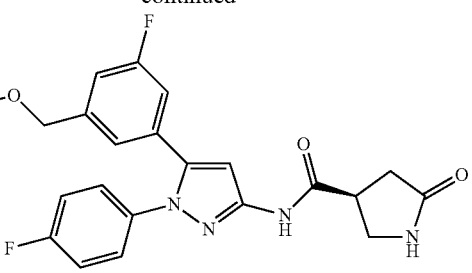
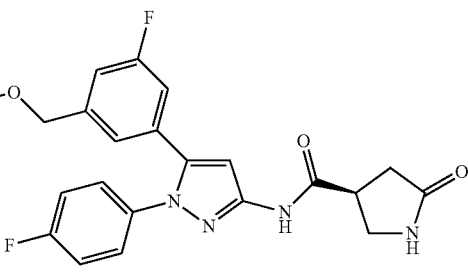
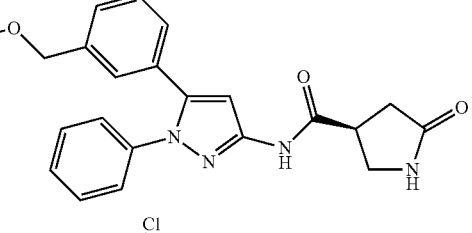
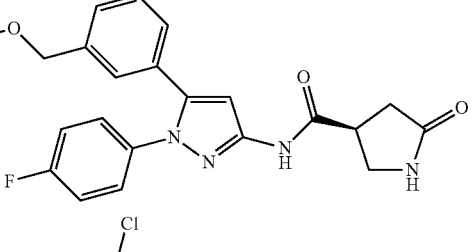
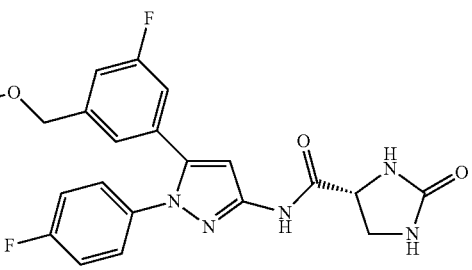
Paragraph 30: A pharmaceutical composition which comprises a compound or a pharmaceutically acceptable salt thereof according to any one of paragraphs 20 to 29 and a pharmaceutically acceptable carrier.

Paragraph 31: A SGLT1 inhibitor which comprises a compound or a pharmaceutically acceptable salt thereof according to any one of paragraphs 20 to 29.

Paragraph 32: An agent for treating or preventing diabetes which comprises a compound or a pharmaceutically acceptable salt thereof according to any one of paragraphs 20 to 29.

Paragraph 33: The agent for treating or preventing diabetes according to paragraph 32, wherein diabetes is type II diabetes mellitus.

Paragraph 34: A method for inhibiting SGLT1 which comprises administrating to mammals a therapeutically effective amount of a compound or a pharmaceutically acceptable salt thereof according to any one of paragraphs 20 to 29.

Paragraph 35: A method for treating or preventing diabetes which comprises administrating to mammals a therapeutically effective amount of a compound or a pharmaceutically acceptable salt thereof according to any one of paragraphs 20 to 29.

Paragraph 36: The method according to paragraph 35, wherein the diabetes is type II diabetes mellitus.

Paragraph 37: Use of a compound or a pharmaceutically acceptable salt thereof according to any one of paragraphs 20 to 29 for manufacturing a SGLT1 inhibitor.

Paragraph 38: Use of a compound or a pharmaceutically acceptable salt thereof according to any one of paragraphs 20 to 29 for manufacturing an agent for treating or preventing diabetes.

Paragraph 39: The use according to paragraph 38 wherein the diabetes is type II diabetes mellitus.

Paragraph 40: A kit for commerce comprising
(a) a pharmaceutical composition which comprises a compound or a pharmaceutically acceptable salt thereof according to any one of paragraphs 20 to 29 as an active ingredient, and
(b) a package insert about the pharmaceutical composition which indicates that the pharmaceutical composition can be used or should be used for treatment or prevention of type II diabetes mellitus.

Paragraph 41: A package for commerce comprising
(a) a pharmaceutical composition which comprises a compound or a pharmaceutically acceptable salt thereof according to any one of paragraphs 20 to 29 as an active ingredient, and
(b) a package insert about the pharmaceutical composition which indicates that the pharmaceutical composition can be used or should be used for treatment or prevention of type II diabetes mellitus.

Effect of the Invention

Since the pyrazole compound or a pharmaceutically acceptable salt thereof in the present invention has SGLT1 inhibitory activity, it is useful for the treatment and/or prevention of diabetes, obesity, diabetic complications (for example, retinopathy, nephropathy and neuropathy which are known as microangiopathy, as well as cerebrovascular disease, ischemic heart disease and membrum-inferius arteriosclerosis obliterans which are known as macroangiopathy), hypertrophic cardiomyopathy, ischemic heart disease, cancer and constipation.

BEST MODE FOR CARRYING OUT THE INVENTION

The definitions of the terms in this description are as follows.

The term "optionally substituted" includes both of cases where the replaceable positions of an intended group are substituted and not substituted (non-substituted). Here, the term "non-substituted" means the case where all the replaceable positions of an intended group are occupied with hydrogen atoms.

For example, the term "optionally substituted by 1 to 4 $C_{1-6}$ alkyl groups" includes both of cases wherein the replaceable positions of an intended group are substituted by 1-4 $C_{1-6}$ alkyl groups and not substituted (non-substituted), and each substituent may be the same or different.

Unless otherwise specified, an explanation of each group is applied to the case wherein the group is a moiety of other groups or a substituent.

A "halogen atom" includes, for example, fluorine atom, chlorine atom, bromine atom and iodine atom.

Preferable one is fluorine atom or chlorine atom.

A "$C_{1-8}$ alkyl" group means a saturated hydrocarbon group of a straight chain or a branched chain having 1-8 carbon atoms, and the term "$C_{1-6}$ alkyl" group means the saturated hydrocarbon group of a straight chain or a branched chain having 1-6 carbon atoms.

Among this group, for example, methyl, ethyl, propyl, isopropyl, n-butyl, isobutyl, sec-butyl, tert-butyl, pentyl, isopentyl, neopentyl, 2-methylpropyl, 1,1-dimethylpropyl, 1-ethylpropyl, hexyl, isohexyl, 1,1-dimethylbutyl, 2,2-dimethylbutyl, 3,3-dimethylbutyl, 2-ethylbutyl are included.

Preferable one is $C_{1-6}$ alkyl group. More preferable are methyl, ethyl, propyl, isopropyl, n-butyl, tert-butyl, isopentyl, 2-methylpropyl, 1,1-dimethylpropyl, hexyl, and 3,3-dimethylbutyl.

Especially preferable are methyl, ethyl, propyl, n-butyl, and isopentyl.

A "$C_{2-8}$ alkenyl" group means a hydrocarbon group having at least one double bond of a straight chain or a branched chain having 2-8 carbon atoms.

As this group, for example vinyl, 1-propenyl, 2-propenyl, isopropenyl, 1-butenyl, 2-butenyl, 3-butenyl, 1-methyl-1-propenyl, 1-methyl-2-propenyl, 2-methyl-1-propenyl, 2-methyl-2-propenyl, 1-ethylvinyl, 1-pentenyl, 2-pentenyl, 3-pentenyl, 4-pentenyl, 1,2-dimethyl-1-propenyl, 1,2-dimethyl-2-propenyl, 1-ethyl-1-propenyl, 1-ethyl-2-propenyl, 1-methyl-1-butenyl, 1-methyl-2-butenyl, 2-methyl-1-butenyl, 1-isopropylvinyl, 2,4-pentadienyl, 1-hexenyl, 2-hexenyl, 3-hexenyl, 4-hexenyl, 5-hexenyl, 2,4-hexadienyl, 1-methyl-1-pentenyl, 3,3-dimethylbutenyl (namely, 3,3-dimethyl but-1-eneyl), are mentioned.

Preferable one is $C_{2-6}$ alkenyl group. More preferable are 1-propenyl, 2-methyl-1-propenyl, and 3,3-dimethyl but-1-eneyl.

A "$C_{2-6}$ alkynyl" group means a hydrocarbon group which has at least one triple bond of a straight chain or a branched chain having 2-6 carbon atoms, and "$C_{2-8}$ alkynyl group" means a hydrocarbon group having at least one triple bond of a straight chain or a branched chain having 2-8 carbon atoms. Specifically, ethynyl, 1-propynyl, 2-propynyl, isopropynyl, 1-butynyl, 2-butynyl, 3-butynyl, 1-methyl-1-propynyl, 1-methyl-2-propynyl, 2-methyl-2-propynyl, 1-ethylethynyl, 3,3-dimethylbutynyl (namely, 3,3-dimethyl but-1-yneyl), are mentioned.

Preferable one is $C_{2-6}$ alkynyl group. More preferable is 3,3-dimethyl but-1-yneyl.

A "$C_{1-6}$ alkoxy" group means an alkoxy group with a straight chain or a branched chain of 1-6 carbon atoms.

Among this group, for example, methoxy, ethoxy, propoxy, isopropoxy, butoxy, isobutoxy, sec-butoxy, tert-butoxy, pentyloxy, isopentyloxy, 2-methylbutoxy, 1,1-dimethylpropoxy, neopentyl oxy, 3,3-dimethylbutoxy, 1-ethylpropoxy and hexyloxy are included.

Preferable one is $C_{1-4}$ alkoxy group. More preferable are methoxy, ethoxy, propoxy, isopropoxy, butoxy, isobutoxy, tert-butoxy, isopentyloxy (namely, 3-methylbutoxy), neopentyl oxy (namely, 2,2-dimethylpropoxy), 1,1-dimethylpropoxy, and 3,3-dimethylbutoxy.

A "$C_{6-10}$ aryl" group means an aromatic hydrocarbon group having 6-10 carbon atoms.

Among this group, for example, phenyl, 1-naphthyl and 2-naphthyl are included.

Preferable one is phenyl.

A "$C_{3-8}$ cycloalkyl" group means a monocycle saturated hydrocarbon group having 3-8 carbon atoms, and the "$C_{3-6}$ cycloalkyl" group means the monocycle saturated hydrocarbon group having 3-6 carbon atoms.

Among this group, for example, cyclopropyl, cyclobutyl, cyclopentyl, cyclohexyl, cycloheptyl and cyclooctyl are included.

Preferable one is $C_{3-7}$ cycloalkyl group. More preferable is cyclopropyl, cyclobutyl, cyclopentyl, cyclohexyl, or cycloheptyl.

A "$C_{3-8}$ cycloalkenyl" group means a monocycle unsaturated hydrocarbon group having 3-8 carbon atoms including one or more double bonds.

Among this group, for example, cyclopropenyl, cyclobutenyl, cyclopentenyl, cyclohexenyl, cycloheptenyl and cyclooctenyl are included. Preferable one is $C_{3-6}$ cycloalkenyl group. More preferable is cyclohexenyl. Especially preferable is 1-cyclohexenyl.

A "saturated heterocycle" group means a group having a 4 to 6-membered ring containing 1 to 2 heteroatoms selected from nitrogen, oxygen, and sulfur in addition to a carbon atom, and whose atomic numbers constituting the ring are 4 to 6, preferably 5 to 6.

Among this group, for example, pyrrolidinyl, pyrrolidino (1-pyrrolidinyl etc.), piperidinyl, piperidino (1-piperidinyl etc.), morpholinyl, morpholino (4-morpholinyl etc.), thiomorpholinyl, thiomorpholino (4-thiomorpholinyl etc.), piperazinyl, piperazino (1-piperazinyl etc.), tetrahydropyranyl ((R)-tetrahydropyran-3-yl, (S)-tetrahydropyran-3-yl etc.), tetrahydropyranyl ((R)-tetrahydrofuran-3-yl, (S)-tetrahydrofuran-3-yl, etc.), oxetanyl, etc. are included.

Preferable one is a saturated heterocycle group with 5 to 6 members having in its ring containing one heteroatom selected from a nitrogen atom or an oxygen atom in addition to a carbon atom. More preferable are tetrahydropyranyl, tetrahydrofuranyl, oxetanyl and pyrrolidinyl. Especially preferable are (R)-tetrahydropyran-3-yl, (S)-tetrahydropyran-3-yl, 4-tetrahydropyranyl, (R)-tetrahydrofuran-3-yl, (S)-tetrahydrofuran-3-yl, oxetane-3-yl, and 1-pyrrolidinyl.

A "halo $C_{1-6}$ alkyl" group means "$C_{1-6}$ alkyl" group of the above-mentioned definition substituted by 1 to 13 "halogen atoms" of the above-mentioned definition. When multiple halogen atoms substitute, each halogen atom is the same or different. Preferable one is a group which is substituted with 1 to 6 "halogen atoms". More preferable is the group which is substituted with 1 to 6 fluorine atoms.

Among this group, for example, 2-fluoroethyl, 2-chloroethyl, 2-bromoethyl, 3-fluoropropyl, 3-chloropropyl, 4-fluorobutyl, 4-chlorobutyl, 1,1-difluoroethyl, 1,1-difluoropropyl, 1,1-difluoro-2-methylpropyl, trifluoromethyl, 2,2,2-trifluoroethyl, 3,3,3-trifluoropropyl, 4,4,4-trifluorobutyl, pentafluoroethyl and 2,2,2-trifluoro-1-trifluoromethylethyl are included.

Preferable one is halo $C_{1-4}$ alkyl group. More preferable is 1,1-difluoroethyl, 1,1-difluoropropyl, 1,1-difluoro-2-methylpropyl, trifluoromethyl, 2,2,2-trifluoroethyl, and 3,3,3-trifluoropropyl.

A "hydroxy $C_{1-6}$ alkyl" group means a group in which the hydroxy group(s) is mono- or di-substituted on the "$C_{1-6}$ alkyl" group of the above-mentioned definition. Preferable one is a group which is mono-substituted by hydroxyl group.

Among this group, for example, hydroxymethyl, 2-hydroxyethyl, 1-hydroxy-1-methylethyl, 1,2-dihydroxyethyl, 3-hydroxypropyl, 1-hydroxy-2,2-dimethylpropyl, 4-hydroxybutyl, 1-hydroxy-2,2-dimethylbutyl, 5-hydroxypentyl and 6-hydroxyhexyl are included.

Preferable one is hydroxy $C_{1-4}$ alkyl group. More preferable are hydroxymethyl, 2-hydroxyethyl, and 1-hydroxy-1-methylethyl, 1-hydroxy-2,2-dimethylpropyl and 1-hydroxy-2,2-dimethylbutyl.

A "$C_{1-6}$ alkoxy $C_{1-6}$ alkyl" group means a group in which the "$C_{1-6}$ alkoxy" group(s) of the above-mentioned definition is mono- or di-substituted on the "$C_{1-6}$ alkyl" group of the above-mentioned definition. When the $C_{1-6}$ alkoxy groups are di-substituted, each $C_{1-6}$ alkoxy group is the same or different.

Among this group, for example, methoxymethyl, ethoxymethyl, n-propoxymethyl, isopropoxymethyl, isobutoxymethyl, tert-butoxymethyl, (R)-sec-butoxymethyl, (S)-sec-butoxymethyl, 2-methoxyethyl, (R)-1-propoxyethyl, (S)-1-propoxyethyl, 1-ethylpropoxymethyl, 1-methoxy-1-methylethyl, 1,2-dimethoxyethyl, 2,2-dimethylpropoxymethyl, 2-methoxy-1,1-dimethylethyl, 1-methyl-1-propoxyethyl, 2-isopropoxyethyl, 3-methoxypropyl, 3-ethoxypropyl, 2,3-diethoxypropyl, 4-methoxybutyl, 5-methoxypentyl, 5-ethoxypentyl, 6-methoxyhexyl, 6-ethoxyhexyl, pentyloxymethyl and hexyloxymethyl are included.

Preferable one is $C_{1-4}$ alkoxy $C_{1-3}$ alkyl group. More preferable are methoxymethyl, ethoxymethyl, n-propoxymethyl, isopropoxymethyl, isobutoxymethyl, 1-methoxy-1-methylethyl, 2-isopropoxyethyl, tert-butoxymethyl, (R)-sec-butoxymethyl, (S)-sec-butoxymethyl, 1-ethylpropoxymethyl, (R)-1-propoxyethyl, (S)-1-propoxyethyl, 1-ethoxy-1-methylethyl, 1-methoxy-1-methylethyl, 2,2-dimethylpropoxymethyl, 2-methoxy-1,1-dimethylethyl, and 1-methyl-1-propoxy-ethyl.

A "$C_{3-8}$ cycloalkyl $C_{1-6}$ alkyl" group means a group in which "$C_{3-8}$ cycloalkyl" group(s) of the above-mentioned definition is mono- or di-substituted on the "$C_{1-6}$ alkyl" group of the above-mentioned definition.

When the $C_{3-8}$ cycloalkyl groups are di-substituted, each $C_{3-8}$ cycloalkyl group is the same or different.

Among this group, for example, cyclopropylmethyl, cyclobutylmethyl, cyclopentylmethyl, cyclohexylmethyl, cycloheptylmethyl, cyclooctylmethyl, 2-cyclopentylethyl, 2-cyclohexylethyl, 2-cycloheptylethyl, 2-cyclooctylethyl, 3-cyclopropylpropyl, 3,3-dicyclopropylpropyl, 3-cyclobutylpropyl, 3-cyclopentylpropyl, 2-cyclohexylpropyl, 3-cyclohexylpropyl, 3-cycloheptylpropyl, 3-cyclooctylpropyl, 4-cyclopropylbutyl, 4-cyclobutylmethyl, 4-cyclopentylbutyl, 4-cyclohexylbutyl, 4-cycloheptylbutyl, 4-cyclooctylbutyl, 5-cyclopropylpentyl, 5-cyclobutylpentyl, 3-cyclopentylpentyl, 5-cyclopentylpentyl, 5-cyclohexylpentyl, 5-cycloheptylpentyl, 5-cyclooctylpentyl, 6-cyclopropylhexyl, 6-cyclobutylhexyl, 6-cyclopentylhexyl, 6-cyclohexylhexyl, 6-cycloheptylhexyl and 6-cyclooctylhexyl are included.

Preferable one is $C_{3-6}$ cycloalkyl $C_{1-3}$ alkyl group. More preferable are cyclohexylmethyl, 2-cyclopentylethyl and 2-cyclohexylethyl.

A "$C_{3-6}$ cycloalkyl $C_{2-6}$ alkynyl" group means a group to which "$C_{3-6}$ cycloalkyl" group(s) of the above-mentioned definition is mono- or di-substituted on the "$C_{2-6}$ alkynyl" group of the above-mentioned definition. When the $C_{3-6}$ cycloalkyl groups are di-substituted, each $C_{3-6}$ cycloalkyl group is the same or different. A Preferable group is a $C_{2-6}$ alkynyl group mono-substituted by the $C_{3-6}$ cycloalkyl group.

As this group, for example, cyclopropylethynyl, cyclobutylethynyl, cyclopentylethynyl, cyclohexylethynyl, cyclopropyl-1-propynyl, are mentioned.

Preferable one is $C_{3-6}$ cycloalkyl $C_{2-4}$ alkynyl. More preferable is cyclopropylethynyl.

A "$C_{6-10}$ aryl $C_{1-6}$ alkyl" group means a group in which the "$C_{6-10}$ aryl" group(s) of the above-mentioned definition is mono- or di-substituted on the "$C_{1-6}$ alkyl" group of the above-mentioned definition.

When the $C_{6-10}$ aryl groups are di-substituted, each $C_{6-10}$ aryl group is the same or different.

Among this group, for example, benzyl, naphthylmethyl, 1-phenylethyl, 2-phenylethyl, 2-naphthylethyl and 3,3-diphenylpropyl are included.

Preferable one is $C_{6-10}$ aryl $C_{1-3}$ alkyl group. More preferable are benzyl and 2-phenylethyl.

A "saturated heterocyclo $C_{1-6}$ alkyl" group means a group in which "saturated heterocyclo" group(s) of the above-mentioned definition is mono- or di-substituted on the "$C_{1-6}$ alkyl" group of the above-mentioned definition. When the saturated heterocycle groups are di-substituted, each saturated heterocycle group is the same or different.

Among this group, for example, (1-pyrrolidinyl)methyl (namely pyrrolidine-1-ylmethyl), (1-piperidinyl)methyl, (4-morpholinyl)methyl, (4-thiomorpholinyl)methyl, (1-piperazinyl)methyl, (4-tetrahydropyranyl)methyl, 2-(1-pyrrolidinyl)ethyl, 2-(1-piperidinyl)ethyl, 2-(4-morpholinyl)ethyl, 2-(4-thiomorpholinyl)ethyl, 2-(1-piperazinyl)ethyl, 2-(4-tetrahydropyranyl)ethyl and 2-(4-tetrahydropyranyl)propyl are included.

Preferable one is a saturated heterocyclo $C_{1-3}$ alkyl group. More preferable are (4-tetrahydropyranyl)methyl, pyrrolidine-1-ylmethyl, 2-(1-pyrrolidinyl)ethyl and 2-(4-tetrahydropyranyl)ethyl.

A "halo $C_{1-6}$ alkoxy" group means a group having 1 to 13 "halogen atoms" of the above-mentioned definition substituted on the "$C_{1-6}$ alkoxy" group of the above-mentioned definition. When multiple halogen atoms are substituted, each halogen atom is the same or different. Preferable one is a group which is substituted by 1 to 6 "halogen atoms". More preferable is a group which is substituted by 1 to 6 fluorine atoms.

Among this group, for example, fluoromethoxy, chloromethoxy, bromomethoxy, 2-fluoroethoxy, 2-chloroethoxy, 2-bromoethoxy, 3-fluoropropoxy, 3-chloropropoxy, 4-fluorobutoxy, 4-chlorobutoxy, 1,1-difluoroethoxy, 2,2-difluoroethoxy, 1,1-difluoropropoxy, 2,2-difluoropropoxy, 3,3-difluoropropoxy, 1,1-difluoro-2-methylpropoxy, trifluoromethoxy, 2,2,2-trifluoroethoxy, 3,3,3-trifluoropropoxy, 4,4,4-trifluorobutoxy, pentafluoroethoxy and 2,2,2-trifluoro-1-trifluoromethylethoxy are included.

Preferable one is halo $C_{1-4}$ alkoxy group. Another preferable group is halo $C_{1-6}$ alkoxy group whose halogens are 1 to 3 fluorine atoms. More preferable are trifluoromethoxy, 2,2,2-trifluoroethoxy and 3,3,3-trifluoropropoxy, 4,4,4-trifluorobutoxy, and 2,2,2-trifluoro-1-trifluoromethylethoxy.

A "hydroxy $C_{1-6}$ alkoxy" group means a group in which the hydroxy group(s) is mono- or di-substituted on the "$C_{1-6}$ alkoxy" group of the above-mentioned definition. Preferable one is a group which is mono-substituted by hydroxy group.

As this group, for example, hydroxymethoxy, 2-hydroxyethoxy, 1-hydroxy-1-methylethoxy, 1,2-dihydroxyethoxy, 3-hydroxypropoxy, 1-hydroxy-2,2-dimethylpropoxy, 4-hydroxybutoxy, 1-hydroxy-2,2-dimethylbutoxy, 5-hydroxypentyloxy, 6-hydroxyhexyloxy, are mentioned.

Preferable one is hydroxy $C_{1-4}$ alkoxy group. More preferable is 2-hydroxyethoxy.

A "carboxy $C_{1-6}$ alkoxy" group means a group in which carboxy(s) is mono- or di-substituted on the "$C_{1-6}$ alkoxy" group of the above-mentioned definition. Preferable one is a group which is mono-substituted by a carboxy.

Among this group, for example, carboxymethoxy, 2-carboxyethoxy, 3-carboxypropoxy, 2-carboxy-1-methylethoxy, 4-carboxybutoxy, 5-carboxypentyloxy and 6-carboxyhexyloxy are included.

Preferable one is carboxy $C_{1-4}$ alkoxy group. More preferable is carboxymethoxy.

A "$C_{1-6}$ alkoxy $C_{1-6}$ alkoxy" group means a group in which the "$C_{1-6}$ alkoxy" of the above-mentioned definition is mono- or di-substituted on the "$C_{1-6}$ alkoxy" group of the above-mentioned definition. When the $C_{1-6}$ alkoxy groups are di-substituted, each $C_{1-6}$ alkoxy group is the same or different.

As this group, for example, methoxymethoxy, ethoxymethoxy, n-propoxymethoxy, isobutoxymethoxy, tert-butoxymethoxy, (R)-sec-butoxymethoxy, (S)-sec-butoxymethoxy, 2-methoxyethoxy, (R)-1-propoxyethoxy, (S)-1-propoxyethoxy, 1-ethylpropoxyethoxy, 1-methoxy-1-methylethoxy, 1,2-dimethoxyethoxy, 2,2-dimethylpropoxymethoxy, 2-methoxy-1,1-dimethylethoxy, 1-methyl-1-propoxy-ethoxy, 2-isopropoxyethoxy, 3-methoxypropoxy, 3-ethoxypropoxy, 2,3-diethoxypropoxy, 4-methoxybutoxy, 5-methoxypentyloxy, 5-ethoxypentyloxy, 6-methoxyhexyloxy, 6-ethoxyhexyloxy, pentyloxymethoxy, hexyloxymethoxy, are mentioned.

Preferable one is $C_{1-3}$ alkoxy $C_{2-4}$ alkoxy group. More preferable is 2-methoxyethoxy.

A "$C_{6-10}$ aryl $C_{1-6}$ alkoxy" group means a group in which the "$C_{6-10}$ aryl" group of the above-mentioned definition is mono- or di-substituted on the "$C_{1-6}$ alkoxy" group of the above-mentioned definition. When the $C_{6-10}$ aryl groups are di-substituted, each $C_{6-10}$ aryl group is the same or different.

As this group, benzyloxy, naphthlmethyloxy, 1-phenylethyloxy, 2-phenylethyloxy, 2-naphthylethyloxy, 3,3-diphenylpropoxy, are mentioned, for example.

Preferable one is $C_{6-10}$ aryl $C_{1-3}$ alkyl group. More preferably it is benzyloxy.

A "halo $C_{1-6}$ alkoxy $C_{1-6}$ alkyl" group means a group in which the "halo $C_{1-6}$ alkoxy" group of the above-mentioned definition is mono- or di-substituted on the "$C_{1-6}$ alkyl" group of the above-mentioned definition. When the halo $C_{1-6}$ alkoxy groups are di-substituted, each halo $C_{1-6}$ alkoxy group is the same or different.

As this group, for example fluoromethoxymethyl, chloromethoxymethyl, bromomethoxymethyl, 2-fluoroethoxymethyl, 2-chloroethoxymethyl, 2-bromoethoxymethyl, 3-fluoropropoxymethyl, 3-chloropropoxymethyl, 4-fluorobutoxymethyl, 4-chlorobutoxymethyl, 1,1-difluoroethoxymethyl, 2,2-difluoroethoxymethyl, 1,1-difluoropropoxymethyl, 2,2-difluoropropoxymethyl, 3,3-difluoropropoxymethyl, 1,1-difluoro-2-methylpropoxymethyl, trifluoromethoxymethyl, 2,3-bis trifluoromethoxypropyl, 2,2,2-trifluoroethoxymethyl, 3,3,3-trifluoropropoxymethyl, 4,4,4-trifluorobutoxymethyl, pentafluoroethoxymethyl, 2,2,2-trifluoro-1-trifluoromethyl-ethoxymethyl, 1-(trifluoromethoxy)ethyl, 1-methyl-2,3-bis-trifluoromethoxypropyl, 1-(2,2,2-trifluoroethoxy)ethyl, 1-(3,3,3-trifluoropropoxy)ethyl, 1-(4,4,4-trifluorobutoxy)ethyl, 1-(2,2,2-trifluoro-1-trifluoromethylethoxy)ethyl, 2-(trifluoromethoxy)ethyl, 2-(2,2, 2-trifluoroethoxy)ethyl, 2-(3,3,3-trifluoropropoxy)ethyl, 2-(4,4,4-trifluorobutoxy)ethyl, 2-(2,2,2-trifluoro-1-trifluoromethyl-ethoxy)ethyl, 1-methyl-1-(trifluoromethoxy)ethyl, 1-methyl-1-(2,2,2-trifluoroethoxy)ethyl, 1-methyl-1-(3,3,3-trifluoropropoxy)ethyl, 1-methyl-1-(4,4,4-trifluorobutoxy) ethyl, 1-methyl-1-(2,2,2-trifluoro-1-trifluoromethyl-ethoxy) ethyl, (R)-2,2,2-trifluoro-1-methylethoxymethyl, (S)-2,2,2-trifluoro-1-methylethoxymethyl, 2,2,2-trifluoro-1,1-dimethyl-ethoxymethyl, 2,2,2-trifluoro-1-trifluoromethyl-ethoxymethyl, 2,2,2-trifluoro-1-methyl-1-trifluoromethyl-ethoxymethyl, 3,3,3-trifluoro-2-(trifluoromethyl) propoxymethyl, 4,4,4-trifluoro-3-(trifluoromethyl) butoxymethyl, 1,1-dimethyl-3,3,3-trifluoropropoxymethyl, 2,2-dimethyl-3,3,3-trifluoropropoxymethyl, 4,4,4-trifluoro-3-(trifluoromethyl)butoxymethyl, 1,1-dimethyl-4,4,4-trifluorobutoxymethyl, 2,2-dimethyl-4,4,4-trifluorobutoxymethyl, 3-methyl-4,4,4-trifluoro-3-(trifluoromethyl)-butoxymethyl, 2-methyl-3,3,3-trifluoro-2-trifluoromethyl-propoxymethyl, are mentioned.

Preferable one is halo $C_{1-4}$ alkoxy $C_{1-3}$ alkyl group. More preferable are trifluoromethoxymethyl, 2,2,2-trifluoroethoxymethyl, 3,3,3-trifluoropropoxymethyl, (R)-2,2,2-trifluoro-1-methylethoxymethyl, (S)-2,2,2-trifluoro-1-methylethoxymethyl, 2,2,2-trifluoro-1,1-dimethyl-ethoxymethyl, 2,2,2-trifluoro-1-trifluoromethyl-ethoxymethyl and 2,2,2-trifluoro-1-methyl-1-trifluoromethyl-ethoxymethyl.

A "halo $C_{3-8}$ cycloalkyl" group means a group in which 1 to 15 "halogen atoms" of the above-mentioned definition is substituted on the "$C_{3-8}$ cycloalkyl" group of the above-mentioned definition. A preferable group is a group which is substituted by 1 to 2 "halogen atoms".

When multiple halogen atoms are substituted, each halogen atom may be the same or different.

Among this group, for example, 2-fluorocyclopropyl, 2-chlorocyclopropyl, 3-fluorocyclobutyl, 3-chlorocyclobutyl, 3-fluorocyclopentyl, 3-chlorocyclopentyl, 4-fluorocyclohexyl, 4-fluorocycloheptyl, 5-fluorocyclooctyl, 2,2-difluorocyclopropyl, 2,2-dichlorocyclopropyl, 3,3-difluorocyclobutyl, 3,3-dichlorocyclobutyl, 3,3-difluorocyclopentyl, 3,3-dichlorocyclopentyl, 4,4-difluorocyclohexyl and 4,4-dichlorocyclohexyl are included.

Preferable one is halo $C_{3-6}$ cycloalkyl group. Another preferable group is halo $C_{3-8}$ cycloalkyl group whose halogen atoms are 1 to 3 fluorine atoms. More preferable is 4,4-difluorocyclohexyl.

A "$C_{1-6}$ alkyl sulfanyl" group means the sulfanyl group substituted by the "$C_{1-6}$ alkyl" group of the above-mentioned definition.

As this group, for example methylsulfanyl, ethylsulfanyl, propylsulfanyl, isopropylsulfanyl, n-butylsulfanyl, isobutylsulfanyl, sec-butylsulfanyl, tert-butylsulfanyl, pentylsulfanyl, 1,1-dimethylpropylsulfanyl, 2,2-dimethylpropylsulfanyl, hexylsulfanyl, are mentioned.

Preferable one is isobutylsulfanyl.

A "$C_{1-6}$ alkyl sulfonyl" group means a sulfonyl group substituted by the "$C_{1-6}$ alkyl" group of the above-mentioned definition.

As this group, for example, methylsulfonyl, ethylsulfonyl, propylsulfonyl, isopropylsulfonyl (namely, propane-2-sulfonyl), n-butylsulfonyl, isobutylsulfonyl (namely, 2-methylpropane-1-sulfonyl), sec-butylsulfonyl, tert-butylsulfonyl (namely, 2-methyl-propane-2-sulfonyl), pentylsulfonyl, 1,1-dimethylpropylsulfonyl, hexylsulfonyl, 2,2-dimethylpropylsulfonyl (namely, 2,2-dimethylpropane-1-sulfonyl), are mentioned.

Preferable are propane-2-sulfonyl, 2-methylpropane-1-sulfonyl, 2-methyl-propane-2-sulfonyl, and 2,2-dimethylpropane-1-sulfonyl.

A "halo $C_{1-6}$ alkyl sulfonyl" group means a sulfonyl group substituted by the "halo $C_{1-6}$ alkyl" group of the above-mentioned definition.

As this group, for example, 2-fluoroethanesulfonyl, 2-chloroethanesulfonyl, 2-bromoethanesulfonyl, 3-fluoropropanesulfonyl, 3-chloropropanesulfonyl, 4-fluorobutanesulfonyl, 4-chlorobutanesulfonyl, 1,1-difluoroethanesulfonyl, 1,1-difluoropropanesulfonyl, 1,1-difluoro-2-methylpropanesulfonyl, trifluoromethanesulfonyl, 2,2,2-trifluoroethanesulfonyl, 3,3,3-trifluoropropanesulfonyl, 4,4,4-trifluorobutanesulfonyl, pentafluoroethanesulfonyl, 2,2,2-trifluoro-1-trifluoromethyl ethanesulfonyl, are mentioned.

Preferable are 2,2,2-trifluoro ethanesulfonyl and 3,3,3-trifluoropropanesulfonyl.

A "$C_{1-8}$ alkyl carbonyl" group means a carbonyl group substituted by the "$C_{1-8}$ alkyl" group of the above-mentioned definition.

As this group, acetyl, propionyl, 2,2-dimethylpropionyl, butyryl, 3-methylbutyryl, 2,2-dimethylbutyryl, pentanoyl, 4-methylpentanoyl, 3,4-dimethylpentanoyl, heptanoyl, nonanoyl, are mentioned, for example.

Preferable are 2,2-dimethylbutyryl and 2,2-dimethylpropionyl.

A "$C_{1-6}$ alkyloxy carbonyl" group means a carbonyl group substituted by the "$C_{1-6}$ alkoxy" group of the above-mentioned definition.

As this group, for example methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, 2-methylbutoxycarbonyl, 1,1-dimethylpropoxycarbonyl, neopentyloxycarbonyl, 3,3-dimethylbutoxycarbonyl, 1-ethylpropoxycarbonyl, hexyloxycarbonyl, are mentioned.

A "$C_{1-6}$ alkoxy carbonyloxy" group means a carbonyloxy group substituted by the "$C_{1-6}$ alkoxy" group of the above-mentioned definition.

As this group, for example methoxycarbonyloxy, ethoxycarbonyloxy, propoxycarbonyloxy, isopropoxycarbonyloxy, buthoxycarbonyloxy, isobuthoxycarbonyloxy, sec-buthoxycarbonyloxy, tert-buthoxycarbonyloxy, pentyloxycarbonyloxy, isopentyloxycarbonyloxy, 2-methyl buthoxycarbonyloxy, 1,1-dimethylpropoxycarbonyloxy, neopentyloxycarbonyloxy, 3,3-dimethyl buthoxycarbonyloxy, 1-ethylpropoxycarbonyloxy, hexyloxycarbonyloxy, are mentioned.

Preferable one is $C_{1-4}$ alkoxy carbonyloxy group. More preferable is tert-buthoxycarbonyloxy. Preferable one is tert-butoxycarbonyl.

A "$C_{1-6}$ alkyl sulfonyl $C_{1-6}$ alkyl" group means a group in which "$C_{1-6}$ alkyl sulfonyl" group of the above-mentioned definition is mono- or di-substituted on the "$C_{1-6}$ alkyl" group of the above-mentioned definition. When the $C_{1-6}$ alkyl sulfonyl groups are di-substituted, each $C_{1-6}$ alkyl sulfonyl group is the same or different. A preferable group is a group which is mono-substituted by $C_{1-6}$ alkyl sulfonyl group.

As this group, for example, methylsulfonylmethyl and ethylsulfonylmethyl (namely, ethanesulfonylmethyl), propylsulfonylmethyl, isopropylsulfonylmethyl (namely, propane-2-sulfonylmethyl), n-butylsulfonylmethyl, isobutylsulfonylmethyl (namely, 2-methylpropane-1-sulfonylmethyl), sec-butylsulfonylmethyl, tert-butylsulfonylmethyl (namely, 2-methyl-propane-2-sulfonylmethyl), pentylsulfonylmethyl, 1,1-dimethylpropylsulfonylmethyl, hexylsulfonylmethyl, 2,2-dimethylpropylsulfonylmethyl (namely, 2,2-dimethylpropane-1-sulfonylmethyl), 1-ethylsulfonylethyl (namely, 1-ethanesulfonylethyl), 1-isopropylsulfonylethyl (namely, 1-(propane-2-sulfonyl)-ethyl), 2-ethylsulfonylethyl (namely, 2-ethanesulfonylethyl), 2-isopropylsulfonylethyl (namely, 2-(propane-2-sulfonyl)-ethyl), 2,3-bis-methanesulfonylpropyl, 2,3-bis-methanesulfonyl-1-methylpropyl etc. are mentioned.

Preferable one is $C_{1-4}$ alkyl sulfonyl $C_{1-3}$ alkyl group. More preferable are ethanesulfonylmethyl and propane-2-sulfonylmethyl.

A "halo $C_{1-6}$ alkyl sulfonyl $C_{1-6}$ alkyl" group means a group in which "halo $C_{1-6}$ alkyl sulfonyl" group of the above-mentioned definition is mono- or di-substituted on the "$C_{1-6}$ alkyl" group of the above-mentioned definition. When the halo $C_{1-6}$ alkyl sulfonyl groups are di-substituted, each halo $C_{1-6}$ alkyl sulfonyl group is the same or different. A preferable group is a group which is mono-substituted by halo $C_{1-6}$ alkyl sulfonyl group.

As this group, for example 2-fluoroethanesulfonylmethyl, 2-chloroethanesulfonylmethyl, 2-bromoethanesulfonylmethyl, 3-fluoropropanesulfonylmethyl, 3-chloropropanesulfonylmethyl, 4-fluorobutanesulfonylmethyl, 4-chlorobutanesulfonylmethyl, 1,1-difluoroethanesulfonylmethyl, 1,1-difluoropropanesulfonylmethyl, 1,1-difluoroisobutanesulfonylmethyl, trifluoromethanesulfonylmethyl, 2,2,2-trifluoroethanesulfonylmethyl, 3,3,3-trifluoropropanesulfonylmethyl, 4,4,4-trifluorobutanesulfonylmethyl, pentafluoroethanesulfonylmethyl, 2,2,2-trifluoro-1-trifluoromethyl-ethanesulfonylmethyl, 1-trifluoromethanesulfonylethyl, 1-(2,2,2-trifluoroethanesulfonyl)-ethyl, 1-(3,3,3-trifluoropropanesulfonyl)-ethyl, 1-(4,4,4-trifluorobutanesulfonyl)-ethyl, 1-(2,2,2-trifluoro-1-trifluoromethyl-ethanesulfonyl)-ethyl, 2-trifluoromethanesulfonylethyl, 2-(2,2,2-trifluoroethane-sulfonyl)-ethyl, 2-(3,3,3-trifluoropropanesulfonyl)-ethyl, 2-(4,4,4-trifluorobutanesulfonyl)-ethyl, 2-(2,2,2-trifluoro-1-trifluoromethylethanesulfonyl)-ethyl, 1-methyl-1-trifluoromethanesulfonylethyl, 1-methyl-1-(2,2,2-trifluoro ethanesulfonyl)-ethyl, 1-methyl-1-(3,3,3-trifluoropropanesulfonyl)-ethyl, 1-methyl-1-(4,4,4-trifluorobutanesulfonyl)-ethyl, 1-methyl-1-(2,2,2-trifluoro-1-trifluoromethyl ethanesulfonyl)-ethyl, 2,3-bis(2,2,2-trifluoroethanesulfonyl) propyl, 1-methyl-2,3-bis(2,2,2-trifluoroethanesulfonyl) propyl, are mentioned.

Preferable one is halo $C_{1-4}$ alkyl sulfonyl $C_{1-3}$ alkyl group. Preferable one is 2,2,2-trifluoro ethanesulfonylmethyl.

A "$C_{1-6}$ alkyl sulfanyl $C_{1-6}$ alkoxy" group means a group in which "$C_{1-6}$ alkyl sulfanyl" group of the above-mentioned definition is mono- or di-substituted on the "$C_{1-6}$ alkoxy" group of the above-mentioned definition. When the $C_{1-6}$ alkyl sulfanyl groups are di-substituted, each $C_{1-6}$ alkyl sulfanyl group is the same or different. A preferable group is a group which is mono-substituted by a $C_{1-6}$ alkyl sulfanyl group.

As this group, for example, 2-methylsulfanylethoxy, 2-ethylsulfanylethoxy, 2-propylsulfanylethoxy, 2-isopropylsulfanylethoxy, 2-n-butylsulfanylethoxy, 2-isobutylsulfanylethoxy, 2-sec-butyl sulfanylethoxy, 2-tert-butyl sulfanylethoxy, 2-pentylsulfanylethoxy, 2-(1,1-dimethylpropylsulfanyl)ethoxy, 2-(2,2-dimethylpropylsulfanyl)ethoxy, 2-hexylsulfanylethoxy, 3-methylsulfanylpropoxy, 3-ethylsulfanylpropoxy, 3-propylsulfanylpropoxy, 3-isopropylsulfanylpropoxy, 3-n-butylsulfanylpropoxy, 3-isobutylsulfanylpropoxy, 3-sec-butylsulfanylpropoxy, 3-tert-butyl sulfanylpropoxy, 3-pentylsulfanylpropoxy, 3-(1,1-dimethylpropylsulfanyl)propoxy, 3-(2,2-dimethylpropylsulfanyl)propoxy, 3-hexylsulfanylpropoxy, 2-methyl-3-methyl sulfanylpropoxy, 2-methyl-3-isopropylsulfanylpropoxy, 2-methyl-3-(2,2-dimethylpropylsulfanyl)-propoxy, 2,3-bis-methyl sulfanylpropoxy, 1-methyl-2,3-bis-methylsulfanylpropoxy are mentioned.

Preferable one is $C_{1-3}$ alkyl sulfanyl $C_{2-4}$ alkoxy. More preferable is 3-methylsulfanylpropoxy.

A "$C_{1-6}$ alkyl sulfonyl $C_{1-6}$ alkoxy" group means a group in which the "$C_{1-6}$ alkylsulfonyl" group of the above-mentioned definition is mono- or di-substituted on the "$C_{1-6}$ alkoxy" group of the above-mentioned definition. When the $C_{1-6}$ alkyl sulfonyl groups are di-substituted, each $C_{1-6}$ alkyl sulfonyl group may be the same or different.

A preferable group is a group which is mono-substituted by a $C_{1-6}$ alkyl sulfonyl group.

As this group, for example, 2-methylsulfonylethoxy, 2-ethylsulfonylethoxy, 2-propylsulfonylethoxy, 2-isopropylsulfonylethoxy, 2-n-butylsulfonylethoxy, 2-isobutylsulfonylethoxy, 2-sec-butylsulfonylethoxy, 2-tert-butylsulfonylethoxy, 2-pentylsulfonylethoxy, 2-(1,1-dimethylpropylsulfonyl)ethoxy, 2-(2,2-dimethylpropylsulfonyl)ethoxy, 2-hexylsulfonylethoxy, 3-methylsulfonylpropoxy, 3-ethylsulfonylpropoxy, 3-propylsulfonylpropoxy, 3-isopropylsulfonylpropoxy, 3-n-butylsulfonylpropoxy, 3-isobutylsulfonylpropoxy, 3-sec-butylsulfonylpropoxy, 3-tert-butylsulfonylpropoxy, 3-pentylsulfonylpropoxy, 3-(1,1-dimethylpropylsulfonyl)propoxy, 3-(2,2-dimethylpropylsulfonyl)propoxy, 3-hexylsulfonylpropoxy, 2-methyl-3-methylsulfonylpropoxy, 2-methyl-3-isopropylsulfonylpropoxy, 2-methyl-3-(2,2-dimethylpropylsulfonyl)-propoxy, 2,3-bis-methylsulfonylpropoxy, 1-methyl-2,3-bis-methylsulfonylpropoxy are mentioned.

Preferable one is $C_{1-3}$ alkyl sulfonyl $C_{2-4}$ alkoxy. More preferable is 3-methanesulfonylpropoxy.

A "halo $C_{1-6}$ alkylamino $C_{1-6}$ alkyl" group means a group in which an amino group, on which the "halo $C_{1-6}$ alkyl" group of the above-mentioned definition is mono- or di-substituted, is mono- or di-substituted on the "$C_{1-6}$ alkyl" group of the above-mentioned definition. A preferable group is a group which is mono-substituted by an amino group on which the halo $C_{1-6}$ alkyl group is mono-substituted.

As this group, for example, 2-fluoroethylaminomethyl, 2-chloroethylaminomethyl, 2-bromoethylaminomethyl, 3-fluoropropylaminomethyl, 3-chloropropylaminomethyl, 4-fluorobutylaminomethyl, 4-chlorobutylaminomethyl, 1,1-difluoroethylaminomethyl, 1,1-difluoropropylaminomethyl, 1,1-difluoro-2-methylpropylaminomethyl, 2,2,2-trifluoroethylaminomethyl, 3,3,3-trifluoropropylaminomethyl, 4,4,4-trifluorobutylaminomethyl, 2,2,3,3,3-pentafluoropropylaminomethyl, 1-(2,2,2-trifluoroethylamino)-ethyl, 2-(2,2,2-trifluoroethylamino)-ethyl, 1-methyl-1-(2,2,2-trifluoroethylamino)-ethyl, bis-(2,2,2-trifluoroethyl) aminomethyl, are mentioned.

Preferable one is halo $C_{1-3}$ alkylamino $C_{1-3}$ alkyl group. More preferable is 2,2,2-trifluoroethyl aminomethyl.

As "$C_{3-8}$ cycloalkyloxy" group, cyclopropyloxy, cyclobutoxy, cyclopentyloxy, cyclohexyloxy, cycloheptyloxy, cyclooctyloxy, are mentioned, for example.

Preferable one is $C_{3-6}$ cycloalkyloxy group. More preferable is cyclopentyloxy and cyclobutoxy.

A "saturated heterocyclo oxy" group means a group in which a chemically acceptable carbon atom in the "saturated heterocycle" group of the above-mentioned definition, and an oxygen atom are combined.

As this group, for example, oxetan-3-yloxy, tetrahydrofuran-3-yloxy, (R)-tetrahydrofuran-3-yloxy, (S)-tetrahydrofuran-3-yloxy, tetrahydropyran-3-yloxy, (R)-tetrahydropyran-3-yloxy, (S)-tetrahydropyran-3-yloxy, tetrahydropyran-4- yloxy, pyrrolidin-3-yloxy, piperidin-3-yloxy, piperidin-4-yloxy, tetrahydrothiopyran-4-yloxy, are mentioned.

Preferable one is oxetan-3-yloxy.

A "saturated heterocyclo oxy $C_{1-6}$ alkyl" group means a group in which the "saturated heterocyclo oxy" group of the above-mentioned definition is mono- or di-substituted on the "$C_{1-6}$ alkyl" group of the above-mentioned definition. When the saturated heterocyclo oxy groups are di-substituted, each saturated heterocyclo oxy group is the same or different.

As this group, for example, oxetan-3-yloxymethyl, tetrahydrofuran-3-yloxymethyl, (R)-tetrahydrofuran-3-yloxymethyl, (S)-tetrahydrofuran-3-yloxymethyl, tetrahydropyran-3-yloxymethyl, (R)-tetrahydropyran-3-yloxymethyl, (S)-tetrahydropyran-3-yloxymethyl, tetrahydropyran-4-yloxymethyl, pyrrolidin-3-yloxymethyl, piperidine-3-yloxymethyl, piperidin-4-yloxymethyl, tetrahydrothiopyran-4-yloxymethyl, 1-(oxetan-3-yloxy)-ethyl, 1-(tetrahydropyran-4-yloxy)-ethyl, 2-(oxetan-3-yloxy)-ethyl, 2-(tetrahydropyran-4-yloxy)-ethyl, etc. are mentioned.

Preferable one is saturated heterocyclo oxy $C_{1-3}$ alkyl group. More preferable are oxetan-3-yloxymethyl, (R)-tetrahydrofuran-3-yloxymethyl, (S)-tetrahydrofuran-3-yloxymethyl, (R)-tetrahydropyran-3-yloxymethyl, (S)-tetrahydropyran-3-yloxymethyl, and tetrahydropyran-4-yloxymethyl.

A "saturated heterocyclo $C_{1-6}$ alkoxy" group means a group in which the "saturated heterocyclo" group of the above-mentioned definition is mono- or di-substituted on the "$C_{1-6}$ alkoxy" group of the above-mentioned definition. When the saturated heterocycle groups are di-substituted, each saturated heterocycle group is the same or different.

As this group, for example, (3-pyrrolidinyl)methoxy (namely, pyrrolidin-3-ylmethoxy), (4-piperidinyl)methoxy, oxetan-3-ylmethoxy, (4-tetrahydropyranyl)methoxy, 2-(1-pyrrolidinyl)ethoxy, 2-(1-piperidinyl)ethoxy, 2-(4-morpholinyl)ethoxy, 2-(4-thio morpholinyl)ethoxy, 2-(1-piperazinyl)ethoxy, 2-oxetan-3-ylethoxy, 2-(4-tetrahydropyranyl)ethoxy, 2-(4-tetrahydropyranyl)propoxy are mentioned.

Preferable one is saturated heterocyclo $C_{1-3}$ alkoxy group. More preferable is oxetan-3-ylmethoxy.

A "$C_{6-10}$ aryl $C_{1-6}$ alkoxy $C_{1-6}$ alkoxy" group means a group in which the "$C_{6-10}$ aryl $C_{1-6}$ alkoxy" group of the above-mentioned definition is mono- or di-substituted on the "$C_{1-6}$ alkoxy" group of the above-mentioned definition. When the $C_{6-10}$ aryl $C_{1-6}$ alkoxy group is di-substituted, each $C_{6-10}$ aryl $C_{1-6}$ alkoxy group is the same or different.

As this group, for example, 2-benzyloxyethoxy, 2-naphthlmethyloxyethoxy, 2-(1-phenylethyloxy)-ethoxy, 2-(2-phenylethyloxy)-ethoxy, 2-(2-naphthylethyloxy)-ethoxy, 2-(3,3-diphenylpropoxy)-ethoxy, 3-benzyloxypropoxy, 3-naphthlmethyloxypropoxy, 3-(1-phenylethyloxy)-propoxy, 3-(2-phenylethyloxy)-propoxy, 3-(2-naphthylethyloxy)-propoxy, 3-(3,3-diphenylpropoxy)-propoxy, 3-benzyloxy-2-methylpropoxy, 2,3-bis-benzyloxypropoxy are mentioned.

Preferable one is $C_{6-10}$ aryl $C_{1-3}$ alkyl $C_{1-3}$ alkoxy group. More preferable is 2-benzyloxyethoxy.

The case as used in "—$(CH_2)_m$—$X^a$—(C=O)—" where $X^a$ is a "bond" means "—$(CH_2)_m$—(C=O)—".

In the general Formula [I], $R^3$ is optionally substituted on carbon atoms in heterocycle within the chemically acceptable range, and is not substituted on heteroatoms.

In the general formula [Ib], $R^{3a}$ and $R^{3b}$ on heterocycles denoted by seven kinds of formulae for the ring $Cy^a$ are optionally substituted on carbon atoms in the heterocycle within the chemically acceptable range, and are not substituted on heteroatoms.

In the case that the ring $Cy^a$ is of the Formula:

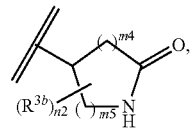

the following Formula:

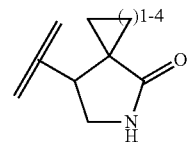

is exemplified for the compound represented by "when two $R^{3b}$ are attached to the same carbon, they optionally form $C_{3-6}$ cycloalkyl group together with the carbon to which they are attached".

In the case that the ring $Cy^a$ is of the Formula:

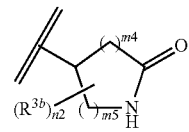

and $R^{3b}$ is $C_{1-6}$ alkyl, the following Formula:

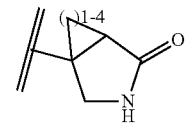

is exemplified for the compound represented by "$R^{3b}$ optionally form $C_{3-6}$ cycloalkyl group together with the carbon to which it is attached and the carbon adjacent thereto".

The preferable embodiments about each group of the compound (it is also henceforth called a "compound of the present invention".) represented by the general formula [I] are explained below.

The preferable embodiment of the ring Cy is $C_{6-10}$ aryl. The preferable examples of the ring Cy are phenyl, cyclopentyl, cyclohexyl, cycloheptyl, 1-cyclohexenyl. A more preferable ring Cy is phenyl.

The preferable example of n1 is 1, 2, 3 or 4. More preferable n1 is 1.

The preferable embodiment of $R^1$ is
(1) a halogen atom,
(2) hydroxy,
(3) carboxy,
(4) a $C_{1-5}$ alkyl group,
(5) a $C_{1-4}$ alkoxy group,
(6) a $C_{3-6}$ cycloalkyl group,
(7) a halo $C_{1-4}$ alkyl group,
(8) a hydroxy $C_{1-4}$ alkyl group,
(9) a $C_{1-4}$ alkoxy $C_{1-3}$ alkyl group,
(10) a halo $C_{1-4}$ alkoxy group or
(11) a carboxy $C_{1-4}$ alkoxy group, provided, when n1 is 2, 3 or 4, $R^1$ each is the same or different.

Another preferable embodiment of $R^1$ is
(1) a halogen atom,
(2) a $C_{1-6}$ alkyl group,
(3) a $C_{1-6}$ alkoxy group,
(4) a halo $C_{1-6}$ alkyl group,
(5) a $C_{1-6}$ alkoxy $C_{1-6}$ alkyl group or
(6) a halo $C_{1-6}$ alkoxy group,
provided, when n1 is 2, 3 or 4, $R^1$ each is the same or different.

The preferable example of $R^1$ is fluoro, chloro, hydroxy, carboxy, methyl, ethyl, propyl, isopropyl, n-butyl, tert-butyl, 2-methylpropyl, 1,1-dimethylpropyl, ethoxy, cyclopropyl, trifluoromethyl, 1,1-difluoroethyl, 1,1-difluoropropyl, 1,1-difluoro-2-methylpropyl, hydroxymethyl, 1-hydroxy-1-methylethyl, 1-methoxy-1-methylethyl, trifluoromethoxy, 2,2,2-trifluoroethoxy, 3,3,3-trifluoropropoxy or carboxymethoxy.

The preferable embodiment of $R^2$ is
(1) a $C_{1-6}$ alkyl group,
(2) a $C_{3-6}$ cycloalkyl $C_{1-3}$ alkyl group,
(3) a $C_{6-10}$ aryl $C_{1-3}$ alkyl group,
(4) a saturated heterocyclo $C_{1-3}$ alkyl group (the saturated heterocycle is of 5-membered to 6-membered saturated heterocycle having 1 to 2 heteroatoms selected from nitrogen, oxygen, and sulfur),
(5) a $C_{3-7}$ cycloalkyl group,
(6) a halo $C_{1-4}$ alkyl group (the halos are 1 to 3 fluorine atoms),
(7) a $C_{1-4}$ alkoxy $C_{1-3}$ alkyl group,
(8) a halo $C_{3-8}$ cycloalkyl group (the halos are 1 to 3 fluorine atoms),
(9) a phenyl group (the phenyl group is optionally substituted by the 1 to 4 substituents selected from
  (a) a halogen atom,
  (b) a $C_{1-3}$ alkyl group,
  (c) a $C_{1-3}$ alkoxy group and
  (d) a carboxy $C_{1-3}$ alkoxy group), or
(10) a saturated heterocycle group (the saturated heterocycle is of 5-membered to 6-membered saturated heterocycle having 1 to 2 heteroatoms selected from nitrogen, oxygen, and sulfur, and is optionally substituted by 1 to 4 $C_{1-3}$ alkyl groups).

Another preferable embodiment of $R^2$ is a $C_{6-10}$ aryl group (the $C_{6-10}$ aryl group is optionally substituted by the 1 to 4 substituents selected from
(a) a halogen atom,
(b) a $C_{1-6}$ alkyl group,
(c) a $C_{1-6}$ alkoxy group, and
(d) a carboxy $C_{1-6}$ alkoxy group).

The preferable examples of $R^2$ are ethyl, propyl, isopropyl, 2-methylpropyl, tert-butyl, 3-methylbutyl, 3,3-dimethylbutyl, hexyl, cyclohexylmethyl, cyclohexylethyl, benzyl, 2-phenylethyl, 4-tetrahydropyranylmethyl, 2-(4-tetrahydropyranyl)ethyl, 2-(1-pyrrolidinyl)ethyl, cyclopentyl, cyclohexyl, cycloheptyl, trifluoromethyl, 2,2,2-trifluoroethyl, 3,3,3-trifluoropropyl, 4,4-difluorocyclohexyl, 2-isopropoxyethyl, 2-cyclopentylethyl, phenyl, 2-chlorophenyl, 3-chlorophenyl, 4-chlorophenyl, 2-fluorophenyl, 3-fluorophenyl, 4-fluorophenyl, 2,4-difluorophenyl, 2-chloro-4-fluorophenyl, 3-fluoro-4-chlorophenyl, 2-methylphenyl, 3-methylphenyl, 4-methylphenyl, 2-methyl-4-fluorophenyl, 2-methoxyphenyl, 3-methoxyphenyl, 4-methoxyphenyl, 3-carboxymethoxyphenyl, 4-tetrahydropyranyl and 2,6-dimethyl-4-tetrahydropyranyl.

More preferable $R^2$ is phenyl group.
The preferable example of n2 is 0, 1 or 2.
More preferable n2 is 0 or 1.

The preferable example of m is 0, 1 or 2.
The preferable example of $R^3$ is methyl, ethyl or 2-hydroxyethyl.
The preferable example of $X^a$ is a bond, NH or N-methyl.
More preferable $X^a$ is a bond.
The preferable example of $X^b$ is NH.
The preferable example of $R^4$ is a hydrogen atom or methyl.

The preferable embodiments of each group of the compound (it is also henceforth called a "compound of the present invention".) represented by the general formula [Ib] are explained below.

The preferable embodiment of the ring Cy is $C_{6-10}$ aryl. The preferable examples of the ring Cy are phenyl, cyclopentyl, cyclohexyl, cycloheptyl, 1-cyclohexenyl. A more preferable ring Cy is phenyl.

The preferable example of n1 is 1, 2, 3 or 4. More preferable n1 is 1 or 2.

The preferable embodiment of $R^{1a}$ is
(1) a halogen atom,
(2) a $C_{1-6}$ alkyl group,
(3) a $C_{1-6}$ alkoxy group,
(4) a $C_{3-6}$ cycloalkyl group,
(5) a halo $C_{1-6}$ alkyl group,
(6) a hydroxy $C_{1-6}$ alkyl group,
(7) a $C_{1-6}$ alkoxy $C_{1-6}$ alkyl group,
(8) a halo $C_{1-6}$ alkoxy $C_{1-6}$ alkyl group,
(9) a $C_{1-6}$ alkylsulfonyl $C_{1-6}$ alkyl group,
(10) a halo $C_{1-6}$ alkylamino $C_{1-6}$ alkyl group,
(11) a halo $C_{1-6}$ alkoxy group,
(12) a carboxy $C_{1-6}$ alkoxy group,
(13) a saturated heterocyclo $C_{1-6}$ alkyl group (the saturated heterocycle is of 4-membered to 6-membered saturated heterocycle having 1 to 2 heteroatoms selected from nitrogen, oxygen, and sulfur) or
(14) a saturated heterocyclo oxy $C_{1-6}$ alkyl group (the saturated heterocycle is of 4-membered to 6-membered saturated heterocycle having 1 to 2 heteroatoms selected from nitrogen, oxygen, and sulfur),
provided when n1 is 2, 3 or 4, $R^{1a}$ each is the same or different.

Another preferable embodiment of $R^{1a}$ is
(1) a halogen atom,
(2) a $C_{1-6}$ alkyl group,
(3) a $C_{1-6}$ alkoxy group,
(4) a halo $C_{1-6}$ alkyl group,
(5) a $C_{1-6}$ alkoxy $C_{1-6}$ alkyl group,
(6) a halo $C_{1-6}$ alkoxy group or
(7) a halo $C_{1-6}$ alkoxy $C_{1-6}$ alkyl group,
provided, when n1 is 2, 3 or 4, $R^{1a}$ each is the same or different.

Another preferable embodiment of $R^{1a}$ is
(1) a halogen atom,
(2) a $C_{1-6}$ alkyl group,
(3) a $C_{1-6}$ alkoxy group or
(4) a halo $C_{1-6}$ alkoxy $C_{1-6}$ alkyl group,
provided, when n1 is 2, 3 or 4, $R^{1a}$ each is the same or different.

Preferable examples of $R^{1a}$ are chloro, fluoro, hydroxy, carboxy, methyl, ethyl, n-butyl, tert-butyl, propyl, isopropyl, 1,1-difluoropropyl, 1,1-dimethylpropyl, 2-methylpropyl, 3,3-dimethylbut-1-enyl, 3,3-dimethyl but-1-ynyl ethoxy, propoxy, 1,1-dimethylpropoxy, 2,2-dimethylpropoxy, isopropoxy, butoxy, isobutoxy, 3,3-dimethylbutoxy, tert-butoxy, 3-methylbutoxy, cyclopropyl, trifluoromethyl, 1,1-difluoroethyl, 1,1-difluoro-2-methylpropyl, 1,1-difluoropropyl, hydroxymethyl, 1-hydroxy-1-methylethyl, 1-hydroxy-2,2-dimethylpropyl, 1-hydroxy-2,2-dimethylbutyl, methoxymethyl, ethoxymethyl, propoxymethyl, isopropoxymethyl, isobutoxymethyl, tert-butoxymethyl, (R)-sec-butoxymethyl, (S)-sec-butoxymethyl, 1-ethylpropoxymethyl, (R)-1-propoxyethyl, (S)-1-propoxyethyl, 1-ethoxy-1-methylethyl, 1-methoxy-1-methylethyl, 2,2-dimethylpropoxymethyl, 2-methoxy-1,1-dimethylethyl, 1-methyl-1-propoxy-ethyl, trifluoromethoxymethyl, 2,2,2-trifluoroethoxymethyl, 3,3,3-trifluoro propoxymethyl, (R)-2,2,2-trifluoro-1-methylethoxymethyl, (S)-2,2,2-trifluoro-1-methylethoxymethyl, 2,2,2-trifluoro-1,1-dimethyl-ethoxymethyl, 2,2,2-trifluoro-1-trifluoromethylethoxymethyl, 2,2,2-trifluoro-1-methyl-1-trifluoromethyl-ethoxymethyl, ethanesulfonylmethyl, propane-2-sulfonylmethyl, 2,2,2-trifluoro ethanesulfonylmethyl, 2,2,2-trifluoroethyl aminomethyl, cyclopropylethynyl, trifluoromethoxy, 2,2,2-trifluoroethoxy, 3,3,3-trifluoropropoxy, 4,4,4-trifluorobutoxy, carboxymethoxy, isobutylsulfanyl, propane-2-sulfonyl, 2-methylpropane-1-sulfonyl, 2-methyl-propane-2-sulfonyl, 2,2-dimethylpropane-1-sulfonyl, 2,2,2-trifluoroethanesulfonyl, 3,3,3-trifluoropropanesulfonyl, 2,2-dimethylbutyryl, 2,2-dimethylpropionyl, tert-butoxycarbonyl, propylcarbamoyl, isopropylcarbamoyl, methylpropylcarbamoyl, 2,2,2-trifluoroethylcarbamoyl, isopropylmethylcarbamoyl, pyrrolidine-1-ylmethyl, (R)-tetrahydrofuran-3-yloxymethyl, (S)-tetrahydrofuran-3-yloxymethyl, (R)-tetrahydropyran-3-yloxymethyl, (S)-tetrahydropyran-3-yloxymethyl, oxetane-3-yloxymethyl and tetrahydropyran-4-yloxymethyl.

More preferable examples of $R^{1a}$ are n-butyl, trifluoromethoxy, 2,2,2-trifluoroethoxymethyl, 2,2,2-trifluoro-1-trifluoromethyl-ethoxymethyl, (R)-2,2,2-trifluoro-1-methylethoxymethyl, (S)-2,2,2-trifluoro-1-methylethoxymethyl and 2,2,2-trifluoro-1,1-dimethylethoxymethyl.

A preferable embodiment of $R^{2a}$ is
(1) a $C_{6-10}$ aryl group (the $C_{6-10}$ aryl group is optionally substituted by 1 to 4 substituents selected from
  (a) a halogen atom,
  (b) hydroxy,
  (c) a $C_{1-6}$ alkyl group,
  (d) a $C_{2-8}$ alkenyl group,
  (e) a $C_{2-6}$ alkynyl group,
  (f) a $C_{1-6}$ alkoxy group,
  (g) a halo $C_{1-6}$ alkyl group,
  (h) a $C_{1-6}$ alkoxy $C_{1-6}$ alkyl group,
  (i) a halo $C_{1-6}$ alkoxy group,
  (j) a hydroxy $C_{1-6}$ alkoxy group,
  (k) a $C_{1-6}$ alkoxy $C_{1-6}$ alkoxy group,
  (l) a carboxy $C_{1-6}$ alkoxy group,
  (m) a $C_{6-10}$ aryl $C_{1-6}$ alkoxy group,
  (n) a $C_{1-6}$ alkylsulfanyl $C_{1-6}$ alkoxy group,
  (o) a $C_{1-6}$ alkyl sulfonyl $C_{1-6}$ alkoxy group,
  (p) a $C_{6-10}$ aryl $C_{1-6}$ alkoxy $C_{1-6}$ alkoxy group,
  (q) a saturated heterocyclo $C_{1-6}$ alkoxy group (the saturated heterocycle is 4-membered to 6-membered saturated heterocycle having 1 to 2 heteroatoms selected from nitrogen, oxygen, and sulfur and is optionally substituted by 1 to 2 $C_{1-6}$ alkyl groups),
  (r) a saturated heterocyclo oxy group (the saturated heterocycle is 4-membered to 6-membered saturated heterocycle having 1 to 2 heteroatoms selected from nitrogen, oxygen and sulfur,
  (s) a $C_{3-8}$ cycloalkyloxy group,
  (t) a $C_{1-6}$ alkoxycarbonyloxy group and
  (u) a $C_{1-6}$ alkylsulfonyl group), or
(2) A saturated heterocycle group (the saturated heterocycle is 4-membered to 6-membered saturated heterocycle having 1 to 2 heteroatoms selected from nitrogen, oxygen and sulfur, and is optionally substituted by 1 to 4 $C_{1-6}$ alkyl groups).

Preferable examples of $R^{2a}$ are ethyl, propyl, isopropyl, 2-methylpropyl, tert-butyl, 3-methylbutyl, 3,3-dimethylbutyl, hexyl, cyclohexylmethyl, cyclohexylethyl, benzyl, 2-cyclopentylethyl, 2-phenylethyl, 4-tetrahydropyranylmethyl, 2-(4-tetrahydropyranyl)ethyl, 2-(1-pyrrolidinyl)ethyl, cyclopentyl, cyclohexyl, cycloheptyl, trifluoromethyl, 2,2,2-trifluoroethyl, 3,3,3-trifluoropropyl, 2-isopropoxyethyl, 4,4-difluorocyclohexyl, phenyl, 2-chlorophenyl, 3-chlorophenyl, 4-chlorophenyl, 2-fluorophenyl, 3-fluorophenyl, 4-fluorophenyl, 2,4-difluorophenyl, 2-chloro-4-fluorophenyl, 3-fluoro-4-chlorophenyl, 5-chloro-2-fluorophenyl, 3-hydroxyphenyl, 4-hydroxyphenyl, 2-methylphenyl, 3-methylphenyl, 4-methylphenyl, 3,5-dimethylphenyl, 2,3-dimethylphenyl, 2,5-dimethylphenyl, 2,6-dimethylphenyl, 2-ethylphenyl, 3-ethylphenyl, 4-ethylphenyl, 3-propylphenyl, 2-isopropylphenyl, 3-isopropylphenyl, 4-isopropylphenyl, 3-isobutylphenyl, 3-(3,3-dimethyl-butyl)phenyl, 3-tert-butylphenyl, 3-(2-methylpropenyl)-phenyl, ((E)-3-propenyl)-phenyl, 3-(3,3-dimethylbut-1-ynyl)-phenyl, 2-methoxypheny, 3-methoxypheny, 4-methoxypheny, 2-ethoxyphenyl, 3-ethoxyphenyl, 4-ethoxyphenyl, 3-propoxyphenyl, 4-propoxyphenyl, 2-isopropoxyphenyl, 3-isopropoxyphenyl, 4-isopropoxyphenyl, 3-isobutoxyphenyl, 3-trifluoromethylphenyl, 4-trifluoromethylphenyl, 3-methoxymethylphenyl, 3-isopropoxymethyl-phenyl, 3-trifluoromethoxy-phenyl, 4-trifluoromethoxy-phenyl, 4-(2,2,2-trifluoro-ethoxy)-phenyl, 4-(3,3,3-trifluoro-propoxy)-phenyl, 3-(2,2,2-trifluoro-ethoxy)-phenyl, 3-(2-hydroxyethoxy)-phenyl, 3-(2-methoxyethoxy)-phenyl, 3-carboxymethoxyphenyl, 3-benzyloxyphenyl, 4-benzyloxyphenyl, 3-(3-methylsulfanylpropoxy)-phenyl, 3-(3-methanesulfonylpropoxy)-phenyl, 3-(2-benzyloxyethoxy)-phenyl, 3-(3-methyloxetan-3-ylmethoxy)-phenyl, 3-(oxetan-3-yloxy)-phenyl, 3-cyclopentyloxyphenyl, 3-cyclobutoxyphenyl, 3-tert-buthoxycarbonyloxyphenyl, 3-methanesulfonylphenyl, 4-tetrahydropyranyl, 2,6-dimethyl-4-tetrahydropyranyl, 4-fluoro-2-methyl-phenyl, 4-fluoro-3-(2-hydroxyethoxy)-phenyl, 4-fluoro-3-(2-methoxyethoxy)-phenyl, 2-fluoro-3-(2-methoxyethoxy)-phenyl, 2-fluoro-5-(2-methoxyethoxy)-phenyl, 2-fluoro-3-(2-methoxyethoxy)-phenyl, 2-fluoro-3-methoxy-phenyl, 4-fluoro-3-methoxy-phenyl, 2-fluoro-5-methoxy-phenyl, 3-fluoro-5-methoxy-phenyl, 3-ethoxy-4-fluoro-phenyl, 3-ethoxy-2-fluoro-phenyl, 5-ethoxy-2-fluoro-phenyl, 3-ethoxy-5-fluoro-phenyl, 4-fluoro-3-isopropoxyphenyl, 2-fluoro-5-isopropoxyphenyl, 3-fluoro-5-isopropoxyphenyl, 2-fluoro-3-isopropoxyphenyl, and 4-fluoro-3-propoxy-phenyl.

More preferable examples of $R^{2a}$ are phenyl, 4-chlorophenyl, 2-fluorophenyl, 3-fluorophenyl and 4-fluorophenyl.

A preferable example of n2 is 0, 1 or 2.
More preferable n2 is 0 or 1.

A preferable example of m2 is 1 or 2, and
a preferable example of m3 is 1 or 2,
provided, the sum of m2 and m3 is 3 or 4.

A preferable example of m4 is 1 or 2, and
a preferable example of m5 is 0, 1 or 2,
provided, the sum of m4 and m5 is 2, 3 or 4.

A preferable example of m6 is 0 or 1, and
a preferable m7 is 0, 1 or 2,
provided, the sum of m6 and m7 is 1 or 2.

A preferable example of m8 is 1.
A preferable example of m9 is 1.

Preferable examples of the ring Cy$^a$ are
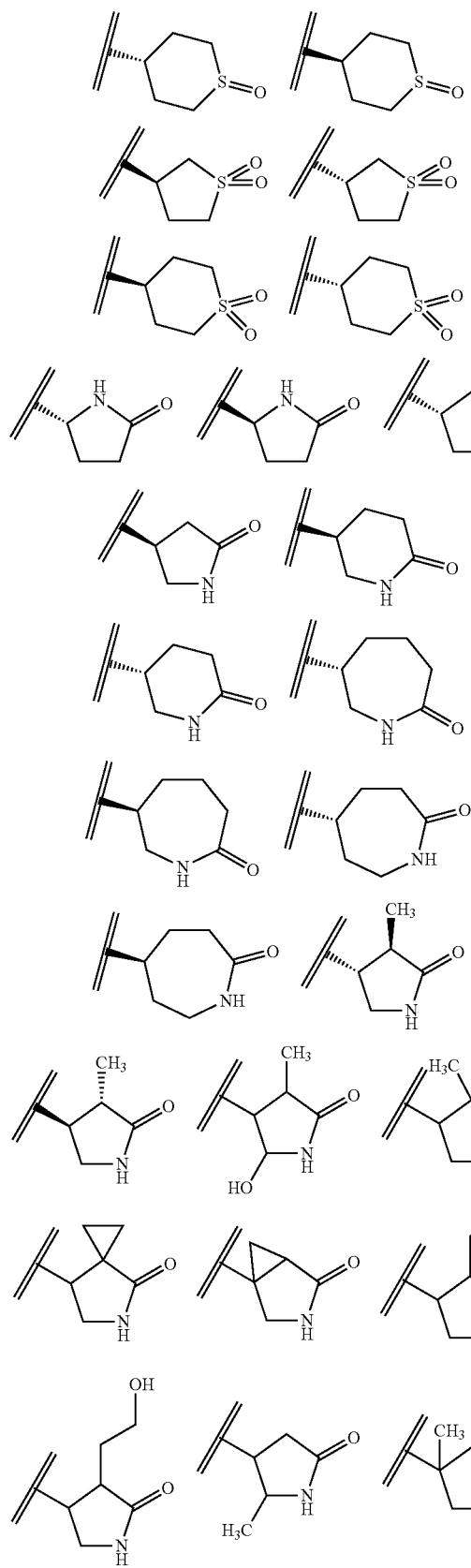
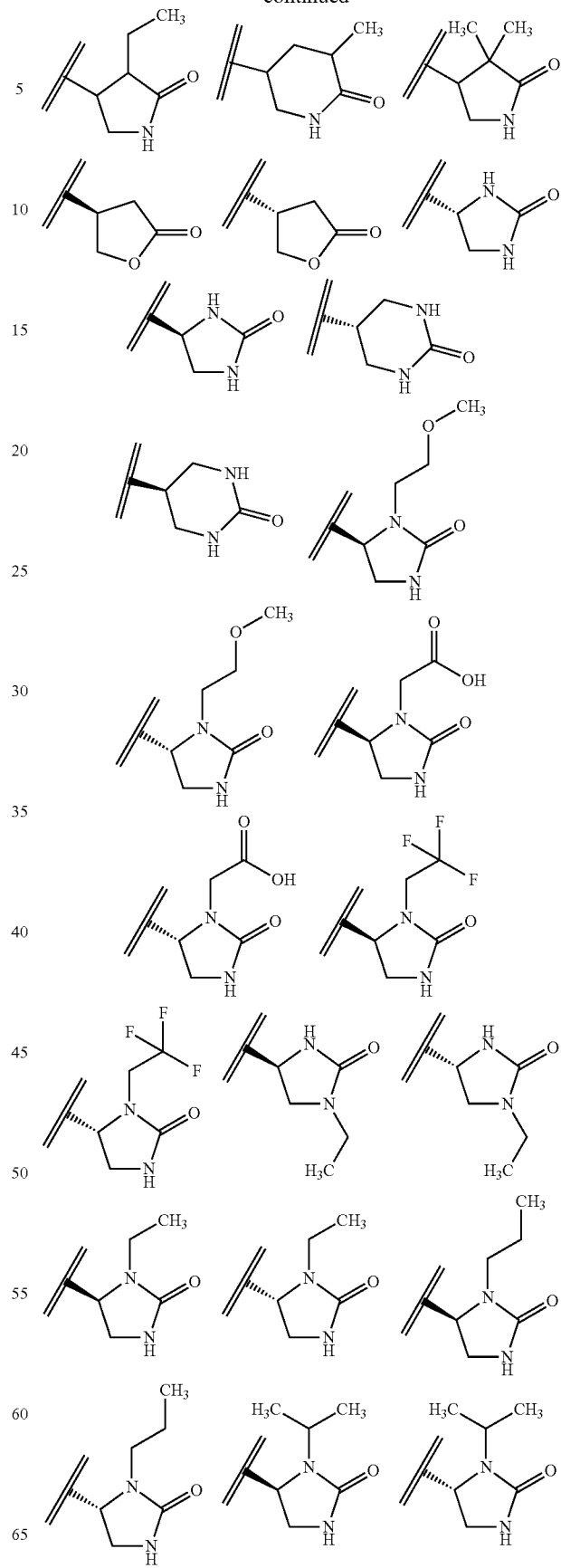

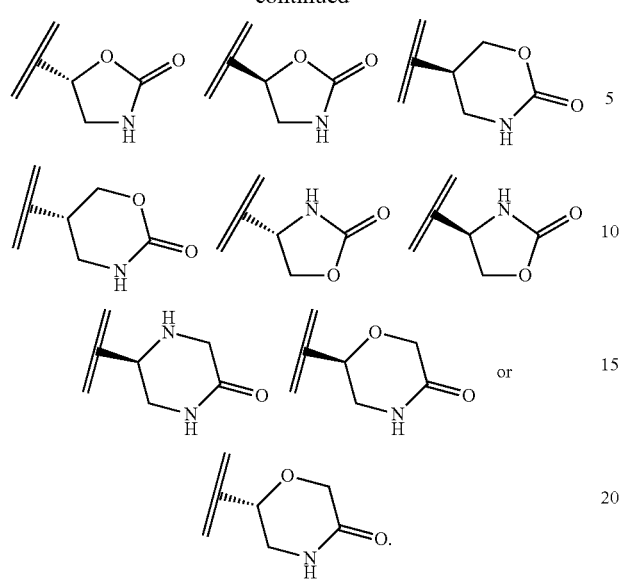
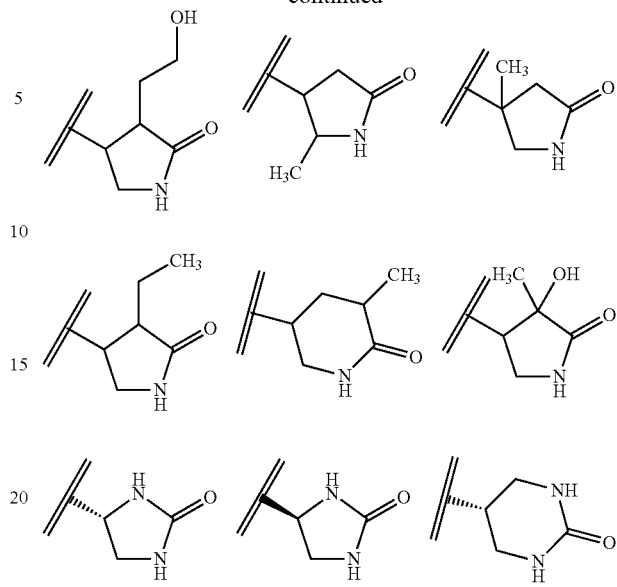
Other preferable examples of the ring Cy$^a$ are
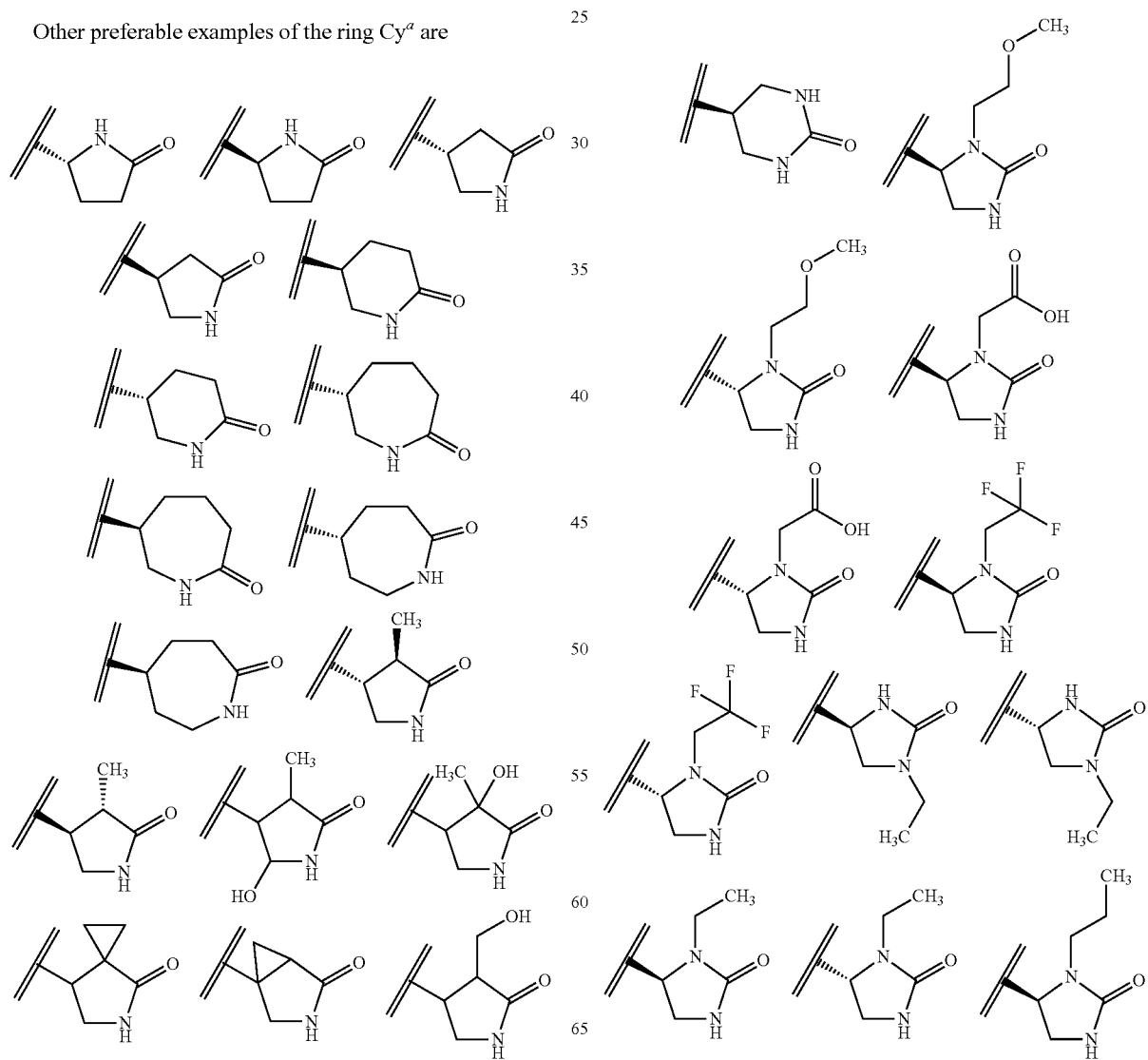

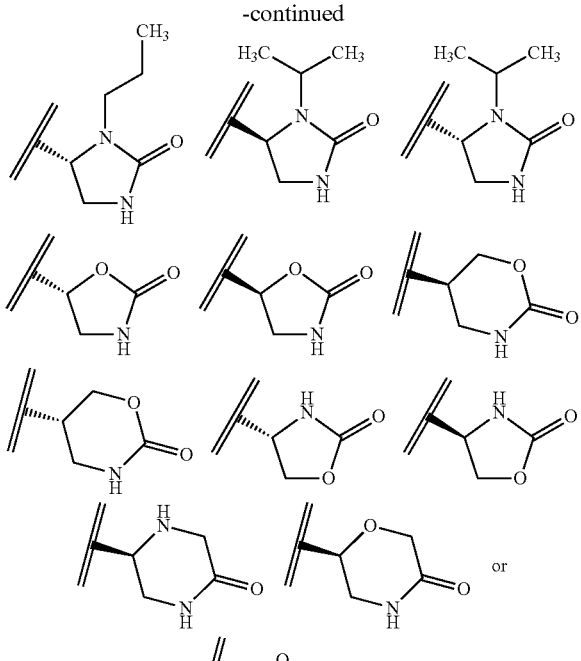
More preferable examples of the ring Cy$^a$ are
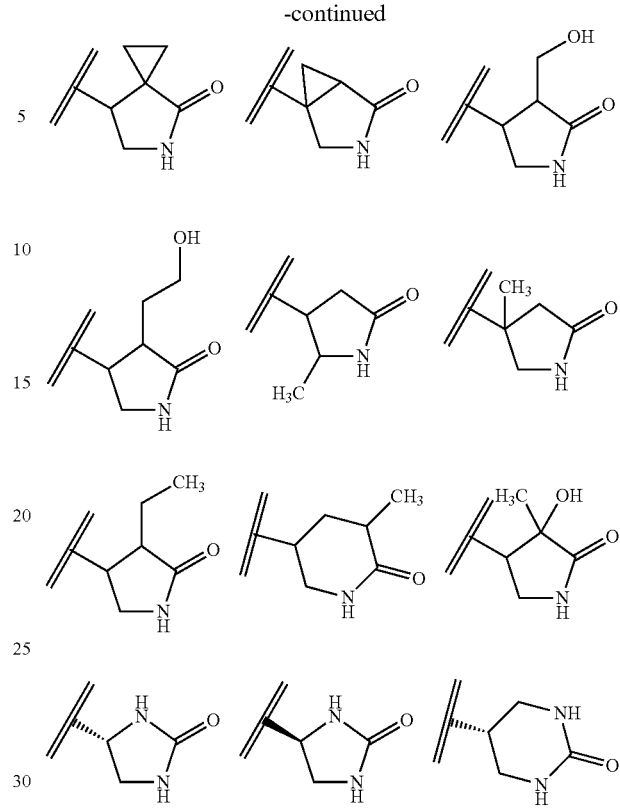
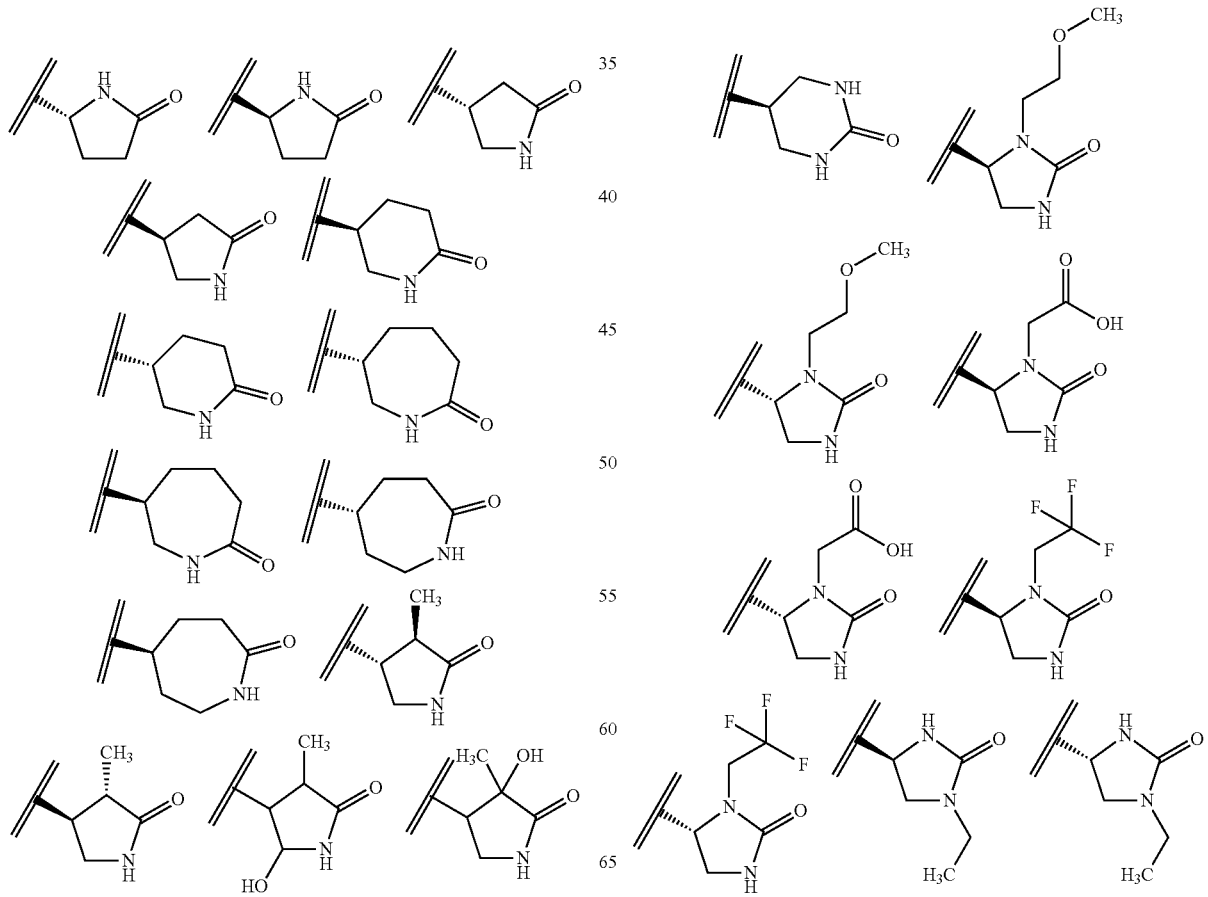

-continued

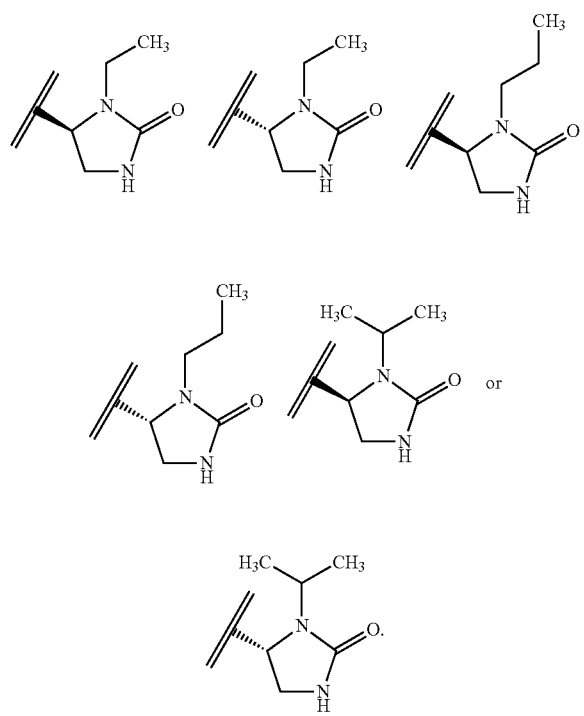

A preferable example of $R^{3a}$ is hydroxy, methyl, ethyl or 2-hydroxyethyl.

A more preferable example of $R^{3a}$ is methyl.

A preferable example of $R^{3b}$ is hydroxy, methyl, ethyl, 2-hydroxyethyl, cyclopropyl group which is formed by combining two methyl groups attached on the same carbon with the carbon to which they are attached, or cyclopropyl group which is formed by joining two methyl groups together with the adjacent carbons to which they are attached.

A more preferable example of $R^{3b}$ is methyl.

A preferable example of $R^{4b}$ is hydrogen atom, methyl, ethyl, propyl, isopropyl, carboxymethyl, 2,2,2-trifluoroethyl or 2-methoxyethyl.

A more preferable example of $R^{4b}$ is hydrogen atom.

A certain preferable embodiment of the compound of the present invention is a compound in general formula [I] wherein the ring Cy is phenyl, n1 is 1, 2, 3 or 4 and $X^b$ is NH, and the compound is represented by the general formula [II]:

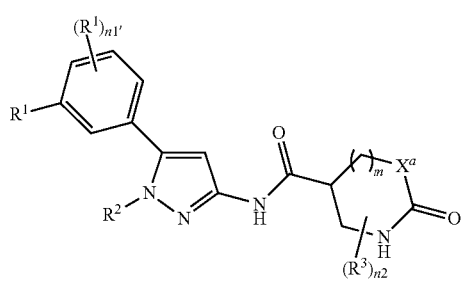

wherein n1' is 0, 1, 2 or 3, and each of other symbols is the same as those defined above.

Another preferable embodiment of the compound of the present invention is a compound in general formula [I] wherein the ring Cy is phenyl, n1 is 1, 2, 3 or 4, n2 is 0, m is 1, $X^a$ is a bond and $X^b$ is NH, and the compound is represented by the general formula [III]:

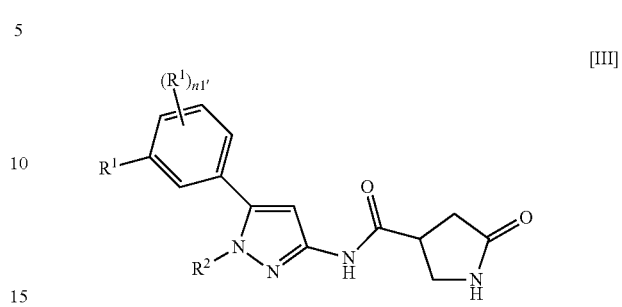

wherein n1' is 0, 1, 2 or 3, and each of other symbols is the same as those defined above.

Another preferable embodiment of the compound of the present invention is a compound in general formula [I] wherein the ring Cy is phenyl, n1 is 1, 2, 3 or 4, n2 is 1, m is 1, $X^a$ is a bond and $X^b$ is NH, and the compound is represented by the general formula [IV]:

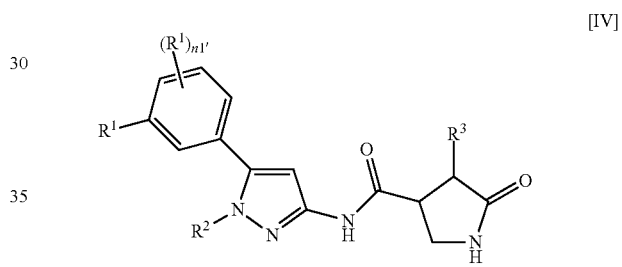

wherein n1' is 0, 1, 2 or 3, and each of other symbols is the same as those defined above.

Another preferable embodiment of the compound of the present invention is a compound in general formula [I] wherein the ring Cy is phenyl, n1 is 1, 2, 3 or 4, n2 is 0, m is 2, $X^a$ is a bond and $X^b$ is NH, and the compound is represented by the general formula [V]:

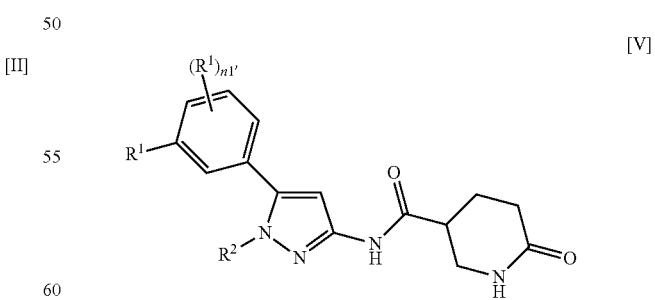

wherein n1' is 0, 1, 2 or 3, and each of other symbols is the same as those defined above.

A certain preferable embodiment of the compound of the present invention is a compound represented by the general Formula [VI]:

[VI]

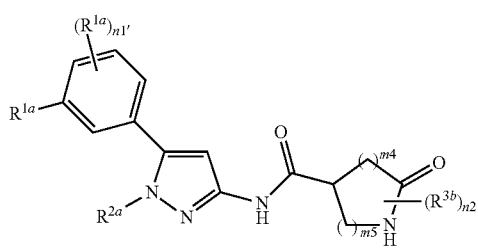

[VIII]

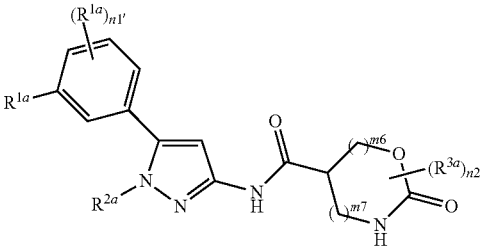

wherein, n1' is 0, 1, 2 or 3, and other symbols are the same as defined above, and the compound is that in the general Formula [Ib], wherein the ring Cy is phenyl and the ring Cy$^a$ is represented by the Formula:

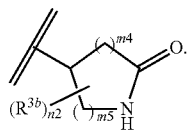

Another preferable embodiment of the compound of the present invention is a compound represented by the general Formula [VII]:

wherein, n1' is 0, 1, 2 or 3, and other symbols are the same as defined above, and the compound is that in the general Formula [Ib], wherein the ring Cy is phenyl and the ring Cy$^a$ is represented by the Formula:

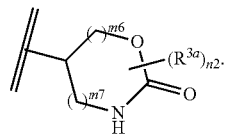

Another preferable embodiment of the compound of the present invention is a compound represented by the general Formula [IX]:

[VII]

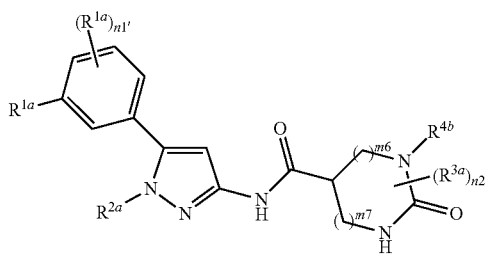

[IX]

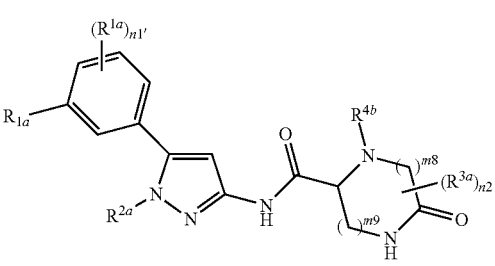

wherein, n1' is 0, 1, 2 or 3, and other symbols are the same as defined above, and the compound is that in the general Formula [Ib], wherein the ring Cy is phenyl and the ring Cy$^a$ is represented by the Formula:

wherein, n1' is 0, 1, 2 or 3, and other symbols are the same as defined above, and the compound is that in the general Formula [Ib], wherein the ring Cy is phenyl and the ring Cy$^a$ is represented by the Formula:

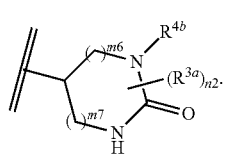

Another preferable embodiment of the compound of the present invention is a compound represented by the general Formula [VIII]:

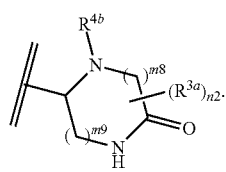

Another preferable embodiment of the compound of the present invention is a compound represented by the general Formula [X]:

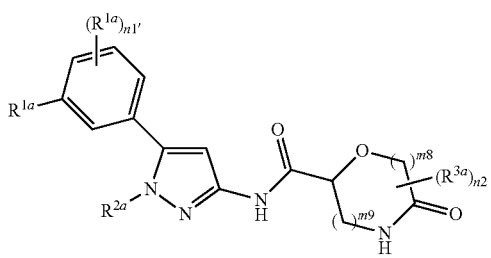
[X]

wherein, n1' is 0, 1, 2 or 3, and other symbols are the same as defined above, and the compound is that in the general Formula [Ib], wherein the ring Cy is phenyl and the ring Cy$^a$ is represented by the Formula:

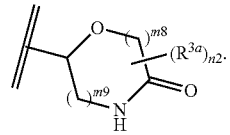

Another preferable embodiment of the compound of the present invention is a compound represented by the general Formula [XI]:

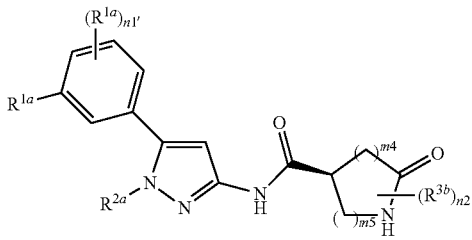
[XI]

wherein, n1' is 0, 1, 2 or 3, and other symbols are the same as defined above, and the compound is that in the general Formula [Ib], wherein the ring Cy is phenyl and the ring Cy$^a$ is represented by the Formula:

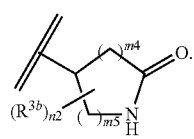

Another preferable embodiment of the compound of the present invention is a compound represented by the general Formula [XII]:

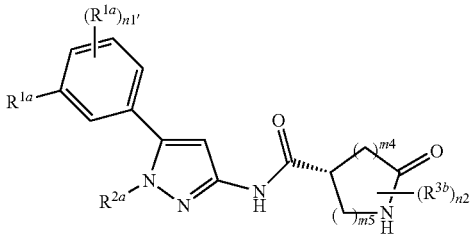
[XII]

wherein, n1' is 0, 1, 2 or 3, and other symbols are the same as defined above, and the compound is that in the general Formula [Ib], wherein the ring Cy is phenyl and the ring Cy$^a$ is represented by the Formula:

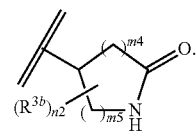

Another preferable embodiment of the compound of the present invention is a compound represented by the general Formula [XIII]:

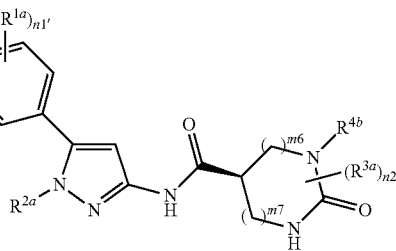
[XIII]

wherein, n1' is 0, 1, 2 or 3, and other symbols are the same as defined above, and the compound is that in the general Formula [Ib], wherein the ring Cy is phenyl and the ring Cy$^a$ is represented by the Formula:

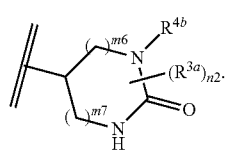

Another preferable embodiment of the compound of the present invention is a compound represented by the general Formula [XIV]:

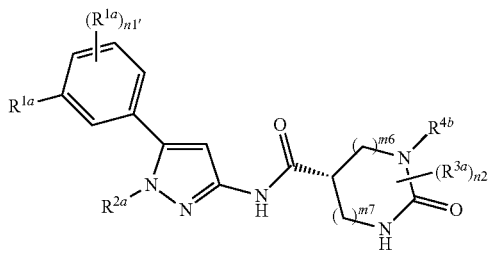

[XIV]

wherein, n1' is 0, 1, 2 or 3, and other symbols are the same as defined above, and the compound is that in the general Formula [Ib], wherein the ring Cy is phenyl and the ring Cy$^a$ is represented by the Formula:

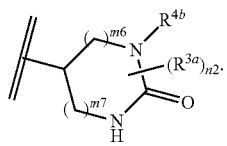

A certain preferable embodiment of the compound of the present invention is a compound represented by the general Formula [XV]:

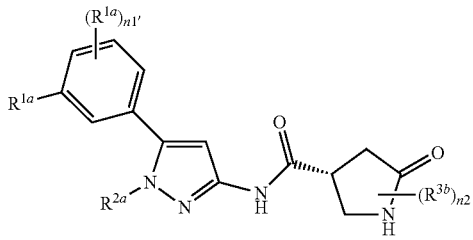

[XV]

wherein, n1' is 0, 1, 2 or 3, and other symbols are the same as defined above.

A certain preferable embodiment of the compound of the present invention is a compound represented by the general Formula [XVI]:

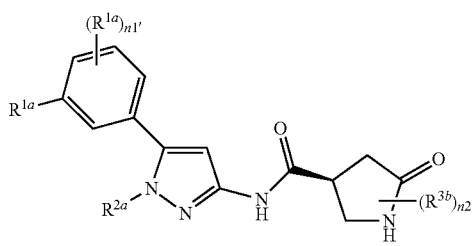

[XVI]

wherein, n1' is 0, 1, 2 or 3, and other symbols are the same as defined above.

Another preferable embodiment of the compound of the present invention is a compound represented by the general Formula [XVII]:

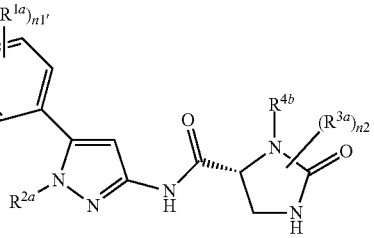

[XVII]

wherein, n1' is 0, 1, 2 or 3, and other symbols are the same as defined above.

A certain preferable embodiment of the compound of the present invention is a compound represented by the general Formula [XVIII]:

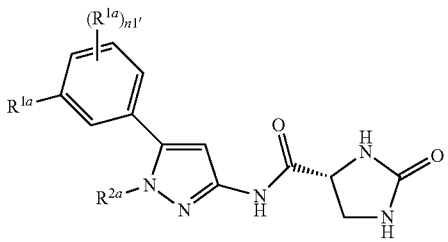

(XVIII)

wherein, n1' is 0, 1, 2 or 3, and other symbols are the same as defined above.

Another preferable embodiment of the compound of the present invention is a compound represented by the general Formula [XIX]:

(XIX)

wherein, n1' is 0, 1, 2 or 3, and other symbols are the same as defined above.

A "pharmaceutically acceptable salt" of a compound of the present invention may be any nonpoisonous salt of a compound of the present invention and include any kind of salts, for example, a salt with an inorganic acid, a salt with an organic acid, a salt with an inorganic base, a salt with an organic base and a salt with amino acid.

As the salt with an inorganic acid, salt with hydrochloric acid, nitric acid, sulfuric acid, phosphoric acid, hydrobromic acid are included, for example.

As the salt with an organic acid, for example, salt with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid and p-toluenesulfonic acid are included.

As the salt with an inorganic base, for example, sodium salt, potassium salt, calcium salt, magnesium salt and ammonium salt are included.

As the salt with an organic base, for example, salts with methylamine, diethylamine, trimethylamine, triethylamine, ethanolamine, diethanolamine, triethanolamine, ethylenediamine, tris (hydroxymethyl)methylamine, dicyclohexylamine, N,N'-dibenzylethylenediamine, guanidine, pyridine, picoline, choline, cinchonine and meglumine are included.

As the salt with amino acid, for example, salts with lysine, arginine, aspartic acid and glutamic acid are included.

In accordance with known methods, each salt may be obtained by reacting a compound of the present invention with an inorganic base, an organic base, an inorganic acid, an organic acid or amino acid.

Various "isomers" exist in the compound of the present invention. For example, E isomer and Z isomer exist as geometrical isomers. When asymmetric carbon atoms exist, the enantiomer and the diastereoisomer as stereoisomers based on these in compounds of the present invention exist. When axial asymmetries exist, the stereoisomers based on these exist. By a case, a compound of the present invention may exist in tautomer. Therefore, these all isomers and mixtures thereof are included in the scope of the present invention.

The compounds represented by the general formulae [I] and [Ib] or pharmaceutically acceptable salts thereof may be in a form of "solvate" thereof. The "solvate" means the compounds represented by the general formulae [I] and [Ib] or pharmaceutically acceptable salts thereof to which is coordinated by a solvent molecules. The solvate which is pharmaceutically acceptable is preferred. The solvate includes, for example, hydrate, ethanolate, dimethyl sulfoxide solvate of the compounds represented by the general formulae [I] and [Ib] or pharmaceutically acceptable salts thereof. Specifically, hemihydrate, monohydrate, dihydrate or mono ethanolate of the compound represented by general formulae [I] and [Ib], or monohydrate of sodium salt of the compound represented by general formulae [I] and [Ib], or 2/3-ethanolate of dihydrochloride of them is mentioned. The solvate may be obtained in accordance with known methods.

A compound of the present invention may be labeled with isotopes (for example, $^{2}H$, $^{3}H$, $^{14}C$, $^{35}S$).

As a compound or a pharmaceutically acceptable salt thereof in the present invention, a compound or a pharmaceutically acceptable salt thereof in the present invention purified substantially is preferred. A compound or a pharmaceutically acceptable salt thereof in the present invention over 80% or more of purities is more preferable.

In the present invention, prodrugs of the compounds represented by the general formulae [I] and [Ib] can also serve as a useful medicine. The "prodrug" means a derivative of the compound of the present invention which has a chemically or metabolically decomposable group, and upon administered to the living body, the derivative restores to the original compound and exerts the original drug action after decomposition by, for example, hydrolysis, solvolysis or decomposition under physiological condition. In the derivatives, a complex and a salt which are not formed by a covalent bond are also included. The prodrug is used for the absorption improvement in oral administration, or for targeting to a targeted position, for example. As a modification site to form a prodrug, functional groups with high reactivity such as hydroxy group, carboxy group, and amino group in the compound of the present invention are included.

A modifying group for hydroxy group includes, specifically, acetyl group, propionyl group, isobutyryl group, pivaloyl group, palmitoyl group, benzoyl group, 4-methylbenzoyl group, dimethylcarbamoyl group, dimethylaminomethylcarbonyl group, sulfo group, alanyl group, fumaryl group, etc. 3-Carboxybenzoyl group and 2-carboxyethylcarbonyl group which are in the form of sodium-salt are also included.

A modifying group for carboxy group includes, specifically, methyl group, ethyl group, propyl group, isopropyl group, butyl group, iso-butyl group, tert-butyl group, pivaloyloxymethyl group, carboxymethyl group, dimethylaminomethyl group, 1-(acetyloxy)ethyl group, 1-(ethoxycarbonyloxy)ethyl group, 1-(isopropyloxycarbonyloxy)ethyl group, 1-(cyclohexyloxycarbonyloxy)ethyl group, (5-methyl-2-oxo-1,3-dioxol-4-yl)methyl group, benzyl group, phenyl group, o-tolyl group, morpholinoethyl group, N,N-diethylcarbamoylmethyl group, phthalidyl group, etc.

A modifying group for amino group includes, specifically, tert-butyl group, docosanoyl group, pivaloylmethyloxy group, alanyl group, hexylcarbamoyl group, pentylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group, (5-methyl-2-oxo-1,3-dioxol-4-yl)methoxycarbonyl group, tetrahydrofuranyl group and pyrrolidylmethyl group, etc.

Since a compound or a pharmaceutically acceptable salt thereof in the present invention has SGLT1 inhibitory activity, it is useful for the treatment and/or prevention of various diseases or conditions of which may be expected to be improved by regulation of SGLT1 activity, for example, diabetes, obesity, diabetic complication (for example, retinopathy, nephropathy and neuropathy which are known as microangiopathy, as well as cerebrovascular disease, ischemic heart disease and membrum-inferius arteriosclerosis obliterans which are known as macroangiopathy), hypertrophic cardiomyopathy, ischemic heart disease, cancer and constipation. Diabetes is type II diabetes mellitus preferably.

"Inhibition of SGLT1" means inhibiting the function of SGLT1, and disappearing or decreasing the activity, and, for example, means inhibiting the function of SGLT1 based on the conditions of the examples of examinations mentioned below. A preferable "inhibition of SGLT1" is "inhibition of human SGLT1". A preferable "SGLT1 inhibitor" is "human SGLT1 inhibitor".

"Treatment" means alleviating or healing symptoms or disease, and/or its accompanying symptoms.

"Prevention" means a method of delaying or preventing the onset of symptoms or disease, and/or its accompanying symptoms, a method of keeping a patient from acquiring symptoms or disease, or a method of reducing a risk of a patient acquiring symptoms or disease.

The pharmaceutical composition of the present invention is manufactured by suitably mixing a compound or a pharmaceutically acceptable salts thereof in the present invention with at least one or more sorts of pharmaceutically acceptable carriers etc. in suitable amounts in accordance with known methods in the technical field of medicinal preparation. Content amounts of a compound or a pharmaceutically acceptable salt thereof in the present invention in the pharmaceutical composition change depending on dosage forms, dose, etc., but are 0.1 to 100% of the weight to the whole pharmaceutical composition, for example.

A "pharmaceutical compositions" include oral preparations such as tablets, capsules, granules, powders, trochiscus, syrups, emulsion, and suspension, and parenteral preparations such as external preparations, suppositories, injections, ophthalmic solutions, intranasal agents, and pulmonary agents.

A "pharmaceutically acceptable carriers" includes various conventional organic or inorganic carrier substances, for example, substances in solid preparations such as excipients, disintegrators, binders, glidants and lubricants, and substances in liquid preparations such as solvents, solubilizing agents, suspending agents, isotonizing agents, buffers and soothing agents. Additives such as preservatives, antioxidants, colorants, and edulcorants, are used if needed.

The "excipients" includes, for example, lactose, white soft sugar, D-mannitol, D-sorbitol, corn starch, dextrin, microcrystalline cellulose, crystalline cellulose, carmellose, carmellose calcium, carboxy-methyl-starch sodium, low substituted hydroxypropylcellulose and acacia.

The "disintegrators" include for example, carmellose, carmellose calcium, carmellose sodium, carboxy-methyl-starch sodium, cross-carmellose sodium, crospovidone, low substituted hydroxypropylcellulose, hydroxypropylmethyl cellulose and crystalline cellulose.

The "binders" include, for example, hydroxypropylcellulose, hydroxypropylmethyl cellulose, povidone, crystalline cellulose, white soft sugar, dextrin, starch, gelatin, carmellose sodium and acacia.

The "glidants" include, for example, light anhydrous silicic acid and magnesium stearate.

The "lubricants" include, for example, magnesium stearate, calcium stearate and talc.

The "solvents" include, for example, purified water, ethanol, propylene glycol, macrogol, sesame oil, corn oil and olive oil.

The "solubilizing agents" include, for example, propylene glycol, D-mannitol, benzyl benzoate, ethanol, triethanolamine, sodium carbonate and sodium citrate.

The "suspending agents" include, for example, benzalkonium chloride, carmellose, hydroxypropylcellulose, propylene glycol, povidone, methylcellulose and glyceryl monostearate.

The "isotonizing agents" include, for example, glucose, D-sorbitol, sodium chloride and D-mannitol.

The "buffers" include, for example, disodium hydrogen phosphate, sodium acetate, sodium carbonate and sodium citrate.

The "soothing agents" include, for example, benzyl alcohol.

The "preservatives" include, for example, ethyl parahydroxybenzoate, chlorobutanol, benzyl alcohol, sodium dehydroacetate, and sorbic acid.

The "antioxidants" include, for example, sodium sulfite and ascorbic acid.

The "colorants" include, for example, food colors (for example, Food Red No. 2 or No. 3, Food Yellow No. 4, or No. 5) and beta-carotene.

The "edulcorant" include, for example, saccharin sodium, glycyrrhizinate dipotassium and aspartame.

The pharmaceutical composition of the present invention can be administered to mammals other than human (for example, mice, rats, hamsters, guinea pigs, rabbits, cats, dogs, pig, cows, horses, sheeps, monkeys) and to human, in oral or parenteral (for example, topical, rectum, intravenous administration) in a therapeutically effective amount. Although the "therapeutically effective amount" changes depending on patients, disease, symptoms, dosage forms, routes of administration, for example, the dose in the case of administering orally to the adult patient (weight: about 60 kg) suffering from diabetes (type II diabetes mellitus etc.) ranges usually from about 1 mg to 1 g per day using, as an active ingredient, a compound or a pharmaceutically acceptable salt thereof in the present invention. Such quantity can be administrated to the patient once or in several times a day.

The pharmaceutical composition comprising a compound or a pharmaceutically acceptable salt thereof in the present invention as an active ingredient or an activator, and the kits (administration, treatment and/or prevention kit), packages (packaging goods etc.), and medicine set (and/or, container) containing the package insert about the pharmaceutical composition which indicate that the pharmaceutical composition can be used or should be used for treatment and/or prevention are also useful. Such kit, the package, and the medicine set may be provided with one or more containers filled with one or more active ingredients and other medicines, or the medicine (or the component) for the above-mentioned pharmaceutical compositions. As examples of such a kit, a package, and a medicine set, the kit for commerce appropriately directed to the treatment and/or prevention of an object disease and the package for commerce are included. As a package insert comprised in such a kit, a package, and a medicine set, notes by the government organization which regulates manufacture, use or sale of a pharmaceutical or biological products, and notes which show the approval of the government organization about manufacture, use or sale of the product relevant to medication to a human are included. In the above-mentioned kit, package and medicine set, the packed product may also be included, and the structure constituted by adopting a suitable medication step (step) may be included, and the structure constituted as could attain the treatment and/or prevention on more preferable medicine including treatment, prevention of an object disease may be included.

A compound or a pharmaceutically acceptable salt thereof in the present invention may be used by the general method currently performed in the medicinal field in combination (henceforth "combination therapy") with one or multiple other drugs (henceforth, a "concomitant drug").

A timing for administration of a compound or a pharmaceutically acceptable salt thereof in the present invention and a concomitant drug is not limited. They may be administrated to the patient as a combination drug, or they may be administrated to the patient simultaneously or in a constant interval. A pharmaceutical kit which is characterized in consisting of a pharmaceutical composition of the present invention and a concomitant drug can be used. The dose of a concomitant drug should comply with the dose in clinical use, and it can be selected suitably depending on patients, disease, symptoms, dosage forms, routes of administration, administration time, combination. The administration method of a concomitant drug is not limited in particular, and a compound or a salt thereof in the present invention and a concomitant drug should just be put together.

The concomitant drug includes, for example,
(1) a therapeutic agent and/or prophylactic of dyslipidemia,
(2) a therapeutic agent and/or prophylactic of obesity,
(3) a therapeutic agent and/or prophylactic of diabetes,
(4) a therapeutic agent and/or prophylactic of diabetic complication, and
(5) a therapeutic agent and/or prophylactic of hypertension, and any one or multiple of these agents and a compound or a pharmaceutically acceptable salt thereof in the present invention may be used in combination.

As an example, a method for preparing compounds for working the present invention is explained as follows, and the method for preparing a compound or a pharmaceutically acceptable salt thereof in the present invention is not intended to be limited thereto.

Unless otherwise specified, effective preparation methods may be carried out by devising such as: introducing any protecting groups into any functional groups, if needed, and then deprotecting at a later step; in each step, treating any functional groups in the forms of their precursor, and converting the same into the corresponding desirable functional groups at an appropriate step; interchanging the order of each preparation method and step; optionally using reagents other than those illustrated below in order to accelerate the progress of reaction, etc.

In each step, aftertreatment of reaction may be performed in a conventional manner, and isolation and purification may be optionally performed by selection from or combination of the conventional procedures, such as crystallization, re-crystallization, distillation, liquid separation, silica gel column chromatography and preparative HPLC, if needed. A reaction may be proceeded to the sequential step without isolation and purification depending on the situation.

[Preparation Method 1]

A method for preparing a compound of the general formula [I] is illustrated as "Preparation Method 1-1" and "Preparation Method 1-2" below. Preparation Method 1-1

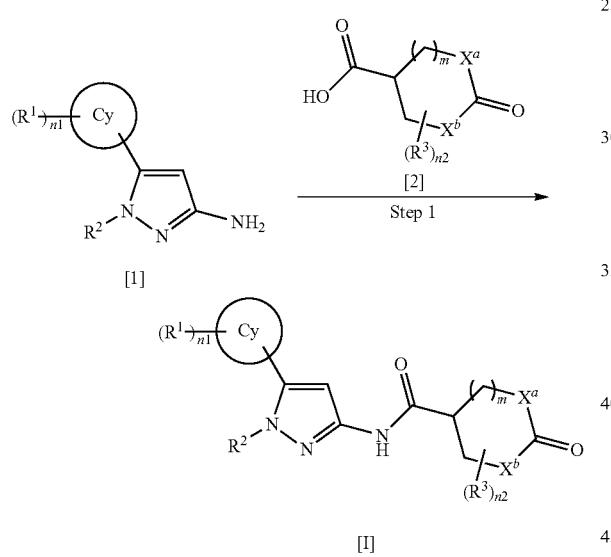

wherein each symbol has the same meaning as defined above.

(Step 1)

Compound [I] may be obtained by reacting Compound [1] or a salt thereof with Compound [2] in a solvent in the presence of a condensing agent and an additive.

A preferable condensing agent is dicyclohexylcarbodiimide (DCC), 1-ethyl-3-(3-dimethylaminopropyl)carbodiimide hydrochloride (WSC.HCl), diisopropylcarbodiimide, 1,1'-carbonyldiimidazole (CDI), O-(7-azabenzotriazol-1-yl)-N,N,N',N'-tetramethyluronium hexafluorophosphate (HATU), (benzotriazol-1-yloxy)tripyrrolidinophosphonium hexafluorophosphate (PyBOP), diphenylphosphoryl azide, etc.

A preferable additive is 1-hydroxybenzotriazole (HOBt), 1-hydroxy-7-azabenzotriazole (HOAt), N-hydroxysuccinimide (HOSu). Optionally, 4-dimethylaminopyridine, etc. may be added as an additive, etc.

A preferable solvent is a halogenated hydrocarbon solvent such as chloroform; an ether solvent such as tetrahydrofuran; a polar solvent such as pyridine, acetonitrile and N,N-dimethylformamide; or a mixed solvent thereof.

The reaction temperature is usually about 0° C. to 100° C., preferably about 0° C. to 40° C.

When a salt of Compound [1] is used, the reaction may be done in the presence of a base such as an organic base such as triethylamine; or an alkali metal salt such as sodium carbonate.

Alternatively, Compound [I] may be obtained by preliminarily converting Compound [2] into an acid chloride thereof, etc., and then reacting the resulting compound with Compound [1] in the presence of a base.

Compound [2] may be commercially available, or may be obtained by using Preparation Method 3 below or a conventional method.

Preparation Method 1-2

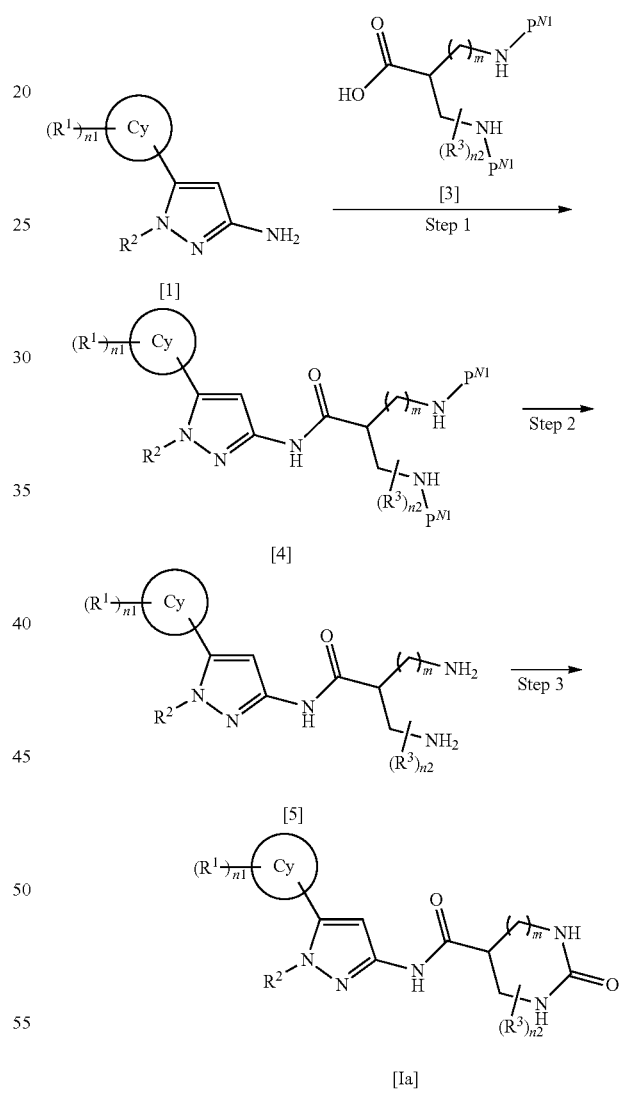

wherein, $P^{N1}$ is a protecting group of an amino group; a preferable $P^{N1}$ is tert-butoxycarbonyl group;
and each of other symbols has the same meaning as defined above.

(Step 1)

Compound [4] may be obtained by reacting Compound [1] or a salt thereof with Compound [3] in a solvent in the presence of a condensing agent and an additive.

A preferable condensing agent is dicyclohexylcarbodiimide (DCC), 1-ethyl-3-(3-dimethylaminopropyl)carbodiimide hydrochloride (WSC.HCl), diisopropylcarbodiimide, 1,1'-carbonyldiimidazole (CDI), O-(7-azabenzotriazol-1-yl)-N,N,N',N'-tetramethyluronium hexafluorophosphate (HATU), (benzotriazol-1-yloxy)tripyrrolidinophosphonium hexafluorophosphate (PyBOP), diphenylphosphoryl azide, etc.

A preferable additive is 1-hydroxybenzotriazole (HOBt), 1-hydroxy-7-azabenzotriazole (HOAt), N-hydroxysuccinimide (HOSu), etc. Optionally, 4-dimethylaminopyridine, etc. may be added as an additive, etc.

A preferable solvent is a halogenated hydrocarbon solvent such as chloroform; an ether solvent such as tetrahydrofuran; a polar solvent such as pyridine, acetonitrile and N,N-dimethylformamide; or a mixed solvent thereof.

The reaction temperature is usually about 0° C. to 100° C., preferably about 0° C. to 40° C.

When a salt of Compound [1] is used, the reaction may be done in the presence of a base such as an organic base such as triethylamine; or an alkali metal salt such as sodium carbonate.

Alternatively, Compound [4] may be obtained by preliminarily converting Compound [3] into an acid chloride thereof, etc., and then reacting the resulting compound with Compound [1] in the presence of a base.

Compound [3] may be commercially available, or may be obtained by a conventional method.

(Step 2)

Compound [5] or a salt thereof may be obtained by removing $P^{N1}$ from Compound [4] in a conventional deprotection reaction. The deprotection reaction may be done by using suitable conditions for each of kinds of $P^{N1}$. For example, when $P^{N1}$ is tert-butoxycarbonyl group, Compound [5] or a salt thereof may be obtained by treating Compound [4] in a solvent under an acidic condition at room temperature. Compound [5] may be isolated as a salt, or as a free form after neutralization.

A preferable solvent is, for example, an alcoholic solvent such as ethanol; an ether solvent such as 1,4-dioxane; an ester solvent such as ethyl acetate; a halogenated hydrocarbon solvent such as chloroform; or a mixed solvent thereof.

A preferable acid used in the reaction is hydrochloric acid or trifluoroacetic acid.

(Step 3)

Compound [Ia] may be obtained by transforming diamino group of Compound [5] or a salt thereof into urea group.

The reagents used in the reaction include, for example, diethyl carbonate, diethyl pyrocarbonate, 1,1'-carbonyldiimidazole (CDI), chloroformate, etc., preferably 1,1'-carbonyldiimidazole (CDI).

A preferable solvent is a halogenated hydrocarbon solvent such as chloroform; an ether solvent such as tetrahydrofuran; a hydrocarbon solvent such as toluene; a polar solvent such as pyridine, acetonitrile and N,N-dimethylformamide; or a mixed solvent thereof.

The reaction temperature is usually about 0° C. to 100° C., preferably about 0° C. to 40° C.

When a salt of Compound [5] is used, the reaction may be done in the presence of a base such as an organic base such as triethylamine; or an alkali metal salt such as sodium carbonate.

When Compound [I] or Compound [Ia] has an enantiomer or a geometric isomer thereof, the reaction may be done by using a commercially available optically active compound or a single diastereomer compound or such a compound obtained by a conventional method. Alternatively, the optically active compound or the single diastereomer of Compound [I] or Compound [Ia] may be obtained by separating and purifying appropriately during the preparation process. The compound which undergoes separation and purification includes Compound [I] or Compound [Ia], etc. A method for separation and purification includes, for example, column chromatography or preparative HPLC.

A method for preparing the compound represented by the general Formula [Ib] is illustrated in the following Preparation Method 1-3.

Preparation Method 1-3

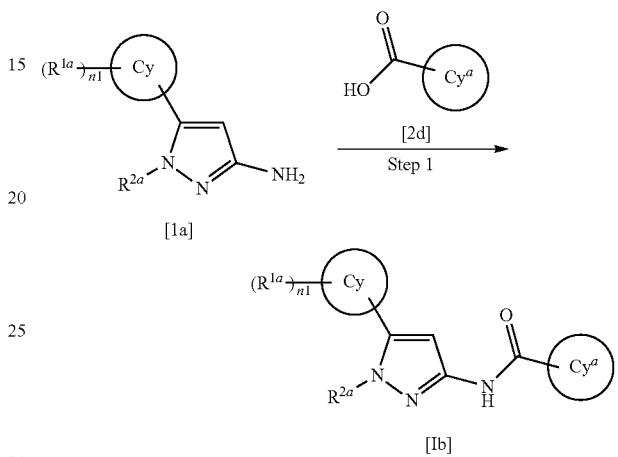

wherein, each symbol has the same meaning as defined above.

(Step 1)

Similarly to Preparation Method 1-1 Step 1, Compound [Ib] or a salt thereof may be obtained.

Compound [2d] or a salt thereof may be commercially available, or it can be obtained by the following Preparation Method 3 or a conventional method.

When Compound [Ib] has an enantiomer or a geometric isomer thereof, the reaction may be done by using a commercially available optically active compound or a single diastereomer compound or such a compound obtained by a conventional method. Alternatively, the optically active compound or single diastereomer of Compound [Ib] may be obtained by separating and purifying during the preparation process. The compound which undergoes separation and purification includes Compound [Ib], etc. A method for separation and purification includes, for example, column chromatography, preparative HPLC.

[Preparation Method 2]

A method for preparing Compound [1] is illustrated as Preparation Method 2-1 to 2-3" below.

Preparation Method 2-1

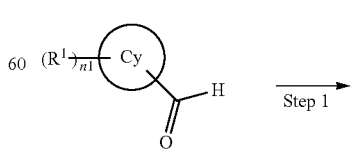

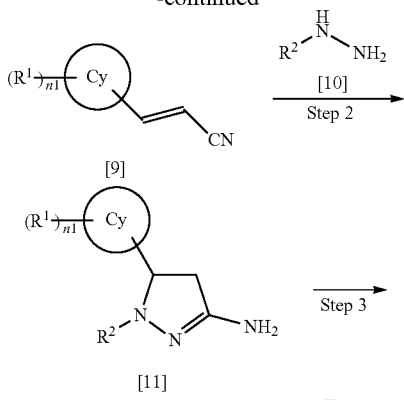

wherein, each symbol has the same meaning as defined above.

(Step 1)

Compound [9] may be obtained by subjecting Compound [8] to Wittig reaction or Horner-Wadsworth-Emmons reaction in a solvent in the presence of a base.

A preferable reagent used in the Wittig Reaction is (cyanomethyl)triphenylphosphonium chloride, and a preferable reagent used in the Horner-Wadsworth-Emmons reaction is diethyl cyanomethylphosphonate.

The base includes, for example, an organic base such as triethylamine; or an alkali metal base such as sodium hydride, potassium tert-butoxide, sodium carbonate and lithium hexamethyldisilazide (LiHMDS), preferably potassium tert-butoxide.

A preferable solvent is, for example, an ether solvent such as tetrahydrofuran; a hydrocarbon solvent such as toluene; a polar solvent such as N,N-dimethylformamide; or a mixed solvent thereof.

The reaction temperature is usually about −78° C. to 100° C., preferably about 0° C. to 40° C.

Compound [8] may be commercially available, or obtained by a conventional method.

(Step 2)

Compound [11] or a salt thereof may be obtained by reacting Compound [9] with Compound [10] or a salt thereof in a solvent in the presence of a base.

The base used in the reaction includes, for example, an organic base such as triethylamine; and an alkali metal base such as sodium hydride, sodium ethoxide, potassium tert-butoxide, sodium carbonate or lithium hexamethyldisilazide (LiHMDS), preferably sodium ethoxide.

A preferable solvent is an alcoholic solvent such as ethanol; an ether solvent such as tetrahydrofuran; a hydrocarbon solvent such as toluene; a polar solvent such as N,N-dimethylformamide; or a mixed solvent thereof.

The reaction temperature is usually about 0° C. to 150° C., preferably about 20° C. to 100° C.

Compound [10] or a salt thereof may be commercially available, or may be obtained by a conventional method.

(Step 3)

Compound [1] or a salt thereof may be obtained by reacting Compound [11] or a salt thereof with an oxidizing agent in a solvent.

A preferable oxidizing agent is 2,3-dichloro-5,6-dicyano-p-benzoquinone (DDQ), p-chloranil, Oxone (Registered Trademark), manganese dioxide, activated carbon, oxygen gas, etc.

A preferable solvent is, for example, an ether solvent such as dioxane; a polar solvent such as N,N-dimethylformamide; a hydrocarbon solvent such as toluene; a halogenated hydrocarbon solvent such as chloroform; or a mixed solvent thereof.

The reaction temperature is usually about 0° C. to 150° C., preferably about 20° C. to 150° C.

Preparation Method 2-2

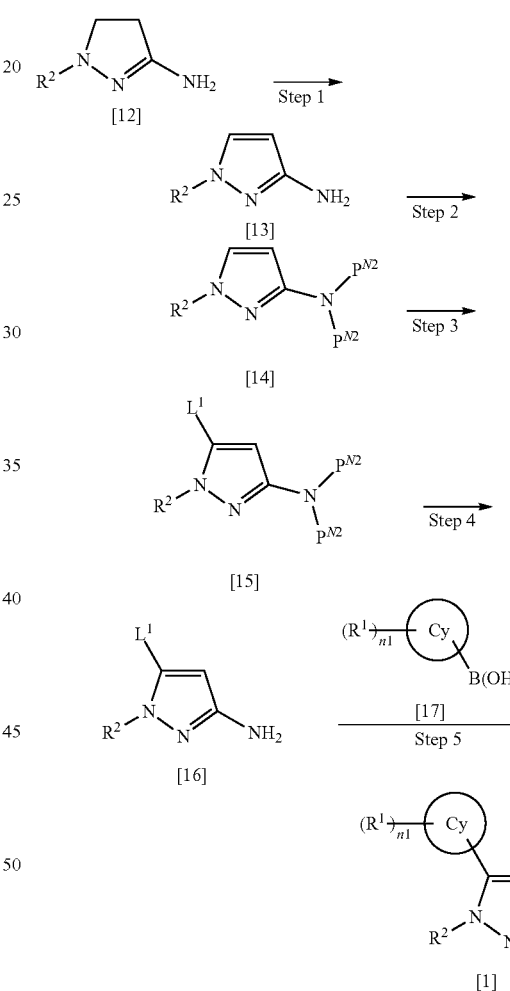

wherein, $P^{N2}$ is hydrogen atom or a protecting group of amino group; preferably, two $P^{N2}$s are combined together with the nitrogen atom to which they are attached to form 2,5-dimethylpyrrole; $L^1$ is a leaving group, preferably bromine atom or iodine atom; each of the other symbols has the same meaning as defined above.

(Step 1)

Compound [13] or a salt thereof may be obtained by the same procedure as Step 3 of Preparation Method 2-1.

Compound [12] or a salt thereof may be commercially available, or may be obtained by a conventional method.

(Step 2)

Compound [14] may be obtained by introducing $P^{N2}$ into amino group of Compound [13] or a salt thereof by a conventional protection reaction. The protection reaction may be done by using suitable conditions for each of kinds of $P^{N2}$. For example, when two $P^{N2}$s together with the nitrogen atom to which they are attached to form 2,5-dimethylpyrrole, Compound [14] may be obtained by reacting with 2,5-hexanedione in a solvent under an acidic condition.

The acid used in the reaction includes, for example, conc. hydrochloric acid, conc. sulfuric acid, amidosulfuric acid, p-toluenesulfonic acid or acetic acid, preferably acetic acid.

A preferable solvent is, for example, an alcoholic solvent such as ethanol; an ether solvent such as tetrahydrofuran; a hydrocarbon solvent such as toluene; a polar solvent such as N,N-dimethylformamide; a halogenated hydrocarbon solvent such as dichloroethane; or a mixed solvent thereof. Alternatively, an organic acid such as acetic acid may be used as the solvent.

The reaction temperature is usually about 0° C. to 150° C., preferably about 20° C. to 120° C.

(Step 3)

Compound [15] may be obtained by introducing $L^1$ into Compound [14] in a solvent in the presence of a base. For example, when $L^1$ is iodine atom, Compound [15] may be obtained by iodination in a solvent in the presence of a base.

The base used in the reaction includes, for example, n-butyllithium, lithium hexamethyldisilazide, or lithium tetramethylpiperidide, preferably n-butyllithium.

The iodination agent includes, for example, iodine, iodine monochloride, N-iodosuccinimide or 1-chloro-2-iodoethane, preferably iodine.

A preferable solvent is, for example, an ether solvent such as tetrahydrofuran; a hydrocarbon solvent such as toluene; or a mixed solvent thereof.

The reaction temperature is usually about −100° C. to 40° C., preferably about −78° C. to 20° C.

(Step 4)

Compound [16] or a salt thereof may be obtained by removing $P^{N2}$ of Compound [15] by a conventional deprotection reaction. The deprotection reaction may be done by using suitable conditions for each of kinds of $P^{N2}$. For example, when two $P^{N2}$s are together with the nitrogen atom to which they are attached to form 2,5-dimethylpyrrole, Compound [16] or a salt thereof may be obtained by treating Compound [15] in a solvent in the presence of hydroxylamine. Compound [16] may be isolated as a salt, or as a free form after neutralization.

A preferable solvent is an alcoholic solvent such as ethanol; water; or a mixed solvent thereof.

The reaction temperature is usually about 40° C. to 150° C., preferably about 80° C. to 130° C.

(Step 5)

Compound [1] or a salt thereof may be obtained by treating Compound [16] or a salt thereof and Compound [17] in Suzuki coupling reaction. For example, Compound [1] or a salt thereof may be obtained by reacting Compound [16] or a salt thereof with Compound [17] in a solvent under heating in the presence of a base and a palladium catalyst.

The palladium catalyst used in the reaction includes, for example, tetrakis(triphenylphosphine)palladium or (bis (diphenylphosphino)ferrocene)palladium dichloride-methylene chloride complex.

The base used in the reaction includes potassium phosphate, sodium carbonate, sodium hydrogen carbonate, potassium carbonate and triethylamine, etc.

A preferable solvent is an ether solvent such as 1,4-dioxane, tetrahydrofuran, diethyl ether and 1,2-dimethoxyethane; an alcoholic solvent such as methanol, ethanol, 1-propanol and 2-propanol; a hydrocarbon solvent such as toluene, n-hexane and xylene; a polar solvent such as N,N-dimethylformamide, dimethylsulfoxide, acetonitrile; or a mixed solvent thereof with water.

Compound [17] may be commercially available, or obtained by a conventional method. Alternatively, the reactions in this step may be done by using boronic acid ester.

By using Compound [12a] and Compound [17a] respectively in place of Compound [12] and Compound [17], Compound [1a] may be obtained similarly to the Preparation Method 2-2.

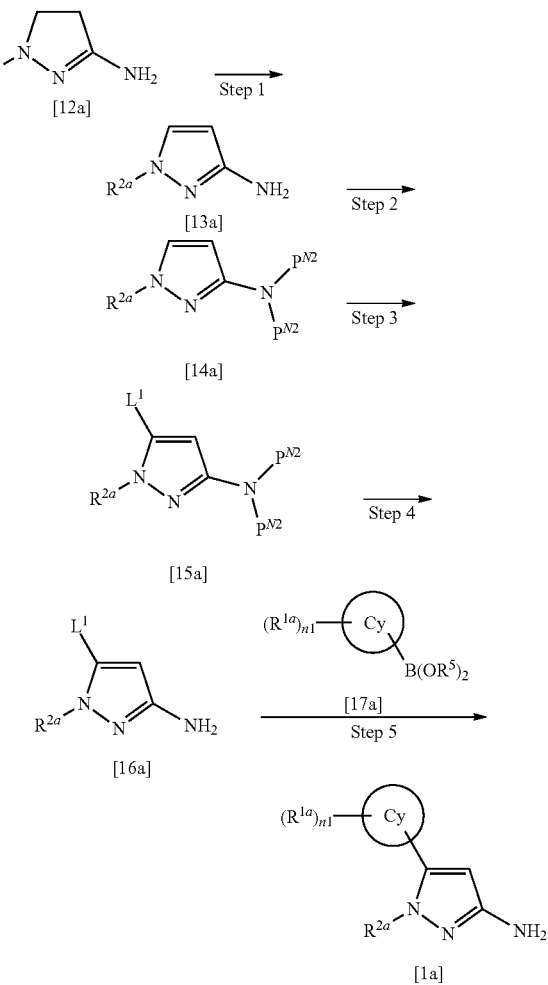

wherein, Compound [17a] is boronic acid ester, and each symbol has the same meaning as defined above.

Compound [12a] or a salt thereof may be commercially available, or may be obtained by a conventional method.

Compound [17a] may be commercially available, or may be obtained by a conventional method. The reactions in this step may be carried out by using boronic acid.

A reagent used for obtaining Compound [17a] includes the following reagents.

For example, when the ring Cy is $C_{6-10}$ aryl group substituted by a leaving group (preferably chlorine atom, bromine atom, iodine atom, p-toluenesulfonyloxy group, methanesulfonyloxy group or trifluoromethanesulfonyloxy group) in addition to $R^{1a}$, palladium catalysts such as palladium acetate, palladium chloride, and tris(dibenzylideneacetone) dipalladium; organic phosphorous compounds such as triphenylphosphine, tricyclohexylphosphine, 1,1'-bis(diphenylphosphino)ferrocene, 2-dicyclohexylphosphino-2',6'-dimethoxybiphenyl, 2-dicyclohexylphosphino-2',4',6'-triisopropylbiphenyl and 2-dicyclohexylphosphino-2'-(N,N-dimethylamino)biphenyl; boron compounds such as bis(pinacolate)diboron; bases such as potassium acetate, sodium carbonate, and potassium carbonate, are included.

For example, when the ring Cy is $C_{6-10}$ aryl group which does not have any substituent other than $R^{1a}$, iridium reagents such as di-μ-methoxobis(1,5-cyclo)(octadiene)diiridium; bipyridine compounds such as 4,4'-di-tert-butyl-2,2'-bipyridine and 4,4'-dimethoxy-2,2'-bipyridine; boron compounds such as bis(pinacolate)diboron are included.

Preparation Method 2-3

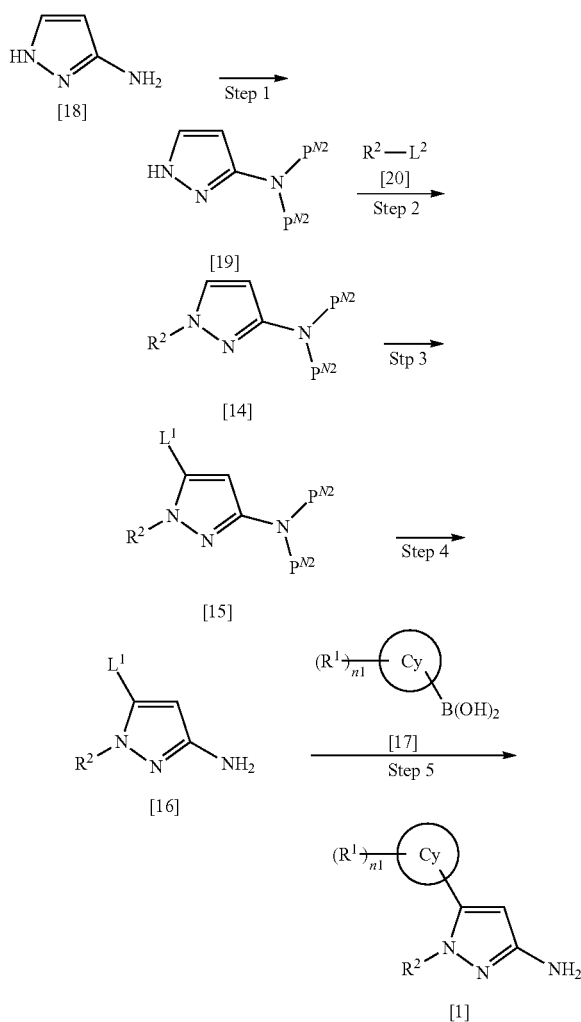

wherein $P^{N2}$ is hydrogen atom or a protecting group of amino group, preferably, two $P^{N2}$s combine together with the nitrogen atom to which they are attached to form 2,5-dimethylpyrrole; $L^1$ is a leaving group, preferably bromine atom or iodine atom; $L^2$ is a leaving group, preferably chlorine atom, bromine atom, iodine atom, dihydroxyboryl group, p-toluenesulfonyloxy group or methanesulfonyloxy group; each of the other symbols has the same meaning as defined above.

(Step 1)
Compound [19] may be obtained by the same procedure as Step 2 of Preparation Method 2-2.

(Step 2)
Compound [14] may be obtained by reacting Compound [19] with Compound [20] in a solvent.

For example, when $R^2$ is $C_{1-8}$ alkyl group or $C_{3-8}$ cycloalkyl group and $L^2$ is chlorine atom, bromine atom, iodine atom, p-toluenesulfonyloxy group or methanesulfonyloxy group, Compound [14] may be obtained by reacting Compound [19] with Compound [20] in a solvent in the presence of a base.

The base used in the reaction includes, for example, potassium hydroxide, potassium carbonate, sodium ethoxide, potassium tert-butoxide, sodium hydride, preferably sodium hydride.

A preferable solvent is, for example, an ether solvent such as tetrahydrofuran; a polar solvent such as N,N-dimethylformamide; an alcoholic solvent such as ethanol; or a mixed solvent thereof.

The reaction temperature is usually about 0° C. to 100° C., preferably about 0° C. to 80° C.

For example, when $R^2$ is $C_{6-10}$ aryl group and $L^2$ is bromine atom or iodine atom, Compound [14] may be obtained by reacting Compound [19] with Compound [20] in a solvent in the presence of a metal reagent, a ligand and a base.

The metal reagent used in the reaction includes, for example, copper (I) iodide, copper (I) oxide, cobalt (II) chloride, manganese (II) chloride or iron (III) chloride, preferably copper (I) oxide.

The ligand used in the reaction includes, for example, salicylaldoxime, trans-1,2-cyclohexanediamine, 8-quinolinol, 1,10-phenanthroline, L-proline, and preferably 8-quinolinol.

The base used in the reaction includes, for example, potassium hydroxide, tripotassium phosphate, potassium carbonate, cesium carbonate or sodium tert-butoxide, preferably cesium carbonate.

A preferable solvent is, for example, a hydrocarbon solvent such as toluene and xylene; a polar solvent such as acetonitrile and N,N-dimethylformamide; or a mixed solvent thereof.

The reaction temperature is usually about 20° C. to 150° C., preferably about 80° C. to 130° C.

For example, when $R^2$ is $C_{6-10}$ aryl group and $L^2$ is dihydroxyboryl group, Compound [14] may be obtained by reacting Compound [19] with Compound [20] in a solvent in the presence of a copper reagent and a base in air at room temperature.

A preferable copper reagent used in the reaction is copper (II) acetate and copper (I) oxide.

A preferable base used in the reaction is an organic base such as pyridine and triethylamine.

A preferable solvent is, for example, an alcoholic solvent such as methanol and ethanol; a halogenated hydrocarbon solvent such as dichloromethane and chloroform; or a mixed solvent thereof.

Compound [20] may be commercially available, or may be obtained by a conventional method.

(Step 3)
Compound [15] may be obtained by the same procedure as Step 3 of Preparation Method 2-2.

(Step 4)
Compound [16] or a salt thereof may be obtained by the same procedure as Step 4 of Preparation Method 2-2.

(Step 5)
Compound [1] or a salt thereof may be obtained by the same procedure as Step 5 of Preparation Method 2-2.

By using Compound [20a] and Compound [17a] respectively in place of Compound [20] and Compound [17], Compound [1a] may be obtained similarly to the Preparation Method 2-3.

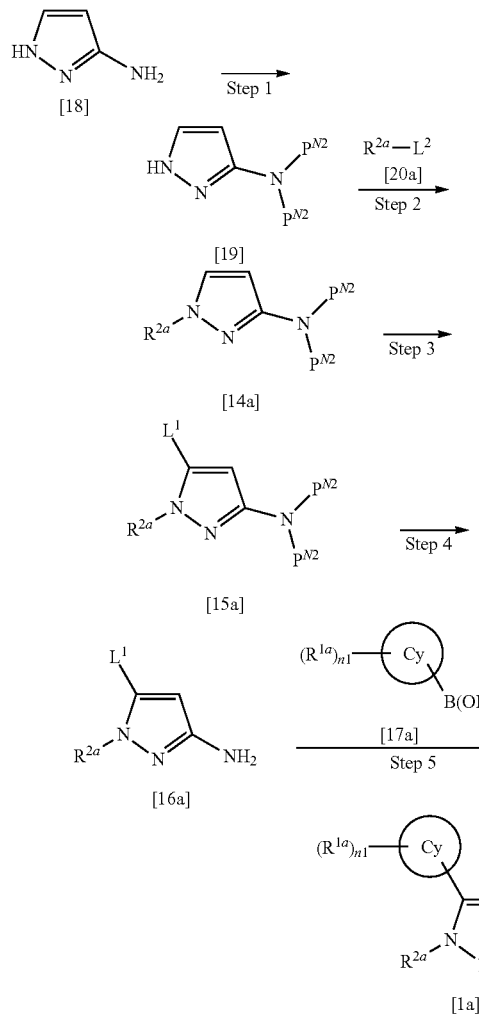

wherein, each symbol has the same meaning as defined above.

Compound [20a] or a salt thereof may be commercially available, or it may be obtained by a conventional method.

The reaction in this step may be carried out using boronic acid in place of Compound [17a].

[Preparation Method 3]

A method for preparing Compound [2] is illustrated as Preparation Methods 3-1 to 3-3 below.

Preparation Method 3-1

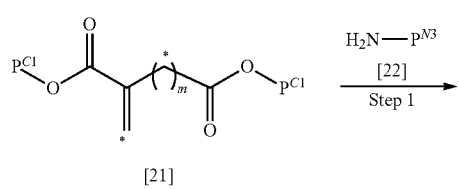

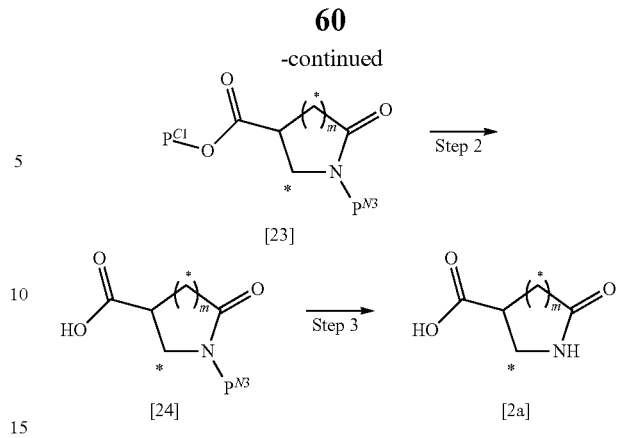

wherein, $P^{C1}$ is a protecting group of carboxy group, preferably methyl group, ethyl group, tert-butyl group or benzyl group; $P^{N3}$ is a protecting group of amino group, preferably 2,4-dimethoxybenzyl group; carbon atoms with * may be optionally substituted by $R^3$ within the chemically acceptable range; each of the other symbols has the same meaning as defined above.

(Step 1)

Compound [23] may be obtained by reacting Compound [21] with Compound [22] in a solvent.

A preferable solvent is, for example, a hydrocarbon solvent such as toluene; an alcoholic solvent such as methanol and ethanol; or a mixed solvent thereof.

The reaction temperature is usually about 20° C. to 150° C., preferably about 80° C. to 130° C.

Compound [21] may be commercially available, or may be obtained by Auxiliary Step 1 below or a conventional method. Compound [22] may be commercially available, or obtained by a conventional method.

Auxiliary Step 1

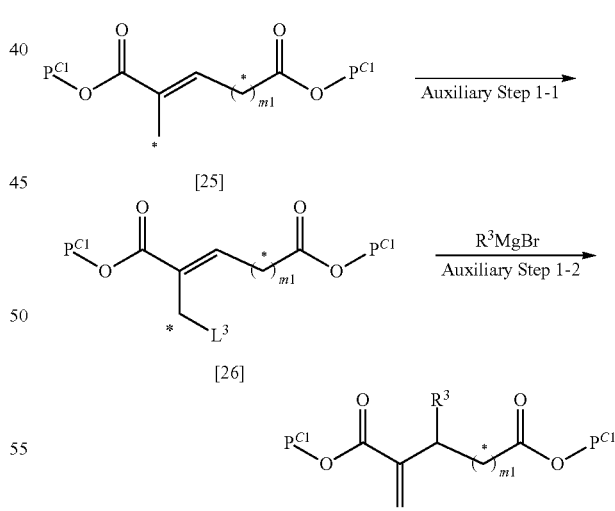

wherein, $P^{C1}$ is a protecting group of carboxy group, preferably methyl group, ethyl group, tert-butyl group or benzyl group; m1 is 0, 1, 2 or 3; $L^3$ is a leaving group, preferably, bromine atom; carbon atoms with * may be optionally substituted by $R^3$ within the chemically acceptable range; each of the other symbols has the same meaning as defined above.

(Auxiliary Step 1-1)

Compound [26] may be obtained by introducing $L^3$ into Compound [25]. For example, when $L^3$ is bromine atom, Compound [26] may be obtained by brominating in a solvent in the presence of a radical reaction initiator.

A preferable radical reaction initiator is azobisisobutyronitrile (AIBN).

A preferable brominating agent is N-bromosuccinimide (NBS).

A preferable solvent is a halogenated hydrocarbon solvent such as dichloromethane and carbon tetrachloride.

The reaction temperature is usually about 20° C. to 130° C., preferably about 40° C. to 100° C.

Compound [25] may be commercially available, or may be obtained by a conventional method.

(Auxiliary Step 1-2)

Compound [21a] may be obtained by introducing $R^3$ into Compound [26]. For example, Compound [21a] may be obtained by reacting Compound [26] with a Grignard reagent in a solvent in the presence of an additive.

A preferable additive is hexamethylphosphoric triamide (HMPA).

A preferable solvent is, for example, an ether solvent such as diethyl ether and tetrahydrofuran; a polar solvent such as N,N-dimethylformamide; or a mixed solvent thereof.

The reaction temperature is usually about −78° C. to 40° C., preferably about −20° C. to 25° C.

The Grinard reagent may be commercially available, or may be obtained by a conventional method.

(Step 2)

Compound [24] or a salt thereof may be obtained by removing $P^{C1}$ of Compound [23] by a conventional deprotection reaction. The deprotection reaction may be done by using suitable conditions for each of kinds of $P^{C1}$. For example, when $P^{C1}$ is methyl group, Compound [24] or a salt thereof may be obtained by hydrolyzing Compound [23] in a solvent in the presence of a base.

The base includes, for example, lithium hydroxide, sodium hydroxide, potassium hydroxide, sodium methoxide, preferably sodium hydroxide.

A preferable solvent is, for example, an alcoholic solvent such as methanol; an ether solvent such as tetrahydrofuran; water; or a mixed solvent thereof.

The reaction temperature is usually about 0° C. to 100° C., preferably about 0° C. to 40° C.

(Step 3)

Compound [2a] or a salt thereof may be obtained by removing $P^{N3}$ of Compound [24] or a salt thereof by a conventional deprotection reaction. The deprotection reaction may be done by using suitable conditions for each of kinds of $P^{N3}$. For example, when $P^{N3}$ is 2,4-dimethoxybenzyl group, Compound [2a] or a salt thereof may be obtained by treating with an acid in a solvent in the presence of an additive.

The acid includes, for example, methanesulfonic acid, p-toluenesulfonic acid, trifluoroacetic acid, preferably trifluoroacetic acid.

The additive includes, for example, anisole and triethylsilane; preferably anisole.

A preferable solvent is, for example, a halogenated hydrocarbon solvent such as dichloromethane; a hydrocarbon solvent such as toluene; water; or a mixed solvent thereof. Alternatively, an organic acid such as trifluoroacetic acid may be used as the solvent.

The reaction temperature is usually about 0° C. to 130° C., preferably about 25° C. to 80° C.

When Compound [2a] has geometric isomers, a single diastereomer may be obtained by separating and purifying appropriately during the preparation process. The compound which undergoes separation and purification includes Compound [23], etc. A method for separation and purification includes, for example, column chromatography, or preparative HPLC. Alternatively, separation and purification may be done after increasing diastereomer excess ratio of a preferable configuration by subjecting Compound [23] to a basic condition.

Enantiomers resulted from an asymmetric carbon atom in the α-position of carboxy group of Compound [2a] may be separated and purified as a single diastereomer by introducing a chiral auxiliary to give an optically active compound thereof. For example, Compounds [2a_chiral_1] and [2a_chiral_2] may be obtained by using (R)-4-benzyl-2-oxazolidinone as the chiral auxiliary for Compound [24] or a salt thereof as shown in Auxiliary Step 2 below.

Auxiliary Step 2

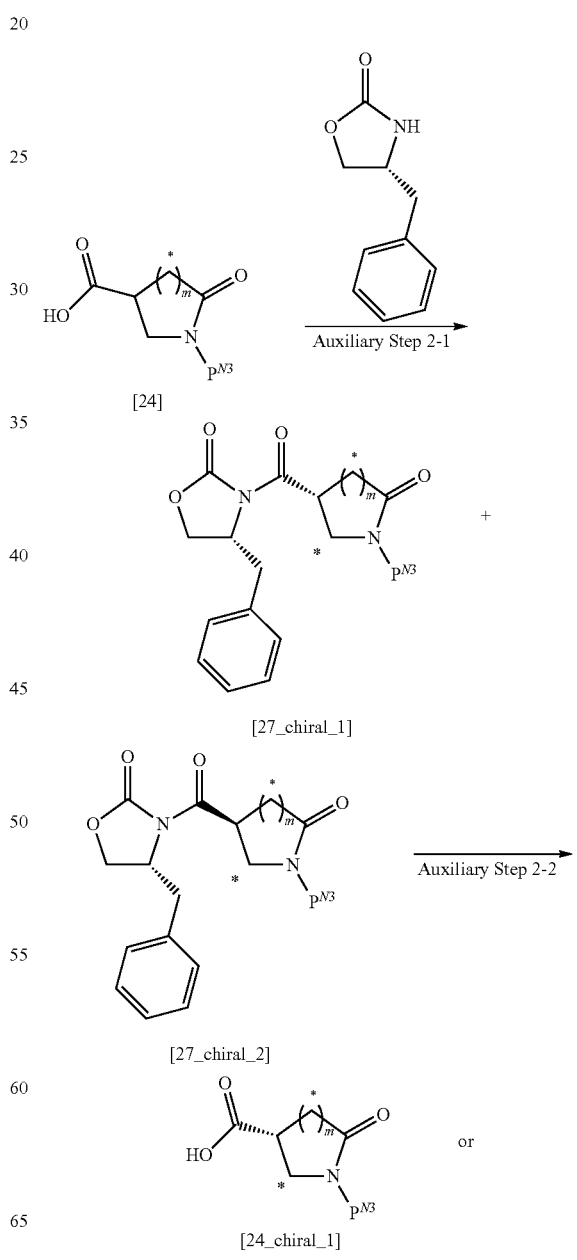

Preparation Method 3-2

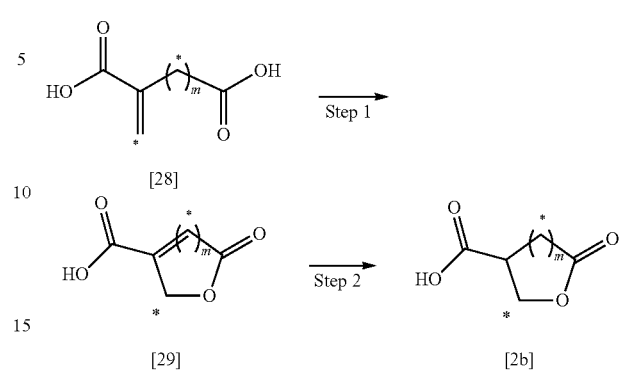

wherein, carbon atoms with * may be optionally substituted by $R^3$ within the chemically acceptable range; each of the other symbols has the same meaning as defined above.

(Step 1)

Compound [29] or a salt thereof may be obtained by treating Compound [28] or a salt thereof with bromine, followed by a base in a solvent.

The base includes, for example, potassium hydroxide, sodium hydrogen carbonate, sodium carbonate, triethylamine, preferably sodium hydrogen carbonate or sodium carbonate.

A preferable solvent is, for example, a halogenated hydrocarbon solvent such as dichloromethane, carbon tetrachloride; water.

The reaction temperature is usually about 0° C. to 100° C., preferably about 25° C. to 80° C.

Compound [28] or a salt thereof may be commercially available, or may be obtained by a conventional method.

(Step 2)

Compound [2b] or a salt thereof may be obtained by reducing Compound [29] or a salt thereof by a catalytic hydrogenation in a solvent in the presence of a metal catalyst under hydrogen atmosphere.

The metal catalyst includes, for example, palladium on carbon, alumina-supported rhodium, Raney nickel, Adams' catalyst, preferably palladium on carbon.

A preferable solvent is, for example, an alcoholic solvent such as methanol and ethanol; an ether solvent such as tetrahydrofuran; an ester solvent such as ethyl acetate; water, or a mixed solvent thereof.

The reaction temperature is usually about 25° C. to 80° C., preferably about 25° C. to 50° C.

Preparation Method 3-3

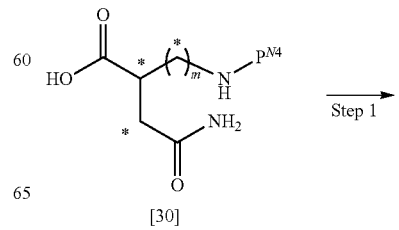

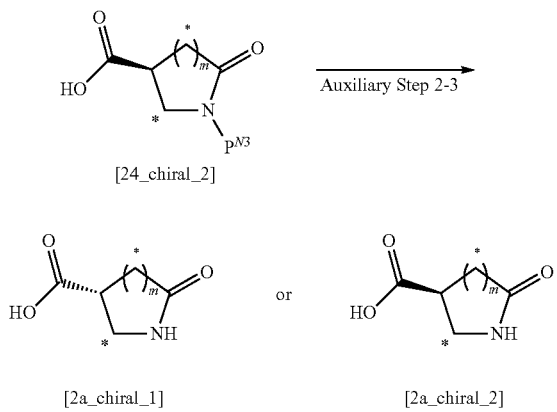

wherein, carbon atoms with * may be optionally substituted by $R^3$ within the chemically acceptable range; each of the other symbols has the same meaning as defined above.

(Auxiliary Step 2-1)

Compound [27_chiral_1] and Compound [27_chiral_2] may be obtained by reacting Compound [24] or a salt thereof with (R)-4-benzyl-2-oxazolidinone in a solvent in the presence of a condensing agent and an additive. At this stage, Compound [27_chiral_1] and Compound [27_chiral_2] may be separated and purified by silica gel column chromatography.

A preferable condensing agent is dicyclohexylcarbodiimide (DCC), 1-ethyl-3-(3-dimethylaminopropyl)carbodiimide hydrochloride (WSC.HCl), etc.

A preferable additive is 4-dimethylaminopyridine, etc.

A preferable solvent is a halogenated hydrocarbon solvent such as chloroform, etc.

The reaction temperature is usually about 0° C. to 100° C., preferably about 0° C. to 40° C.

Alternatively, Compound [27_chiral_1] and Compound [27_chiral_2] may be obtained by preliminarily converting Compound [24] into an acid chloride thereof, etc., and then reacting the resulting compound with (R)-4-benzyl-2-oxazolidinone in the presence of a base.

(Auxiliary Step 2-2)

Compound [24_chiral_1] or a salt thereof (or Compound [24_chiral_2] or a salt thereof) may be obtained by reacting Compound [27_chiral_1] (or Compound [27_chiral_2]) in a solvent in the presence of a base and an aqueous hydrogen peroxide.

The base used in the reaction includes, for example, sodium hydroxide, lithium hydroxide, preferably lithium hydroxide.

A preferable solvent is, for example, an ether solvent such as tetrahydrofuran; water; or a mixed solvent thereof.

The reaction temperature is usually about 0° C. to 50° C., preferably about 0° C. to 25° C.

(Auxiliary Step 2-3)

Compound [2a_chiral_1] or a salt thereof (or Compound [2a_chiral_2] or a salt thereof) may be obtained by the same procedure as Step 3 of Preparation Method 3-1.

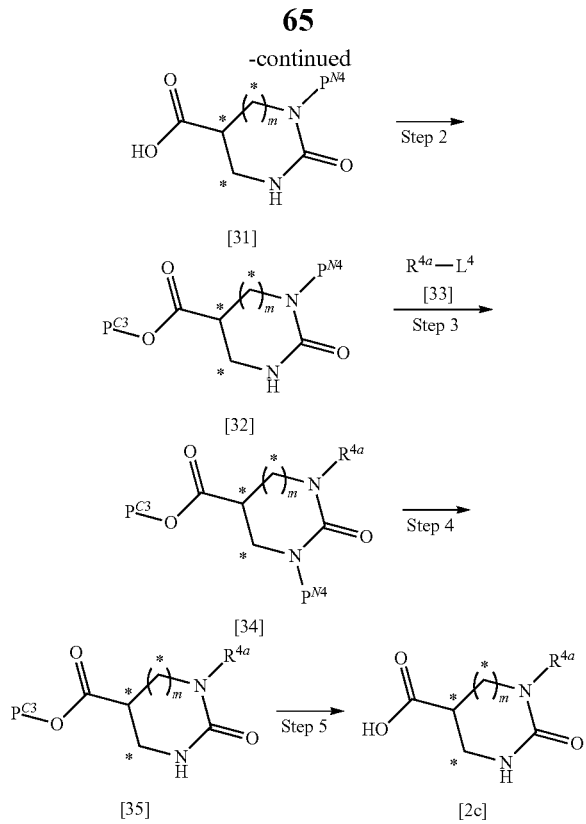

wherein, $P^{N4}$ is a protecting group of amino group, preferably benzyloxycarbonyl group; $P^{C3}$ is a protecting group of carboxy group, preferably methyl group, ethyl group, tert-butyl group or benzyl group; $R^{4a}$ is $C_{1-6}$ alkyl group; $L^4$ is a leaving group, preferably halogen atom; carbon atoms with * may be optionally substituted by $R^3$ within the chemically acceptable range; each of the other symbols has the same meaning as defined above.

(Step 1)

Compound [31] or a salt thereof may be obtained by subjecting Compound [30] or a salt thereof to Hofmann rearrangement reaction in the presence of a base and bromine, followed by intramolecular cyclization reaction in a solvent.

The base includes, for example, sodium hydroxide, potassium hydroxide, sodium methoxide, preferably sodium hydroxide.

A preferable solvent is, for example, an alcoholic solvent such as methanol and ethanol; an ether solvent such as 1,4-dioxane; water; or a mixed solvent thereof.

The reaction temperature is usually about −78° C. to 100° C., preferably about −40° C. to 80° C.

Compound [30] or a salt thereof may be commercially available, or may be obtained by a conventional method.

(Step 2)

Compound [32] may be obtained by introducing $P^{C3}$ into carboxy group of Compound [31] or a salt thereof by a conventional protection reaction. The protection reaction may be done by using suitable conditions for each of kinds of $P^{C3}$. For example, $P^{C3}$ is tert-butyl group, Compound [32] may be obtained by preliminarily converting Compound [31] into an acid chloride thereof in a solvent, etc., and then reacting the resulting compound with tert-butyl alcohol in the presence of a base The reagent used in the reaction is, for example, thionyl chloride, oxalyl chloride, phosphorous oxychloride, preferably phosphorous oxychloride.

The base includes, for example, an organic amine such as triethylamine and pyridine; an alkali metal carbonate such as sodium carbonate, potassium carbonate and sodium hydrogen carbonate, preferably pyridine.

A preferable solvent is, for example, a hydrocarbon solvent such as toluene; an ether solvent such as tetrahydrofuran; a halogenated hydrocarbon solvent such as chloroform; or a mixed solvent thereof.

The reaction temperature is usually about 0° C. to 130° C., preferably about 25° C. to 80° C.

(Step 3)

Compound [34] may be obtained by rearranging $P^{N4}$ of Compound [32], followed by introducing $R^{4a}$ into the rearranged compound in a solvent in the presence of a base.

A preferable base is sodium hydride.

A preferable solvent is, for example, an ether solvent such as tetrahydrofuran; a polar solvent such as N,N-dimethylformamide; or a mixed solvent thereof.

The reaction temperature is usually about 0° C. to 80° C., preferably about 0° C. to 25° C.

Compound [33] may be commercially available, or may be obtained by a conventional method.

(Step 4)

Compound [35] may be obtained by removing $P^{N4}$ from Compound [34] by a conventional deprotection reaction. The deprotection reaction may be done by using suitable conditions for each of kinds of $P^{N4}$. For example, when $P^{N4}$ is benzyloxycarbonyl group, Compound [35] may be obtained by reducing Compound [34] by a catalytic hydrogenation in a solvent in the presence of a palladium catalyst under hydrogen atmosphere.

The palladium catalyst includes, for example, palladium on carbon, palladium (II) hydroxide, preferably palladium on carbon.

A preferable solvent is, for example, an alcoholic solvent such as methanol; an ether solvent such as tetrahydrofuran; an ester solvent such as ethyl acetate; or a mixed solvent thereof.

The reaction temperature is usually about 25° C. to 80° C., preferably about 25° C. to 50° C.

(Step 5)

Compound [2c] or a salt thereof may be obtained by removing $P^{C3}$ from Compound [35] by a conventional deprotection reaction. The deprotection reaction may be done by using suitable conditions for each of kinds of $P^{C3}$. For example, when $P^{C3}$ is tert-butyl group, Compound [2c] may be obtained by treating Compound [35] in a solvent under an acidic condition.

The acid includes, for example, hydrochloric acid, sulfuric acid, trifluoroacetic acid, preferably trifluoroacetic acid.

A preferable solvent is, for example, an ether solvent such as 1,4-dioxane; a halogenated hydrocarbon solvent such as chloroform; an ester solvent such as ethyl acetate; an alcoholic solvent such as methanol; water; or a mixed solvent thereof.

The reaction temperature is usually about 0° C. to 80° C., preferably about 0° C. to 40° C.

When Compound [2c] has an enantiomer thereof, the reaction may be done by using a commercially available optically active compound or using a product obtained therefrom by a conventional method.

Preparation Method 3-4

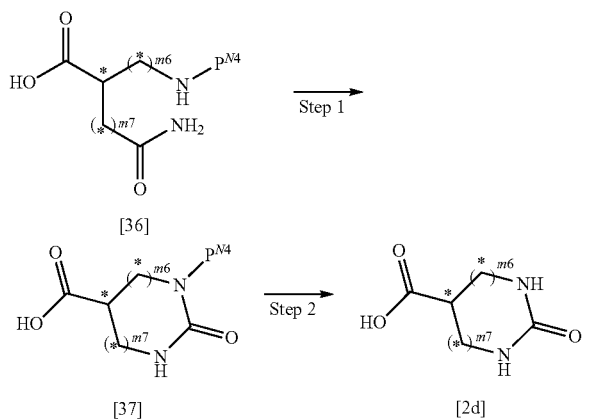

wherein, carbon atoms indicated by * in the Formula may be optionally substituted by $R^{3a}$ within the chemically acceptable range, each of the other symbols has the same meaning as defined above.
(Step 1)
Compound [37] or a salt thereof may be obtained by the same procedure as Step 1 of Preparation Method 3-3.
Compound [36] or a salt thereof may be commercially available, or may be obtained by a conventional method.
(Step 2)
Compound [2d] or a salt thereof may be obtained by the same procedure as Step 4 of Preparation Method 3-3.
When Compound [2d] has an enantiomer thereof, the reaction may be carried out by using a commercially available optically active compound or using a product obtained therefrom by a conventional method.

Preparation Method 3-5

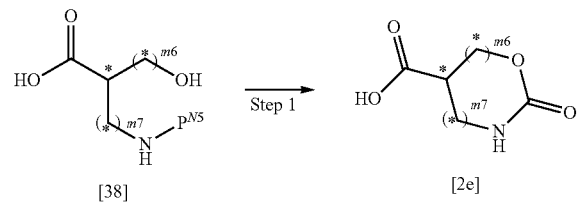

wherein, $P^{N5}$ is a protecting group of amino group, preferably benzyloxycarbonyl group; carbon atoms indicated by * may be optionally substituted by $R^{3a}$ within the chemically acceptable range; each of the other symbols has the same meaning as defined above.
(Step 1)
Compound [2e] or a salt thereof may be obtained by reacting Compound [38] or a salt thereof in the presence of a base in a solvent.
The base includes, for example, sodium hydroxide, potassium hydroxide, sodium methoxide, preferably sodium hydroxide.
A preferable solvent is, for example, an alcoholic solvent such as methanol and ethanol; an ether solvent such as 1,4-dioxane; water; or a mixed solvent thereof.
The reaction temperature is usually about 0 to 100° C., preferably about 25 to 50° C.
Compound [38] or a salt thereof may be commercially available, or may be obtained by a conventional method.

When Compound [2e] has an enantiomer thereof, the reaction may be carried out using a commercially available optically active compound or using a product obtained therefrom by a conventional method.

Preparation Method 3-6

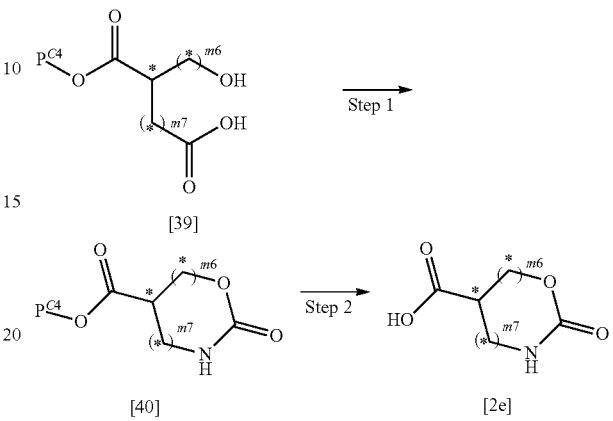

wherein, $P^{C4}$ is a protecting group of carboxy group, preferably methyl group, ethyl group, tert-butyl group, or benzyl group; carbon atoms indicated by * may be optionally substituted by $R^{3a}$ within the chemically acceptable range; each of the other symbols has the same meaning as defined above.
(Step 1)
Compound [40] may be obtained by subjecting Compound [39] or a salt thereof to Curtius rearrangement reaction, followed by an intramolecular cyclization reaction in a solvent.
The reagent used for the reaction includes, for example, diphenylphosphoryl azide.
A preferable solvent is, for example, a hydrocarbon solvent such as toluene; an alcoholic solvent such as ethanol and tert-butanol; an ether solvent such as 1,4-dioxane; or a mixed solvent thereof.
The reaction temperature is usually about 40 to 140° C., preferably about 80 to 120° C.
Compound [39] or a salt thereof may be commercially available, or may be obtained by a conventional method.
(Step 2)
Compound [2e] or a salt thereof may be obtained by removing $P^{C4}$ of Compound [40] by a conventional deprotection reaction. The deprotection reaction may be carried out using suitable conditions for each of kinds of $P^{C4}$, for example, when $P^{C4}$ is benzyl group, Compound [2e] or a salt thereof may be obtained by reducing Compound [40] by a catalytic hydrogenation in the presence of a palladium catalyst in a solvent under hydrogen atmosphere.
The palladium catalyst includes, for example, palladium on carbon, palladium (II) hydroxide, preferably palladium on carbon.
A preferable solvent is an alcoholic solvent such as methanol; an ether solvent such as tetrahydrofuran; an ester solvent such as ethyl acetate; or a mixed solvent thereof.
The reaction temperature is usually about 25 to 80° C., preferably about 25 to 50° C.
When Compound [2e] has an enantiomer thereof, the reaction may be carried out using a commercially available optically active compound or using a product obtained therefrom by a conventional method.

Preparation Method 3-7

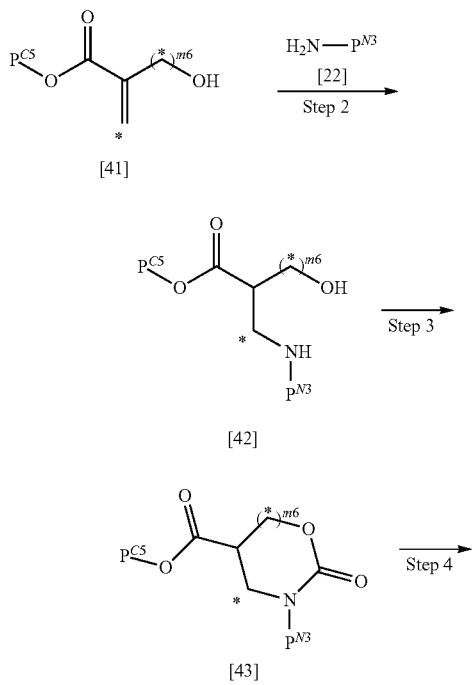

wherein, $P^{C5}$ is a protecting group of carboxy group, preferably methyl group, ethyl group, tert-butyl group or benzyl group; carbon atoms indicated by * may be optionally substituted by $R^{3a}$ within the chemically acceptable range; each of the other symbols has the same meaning as defined above.

(Step 1)

Compound [42] may be obtained by reacting Compound [41] with Compound [22] in a solvent. Compound [22] itself may be used as a solvent.

A preferable solvent is, for example, a hydrocarbon solvent such as toluene; an alcoholic solvent such as methanol and ethanol; or a mixed solvent thereof.

The reaction temperature is usually about 20 to 150° C., preferably about 80 to 130° C.

Compound [41] may be commercially available, or may be obtained by a conventional method.

Compound [22] may be commercially available, or may be obtained by a conventional method.

(Step 2)

Compound [43] may be obtained by converting amino group and hydroxy group of Compound [42] into carbamate group in a solvent.

The reagent used for the reaction includes, for example, diethylcarbonate, diethylpyrocarbonate, 1,1'-carbonyldiimidazole (CDI), chloroformate, preferably 1,1'-carbonyldiimidazole (CDI).

A preferable solvent is, for example, a halogenated hydrocarbon solvent such as chloroform; an ether solvent such as tetrahydrofuran; a hydrocarbon solvent such as toluene; a polar solvent such as pyridine, acetonitrile and N,N-dimethylformamide; or a mixed solvent thereof.

The reaction temperature is usually about 0 to 100° C., preferably about 0 to 40° C.

(Step 3).

Compound [2f] or a salt thereof may be obtained by removing $P^{N3}$ and $P^{C5}$ of Compound [43] by a conventional deprotection reaction. The deprotection reaction may be carried out using suitable conditions for each of kinds of $P^{N3}$ and $P^{C5}$, and for example, when $P^{N3}$ is 2,4-dimethoxybenzyl group and $P^{C5}$ is tert-butyl group, Compound [2f] or a salt thereof may be obtained by treating with an acid in the presence of an additive in a solvent.

The acid includes, for example, methanesulfonic acid, p-toluenesulfonic acid, trifluoroacetic acid, preferably trifluoroacetic acid.

The additive includes, for example, anisole, triethylsilane, preferably anisole.

A preferable solvent is, for example, a halogenated hydrocarbon solvent such as dichloromethane; a hydrocarbon solvent such as toluene; water; or a mixed solvent thereof. The organic acid itself such as trifluoroacetic acid may be used as a solvent.

The reaction temperature is usually about 0 to 130° C., preferably about 25 to 80° C.

Preparation Method 3-8

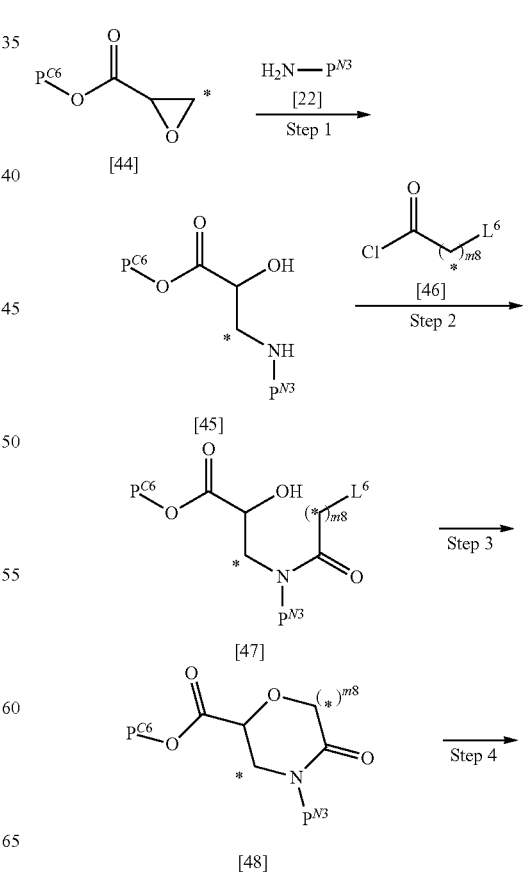

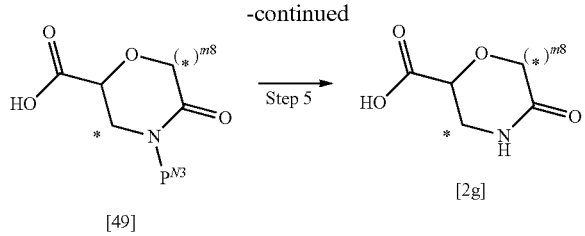

wherein, $P^{C6}$ is a protecting group of carboxy group, preferably methyl group, ethyl group, tert-butyl group or benzyl group; $L^6$ is a leaving group, preferably chlorine atom or bromine atom; carbon atoms indicated by * may be optionally substituted by $R^{3a}$ within the chemically acceptable range; each of the other symbols has the same meaning as defined above.

(Step 1)

Compound [45] may be obtained by reacting Compound [44] with Compound [22] in a solvent. Compound [22] itself may be used as a solvent.

A preferable solvent is, for example, a hydrocarbon solvent such as toluene; an alcoholic solvent such as ethanol and tert-butanol; a polar solvent such as acetonitrile and N,N-dimethylformamide; or a mixed solvent thereof.

The reaction temperature is usually about 20 to 150° C., preferably about 80 to 130° C.

Compound [44] may be commercially available, or may be obtained by a conventional method.

(Step 2)

Compound [47] may be obtained by reacting Compound [45] with Compound [46] in the presence of a base in a solvent.

The base includes, for example, an organic amine such as triethylamine and pyridine; an alkali metal carbonate such as sodium carbonate, potassium carbonate and sodium hydrogen carbonate, preferably triethylamine A preferable solvent is, for example, a hydrocarbon solvent such as toluene; an ether solvent such as tetrahydrofuran; a halogenated hydrocarbon solvent such as chloroform; a polar solvent such as acetonitrile; or a mixed solvent thereof.

The reaction temperature is usually about −20 to 130° C., preferably about 0 to 80° C.

Compound [48] may be commercially available, or may be obtained by a conventional method.

(Step 3)

Compound [48] may be obtained by reacting Compound [47] in the presence of a base in a solvent.

The base includes, for example, an alkali metal carbonate such as sodium carbonate, potassium carbonate and cesium carbonate; potassium tert-butoxide, sodium hydride, preferably potassium tert-butoxide.

The solvent includes, for example, a hydrocarbon solvent such as toluene; an ether solvent such as tetrahydrofuran; an alcoholic solvent such as tert-butanol; a polar solvent such as N,N-dimethylformamide; or a mixed solvent thereof.

The reaction temperature is usually about 0 to 130° C., preferably about 25 to 80° C.

(Step 4)

Compound [59] or a salt thereof may be obtained by the same procedure as Step 2 of Preparation Method 3-1.

(Step 5)

Compound [2g] or a salt thereof may be obtained by the same procedure as Step 3 of Preparation Method 3-1.

An enantiomer derived from an asymmetric carbon atom of the alpha position of carboxy group of Compound [2g] may be obtained by the same procedure as Auxiliary step 2 of Preparation Method 3-1.

Preparation Method 3-9

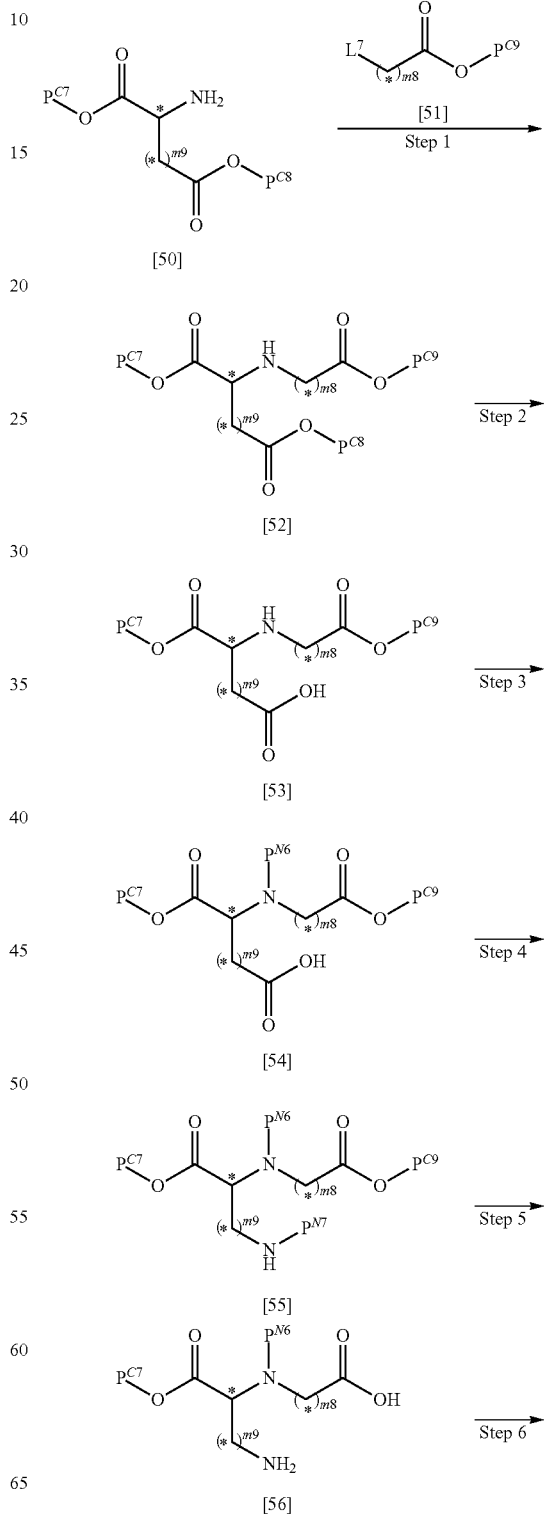

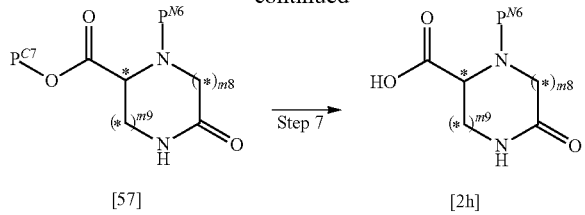

wherein, $P^{C7}$ is a protecting group of carboxy group, preferably methyl group, ethyl group, tert-butyl group or benzyl group; $P^{C8}$ is a protecting group of carboxy group, preferably methyl group, ethyl group, tert-butyl group or benzyl group; $P^{C9}$ is a protecting group of carboxy group, preferably methyl group, ethyl group, tert-butyl group or benzyl group; $P^{N6}$ is a protecting group of amino group, preferably tert-butoxycarbonyl group; $P^{N7}$ is a protecting group of amino group, preferably benzyloxycarbonyl group: $L^7$ is a leaving group, preferably chlorine atom or bromine atom: carbon atoms indicated by * may be optionally substituted by $R^{3a}$ within the chemically acceptable range; each of the other symbols has the same meaning as defined above.

(Step 1)

Compound [52] or a salt thereof may be obtained by reacting Compound [50] or a salt thereof with Compound [51] in the presence of a base in a solvent.

The base includes, for example, an organic amine such as triethylamine and pyridine; an alkali metal carbonate such as sodium carbonate, potassium carbonate and sodium hydrogen carbonate, preferably potassium carbonate.

A preferable solvent is, for example, a hydrocarbon solvent such as toluene; an ether solvent such as tetrahydrofuran; a halogenated hydrocarbon solvent such as chloroform; a polar solvent such as acetonitrile; or a mixed solvent thereof.

The reaction temperature is usually about 0 to 130° C., preferably about 25 to 80° C.

Compound [50] or a salt thereof may be commercially available, or may be obtained by a conventional method. Compound [51] may be commercially available, or may be obtained by a conventional method.

(Step 2)

Compound [53] or a salt thereof may be obtained by removing $P^{C8}$ of Compound [52] or a salt thereof by a conventional deprotection reaction. The deprotection reaction may be carried out using suitable conditions for each of kinds of $P^{C8}$, for example, when $P^{C3}$ is tert-butyl group, Compound [53] or a salt thereof may be obtained by the same procedure as Step 5 of Preparation Method 3-3.

(Step 3)

Compound [54] or a salt thereof may be obtained by introducing $P^{N6}$ into amino group of Compound [53] or a salt thereof by a conventional protection reaction. The protection reaction may be carried out using suitable conditions for each of kinds of $P^{N6}$, for example, when $P^{N6}$ is tert-butoxycarbonyl group, Compound [54] or a salt thereof may be obtained by reacting with di-tert-butyl dicarbonate in the presence of a base in a solvent.

The base includes, for example, an organic amine such as triethylamine and pyridine; an alkali metal carbonate such as sodium carbonate, potassium carbonate and sodium hydrogen carbonate, preferably triethylamine.

A preferable solvent is, for example, a hydrocarbon solvent such as toluene; an ether solvent such as tetrahydrofuran; a halogenated hydrocarbon solvent such as chloroform; a polar solvent such as acetonitrile; water; or a mixed solvent thereof.

The reaction temperature is usually about 0 to 130° C., preferably about 25 to 50° C.

(Step 4)

Compound [55] may be obtained by subjecting Compound [54] or a salt thereof to Curtius rearrangement reaction in the presence of an alcohol in a solvent.

The reagent used for the reaction includes, for example, diphenylphosphoryl azide.

The alcohol used for the reaction includes, for example, benzyl alcohol, tert-butanol, preferably benzyl alcohol.

A preferable solvent is, for example, a hydrocarbon solvent such as toluene; an ether solvent such as 1,4-dioxane; or a mixed solvent thereof.

The reaction temperature is usually about 25 to 140° C., preferably about 80 to 120° C.

(Step 5)

Compound [56] or a salt thereof may be obtained by removing $P^{N7}$ and $P^{C9}$ of Compound [55] by a conventional deprotection reaction. The deprotection reaction may be carried out using suitable conditions for each of kinds of $P^{N7}$ and $P^{C9}$, for example, when $P^{N7}$ is benzyloxycarbonyl group and $P^{C9}$ is benzyl group, Compound [58] or a salt thereof may be obtained by reducting Compound [57] by a catalytic hydrogenations in the presence of a metal catalyst in a solvent under hydrogen atmosphere.

The metal catalyst includes, for example, palladium on carbon, palladium black, palladium (II) hydroxide, preferably palladium on carbon.

A preferable solvent is, for example, an alcoholic solvent such as methanol and ethanol; an ether solvent such as tetrahydrofuran an ester solvent such as ethyl acetate water or a mixed solvent thereof.

The reaction temperature is usually about 25 to 80° C., preferably about 25 to 50° C.

(Step 6)

Compound [57] may be obtained by reacting Compound [56] or a salt thereof in the presence of a condensing agent and an additive in a solvent.

A preferable condensing agent is dicyclohexylcarbodiimide (DCC), 1-ethyl-3-(3-dimethylaminopropyl)carbodiimide hydrochloride (WSC.HCl), diisopropylcarbodiimide, 1,1'-carbonyldiimidazole (CDI), O-(7-azabenzotriazol-1-yl)-N,N,N',N'-tetramethyluronium hexafluorophosphate (HATU), (benzotriazol-1-yloxy)tripyrrolidinophosphonium hexafluorophosphate (PyBOP) or diphenylphosphoryl azide, etc.

A preferable additive is 1-hydroxybenzotriazol (HOBt), 1-hydroxy-7-azabenzotriazol (HOAt), N-hydroxysuccinimide (HOSu), etc. 4-Dimethylaminopyridine etc. may be optionally added as an additive.

A preferable solvent is a halogenated hydrocarbon solvent such as chloroform; an ether solvent such as tetrahydrofuran; a polar solvent such as pyridine, acetonitrile and N,N-dimethylformamide; or a mixed solvent thereof.

The reaction temperature is usually about 0 to 100° C., and preferably is about 0 to 40° C.

When an acidic salt of Compound [56] is used, the reaction may be carried out in the presence of a base including an organic base such as triethylamine; an alkali metal salt such as sodium carbonate; etc.

(Step 7)

Compound [2h] or a salt thereof may be obtained by removing $P^{C7}$ of Compound [57] by a conventional deprotection reaction. The deprotection reaction may be carried out using suitable conditions for each of kinds of $P^{C7}$. For example, when $P^{C7}$ is methyl group, Compound [2h] or a salt thereof may be obtained by hydrolyzing Compound [57] in the presence of a base in a solvent.

The base includes, for example, lithium hydroxide, sodium hydroxide, potassium hydroxide, preferably sodium hydroxide.

A preferable solvent is, for example, an alcoholic solvent such as methanol; an ether solvent such as tetrahydrofuran; water; or a mixed solvent thereof.

The reaction temperature is usually about 0 to 100° C., preferably about 0 to 40° C.

When Compounds [2h] has an enantiomer thereof, the reaction may be carried out using a commercially available optically active compound or using a product obtained therefrom by a conventional method.

When Compound [2h] or a salt thereof is used, Compound [Ib] or a salt thereof may be obtained by treating by the same procedure as Preparation Method 1-3, followed by removing $P^{N6}$ by a conventional deprotection reaction. The deprotection reaction may be carried out using suitable conditions for each of kinds of $P^{N6}$. For example, when $P^{N6}$ is tert-butoxycarbonyl group, Compound [Ib] or a salt thereof may be obtained by the same procedure as Step 2 of Preparation Method 1-2.

EXAMPLES

Preparations of a compound or a pharmaceutically acceptable salt thereof in the present invention are specifically illustrated by Examples. However, the present invention is not intended to be limited thereto.

Stereochemistry in chemical structural formulae of compounds are partially abbreviated in the Examples.

Measurement apparatuses and conditions used in the Examples are as follows.

HPLC Analysis Condition 1
Preparation for solvent A: Sodium dihydrogen phosphate dihydrate (2.34 g) was dissolved in water (3000 ml) to be adjusted to pH 2.6 by using phosphoric acid (1.02 ml).
Measurement instrument: HPLC system SHIMADZU CORPORATION High Performance Liquid Chromatograph Prominence
Column: DAICEL CHIRALPAK AD-3R 4.6 mmϕ×150 mm
Column temperature: 40° C.
Mobile phase: (solvent A) 10 mM phosphate (sodium) buffer (pH 2.6), (solvent B) acetonitrile solvent A: solvent B=60:40 constant (12 minutes flow)
Flow rate: 0.5 ml/min
Detection: UV (220 nm)
HPLC Analysis Condition 2
Preparation for solvent A: Sodium dihydrogenphosphate dihydrate (2.34 g) was dissolved in water (3000 ml), and to be adjusted to pH 2.6 by using phosphoric acid (1.02 ml).
Measurement instrument: HPLC system SHIMADZU CORPORATION High Performance Liquid Chromatograph Prominence
Column: DAICEL CHIRALPAK AD-3R 4.6 mmϕ×150 mm
Column temperature: 40° C.
Mobile phase: (solvent A) 10 mM phosphate (sodium) buffer (pH 2.6), (solvent B) acetonitrile
Solvent A: Solvent B=50:50 constant (12 minutes flow)
Flow rate: 0.5 ml/min
Detection: UV (220 nm)
HPLC Analysis Condition 3
Measurement instrument: HPLC system SHIMADZU CORPORATION High Performance Liquid Chromatograph Prominence
Column: DAICEL CHIRALCEL OD 4.6 mmϕ×250 mm
Column temperature: 40° C.
Mobile phase: (solvent A) n-hexane, (solvent B) 2-propanol
Solvent A:Solvent B=10:90 constant (30 minutes flow)
Flow rate: 0.3 ml/min
Detection: UV (254 nm)
NMR was used with 400 MHz.

Preparation 1

Synthesis of 4-methyl-5-oxopyrrolidine-3-carboxylic acid

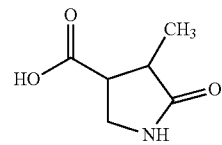

(1) (Z)-2-Bromomethyl-2-butenedioic acid dimethyl ester

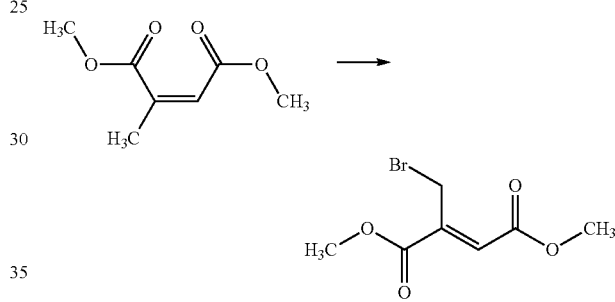

To a solution of (Z)-2-methyl-2-butenedioic acid dimethyl ester (15.3 g) in carbon tetrachloride (300 ml) were added N-bromosuccinimide (25.8 g) and 2,2'-azobis(isobutyronitrile) (319 mg), and the mixture was stirred for 36 hours at reflux. After cooling the mixture to room temperature, the insoluble substance was filtered off, and the filtrate was concentrated. The resulting residue was purified by silica gel column chromatography (eluent: n-hexane/ethyl acetate=1/0 to 18/1) to give the titled compound (19.6 g).

$^1$H-NMR (CDCl$_3$) δ: 3.83 (s, 3H), 3.88 (s, 3H), 4.72 (s, 2H), 6.84 (s, 1H).

(2) 2-Methyl-3-methylenesuccinic acid dimethyl ester

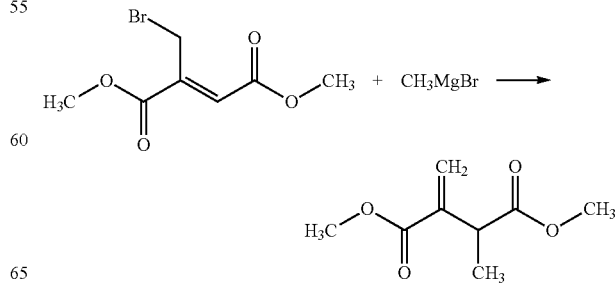

To a solution of (Z)-2-bromomethyl-2-butenedioic acid dimethyl ester (19.3 g) and hexamethylphosphoric acid triamide (70 ml) in diethyl ether (200 ml) was added dropwise methyl magnesium bromide (1.12 M solution in tetrahydrofuran, 100 ml) over 1 hour at −20° C. and stirred for additional 1 hour. To this reaction mixture were added a 6M aqueous solution of hydrochloric acid (18 ml) and a saturated aqueous solution of ammonium chloride (100 ml), and then the mixture was warmed to room temperature and extracted with diethyl ether (200 ml). The resulting organic layer was washed with water twice, followed by a saturated aqueous solution of sodium chloride once, dried over anhydrous sodium sulfate, and concentrated under reduced pressure. The resulting residue was purified by silica gel column chromatography (eluent: n-hexane/chloroform=1/1 to 0/1) to give the titled compound (9.92 g).

$^1$H-NMR (CDCl$_3$) δ: 1.38 (d, 3H, J=7.2 Hz), 3.62 (q, 1H, J=7.2 Hz), 3.69 (s, 3H), 3.77 (s, 3H), 5.72 (s, 1H), 6.34 (s, 1H).

(3) Mixture of (cis)-1-(2,4-dimethoxybenzyl)-4-methyl-5-oxopyrrolidine-3-carboxylic acid methyl ester and (trans)-1-(2,4-dimethoxybenzyl)-4-methyl-5-oxopyrrolidine-3-carboxylic acid methyl ester

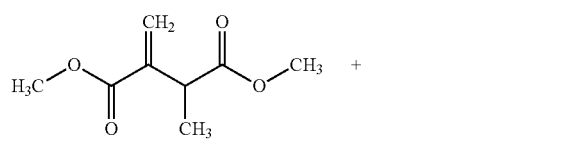

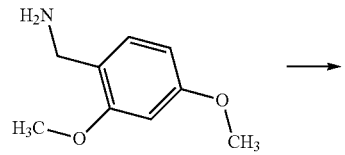

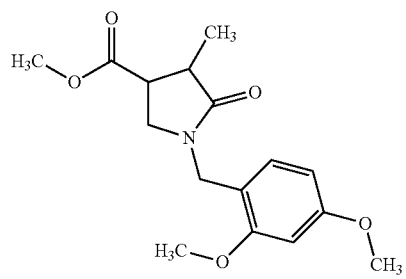

To a solution of 2-methyl-3-methylenesuccinic acid dimethyl ester (9.81 g) in toluene (100 ml) was added 2,4-dimethoxybenzylamine (9.72 g) and the mixture was stirred for 3 days at reflux. This reaction solution was cooled to room temperature and then purified by silica gel column chromatography (eluent: n-hexane/chloroform=1/1 to 0/1) to give the titled compound (14.2 g).

$^1$H-NMR (CDCl$_3$) cis δ: 1.13 (d, 3H, J=7.5 Hz), 2.75-2.86 (m, 1H), 3.22-3.34 (m, 2H), 3.48-3.56 (m, 1H), 3.69 (s, 3H), 3.80 (bs, 6H), 4.41 (d, 1H, J=14.4 Hz), 4.47 (d, 1H, J=14.4 Hz), 6.42-6.48 (m, 2H), 7.13-7.17 (m, 1H). trans δ: 1.30 (d, 3H, J=6.6 Hz), 2.66-2.80 (m, 2H), 3.31-3.43 (m, 2H), 3.71 (s, 3H), 3.80 (s, 6H), 4.41 (d, 1H, J=14.4 Hz), 4.45 (d, 1H, J=14.4 Hz), 6.41-6.47 (m, 2H), 7.10-7.15 (m, 1H).

(4) (Trans)-1-(2,4-dimethoxybenzyl)-4-methyl-5-oxopyrrolidine-3-carboxylic acid

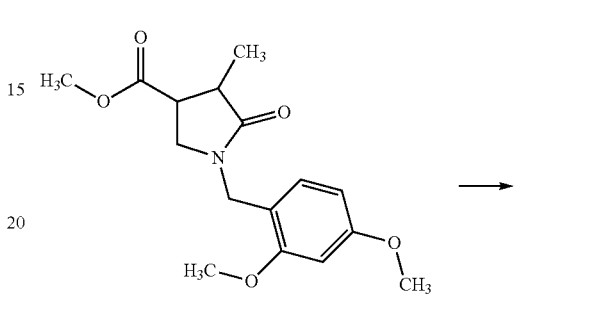

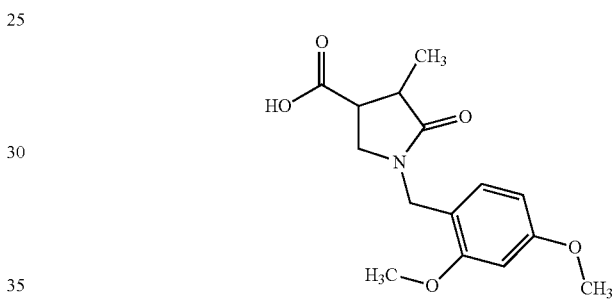

To a solution of a mixture of (cis)-1-(2,4-dimethoxybenzyl)-4-methyl-5-oxopyrrolidine-3-carboxylic acid methyl ester and (trans)-1-(2,4-dimethoxybenzyl)-4-methyl-5-oxopyrrolidine-3-carboxylic acid methyl ester (14.2 g) in methanol (150 ml) was added sodium methoxide (about 5M solution in methanol, 28 ml), and the mixture was stirred at room temperature for 16 hours, and then heated to 55° C. and stirred for 3 hours. To this reaction solution was added sodium methoxide (about 5M solution in methanol, 10 ml), and the mixture was stirred at 55° C. for additional 2 hours. This reaction solution was cooled to room temperature, and then water (50 ml) was added thereto, and the mixture was stirred overnight. The reaction solution was concentrated under reduced pressure to remove methanol. To the resulting residue was added a 2M aqueous solution of hydrochloric acid (105 ml), and the mixture was extracted with ethyl acetate (300 ml). The resulting organic layer was washed with a saturated aqueous solution of sodium chloride, and then dried over anhydrous sodium sulfate, and concentrated under reduced pressure to give a crude product of the titled compound (14.0 g).

$^1$H-NMR (CDCl$_3$) δ: 1.32 (d, 3H, J=6.6 Hz), 2.69-2.84 (m, 2H), 3.35-3.46 (m, 2H), 3.80 (s, 6H), 4.43 (s, 2H), 6.41-6.47 (m, 2H), 7.10-7.15 (m, 1H).

(5) Optically active compound of (R)-4-benzyl-3-[(trans)-1-(2,4-dimethoxybenzyl)-4-methyl-5-oxopyrrolidine-3-carbonyl]-2-oxazolidinone

(6) Optically active compound of (trans)-1-(2,4-dimethoxybenzyl)-4-methyl-5-oxopyrrolidine-3-carboxylic acid

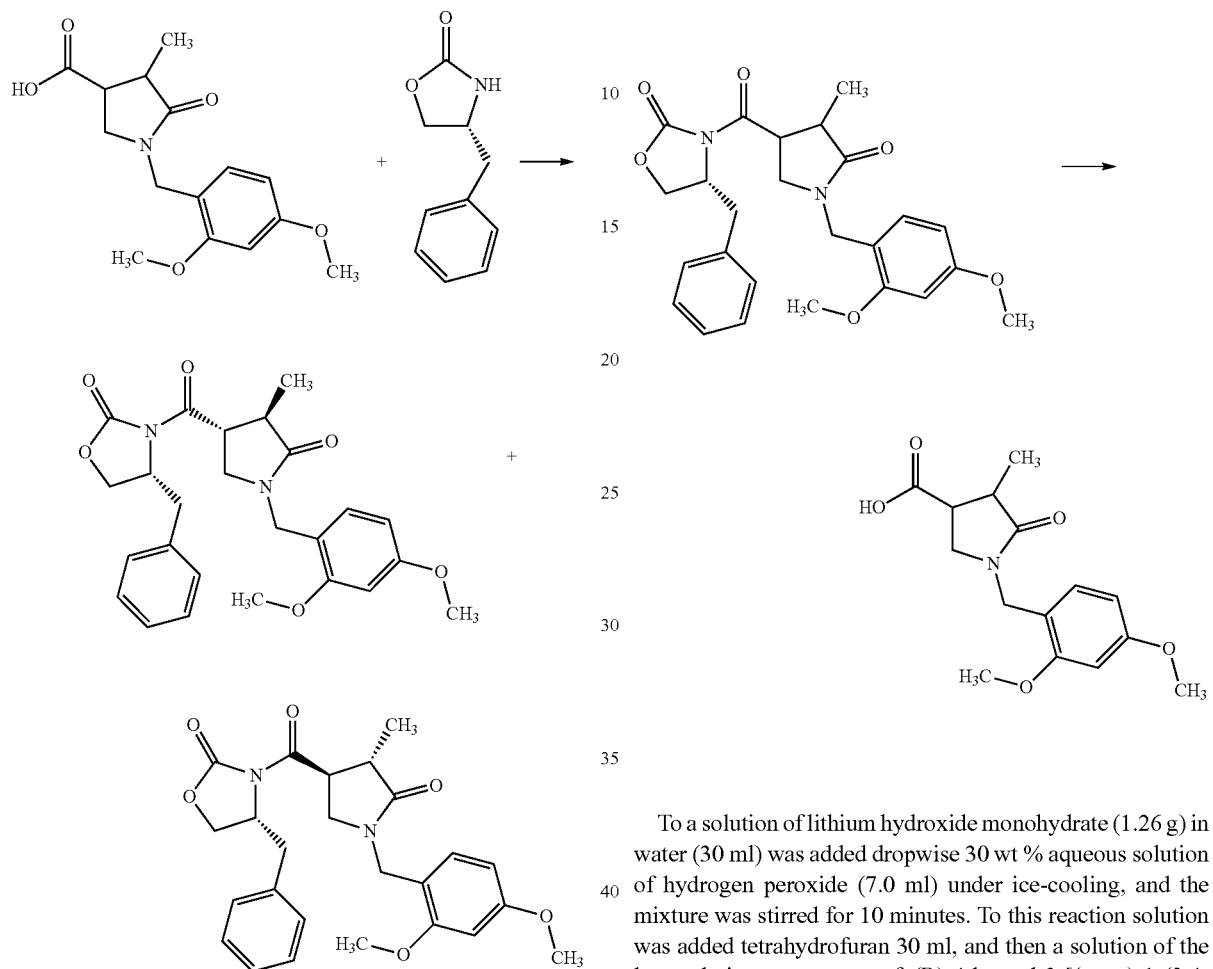

To a solution of the crude product of (trans)-1-(2,4-dimethoxybenzyl)-4-methyl-5-oxopyrrolidine-3-carboxylic acid (14.0 g) in chloroform (60 ml) were sequentially added (R)-4-benzyl-2-oxazolidinone (8.15 g), WSC.HCl (9.70 g), 4-dimethylaminopyridine (2.81 g), and the mixture was stirred overnight at room temperature. This reaction solution was purified by silica gel column chromatography (eluent: n-hexane/ethyl acetate=4/1 to 1/3) to give the titled compound (low-polarity component 11.4 g, high-polarity component 10.1 g).

$^1$H-NMR (CDCl$_3$) low-polarity component δ: 1.31 (d, 3H, J=7.3 Hz), 2.77-2.85 (m, 1H), 2.94-3.03 (m, 1H), 3.19-3.30 (m, 2H), 3.51-3.58 (m, 1H), 3.79 (s, 3H), 3.80 (s, 3H), 3.96-4.03 (m, 1H), 4.19-4.23 (m, 2H), 4.41 (d, 1H, J=15.8 Hz), 4.49 (d, 1H, J=15.8 Hz), 4.63-4.70 (m, 1H), 6.42-6.46 (m, 2H), 7.10-7.21 (m, 3H), 7.27-7.37 (m, 3H). high-polarity component δ: 1.26 (d, 3H, J=7.3 Hz), 2.67-2.75 (m, 1H), 2.97-3.08 (m, 1H), 3.15-3.24 (m, 1H), 3.63-3.93 (m, 8H), 4.17-4.28 (m, 3H), 4.36-4.56 (m, 2H), 4.63-4.73 (m, 1H), 6.39-6.56 (m, 2H), 7.11-7.21 (m, 3H), 7.27-7.39 (m, 3H).

To a solution of lithium hydroxide monohydrate (1.26 g) in water (30 ml) was added dropwise 30 wt % aqueous solution of hydrogen peroxide (7.0 ml) under ice-cooling, and the mixture was stirred for 10 minutes. To this reaction solution was added tetrahydrofuran 30 ml, and then a solution of the low-polarity component of (R)-4-benzyl-3-[(trans)-1-(2,4-dimethoxybenzyl)-4-methyl-5-oxopyrrolidine-3-carbonyl]-2-oxazolidinone (11.4 g) in tetrahydrofuran (90 ml) was added dropwise thereto, and then the mixture was stirred for additional 1 hour. To this reaction solution was added dropwise a solution of sodium hydrogen sulfite (7.18 g) in water (50 ml), and then the mixture was warmed to room temperature, and stirred for 1 hour. This mixture was extracted with ethyl acetate, and the resulting organic layer was washed with a saturated aqueous solution of sodium chloride, and then dried over anhydrous sodium sulfate, and concentrated under reduced pressure. The resulting residue was purified by silica gel column chromatography (eluent: chloroform/ethyl acetate=1/1 to 1/2, chloroform/methanol=5/1) to give a crude product of the titled compound (8.11 g). An analysis of the solid by HPLC analysis condition 1 showed that an isomer with shorter retention time was a main product.

An isomer with shorter retention time (retention time 5.7 minutes)

An isomer with longer retention time (retention time 6.5 minutes)

Alternatively, the titled compound can be prepared according to the following method.

(6)-(1) Diastereomeric salt of an optically active compound of (trans)-1-(2,4-dimethoxybenzyl)-4-methyl-5-oxopyrrolidine-3-carboxylic acid and (1R,2R)-(−)-2-amino-1-(4-nitrophenyl)-1,3-propanediol

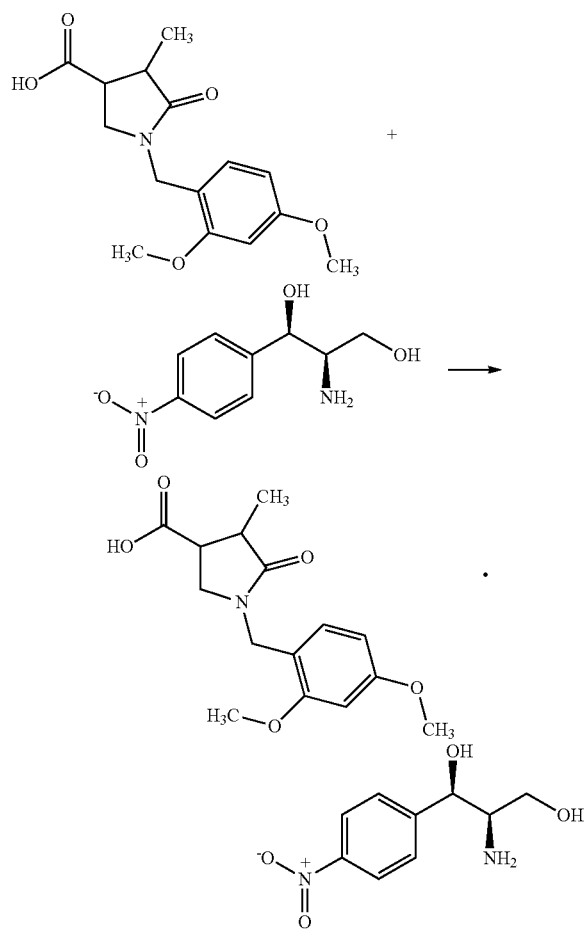

(Trans)-1-(2,4-dimethoxybenzyl)-4-methyl-5-oxopyrrolidine-3-carboxylic acid (1.0 g), (1R,2R)-(−)-2-amino-1-(4-nitrophenyl)-1,3-propanediol (434 mg), acetonitrile (10 ml) and water (0.9 ml) were mixed, and stirred at reflux to dissolve. This mixed solution was stirred at 50° C. for 6 hours, and then stirred at room temperature overnight. A solid precipitated from this mixed solution was collected by filtration, washed with acetonitrile (6 ml), and dried under reduced pressure to give a solid 1 of the titled compound (572 mg). An analysis of the solid 1 by HPLC analysis condition 1 showed that an isomer with shorter retention time was a main product.

An isomer with shorter retention time (retention time 5.7 minutes)

An isomer with longer retention time (retention time 6.5 minutes)

$^1$H-NMR (DMSO-D$_6$) δ: 1.11 (d, 3H, J=7.3 Hz), 2.43-2.53 (m, 1H), 2.55-2.64 (m, 1H), 2.85-2.92 (m, 1H), 3.14-3.22 (m, 2H), 3.27 (dd, 1H, J=9.3, 9.3 Hz), 3.38 (dd, 1H, J=11.3, 4.8 Hz), 3.73 (s, 3H), 3.76 (s, 3H), 4.19 (d, 1H, J=14.5 Hz), 4.29 (d, 1H, J=14.5 Hz), 4.73 (d, 1H, J=6.0 Hz), 6.46 (dd, 1H, J=8.1, 2.4 Hz), 6.54 (d, 1H, J=2.4 Hz), 6.97 (d, 1H, J=8.1 Hz), 7.61 (d, 2H, J=8.5 Hz), 8.19 (d, 2H, J=8.5 Hz).

An X ray crystal structural analysis of the crystal obtained by recrystallization of the solid 1 from methyl isobutyl ketone showed that this crystal was a diastereomeric salt of (3R,4R)-1-(2,4-dimethoxybenzyl)-4-methyl-5-oxopyrrolidine-3-carboxylic acid and (1R,2R)-(−)-2-amino-1-(4-nitrophenyl)-1,3-propanediol.

(6)-(2) (3R,4R)-1-(2,4-Dimethoxybenzyl)-4-methyl-5-oxopyrrolidine-3-carboxylic acid

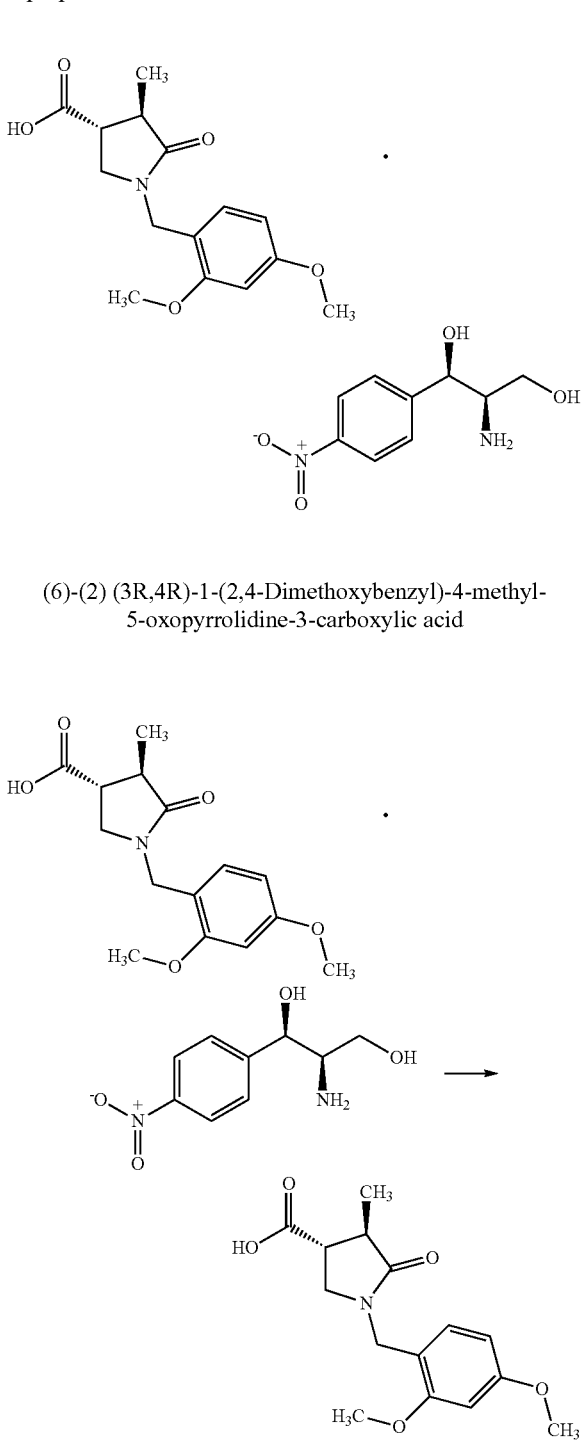

A diastereomeric salt of (3R,4R)-1-(2,4-dimethoxybenzyl)-4-methyl-5-oxopyrrolidine-3-carboxylic acid and (1R,2R)-(−)-2-amino-1-(4-nitrophenyl)-1,3-propanediol (10.0 g) was mixed with ethyl acetate (38 ml), potassium hydrogen sulfate (2.4 g) and water (38 ml), and stirred at room temperature for 30 minutes. An organic layer was separated, and a separated aqueous layer was again extracted twice with ethyl acetate (15 ml). The combined organic layer was washed with a saturated aqueous solution of sodium chloride, dried over anhydrous sodium sulfate, and concentrated under reduced pressure. To the resulting residue were added 2-propanol (2.2 ml) and diisopropyl ether (45 ml), and the mixture was stirred. The insoluble substance was collected by filtration, washed with a small amount of diisopropyl ether, and dried under reduced pressure to give the titled compound (4.3 g). An analysis of this solid by HPLC analysis condition 1 showed that an isomer with shorter retention time was a main product.

An isomer with shorter retention time (retention time 5.7 minutes)

An isomer with longer retention time (retention time 6.5 minutes)

(7) (3R,4R)-4-Methyl-5-oxopyrrolidine-3-carboxylic acid

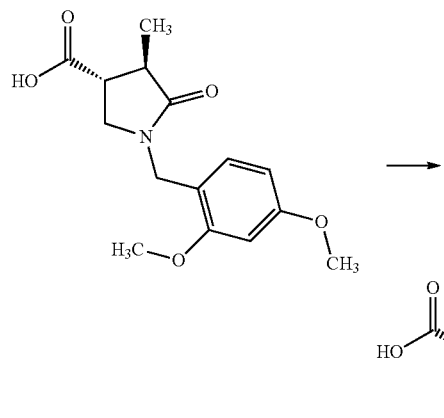

To a crude product of (3R,4R)-1-(2,4-dimethoxybenzyl)-4-methyl-5-oxopyrrolidine-3-carboxylic acid (8.11 g) were added anisole (3.76 ml) and trifluoroacetic acid (40 ml), and the mixture was stirred at 80° C. for 5 hours. This reaction solution was cooled to room temperature, and concentrated under reduced pressure. To the resulting residue was added diisopropyl ether, and the mixture was stirred. The insoluble substance was collected by filtration, and dried under reduced pressure to give a crude product of the titled compound (2.23 g). To the resulting solid was added ethanol (8 ml), and the mixture was heated at reflux to dissolve, and then the solution was stirred at room temperature. A solid precipitated from the mixed solution was collected by filtration, washed with a small amount of cooled ethanol, and dried under reduced pressure to give the titled compound (1.36 g).

$^1$H-NMR (DMSO-D$_6$) δ: 1.10 (d, 3H, J=7.3 Hz), 2.40 (dq, 1H, J=9.0, 7.3 Hz), 2.83 (ddd, 1H, J=9.0, 8.6, 7.6 Hz), 3.22 (dd, 1H, J=10.0, 7.6 Hz), 3.37 (dd, 1H, J=10.0, 8.6 Hz), 7.66 (s, 1H), 12.58 (s, 1H).

Also, the high-polarity component of (R)-4-benzyl-3-[(trans)-1-(2,4-dimethoxybenzyl)-4-methyl-5-oxopyrrolidine-3-carbonyl]-2-oxazolidinone (10.1 g) was subjected to the similar reactions and post-treatment as described above to give (3S,4S)-4-methyl-5-oxopyrrolidine-3-carboxylic acid (1.53 g) as the optical isomer of the titled compound.

$^1$H-NMR (DMSO-D$_6$) δ: 1.10 (d, 3H, J=7.3 Hz), 2.40 (dq, 1H, J=9.0, 7.3 Hz), 2.83 (ddd, 1H, J=9.0, 8.6, 7.6 Hz), 3.22 (dd, 1H, J=10.0, 7.6 Hz), 3.37 (dd, 1H, J=10.0, 8.6 Hz), 7.66 (s, 1H), 12.58 (s, 1H).

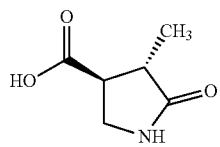

Preparation 2

Example 1

Synthesis of ((3R,4R)-4-methyl-5-oxopyrrolidine-3-carboxylic acid[1-phenyl-5-(3-trifluoromethoxyphenyl)-1H-pyrazol-3-yl]amide)

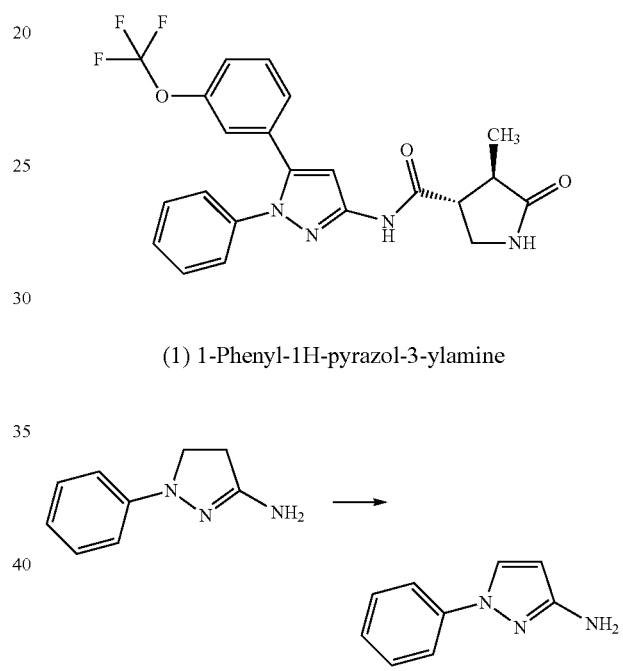

(1) 1-Phenyl-1H-pyrazol-3-ylamine

To a solution of 1-phenyl-4,5-dihydro-1H-pyrazol-3-ylamine (50.0 g) in N,N-dimethylformamide (150 ml) and 1,4-dioxane (500 ml) was added 3,4,5,6-tetrachloro-1,4-benzoquinone (84.0 g) under ice-cooling over 20 minutes, and the mixture was stirred at room temperature for 4.5 hours. To the reaction mixture was added a 2M aqueous solution of sodium hydroxide (400 ml) under ice-cooling over 25 minutes, and the mixture was stirred at room temperature for 1 hour. The mixture was filtered through Celite to remove the insoluble substance, and eluted with ethyl acetate (250 ml×3), and then the filtrate was extracted with ethyl acetate (300 ml). The resulting organic layer was sequentially washed with water (300 ml) and a saturated aqueous solution of sodium chloride (300 ml). The separated aqueous layer was extracted twice with ethyl acetate (300 ml). To the combined organic layer were added anhydrous sodium sulfate (50 g) and silica gel (50 g), and the mixture was stirred at room temperature for 1 hour. This mixture was filtered with silica gel (100 g) on Celite, and subjected to elution with ethyl acetate (250 ml×3). The filtrate was concentrated, and diisopropyl ether (500 ml) was added to the resulting residue, and the mixture was stirred at room temperature. The insoluble substance was collected by filtration, washed twice with diisopropyl ether (100 ml), and dried under reduced pressure to give the titled compound (12.2 g).

¹H-NMR (CDCl₃) δ: 3.81 (br s, 2H), 5.85 (d, 1H, J=2.4 Hz), 7.16-7.19 (m, 1H), 7.38-7.40 (m, 2H), 7.55-7.57 (m, 2H), 7.69 (d, 1H, J=2.4 Hz).

(2) 3-(2,5-Dimethylpyrrol-1-yl)-1-phenyl-1H-pyrazole

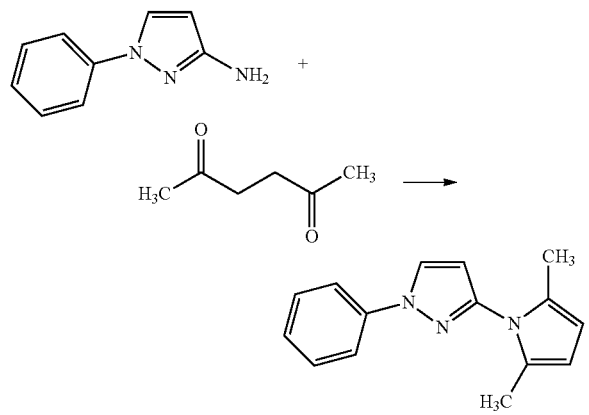

To a solution of 1-phenyl-1H-pyrazol-3-ylamine (32.7 g) in acetic acid (330 ml) was added 2,5-hexanedione (25 ml), and the mixture was stirred for 3 hours at reflux. This reaction solution was cooled to room temperature, and then acetic acid was concentrated under reduced pressure, and then toluene (100 ml) was added thereto, and the mixture was further concentrated. The resulting residue was purified by silica gel column chromatography (eluent: n-hexane/ethyl acetate 100/1 to 20/1) to give the titled compound (41.8 g).

¹H-NMR (CDCl₃) δ: 2.19 (s, 6H), 5.90 (s, 2H), 6.39 (d, 1H, J=2.4 Hz), 7.29-7.31 (m, 1H), 7.46-7.48 (m, 2H), 7.72-7.73 (m, 2H), 7.98 (d, 1H, J=2.4 Hz).

(3) 3-(2,5-Dimethylpyrrol-1-yl)-5-iodo-1-phenyl-1H-pyrazole

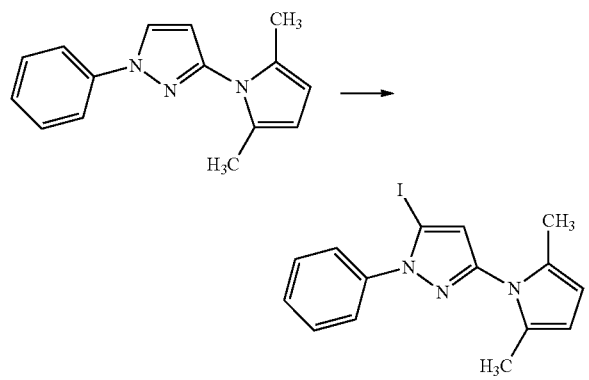

To a solution of 3-(2,5-dimethylpyrrol-1-yl)-1-phenyl-1H-pyrazole (14.6 g) in tetrahydrofuran (80 ml) cooled to −78° C. was added n-butyllithium (1.6M solution in n-hexane, 24 ml) over 5 minutes, and then the mixture was stirred for 1 hour. To this mixture was added a solution of iodine (15.7 g) in tetrahydrofuran (30 ml) over 10 minutes, and the mixture was stirred for additional 1.5 hours. To this mixture were sequentially added water (5 ml) and a saturated aqueous solution of sodium hydrogen sulfite (30 ml), and then the mixture was warmed to 0° C., and additional water (150 ml) was added thereto, and the mixture was stirred at room temperature for 1 hour. A precipitated solid was collected by filtration, washed with water and a small amount of methanol, and dried under reduced pressure to give the titled compound (13.0 g).

¹H-NMR (CDCl₃) δ: 2.19 (s, 6H), 5.88 (s, 2H), 6.55 (s, 1H), 7.44-7.53 (m, 3H), 7.57-7.60 (m, 2H).

(4) 5-Iodo-1-phenyl-1H-pyrazol-3-ylamine

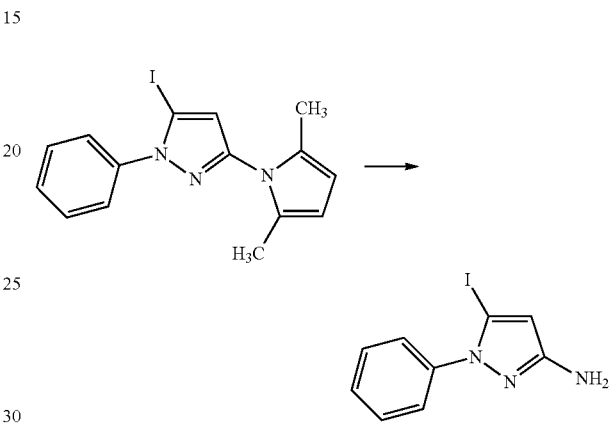

To a solution of 3-(2,5-dimethylpyrrol-1-yl)-5-iodo-1-phenyl-1H-pyrazole (12.2 g) in ethanol/water (2/1, 180 ml) were sequentially added hydroxylammonium chloride (46.6 g) and triethylamine (9.3 ml), and the mixture was stirred at 95° C. for 72 hours. This reaction mixture was cooled to room temperature, and concentrated under reduced pressure. To the resulting residue was added a 8M aqueous solution of sodium hydroxide (80 ml), and then the mixture was extracted with ethyl acetate (50 ml). This organic layer was sequentially washed with water and a saturated aqueous solution of sodium chloride, dried over anhydrous sodium sulfate, and concentrated under reduced pressure. The resulting residue was purified by silica gel column chromatography (eluent: n-hexane/ethyl acetate=3/1) to give the titled compound (9.1 g).

¹H-NMR (CDCl₃) δ: 3.77 (br s, 2H), 6.01 (s, 1H), 7.35-7.51 (m, 5H).

(5) 1-Phenyl-5-(3-(trifluoromethoxy)phenyl)-1H-pyrazol-3-ylamine

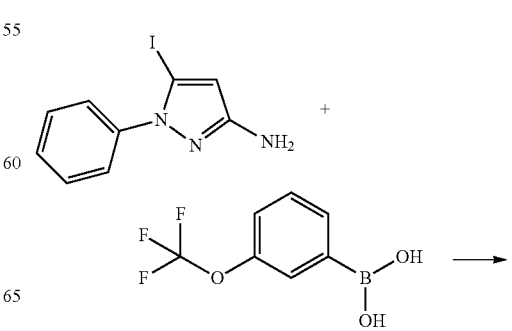

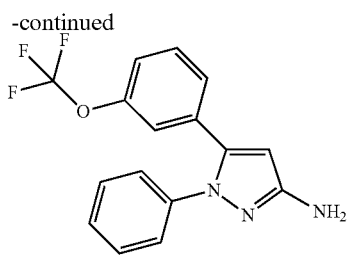

To a solution of 5-iodo-1-phenyl-1H-pyrazol-3-ylamine (605 mg) in ethylene glycol dimethyl ether (12 ml) were sequentially added 3-(trifluoromethoxy)phenyl boronic acid (481 mg), a 2M aqueous solution of sodium carbonate (6 ml), tricyclohexylphosphine (119 mg), palladium acetate (48 mg), and the mixture was stirred for 2 hours at reflux. This reaction mixture was cooled to room temperature, and a saturated aqueous solution of sodium hydrogen carbonate was added thereto, and then the mixture was filtered through Celite. The filtrate was extracted with ethyl acetate. The resulting organic layer was washed with a saturated aqueous solution of sodium chloride, dried over anhydrous sodium sulfate, and concentrated under reduced pressure. The resulting residue was purified by silica gel column chromatography (eluent: n-hexane/ethyl acetate=2/1) to give the titled compound (298 mg).

$^1$H-NMR (CDCl$_3$) δ: 3.79 (br s, 2H), 5.95 (s, 1H), 7.04 (s, 1H), 7.13-7.34 (m, 8H).

(6) (3R,4R)-4-Methyl-5-oxopyrrolidine-3-carboxylic acid[1-phenyl-5-(3-(trifluoromethoxy)phenyl)-1H-pyrazol-3-yl]amide

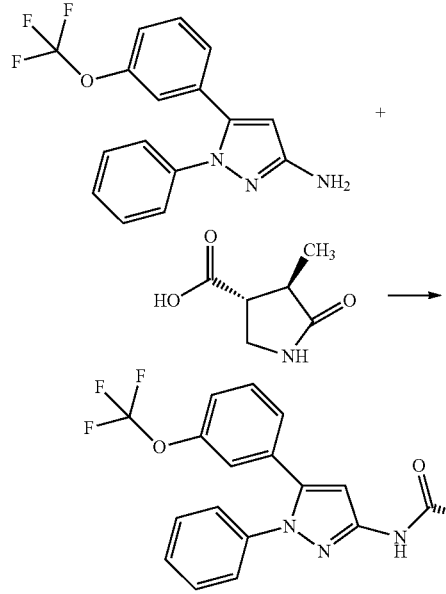

To a solution of 1-phenyl-5-(3-(trifluoromethoxy)phenyl)-1H-pyrazol-3-ylamine (79 mg) in N,N-dimethylformamide (0.8 ml) were sequentially added (3R,4R)-4-methyl-5-oxopyrrolidine-3-carboxylic acid (46 mg) prepared in Preparation 1, HOBt.H$_2$O (57 mg) and WSC.HCl (71 mg), and the mixture was stirred at room temperature for 2 hours. To this reaction solution were added water and a saturated aqueous solution of sodium hydrogen carbonate, and the mixture was extracted with ethyl acetate. The separated organic layer was washed with a saturated aqueous solution of sodium chloride, dried over anhydrous sodium sulfate, and then concentrated under reduced pressure. The resulting residue was purified by silica gel thin-layer chromatography (eluent: chloroform/methanol=10/1) to give the titled compound (63 mg).

$^1$H-NMR (DMSO-D$_6$) δ: 1.08 (d, 3H, J=7.3 Hz), 2.55 (ddd, 1H, J=9.3, 8.8, 8.8 Hz), 3.04 (dq, 1H, J=9.3, 7.3 Hz), 3.23 (dd, 1H, J=8.8, 8.8 Hz), 3.45 (dd, 1H, J=8.8, 8.8 Hz), 7.03 (s, 1H), 7.09 (s, 1H), 7.26 (t, 2H, J=6.7 Hz), 7.35-7.45 (m, 5H), 7.52 (t, 1H, J=8.0 Hz), 7.68 (s, 1H), 10.99 (s, 1H).

(7) Crystals of (3R,4R)-4-methyl-5-oxopyrrolidine-3-carboxylic acid[1-phenyl-5-(3-(trifluoromethoxy)phenyl)-1H-pyrazol-3-yl]amide The titled compound was dissolved in ethyl acetate at 90° C., and recrystallized by an addition of heptane thereto at the same temperature to give a crystal of the titled compound. Furthermore, the corresponding crystal as above was suspended in water at 100° C. to give an another crystal of the titled compound.

Preparation 3

Example 2

Synthesis of ((3R,4R)-4-methyl-5-oxopyrrolidine-3-carboxylic acid[1-(4-fluorophenyl)-5-(3-(trifluoromethoxy)phenyl)-1H-pyrazol-3-yl]amide)

(1) Mixture of (E)-3-(3-(trifluoromethoxy)phenyl) acrylonitrile and (Z)-3-(3-(trifluoromethoxy)phenyl) acrylonitrile

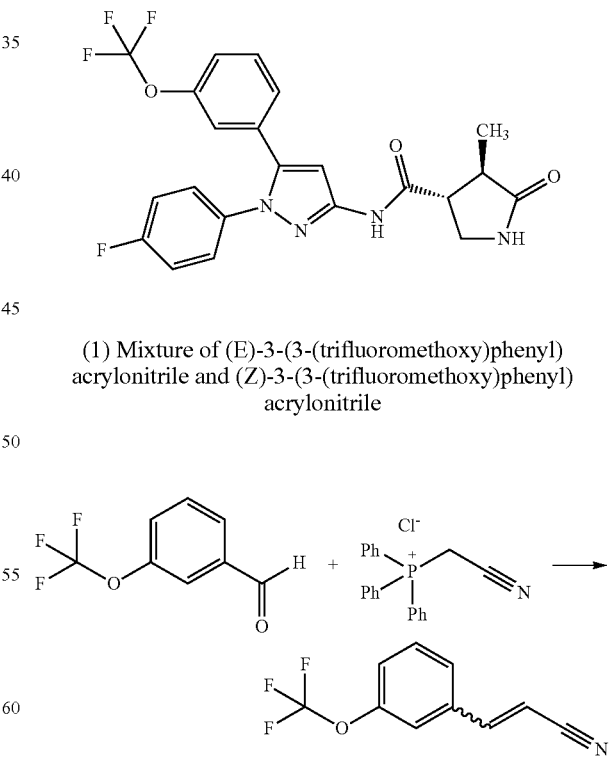

To a suspension of (cyanomethyl)triphenylphosphonium chloride (2.89 g) in tetrahydrofuran (10 ml) was added potassium tert-butoxide (942 mg) under ice-cooling, and the mixture was stirred at room temperature for 1 hour. To this reaction solution was added 3-trifluoromethoxybenzaldehyde (1.33 g) under ice-cooling, and then the mixture was stirred at room temperature overnight. To this reaction solution was added n-hexane (20 ml), and the insoluble substance was filtered off, and then the filtrate was concentrated. The resulting residue was purified by silica gel column chromatography (eluent: n-hexane/ethyl acetate=1/0 to 10/1) to give the titled compound (1.28 g).

$^1$H-NMR (CDCl$_3$) (E)-isomer δ: 5.92 (1H, d, J=16.8 Hz), 7.27-7.49 (5H, m).

(Z)-isomer δ: 5.55 (1H, d, J=12.0 Hz), 7.12 (1H, d, J=12.0 Hz), 7.35-7.52 (2H, m), 7.60 (1H, s), 7.79 (1H, d, J=8.0 Hz).

(2) 1-(4-Fluorophenyl)-5-(3-(trifluoromethoxy)phenyl)-4,5-dihydro-1H-pyrazol-3-ylamine

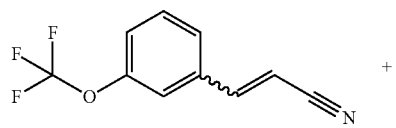

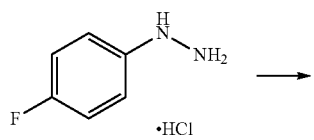

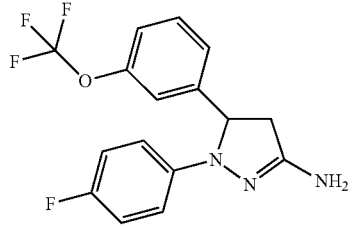

To a solution of a mixture of (E)-3-(3-(trifluoromethoxy)phenyl)acrylonitrile and (Z)-3-(3-(trifluoromethoxy)phenyl)acrylonitrile (1.28 g) in ethanol (13 ml) were sequentially added 4-fluorophenylhydrazine hydrochloride (979 mg) and sodium ethoxide (20 wt % in ethanol, 5.0 ml), and the mixture was stirred overnight at reflux. This reaction solution was concentrated under reduced pressure, and then water was added thereto, and the mixture was extracted with ethyl acetate. This organic layer was sequentially washed with water and a saturated aqueous solution of sodium chloride, and then concentrated under reduced pressure. The resulting residue was purified by silica gel column chromatography (eluent: n-hexane/ethyl acetate=2/1 to 1/1) to give the titled compound (1.29 g).

$^1$H-NMR (CDCl$_3$) δ: 2.79 (dd, 1H, J=16.3, 8.8 Hz), 3.41 (dd, 1H, J=16.3, 11.0 Hz), 3.98 (s, 2H), 4.83 (dd, 1H, J=11.0, 8.8 Hz), 6.72-6.87 (m, 4H), 7.14 (d, 1H, J=7.9 Hz), 7.25 (s, 1H), 7.32 (d, 1H, J=7.7 Hz), 7.38 (dd, 1H, J=7.9, 7.7 Hz).

(3) 1-(4-Fluorophenyl)-5-(3-(trifluoromethoxy)phenyl)-1H-pyrazol-3-ylamine

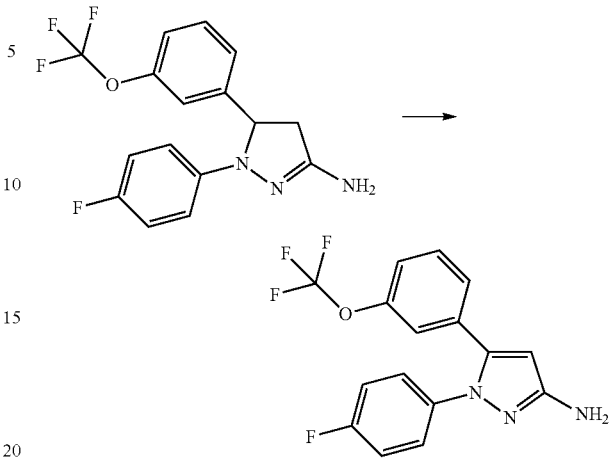

To a solution of 1-(4-fluorophenyl)-5-(3-(trifluoromethoxy)phenyl)-4,5-dihydro-1H-pyrazol-3-ylamine (1.29 g) in toluene (10 ml) was added activated carbon (pH5 to 8, 0.64 g), and the mixture was stirred for 2 hours under oxygen atmosphere under cooling to reflux. After cooling to room temperature, the activated carbon was filtered off through Celite eluting with ethyl acetate. This filtrate was concentrated under reduced pressure. To the resulting residue, a mixed solvent of diisopropyl ether/n-hexane was added and the mixture was stirred at room temperature. The insoluble substance was collected by filtration, and then dried under reduced pressure to give the titled compound (652 mg).

$^1$H-NMR (CDCl$_3$) δ: 3.78 (bs, 1H), 5.95 (s, 1H), 6.97-7.05 (m, 3H), 7.13-7.21 (m, 4H), 7.334 (t, 1H, J=8.0 Hz).

(4) (3R,4R)-4-Methyl-5-oxopyrrolidine-3-carboxylic acid[1-(4-fluorophenyl)-5-(3-(trifluoromethoxy)phenyl)-1H-pyrazol-3-yl]amide

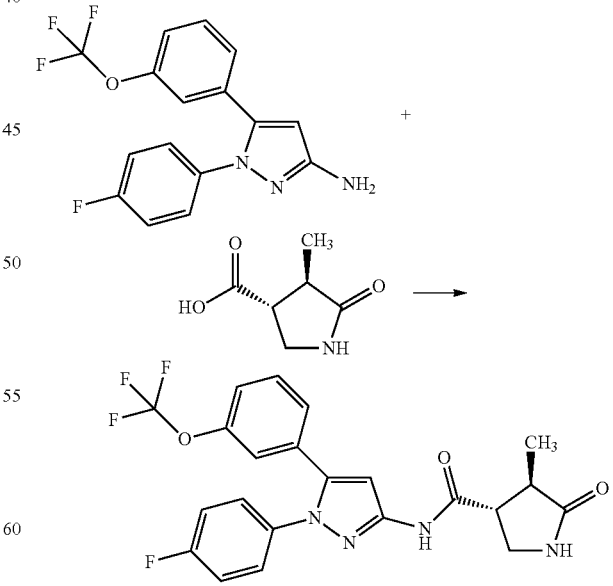

To a solution of 1-(4-fluorophenyl)-5-(3-(trifluoromethoxy)phenyl)-1H-pyrazol-3-ylamine (90 mg) in N,N-dimethylformamide (0.9 ml) were added (3R,4R)-4-methyl- 5-oxopyrrolidine-3-carboxylic acid (50 mg) prepared in Preparation 1, HOBt.H₂O (61 mg) and WSC.HCl (77 mg), and the mixture was stirred at room temperature for 2 hours. To this mixture were added water and a saturated aqueous solution of sodium hydrogen carbonate, and the mixture was extracted with ethyl acetate. The separated organic layer was washed with a saturated aqueous solution of sodium chloride, dried over anhydrous sodium sulfate, and then concentrated under reduced pressure. The resulting residue was purified by silica gel thin-layer chromatography (eluent: chloroform/methanol=10/1) to give the titled compound (80 mg).

1H-NMR (DMSO-D6) δ: 1.08 (d, 3H, J=7.1 Hz), 2.54 (dq, 1H, J=9.3, 7.1 Hz), 3.04 (ddd, 1H, J=9.3, 9.2, 8.4 Hz), 3.23 (dd, 1H, J=9.2, 8.6 Hz), 3.44 (dd, 1H, J=8.6, 8.4 Hz), 7.03 (s, 1H), 7.11 (s, 1H), 7.25-7.38 (m, 6H), 7.53 (dd, 1H, J=8.2, 7.9 Hz), 7.68 (s, 1H), 10.98 (s, 1H).

Preparation 4

Example 3

Synthesis of ((3R,4R)-4-methyl-5-oxopyrrolidine-3-carboxylic acid[1-(3-fluorophenyl)-5-(3-(trifluoromethoxy)phenyl)-1H-pyrazol-3-yl]amide)

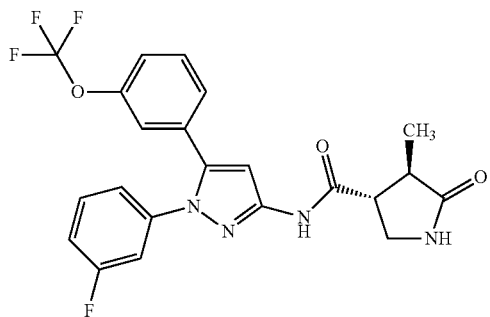 [SMILES: C[C@H]1C(=O)NC[C@@H]1C(=O)Nc1cc(-c2cccc(OC(F)(F)F)c2)n(-c2cccc(F)c2)n1]

(1) 3-(2,5-Dimethylpyrrol-1-yl)-1H-pyrazole

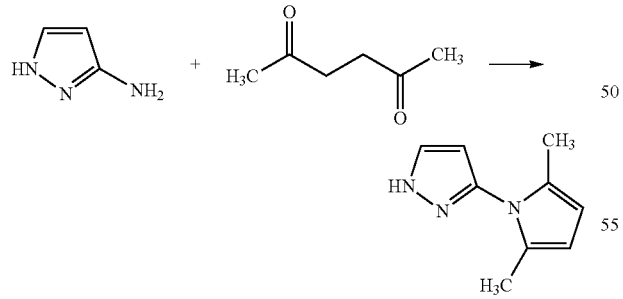

To a solution of 3-aminopyrazole (100 g) in acetic acid (1000 ml) was added 2,5-hexanedione (148 ml), and the mixture was stirred for 2.4 hours at reflux. This reaction solution was cooled to room temperature, water (1000 ml) was added thereto, and the precipitated solid was collected by filtration. The resulting solid was washed with water (1000 ml), and dried under reduced pressure to give the titled compound (183 g).

¹H-NMR (DMSO-D₆) δ: 2.00 (s, 6H), 5.74 (s, 2H), 6.27 (d, 1H, J=2.1 Hz), 7.84 (d, 1H, J=2.1 Hz), 12.90 (s, 1H).

(2) 3-(2,5-Dimethylpyrrol-1-yl)-1-(3-fluorophenyl)-1H-pyrazole

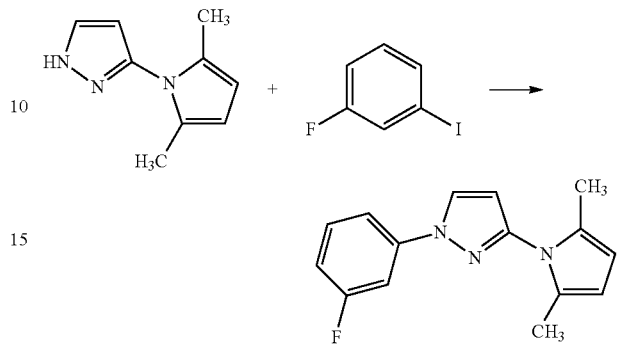

To a solution of 3-(2,5-dimethylpyrrol-1-yl)-1H-pyrazole (6.8 g) in N-methyl-2-pyrrolidone (68 ml) were sequentially added cesium carbonate (27.4 g), 8-quinolinol (1.2 g), copper oxide (I) (0.6 g) and 1-fluoro-3-iodobenzene (7.4 ml), and the mixture was stirred at 110° C. for 2 hours. This reaction mixture was cooled to room temperature, and toluene (80 ml) was added thereto, and then the mixture was filtered through Celite. After adding a 1M aqueous solution of sodium hydroxide (80 ml) to the filtrate, the mixture was extracted with toluene. The resulting organic layer was sequentially washed with water and a saturated aqueous solution of sodium chloride, dried over anhydrous sodium sulfate, and concentrated under reduced pressure. The resulting residue was purified by silica gel column chromatography (eluent: n-hexane/ethyl acetate=9/1) to give the titled compound (10.4 g).

¹H-NMR (CDCl₃) δ: 2.19 (s, 6H), 5.90 (s, 2H), 6.41 (d, 1H, J=2.6 Hz), 6.97-7.02 (m, 1H), 7.39-7.45 (m, 1H), 7.48-7.49 (m, 1H), 7.49-7.52 (m, 1H), 7.97 (d, 1H, J=2.6 Hz).

(3) 3-(2,5-Dimethylpyrrol-1-yl)-1-(3-fluorophenyl)-5-iodo-1H-pyrazole

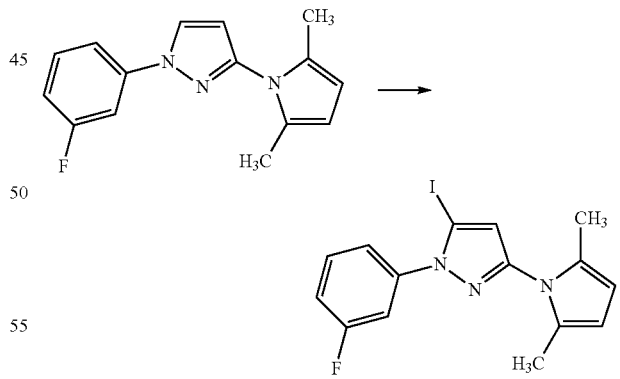

To a solution of 3-(2,5-dimethylpyrrol-1-yl)-1-(3-fluorophenyl)-1H-pyrazole (10.4 g) in tetrahydrofuran (100 ml) cooled to −78° C. was added n-butyllithium (1.6M solution in n-hexane, 31 ml) over 10 minutes, and then the mixture was stirred for 30 minutes. To the mixture was added dropwise a solution of iodine (12.4 g) in tetrahydrofuran (20 ml) over 10 minutes, and the mixture was stirred for additional 30 minutes. To the mixture were sequentially added a 20 wt % aqueous solution of sodium thiosulfate and a saturated aqueous ammonia, and then the mixture was warmed to room temperature, and extracted with ethyl acetate. The separated organic layer was washed with a saturated aqueous solution of sodium chloride, dried over anhydrous sodium sulfate, and concentrated under reduced pressure. To the resulting residue was added a mixed solvent of n-hexane/ethyl acetate (2/1), and the mixture was stirred. The insoluble substance was collected by filtration, and dried under reduced pressure to give the titled compound (4.5 g).

$^1$H-NMR (CDCl$_3$) δ: 2.19 (s, 6H), 5.88 (s, 2H), 6.56 (s, 1H), 7.15-7.19 (m, 1H), 7.35-7.37 (m, 1H), 7.41-7.50 (m, 2H).

(4) 1-(3-Fluorophenyl)-5-iodo-1H-pyrazol-3-ylamine

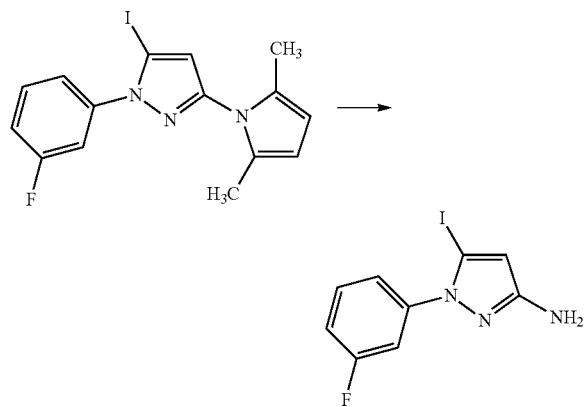

To a solution of 3-(2,5-dimethylpyrrol-1-yl)-1-(3-fluorophenyl)-5-iodo-1H-pyrazole (4.5 g) in ethanol/water (2/1, 81 ml) were sequentially added hydroxylammonium chloride (16.3 g) and triethylamine (3.3 ml), and the mixture was stirred at 95° C. for 17 hours. This reaction mixture was cooled to room temperature and concentrated under reduced pressure. To the resulting residue was added an 8M aqueous solution of sodium hydroxide, and the mixture was extracted with ethyl acetate. This organic layer was sequentially washed with water and a saturated aqueous solution of sodium chloride, dried over anhydrous sodium sulfate, and concentrated under reduced pressure. The resulting residue was purified by silica gel column chromatography (eluent: n-hexane/ethyl acetate=2/1) to give the titled compound (3.2 g).

$^1$H-NMR (CDCl$_3$) δ: 3.78 (br s, 2H), 6.03 (s, 1H), 7.05-7.09 (m, 1H), 7.26-7.29 (m, 1H), 7.32-7.43 (m, 2H).

(5) 1-(3-Fluorophenyl)-5-(3-(trifluoromethoxy)phenyl)-1H-pyrazol-3-ylamine

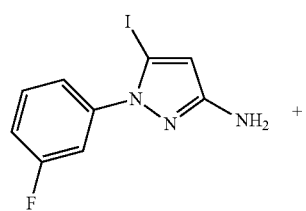 +

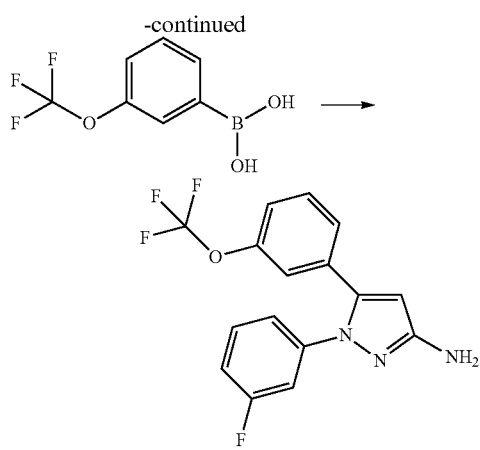

To a solution of 1-(3-fluorophenyl)-5-iodo-1H-pyrazol-3-ylamine (263 mg) in ethylene glycol dimethyl ether (5 ml) were sequentially added 3-(trifluoromethoxy)phenylboronic acid (197 mg), a 2M aqueous solution of sodium carbonate (2.5 ml), tricyclohexylphosphine (49 mg), palladium acetate (20 mg), and the mixture was stirred for 2 hours at reflux. This reaction mixture was cooled to room temperature, a saturated aqueous solution of sodium hydrogen carbonate was added thereto, and then the mixture was filtered through Celite. The filtrate was extracted with ethyl acetate, the resulting organic layer was washed with a saturated aqueous solution of sodium chloride, dried over anhydrous sodium sulfate, and concentrated under reduced pressure. The resulting residue was purified by silica gel column chromatography (eluent: n-hexane/ethyl acetate=2/1) to give the titled compound (234 mg).

$^1$H-NMR (CDCl$_3$) δ: 3.82 (br s, 2H), 5.96 (s, 1H), 6.92-7.02 (m, 3H), 7.05-7.07 (m, 1H), 7.17-7.38 (m, 4H).

(6) (3R,4R)-4-Methyl-5-oxopyrrolidine-3-carboxylic acid[1-(3-fluorophenyl)-5-(3-(trifluoromethoxy)phenyl)-1H-pyrazol-3-yl]amide

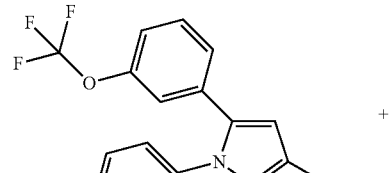 +

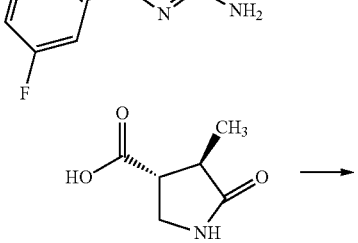

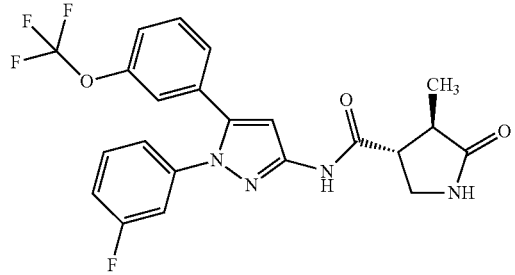

To a solution of 1-(3-fluorophenyl)-5-(3-(trifluoromethoxy)phenyl)-1H-pyrazol-3-ylamine (68 mg) in N,N- dimethylformamide (0.7 ml) were sequentially added (3R, 4R)-4-methyl-5-oxopyrrolidine-3-carboxylic acid (38 mg) prepared in Preparation 1, HOBt.H₂O (46 mg) and WSC.HCl (58 mg), and the mixture was stirred at room temperature for 2 hours. To this reaction solution were added water and a saturated aqueous solution of sodium hydrogen carbonate, and the mixture was extracted with ethyl acetate. The separated organic layer was washed with a saturated aqueous solution of sodium chloride, dried over anhydrous sodium sulfate, and then concentrated under reduced pressure. The resulting residue was purified by silica gel thin-layer chromatography (eluent: chloroform/methanol=10/1) to give the titled compound (33 mg).

¹H-NMR (DMSO-D₆) δ: 1.08 (d, 3H, J=7.3 Hz), 2.54 (dq, 1H, J=9.3, 7.3 Hz), 3.04 (ddd, 1H, J=9.3, 8.9, 8.5 Hz), 3.23 (dd, 1H, J=8.9, 8.7 Hz), 3.45 (dd, 1H, J=8.7, 8.5 Hz), 7.04 (s, 1H), 7.05-7.07 (m, 1H), 7.14-7.18 (m, 2H), 7.22-7.26 (m, 1H), 7.39-7.48 (m, 3H), 7.56 (t, 1H, J=8.0 Hz), 7.68 (s, 1H), 11.03 (s, 1H).

Preparation 5

Synthesis of (R) and (S)-5-oxopyrrolidine-3-carboxylic acid

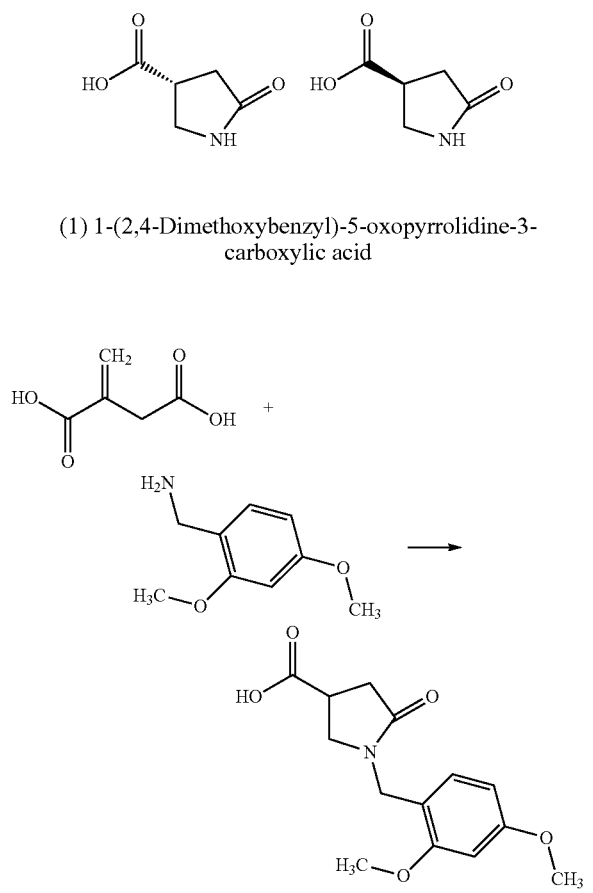

(1) 1-(2,4-Dimethoxybenzyl)-5-oxopyrrolidine-3-carboxylic acid

To a solution of itaconic acid (65.3 g) in toluene (400 ml) was added a solution of 2,4-dimethoxybenzylamine (84.0 g) in toluene (100 ml), and the mixture was stirred for 15 hours at reflux. This reaction solution was cooled to room temperature, and concentrated under reduced pressure. To the resulting residue was added diethyl ether (600 ml), and the mixture was stirred. The precipitated solid was collected by filtration, washed with diethyl ether and a small amount of ethyl acetate, and then dried under reduced pressure to give the titled compound (127 g).

¹H-NMR (CDCl₃) δ: 2.66-2.82 (m, 2H), 3.20 (dt, 1H, J=17.3, 7.6 Hz), 3.49-3.53 (m, 2H), 3.80 (s, 6H), 4.40 (d, 1H, J=14.6 Hz), 4.46 (d, 1H, J=14.6 Hz), 6.42-6.47 (m, 2H), 7.14 (t, 1H, J=4.5 Hz).

(2) Optically active compound of (R)-4-benzyl-3-[1-(2,4-dimethoxybenzyl)-5-oxopyrrolidine-3-carbonyl]-2-oxazolidinone

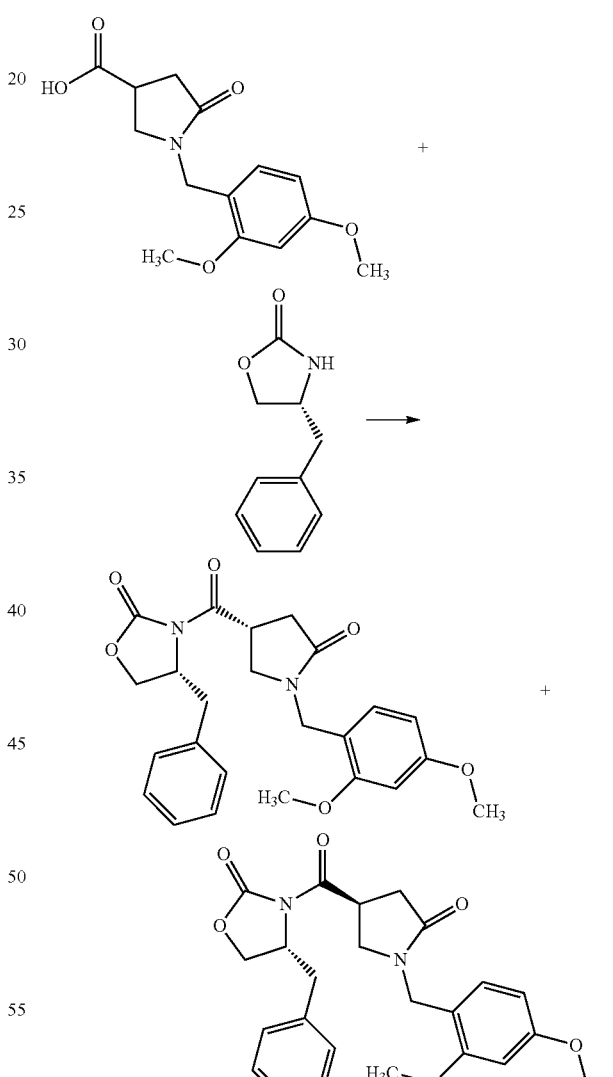

To a solution of 1-(2,4-dimethoxybenzyl)-5-oxopyrrolidine-3-carboxylic acid (31.7 g) in chloroform (300 ml) were sequentially added (R)-4-benzyl-2-oxazolidinone (20.0 g), WSC.HCl (23.8 g) and 4-dimethylaminopyridine (6.90 g) under ice-cooling, the mixture was stirred for 15 minutes, warmed to room temperature and stirred for 18 hours. This reaction mixture was purified by silica gel column chromatography (eluent: n-hexane/ethyl acetate=1/1 to 1/9) to give the titled compound (low-polarity component 26.4 g, high-polarity component 13.3 g).

$^1$H-NMR (CDCl$_3$) low-polarity component δ: 2.72-2.83 (m, 3H), 3.27 (dd, 1H, J=13.4, 3.5 Hz), 3.46-3.57 (m, 2H), 3.80 (s, 3H), 3.80 (s, 3H), 4.15-4.29 (m, 3H), 4.40-4.48 (m, 2H), 4.61-4.69 (m, 1H), 6.42-6.47 (m, 2H), 7.12-7.21 (m, 3H), 7.27-7.37 (m, 3H). high-polarity component δ: 2.62-2.72 (m, 2H), 2.86 (dd, 1H, J=16.9, 5.8 Hz), 3.17 (dd, 1H, J=13.4, 3.2 Hz), 3.40 (dd, 1H, J=10.4, 5.1 Hz), 3.66 (dd, 1H, J=10.4, 8.8 Hz), 3.72 (s, 3H), 3.81 (s, 3H), 4.16-4.26 (m, 3H), 4.40 (d, 1H, J=14.6 Hz), 4.50 (d, 1H, J=14.6 Hz), 4.61-4.69 (m, 1H), 6.40-6.45 (m, 2H), 7.11-7.17 (m, 3H), 7.27-7.34 (m, 3H).

(3) Optically active compound of 1-(2,4-dimethoxy-benzyl)-5-oxopyrrolidine-3-carboxylic acid

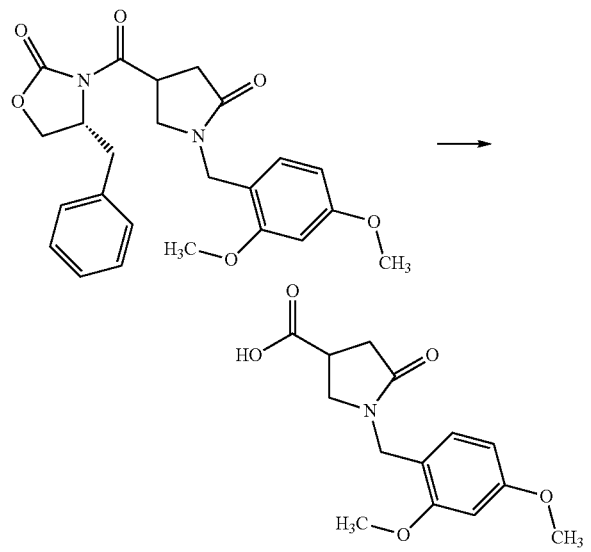

To a solution of lithium hydroxide monohydrate (3.29 g) in water (50 ml) was added dropwise 30 wt % aqueous solution of hydrogen peroxide (17.5 ml) under cooling with an ice-sodium chloride bath, and the mixture was stirred for 15 minutes. To this reaction solution was added tetrahydrofuran (30 ml), and then a solution of the low-polarity component of (R)-4-benzyl-3-[1-(2,4-dimethoxybenzyl)-5-oxopyrrolidine-3-carbonyl]-2-oxazolidinone (26.4 g) in tetrahydrofuran (150 ml) was added dropwise thereto, and the mixture was stirred for additional 1 hour. To this reaction solution was slowly added a solution of sodium hydrogen sulfite (18.7 g) in water (60 ml), and the mixture was warmed to room temperature by removing the bath, and then extracted with ethyl acetate (100 ml). The resulting organic layer was washed with a saturated aqueous solution of sodium chloride, dried over anhydrous sodium sulfate, and then concentrated under reduced pressure. The resulting residue was purified by silica gel column chromatography (eluent: chloroform/ethyl acetate=1/1 to 1/2, chloroform/methanol=5/1) to give the titled compound (14.3 g). An analysis of this solid by HPLC analysis condition 2 showed that an isomer with shorter retention time was a main product.

An isomer with shorter retention time (retention time 4.1 minutes)

An isomer with longer retention time (retention time 4.6 minutes)

$^1$H-NMR (CDCl$_3$) δ: 2.66-2.82 (m, 2H), 3.20 (dt, 1H, J=17.3, 7.6 Hz), 3.49-3.53 (m, 2H), 3.80 (s, 6H), 4.40 (d, 1H, J=14.6 Hz), 4.46 (d, 1H, J=14.6 Hz), 6.42-6.47 (m, 2H), 7.14 (t, 1H, J=4.5 Hz).

(4) Optically active compound of 5-oxopyrrolidine-3-carboxylic acid

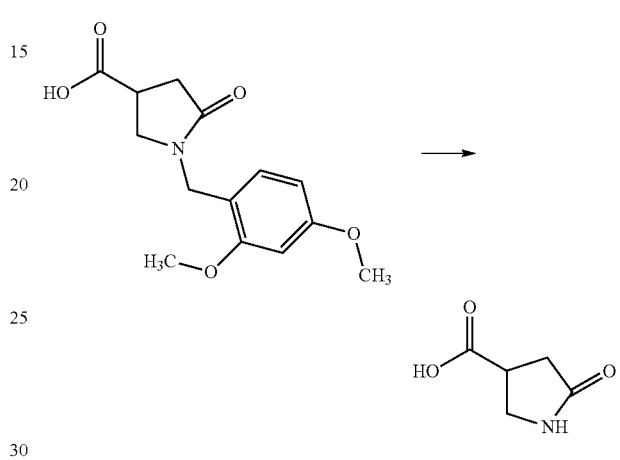

To an optically active compound of 1-(2,4-dimethoxybenzyl)-5-oxopyrrolidine-3-carboxylic acid (14.3 g) were added anisole (8.4 ml) and trifluoroacetic acid (100 ml), and the mixture was stirred at 80° C. for 5 hours. This reaction solution was cooled to room temperature, and concentrated under reduced pressure. To the resulting residue was added diisopropyl ether (100 ml), and the mixture was stirred at room temperature. The insoluble substance was collected by filtration, washed with diisopropyl ether, and dried under reduced pressure to give the titled compound (4.96 g).

$^1$H-NMR (DMSO-D$_6$) δ: 2.26-2.40 (m, 2H), 3.18-3.28 (m, 1H), 3.30-3.35 (m, 1H), 3.40-3.47 (m, 1H), 7.64 (s, 1H), 12.58 (s, 1H); $[α]_D^{25}$+37 (c 0.10, CH$_3$OH).

It was shown that the resulting compound was (R)-5-oxopyrrolidine-3-carboxylic acid by comparing a specific rotation of the compound with those described in the literature (Tetrahedron: Asymmetry 12 (2001) 3241-3249).

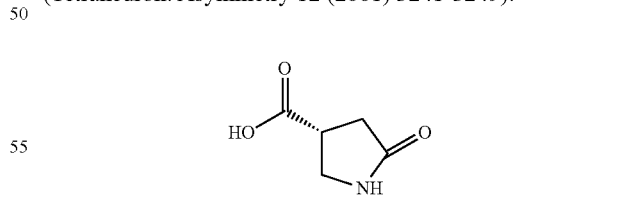

Also, the high-polarity component of (R)-4-benzyl-3-[1-(2,4-dimethoxybenzyl)-5-oxopyrrolidine-3-carbonyl]-2-oxazolidinone was subjected to the same reactions and post-treatment as described above to give (S)-5-oxopyrrolidine-3-carboxylic acid (2.83 g) as the optical isomer.

$^1$H-NMR (DMSO-D$_6$) δ: 2.26-2.40 (m, 2H), 3.18-3.28 (m, 1H), 3.30-3.35 (m, 1H), 3.40-3.47 (m, 1H), 7.64 (s, 1H), 12.58 (s, 1H); $[α]_D^{25}$-40 (c 0.10, CH$_3$OH).

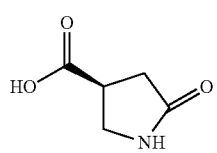

Preparation 6

Example 4

Synthesis of ((R)-5-oxopyrrolidine-3-carboxylic acid [1-phenyl-5-(3-trifluoromethoxyphenyl)-1H-pyrazol-3-yl]amide)

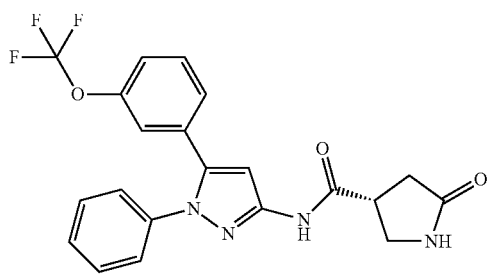 [SMILES: O=C1C[C@@H](C(=O)Nc2cc(-c3cccc(OC(F)(F)F)c3)n(-c3ccccc3)n2)CN1]

(1) (R)-5-Oxopyrrolidine-3-carboxylic acid[1-phenyl-5-(3-trifluoromethoxyphenyl)-1H-pyrazol-3-yl]amide

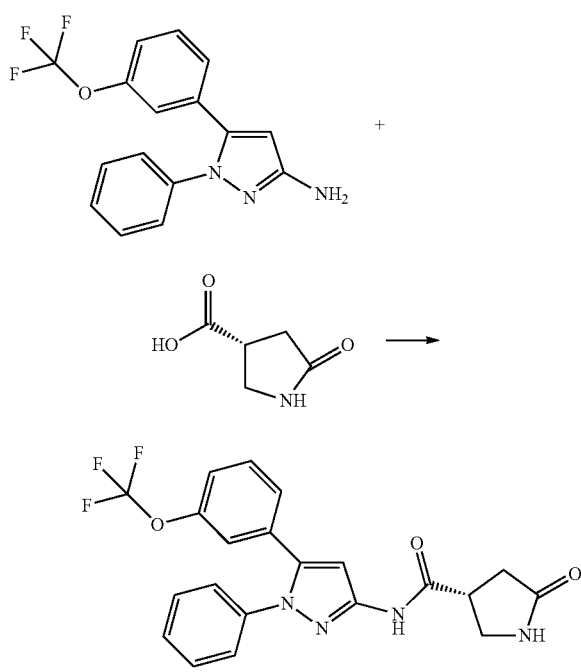

To a solution of 1-phenyl-5-(3-(trifluoromethoxy)phenyl)-1H-pyrazol-3-ylamine (40 mg) prepared according to the same procedures as Preparation 2 in N,N-dimethylformamide (0.3 ml) were sequentially added (R)-5-oxopyrrolidine-3-carboxylic acid (24 mg) prepared in Preparation 5, HOBt.H₂O (29 mg) and WSC.HCl (36 mg), and the mixture was stirred at room temperature overnight. To this reaction solution were added a saturated aqueous solution of sodium hydrogen carbonate and water, and the mixture was stirred. The insoluble substance was collected by filtration, washed with water, and dried under reduced pressure to give the titled compound (45 mg).

$^1$H-NMR (DMSO-D₆) δ: 2.35-2.42 (m, 2H), 3.31-3.54 (m, 3H), 7.01 (s, 1H), 7.08 (s, 1H), 7.22-7.28 (m, 2H), 7.32-7.46 (m, 5H), 7.52 (t, 1H, J=8.0 Hz), 7.64 (s, 1H), 10.90 (s, 1H).

Preparation 7

Synthesis of optically active compound of 6-oxopiperidine-3-carboxylic acid

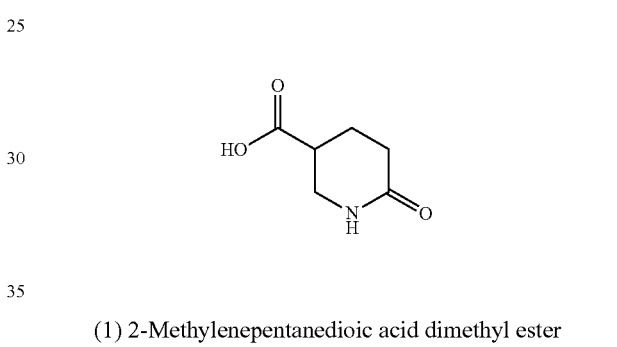

(1) 2-Methylenepentanedioic acid dimethyl ester

To a solution of 2,8,9-triisopropyl-2,5,8,9-tetraaza-1-phosphabicyclo(3,3,3)indecane (4.62 g) in tetrahydrofuran (180 ml) was added dropwise a solution of methyl acrylate (40.5 ml) in tetrahydrofuran (20 ml) at room temperature, and then the mixture was stirred overnight. This reaction solution was concentrated under reduced pressure, and then diisopropyl ether, n-hexane and chloroform were added to the resulting residue, and the mixture was again concentrated under reduced pressure. To the precipitated solid was added diisopropyl ether, the mixture was stirred, and then the insoluble substance was filtered off. The filtrate was concentrated under reduced pressure, and the resulting residue was purified by silica gel column chromatography (eluent: n-hexane/ethyl acetate=9/1 to 4/1) to give the titled compound (19.2 g).

¹H-NMR (CDCl₃) δ: 2.53 (td, 2H, J=7.6, 1.3 Hz), 2.65 (t, 2H, J=7.6 Hz), 3.67 (s, 3H), 3.76 (s, 3H), 5.61 (q, 1H, J=1.3 Hz), 6.20 (d, 1H, J=1.3 Hz).

(2) 1-(2,4-Dimethoxybenzyl)-6-oxopiperidine-3-carboxylic acid methyl ester

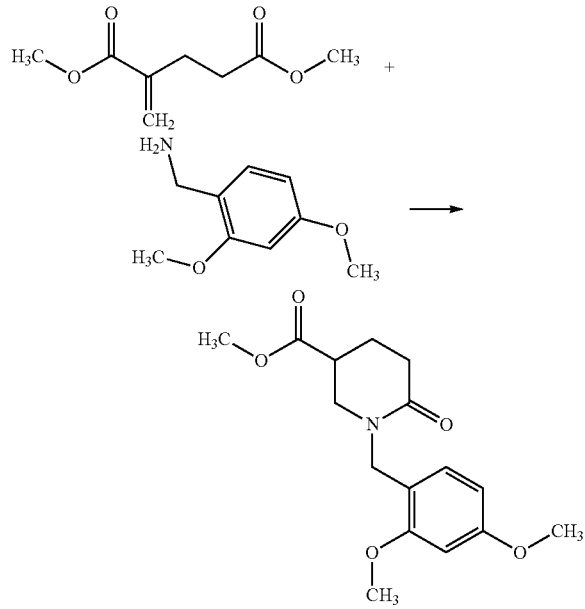

To a solution of 2-methylenepentanedioic acid dimethyl ester (19.2 g) in toluene (195 ml) was added 2,4-dimethoxybenzylamine (16.6 ml), and the mixture was stirred for 3 days at reflux. This reaction solution was cooled to room temperature, and then washed with a 1M aqueous solution of hydrochloric acid, water and a saturated aqueous solution of sodium chloride, dried over anhydrous sodium sulfate, and concentrated under reduced pressure to give a crude product of the titled compound (26.8 g).

¹H-NMR (CDCl₃) δ: 1.93-2.05 (m, 1H), 2.08-2.17 (m, 1H), 2.40-2.50 (m, 1H), 2.52-2.62 (m, 1H), 2.74-2.83 (m, 1H), 3.45 (d, 2H, J=7.4 Hz), 3.68 (s, 3H), 3.81 (s, 3H), 3.81 (s, 3H), 4.54 (d, 1H, J=14.6 Hz), 4.62 (d, 1H, J=14.6 Hz), 6.44-6.48 (m, 2H), 7.15-7.19 (m, 1H).

(3) 1-(2,4-Dimethoxybenzyl)-6-oxopiperidine-3-carboxylic acid

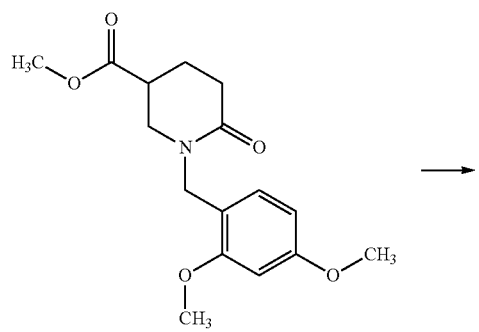

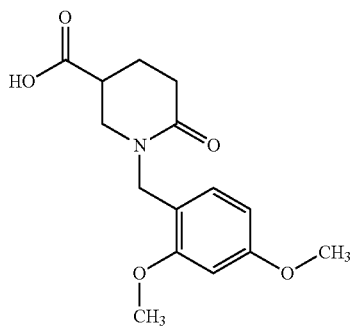

To a solution of the crude product of 1-(2,4-dimethoxybenzyl)-6-oxopiperidine-3-carboxylic acid methyl ester (26.8 g) in methanol/tetrahydrofuran (1/1, 174 ml) was added a 1M aqueous solution of sodium hydroxide (174 ml) at room temperature, and the mixture was stirred overnight. To this reaction solution was added a 1M aqueous solution of hydrochloric acid (174 ml), the mixture was stirred. The precipitated solid was collected by filtration, washed with water, and dried under reduced pressure to give the titled compound (15.1 g).

¹H-NMR (DMSO-D₆) δ: 1.77-1.90 (m, 1H), 1.95-2.06 (m, 1H), 2.25-2.41 (m, 2H), 2.75-2.86 (m, 1H), 3.31 (d, 2H, J=7.1 Hz), 3.74 (s, 3H), 3.78 (s, 3H), 4.34 (d, 1H, J=15.2 Hz), 4.43 (d, 1H, J=15.2 Hz), 6.47 (dd, 1H, J=8.4, 2.4 Hz), 6.56 (d, 1H, J=2.4 Hz), 7.00 (d, 1H, J=8.4 Hz), 12.56 (br s, 1H).

(4) Optically active compound of 5-((R)-4-benzyl-2-oxooxazolidine-3-carbonyl)-1-(2,4-dimethoxybenzyl)piperidin-2-one

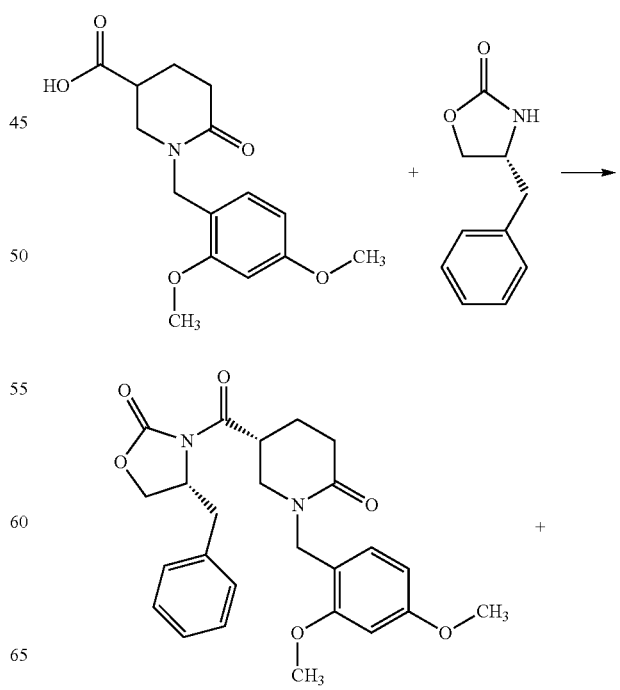

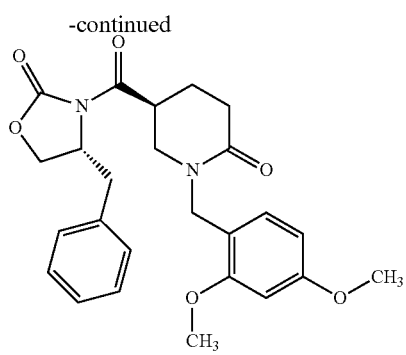

To a solution of 1-(2,4-dimethoxybenzyl)-6-oxopiperidine-3-carboxylic acid (3.39 g) in chloroform (15 ml) were sequentially added (R)-4-benzyl-2-oxazolidinone (2.04 g), WSC.HCl (2.44 g) and 4-dimethylaminopyridine (706 mg) at room temperature, and the mixture was stirred overnight. This reaction mixture was purified by silica gel column chromatography (eluent: chloroform/ethyl acetate=4/1 to 1/1) to give the titled compound (low-polarity component 3.37 g, high-polarity component 2.72 g).

$^1$H-NMR (CDCl$_3$) low-polarity component δ: 1.91-2.02 (m, 1H), 2.14-2.24 (m, 1H), 2.50-2.66 (m, 2H), 2.73-2.81 (m, 1H), 3.18-3.25 (m, 1H), 3.34-3.41 (m, 1H), 3.51-3.60 (m, 1H), 3.78 (s, 3H), 3.80 (s, 3H), 3.84-3.93 (m, 1H), 4.05-4.20 (m, 2H), 4.53-4.65 (m, 3H), 6.42-6.47 (m, 2H), 7.14-7.38 (m, 6H). high-polarity component $^1$H-NMR (CDCl$_3$) δ: 1.92-2.14 (m, 2H), 2.47-2.67 (m, 3H), 3.14-3.23 (m, 1H), 3.44-3.59 (m, 2H), 3.77 (s, 3H), 3.81 (s, 3H), 3.91-4.01 (m, 1H), 4.14-4.26 (m, 2H), 4.54-4.68 (m, 3H), 6.42-6.49 (m, 2H), 7.15-7.21 (m, 3H), 7.25-7.35 (m, 3H).

(5) Optically active compound of 1-(2,4-dimethoxybenzyl)-6-oxopiperidine-3-carboxylic acid

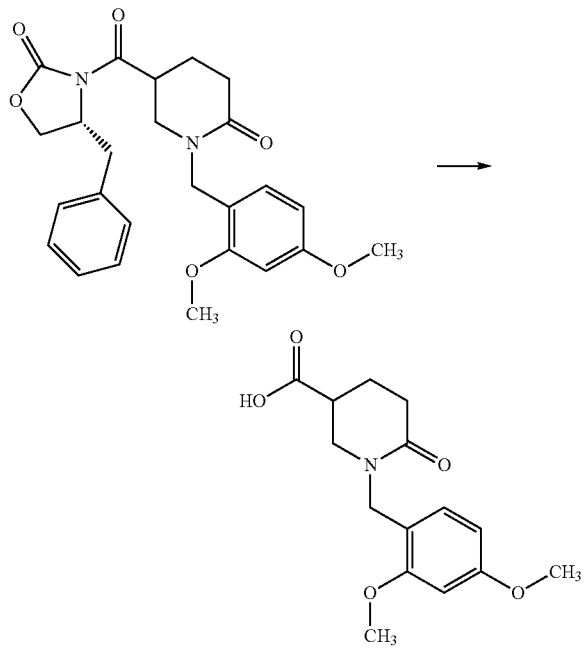

To a solution of lithium hydroxide monohydrate (316 mg) in water (10 ml) was added dropwise a 30 wt % aqueous solution of hydrogen peroxide (1.8 ml) under ice-cooling and the mixture was stirred for 10 minutes. To this reaction solution was added tetrahydrofuran (10 ml), and then a solution of the low-polarity component of 5-((R)-4-benzyl-2-oxooxazolidine-3-carbonyl)-1-(2,4-dimethoxybenzyl)piperidin-2-one (3.37 g) in tetrahydrofuran (20 ml) was added dropwise thereto, and the mixture was stirred for additional 1 hour. To this reaction solution was added an aqueous solution of sodium hydrogen sulfite (1.81 g) was added dropwise, and then the mixture was warmed to room temperature, and stirred for 30 minutes. This mixed solution was extracted with ethyl acetate, and the resulting organic layer was washed with a saturated aqueous solution of sodium chloride, and then dried over anhydrous sodium sulfate, and concentrated under reduced pressure. To the resulting residue was added ethyl acetate, and the mixture was stirred at room temperature. The insoluble substance was collected by filtration, and dried under reduced pressure to give the titled compound (1.36 g). An analysis of this solid by HPLC analysis condition 2 showed that an isomer with shorter retention time was a main product.

An isomer with shorter retention time (retention time 4.5 minutes)

An isomer with longer retention time (retention time 6.6 minutes)

(6) Optically active compound of 6-oxopiperidine-3-carboxylic acid

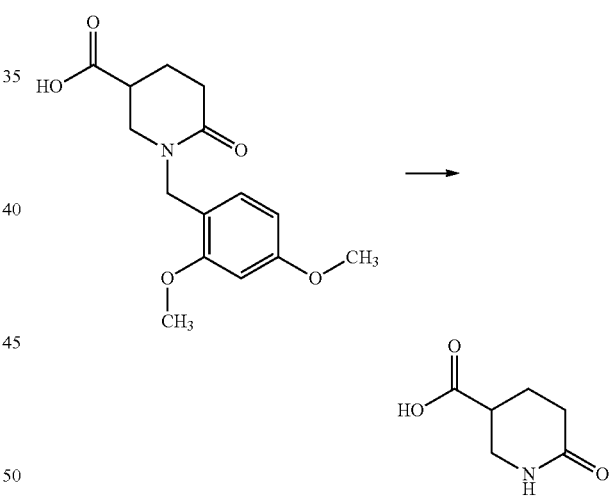

To an optically active compound of 1-(2,4-dimethoxybenzyl)-6-oxopiperidine-3-carboxylic acid (1.36 g) were added anisole (758 μl) and trifluoroacetic acid (10 ml), and the mixture was stirred at 80° C. for 6 hours. This reaction solution was cooled to room temperature, and then concentrated under reduced pressure. To the resulting residue was added diisopropyl ether, and the mixture was stirred at room temperature. The insoluble substance was collected by filtration, and dried under reduced pressure to give the titled compound (628 mg).

$^1$H-NMR (DMSO-D$_6$) δ: 1.75-1.88 (m, 1H), 1.91-2.01 (m, 1H), 2.11-2.24 (m, 2H), 2.66-2.73 (m, 1H), 3.21-3.32 (m, 2H), 7.45 (s, 1H), 12.51 (br s, 1H).

Also, the high-polarity component of 5-((R)-benzyl-2-oxoxazolidinone-3-carbonyl)-1-(2,4-dimethoxybenzyl)piperidin-2-on was subjected to the same reactions and post-treatment as described above to give an optical isomer of the titled compound (485 mg).

$^1$H-NMR (DMSO-D$_6$) δ: 1.75-1.88 (m, 1H), 1.91-2.01 (m, 1H), 2.11-2.24 (m, 2H), 2.66-2.73 (m, 1H), 3.21-3.32 (m, 2H), 7.45 (s, 1H), 12.51 (br s, 1H).

Preparation 8

Example 5

Synthesis of optically active compound of (6-oxopiperidine-3-carboxylic acid[1-phenyl-5-(3-propylphenyl)-1H-pyrazol-3-yl]amide)

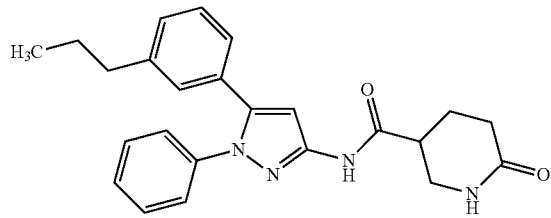 [SMILES: CCCc1cccc(-c2cc(NC(=O)C3CCC(=O)NC3)nn2-c2ccccc2)c1]

(1) 1-Bromo-3-propylbenzene

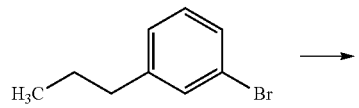

To a solution of 3-bromopropiophenone (25 g) in trifluoroacetic acid (250 ml) was added dropwise triethylsilane (94 ml) under ice-cooling over 20 minutes, and the mixture was stirred for additional 20 minutes. This reaction solution was heated to 80° C., and stirred overnight. This reaction solution was cooled to room temperature, concentrated under reduced pressure, and again concentrated under reduced pressure after adding toluene thereto. The resulting residue was purified by silica gel column chromatography (eluent: n-hexane) to give the titled compound (16.6 g).

$^1$H-NMR (CDCl$_3$) δ: 0.95 (t, 3H, J=7.4 Hz), 1.64 (tq, 2H, J=7.7, 7.4 Hz), 2.57 (t, 2H, J=7.7 Hz), 7.08-7.13 (m, 1H), 7.13-7.18 (m, 1H), 7.30-7.35 (m, 2H).

(2) 3-Propylbenzaldehyde

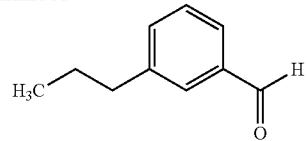

To a solution of 1-bromo-3-propylbenzene (16.6 g) in tetrahydrofuran (83 ml) cooled to −78° C. was added dropwise n-butyllithium (2.66M solution in n-hexane, 34 ml) over 9 minutes, and then the mixture was stirred for 1 hour. To this reaction solution was added dropwise N,N-dimethylformamide (7.7 ml) over 6 minutes, and the mixture was stirred for additional 20 minutes. To this reaction solution was added dropwise a 4M solution of hydrogen chloride in 1,4-dioxane (23 ml) over 5 minutes, and then the mixture was stirred after warming to room temperature. To this mixed solution was added water (83 ml), followed by a 6M aqueous solution of hydrochloric acid (12 ml), and then the mixture was extracted with n-hexane (80 ml). The resulting organic layer was washed with a saturated aqueous solution of sodium chloride, dried over anhydrous magnesium sulfate, and concentrated under reduced pressure to give a crude product of the titled compound (14.0 g).

$^1$H-NMR (CDCl$_3$) δ: 0.95 (t, 3H, J=7.3 Hz), 1.68 (tq, 2H, J=7.7, 7.3 Hz), 2.67 (t, 2H, J=7.7 Hz), 7.42-7.47 (m, 2H), 7.67-7.72 (m, 2H), 9.98-10.01 (m, 1H).

(3) Mixture of (E)-3-(3-propylphenyl)acrylonitrile and (Z)-3-(3-propylphenyl)acrylonitrile

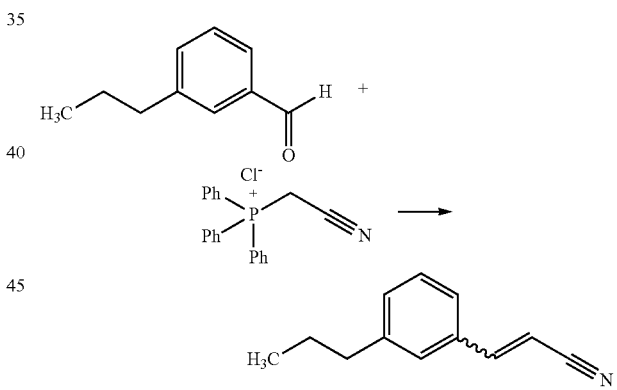

To a suspension of (cyanomethyl)triphenylphosphonium chloride (34 g) in tetrahydrofuran (110 ml) was added portionwise potassium tert-butoxide (13 g) under ice-cooling, and then the mixture was stirred for 1 hour. To this reaction solution was added dropwise a solution of a crude product of 3-propyl benzaldehyde (14.0 g) in tetrahydrofuran (30 ml) over 7 minutes under ice-cooling, and then the mixture was stirred at room temperature overnight. To this mixture was added n-hexane (280 ml), and the mixture was stirred for 1 hour under ice-cooling, and then the insoluble substance was filtered off through Celite, and eluted with n-hexane (840 ml). To the resulting residue by concentrating the filtrate was added a mixed solvent of n-hexane/ethyl acetate (5/1, 120 ml), and the mixture was stirred. The insoluble substance was filtered off through Celite, and eluted with a mixed solvent of n-hexane/ethyl acetate (10/1). The filtrate was concentrated, and the resulting residue was purified by silica gel column chromatography (eluent: n-hexane/ethyl acetate=1/0 to 25/1) to give the titled compound (11.4 g).

¹H-NMR (CDCl₃) (E)-isomer δ: 0.95 (t, 3H, J=7.5 Hz), 1.65 (tq, 2H, J=7.7, 7.5 Hz), 2.60 (t, 2H, J=7.7 Hz), 5.87 (d, 1H, J=16.5 Hz), 7.22-7.41 (m, 5H). (Z)-isomer δ: 0.95 (t, 3H, J=7.5 Hz), 1.67 (tq, 2H, J=7.7, 7.5 Hz), 2.64 (t, 2H, J=7.7 Hz), 5.42 (d, 1H, J=12.1 Hz), 7.11 (d, 1H, J=12.1 Hz), 7.23-7.42 (m, 2H), 7.58-7.66 (m, 2H).

(4) 1-Phenyl-5-(3-propylphenyl)-4,5-dihydro-1H-pyrazol-3-ylamine

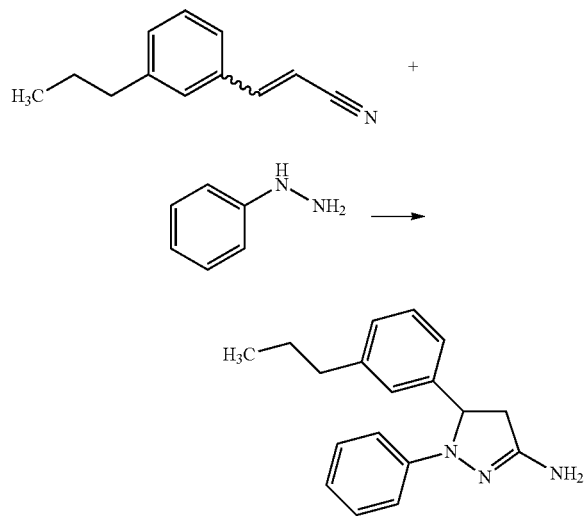

To a solution of sodium ethoxide (20 wt % in ethanol, 31 ml) in ethanol (66 ml) was stirred and added dropwise phenylhydrazine (6.4 ml) at room temperature, and then the mixture was stirred for 40 minutes. To this reaction solution was added dropwise a solution of the mixture of (E)-3-(3-propylphenyl)acrylonitrile and (Z)-3-(3-propylphenyl)acrylonitrile (11.1 g) in ethanol (33 ml), and then the mixture was stirred overnight at reflux. This reaction solution was cooled to room temperature, and water (30 ml) was added thereto. Next, pH of the reaction solution was adjusted to 7 by adding a 6M aqueous solution of hydrochloric acid under ice-cooling. This mixed solution was extracted with ethyl acetate, and the resulting organic layer was washed with a saturated aqueous solution of sodium chloride, dried over anhydrous sodium sulfate, and concentrated under reduced pressure. To the resulting residue was added toluene, and the mixture was dried over anhydrous magnesium sulfate, and then concentrated under reduced pressure. To the resulting residue was added toluene, and again concentrated under reduced pressure to give a crude product of the titled compound (18.6 g).

¹H-NMR (CDCl₃) δ: 0.91 (t, 3H, J=7.5 Hz), 1.61 (tq, 2H, J=7.7, 7.5 Hz), 2.56 (t, 2H, J=7.7 Hz), 2.78 (dd, 1H, J=16.3, 8.5 Hz), 3.41 (dd, 1H, J=16.3, 11.3 Hz), 3.96 (s, 2H), 4.90 (dd, 1H, J=11.3, 8.5 Hz), 6.67-6.72 (m, 1H), 6.80-6.87 (m, 2H), 7.02-7.37 (m, 6H).

(5) 1-Phenyl-5-(3-propylphenyl)-1H-pyrazol-3-ylamine

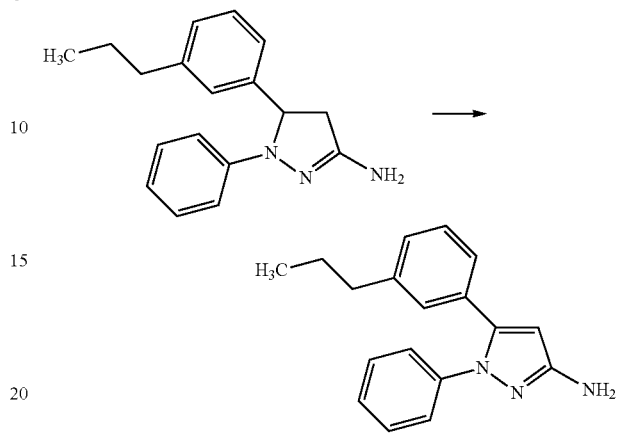

To a solution of the crude product of 1-phenyl-5-(3-propylphenyl)-4,5-dihydro-1H-pyrazol-3-ylamine (18.6 g) in toluene (185 ml) was added activated carbon (pH5 to 8, 9.29 g), and the mixture was stirred overnight under oxygen atmosphere at reflux. This reaction solution was cooled to room temperature, and then the activated carbon was filtered off through Celite, and eluted with ethyl acetate. This filtrate was concentrated under reduced pressure, the resulting residue was dissolved in toluene (185 ml), and to the solution was added fresh activated carbon (pH5 to 8, 9.29 g), and the mixture was stirred overnight under oxygen atmosphere at reflux. This reaction solution was cooled to room temperature, and then the activated carbon was filtered off through Celite, and eluted with ethyl acetate. This filtrate was concentrated under reduced pressure, and the resulting residue was purified by silica gel column chromatography (eluent: n-hexane/ethyl acetate=4/1 to 1/1) to give the titled compound (8.68 g).

¹H-NMR (CDCl₃) δ: 0.82 (t, 3H, J=7.3 Hz), 1.49 (tq, 2H, J=7.6, 7.3 Hz), 2.47 (t, 2H, J=7.6 Hz), 3.75 (s, 2H), 5.90 (s, 1H), 6.96-7.00 (m, 1H), 7.02-7.12 (m, 2H), 7.15-7.30 (m, 6H).

(6) Optically active compound of 6-oxopiperidine-3-carboxylic acid[1-phenyl-5-(3-propylphenyl)-1H-pyrazol-3-yl]amide

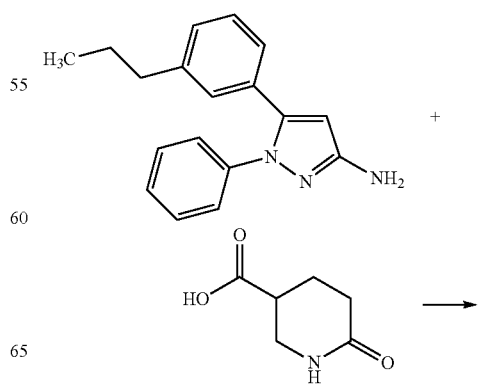

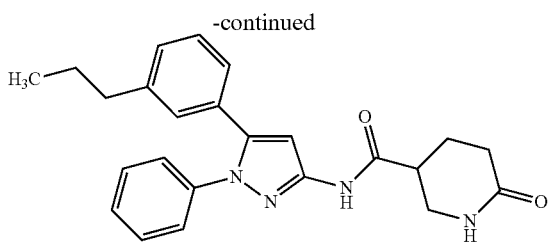

To a solution of 1-phenyl-5-(3-propylphenyl)-1H-pyrazol-3-ylamine (56 mg) in tetrahydrofuran (1.5 ml) were sequentially added an optically active compound of 6-oxopiperidine-3-carboxylic acid (43 mg) synthesized in Preparation 7 (derived from the low-polarity component of 5-((R)-4-benzyl-2-oxoxazolidine-3-carbonyl)-1-(2,4-dimethoxybenzyl)piperidin-2-one), HOBt.H₂O (46 mg) and WSC.HCl (58 mg), and the mixture was stirred at room temperature overnight. To this reaction solution was added a saturated aqueous solution of sodium hydrogen carbonate, and the mixture was extracted with ethyl acetate. The separated organic layer was concentrated under reduced pressure, the resulting residue was purified by silica gel thin-layer chromatography (eluent: chloroform/methanol=10/1) to give the titled compound (50 mg).

¹H-NMR (DMSO-D₆) δ: 0.77 (t, 3H, J=7.3 Hz), 1.44 (tq, 2H, J=7.5, 7.3 Hz), 1.83-2.03 (m, 2H), 2.12-2.30 (m, 2H), 2.46 (t, 2H, J=7.5 Hz), 2.84 (tt, 1H, J=10.7, 3.6 Hz), 3.24-3.31 (m, 2H), 6.89 (s, 1H), 7.00 (s, 1H), 7.06 (d, 1H, J=7.7 Hz), 7.17 (d, 1H, J=7.7 Hz), 7.19-7.43 (m, 6H), 7.51 (s, 1H), 10.83 (s, 1H).

Preparation 9

Synthesis of (R)-3-methyl-2-oxoimidazolidine-4-carboxylic acid and (S)-3-methyl-2-oxoimidazolidine-4-carboxylic acid

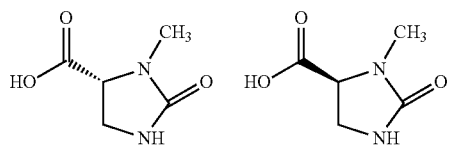

(1) (R)-2-Oxoimidazolidine-1,5-dicarboxylic acid 1-benzyl ester

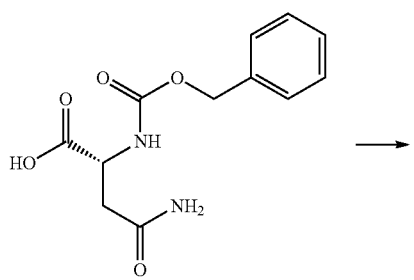

To a solution of sodium hydroxide (743 mg) in water (15 ml) was added dropwise bromine (318 μl) under ice-cooling over 30 minutes. To this reaction solution was added Z-D-asparagine (1.5 g), and then the mixture was heated to 55° C., and stirred for 3 hours. This reaction solution was cooled to room temperature, and washed twice with diethyl ether (15 ml). To the resulting aqueous layer was added dropwise a 6M aqueous solution of hydrochloric acid until the pH reached 1. This mixed solution was left to stand at 4° C. overnight. The precipitated solid was collected by filtration, washed with water, and dried under reduced pressure to give the titled compound (1.1 g).

¹H-NMR (DMSO-D₆) δ: 3.22 (dd, 1H, J=10.0, 3.3 Hz), 3.65 (dd, 1H, J=10.0, 10.2 Hz), 4.68 (dd, 1H, J=10.2, 3.3 Hz), 5.16 (d, 1H, J=14.8 Hz), 5.19 (d, 1H, J=14.8 Hz), 7.29-7.39 (m, 5H), 7.57 (s, 1H), 13.25 (br s, 1H).

(2) (R)-2-Oxoimidazolidine-1,5-dicarboxylic acid 1-benzyl ester 5-tert-butyl ester

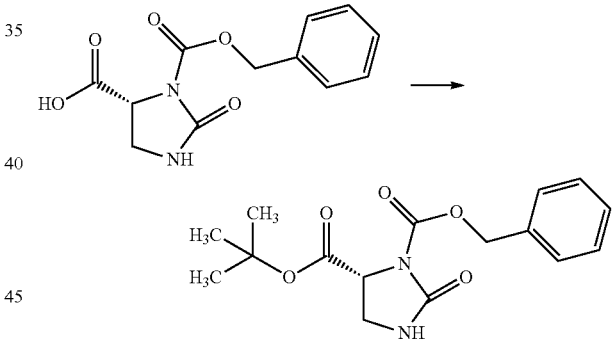

To a solution of (R)-2-oxoimidazolidine-1,5-dicarboxylic acid 1-benzyl ester (534 mg) in chloroform (2.6 ml) were sequentially added pyridine (1.0 ml) and tert-butylalcohol (1.5 ml) at room temperature, and the mixture was stirred. This reaction solution was iced, and phosphorous oxychloride (0.23 ml) was added thereto, and then the mixture was stirred at room temperature for 5 hours. This reaction solution was iced, and a 20 wt % aqueous solution of sodium acetate (20 ml) was added thereto, and then chloroform (5 ml) was further added at room temperature, and the mixture was stirred for 30 minutes. This mixed solution was extracted with chloroform, and the resulting organic layer was washed with a 0.1M aqueous solution of hydrochloric acid, water, a saturated aqueous solution of sodium hydrogen carbonate and a saturated aqueous solution of sodium chloride, and then dried over anhydrous sodium sulfate, and concentrated under reduced pressure to give a crude product of the titled compound (467 mg).

¹H-NMR (CDCl₃) δ: 1.39 (s, 9H), 3.38 (dd, 1H, J=9.8, 3.3 Hz), 3.71 (dd, 1H, J=9.8, 9.8 Hz), 4.62 (dd, 1H, J=9.8, 3.3 Hz), 5.24 (d, 1H, J=12.6 Hz), 5.29 (d, 1H, J=12.6 Hz), 6.00 (br s, 1H), 7.28-7.41 (m, 5H).

(3) (R)-3-Methyl-2-oxoimidazolidine-1,4-dicarboxylic acid 1-benzyl ester 4-tert-butyl ester

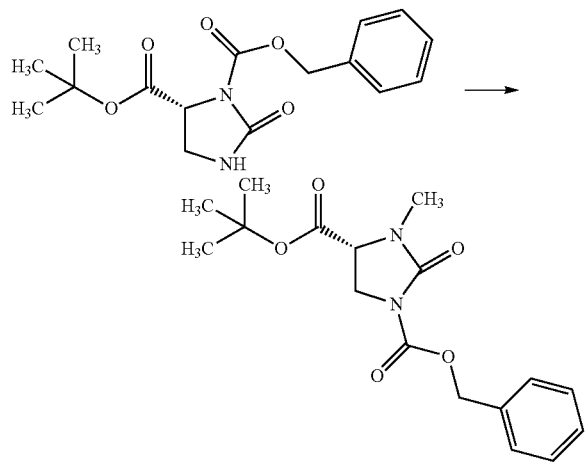

To a solution of the crude product of (R)-2-oxoimidazolidine-1,5-dicarboxylic acid 1-benzyl ester 5-tert-butyl ester (318 mg) in N,N-dimethylformamide (3 ml) was added sodium hydride (42 mg) under ice-cooling, and the mixture was stirred for 40 minutes. To this reaction solution was added methyl iodide (309 μl), and then the mixture was warmed to room temperature, and stirred for 4 hours. This reaction solution was iced, and water and ethyl acetate were added thereto, and the mixture was stirred. This mixed solution was extracted with ethyl acetate, and the resulting organic layer was washed with a saturated aqueous solution of sodium chloride, and then dried over anhydrous sodium sulfate, and concentrated under reduced pressure. The resulting residue was purified by silica gel column chromatography (eluent: n-hexane/ethyl acetate=1/1) to give the titled compound (167 mg).

¹H-NMR (CDCl₃) δ: 1.48 (s, 9H), 2.91 (s, 3H), 3.81-3.85 (m, 1H), 3.96-4.02 (m, 2H), 5.27 (d, 1H, J=13.1 Hz), 5.30 (d, 1H, J=13.1 Hz), 7.29-7.45 (m, 5H).

(4) (R)-3-Methyl-2-oxoimidazolidine-4-carboxylic acid tert-butyl ester

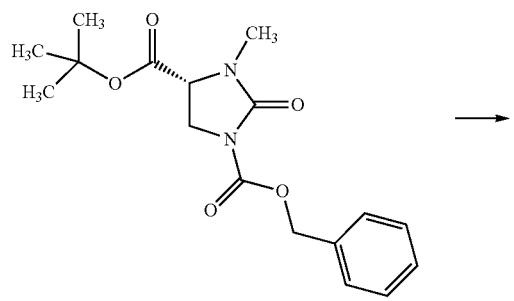

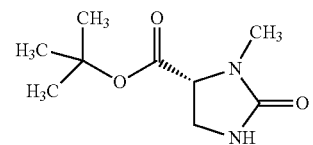

To a solution of (R)-3-methyl-2-oxoimidazolidine-1,4-dicarboxylic acid 1-benzyl ester 4-tert-butyl ester (167 mg) in methanol (1.7 ml) was added 10 wt % palladium on carbon at room temperature, and the mixture was stirred for 15 hours under one atom. of hydrogen. Under nitrogen atmosphere, this reaction solution was filtered through Celite, and eluted with methanol. The filtrate was concentrated under reduced pressure to give the titled compound (94 mg).

¹H-NMR (CDCl₃) δ: 1.50 (s, 9H), 2.86 (s, 3H), 3.41-3.46 (m, 1H), 3.62-3.67 (m, 1H), 4.05 (dd, 1H, J=9.8, 6.1 Hz), 4.38 (br s, 1H).

(5) (R)-3-Methyl-2-oxoimidazolidine-4-carboxylic acid

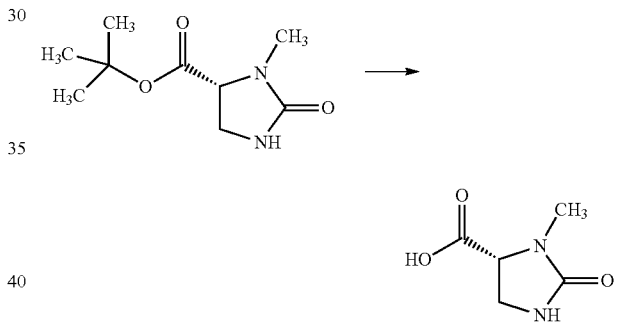

To a solution of (R)-3-methyl-2-oxoimidazolidine-4-carboxylic acid tert-butyl ester (94 mg) in chloroform (2 ml) was added trifluoroacetic acid (1 ml) at room temperature, and the mixture was stirred for 3 hours. This reaction solution was concentrated under reduced pressure, additional toluene (3 ml) was added thereto, and the mixture was again concentrated. To the resulting residue was added diethyl ether (0.5 ml) at room temperature, and the mixture was stirred. Next, n-hexane (2 ml) was added thereto, and the mixture was further stirred. The insoluble substance was collected by filtration, and dried under reduced pressure to give the titled compound (52 mg).

¹H-NMR (DMSO-D₆) δ: 2.66 (s, 3H), 3.18 (dd, 1H, J=9.2, 5.7 Hz), 3.51 (dd, 1H, J=9.2, 9.9 Hz), 4.12 (dd, 1H, J=9.9, 5.7 Hz), 6.42 (br s, 1H), 12.99 (br s, 1H).

Also, Z-L-asparagine was subjected to the same reactions and post-treatment as described above to give (S)-3-methyl-2-oxoimidazolidine-4-carboxylic acid (686 mg) as the optical isomer of the titled compound.

¹H-NMR (DMSO-D₆) δ: 2.66 (s, 3H), 3.18 (dd, 1H, J=9.2, 5.7 Hz), 3.51 (dd, 1H, J=9.2, 9.9 Hz), 4.12 (dd, 1H, J=9.9, 5.7 Hz), 6.42 (br s, 1H), 12.99 (br s, 1H).

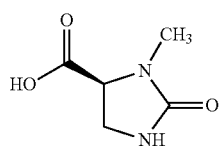

Preparation 10

Example 6

Synthesis of ((R)-3-methyl-2-oxoimidazolidine-4-carboxylic acid [1-phenyl-5-(3-propylphenyl)-1H-pyrazol-3-yl]amide)

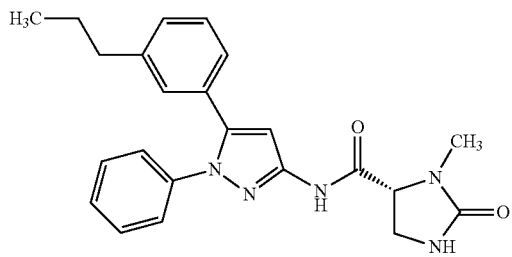 [SMILES: CCCc1cccc(-c2cc(NC(=O)[C@H]3CNC(=O)N3C)nn2-c2ccccc2)c1]

(1) (R)-3-methyl-2-oxoimidazolidine-4-carboxylic acid[1-phenyl-5-(3-propylphenyl)-1H-pyrazol-3-yl]amide

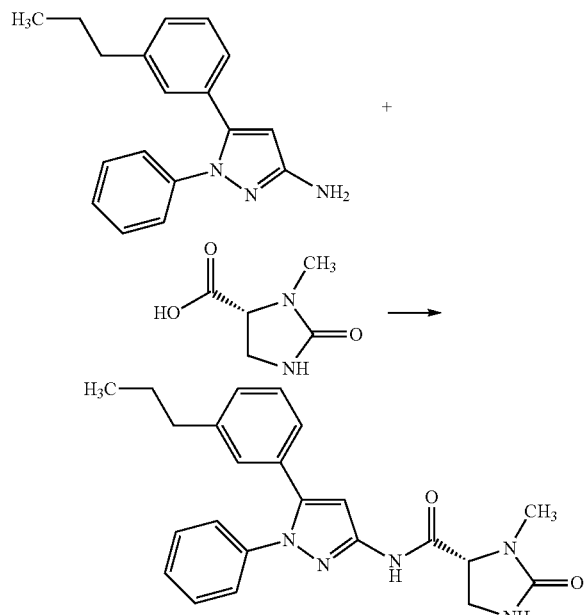

To a solution of 1-phenyl-5-(3-propylphenyl)-1H-pyrazol-3-ylamine (56 mg) prepared according to the same procedures as Preparation 8 in N,N-dimethylformamide (0.6 ml) were sequentially added (R)-3-methyl-2-oxoimidazolidine-4-carboxylic acid (38 mg) prepared in Preparation 9, HOBt.H$_2$O (46 mg) and WSC.HCl (58 mg), and the mixture was stirred at room temperature for 2 hours. To this reaction solution were added a saturated aqueous solution of sodium hydrogen carbonate and water, and the mixture was extracted with ethyl acetate. The separated organic layer was washed with water and a saturated aqueous solution of sodium chloride, dried over anhydrous sodium sulfate, and concentrated under reduced pressure. The resulting residue was purified by silica gel thin-layer chromatography (eluent: chloroform/methanol=10/1) to give the titled compound (40 mg).

$^1$H-NMR (DMSO-D$_6$) δ: 0.77 (t, 3H, J=7.3 Hz), 1.44 (tq, 2H, J=7.5, 7.3 Hz), 2.46 (t, 3H, J=7.5 Hz), 2.64 (s, 3H), 3.21 (dd, 1H, J=8.8, 6.3 Hz), 3.54 (dd, 1H, J=9.4, 8.8 Hz), 4.28 (dd, 1H, J=9.4, 6.3 Hz), 6.44 (s, 1H), 6.92 (s, 1H), 7.01 (s, 1H), 7.08 (d, 1H, J=7.0 Hz), 7.17 (d, 1H, J=7.0 Hz), 7.20-7.44 (m, 6H), 11.02 (s, 1H).

Preparation 11

Synthesis of 5-oxotetrahydrofuran-3-carboxylic acid

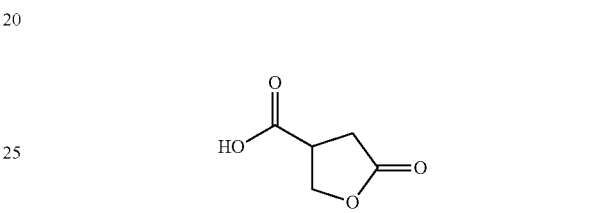

(1) Sodium 5-oxo-2,5-dihydrofuran-3-carboxylate

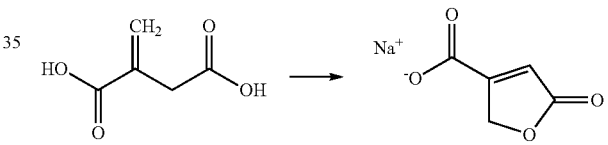

To a solution of itaconic acid (26.0 g) in water (35 ml) was added dropwise bromine (10.3 ml) at room temperature while keeping a temperature of the reaction solution below 45° C., and then the mixture was stirred at 30° C. for 15 minutes. To this reaction solution was added portionwise sodium hydrogen carbonate (33.6 g), and then the mixture was heated to 55° C. To this reaction solution was added dropwise a solution of sodium carbonate (10.6 g) in water (15 ml), and then the mixture was stirred for 20 minutes. This reaction solution was iced, and stirred for 1 hour. The precipitated solid was collected by filtration, washed with cold water and ethanol, and then dried under reduced pressure to give the titled compound (16.8 g).

$^1$H-NMR (DMSO-d$_6$) δ: 4.83 (d, 2H, J=2.0 Hz), 5.93-5.95 (m, 1H).

(2) 5-Oxotetrahydrofuran-3-carboxylic acid

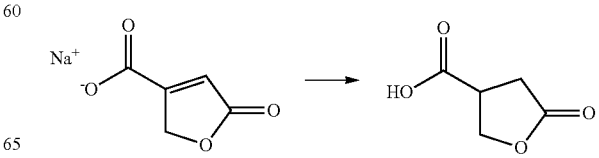

To a solution of sodium 5-oxo-2,5-dihydrofuran-3-carboxylate (150 mg) in water (3 ml) was added 10 wt % palladium on carbon (30 mg), and the mixture was stirred for 18 hours at room temperature under one atm. of hydrogen. Under nitrogen atmosphere, an appropriate amount of amberlite IR-120 was added to the reaction solution, the mixture was stirred at room temperature for 10 minutes, and then filtered through Celite. The filtrate was concentrated under reduced pressure, ethyl acetate was added to the resulting residue, the mixture was dried over sodium sulfate, and then again concentrated under reduced pressure to give the titled compound (83 mg).

$^1$H-NMR (DMSO-d$_6$) δ: 2.64 (dd, 1H, J=17.6, 6.2 Hz), 2.75 (dd, 1H, J=17.6, 9.4 Hz), 3.39-3.49 (m, 1H), 4.34 (dd, 1H, J=8.8, 5.4 Hz), 4.44 (dd, 1H, J=8.8, 8.2 Hz), 12.82 (br s, 1H).

Preparation 12

Example 7

Synthesis of (5-oxotetrahydrofuran-3-carboxylic acid[1-phenyl-5-(3-propylphenyl)-1H-pyrazol-3-yl]amide)

(1) 5-Oxotetrahydrofuran-3-carboxylic acid[1-phenyl-5-(3-propylphenyl)-1H-pyrazol-3-yl]amide

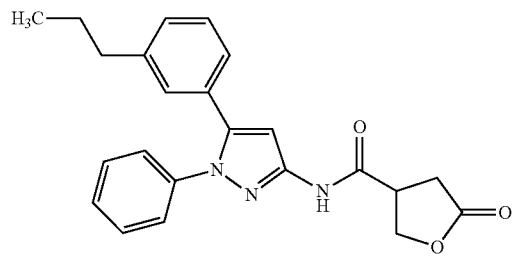 [SMILES: CCCc1cccc(-c2cc(NC(=O)C3COC(=O)C3)nn2-c2ccccc2)c1]

+

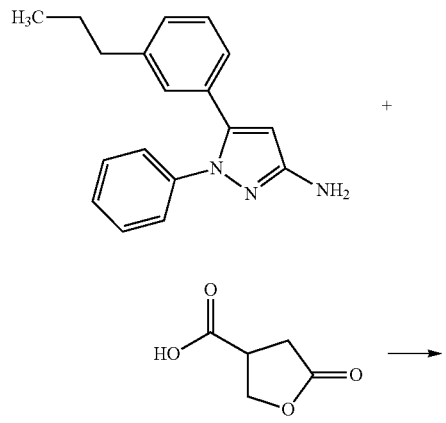

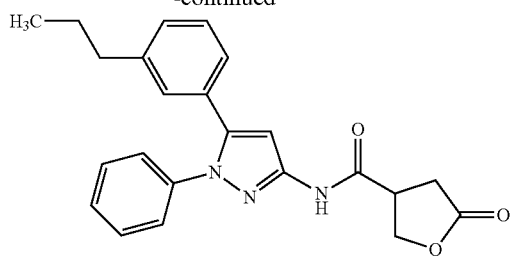

To a solution of 1-phenyl-5-(3-propylphenyl)-1H-pyrazol-3-ylamine (109 mg) prepared according to the same procedures as Preparation 8 in N,N-dimethylformamide/tetrahydrofuran (1/1, 2 ml) were sequentially added 5-oxotetrahydrofuran-3-carboxylic acid (82 mg) prepared in Preparation 9, HOBt.H$_2$O (96 mg) and WSC.HCl (121 mg), and the mixture was stirred at room temperature overnight. To this reaction solution was added a saturated aqueous solution of sodium hydrogen carbonate, and the mixture was extracted with ethyl acetate. The separated organic layer was concentrated under reduced pressure, and the resulting residue was purified by silica gel thin-layer chromatography (eluent: chloroform/methanol=10/1) to give the titled compound (96 mg).

$^1$H-NMR (DMSO-D$_6$) δ: 0.77 (t, 3H, J=7.3 Hz), 1.38-1.50 (m, 2H), 2.46 (t, 2H, J=7.5 Hz), 2.69 (dd, 1H, J=17.4, 5.9 Hz), 2.81 (dd, 1H, J=17.4, 9.0 Hz), 3.56-3.65 (m, 1H), 4.34 (dd, 1H, J=8.8, 5.0 Hz), 4.47-4.55 (m, 1H), 6.89 (s, 1H), 7.00 (s, 1H), 7.07 (d, 1H, J=7.5 Hz), 7.17 (d, 1H, J=7.1 Hz), 7.20-7.30 (3H, m), 7.31-7.43 (3H, m), 11.00 (s, 1H).

Preparation 13

Example 8

Synthesis of ((R)-2-oxoimidazolidine-4-carboxylic acid[1-phenyl-5-(3-propylphenyl)-1H-pyrazol-3-yl]amide)

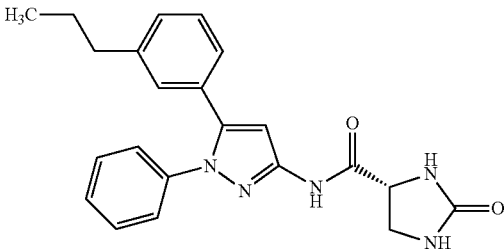 [SMILES: CCCc1cccc(-c2cc(NC(=O)[C@H]3CNC(=O)N3)nn2-c2ccccc2)c1]

(1) (R)-2,3-Bis-tert-butoxycarbonylaminopropionic acid

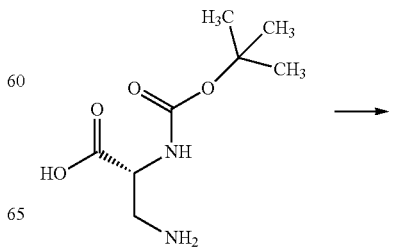

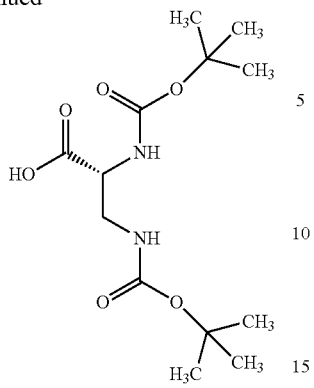
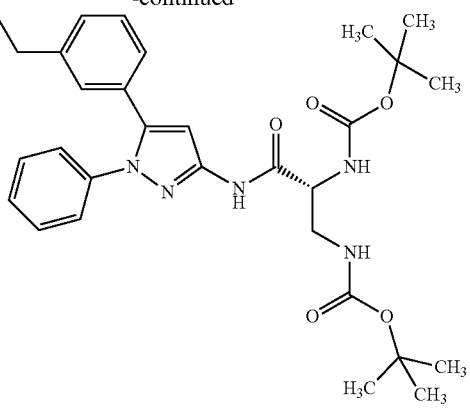

To a solution of di-tert-butyl dicarbonate (513 mg) in 1,4-dioxane (4 ml) was added N-Boc-(R)-2,3-diaminopropionic acid (400 mg) at room temperature, and the mixture was stirred for 20 minutes, and then heated to 50° C., and stirred for 20 minutes. The mixture was again cooled to room temperature, and then triethylamine (546 μl) was added thereto, and the mixture was stirred for 2 hours. To this reaction solution were added water and a 10 wt % aqueous solution of citric acid, and the mixture was extracted with ethyl acetate. The resulting organic layer was washed twice with water, dried over anhydrous magnesium sulfate, and concentrated under reduced pressure. The resulting residue was purified by silica gel column chromatography (eluent: chloroform/ethanol=1/0 to 10/1) to give the titled compound (557 mg).

$^1$H-NMR (DMSO-D$_6$) δ: 1.37 (s, 9H), 1.38 (s, 9H), 3.23 (dd, 2H, J=6.2, 6.0 Hz), 3.99 (dt, 1H, J=8.2, 6.2 Hz), 6.78 (t, 1H, J=6.0 Hz), 6.86 (d, 1H, J=8.2 Hz), 12.52 (br s, 1H).

(2) {(R)-2-tert-Butoxycarbonylamino-2-[1-phenyl-5-(3-propylphenyl)-1H-pyrazol-3-ylcarbamoyl]-ethyl}carbamic acid tert-butyl ester To a solution of 1-phenyl-5-(3-propylphenyl)-1H-pyrazol-3-ylamine (177 mg) prepared according to the same procedures as Preparation 8 in DMF (1.8 ml) were added (R)-2,3-bis-tert-butoxycarbonylaminopropionic acid (292 mg), HOBt.H$_2$O (147 mg) and WSC.HCl (184 mg), and the mixture was stirred at room temperature for 2 hours. To this reaction solution were added water and a saturated aqueous solution of sodium hydrogen carbonate, and the mixture was extracted with ethyl acetate. The separated organic layer was washed with a saturated aqueous solution of sodium chloride, dried over anhydrous sodium sulfate, and then concentrated under reduced pressure. The resulting residue was purified by silica gel column chromatography (eluent: n-hexane/ethyl acetate=2/1) to give the titled compound (329 mg).

$^1$H-NMR (CDCl$_3$) δ: 0.83 (t, 3H, J=7.3 Hz), 1.45 (s, 9H), 1.48 (s, 9H), 1.50 (tq, 2H, J=7.3, 7.5 Hz), 2.49 (t, 2H, J=7.5 Hz), 3.61-3.64 (br m, 2H), 4.38-4.41 (br m, 1H), 5.06 (br s, 1H), 5.94 (br s, 1H), 7.01 (s, 1H), 7.05-7.35 (m, 9H), 8.94 (br s, 1H).

(3) (R)-2,3-Diamino-N-[1-phenyl-5-(3-propylphenyl)-1H-pyrazol-3-yl]-propionamide dihydrochloride

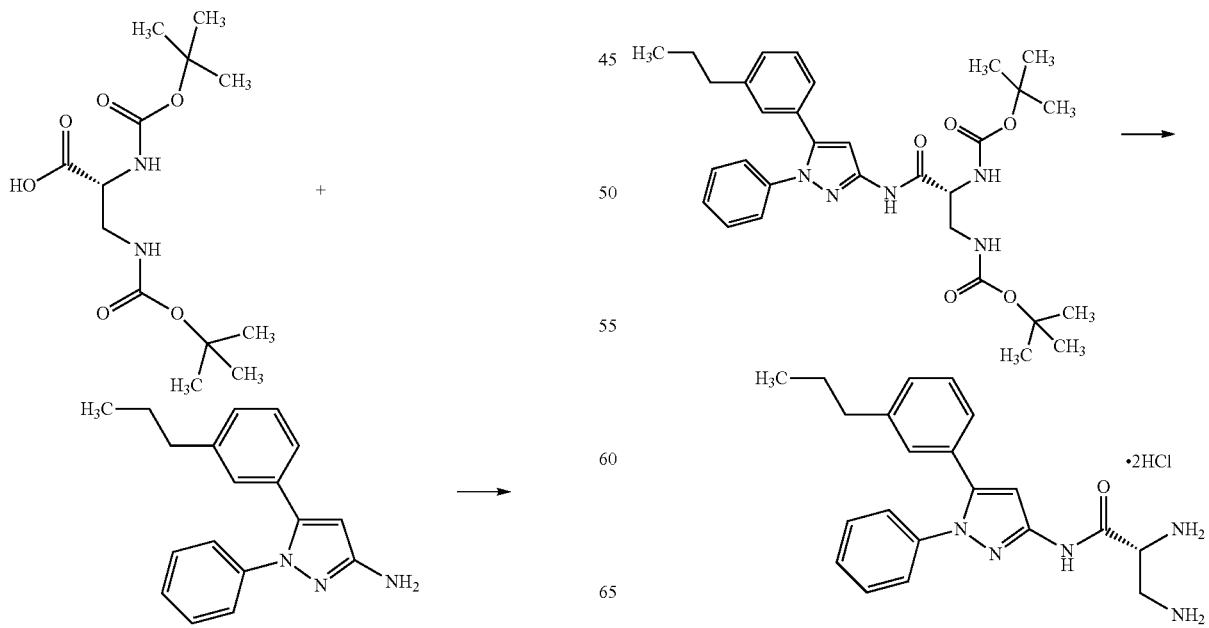

To a solution of [(R)-2-tert-butoxycarbonylamino-2-[1-phenyl-5-(3-propylphenyl)-1H-pyrazol-3-ylcarbamoyl]ethyl]carbamic acid tert-butyl ester (328 mg) in 1,4-dioxane (3 ml) was added a 4M solution of hydrogen chloride in 1,4-dioxane (3 ml) at room temperature, and the mixture was stirred for 2 hours. This reaction solution was concentrated, and then n-hexane (4 ml) was added thereto, and the mixture was stirred. The insoluble substance was collected by filtration, washed with n-hexane, and dried under reduced pressure to give the titled compound (181 mg).

$^1$H-NMR (DMSO-D$_6$) δ: 0.77 (t, 3H, J=7.3 Hz), 1.44 (tq, 2H, J=7.5, 7.3 Hz), 2.46 (t, 2H, J=7.5 Hz), 3.41-3.46 (m, 2H), 3.57 (s, 1H), 4.38-4.41 (m, 1H), 6.91 (s, 1H), 7.11-7.31 (m, 9H), 8.56 (br s, 4H).

(4) (R)-2-Oxoimidazolidine-4-carboxylic acid[1-phenyl-5-(3-propyl-phenyl)-1H-pyrazol-3-yl]amide

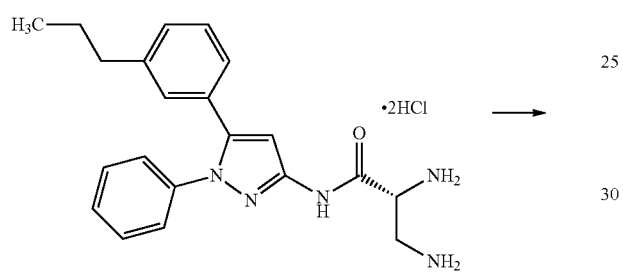

To a solution of (R)-2,3-diamino-N-[1-phenyl-5-(3-propylphenyl)-1H-pyrazol-3-yl]-propionamide dihydrochloride (181 mg) in N,N-dimethylformamide (3 ml) were added 1,1'-carbonyldiimidazole (67 mg), and triethylamine (116 µl) at room temperature, and the mixture was stirred for 16 hours. To this reaction solution was added water, and the mixture was extracted with ethyl acetate. The resulting organic layer was washed with water and a saturated aqueous solution of sodium chloride, dried over anhydrous sodium sulfate, and then concentrated under reduced pressure. The resulting residue was purified by silica gel thin-layer chromatography (eluent: chloroform/methanol=10/1) to give the titled compound (76 mg).

$^1$H-NMR (DMSO-D$_6$) δ: 0.77 (t, 3H, J=7.4 Hz), 1.44 (tq, 2H, J=7.5, 7.4 Hz), 2.46 (t, 2H, J=7.5 Hz), 3.35 (dd, 1H, J=9.4, 5.6 Hz), 3.59 (dd, 1H, J=9.4, 9.4 Hz), 4.32 (dd, 1H, J=9.4, 5.6 Hz), 6.34 (s, 1H), 6.61 (s, 1H), 6.90 (s, 1H), 7.00 (s, 1H), 7.06-7.41 (m, 8H), 10.71 (s, 1H).

Preparation 14

Synthesis of (S)-5-oxopyrrolidine-3-carboxylic acid

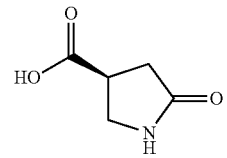

(1) (S)-4-Benzyl-3-[(S)-1-(2,4-dimethoxybenzyl)-5-oxopyrrolidine-3-carbonyl]-2-oxazolidinone

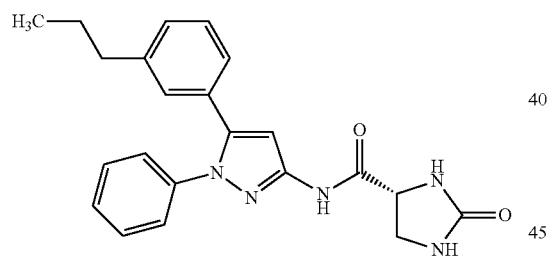

To a solution of 1-(2,4-dimethoxybenzyl)-5-oxopyrrolidine-3-carboxylic acid (20 g) prepared according to the same procedures as Preparation 5 in chloroform (200 ml) were sequentially added (S)-4-benzyl-2-oxazolidinone (15.2 g) and WSC.HCl (16.4 g), 4-(dimethylamino)pyridine (4.4 g) at room temperature, and the mixture was stirred for 3 hours. This reaction solution was washed with a 5 wt % aqueous solution of sodium hydrogen carbonate and a saturated aqueous solution of sodium chloride, dried over anhydrous sodium sulfate, and then concentrated under reduced pressure. The resulting residue was purified by silica gel column chromatography (eluent: n-hexane/ethyl acetate=1/1 to 1/3), subjected to azeotropic drying with toluene, and dried under reduced pressure to give the titled compound (17.2 g).

H-NMR (CDCl₃) δ: 2.72-2.83 (m, 3H), 3.27 (dd, 1H, J=13.4, 3.5 Hz), 3.46-3.57 (m, 2H), 3.80 (s, 3H), 3.80 (s, 3H), 4.15-4.29 (m, 3H), 4.40-4.48 (m, 2H), 4.61-4.69 (m, 1H), 6.42-6.47 (m, 2H), 7.12-7.21 (m, 3H), 7.27-7.37 (m, 3H).

(2) (S)-1-(2,4-dimethoxybenzyl)-5-oxopyrrolidine-3-carboxylic acid

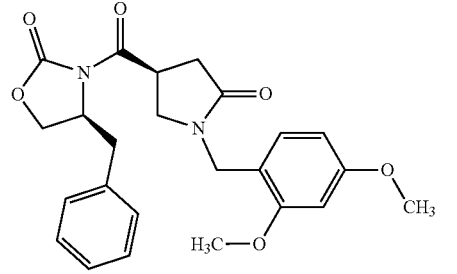

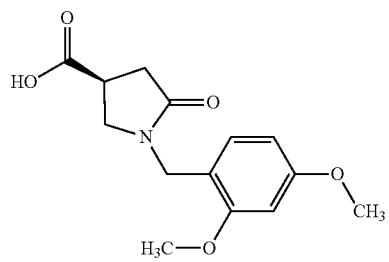

To a solution of lithium hydroxide monohydrate (2.0 g) in water (45 ml) was added dropwise 30 wt % aqueous solution of hydrogen peroxide solution (11 ml)) in an ice-sodium chloride cooling bath, and the mixture was stirred for 15 minutes. To this reaction solution was added tetrahydrofuran (36 ml), and then a solution of (S)-4-benzyl-3-[(S)-1-(2,4-dimethoxybenzyl)-5-oxopyrrolidine-3-carbonyl]-2-oxazolidinone (17.2 g) in tetrahydrofuran (144 ml) was added dropwise thereto, and the mixture was stirred for additional 20 minutes. To this reaction solution was slowly added a 10 wt % aqueous solution of sodium hydrogen sulfite (131 ml), and the mixture was stirred at room temperature for 1 hour after removing the bath, and then extracted with ethyl acetate (180 ml). The resulting organic layer was washed with a saturated aqueous solution of sodium chloride, dried over anhydrous sodium sulfate, and then concentrated under reduced pressure. The resulting residue was purified by silica gel column chromatography (eluent: ethyl acetate to chloroform/methanol=9/1). To the resulting product (6.7 g) was added diisopropyl ether (13.4 ml), the mixture was stirred at 70° C., and then cooled to 0° C. with stirring. A solid was collected from this suspension by filtration, dried under reduced pressure to give the titled compound (5.5 g). An analysis of this solid by HPLC analysis condition 1 showed that an isomer with longer retention time was a main product.

An isomer with shorter retention time (retention time 4.7 minutes)

An isomer with longer retention time (retention time 5.4 minutes)

¹H-NMR (CDCl₃) δ: 2.66-2.82 (m, 2H), 3.20 (dt, 1H, J=17.3, 7.6 Hz), 3.49-3.53 (m, 2H), 3.80 (s, 6H), 4.40 (d, 1H, J=14.6 Hz), 4.46 (d, 1H, J=14.6 Hz), 6.42-6.47 (m, 2H), 7.14 (t, 1H, J=4.5 Hz).

(3) (S)-5-oxopyrrolidine-3-carboxylic acid

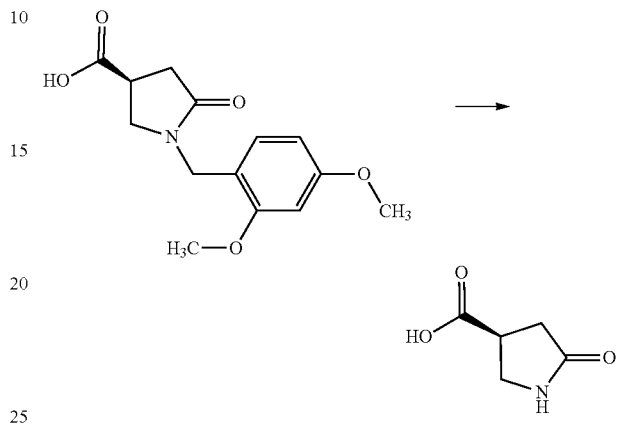

To (S)-1-(2,4-dimethoxybenzyl)-5-oxopyrrolidine-3-carboxylic acid (5.3 g) were added anisole (3.1 ml) and trifluoroacetic acid (26.5 ml) at room temperature, and the mixture was stirred for 4 hours at reflux. This reaction solution was cooled to room temperature, concentrated under reduced pressure, azeotropic-dried with toluene. To the resulting residue was added diisopropyl ether (53 ml), and the mixture was stirred at room temperature. A solid was collected from this suspension by filtration, washed with diisopropyl ether, and dried under reduced pressure to give the titled compound (2.4 g).

¹H-NMR (DMSO-D₆) δ: 2.26-2.40 (m, 2H), 3.18-3.28 (m, 1H), 3.30-3.35 (m, 1H), 3.40-3.47 (m, 1H), 7.64 (s, 1H), 12.58 (s, 1H)

Preparation 15

Example 235

Synthesis of ((S)-5-oxopyrrolidine-3-carboxylic acid{5-[3-fluoro-5-((R)-2,2,2-trifluoro-1-methyl-ethoxymethyl)phenyl]-1-phenyl-1H-pyrazol-3-yl}amide)

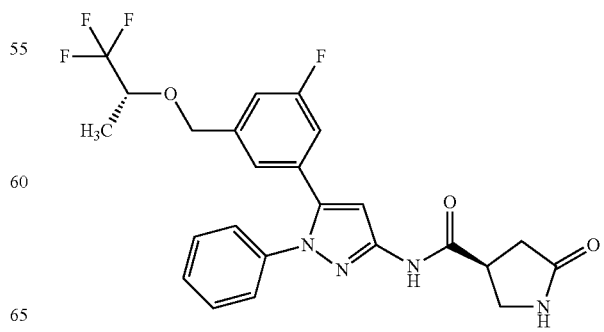

(1) 1-Fluoro-3-((R)-2,2,2-trifluoro-1-methyl-ethoxymethyl)benzene

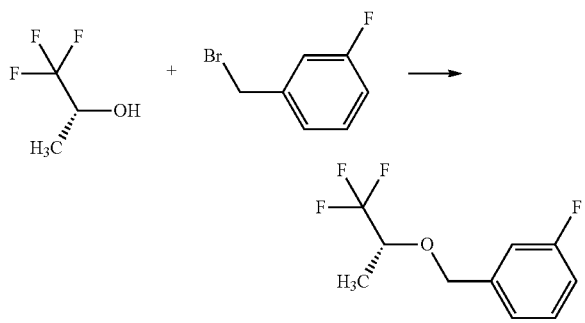

Under argon atmosphere, a suspension of sodium hydride (76 mg, 60 wt % oil dispersion) in N,N-dimethylformamide (2.0 ml) was cooled to 0° C., a solution of N,N-dimethylformamide (2.0 ml) in (R)-1,1,1-trifluoropropan-2-ol (219 mg) was added thereto, and the mixture was stirred for 25 minutes. Then, a solution of 1-bromomethyl-3-fluorobenzene (297 mg) in N,N-dimethylformamide (2.0 ml) was added thereto, and then the mixture was stirred for 2 hours. To this reaction mixture was added water, and the mixture was extracted with ethyl acetate. This organic layer was washed with a saturated aqueous solution of sodium chloride, dried over anhydrous magnesium sulfate, and then concentrated under reduced pressure. The resulting residue was purified by silica gel thin-layer chromatography (eluent: n-hexane/ethyl acetate=9/1) to give the titled compound (242 mg).

$^1$H-NMR (CDCl$_3$) δ: 1.35 (d, 3H, J=6.47 Hz), 3.84 (qq, 1H, J=6.47, 9.40 Hz), 4.63 (d, 1H, J=12.00 Hz), 4.76 (d, 1H, J=12.00 Hz), 6.98-7.03 (m, 1H), 7.06-7.12 (m, 2H), 7.29-7.35 (m, 1H).

(2) 2-[3-Fluoro-5-((R)-2,2,2-trifluoro-1-methyl-ethoxymethyl)phenyl]-4,4,5,5-tetramethyl-[1,3,2]dioxaborolane

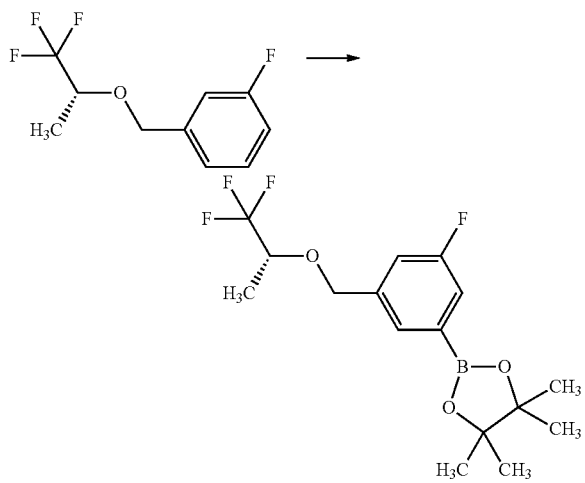

Under argon atmosphere, to a solution of 1-fluoro-3-((R)-2,2,2-trifluoro-1-methylethoxymethyl)benzene (159 mg) in tetrahydrofuran (3.0 ml) were sequentially added bispinacolate diboron (202 mg), 4,4'-di-tert-butyl-2,2'-dipyridyl (10 mg) and di-μ-methoxobis(1,5-cyclooctadiene)diiridium (I) (12 mg) at room temperature, and then the mixture was stirred for 16 hours at reflux. This reaction mixture was cooled to room temperature, and then a saturated aqueous solution of sodium hydrogen carbonate and ethyl acetate were added thereto, the mixture was filtered through Celite, and extracted with ethyl acetate. The filtrate was extracted with ethyl acetate, the separated organic layer was washed with a saturated aqueous solution of sodium chloride, dried over anhydrous magnesium sulfate, and then concentrated under reduced pressure. The resulting residue was purified by silica gel thin-layer chromatography (eluent: n-hexane/ethyl acetate=85/15) to give the titled compound (49 mg).

$^1$H-NMR (CDCl$_3$) δ: 1.35 (m, 15H), 3.83 (qq, 1H, J=6.47, 9.40 Hz), 4.62 (d, 1H, J=12.00 Hz), 4.75 (d, 1H, J=12.00 Hz), 7.19 (d, 1H, J=9.60 Hz), 7.43 (d, 1H, J=9.60 Hz), 7.49 (s, 1H).

(3) 5-[3-Fluoro-5-((R)-2,2,2-trifluoro-1-methyl-ethoxymethyl)phenyl]-1-phenyl-1H-pyrazol-3-ylamine

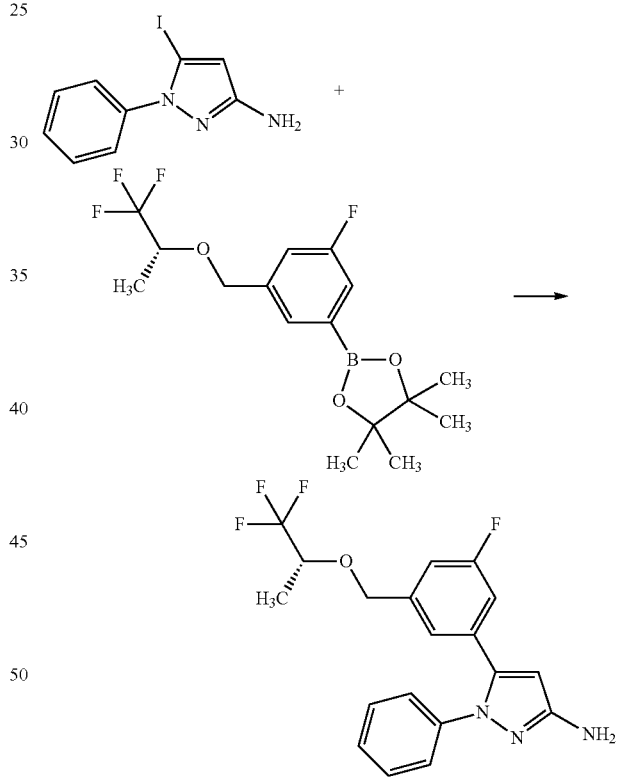

To 2-[3-fluoro-5-((R)-2,2,2-trifluoro-1-methylethoxymethyl)phenyl]-4,4,5,5-tetramethyl-[1,3,2]dioxaborolane (49 mg) were sequentially added a solution of 5-iodo-1-phenyl-1H-pyrazol-3-ylamine (36 mg) prepared according to the same procedures as Preparation 2 in 1,2-dimethoxyethane (1.0 ml), a 2M aqueous solution of sodium carbonate (0.5 ml), tricyclohexylphosphine (7.3 mg) and palladium (II) acetate (3.0 mg) at room temperature, and the mixture was stirred at 100° C. for 2 hours. This reaction mixture was cooled to room temperature, a saturated aqueous solution of sodium hydrogen carbonate and ethyl acetate were added thereto, the mixture was filtered through Celite, and extracted with ethyl acetate. The filtrate was extracted with ethyl acetate, the separated organic layer was washed with a saturated aqueous solution of sodium chloride, dried over anhydrous magnesium sulfate, and then concentrated under reduced pressure. The resulting residue was purified by silica gel thin-layer chromatography (eluent: chloroform/methanol=9/1) to give the titled compound (37 mg).

(4) (S)-5-Oxopyrrolidine-3-carboxylic acid{5-[3-fluoro-5-((R)-2,2,2-trifluoro-1-methylethoxymethyl)phenyl]-1-phenyl-1H-pyrazol-3-yl}amide

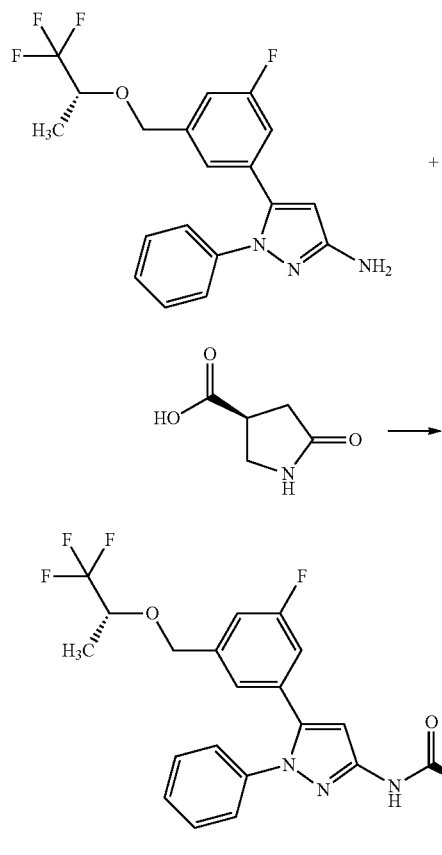

To a solution of 5-[3-fluoro-5-((R)-2,2,2-trifluoro-1-methylethoxymethyl)phenyl]-1-phenyl-1H-pyrazol-3-ylamine (37 mg) in N,N-dimethylacetamide (1.0 ml) were sequentially added (S)-5-oxopyrrolidine-3-carboxylic acid (16 mg) prepared in Preparation 14 and WSC.HCl (23 mg) at room temperature, the mixture was stirred for 5.2 hours. To this reaction mixture was added water, and then the precipitated solid was collected by filtration. This solid was purified by silica gel thin-layer chromatography (eluent: chloroform/methanol=9/1). To the resulting solid were added water and a small amount of methanol, and the mixture was stirred. A solid was collected from this suspension by filtration, and was dried under reduced pressure to give the titled compound (20 mg).

$^1$H-NMR (DMSO-D6) δ: 1.18 (d, 3H, J=6.5 Hz), 2.36-2.38 (m, 2H), 3.32-3.33 (m, 1H), 3.37-3.41 (m, 1H), 3.46-3.49 (m, 1H), 4.10 (qq, 1H, J=6.5, 9.4 Hz), 4.57 (d, 1H, J=12.7 Hz), 4.61 (d, 1H, J=12.7 Hz), 6.96-3.98 (m, 2H), 7.09 (s, 1H), 7.15-7.18 (m, 1H), 7.25-7.27 (m, 2H), 7.35-7.44 (m, 3H), 7.63 (s, 1H), 10.88 (s, 1H).

Preparation 16

Example 236

Synthesis of ((S)-5-oxopyrrolidine-3-carboxylic acid{1-(4-chlorophenyl)-5-[3-fluoro-5-((R)-2,2,2-trifluoro-1-methylethoxymethyl)phenyl]-1H-pyrazol-3-yl}amide)

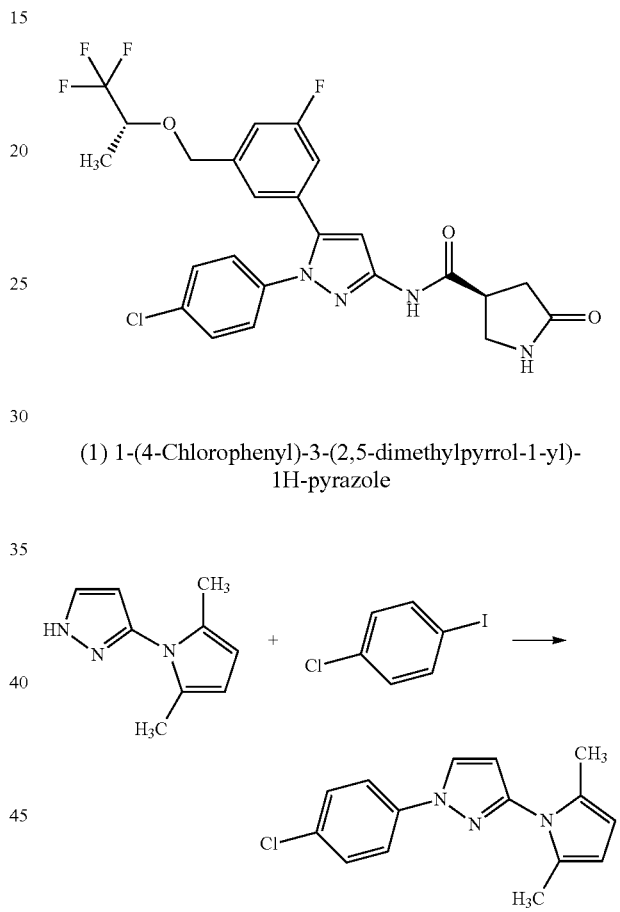

(1) 1-(4-Chlorophenyl)-3-(2,5-dimethylpyrrol-1-yl)-1H-pyrazole

Under argon atmosphere, to a solution of 3-(2,5-dimethylpyrrol-1-yl)-1H-pyrazole (3.06 g) prepared according to the same procedures as Preparation 4 in N-methylpyrrolidone (31 ml) were sequentially added cesium carbonate (12.37 g), 8-quinolinol (0.55 g), copper (I) oxide (0.27 g) and 1-chloro-4-iodobenzene (6.79 g) at room temperature, the mixture was stirred at 110° C. for 2 hours. This reaction mixture was cooled to room temperature, and then toluene (30 ml) was added thereto, the mixture was filtered through Celite, and further subjected to elution with toluene. The filtrate was sequentially washed with a 1N aqueous solution of sodium hydroxide, water, a saturated aqueous solution of sodium chloride, dried over anhydrous sodium sulfate, and then concentrated under reduced pressure. The resulting residue was purified by silica gel column chromatography (eluent: n-hexane/ethyl acetate=1/0 to 9/1) to give the titled compound (4.98 g).

$^1$H-NMR (CDCl$_3$) δ: 2.19 (s, 6H), 5.90 (s, 2H), 6.40 (d, 1H, J=2.65 Hz), 7.43 (d, 2H, J=8.82 Hz), 7.66 (d, 2H, J=8.82 Hz), 7.94 (d, 1H, J=2.65 Hz).

(2) 1-(4-Chlorophenyl)-3-(2,5-dimethylpyrrol-1-yl)-5-iodo-1H-pyrazole

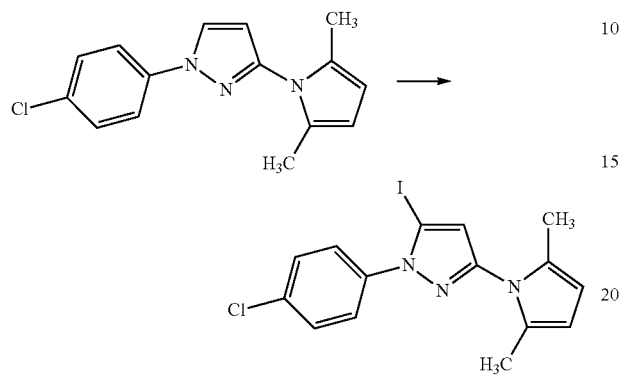

Under argon atmosphere, a solution of 3-(2,5-dimethylpyrrol-1-yl)-1-(4-chlorophenyl)-1H-pyrazole (4.98 g) in tetrahydrofuran (40 ml) was cooled to −78° C., n-butyllithium (13.7 ml, 1.6M solution in n-hexane) was added dropwise thereto, and the mixture was stirred for 30 minutes. To this reaction solution was added dropwise a solution of iodine (5.58 g) in tetrahydrofuran (10 ml), the mixture was stirred for 30 minutes. To this reaction solution were added a 20 wt % aqueous solution of sodium sulfite and a saturated aqueous solution of ammonium chloride, the mixture was extracted with ethyl acetate. The organic layer was washed with a saturated aqueous solution of sodium chloride, dried over anhydrous sodium sulfate, and then concentrated under reduced pressure. To the resulting solid residue was added a mixed solvent of ethyl acetate/n-hexane=1/2, the mixture was stirred. A solid was collected from this suspension by filtration, and was dried under reduced pressure to give the titled compound (4.19 g).

$^1$H-NMR (CDCl$_3$) δ: 2.18 (s, 6H), 5.88 (s, 2H), 6.55 (s, 1H), 7.47 (d, 2H, J=9.04 Hz), 7.55 (d, 2H, J=9.04 Hz).

(3) 1-(4-Chlorophenyl)-5-iodo-1H-pyrazol-3-ylamine

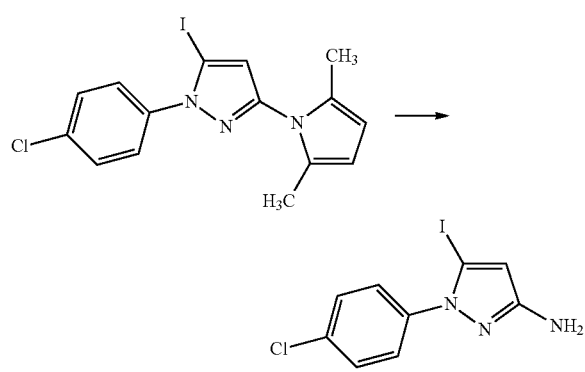

To a suspension of 1-(4-chlorophenyl)-3-(2,5-dimethylpyrrol-1-yl)-5-iodo-1H-pyrazole (4.19 g) in ethanol/water (2/1, 72 ml) were sequentially added hydroxylammonium chloride (14.64 g) and triethylamine (2.9 ml) at room temperature, and the mixture was stirred at 95° C. for 86 hours. This reaction mixture was cooled to room temperature, and concentrated under reduced pressure. To the resulting residue was added an 8M aqueous solution of sodium hydroxide, and then the mixture was extracted with ethyl acetate. This organic layer was sequentially washed with water and a saturated aqueous solution of sodium chloride, dried over anhydrous sodium sulfate, and then concentrated under reduced pressure. The resulting residue was purified by silica gel column chromatography (eluent: n-hexane/ethyl acetate=2/1) to give the titled compound (1.87 g).

$^1$H-NMR (CDCl$_3$) δ: 3.77 (br s, 2H), 6.01 (s, 1H), 7.39-7.50 (m, 4H).

(4) 1-(4-Chlorophenyl)-5-[3-fluoro-5-((R)-2,2,2-trifluoro-1-methylethoxymethyl)phenyl]-1H-pyrazol-3-ylamine

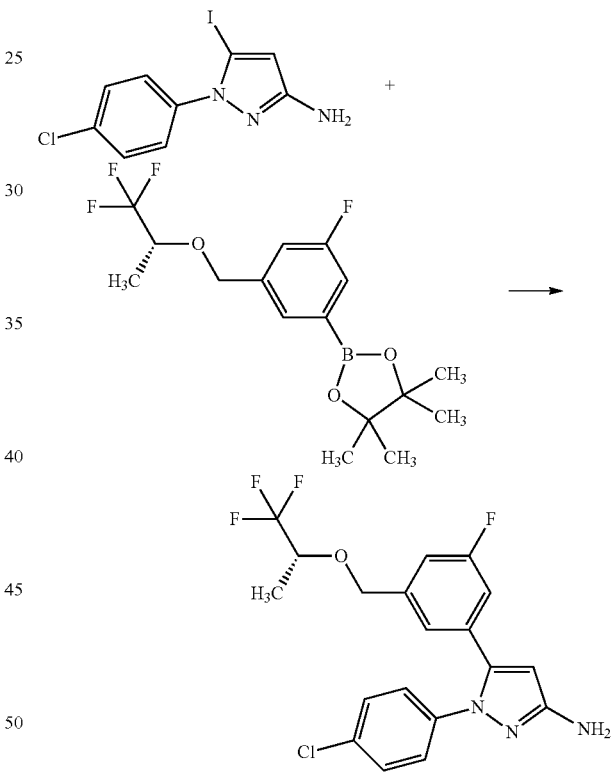

Under argon atmosphere, to a solution of 1-(4-chlorophenyl)-5-iodo-1H-pyrazol-3-ylamine (35 mg) in 1,2-dimethoxyethane (0.7 ml) were sequentially added 2-[3-fluoro-5-((R)-2,2,2-trifluoro-1-methylethoxymethyl)phenyl]-4,4,5,5-tetramethyl-[1,3,2]dioxaborolane (46 mg) prepared according to the same procedures as Preparation 15, a 2M aqueous solution of sodium carbonate (0.35 ml), tricyclohexylphosphine (6.1 mg) and palladium (II) acetate (2.5 mg) at room temperature, and the mixture was stirred at 100° C. for 2 hours. This reaction mixture was cooled to room temperature, filtered through Celite, was subjected to elution with ethyl acetate. The filtrate was dried over anhydrous magnesium sulfate, and then concentrated under reduced pressure. The resulting residue was purified by silica gel thin-layer chromatography (eluent: n-hexane/ethyl acetate=1/1) to give the titled compound.

(5) (S)-5-Oxopyrrolidine-3-carboxylic acid{1-(4-chlorophenyl)-5-[3-fluoro-5-((R)-2,2,2-trifluoro-1-methylethoxymethyl)phenyl]-1H-pyrazol-3-yl}amide

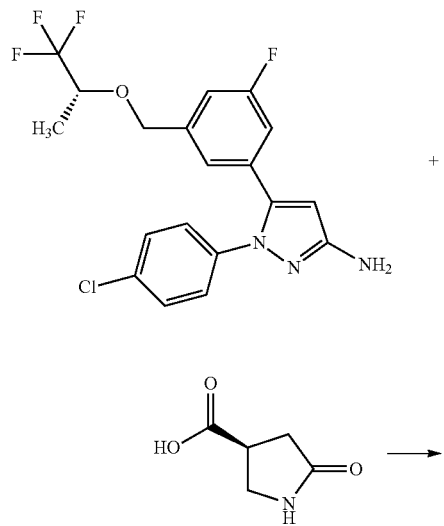

To a solution of 1-(4-chlorophenyl)-5-[3-fluoro-5-((R)-2,2,2-trifluoro-1-methylethoxymethyl)phenyl]-1H-pyrazol-3-ylamine (about 0.110 mol) prepared in the previous step in N,N-dimethylacetamide (0.5 ml) were sequentially added (S)-5-oxopyrrolidine-3-carboxylic acid (17 mg) prepared in Preparation 14 and WSC.HCl (32 mg) at room temperature, and the mixture was stirred for 0.5 hours. To this reaction mixture was added water, and then the precipitated solid was collected by filtration. The resulting solid was purified by silica gel thin-layer chromatography (eluent: chloroform/methanol=9/1) to give the titled compound (18 mg).

$^1$H-NMR (DMSO-D6) δ: 1.20 (d, 3H, J=6.5 Hz), 2.38-2.40 (m, 2H), 3.33-3.35 (m, 1H), 3.40-3.44 (m, 1H), 3.48-3.51 (m, 1H), 4.10-4.15 (m, 1H), 4.63 (s, 2H), 6.99 (s, 1H), 7.06 (s, 1H), 7.08 (d, 1H, J=9.3 Hz), 7.19 (d, 1H, J=9.3 Hz), 7.27 (dd, 2H, J=6.6, 2.0 Hz), 7.48 (dd, 2H, J=6.6, 2.0 Hz), 7.63 (s, 1H), 10.91 (s, 1H).

Preparation 17

Example 237

Synthesis of ((S)-5-oxopyrrolidine-3-carboxylic acid{1-(2-fluorophenyl)-5-[3-fluoro-5-((R)-2,2,2-trifluoro-1-methylethoxymethyl)phenyl]-1H-pyrazol-3-yl}amide)

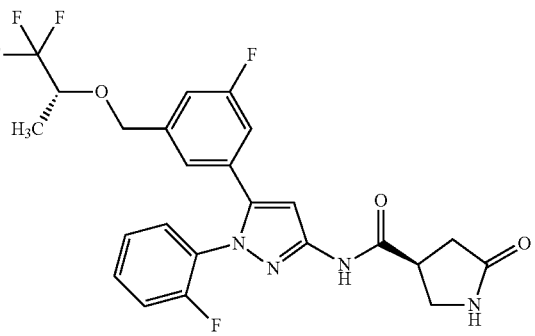

(1) 3-(2,5-Dimethylpyrrol-1-yl)-1-(2-fluorophenyl)-1H-pyrazole

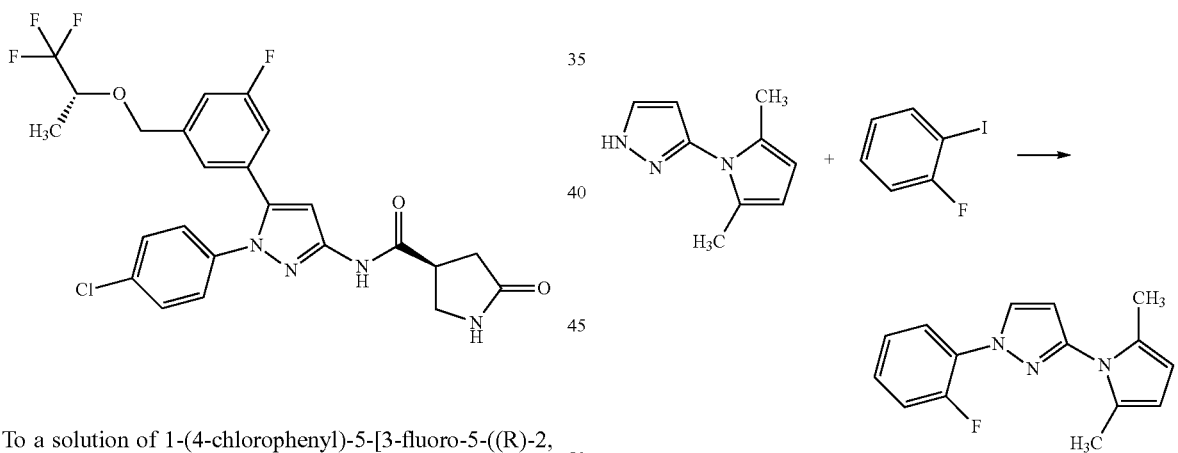

To a solution of 3-(2,5-dimethylpyrrol-1-yl)-1H-pyrazole (1.00 g) prepared according to the same procedures as Preparation 4 in N-methylpyrrolidone (10 ml) were sequentially added 1-fluoro-2-iodobenzene (1.08 ml), copper (I) oxide (89 mg), 8-quinolinol (180 mg) and cesium carbonate (4.04 g) at room temperature, and the mixture was stirred at 110° C. for 3 hours. This reaction mixture was cooled to room temperature, and then toluene was added thereto, and the mixture was filtered through Celite. The filtrate was sequentially washed with a 2N aqueous solution of sodium hydroxide, water and a saturated aqueous solution of sodium chloride, dried over anhydrous sodium sulfate, and then concentrated under reduced pressure. The resulting residue was purified by silica gel column chromatography (eluent: n-hexane/ethyl acetate=1/0 to 10/1) to give the titled compound (1.19 g).

(2) 3-(2,5-Dimethylpyrrol-1-yl)-1-(2-fluorophenyl)-5-iodo-1H-pyrazole

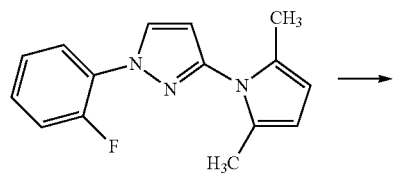

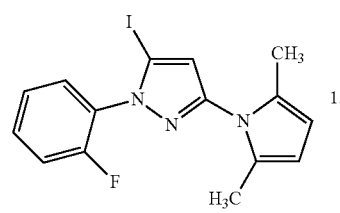

Under nitrogen atmosphere, a solution of 3-(2,5-dimethylpyrrol-1-yl)-1-(2-fluorophenyl)-1H-pyrazole (1.19 g) in tetrahydrofuran (10 ml) was cooled to −78° C., n-butyllithium (3.5 ml, 1.6M solution in n-hexane) was added dropwise thereto, and the mixture was stirred for 30 minutes. To this reaction solution was added dropwise a solution of iodine (1.42 g) in tetrahydrofuran (5 ml), and the mixture was stirred for 30 minutes. To this reaction mixture was added a saturated aqueous solution of sodium sulfite and a saturated aqueous solution of ammonium chloride, and the mixture was extracted with ethyl acetate. This organic layer was washed with a saturated aqueous solution of sodium chloride, dried over anhydrous sodium sulfate, and then concentrated under reduced pressure. To the resulting residue was added a mixed solvent of n-hexane/ethyl acetate (=6/1), the mixture was stirred. A solid was collected from this suspension by filtration, and was dried under reduced pressure to give the titled compound (1.23 g).

(3) 1-(2-Fluorophenyl)-5-iodo-1H-pyrazol-3-ylamine

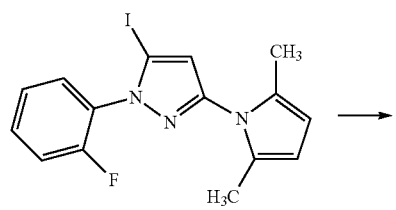

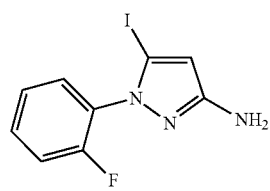

To a solution of 3-(2,5-dimethylpyrrol-1-yl)-1-(2-fluorophenyl)-5-iodo-1H-pyrazole (1.23 g) in ethanol/water (2/1, 18 ml) were sequentially added hydroxylammonium chloride (4.47 g) and triethylamine (0.9 ml) at room temperature, and the mixture was stirred at 90° C. for 24 hours. This reaction mixture was cooled to room temperature, concentrated under reduced pressure. To the resulting residue was added a 8M aqueous solution of sodium hydroxide, and then the mixture was extracted with ethyl acetate. This organic layer was washed with a saturated aqueous solution of sodium chloride, dried over anhydrous sodium sulfate, and then concentrated under reduced pressure. The resulting residue was purified by silica gel column chromatography (eluent: n-hexane/ethyl acetate=4/1 to 1/1) to give the titled compound (0.61 g).

$^1$H-NMR (CDCl$_3$) δ: 3.76 (br s, 2H), 6.03 (s, 1H), 7.19-7.25 (m, 2H), 7.38-7.46 (m, 2H).

(4) 1-(2-Fluorophenyl)-5-[3-fluoro-5-((R)-2,2,2-trifluoro-1-methylethoxymethyl)phenyl]-1H-pyrazol-3-ylamine

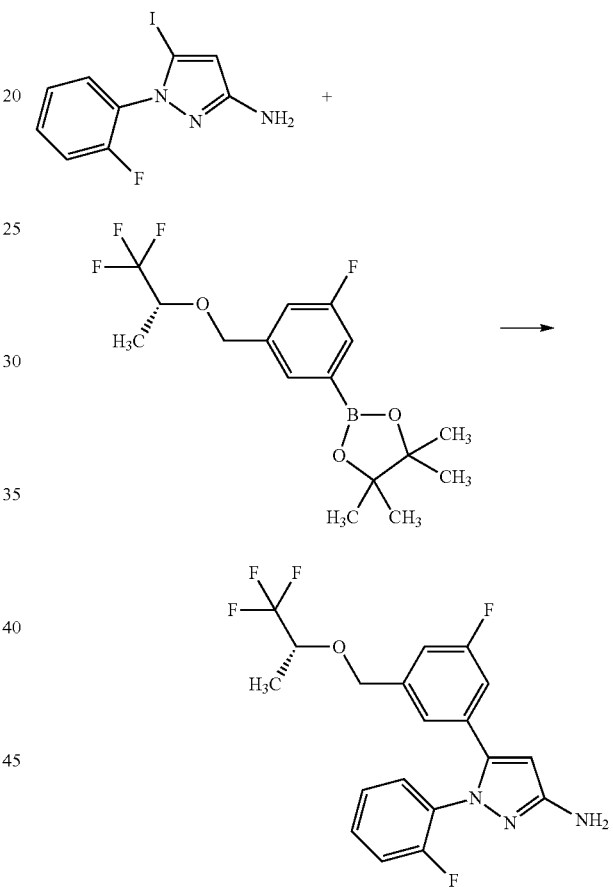

To a solution of 1-(2-fluorophenyl)-5-iodo-1H-pyrazol-3-ylamine (38 mg) in 1,4-dioxane (0.4 ml) were sequentially added 2-[3-fluoro-5-((R)-2,2,2-trifluoro-1-methylethoxymethyl)-phenyl]-4,4,5,5-tetramethyl-[1,3,2]dioxaborolane (52 mg) prepared according to the same procedures as Preparation 15, palladium (II) acetate (3 mg), tricyclohexylphosphine (7 mg), 2M aqueous solution of potassium carbonate (0.2 ml) at room temperature, and the mixture was stirred at 105° C. for 4 hours. After removing the aqueous layer of this reaction mixture, the organic layer was filtered through silica gel (5 g), and subjected to elution with ethyl acetate. The filtrate was concentrated under reduced pressure, and the resulting residue was purified by silica gel thin-layer chromatography (eluent: n-hexane/ethyl acetate 1/1) to give the titled compound.

133

(5) (S)-5-Oxopyrrolidine-3-carboxylic acid{1-(2-fluorophenyl)-5-[3-fluoro-5-((R)-2,2,2-trifluoro-1-methylethoxymethyl)phenyl]-1H-pyrazol-3-yl}amide

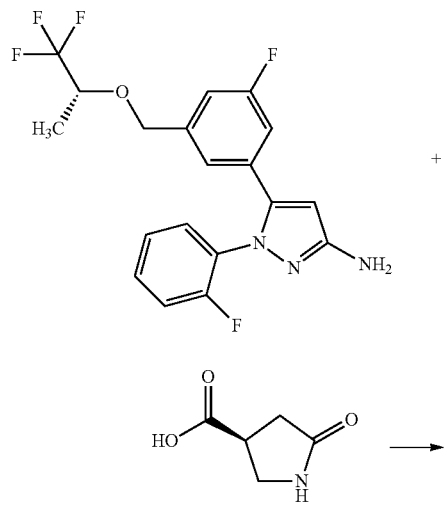

To a solution of 1-(2-fluorophenyl)-5-[3-fluoro-5-((R)-2,2,2-trifluoro-1-methylethoxymethyl)phenyl]-1H-pyrazol-3-ylamine (about 0.125 mmol) prepared in the previous step in dimethylformamide (0.5 ml) were sequentially added (S)-5-oxopyrrolidine-3-carboxylic acid (18 mg) prepared in Preparation 14 and WSC.HCl (29 mg) at room temperature, and the mixture was stirred for 3 hours. To this reaction mixture was added water, and the mixture was extracted with ethyl acetate. This organic layer was concentrated under reduced pressure, and the resulting residue was purified by silica gel thin-layer chromatography (eluent: chloroform/methanol=10/1). To the resulting solid were added water and a small amount of methanol, and the mixture was stirred. A solid was collected from this suspension by filtration, and was dried under reduced pressure to give the titled compound (32 mg).

$^1$H-NMR (CDCl$_3$) δ: 1.29 (d, 3H, J=6.4 Hz), 2.59 (dd, 1H, J=17.2, 9.6 Hz), 2.78 (dd, 1H, J=17.2, 8.8 Hz), 3.29-3.40 (m, 1H), 3.60 (dd, 1H, J=9.2 Hz), 3.67-3.80 (m, 2H), 4.52 (d, 1H, J=12.0 Hz), 4.63 (d, 1H, J=12.0 Hz), 6.08 (s, 1H), 6.85 (dt, 1H, J=9.6, 2.0 Hz), 6.98-7.04 (m, 2H), 7.09-7.17 (m, 2H), 7.22 (t, 1H, J=8.0 Hz), 7.34-7.22 (m, 2H), 8.69 (s, 1H).

134

Preparation 18

Example 238

Synthesis of ((S)-5-oxopyrrolidine-3-carboxylic acid{1-(4-fluorophenyl)-5-[3-((R)-2,2,2-trifluoro-1-methylethoxymethyl)phenyl]-1H-pyrazol-3-yl}amide)

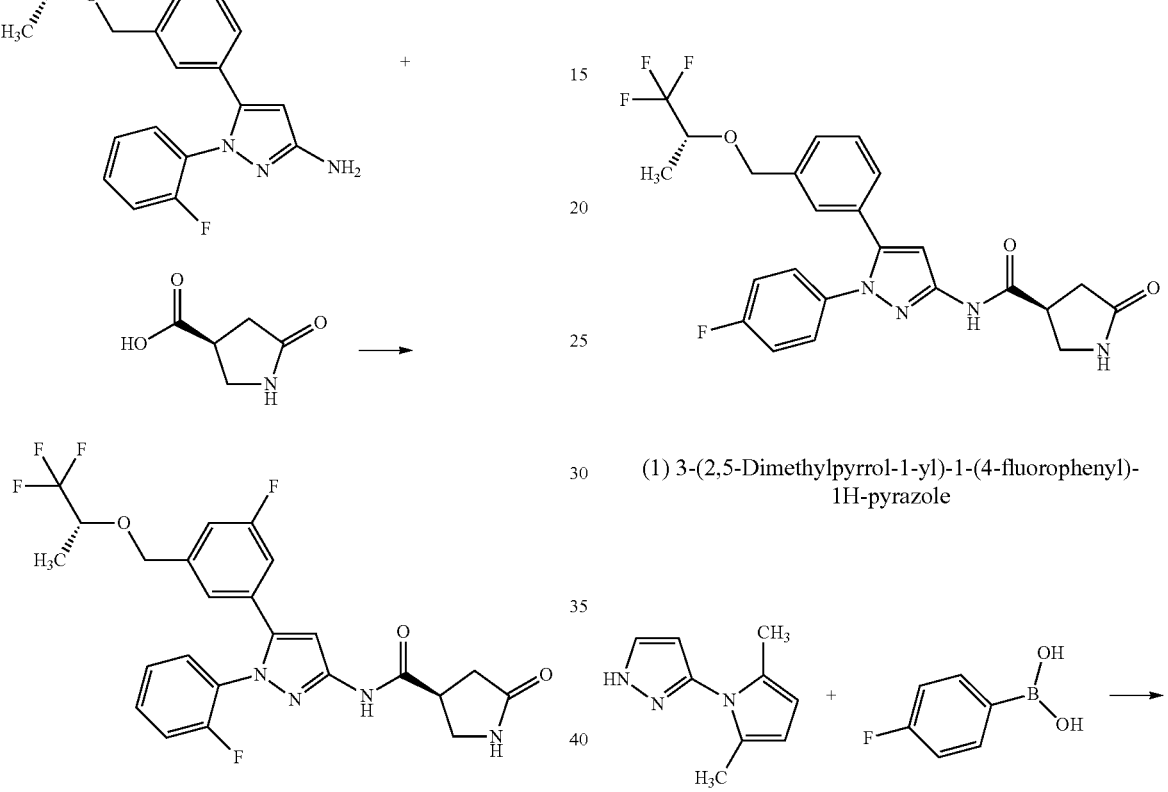

(1) 3-(2,5-Dimethylpyrrol-1-yl)-1-(4-fluorophenyl)-1H-pyrazole

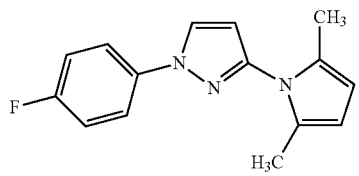

To a solution of 3-(2,5-dimethylpyrrol-1-yl)-1H-pyrazole (500 mg) prepared according to the same procedures as Preparation 4,4-fluorophenyl boronic acid (651 mg) and copper (II) acetate (563 mg) in chloroform (5 ml) was added pyridine (0.50 ml) at room temperature, the mixture was stirred for 40 hours. This reaction solution was filtered through silica gel, and subjected to elution with ethyl acetate. The filtrate was concentrated under reduced pressure, the resulting residue was purified by silica gel column chromatography (eluent: n-hexane/ethyl acetate=9/1) to give the titled compound (599 mg).

¹H-NMR (CDCl₃) δ: 2.19 (s, 6H), 5.90 (s, 2H), 6.39 (d, 1H, J=2.56 Hz), 7.15-7.17 (m, 2H), 7.67-7.70 (m, 2H), 7.91 (d, 1H, J=2.56 Hz).

(2) 3-(2,5-Dimethylpyrrol-1-yl)-1-(4-fluorophenyl)-5-iodo-1H-pyrazole

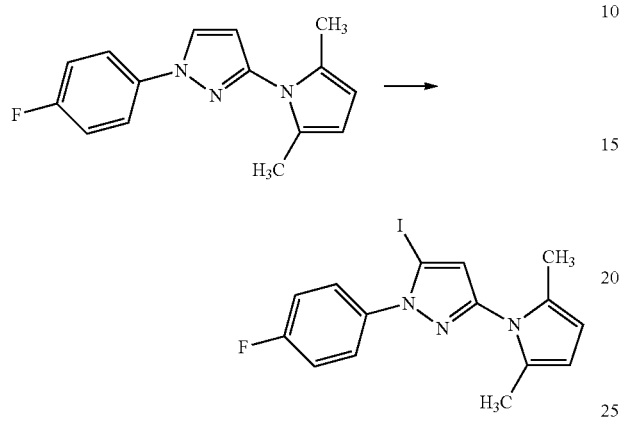

Under argon atmosphere, a solution of 3-(2,5-dimethylpyrrol-1-yl)-1-(4-fluorophenyl)-1H-pyrazole (599 mg) in tetrahydrofuran (4 ml) was cooled to −78° C., n-butyllithium (1.8 ml, 1.6M solution in n-hexane) was added dropwise thereto, and the mixture was stirred for 30 minutes. To this reaction solution was added dropwise a solution of iodine (715 mg) in tetrahydrofuran (2 ml), the mixture was stirred for additional 30 minutes. To this reaction mixture was added a saturated aqueous solution of sodium sulfite, and the mixture was extracted with ethyl acetate. The resulting organic layer was washed with a saturated aqueous solution of sodium chloride, dried over anhydrous sodium sulfate, and then concentrated under reduced pressure. To the resulting solid residue was added a mixed solvent of ethyl acetate/n-hexane (=1/5), and the mixture was stirred. A solid was collected from this suspension by filtration, dried under reduced pressure to give the titled compound (625 mg).

¹H-NMR (CDCl₃) δ: 2.18 (s, 6H), 5.88 (s, 2H), 6.54 (s, 1H), 7.18-7.20 (m, 2H), 7.54-7.57 (m, 2H).

(3) 1-(4-Fluorophenyl)-5-iodo-1H-pyrazol-3-ylamine

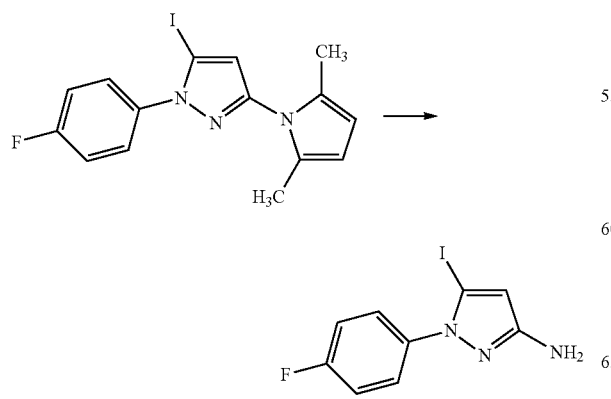

To a suspension of 3-(2,5-dimethylpyrrol-1-yl)-1-(4-fluorophenyl)-5-iodo-1H-pyrazole (625 mg) in ethanol/water (2/1, 12.5 ml) were sequentially added hydroxylammonium chloride (2.28 g) and triethylamine (0.46 ml) at room temperature, and the mixture was stirred at 95° C. for 15 hours. This reaction mixture was cooled to room temperature, concentrated under reduced pressure. To the resulting residue was added a 8M aqueous solution of sodium hydroxide, and then the mixture was extracted with ethyl acetate. This organic layer was sequentially washed with water and a saturated aqueous solution of sodium chloride, dried over anhydrous sodium sulfate, and then concentrated under reduced pressure. The resulting residue was purified by silica gel column chromatography (eluent: n-hexane/ethyl acetate=1/1) to give the titled compound (318 mg).

¹H-NMR (CDCl₃) δ: 3.75 (br s, 2H), 6.00 (s, 1H), 7.11-7.15 (m, 2H), 7.44-7.47 (m, 2H).

(4) (R)-3-[1,1,1-Trifluoropropan-2-yloxy]phenyl boronic acid

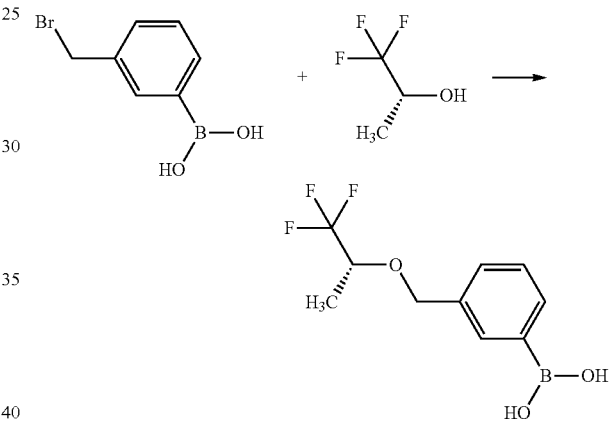

A solution of (R)-1,1,1-trifluoropropan-2-ol (212 mg) in N,N-dimethylformamide (1.5 ml) was cooled to 0° C., sodium hydride (74 mg, 60 wt. % oil dispersion) and 3-(bromomethyl)phenyl boronic acid (100 mg) were sequentially added thereto, and the mixture was stirred at room temperature for 2 hours. To this reaction mixture were added water and an 1M aqueous solution of hydrochloric acid, and the mixture was extracted with ethyl acetate. This organic layer was washed with water and a saturated aqueous solution of sodium chloride, dried over anhydrous sodium sulfate, and then concentrated under reduced pressure to give the titled compound (147 mg).

(5) 1-(4-Fluorophenyl)-5-[3-((R)-2,2,2-trifluoro-1-methylethoxymethyl)phenyl]-1H-pyrazol-3-ylamine

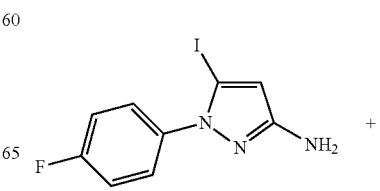

-continued

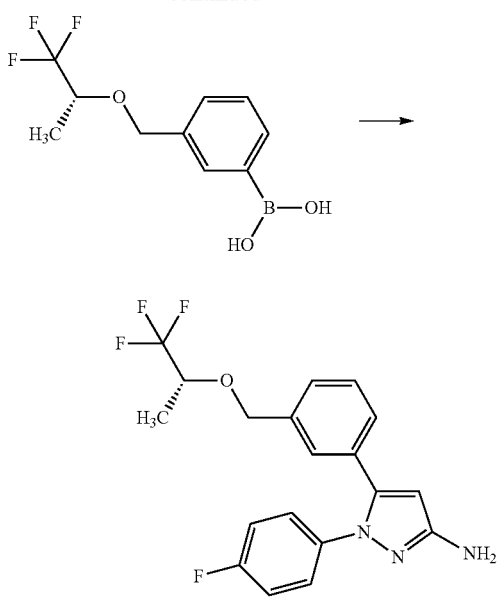

To a solution of 1-(4-fluorophenyl)-5-iodo-1H-pyrazol-3-ylamine (70 mg) in 1,2-dimethoxyethane (0.7 ml) were sequentially added (R)-3-(1,1,1-trifluoropropan-2-yloxy)phenyl boronic acid (104 mg), a 2M aqueous solution of sodium carbonate (0.35 ml), tricyclohexylphosphine (13.0 mg) and palladium (II) acetate (5.2 mg) at room temperature, and the mixture was stirred at 100° C. for 15 hours. This reaction mixture was cooled to room temperature, filtered through Celite, and subjected to elution with ethyl acetate. The filtrate was extracted with ethyl acetate, the resulting organic layer was washed with a saturated aqueous solution of sodium chloride, dried over anhydrous sodium sulfate, and then concentrated under reduced pressure. The resulting residue was purified by silica gel column chromatography (eluent: n-hexane/ethyl acetate=1/1) to give the titled compound (52 mg).

$^1$H-NMR (CDCl$_3$) δ: 1.28 (d, 3H, J=6.51 Hz), 3.74-3.80 (m, 2H), 3.76-3.78 (m, 1H), 4.56 (d, 1H, J=11.86 Hz), 4.66 (d, 1H, J=11.86 Hz), 5.92 (s, 1H), 6.96-6.99 (m, 2H), 7.15-7.21 (m, 4H), 7.29-7.29 (m, 2H).

(6) (S)-5-Oxopyrrolidine-3-carboxylic acid{1-(4-fluorophenyl)-5-[3-((R)-2,2,2-trifluoro-1-methylethoxymethyl)phenyl]-1H-pyrazol-3-yl}amide -continued

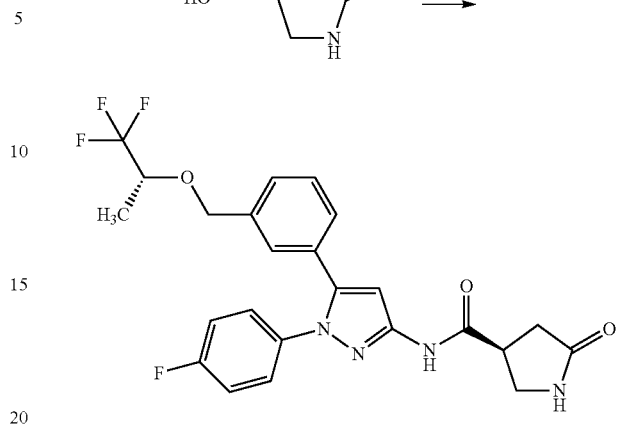

To a solution of 1-(4-fluorophenyl)-5-[3-((R)-2,2,2-trifluoro-1-methylethoxymethyl)phenyl]-1H-pyrazol-3-ylamine (52 mg) in N,N-dimethylacetamide (0.5 ml) were sequentially added (S)-5-oxopyrrolidine-3-carboxylic acid (20 mg) prepared according to the same procedures as Preparation 5 and WSC.HCl (40 mg) at room temperature, and the mixture was stirred for 0.5 hours. To this reaction mixture was added water, and then the precipitated solid was collected by filtration. This solid was purified by silica gel thin-layer chromatography (eluent: chloroform/methanol=9/1). To the resulting solid were added water and a small amount of methanol, and the mixture was stirred. A solid was collected by filtration from this suspension, and dried under reduced pressure to give the titled compound (37 mg).

$^1$H-NMR (DMSO-D6) δ: 1.20 (d, 3H, J=6.5 Hz), 2.38-2.39 (m, 2H), 3.33-3.34 (m, 1H), 3.39-3.43 (m, 1H), 3.49-3.51 (m, 1H), 4.09-4.11 (m, 1H), 4.59 (d, 1H, J=12.1 Hz), 4.63 (d, 1H, J=12.1 Hz), 6.92 (s, 1H), 7.18-7.39 (m, 8H), 7.63 (s, 1H), 10.85 (s, 1H).

Preparation 19

Example 239

Synthesis of ((S)-5-oxopyrrolidine-3-carboxylic acid{1-(4-fluorophenyl)-5-[3-fluoro-5-((R)-2,2,2-trifluoro-1-methylethoxymethyl)phenyl]-1H-pyrazol-3-yl}amide)

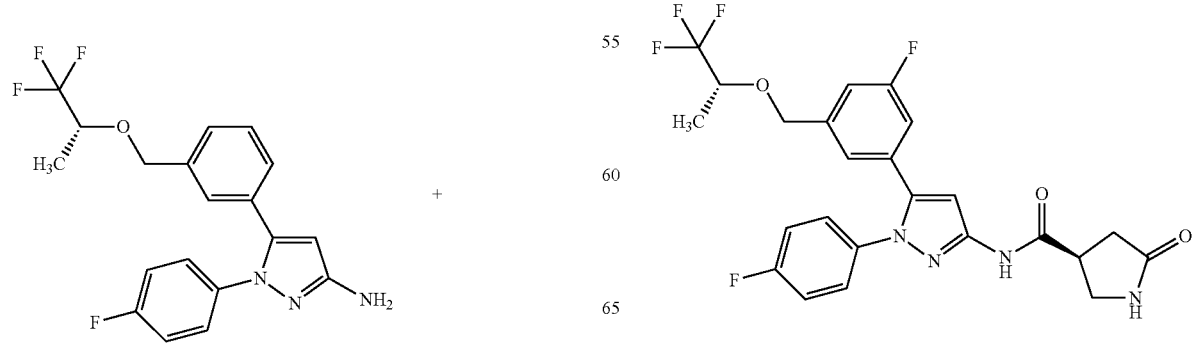

(1) 1-(4-Fluorophenyl)-5-[3-fluoro-5-((R)-2,2,2-trifluoro-1-methylethoxymethyl)phenyl]-1H-pyrazol-3-ylamine

(2) (S)-5-Oxopyrrolidine-3-carboxylic acid{1-(4-fluorophenyl)-5-[3-fluoro-5-((R)-2,2,2-trifluoro-1-methylethoxymethyl)phenyl]-1H-pyrazol-3-yl}amide

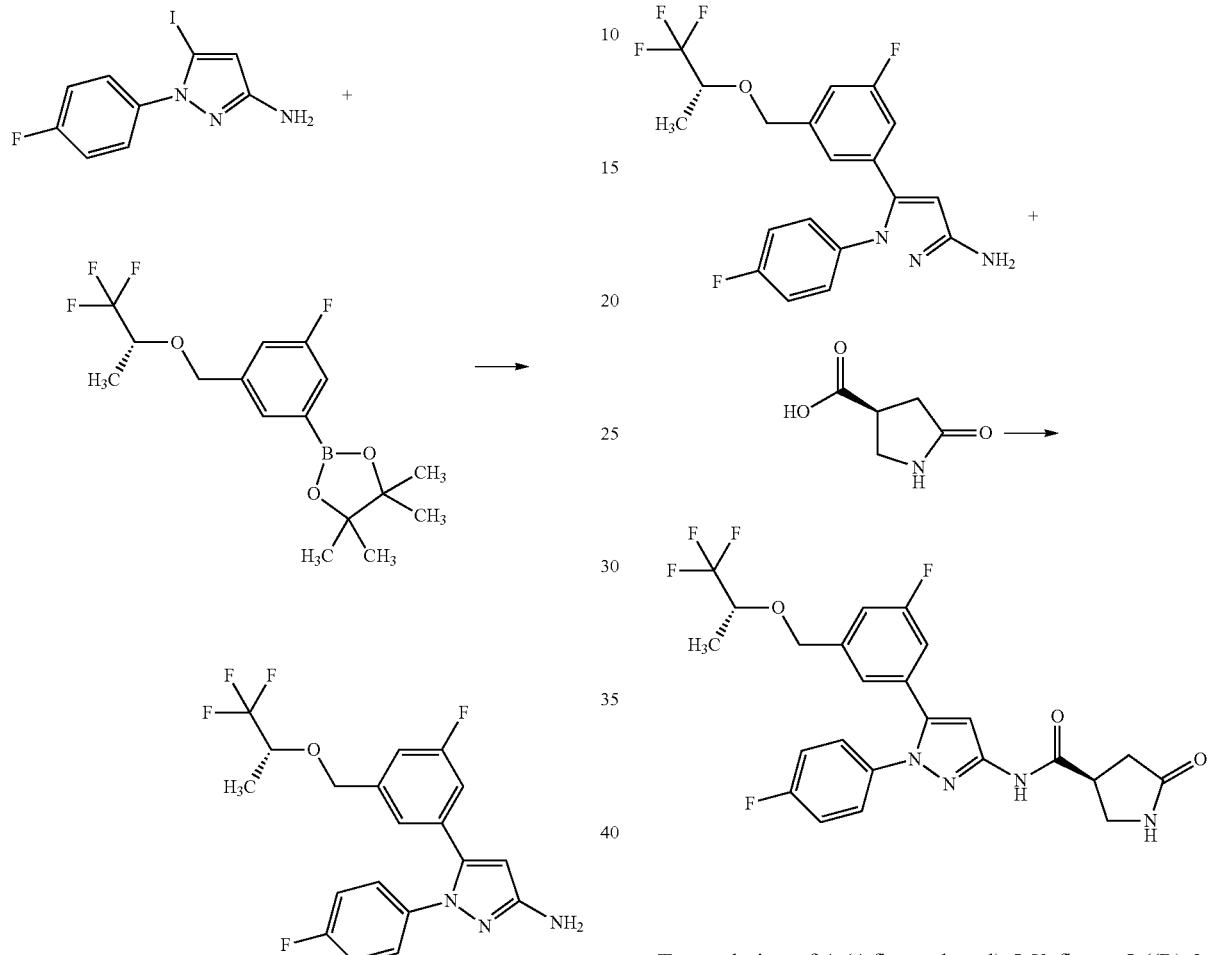

To a solution of 1-(4-fluorophenyl)-5-iodo-1H-pyrazol-3-ylamine (38 mg) prepared in Preparation 18 in 1,4-dioxane (0.4 ml) were sequentially added 2-[3-fluoro-5-((R)-2,2,2-trifluoro-1-methylethoxymethyl)phenyl]-4,4,5,5-tetramethyl-[1,3,2]dioxaborolane (52 mg) prepared according to the same procedures as Preparation 15, palladium (II) acetate (3 mg), tricyclohexylphosphine (7 mg) and a 2M aqueous solution of potassium carbonate (0.2 ml) at room temperature, and the mixture was stirred at 105° C. for 4 hours. After removing an aqueous layer of the reaction mixture, an organic layer was filtered through silica gel (5 g), and subjected to elution with ethyl acetate. The filtrate was concentrated under reduced pressure, the resulting residue was purified by silica gel thin-layer chromatography (eluent: n-hexane/ethyl acetate=1/1) to give the titled compound.

To a solution of 1-(4-fluorophenyl)-5-[3-fluoro-5-((R)-2,2,2-trifluoro-1-methylethoxymethyl)phenyl]-1H-pyrazol-3-ylamine prepared in the previous step (about 0.125 mmol) in dimethylformamide (0.5 ml) were sequentially added (S)-5-oxopyrrolidine-3-carboxylic acid (18 mg) prepared according to the same procedures as Preparation 14 and WSC.HCl (29 mg) at room temperature, and the mixture was stirred for 3 hours. To this reaction mixture was added water, and the mixture was extracted with ethyl acetate. This organic layer was concentrated under reduced pressure, the resulting residue was purified by silica gel thin-layer chromatography (eluent: chloroform/methanol=10/1). To the resulting solid were added water and a small amount of methanol, and the mixture was stirred. A solid was collected from this suspension by filtration, and was dried under reduced pressure to give the titled compound (31 mg).

$^1$H-NMR (CDCl$_3$) δ: 1.31 (d, 3H, J=6.4 Hz), 2.61 (dd, 1H, J=16.8, 9.6 Hz), 2.78 (dd, 1H, J=16.8, 8.4 Hz), 3.31-3.42 (m, 1H), 3.61 (t, 1H, J=8.8 Hz), 3.67-3.83 (m, 2H), 4.55 (d, 1H, J=12.0 Hz), 4.65 (d, 1H, J=12.0 Hz), 6.04 (s, 1H), 6.85 (d, 1H, J=9.2 Hz), 6.98-7.10 (m, 5H), 7.19-7.25 (m, 2H), 8.48 (s, 1H).

Preparation 20

Synthesis of (R)-2-oxoimidazolidine-4-carboxylic acid (1) (R)-2-Oxoimidazolidine-1,5-dicarboxylic acid 1-benzyl ester Under ice-cooling, to a 1M aqueous solution of sodium hydroxide (124 ml) was added dropwise bromine (6.60 ml), and then after adding (R)-2-benzyloxycarbonylaminosuccinamic acid (10.0 g), the mixture was stirred at 55° C. for 3 hours. This reaction solution was cooled to room temperature, washed twice with diethyl ether, and then a 6M aqueous solution of hydrochloric acid (21 ml) was added thereto. This reaction mixture was left to stand at 4° C. for 3 days, and a precipitated solid was collected by filtration to give the titled compound (6.16 g).

$^1$H-NMR (DMSO-D$_6$) δ: 3.19-3.22 (m, 1H), 3.63 (dd, 1H, J=10.2, 5.0 Hz), 4.67 (dd, 1H, J=10.2, 3.3 Hz), 5.14-5.18 (m, 2H), 7.28-7.40 (m, 5H), 7.56 (s, 1H), 13.24 (br s, 1H).

(2) (R)-2-Oxoimidazolidine-4-carboxylic acid

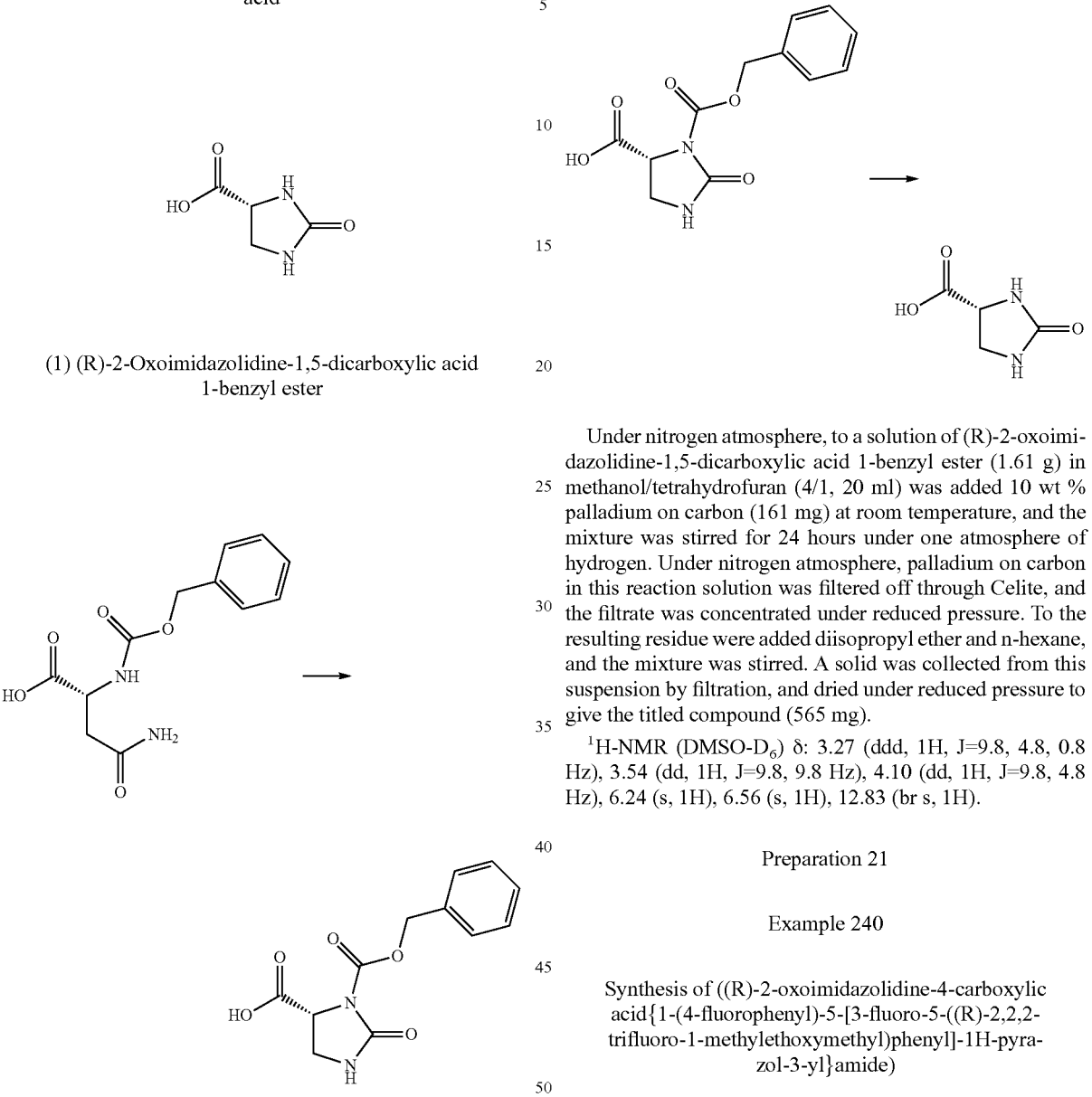

Under nitrogen atmosphere, to a solution of (R)-2-oxoimidazolidine-1,5-dicarboxylic acid 1-benzyl ester (1.61 g) in methanol/tetrahydrofuran (4/1, 20 ml) was added 10 wt % palladium on carbon (161 mg) at room temperature, and the mixture was stirred for 24 hours under one atmosphere of hydrogen. Under nitrogen atmosphere, palladium on carbon in this reaction solution was filtered off through Celite, and the filtrate was concentrated under reduced pressure. To the resulting residue were added diisopropyl ether and n-hexane, and the mixture was stirred. A solid was collected from this suspension by filtration, and dried under reduced pressure to give the titled compound (565 mg).

$^1$H-NMR (DMSO-D$_6$) δ: 3.27 (ddd, 1H, J=9.8, 4.8, 0.8 Hz), 3.54 (dd, 1H, J=9.8, 9.8 Hz), 4.10 (dd, 1H, J=9.8, 4.8 Hz), 6.24 (s, 1H), 6.56 (s, 1H), 12.83 (br s, 1H).

Preparation 21

Example 240

Synthesis of ((R)-2-oxoimidazolidine-4-carboxylic acid{1-(4-fluorophenyl)-5-[3-fluoro-5-((R)-2,2,2-trifluoro-1-methylethoxymethyl)phenyl]-1H-pyrazol-3-yl}amide)

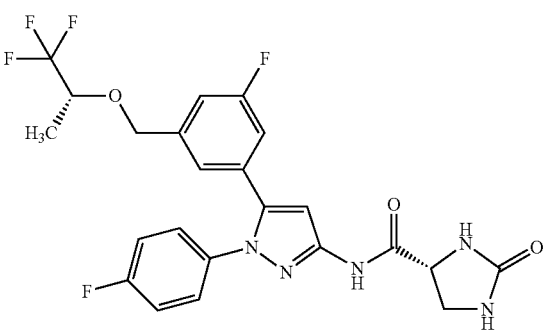 [SMILES: C[C@@H](OCc1cc(F)cc(-c2cc(NC(=O)[C@H]3CNC(=O)N3)nn2-c2ccc(F)cc2)c1)C(F)(F)F]

(1) 1-(4-Fluorophenyl)-5-[3-fluoro-5-((R)-2,2,2-trifluoro-1-methylethoxymethyl)phenyl]-1H-pyrazol-3-ylamine (2) (R)-2-Oxoimidazolidine-4-carboxylic acid{1-(4-fluorophenyl)-5-[3-fluoro-5-((R)-2,2,2-trifluoro-1-methylethoxymethyl)phenyl]-1H-pyrazol-3-yl}amide

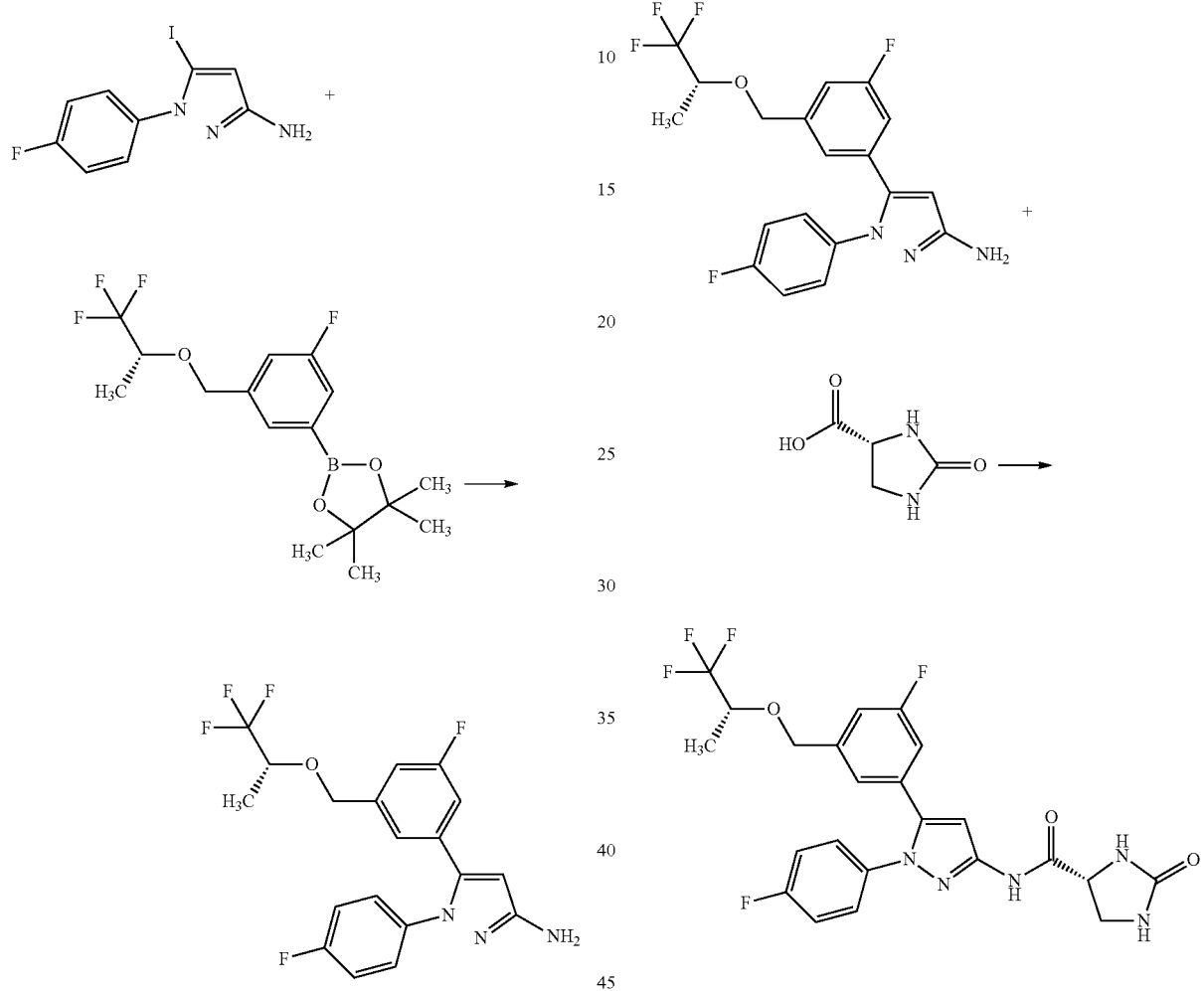

To a solution of 1-(4-fluorophenyl)-5-iodo-1H-pyrazol-3-ylamine (84 mg) prepared according to the same procedures as Preparation 18 in 1,4-dioxane (1.0 ml) were sequentially added 2-[3-fluoro-5-((R)-2,2,2-trifluoro-1-methylethoxymethyl)phenyl]-4,4,5,5-tetramethyl-[1,3,2]dioxaborolane (106 mg) prepared according to the same procedures as Preparation 15, palladium (II) acetate (7 mg), tricyclohexylphosphine (17 mg) and a 2M aqueous solution of potassium carbonate (0.5 ml) at room temperature, and the mixture was stirred at 105° C. for 2 hours. This reaction mixture was cooled to room temperature and after removing an aqueous layer, an organic layer was filtered through silica gel (5 g), and subjected to elution with ethyl acetate. The filtrate was concentrated under reduced pressure, and the resulting residue was purified by silica gel thin-layer chromatography (eluent: n-hexane/ethyl acetate=3/2) to give the titled compound.

To a solution of 1-(4-fluorophenyl)-5-[3-fluoro-5-((R)-2,2,2-trifluoro-1-methylethoxymethyl)phenyl]-1H-pyrazol-3-ylamine (about 0.277 mmol) prepared in the previous step in chloroform (1 ml) were sequentially added (R)-2-oxoimidazolidine-4-carboxylic acid (40 mg) and WSC.HCl (64 mg) at room temperature, and the mixture was stirred for 3 hours. This reaction mixture was purified by silica gel thin-layer chromatography (eluent: chloroform/methanol=10/1). To the resulting solid were added water and a small amount of methanol, and the mixture was stirred. A solid was collected from this suspension by filtration and was dried under reduced pressure to give the titled compound (56 mg).

$^1$H-NMR (DMSO-D$_6$) δ: 1.20 (d, 3H, J=6.0 Hz), 3.35 (dd, 1H, J=8.6, 6.2 Hz), 3.58 (dd, 1H, J=9.3, 8.6 Hz), 4.12 (tq, 1H, J=9.7, 6.0 Hz), 4.31 (dd, 1H, J=9.3, 6.2 Hz), 4.60 (d, 1H, J=12.5 Hz), 4.63 (d, 1H, J=12.5 Hz), 6.33 (s, 1H), 6.59 (s, 1H), 6.98 (s, 1H), 7.02-7.07 (m, 2H), 7.18 (d, 1H, J=9.6 Hz), 7.23-7.35 (m, 4H), 10.72 (s, 1H).

Preparation 22

Example 241

Synthesis of ((S)-5-oxopyrrolidine-3-carboxylic acid{5-[3-chloro-5-((R)-2,2,2-trifluoro-1-methyl-ethoxymethyl)phenyl]-1-phenyl-1H-pyrazol-3-yl}amide)

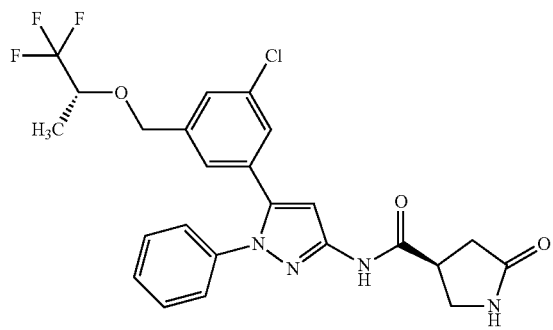 [SMILES: C[C@@H](OCc1cc(Cl)cc(-c2cc(NC(=O)[C@@H]3CNC(=O)C3)nn2-c2ccccc2)c1)C(F)(F)F]

(1) 1-Chloro-3-((R)-2,2,2-trifluoro-1-methyl-ethoxymethyl)benzene

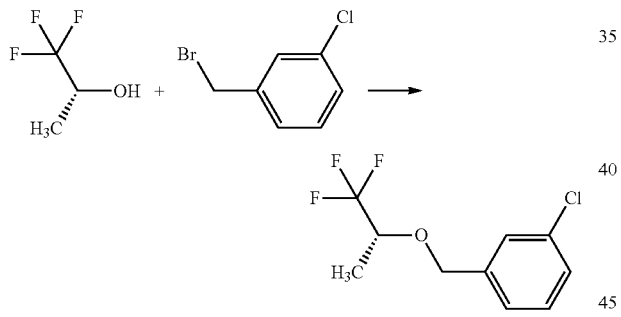

Under argon atmosphere, a suspension of sodium hydride (77 mg, 60 wt % oil dispersion) in N,N-dimethylformamide (2.0 ml) was cooled to 0° C., a solution of (R)-1,1,1-trifluoropropan-2-ol (213 mg) in N,N-dimethylformamide (2.0 ml) was added thereto, and the mixture was stirred for 15 minutes. Then, a solution of 1-bromomethyl-3-chlorobenzene (311 mg) in N,N-dimethylformamide (2.0 ml) was added thereto, and then the mixture was stirred at room temperature for 2.5 hours. To this reaction mixture was added water, and the mixture was extracted with ethyl acetate. This organic layer was washed with a saturated aqueous solution of sodium chloride, dried over magnesium sulfate, and then concentrated under reduced pressure. The resulting residue was purified by silica gel chromatography (eluent: n-hexane/ethyl acetate=1/0 to 19/1) to give the titled compound (307 mg).

$^1$H-NMR (CDCl$_3$) δ: 1.35 (d, 3H, J=6.47 Hz), 3.84 (qq, 1H, J=6.47, 9.40 Hz), 4.62 (d, 1H, J=12.00 Hz), 4.73 (d, 1H, J=12.00 Hz), 7.21-7.24 (m, 1H), 7.27-7.30 (m, 2H), 7.34 (s 1H)

(2) 2-[3-Chloro-5-((R)-2,2,2-trifluoro-1-methyl-ethoxymethyl)phenyl]-4,4,5,5-tetramethyl[1,3,2]dioxaborolane

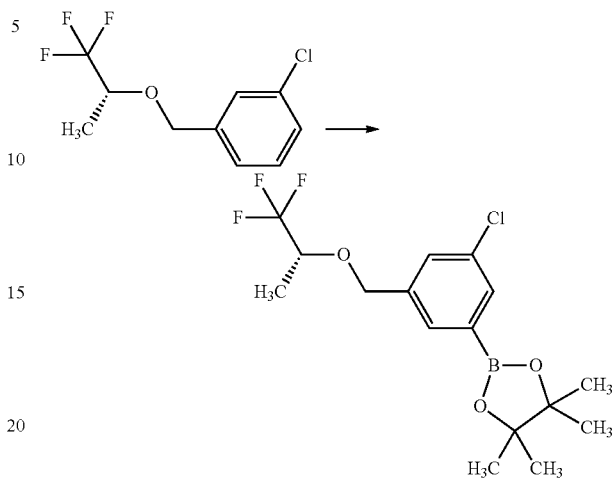

Under argon atmosphere, to a solution of 1-chloro-3-((R)-2,2,2-trifluoro-1-methylethoxymethyl)benzene (307 mg) in tetrahydrofuran (6.0 ml) were sequentially added bispinacolate diboron (362 mg), 4,4'-di-tert-butyl-2,2'-dipyridyl (18 mg) and di-μ-methoxobis(1,5-cyclooctadiene)diiridium (I) (22 mg) at room temperature, and then the mixture was heated to reflux for 13 hours. After cooling this reaction mixture to room temperature, a saturated aqueous solution of sodium hydrogen carbonate and ethyl acetate were added thereto, the mixture was filtered through Celite. The filtrate was extracted with ethyl acetate. The resulting organic layer was washed with a saturated aqueous solution of sodium chloride, dried over anhydrous magnesium sulfate, and then concentrated under reduced pressure. The resulting residue was purified by silica gel thin-layer chromatography (eluent: n-hexane/ethyl acetate=9/1) to give the titled compound (374 mg).

$^1$H-NMR (CDCl$_3$) δ: 1.35 (m, 15H), 3.83 (qq, 1H, J=6.47, 9.40 Hz), 4.59 (d, 1H, J=12.00 Hz), 4.73 (d, 1H, J=12.00 Hz), 7.46 (s, 1H), 7.59 (d, 1H, J=9.60 Hz), 7.72 (s, 1H).

(3) 5-[3-Chloro-5-((R)-2,2,2-trifluoro-1-methyl-ethoxymethyl)phenyl]-1-phenyl-1H-pyrazol-3-ylamine

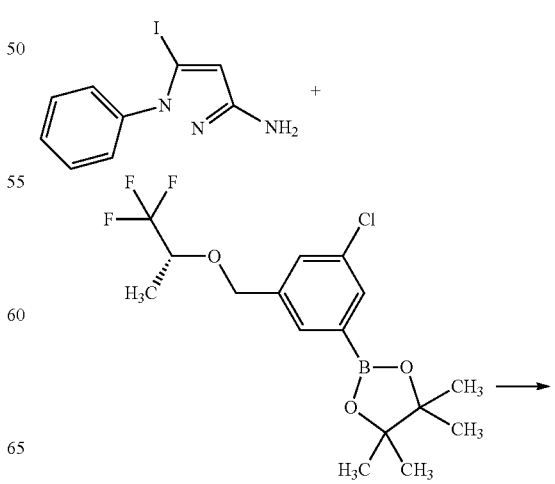

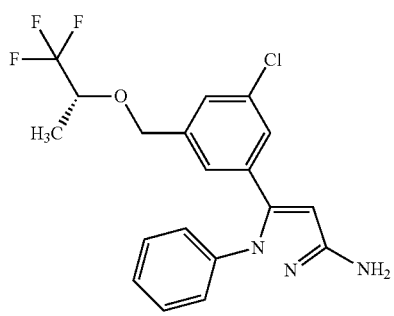

Under argon atmosphere, to 2-[3-chloro-5-((R)-2,2,2-trifluoro-1-methylethoxymethyl)phenyl]-4,4,5,5-tetramethyl[1,3,2]dioxaborolane (269 mg) were sequentially added a solution of 5-iodo-1-phenyl-1H-pyrazol-3-ylamine (181 mg) prepared according to the same procedures as Preparation 2 in 1,2-dimethoxyethane (2.0 ml), a 2M aqueous solution of sodium carbonate (1.0 ml), tricyclohexylphosphine (36 mg) and palladium (II) acetate (15 mg) at room temperature, and the mixture was stirred at 100° C. for 2 hours. This reaction mixture was cooled to room temperature, a saturated aqueous solution of sodium hydrogen carbonate and ethyl acetate were added thereto, the mixture was filtered through Celite, and subjected to elution with ethyl acetate. The filtrate was extracted with ethyl acetate. The resulting organic layer was washed with a saturated aqueous solution of sodium chloride, dried over anhydrous magnesium sulfate, and then concentrated under reduced pressure. The resulting residue was purified by silica gel thin-layer chromatography (eluent: n-hexane/ethyl acetate=3/7) to give the titled compound (196 mg).

(4) (S)-5-Oxopyrrolidine-3-carboxylic acid{5-[3-chloro-5-((R)-2,2,2-trifluoro-1-methylethoxymethyl)phenyl]-1-phenyl-1H-pyrazol-3-yl}amide

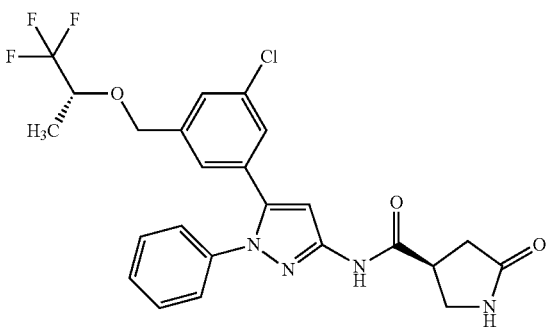

To a solution of 5-[3-chloro-5-((R)-2,2,2-trifluoro-1-methylethoxymethyl)phenyl]-1-phenyl-1H-pyrazol-3-ylamine (79 mg) in N,N-dimethylacetamide (1.0 ml) were sequentially added (S)-5-oxopyrrolidine-3-carboxylic acid (31 mg) prepared according to the same procedures as Preparation 14 and WSC.HCl (47 mg) at room temperature, and the mixture was stirred overnight. To this reaction mixture was added water, and then the precipitated solid was collected by filtration. This solid was purified by silica gel thin-layer chromatography (eluent: chloroform/methanol=9/1). To the resulting solid were added water and a small amount of methanol, and the mixture was stirred. A solid was collected from this suspension by filtration and was dried under reduced pressure to give the titled compound (60 mg).

¹H-NMR (DMSO-D6) δ: 1.18 (d, 3H, J=6.5 Hz), 2.36-2.38 (m, 2H), 3.32-3.33 (m, 1H), 3.37-3.41 (m, 1H), 3.46-3.49 (m, 1H), 4.10 (qq, 1H, J=6.5, 9.4 Hz), 4.57 (d, 1H, J=12.7 Hz), 4.61 (d, 1H, J=12.7 Hz), 6.98 (s, 1H), 7.19-7.20 (m, 2H), 7.25-7.27 (m, 2H), 7.35-7.45 (m, 4H), 7.63 (s, 1H), 10.88 (s, 1H).

Preparation 23

Example 242

Synthesis of ((S)-5-oxopyrrolidine-3-carboxylic acid{5-[3-chloro-5-((R)-2,2,2-trifluoro-1-methylethoxymethyl)phenyl]-1-(4-fluorophenyl)-1H-pyrazol-3-yl}amide)

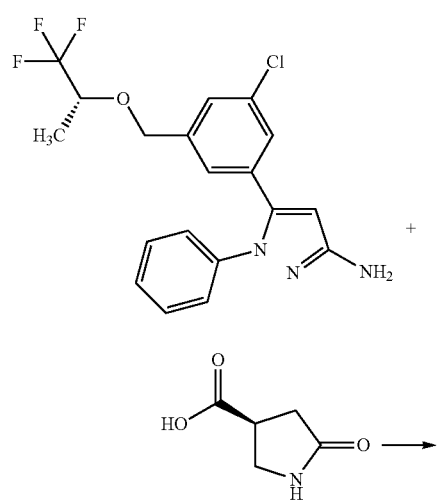

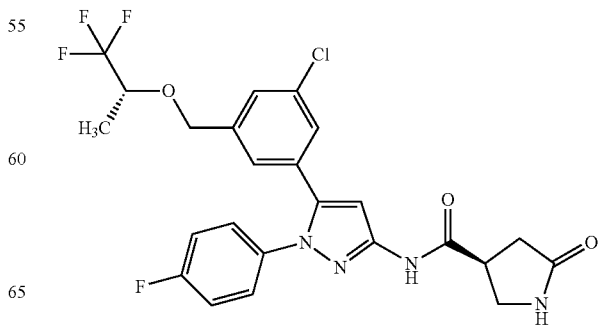

(1) 5-[3-Chloro-5-((R)-2,2,2-trifluoro-1-methyl-ethoxymethyl)phenyl]-1-(4-fluorophenyl)-1H-pyrazol-3-ylamine

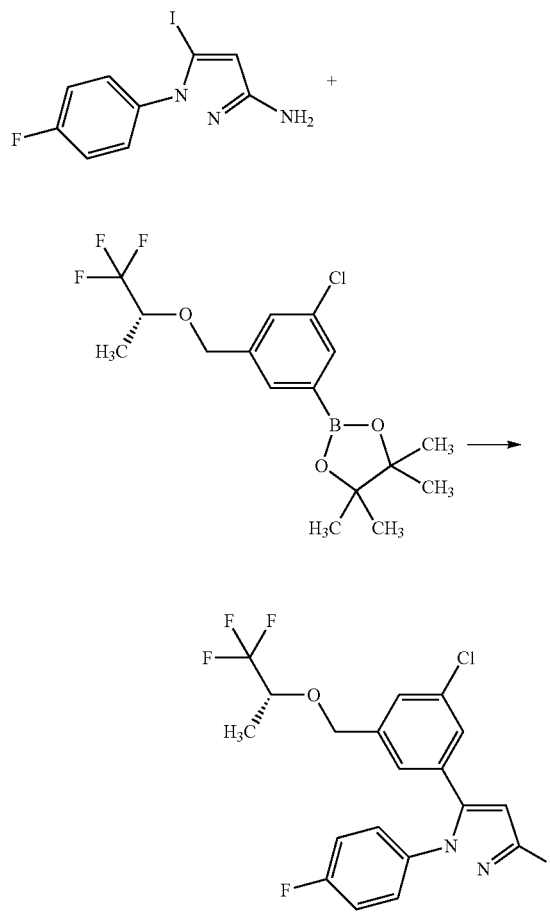

To a solution of 1-(4-fluorophenyl)-5-iodo-1H-pyrazol-3-ylamine (50 mg) prepared according to the same procedures as Preparation 18 in 1,2-dimethoxyethane (0.5 ml) were sequentially added 2-[3-chloro-5-((R)-2,2,2-trifluoro-1-methylethoxymethyl)phenyl]-4,4,5,5-tetramethyl-[1,3,2]dioxaborolane (72 mg) prepared according to the same procedures as Preparation 22, a 2M aqueous solution of sodium carbonate (0.25 ml), tricyclohexylphosphine (9.3 mg) and palladium (II) acetate (3.7 mg) at room temperature, and the mixture was stirred at 100° C. for 2 hours. This reaction mixture was cooled to room temperature, filtered through Celite, and subjected to elution with ethyl acetate. The filtrate was extracted with ethyl acetate, the resulting organic layer was washed with a saturated aqueous solution of sodium chloride, dried over anhydrous magnesium sulfate, and then concentrated under reduced pressure. The resulting residue was purified by silica gel column chromatography (eluent: n-hexane/ethyl acetate=1/1) to give the titled compound (79 mg).

¹H-NMR (CDCl₃) δ: 1.29 (d, 3H, J=6.47 Hz), 3.75 (qq, 1H, J=6.47, 9.40 Hz), 3.78 (br s, 2H), 4.50 (d, 1H, J=12.02 Hz), 4.61 (d, 1H, J=12.02 Hz), 5.93 (s, 1H), 6.99-7.02 (m, 3H), 7.18-7.20 (m, 3H), 7.26-7.28 (m, 1H).

(2) (S)-5-Oxopyrrolidine-3-carboxylic acid{5-[3-chloro-5-((R)-2,2,2-trifluoro-1-methylethoxymethyl)phenyl]-1-(4-fluorophenyl)-1H-pyrazol-3-yl}amide

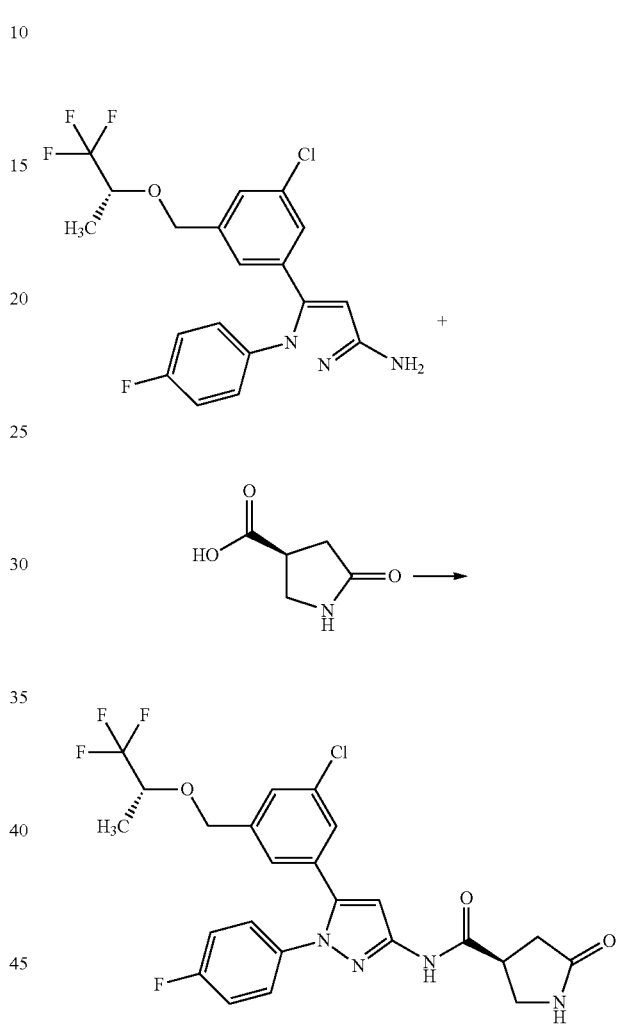

To a solution of 5-[3-chloro-5-((R)-2,2,2-trifluoro-1-methylethoxymethyl)phenyl]-1-(4-fluorophenyl)-1H-pyrazol-3-ylamine (79 mg) in chloroform (0.4 ml) were sequentially added (S)-5-oxopyrrolidine-3-carboxylic acid (26 mg) prepared according to the same procedures as Preparation 14 and WSC.HCl (47 mg) at room temperature, and the mixture was stirred for 2 hours. This reaction mixture was purified by silica gel thin-layer chromatography (eluent: chloroform/methanol=9/1). To the resulting solid were added water and a small amount of methanol, and the mixture was stirred. A solid was collected from this suspension by filtration and was dried under reduced pressure to give the titled compound (43 mg).

¹H-NMR (DMSO-D6) δ: 1.18 (d, 3H, J=6.5 Hz), 2.36-2.38 (m, 2H), 3.32-3.33 (m, 1H), 3.37-3.41 (m, 1H), 3.46-3.49 (m, 1H), 4.10 (qq, 1H, J=6.5, 9.4 Hz), 4.57 (d, 1H, J=12.7 Hz), 4.61 (d, 1H, J=12.7 Hz), 6.97 (s, 1H), 7.13 (s, 1H), 7.23-7.32 (m, 5H), 7.37 (s, 1H), 7.61 (s, 1H), 10.86 (s, 1H).

Preparation 24

Example 243

Synthesis of (S)-5-oxopyrrolidine-3-carboxylic acid [5-[3-chloro-5-(2,2,2-trifluoro-1,1-dimethyl-ethoxymethyl)phenyl]-1-phenyl-1H-pyrazol-3-yl] amide)

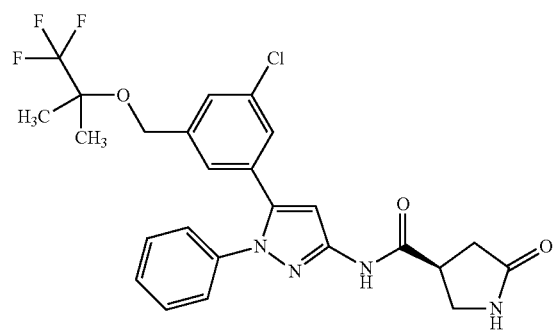 [SMILES: CC(C)(OCc1cc(Cl)cc(-c2cc(NC(=O)[C@@H]3CNC(=O)C3)nn2-c2ccccc2)c1)C(F)(F)F]

(1) 1-Chloro-3-(2,2,2-trifluoro-1,1-dimethyl-ethoxymethyl)benzene

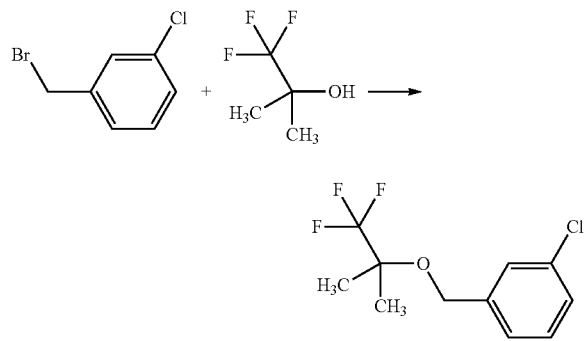

To a suspension cooled to 0° C. of sodium hydride (126 mg, 60 wt. % oil dispersion) in N,N-dimethylformamide (5 ml) was added dropwise, 1,1,1-trifluoro-2-methylpropan-2-ol (320 μL) under argon atmosphere, and the mixture was stirred for 15 minutes. To this reaction mixture was added dropwise 1-bromomethyl-3-chlorobenzene (320 μL), and the mixture was stirred for 3 hours. To this reaction mixture was added water, and the mixture was extracted with ethyl acetate. This organic layer was washed with water and a saturated aqueous solution of sodium chloride, dried over anhydrous sodium sulfate, and then concentrated under reduced pressure. The resulting residue was purified by silica gel column chromatography (eluent: n-hexane/ethyl acetate=1/0 to 40/1) to give the titled compound (389 mg).

$^1$H-NMR (CDCl$_3$) δ: 1.45 (s, 6H), 4.50 (s, 2H), 7.15-7.30 (m, 3H), 7.34 (s, 1H).

(2) 2-[3-Chloro-5-(2,2,2-trifluoro-1,1-dimethyl-ethoxymethyl)phenyl]-4,4,5,5-tetramethyl-[1,3,2]dioxaborolane

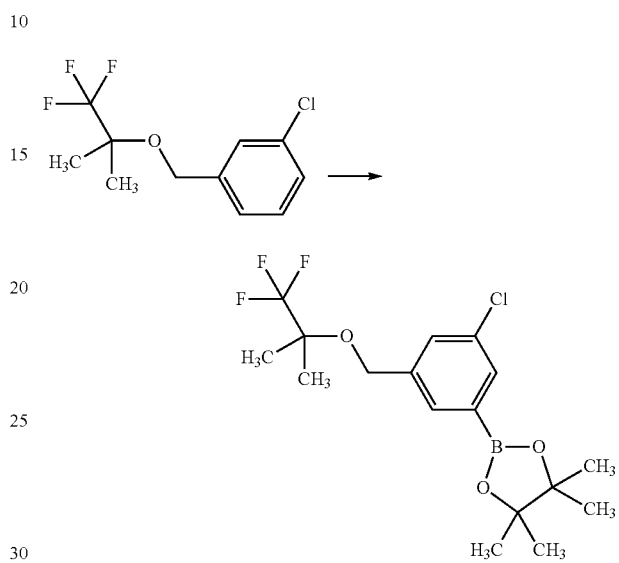

Under argon atmosphere, to a solution of 1-chloro-3-(2,2,2-trifluoro-1,1-dimethylethoxymethyl)benzene (389 mg) in tetrahydrofuran (4 ml) were sequentially added bispinacolate diboron (430 mg), 4,4'-di-tert-butyl-2,2'-dipyridyl (21 mg), di-μ-methoxobis(1,5-cyclooctadiene)diiridium (I) (29 mg) at room temperature, and the mixture was heated to reflux for 13 hours. This reaction mixture was cooled to room temperature, a saturated aqueous solution of sodium hydrogen carbonate was added thereto, and the mixture was extracted with ethyl acetate. This organic layer was dried over anhydrous sodium sulfate, and concentrated under reduced pressure. The resulting residue was purified by silica gel column chromatography (eluent: n-hexane/ethyl acetate=100/1 to 20/1) to give the titled compound (481 mg).

$^1$H-NMR (CDCl$_3$) δ: 1.34 (s, 12H), 1.44 (s, 6H), 4.57 (s, 2H), 7.45 (s, 1H), 7.57 (s, 1H), 7.69 (s, 1H).

(3) 5-[3-Chloro-5-(2,2,2-trifluoro-1,1-dimethyl-ethoxymethyl)phenyl]-1-phenyl-1H-pyrazol-3-ylamine

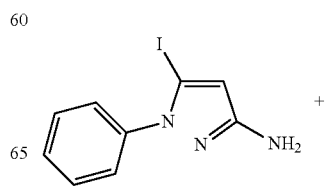

153
-continued

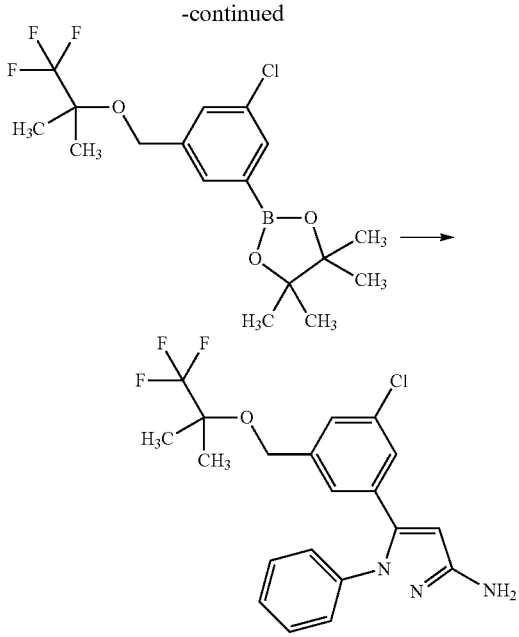

Under argon atmosphere, to a solution of 5-iodo-1-phenyl-1H-pyrazol-3-ylamine (40 mg) prepared according to the same procedures as Preparation 2 in 1,2-dimethoxyethane (1.0 ml) were sequentially added 2-[3-chloro-5-(2,2,2-trifluoro-1,1-dimethylethoxymethyl)phenyl]-4,4,5,5-tetramethyl-[1,3,2]dioxaborolane (64 mg), palladium (II) acetate (3 mg), tricyclohexylphosphine (8 mg) and a 2M aqueous solution of sodium carbonate (0.5 ml) at room temperature, and the mixture was stirred at 100° C. for 13 hours. This reaction mixture was cooled to room temperature, and then purified by silica gel column chromatography (eluent: n-hexane/ethyl acetate 3/2 to 1/1) to give the titled compound (62 mg).

$^1$H-NMR (CDCl$_3$) δ: 1.35 (s, 6H), 3.77 (br s, 2H), 4.46 (s, 2H), 5.93 (s, 1H), 7.00 (s, 1H), 7.15 (s, 1H), 7.20-7.26 (m, 4H), 7.28-7.33 (m, 2H).

(4) (S)-5-Oxopyrrolidine-3-carboxylic acid{5-[3-chloro-5-(2,2,2-trifluoro-1,1-dimethylethoxymethyl)phenyl]-1-phenyl-1H-pyrazol-3-yl}amide)

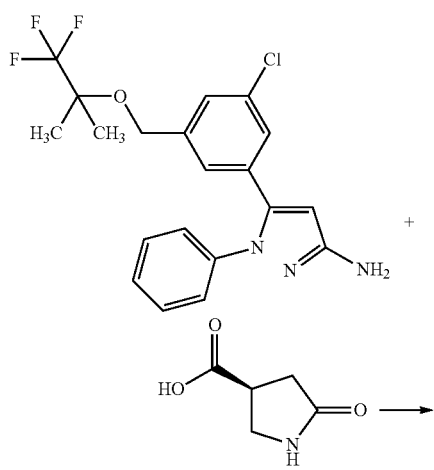

154
-continued

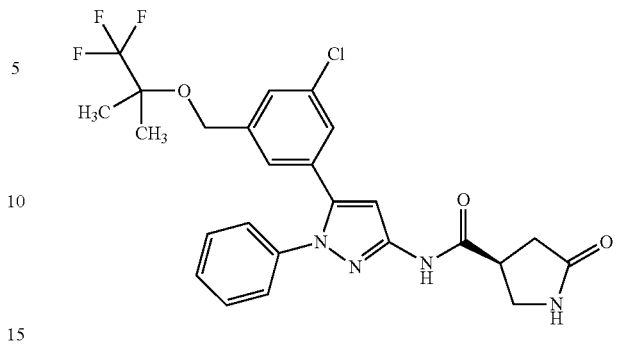

Under argon atmosphere, to a solution of 5-[3-chloro-5-(2,2,2-trifluoro-1,1-dimethylethoxymethyl)phenyl]-1-phenyl-1H-pyrazol-3-ylamine (62 mg) in N,N-dimethylacetamide (1 ml) were sequentially added (S)-5-oxopyrrolidine-3-carboxylic acid (26 mg) prepared according to the same procedures as Preparation 14, WSC.HCl (40 mg) at room temperature, and the mixture was stirred for 1 hour. To this reaction mixture was added water, and the mixture was extracted with ethyl acetate. This organic layer was washed with a saturated aqueous solution of sodium chloride, dried over anhydrous sodium sulfate, and then concentrated under reduced pressure. The resulting residue was purified by silica gel thin-layer chromatography (eluent: chloroform/methanol=9/1). To the resulting solid were added water and a small amount of methanol, and the mixture was stirred. A solid was collected from this suspension by filtration, and was dried under reduced pressure to give the titled compound (35 mg).

$^1$H-NMR (DMSO-D$_6$) δ: 1.32 (s, 6H), 2.37-2.42 (m, 2H), 3.33-3.53 (m, 3H), 4.53 (s, 2H), 6.98 (s, 1H), 7.16 (s, 1H), 7.19 (s, 1H), 7.23-7.28 (m, 2H), 7.33-7.45 (m, 4H), 7.63 (s, 1H), 10.89 (s, 1H).

Preparation 25

Example 244

Synthesis of ((S)-5-oxopyrrolidine-3-carboxylic acid{1-(4-chlorophenyl)-5-[3-((R)-2,2,2-trifluoro-1-methylethoxymethyl)phenyl]-1H-pyrazol-3-yl}amide)

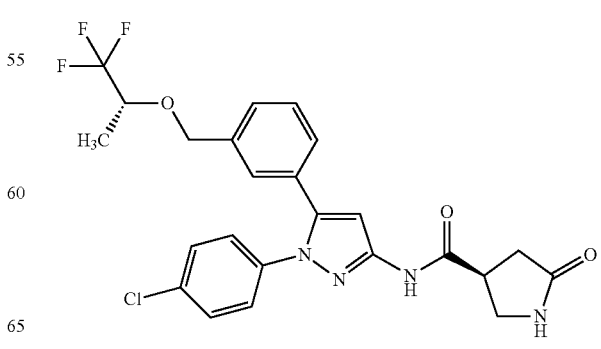

(1) 2-(3-Bromomethylphenyl)-4,4,5,5-tetramethyl-[1,3,2]dioxaborolane

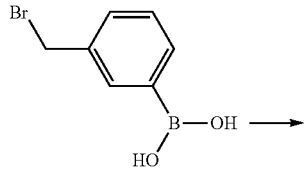

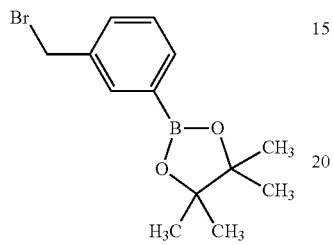

To a solution of 3-(bromomethyl)phenyl boronic acid (3.13 g) in ethyl acetate (45 ml) were sequentially added pinacol (1.72 g) and anhydrous magnesium sulfate (15 g) at room temperature, and the mixture was stirred for 8 hours. The insoluble substance was filtered off, and the filtrate was concentrated under reduced pressure to give the titled compound (4.43 g).

$^1$H-NMR (CDCl$_3$) δ: 1.33 (s, 12H), 4.49 (s, 2H), 7.31-7.37 (m, 1H), 7.46-7.50 (m, 1H), 7.70-7.74 (m, 1H), 7.79-7.82 (m, 1H).

(2) 4,4,5,5-Tetramethyl-2-[3-((R)-2,2,2-trifluoro-1-methylethoxymethyl)phenyl)-[1,3,2]dioxaborolane

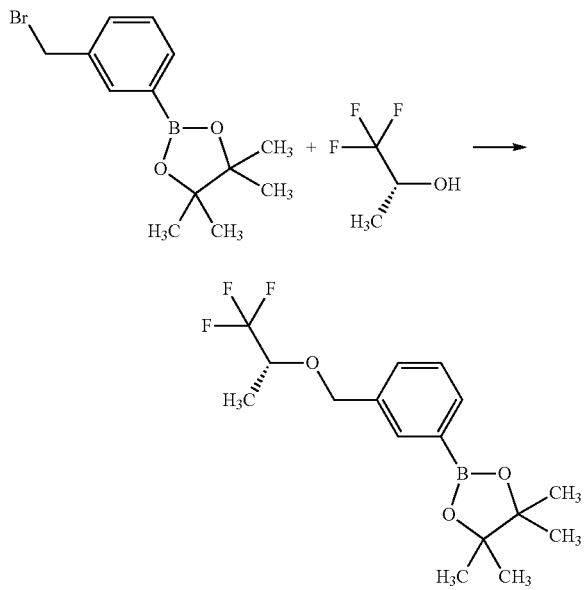

Under argon stream, to a solution of (R)-1,1,1-trifluoropropan-2-ol (3.32 g) in N,N-dimethylformamide (43 ml) was added portionwise sodium hydride (1.16 g, 60 wt % oil dispersion) at 0° C., and the mixture was stirred for 20 minutes. Then, 2-(3-bromomethylphenyl)-4,4,5,5-tetramethyl-[1,3,2] dioxaborolane (4.32 g) was added thereto, and then the mixture was stirred at room temperature overnight. To this reaction mixture were sequentially added water and a 2M aqueous solution of hydrochloric acid, and the mixture was extracted with ethyl acetate. This organic layer was washed with a saturated aqueous solution of sodium chloride, dried over anhydrous magnesium sulfate, and then concentrated under reduced pressure. The resulting residue was purified by silica gel column chromatography (eluent: n-hexane/ethyl acetate=1/0 to 19/1) to give the titled compound (3.43 g).

$^1$H-NMR (CDCl$_3$) δ: 1.31 (d, 3H, J=6.6 Hz), 1.35 (s, 12H), 3.77-3.89 (m, 1H), 4.62 (d, 1H, J=11.7 Hz), 4.76 (d, 1H, J=11.7 Hz), 7.35-7.43 (m, 1H), 7.46-7.54 (m, 1H), 7.71-7.81 (m, 2H).

(3) 1-(4-Chlorophenyl)-5-[3-((R)-2,2,2-trifluoro-1-methylethoxymethyl)phenyl]-1H-pyrazol-3-ylamine

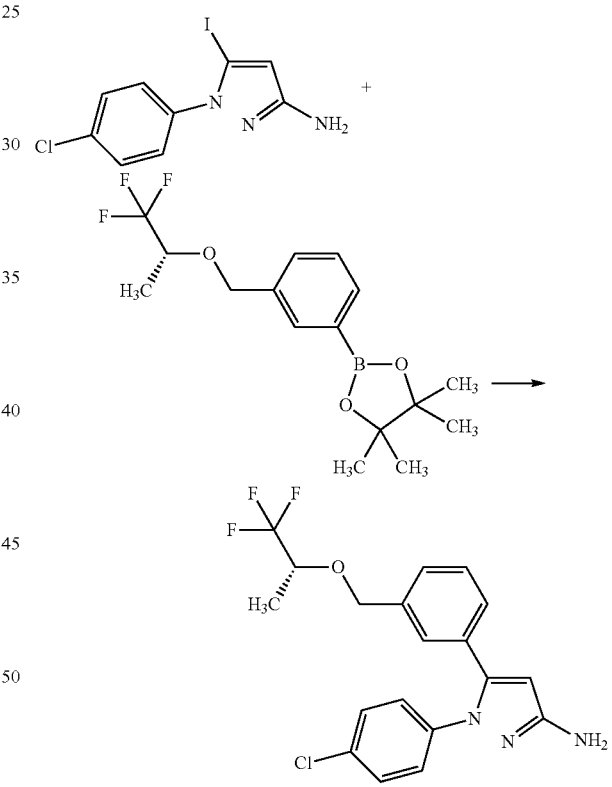

To a solution of 11-(4-chlorophenyl)-5-iodo-1H-pyrazol-3-ylamine (40 mg) prepared in Preparation 16 in 1,4-dioxane (0.4 ml) were sequentially added 4,4,5,5-tetramethyl-2-[3-((R)-2,2,2-trifluoro-1-methylethoxymethyl)phenyl)-[1,3,2] dioxaborolane (50 mg), palladium (II) acetate (3 mg), tricyclohexylphosphine (7 mg) and a 2M aqueous solution of potassium carbonate (0.2 ml) at room temperature, and the mixture was stirred at 105° C. for 4 hours. After removing an aqueous layer of the reaction mixture, an organic layer was filtered through silica gel (5 g), and subjected to elution with ethyl acetate. The filtrate was concentrated under reduced pressure, the resulting residue was purified by silica gel thin-layer chromatography (eluent: n-hexane/ethyl acetate=1/1) to give the titled compound.

(4) (S)-5-Oxopyrrolidine-3-carboxylic acid{1-(4-chlorophenyl)-5-[3-((R)-2,2,2-trifluoro-1-methyl-ethoxymethyl)phenyl]-1H-pyrazol-3-yl}amide

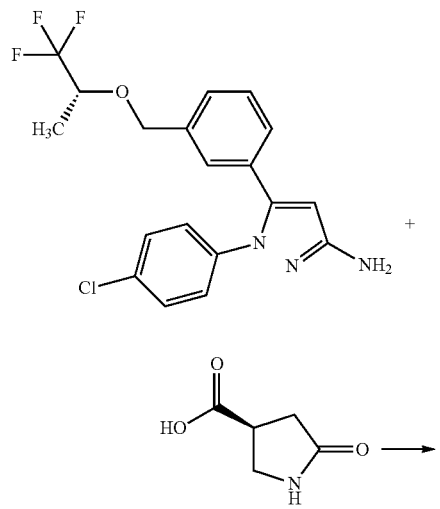

To a solution of 1-(4-chlorophenyl)-5-[3-((R)-2,2,2-trifluoro-1-methylethoxymethyl)phenyl]-1H-pyrazol-3-ylamine (about 0.125 mmol) prepared in the previous step in N,N-dimethylformamide (1 ml) were sequentially added (S)-5-oxopyrrolidine-3-carboxylic acid prepared according to the same procedures as preparation 14 (18 mg) and WSC.HCl (29 mg) at room temperature, and the mixture was stirred for 3 hours. To this reaction mixture was added water, and the mixture was extracted with ethyl acetate. The resulting organic layer was concentrated under reduced pressure, the resulting residue was purified by silica gel thin-layer chromatography (eluent: chloroform/methanol=10/1). To the resulting solid were added water and a small amount of methanol, and the mixture was stirred. A solid was collected from this suspension by filtration, and was dried under reduced pressure to give the titled compound (33 mg).

$^1$H-NMR (CDCl$_3$) δ: 1.29 (d, 3H, J=6.8 Hz), 2.61 (dd, 1H, J=17.2, 9.6 Hz), 2.78 (dd, 1H, J=17.2, 8.8 Hz), 3.30-3.40 (m, 1H), 3.61 (t, 1H, J=8.8 Hz), 3.68-3.82 (m, 2H), 4.57 (d, 1H, J=12.0 Hz), 4.68 (d, 1H, J=12.0 Hz), 5.90 (s, 1H), 7.04 (s, 1H), 7.15-7.20 (m, 3H), 7.24 (br s, 1H), 7.28-7.35 (m, 4H), 8.38 (s, 1H).

Preparation 26

Example 245

Synthesis of ((R)-2-oxoimidazolidine-4-carboxylic acid[5-(3-butylphenyl)-1-phenyl-1H-pyrazol-3-yl]amide)

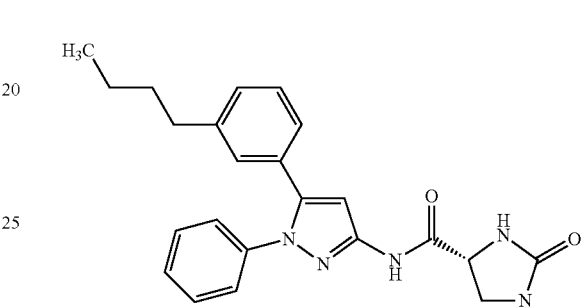

(1) 1-Bromo-3-butylbenzene

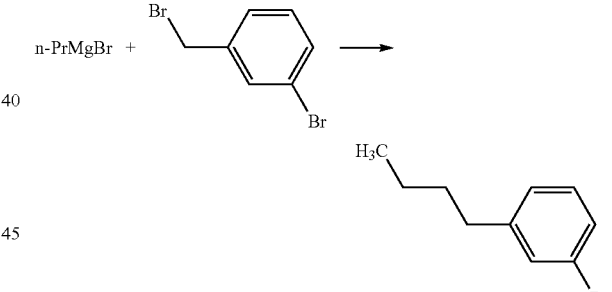

Under nitrogen stream, to a solution of 1-bromo-3-bromomethylbenzene (25 g) in tetrahydrofuran (200 ml) were sequentially added dropwise n-propylmagnesium bromide (60 ml, 2M solution in tetrahydrofuran) and lithium tetrachlorocuprate (5 ml, 0.1M solution in tetrahydrofuran) at −78° C. Then, this reaction mixture was stirred at 0° C. for 2 hours. Under ice-cooling, to this reaction mixture were sequentially added a saturated aqueous solution of ammonium chloride (100 ml) and water (100 ml), and the mixture was extracted with ethyl acetate (200 ml). The resulting aqueous layer was again extracted with ethyl acetate (100 ml), the combined organic layer was washed with a saturated aqueous solution of sodium chloride (100 ml), and dried over anhydrous sodium sulfate. This organic layer was concentrated under reduced pressure, the resulting residue was purified by silica gel chromatography (eluent: n-hexane/ethyl acetate=1/0 to 100/1) to give the titled compound (8.5 g).

¹H-NMR (CDCl₃) δ: 0.91 (t, 3H, J=7.4 Hz), 1.31-1.35 (m, 2H), 1.55-1.59 (m, 2H), 2.56 (t, 2H, J=7.8 Hz), 7.06-7.13 (m, 2H), 7.27-7.32 (m, 2H).

(2) 2-(3-Butylphenyl)-4,4,5,5-tetramethyl-[1,3,2]dioxaborolane

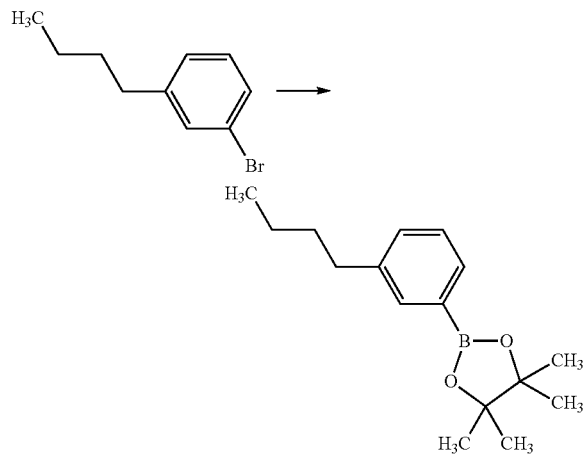

Under argon atmosphere, to a solution of 1-bromo-3-butylbenzene (1.44 g) in 1,4-dioxane (15 ml) were added bispinacolate diboron (1.97 g), [1,1'-bis(diphenylphosphino)ferrocene]dichloropalladium (II) dichloromethane adduct (287 mg) and potassium acetate (2.07 g) at room temperature, and the mixture was stirred at 80° C. for 15 hours. The mixture was cooled to room temperature, and the insoluble substance was filtered off through Celite. The filtrate was washed with water and a saturated aqueous solution of sodium chloride, dried over anhydrous sodium sulfate, and then concentrated under reduced pressure. The resulting residue was purified by silica gel column chromatography (eluent: n-hexane/ethyl acetate=30/1 to 10/1) to give the titled compound (1.37 g).

¹H-NMR (CDCl₃) δ: 0.92 (t, 3H, J=7.3 Hz), 1.31-1.41 (m, 14H), 1.59-1.61 (m, 2H), 2.61 (t, 2H, J=7.9 Hz), 7.24-7.30 (m, 2H), 7.59-7.65 (m, 2H).

(3) 5-(3-Butylphenyl)-1-phenyl-1H-pyrazol-3-ylamine

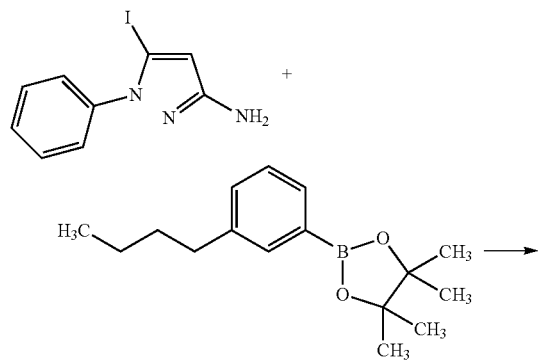

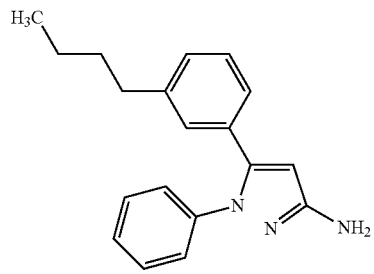

To a solution of 5-iodo-1-phenyl-1H-pyrazol-3-ylamine (1.00 g) prepared according to the same procedures as Preparation 2 in 1,2-dimethoxyethane (20 ml) were sequentially added 2-(3-butylphenyl)-4,4,5,5-tetramethyl-[1,3,2]dioxaborolane (1.37 g), a 2M aqueous solution of sodium carbonate (10 ml), tricyclohexylphosphine (197 mg) and palladium acetate (79 mg) at room temperature, and the mixture was stirred at reflux for 3 hours. This reaction mixture was cooled to room temperature, a saturated aqueous solution of sodium hydrogen carbonate was added thereto, and then the insoluble substance was filtered off through Celite. The filtrate was extracted with ethyl acetate, the resulting organic layer was washed with a saturated aqueous solution of sodium chloride, dried over anhydrous sodium sulfate, and concentrated under reduced pressure. The resulting residue was purified by silica gel column chromatography (eluent: n-hexane/ethyl acetate=2/1 to 2/3) to give the titled compound (880 mg).

¹H-NMR (CDCl₃) δ: 0.85 (t, 3H, J=7.3 Hz), 1.17-1.27 (m, 2H), 1.40-1.47 (m, 2H), 2.49 (t, 2H, J=7.6 Hz), 3.75 (br s, 2H), 5.90 (s, 1H), 6.97 (s, 1H), 7.02-7.12 (m, 2H), 7.13-7.29 (m, 6H).

(4) (R)-2-Oxoimidazolidine-4-carboxylic acid[5-(3-butylphenyl)-1-phenyl-1H-pyrazol-3-yl]amide

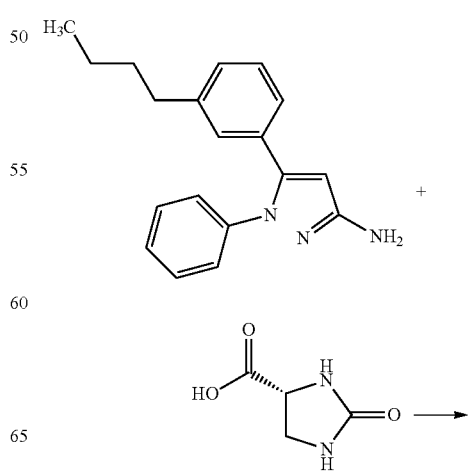

-continued

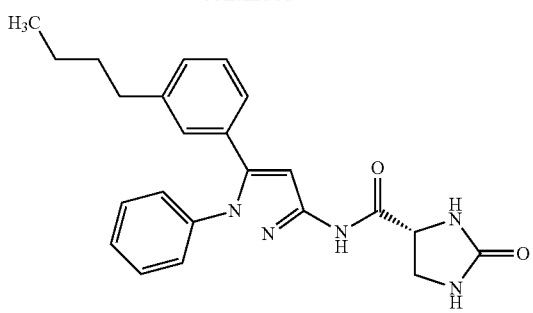

To a solution of 5-(3-butylphenyl)-1-phenyl-1H-pyrazol-3-ylamine (40 mg) in N,N-dimethylformamide (0.4 ml) were sequentially added (R)-2-oxoimidazolidine-4-carboxylic acid (21 mg) prepared by the same procedures as Preparation 20, HATU (63 mg), diisopropylethylamine (29 μL) at room temperature, and the mixture was stirred for 2 hours. To this reaction mixture was added water, and the mixture was extracted with ethyl acetate. The resulting organic layer was washed with water and a saturated aqueous solution of sodium chloride, dried over anhydrous sodium sulfate, and then concentrated under reduced pressure. The resulting residue was purified by silica gel thin-layer chromatography (eluent: n-hexane/acetone=1/5). To the resulting solid was added diisopropyl ether, and the mixture was stirred. A solid was collected from this suspension by filtration, and was dried under reduced pressure to give the titled compound (12 mg).

$^1$H-NMR (DMSO-D6) δ: 0.82 (t, 3H, J=7.4 Hz), 1.15 (tq, 2H, J=7.4 Hz, 7.4 Hz), 1.39 (tt, 2H, J=7.4 Hz, 7.4 Hz), 2.48 (t, 2H, J=7.4 Hz), 3.36 (dd, 1H, J=9.2 Hz, 5.6 Hz), 3.59 (dd, 1H, J=9.2 Hz, 9.2 Hz), 4.32 (dd, 1H, J=9.2 Hz, 5.6 Hz), 6.33 (s, 1H), 6.60 (s, 1H), 6.90 (s, 1H), 6.98 (s, 1H), 7.09 (d, 1H, J=7.6 Hz), 7.17 (d, 1H, J=7.6 Hz), 7.20-7.30 (m, 3H), 7.32-7.43 (m, 3H), 10.70 (s, 1H).

Preparation 27

Example 246

Synthesis of ((S)-5-oxopyrrolidine-3-carboxylic acid{1-phenyl-5-[3-(2,2,2-trifluoro-1-trifluoromethylethoxymethyl)phenyl]-1H-pyrazol-3-yl}amide)

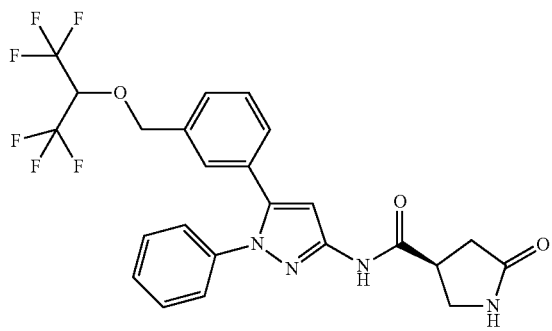 [SMILES: O=C1C[C@H](C(=O)Nc2cc(-c3cccc(COC(C(F)(F)F)C(F)(F)F)c3)n(-c3ccccc3)n2)CN1]

(1) 3-(1,1,1,3,3,3-Hexafluoropropan-2-yloxy)phenyl boronic acid

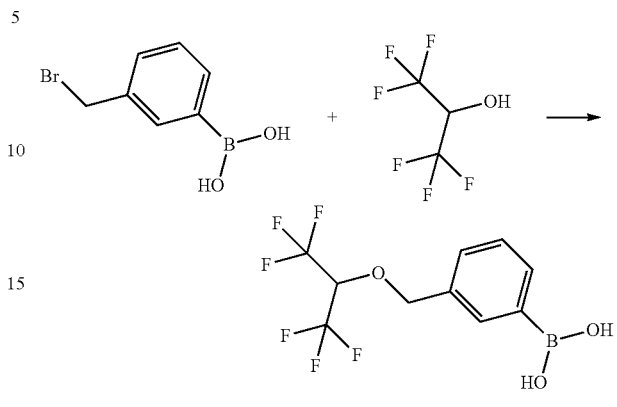

A suspension of sodium hydride (149 mg, 60 wt. % oil dispersion) in N,N-dimethylformamide (3.0 ml) was cooled to 0° C., (R)-1,1,1,3,3,3-hexafluoropropan-2-ol (392 mg) was added thereto, and the mixture was stirred for 15 minutes. Then, 3-(bromomethyl)phenyl boronic acid (200 mg) was added thereto, and then the mixture was stirred at room temperature for 2 hours. To this reaction mixture were sequentially added water and a 1M aqueous solution of hydrochloric acid, and the mixture was extracted with ethyl acetate. This organic layer was washed with a saturated aqueous solution of sodium chloride, dried over magnesium sulfate, and then concentrated under reduced pressure to give a crude product of the titled compound (1.0 g).

(2) 1-Phenyl-5-[3-(2,2,2-trifluoro-1-trifluoromethylethoxymethyl)phenyl]-1H-pyrazol-3-ylamine

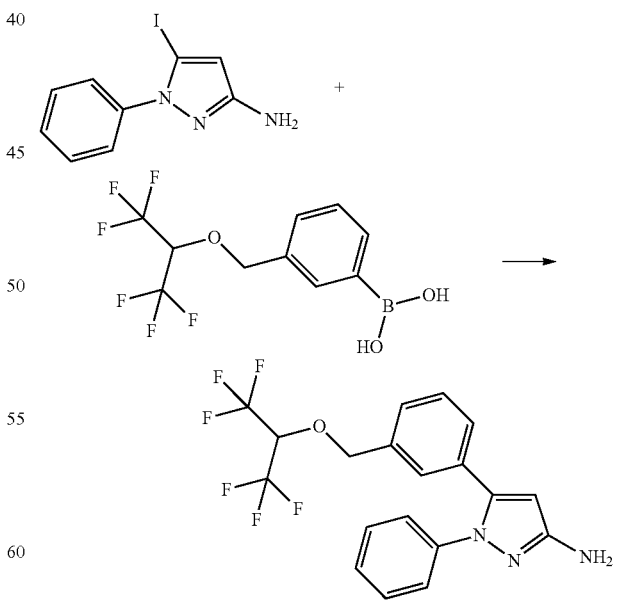

To 3-(1,1,1,3,3,3-hexafluoropropan-2-yloxy)phenyl boronic acid (1.0 g) were sequentially added a solution of 5-iodo-1-phenyl-1H-pyrazol-3-ylamine (180 mg) prepared according to the same procedures as Preparation 2 in 1,2- dimethoxyethane (2.0 ml), a 2M aqueous solution of sodium carbonate (1.0 ml), tricyclohexylphosphine (35 mg) and palladium (II) acetate (18 mg) at room temperature, and the mixture was stirred at 100° C. for 2 hours. This reaction mixture was cooled to room temperature, filtered through Celite, and subjected to elution with ethyl acetate. The filtrate was extracted with ethyl acetate, the resulting organic layer was washed with a saturated aqueous solution of sodium chloride, dried over magnesium sulfate, and then concentrated under reduced pressure. The resulting residue was purified by silica gel thin-layer chromatography (eluent: n-hexane/ethyl acetate=3/7) to give the titled compound (151 mg).

(3) (S)-5-Oxopyrrolidine-3-carboxylic acid{1-phenyl-5-[3-(2,2,2-trifluoro-1-trifluoromethylethoxymethyl)phenyl]-1H-pyrazol-3-yl}amide

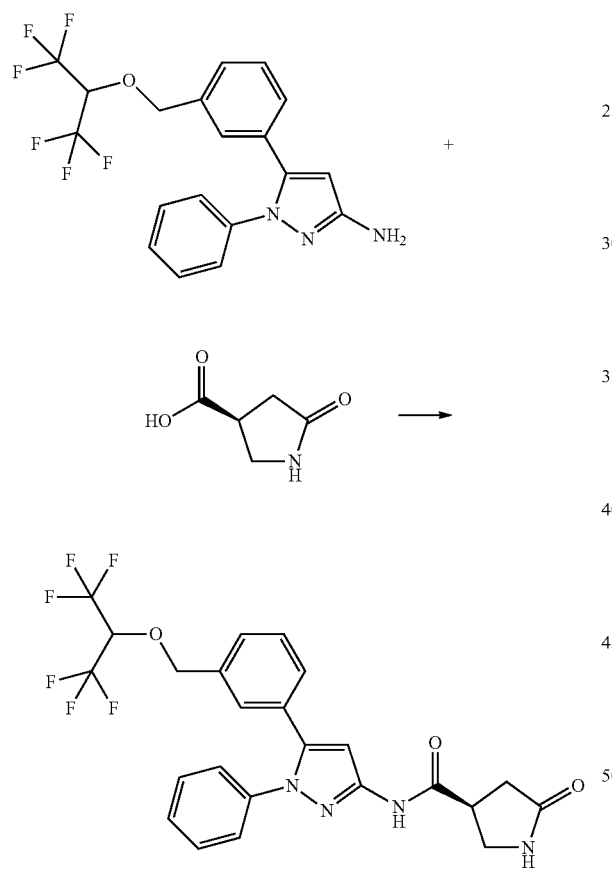

To a solution of 1-phenyl-5-[3-(2,2,2-trifluoro-1-trifluoromethyl-ethoxymethyl)phenyl]-1H-pyrazol-3-ylamine (78 mg) in N,N-dimethylacetamide (1.0 ml) were sequentially added (S)-5-oxopyrrolidine-3-carboxylic acid (29 mg) prepared according to the same procedures as Preparation 5 and WSC.HCl (44 mg) at room temperature, and the mixture was stirred overnight. To this reaction mixture was added water, and then the precipitated solid was collected by filtration. The resulting solid was purified by silica gel thin-layer chromatography (eluent: chloroform/methanol=9/1). To the resulting solid were added water and a small amount of methanol, and the mixture was stirred. A solid was collected from this suspension by filtration, and was dried under reduced pressure to give the titled compound (54 mg).

$^1$H-NMR (DMSO-D6) δ: 2.36-2.38 (m, 2H), 3.32-3.33 (m, 1H), 3.37-3.41 (m, 1H), 3.46-3.49 (m, 1H), 4.85 (m, 2H), 5.53-5.59 (m, 1H), 6.94 (s, 1H), 7.17-7.18 (m, 1H), 7.22-7.24 (m, 2H), 7.34-7.41 (m, 6H), 7.63 (s, 1H), 10.88 (s, 1H).

Preparation 28

Example 247

Synthesis of ((S)-5-oxopyrrolidine-3-carboxylic acid{1-(4-fluorophenyl)-5-[3-(2,2,2-trifluoroethoxymethyl)phenyl]-1H-pyrazol-3-yl}amide)

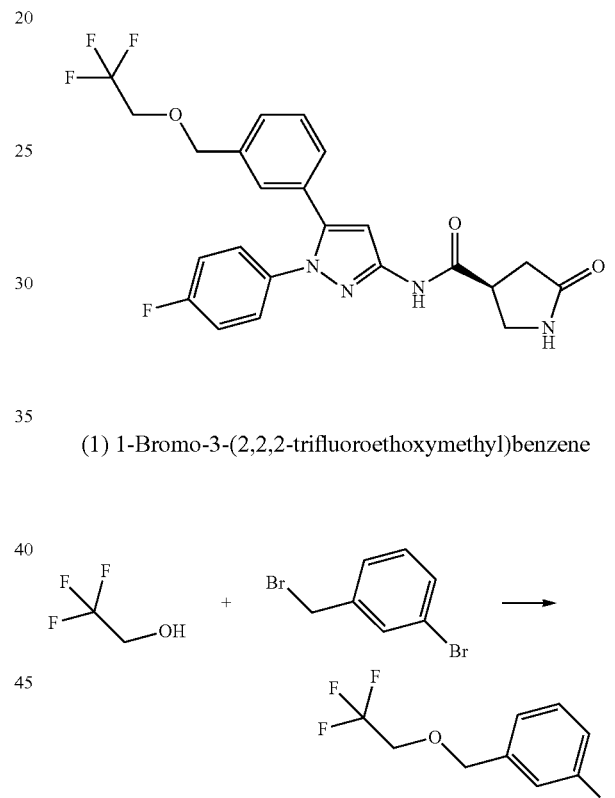

(1) 1-Bromo-3-(2,2,2-trifluoroethoxymethyl)benzene

Under nitrogen atmosphere, a suspension of sodium hydride (352 mg, 60 wt. % oil dispersion) in tetrahydrofuran (10 ml) was cooled to 0° C., 2,2,2-trifluoroethanol (0.63 ml) was added thereto, and the mixture was stirred for 5 minutes. Then, 3-bromobenzyl bromide (2.00 g) was added thereto, and then the mixture was stirred at reflux for 1 hour. This reaction mixture was cooled to room temperature, a saturated aqueous solution of ammonium chloride was added thereto, and the mixture was extracted with ethyl acetate. This organic layer was washed with a saturated aqueous solution of sodium chloride, dried over anhydrous sodium sulfate, and then concentrated under reduced pressure. The resulting residue was purified by silica gel column chromatography (eluent: n-hexane/ethyl acetate=1/0 to 10/1) to give the titled compound (2.05 g).

$^1$H-NMR (CDCl$_3$) δ: 3.84 (q, 2H, J=8.68 Hz), 4.65 (s, 2H), 7.22-7.28 (m, 2H), 7.45-7.47 (m, 1H), 7.49-7.51 (m, 1H).

(2) 4,4,5,5-Tetramethyl-2-[3-(2,2,2-trifluoroethoxymethyl)phenyl]-[1,3,2]dioxaborolane

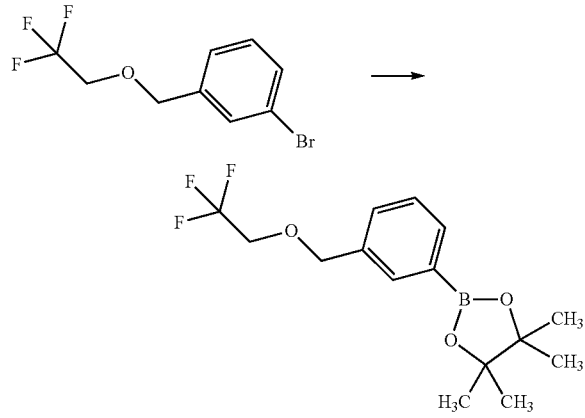

Under argon atmosphere, to a solution of 1-bromo-3-(2,2,2-trifluoroethoxymethyl)benzene (2.05 g) in 1,4-dioxane (21 ml) were sequentially added bispinacolate diboron (2.12 g), potassium acetate (2.24 g) and [1,1'-bis(diphenylphosfino)ferrocene]dichloropalladium (II) dichloromethane adduct (310 mg) at room temperature, and the mixture was stirred at 80° C. for 19 hours. This reaction mixture was cooled to room temperature, filtered through Celite, and then subjected to elution with ethyl acetate. The filtrate was concentrated under reduced pressure, the resulting residue was purified by silica gel column chromatography (eluent: n-hexane/ethyl acetate=30/1) to give the titled compound (1.69 g).

$^1$H-NMR (CDCl$_3$) δ: 1.35 (s, 12H), 3.81 (q, 2H, J=8.67 Hz), 4.68 (s, 2H), 7.38-7.40 (m, 1H), 7.47-7.48 (m, 1H), 7.76-7.78 (m, 2H).

(3) 1-(4-Fluorophenyl)-5-[3-(2,2,2-trifluoroethoxymethyl)phenyl]-1H-pyrazol-3-ylamine

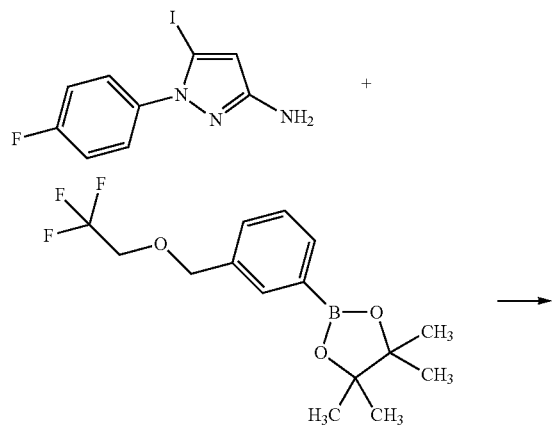

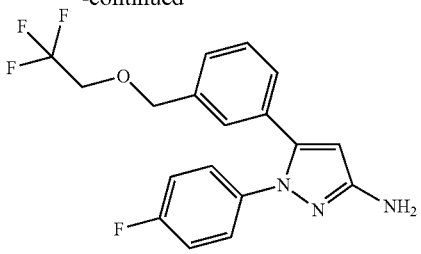

Under argon atmosphere, to a solution of 1-(4-fluorophenyl)-5-iodo-1H-pyrazol-3-ylamine (70 mg) prepared in Preparation 18 in 1,2-dimethoxyethane (0.7 ml) were sequentially added 4,4,5,5-tetramethyl-2-[3-(2,2,2-trifluoroethoxymethyl)phenyl]-[1,3,2]dioxaborolane (80 mg), a 2M aqueous solution of sodium carbonate (0.35 ml), tricyclohexylphosphine (13.0 mg) and palladium (II) acetate (5.2 mg) at room temperature, and the mixture was stirred at 100° C. for 2 hours. This reaction mixture was cooled to room temperature, filtered through Celite, and subjected to elution with ethyl acetate. The filtrate was extracted with ethyl acetate, the resulting organic layer was washed with a saturated aqueous solution of sodium chloride, dried over anhydrous sodium sulfate, and then concentrated under reduced pressure. The resulting residue was purified by silica gel column chromatography (eluent: n-hexane/ethyl acetate=1/1) to give the titled compound (43 mg).

$^1$H-NMR (CDCl$_3$) δ: 3.74 (q, 2H, J=8.61 Hz), 3.77 (br s, 2H), 4.60 (s, 2H), 5.93 (s, 1H), 6.97-6.99 (m, 2H), 7.16-7.21 (m, 4H), 7.29-7.31 (m, 2H).

(4) (S)-5-Oxopyrrolidine-3-carboxylic acid{1-(4-fluorophenyl)-5-[3-(2,2,2-trifluoroethoxymethyl)phenyl]-1H-pyrazol-3-yl}amide

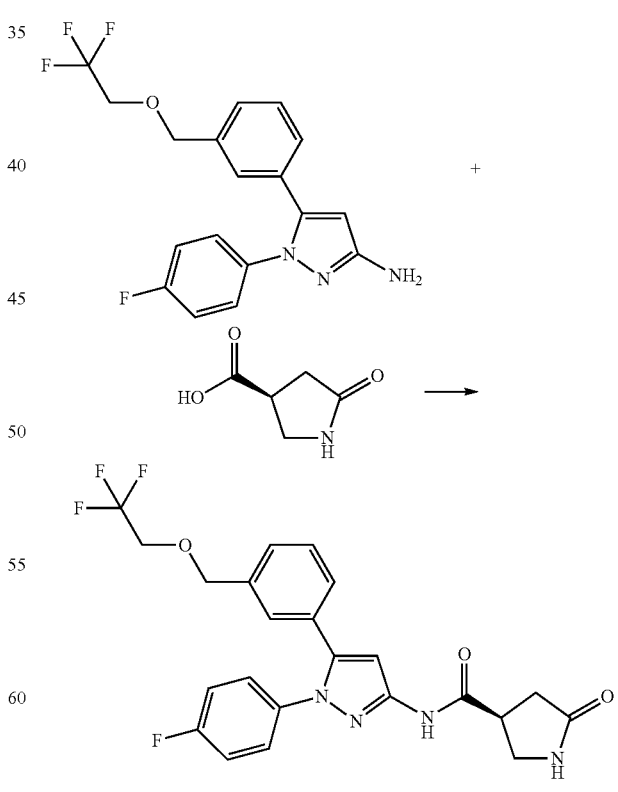

To a solution of 1-(4-fluorophenyl)-5-[3-(2,2,2-trifluoroethoxymethyl)phenyl]-1H-pyrazol-3-ylamine (43 mg) in N,N-dimethylacetamide (0.4 ml) were sequentially added (S)-5-oxopyrrolidine-3-carboxylic acid (17 mg) prepared according to the same procedures as Preparation 5 and WSC.HCl (34 mg) at room temperature, and the mixture was stirred for 0.5 hours. To this reaction mixture was added water, and then the precipitated solid was collected by filtration. This solid was purified by silica gel thin-layer chromatography (eluent: chloroform/methanol=9/1). To the resulting solid were added water and a small amount of methanol, and the mixture was stirred. A solid was collected from this suspension by filtration, and was dried under reduced pressure to give the titled compound (26 mg).

$^1$H-NMR (DMSO-D6) δ: 2.38-2.40 (m, 2H), 3.32-3.35 (m, 1H), 3.40-3.45 (m, 1H), 3.48-3.52 (m, 1H), 3.98 (q, 2H, J=9.3 Hz), 4.61 (s, 2H), 6.93 (s, 1H), 7.18-7.40 (m, 8H), 7.63 (s, 1H), 10.86 (s, 1H).

Preparation 29

Example 248

Synthesis of ((S)-5-oxopyrrolidine-3-carboxylic acid{1-(4-fluorophenyl)-5-[3-fluoro-5-(2,2,2-trifluoroethoxymethyl)phenyl]-1H-pyrazol-3-yl}amide)

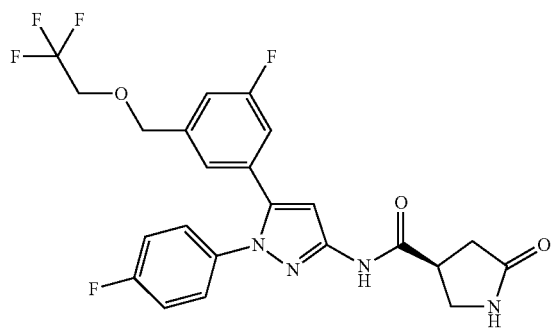 [SMILES: O=C1C[C@H](C(=O)Nc2cc(-c3cc(F)cc(COCC(F)(F)F)c3)n(-c3ccc(F)cc3)n2)CN1]

(1) 1-Chloro-3-fluoro-5-(2,2,2-trifluoroethoxymethyl)benzene

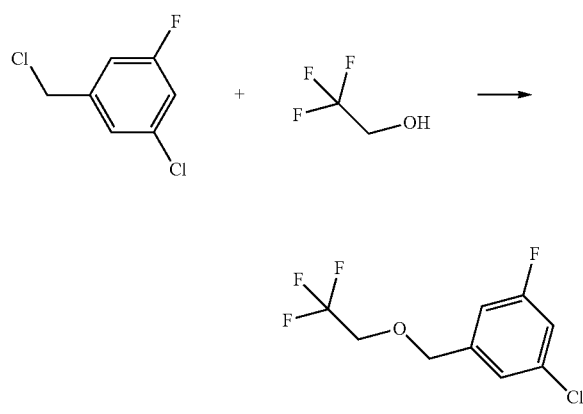

Under argon stream, to a suspension of sodium hydride (601 mg, 60 wt. % oil dispersion) in dimethylformamide (13 ml) was added dropwise trifluoroethanol (1.08 ml) at 0° C., and the mixture was stirred for 15 minutes. To this reaction solution was added dropwise a solution of 1-chloro-3-fluoro-5-chloromethylbenzene (2.23 g) in dimethylformamide (9 ml), and then the mixture was stirred at room temperature for 1 hour. To this reaction mixture was added water, and the mixture was extracted with a mixed solvent of n-hexane/ethyl acetate=1/1. This organic layer was washed with a saturated aqueous solution of sodium chloride, dried over anhydrous magnesium sulfate, and concentrated under reduced pressure. The resulting residue was purified by silica gel column chromatography (eluent: n-hexane/ethyl acetate=1/0 to 9/1) to give the titled compound (2.85 g).

$^1$H-NMR (CDCl$_3$) δ: 3.87 (q, 2H, J=8.8 Hz), 4.64 (s, 2H), 6.97 (d, 1H, J=8.8 Hz), 7.05 (dt, 1H, J=8.8, 2.4 Hz), 7.13 (br s, 1H).

(2) 2-[3-Fluoro-5-(2,2,2-trifluoroethoxymethyl)phenyl]-4,4,5,5-tetramethyl-[1,3,2]dioxaborolane

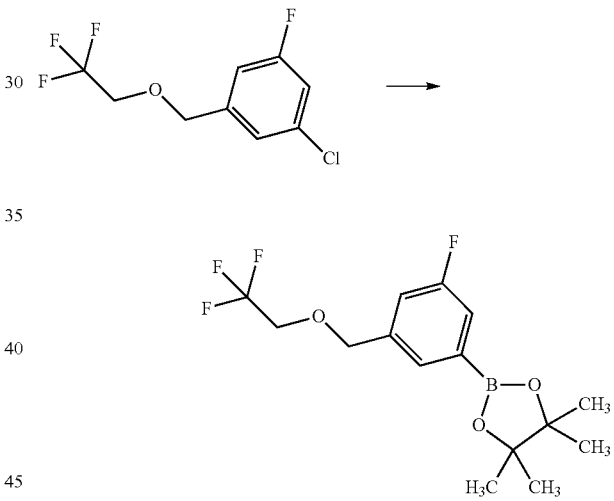

Under argon atmosphere, to a solution of 1-chloro-3-fluoro-5-(2,2,2-trifluoroethoxymethyl)benzene (2.65 g) in 1,4-dioxane (60 ml) were sequentially added bispinacolate diboron (3.41 g), potassium acetate (3.33 g), 2-dicyclohexylphosphino-2',4',6'-triisopropylbiphenyl (521 mg) and tris(dibenzylideneacetone)dipalladium (0) (253 mg) at room temperature, and the mixture was stirred at reflux for 6 hours. This reaction mixture was cooled to room temperature, and then filtered through Celite, and subjected to elution with ethyl acetate. The filtrate was concentrated under reduced pressure, the resulting residue was purified by silica gel column chromatography (eluent: n-hexane/ethyl acetate=1/0 to 19/1). The resulting crude product was suspended in n-hexane, and the insoluble substance was filtered off. The filtrate was concentrated under reduced pressure to give the titled compound (2.71 g).

$^1$H-NMR (CDCl$_3$) δ: 1.35 (s, 12H), 3.83 (q, 2H, J=8.8 Hz), 4.67 (s, 2H), 7.18 (d, 1H, J=8.8 Hz), 7.44 (dd, 1H, J=8.8, 2.4 Hz), 7.50 (br s, 1H).

(3) 1-(4-Chlorophenyl)-5-[3-fluoro-5-(2,2,2-trifluoroethoxymethyl)phenyl]-1H-pyrazol-3-ylamine

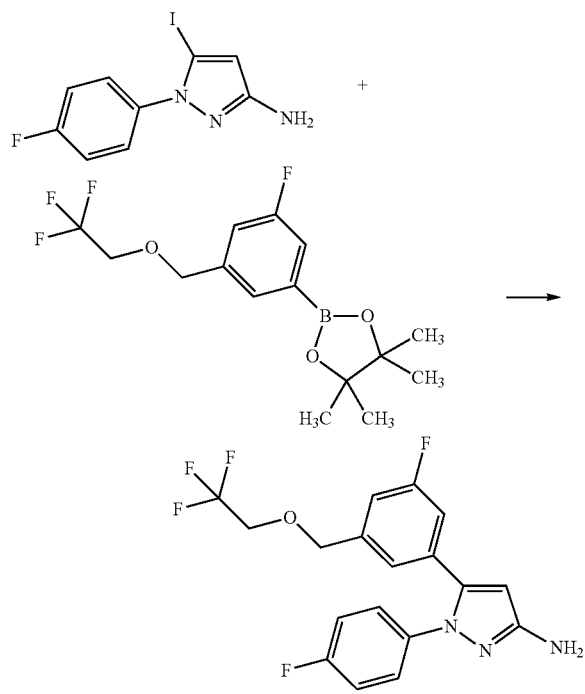

To a solution of 1-(4-fluorophenyl)-5-iodo-1H-pyrazol-3-ylamine (38 mg) prepared in Preparation 18 in 1,4-dioxane (0.4 ml) were sequentially added 2-[3-fluoro-5-(2,2,2-trifluoroethoxymethyl)phenyl]-4,4,5,5-tetramethyl-[1,3,2]dioxaborolane (50 mg), palladium (II) acetate (3 mg), tricyclohexylphosphine (7 mg) and a 2M aqueous solution of potassium carbonate (0.2 ml) at room temperature, and the mixture was stirred at 105° C. for 4 hours. After removing an aqueous layer of the reaction mixture, an organic layer was filtered through silica gel (5 g), and subjected to elution with ethyl acetate. The filtrate was concentrated under reduced pressure, the resulting residue was purified by silica gel thin-layer chromatography (eluent: n-hexane/ethyl acetate 1/1) to give the titled compound.

(4) Synthesis of (S)-5-oxopyrrolidine-3-carboxylic acid{1-(4-fluorophenyl)-5-[3-fluoro-5-(2,2,2-trifluoroethoxymethyl)phenyl]-1H-pyrazol-3-yl}amide

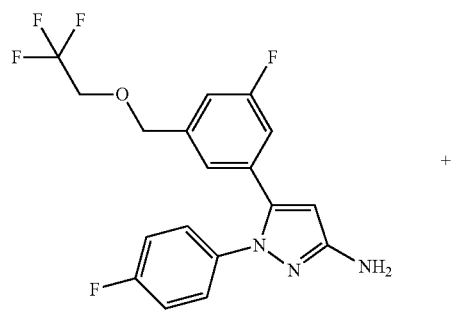

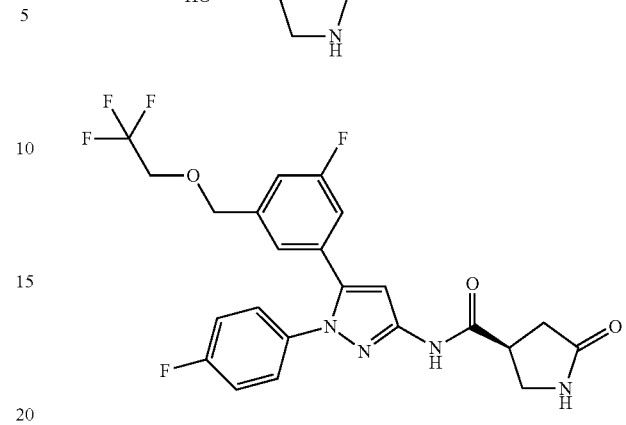

To a solution of 1-(4-chlorophenyl)-5-[3-fluoro-5-(2,2,2-trifluoroethoxymethyl)phenyl]-1H-pyrazol-3-ylamine (about 0.125 mmol) prepared in the previous step in N,N-dimethylformamide (0.5 ml) were sequentially added (S)-5-oxopyrrolidine-3-carboxylic acid (18 mg) prepared according to the same procedures as preparation 14 and WSC.HCl (29 mg) at room temperature, and the mixture was stirred for 3 hours. To this reaction mixture was added water, and the mixture was extracted with ethyl acetate. This organic layer was concentrated under reduced pressure, the resulting residue was purified by silica gel thin-layer chromatography (eluent: chloroform/methanol=10/1). To the resulting solid were added water and a small amount of methanol, and the mixture was stirred. A solid was collected from this suspension by filtration and was dried under reduced pressure to give the titled compound (33 mg).

$^1$H-NMR (CDCl$_3$) δ: 2.61 (dd, 1H, J=17.2, 9.6 Hz), 2.78 (dd, 1H, J=17.2, 8.8 Hz), 3.32-3.42 (m, 1H), 3.61 (t, 1H, J=8.8 Hz), 3.71 (dd, 1H, J=9.6, 7.2 Hz), 3.79 (q, 2H, J=8.8 Hz), 4.59 (s, 2H), 6.04 (s, 1H), 6.89 (d, 1H, J=9.2 Hz), 6.99-7.10 (m, 5H), 7.19-7.24 (m, 2H), 8.48 (s, 1H).

Preparation 30

Example 249

Synthesis of (4-oxo-3-azabicyclo[3.1.0]hexane-1-carboxylic acid[1-phenyl-5-(3-propylphenyl)-1H-pyrazol-3-yl]amide)

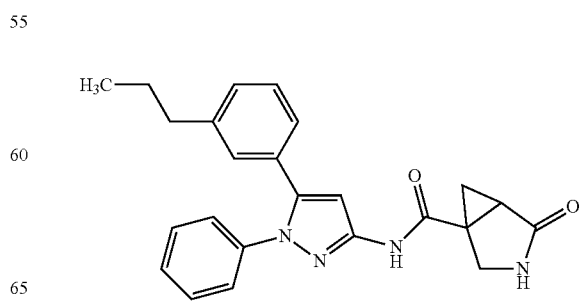

(1) 2-(tert-Butyldimethylsilanyloxymethyl)-2-propen-1-ol

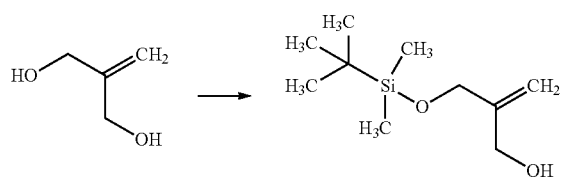

Under argon atmosphere, to a suspension of sodium hydride (490 mg, 60 wt. % oil dispersion) in tetrahydrofuran (10 ml) were sequentially added 2-methylene-1,3-propanediol (1 ml) and tert-butyldimethylchlorosilane (2.22 g) at 0° C., and then the mixture was stirred at room temperature for 1 hour. To this reaction mixture was added a saturated aqueous solution of ammonium chloride, and the mixture was extracted with ethyl acetate. This organic layer was washed with a saturated aqueous solution of sodium chloride, dried over anhydrous sodium sulfate, and then concentrated under reduced pressure. The resulting residue was purified by silica gel column chromatography (eluent: n-hexane/ethyl acetate=3/1) to give the titled compound (1.62 g).

$^1$H-NMR (CDCl$_3$) δ: 0.09 (s, 6H), 0.91 (s, 9H), 1.96 (t, 1H, J=3.09 Hz), 4.18 (d, 2H, J=3.09 Hz), 4.25 (s, 2H), 5.08 (d, 1H, J=1.32 Hz), 5.10 (d, 1H, J=1.32 Hz).

(2) [2-(tert-Butyldimethylsilanyloxymethyl)allyl]-(2,4-dimethoxybenzyl)amine

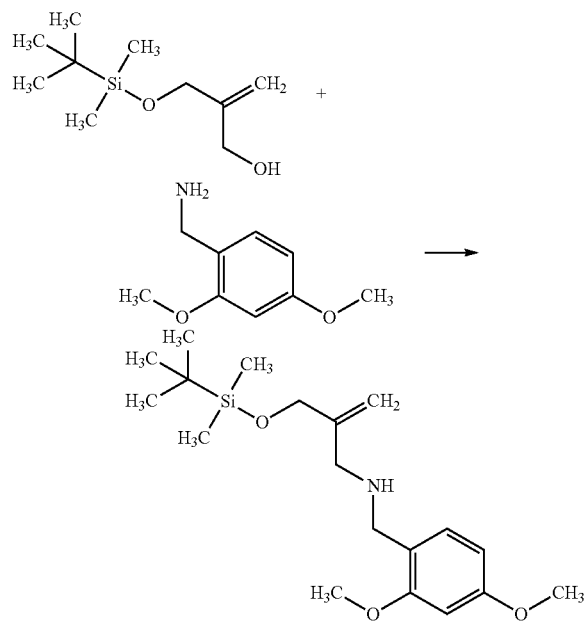

To a solution of 2-(tert-butyldimethylsilanyloxymethyl)-2-propen-1-ol (1.58 g) in chloroform (16 ml) were sequentially added triethylamine (2.2 ml) and methanesulfonyl chloride (0.73 ml) at 0° C., and then the mixture was stirred for 2 hours. To this reaction solution were sequentially added triethylamine (1.2 ml) and 2,4-dimethoxybenzylamine (1.3 ml), and then the mixture was stirred at room temperature for 15 hours. To this reaction mixture was added water, and an organic layer was separated from the mixture, and concentrated under reduced pressure. The resulting residue was purified by silica gel column chromatography (eluent: n-hexane/ethyl acetate=1/1) to give the titled compound (1.14 g).

$^1$H-NMR (CDCl$_3$) δ: 0.07 (s, 6H), 0.91 (s, 9H), 3.21 (s, 2H), 3.69 (s, 2H), 3.80 (s, 6H), 4.18 (s, 2H), 5.02 (s, 1H), 5.13 (s, 1H), 6.41-6.45 (m, 2H), 7.12 (d, 1H, J=7.91 Hz).

(3) (E)-2-(2-Tosylhydrazono)acetic acid

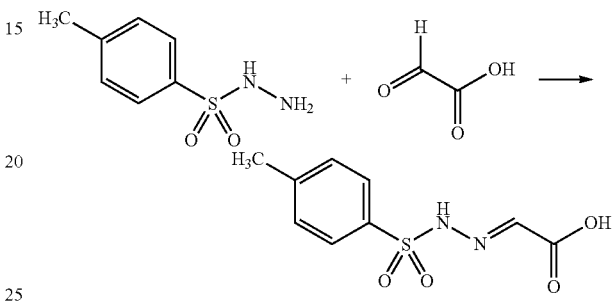

To glyoxylic acid monohydrate (644 mg) was added water (7 ml). The resulting suspension was dissolved in water by heating to 65° C., a solution of p-toluenehydrazide (1.30 g) in a 2.5M aqueous solution of hydrochloric acid (4.2 ml) was added thereto, and the mixture was stirred for 15 minutes. This reaction mixture was cooled to room temperature, the precipitated solid was collected by filtration, and washed with water. The resulting solid was dried under reduced pressure to give the titled compound (1.42 g).

$^1$H-NMR (CDCl$_3$) δ: 2.46 (s, 3H), 7.14 (s, 1H), 7.38 (d, 2H, J=8.14 Hz), 7.83 (d, 2H, J=8.14 Hz), 8.46 (s, 1H).

(4) Diazoacetic acid 2,5-dioxopyrrolidin-1-yl ester

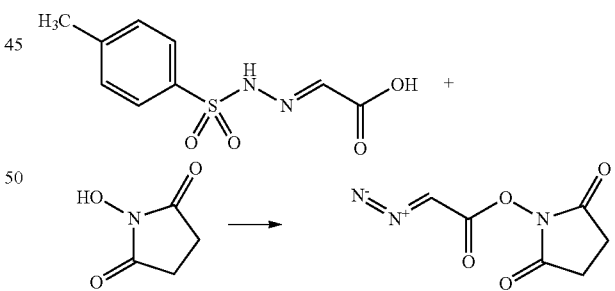

Under argon atmosphere, to a solution of (E)-2-(2-tosylhydrazono)acetic acid (1.42 g) in 1,4-dioxane (14 ml) were sequentially added N-hydroxysuccinimide (677 mg) and dicyclohexylcarbodiimide (1.21 g) at room temperature, and the mixture was stirred for 17 hours. This reaction mixture was filtered through Celite, and eluted with 1,4-dioxane. This filtrate was concentrated under reduced pressure, the resulting residue was purified by silica gel column chromatography (eluent: n-hexane/diethyl ether=1/3) to give the titled compound (579 mg).

$^1$H-NMR (CDCl$_3$) δ: 2.85 (s, 4H), 5.11 (s, 1H).

(5) N-[2-(tert-Butyldimethylsilanyloxymethyl)allyl]-2-diazo-N-(2,4-dimethoxybenzyl)acetamide

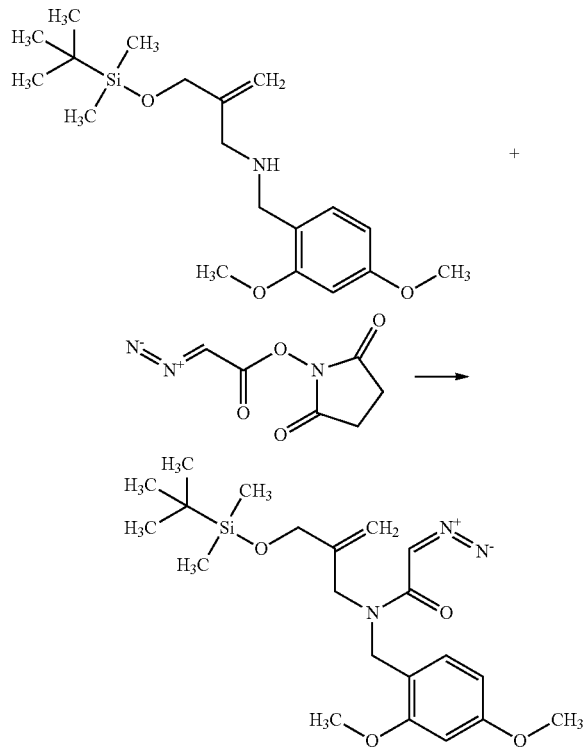

To a solution of [2-(tert-butyldimethylsilanyloxymethyl)allyl]-(2,4-dimethoxybenzyl)amine (384 mg) in chloroform (3.8 ml) were sequentially added triethylamine (0.23 ml) and diazoacetic acid 2,5-dioxopyrrolidin-1-yl ester (200 mg) at room temperature, and the mixture was stirred for 16 hours. This reaction mixture was concentrated under reduced pressure, the resulting residue was purified by silica gel column chromatography (eluent: n-hexane/ethyl acetate=4/1) to give the titled compound (223 mg).

$^1$H-NMR (CDCl$_3$) δ: 0.06 (s, 6H), 0.90 (s, 9H), 3.79 (s, 3H), 3.80 (s, 3H), 3.88-3.91 (m, 2H), 4.08 (s, 2H), 4.93 (s, 1H), 5.04 (s, 1H), 5.18 (s, 1H), 6.43-6.47 (m, 3H).

(6) 5-(tert-Butyldimethylsilanyloxymethyl)-3-(2,4-dimethoxybenzyl)-3-azabicyclo[3.1.0]hexan-2-one

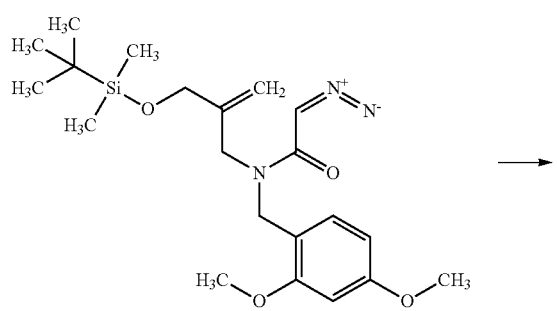

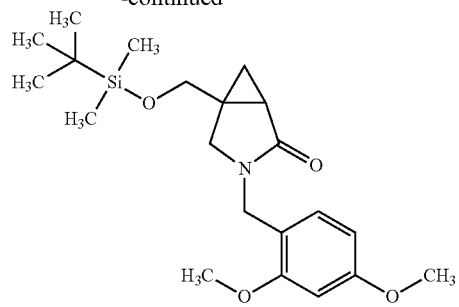

Under argon atmosphere, to a solution of N-[2-(tert-butyldimethylsilanyloxymethyl)allyl]-2-diazo-N-(2,4-dimethoxybenzyl)acetamide (43 mg) in benzotrifluoride (0.4 ml) was added rhodium (II) acetate dimer dihydrate (2.4 mg) at room temperature, and the mixture was stirred at 50° C. for 24 hours. This reaction mixture was concentrated under reduced pressure, the resulting residue was purified by silica gel column chromatography (eluent: n-hexane/ethyl acetate=2/1) to give the titled compound (14.2 mg).

$^1$H-NMR (CDCl$_3$) δ: 0.01 (s, 6H), 0.72 (dd, 1H, J=4.42, 3.61 Hz), 0.85 (s, 9H), 1.11 (dd, 1H, J=8.84, 4.42 Hz), 1.81 (dd, 1H, J=8.84, 3.61 Hz), 3.16 (d, 1H, J=10.47 Hz), 3.36 (d, 1H, J=10.47 Hz), 3.62 (d, 1H, J=10.70 Hz), 3.70 (d, 1H, J=10.70 Hz), 3.79 (s, 3H), 3.79 (s, 3H), 4.25 (d, 1H, J=14.65 Hz), 4.38 (d, 1H, J=14.65 Hz), 6.40-6.44 (m, 2H), 7.06-7.09 (m, 1H).

(7) 3-(2,4-Dimethoxybenzyl)-5-hydroxymethyl-3-azabicyclo[3.1.0]hexan-2-one

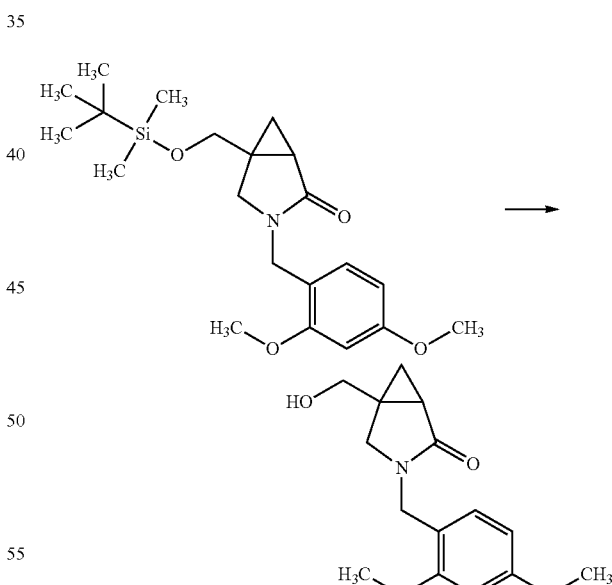

To a solution of 5-(tert-butyldimethylsilanyloxymethyl)-3-(2,4-dimethoxybenzyl)-3-azabicyclo[3.1.0]hexan-2-one (14.2 mg) in tetrahydrofuran (0.3 ml) was added n-butylammonium fluoride (54 μl, 1.0M solution in tetrahydrofuran) at room temperature, and the mixture was stirred for 1 hour. This reaction mixture was concentrated under reduced pressure, the resulting residue was purified by silica gel column chromatography (eluent: ethyl acetate, to chloroform/methanol=9/1) to give the titled compound (9.2 mg).

$^1$H-NMR (CDCl$_3$) δ: 0.77 (dd, 1H, J=4.84, 3.43 Hz), 1.12 (dd, 1H, J=8.87, 4.84 Hz), 1.85 (dd, 1H, J=8.87, 3.43 Hz), 3.23 (d, 1H, J=10.07 Hz), 3.45 (d, 1H, J=10.07 Hz), 3.66 (d, 1H, J=11.69 Hz), 3.70 (d, 1H, J=11.69 Hz), 3.79 (s, 3H), 3.79 (s, 3H), 4.21 (d, 1H, J=14.51 Hz), 4.43 (d, 1H, J=14.51 Hz), 6.41-6.44 (m, 2H), 7.07-7.10 (m, 1H).

(8) 3-(2,4-Dimethoxybenzyl)-4-oxo-3-azabicyclo[3.1.0]hexane-1-carbaldehyde

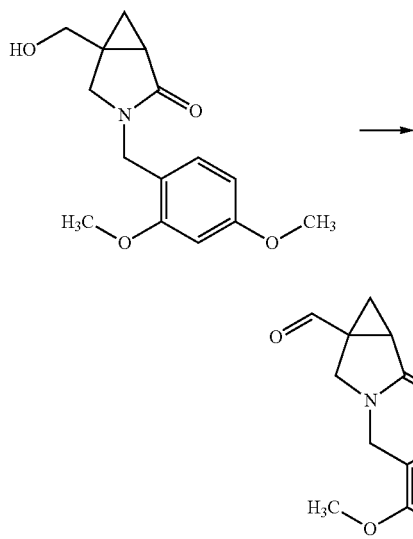

Under argon atmosphere, to a solution of 3-(2,4-dimethoxybenzyl)-5-hydroxymethyl-3-azabicyclo[3.1.0]hexan-2-one (9.2 mg) in dimethylsulfoxide/chloroform (2/1, 135 μl) were sequentially added triethylamine (23 μl) and sulfur trioxide-pyridine complex (10.6 mg) at room temperature, and the mixture was stirred for 2 hours. To this reaction mixture was added water, and the mixture was extracted with ethyl acetate. This organic layer was washed with water, a saturated aqueous solution of sodium chloride, dried over anhydrous sodium sulfate, and then concentrated under reduced pressure to give a crude product of the titled compound (10.8 mg).

(9) 3-(2,4-Dimethoxybenzyl)-4-oxo-3-azabicyclo[3.1.0]hexane-1-carboxylic acid

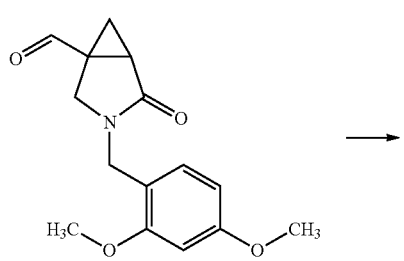

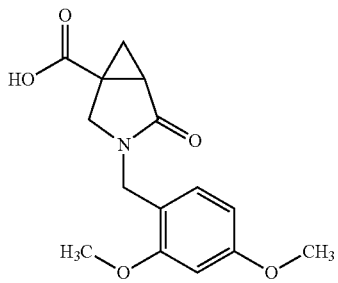

Under argon atmosphere, to a solution of 3-(2,4-dimethoxybenzyl)-4-oxo-3-azabicyclo[3.1.0]hexane-1-carbaldehyde (10.8 mg) in tert-butanol/tetrahydrofuran/water (4/3/1, 0.5 ml) was added sodium dihydrogenphosphate dihydrate (20.2 mg) at room temperature. This reaction mixture was cooled to 0° C., 2-methyl-2-butene (18 μl) and sodium chlorite (9.0 mg) were sequentially added thereto, and then the mixture was stirred at room temperature for 24 hours. This reaction mixture was cooled to 0° C., and then water was added thereto, and the mixture was extracted with ethyl acetate. This organic layer was washed with a saturated aqueous solution of sodium chloride, dried over anhydrous sodium sulfate, and then concentrated under reduced pressure. The resulting residue was purified by silica gel thin-layer chromatography (eluent: chloroform/methanol=9/1) to give the titled compound (3.7 mg).

$^1$H-NMR (CDCl$_3$) δ: 0.69-0.71 (m, 1H), 1.68-1.71 (m, 1H), 2.25-2.28 (m, 1H), 3.11 (d, 1H, J=11.28 Hz), 3.49 (s, 1H), 3.71 (s, 3H), 3.73 (s, 3H), 3.75 (d, 1H, J=11.28 Hz), 3.98 (d, 1H, J=13.30 Hz), 4.42 (d, 1H, J=13.30 Hz), 6.33-6.38 (m, 2H), 6.95-6.98 (m, 1H).

(10) 3-(2,4-Dimethoxybenzyl)-4-oxo-3-azabicyclo[3.1.0]hexane-1-carboxylic acid[1-phenyl-5-(3-propylphenyl)-1H-pyrazol-3-yl]amide

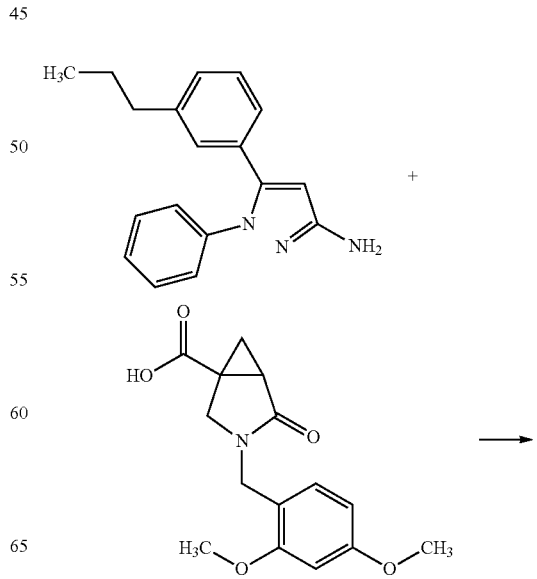

-continued

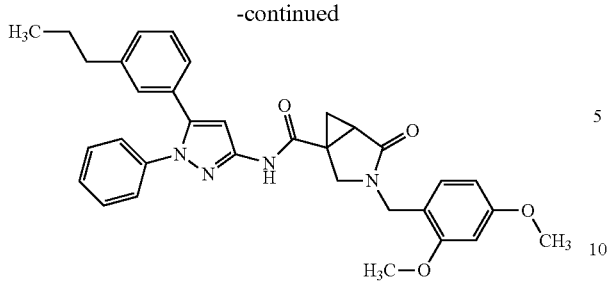

To a solution of 1-phenyl-5-(3-propylphenyl)-1H-pyrazol-3-ylamine (3.5 mg) prepared according to the same procedures as Preparation 2-2 in N,N-dimethylformamide (0.5 ml) were sequentially added 3-(2,4-dimethoxybenzyl)-4-oxo-3-azabicyclo[3.1.0]hexane-1-carboxylic acid (3.7 mg) and WSC.HCl (3.6 mg) at room temperature, and the mixture was stirred for 14 hours. To this reaction mixture were added diisopropylethylamine (3.3 µl) and HATU (7.3 mg), and the mixture was stirred at room temperature for additional 72 hours. To this reaction mixture was added water, and the mixture was extracted with ethyl acetate. This organic layer was washed with water and a saturated aqueous solution of sodium chloride, dried over anhydrous sodium sulfate, and then concentrated under reduced pressure to give the titled compound (6.3 mg).

(11) 4-Oxo-3-azabicyclo[3.1.0]hexane-1-carboxylic acid[1-phenyl-5-(3-propylphenyl)-1H-pyrazol-3-yl]amide

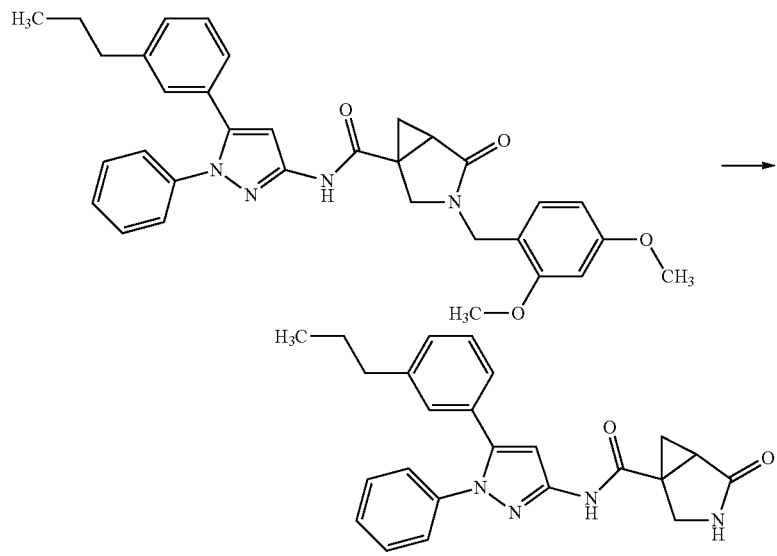

To 3-(2,4-dimethoxybenzyl)-4-oxo-3-azabicyclo[3.1.0]hexane-1-carboxylic acid[1-phenyl-5-(3-propylphenyl)-1H-pyrazol-3-yl]amide (6.3 mg) were sequentially added anisole (2 µl) and trifluoroacetic acid (0.5 ml) at room temperature, and the mixture was stirred at 80° C. for 3 hours. This reaction mixture was concentrated under reduced pressure, the resulting residue was purified by silica gel thin-layer chromatography (eluent: chloroform/methanol=9/1) to give the titled compound (0.3 mg).

1H-NMR (CDCl3) δ: 0.83-0.88 (m, 4H), 1.22-1.28 (m, 3H), 1.95 (dd, 1H, J=9.3, 4.8 Hz), 2.49 (t, 2H, J=8.5 Hz), 3.60 (d, 1H, J=10.1 Hz), 4.01 (d, 1H, J=10.1 Hz), 5.14 (s, 1H), 6.99 (s, 1H), 7.04-7.34 (m, 9H), 7.83 (s, 1H).

Preparation 31

Example 250

Synthesis of (4-oxo-5-azabispiro[2.4]heptane-7-carboxylic acid{1-phenyl-5-[3-(2,2,2-trifluoroethoxymethyl)phenyl]-1H-pyrazol-3-yl}amide)

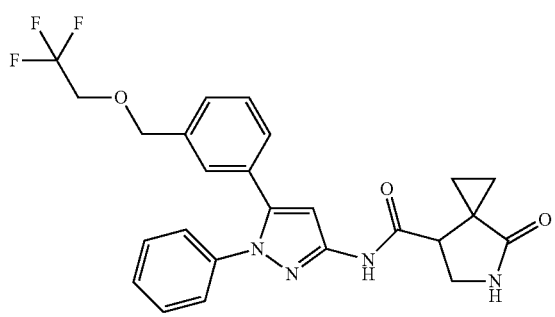 [SMILES: O=C(Nc1cc(-c2cccc(COCC(F)(F)F)c2)n(-c2ccccc2)n1)C1CNC(=O)C12CC2]

(1) 1-Acetylcyclopropanecarboxylic acid methyl ester

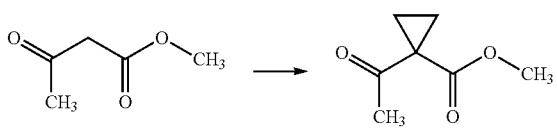

To a solution of methyl acetoacetate (3 ml) in acetone (30 ml) were sequentially added potassium carbonate (11.54 g) and 1,2-dibromoethane (2.4 ml) at room temperature, and the mixture was stirred at 65° C. for 17 hours. This reaction mixture was filtered, the filtrate was concentrated under reduced pressure, and the resulting residue was purified by silica gel column chromatography (eluent: n-hexane/ethyl acetate=10/1) to give the titled compound (2.17 g).

$^1$H-NMR (CDCl$_3$) δ: 1.48 (s, 4H), 2.47 (s, 3H), 3.75 (s, 3H).

(2) 1-(1-Trifluoromethanesulfonyloxyvinyl)cyclopropane carboxylic acid methyl ester

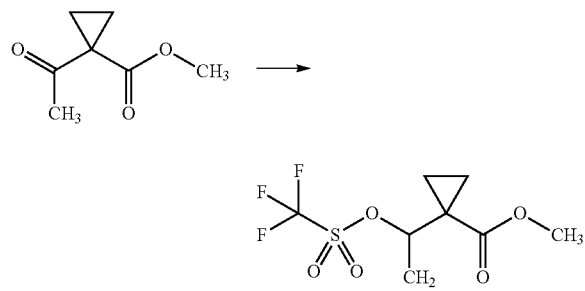

Under argon atmosphere, to a solution of diisopropylamine (2.37 ml) in tetrahydrofuran (11 ml) was added n-butyllithium (10.4 ml, 1.6M solution in n-hexane) at 0° C., and the mixture was stirred for 0.5 hours. At −78° C., a solution of 1-accetylcyclopropane carboxylic acid methyl ester (2.17 g) in tetrahydrofuran (11 ml) was added thereto, and the mixture was stirred for 0.5 hours. Then, N-phenylbis(trifluoromethanesulfonimide) (6.00 g) was added thereto, and the mixture was stirred for 0.5 hours, and then stirred at 0° C. for additional 1 hour. To this reaction mixture was added water, and the mixture was extracted with ethyl acetate. This organic layer was washed with a saturated aqueous solution of sodium chloride, dried over anhydrous sodium sulfate, and then concentrated under reduced pressure to give the titled compound (4.36 g).

(3) 1-(1-Methoxycarbonylvinyl)cyclopropanecarboxylic acid methyl ester

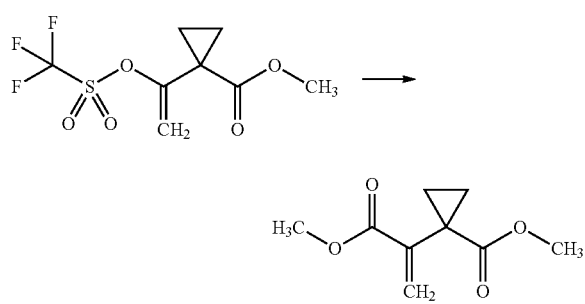

To a solution of 1-(1-trifluoromethanesulfonyloxyvinyl)cyclopropane carboxylic acid methyl ester (4.36 g) prepared in the previous step in N,N-dimethylformamide/methanol (1/2, 66 ml) were sequentially added triethylamine (6.4 ml) and bis(triphenylphosphine)palladium (II) dichloride (1.07 g) at room temperature, and the air in reaction vessel was replaced with carbon monooxide at normal pressure. This reaction solution was stirred at 50° C. for 18 hours, and then cooled to room temperature, and carbon monooxide in the reaction vessel was replaced with nitrogen. To this reaction mixture were added water and ethyl acetate, the mixture was filtered through Celite, and subjected to elution with ethyl acetate. The filtrate was extracted with ethyl acetate, the separated organic layer was washed with a saturated aqueous solution of sodium chloride, dried over anhydrous sodium sulfate, and then concentrated under reduced pressure. The resulting residue was purified by silica gel column chromatography (eluent: n-hexane/ethyl acetate=8/1) to give the titled compound (720 mg).

$^1$H-NMR (CDCl$_3$) δ: 1.03 (dd, 2H, J=7.33, 4.07 Hz), 1.51 (dd, 2H, J=7.33, 4.07 Hz), 3.65 (s, 3H), 3.78 (s, 3H), 5.64 (d, 1H, J=0.93 Hz), 6.31 (d, 1H, J=0.93 Hz).

(4) 5-(2,4-Dimethoxybenzyl)-4-oxo-5-azaspiro[2.4]heptane-7-carboxylic acid methyl ester

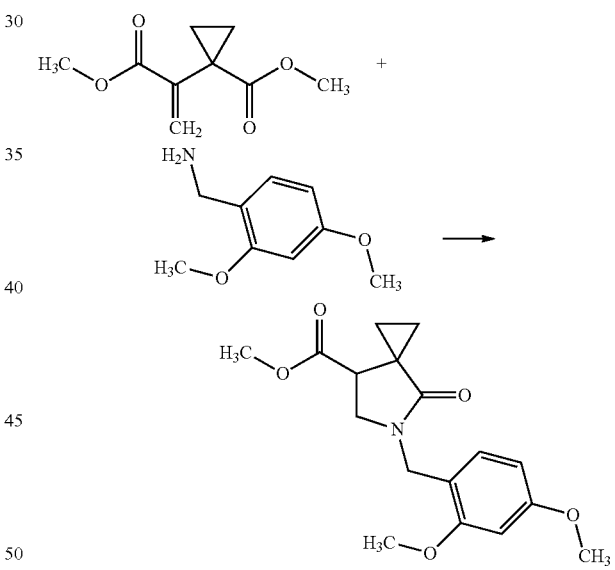

To a solution of 1-(1-methoxycarbonylvinyl)cyclopropanecarboxylic acid methyl ester (720 mg) in toluene (3.6 ml) was added 2,4-dimethoxybenzylamine (587 μl) at room temperature, and then the mixture was stirred at reflux for 20 hours. This reaction mixture was concentrated under reduced pressure, the resulting residue was purified by silica gel column chromatography (eluent: n-hexane/ethyl acetate=1/1) to give the titled compound (567 mg).

$^1$H-NMR (CDCl$_3$) δ: 0.81-0.84 (m, 2H), 1.09-1.12 (m, 1H), 1.22-1.28 (m, 1H), 3.10 (dd, 1H, J=8.84, 5.23 Hz), 3.48 (dd, 1H, J=10.00, 8.84 Hz), 3.66 (dd, 1H, J=10.00, 5.23 Hz), 3.67 (s, 3H), 3.80 (s, 3H), 3.81 (s, 3H), 4.45 (d, 1H, J=14.77 Hz), 4.51 (d, 1H, J=14.77 Hz), 6.45-6.47 (m, 2H), 7.16-7.18 (m, 1H).

(5) 5-(2,4-Dimethoxybenzyl)-4-oxo-5-azaspiro[2.4]heptane-7-carboxylic acid

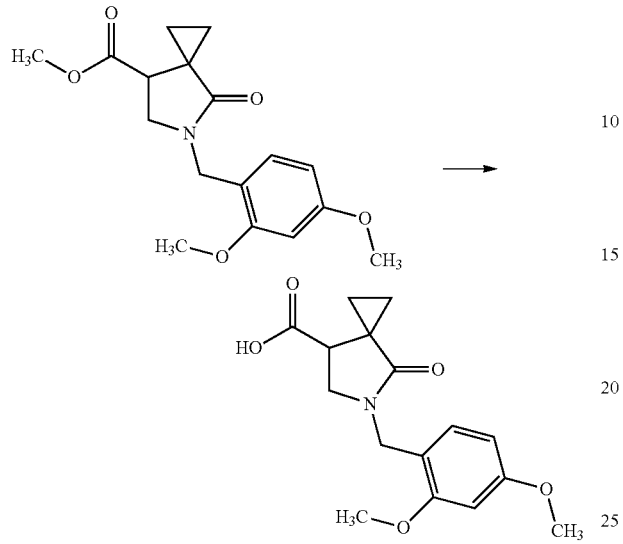

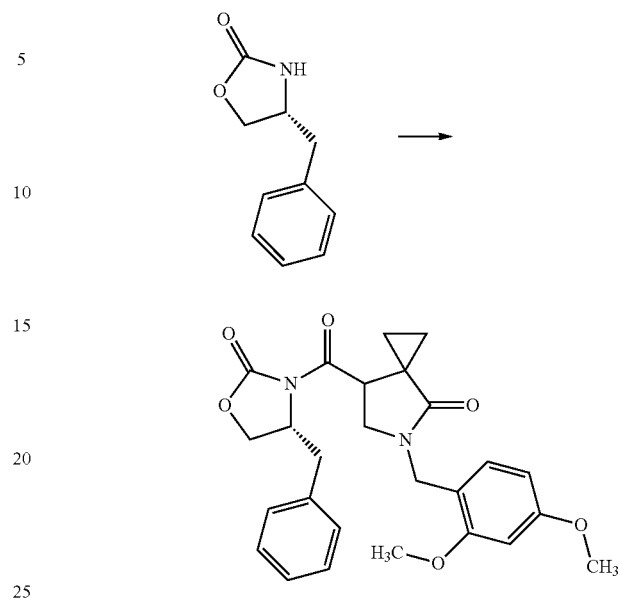

To a solution of 5-(2,4-dimethoxybenzyl)-4-oxo-5-azaspiro[2.4]heptane-7-carboxylic acid methyl ester (2.02 g) in tetrahydrofuran/methanol (1/1, 12 ml) was added a 1M aqueous solution of sodium hydroxide (12 ml) at room temperature, and the mixture was stirred for 1 hour. To this reaction solution was added a 2M aqueous solution of hydrochloric acid (6 ml), and the mixture was stirred, and then concentrated under reduced pressure. The resulting residue was dissolved in ethyl acetate, the solution was washed with a saturated aqueous solution of sodium chloride, dried over anhydrous sodium sulfate, and then concentrated under reduced pressure. To the resulting solid was added diisopropyl ether (8 ml), and the mixture was stirred. A solid was collected from this suspension by filtration, and was dried under reduced pressure to give the titled compound (1.59 g).

$^1$H-NMR (CDCl$_3$) δ: 0.83-0.88 (m, 1H), 0.95-1.00 (m, 1H), 1.12-1.18 (m, 1H), 1.21-1.28 (m, 1H), 3.10 (dd, 1H, J=8.61, 5.12 Hz), 3.49 (dd, 1H, J=10.23, 8.61 Hz), 3.64 (dd, 1H, J=10.23, 5.12 Hz), 3.78 (s, 3H), 3.79 (s, 3H), 4.43 (d, 1H, J=14.65 Hz), 4.50 (d, 1H, J=14.65 Hz), 6.42-6.45 (m, 2H), 7.13-7.16 (m, 1H).

(6) Optically active compound of 7-((R)-4-Benzyl-2-oxooxazolidine-3-carbonyl)-5-(2,4-dimethoxybenzyl)-5-azaspiro[2.4]heptan-4-one

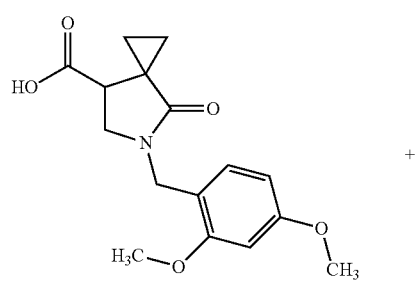

+

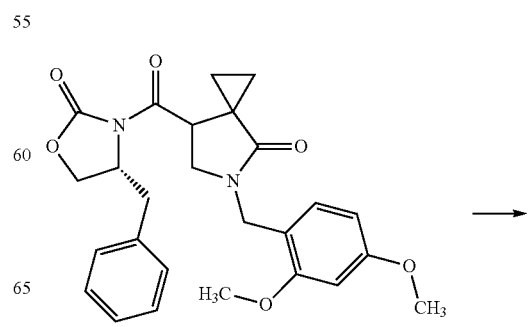

To a solution of 5-(2,4-dimethoxybenzyl)-4-oxo-5-azaspiro[2.4]heptane-7-carboxylic acid (1.59 g) in chloroform (16 ml) were sequentially added (R)-4-benzyl-2-oxazolidinone (1.11 g), WSC.HCl (1.20 g) and N,N-dimethyl-4-aminopyridine (318 mg) at room temperature, and the mixture was stirred for 4 hours. To this reaction mixture was added water, and the organic layer was separated from the solution, and concentrated under reduced pressure. The resulting residue was purified by silica gel column chromatography (eluent: n-hexane/ethyl acetate=2/1) to separate a low-polarity component as the titled compound (1.39 g).

$^1$H-NMR (CDCl$_3$) δ: 0.77-0.82 (m, 1H), 1.11-1.17 (m, 2H), 1.26-1.30 (m, 1H), 2.67 (dd, 1H, J=13.23, 10.37 Hz), 3.38 (dd, 1H, J=13.23, 3.42 Hz), 3.49-3.55 (m, 1H), 3.65 (dd, 1H, J=10.37, 3.42 Hz), 3.81 (s, 3H), 3.81 (s, 3H), 4.17-4.19 (m, 2H), 4.34-4.36 (m, 1H), 4.48 (d, 1H, J=15.00 Hz), 4.57 (d, 1H, J=15.00 Hz), 4.64-4.68 (m, 1H), 6.45-6.50 (m, 2H), 7.21-7.24 (m, 3H), 7.29-7.37 (m, 3H).

(7) Optically active compound of 5-(2,4-Dimethoxybenzyl)-4-oxo-5-azaspiro[2.4]heptane-7-carboxylic acid

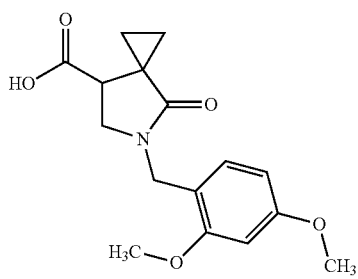

To a solution of lithium hydroxide monohydrate (142 mg) in water (5 ml) was added 30 wt % aqueous solution of hydrogen peroxide (0.8 ml) at −5° C., and the mixture was stirred for 15 minutes. To this reaction mixture were sequentially added tetrahydrofuran (5 ml) and a solution of an optically active compound of 7-((R)-4-benzyl-2-oxooxazolidine-3-carbonyl)-5-(2,4-dimethoxybenzyl)-5-azaspiro[2.4]heptan-4-one (1.39 g) in tetrahydrofuran (10 ml), and the mixture was stirred for additional 1 hour. To this reaction mixture was added a solution of sodium hydrogen sulfite (815 mg) in water (5 ml), and the mixture was stirred at room temperature for 1 hour, and then extracted with ethyl acetate. This organic layer was washed with a saturated aqueous solution of sodium chloride, dried over anhydrous sodium sulfate, and then concentrated under reduced pressure. The resulting residue was purified by silica gel column chromatography (eluent: ethyl acetate only). To the resulting solid was added diisopropyl ether/ethyl acetate/n-hexane (10/1/5, 10 ml), and the mixture was stirred. A solid was collected from this suspension by filtration, and dried under reduced pressure to give the titled compound (372 mg).

$^1$H-NMR (DMSO-D$_6$) δ: 0.83-0.89 (m, 3H), 0.94-0.97 (m, 1H), 3.07-3.11 (m, 1H), 3.42-3.51 (m, 2H), 3.75 (s, 3H), 3.78 (s, 3H), 4.28 (d, 1H, J=14.89 Hz), 4.34 (d, 1H, J=14.89 Hz), 6.49 (dd, 1H, J=8.37, 2.33 Hz), 6.57 (d, 1H, J=2.33 Hz), 7.04 (d, 1H, J=8.37 Hz), 12.56 (br s, 1H).

(8) Optically active compound of 4-Oxo-5-azaspiro[2.4]heptane-7-carboxylic acid

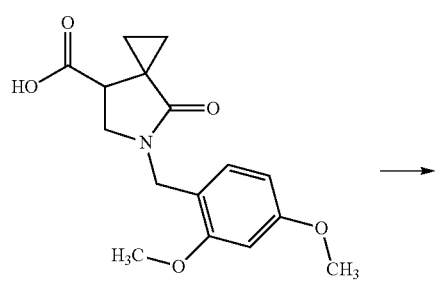

→

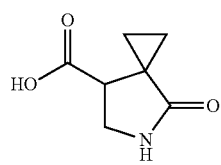

To an optically active compound of 5-(2,4-dimethoxybenzyl)-4-oxo-5-azaspiro[2.4]heptane-7-carboxylic acid (372 mg) were sequentially added anisole (159 μl) and trifluoroacetic acid (5.6 ml) at room temperature, and the mixture was stirred at 80° C. for 4 hours. This reaction mixture was concentrated under reduced pressure, and diisopropyl ether (10 ml) was added thereto. The precipitated solid was collected by filtration to give the titled compound (144 mg).

$^1$H-NMR (DMSO-D$_6$) δ: 0.77-0.82 (m, 3H), 0.86-0.91 (m, 1H), 3.12 (t, 1H, J=6.75 Hz), 3.48 (d, 2H, J=6.75 Hz), 7.70 (br s, 1H), 12.51 (br s, 1H).

(9) 1-Phenyl-5-[3-(2,2,2-trifluoroethoxymethyl)phenyl]-1H-pyrazol-3-ylamine

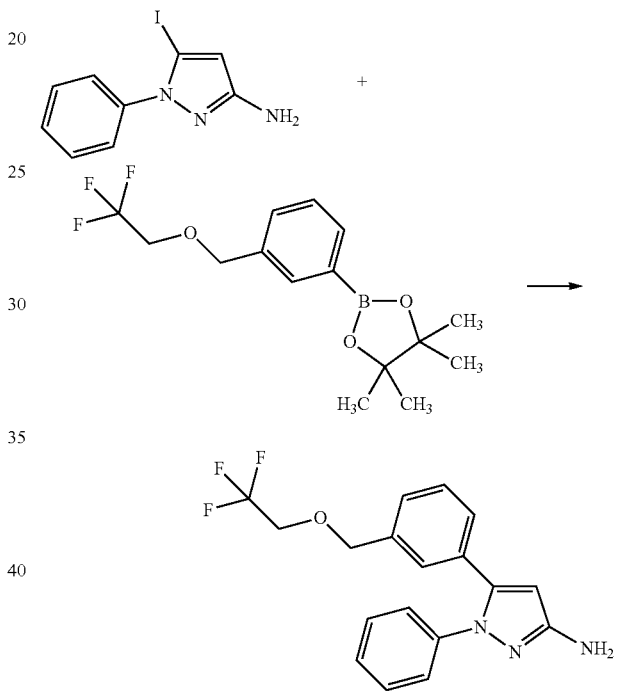

To a solution of 5-iodo-1-phenyl-1H-pyrazol-3-ylamine (221 mg) prepared according to the same procedures as Preparation 2 in 1,2-dimethoxyethane (2.2 ml) were sequentially added 4,4,5,5-tetramethyl-2-[3-(2,2,2-trifluoroethoxymethyl)phenyl]-[1,3,2]dioxaborolane (269 mg) prepared in Preparation 28, a 2M aqueous solution of sodium carbonate (1.1 ml), tricyclohexylphosphine (43.4 mg) and palladium (II) acetate (17.4 mg) at room temperature, and the mixture was stirred at 100° C. for 12 hours. To this reaction mixture was added a saturated aqueous solution of sodium hydrogen carbonate at room temperature, and then the mixture was filtered through Celite, and subjected to elution with ethyl acetate. The filtrate was extracted with ethyl acetate, the resulting organic layer was washed with was a saturated aqueous solution of sodium chloride, dried over anhydrous sodium sulfate, and then concentrated under reduced pressure. The resulting residue was purified by silica gel column chromatography (eluent: n-hexane/ethyl acetate=2/1) to give the titled compound (258 mg).

¹H-NMR (CDCl₃) δ: 3.66 (q, 2H, J=8.7 Hz), 3.77 (br s, 2H), 4.57 (s, 2H), 5.92 (s, 1H), 7.12-7.33 (m, 9H).

(10) Optically active compound of 4-Oxo-5-aza bispiro[2.4]heptane-7-carboxylic acid{1-phenyl-5-[3-(2,2-trifluoroethoxymethyl)phenyl]-1H-pyrazol-3-yl}amide

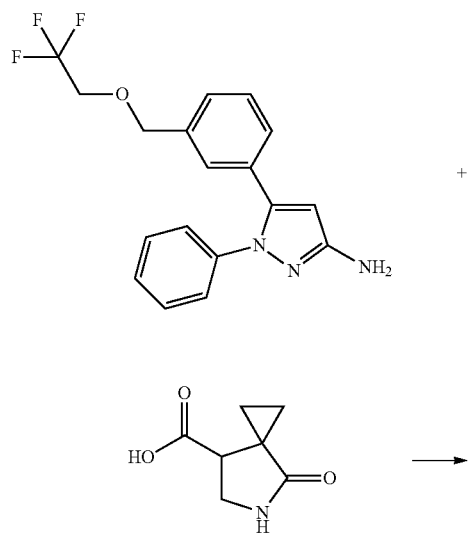

+

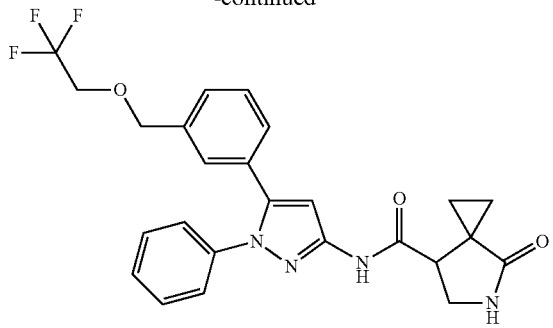

To a solution of 1-phenyl-5-[3-(2,2-trifluoroethoxymethyl)phenyl]-1H-pyrazol-3-ylamine (19.5 mg) in N,N-dimethylacetamide (0.2 ml) were sequentially added an optically active compound of 4-oxo-5-azaspiro[2.4]heptane-7-carboxylic acid (10.5 mg) and WSC.HCl (16.1 mg) at room temperature, and the mixture was stirred for 0.5 hours. To this reaction mixture was added water, and then the precipitated solid was collected by filtration, and dried under reduced pressure to give the titled compound (15.4 mg).

¹H-NMR (DMSO-D₆) δ: 0.66-0.71 (m, 1H), 0.78-0.82 (m, 1H), 0.88-0.99 (m, 2H), 3.33-3.37 (m, 1H), 3.50-3.54 (m, 1H), 3.56-3.60 (m, 1H), 3.97 (q, 2H, J=9.30 Hz), 4.61 (s, 2H), 6.93 (s, 1H), 7.15-7.17 (m, 1H), 7.22-7.26 (m, 3H), 7.31-7.41 (m, 5H), 7.72 (s, 1H), 10.73 (s, 1H).

Compounds of Examples 9 to 234 and 251 to 605 were prepared according to the same procedures as Preparations described in above. The compounds of Examples 9 to 234 are shown in the following Tables 1 together with Compounds of Examples 1-8. The compounds of Examples 251 to 605 are shown in the following Tables 2 together with Compounds of Examples 235-250.

TABLE 1

| Ex. No. | Molecular Structure | NMR | MS (M + H) | MS (M − H) | Comments |
|---|---|---|---|---|---|
| 1 | 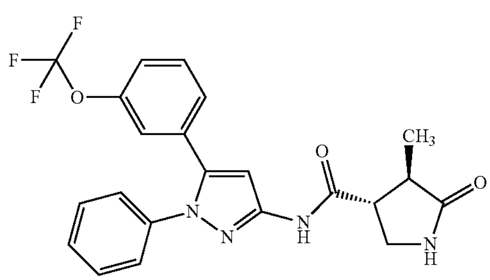 [SMILES: C[C@H]1C(=O)NC[C@@H]1C(=O)Nc1cc(-c2cccc(OC(F)(F)F)c2)n(-c2ccccc2)n1] | 1H-NMR (DMSO-D6) δ: 1.08 (d, 3H, J = 7.3 Hz), 2.55 (dq, 1H, J = 9.2, 7.3 Hz), 3.04 (ddd, 1H, J = 9.2, 8.7, 8.5 Hz), 3.23 (dd, 1H, J = 9.2, 8.7 Hz), 3.45 (dd, 1H, J = 9.2, 8.5 Hz), 7.03 (s, 1H), 7.09 (s, 1H), 7.25-7.27 (m, 2H), 7.35-7.45 (m, 5H), 7.52 (t, 1H, J = 8.0 Hz), 7.68 (s, 1H), 10.99 (s, 1H). | 445 | 443 | (3R,4R)-form |
| 2 | 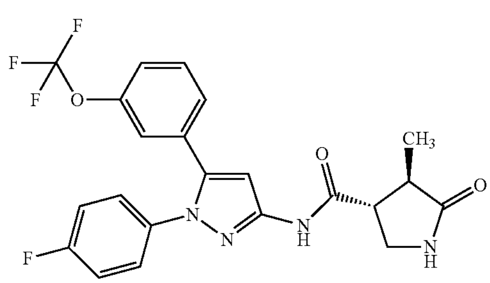 [SMILES: C[C@H]1C(=O)NC[C@@H]1C(=O)Nc1cc(-c2cccc(OC(F)(F)F)c2)n(-c2ccc(F)cc2)n1] | 1H-NMR (DMSO-D6) δ: 1.08 (d, 3H, J = 7.1 Hz), 2.54 (dq, 1H, J = 9.3, 7.1 Hz), 3.04 (ddd, 1H, J = 9.3, 9.2, 8.4 Hz), 3.23 (dd, 1H, J = 9.2, 8.6 Hz), 3.44 (dd, 1H, J = 8.6, 8.4 Hz), 7.03 (s, 1H), 7.11 (s, 1H), 7.25-7.38 (m, 6H), 7.53 (dd, 1H, J = 8.2, 7.9 Hz), 7.68 (s, 1H), 10.98 (s, 1H). | 463 | 461 | (3R,4R)-form |

TABLE 1-continued

| Ex. No. | Molecular Structure | NMR | MS (M + H) | MS (M − H) | Comments |
|---|---|---|---|---|---|
| 3 | 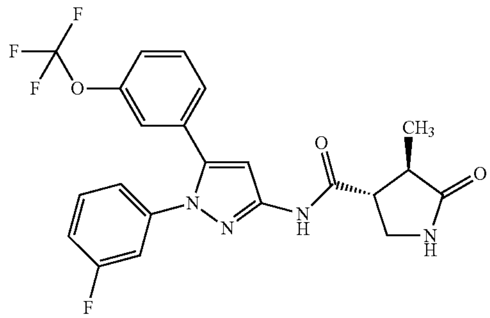 [SMILES: C[C@H]1C(=O)NC[C@@H]1C(=O)Nc1cc(-c2cccc(OC(F)(F)F)c2)n(-c2cccc(F)c2)n1] | 1H-NMR (DMSO-D6) δ: 1.08 (d, 3H, J = 7.3 Hz), 2.54 (dq, 1H, J = 9.3, 7.3 Hz), 3.04 (ddd, 1H, J = 9.3, 8.9, 8.5 Hz), 3.23 (dd, 1H, J = 8.9, 8.7 Hz), 3.45 (dd, 1H, J = 8.7, 8.5 Hz), 7.04 (s, 1H), 7.05-7.07 (m, 1H), 7.14-7.18 (m, 2H), 7.22-7.26 (m, 1H), 7.39-7.48 (m, 3H), 7.56 (t, 1H, J = 8.0 Hz), 7.68 (s, 1H), 11.03 (s, 1H). | 463 | 461 | (3R,4R)-form |
| 4 | 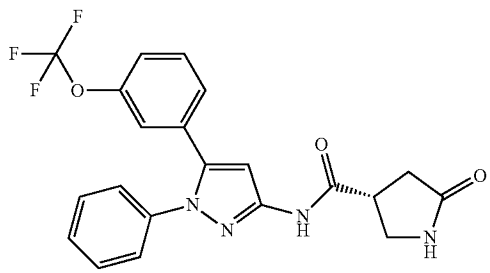 [SMILES: O=C1C[C@@H](C(=O)Nc2cc(-c3cccc(OC(F)(F)F)c3)n(-c3ccccc3)n2)CN1] | 1H-NMR (DMSO-D6) δ: 2.35-2.42 (m, 2H), 3.31-3.54 (m, 3H), 7.01 (s, 1H), 7.08 (s, 1H), 7.22-7.28 (m, 2H), 7.32-7.46 (m, 5H), 7.52 (t, 1H, J = 8.0 Hz), 7.64 (s, 1H), 10.90 (s, 1H). | 431 | 429 | R-form |
| 5 | 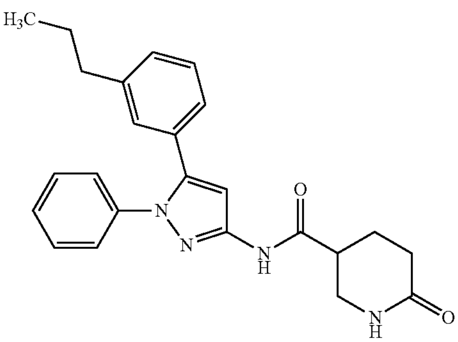 [SMILES: CCCc1cccc(-c2cc(NC(=O)C3CCC(=O)NC3)nn2-c2ccccc2)c1] | 1H-NMR (DMSO-D6) δ: 0.77 (t, 3H, J = 7.3 Hz), 1.44 (tq, 2H, J = 7.5, 7.3 Hz), 1.83-2.03 (m, 2H), 2.12-2.30 (m, 2H), 2.46 (t, 2H, J = 7.5 Hz), 2.84 (tt, 1H, J = 10.7, 3.6 Hz), 3.24-3.31 (m, 2H), 6.89 (s, 1H), 7.00 (s, 1H), 7.06 (d, 1H, J = 7.7 Hz), 7.17 (d, 1H, J = 7.7 Hz), 7.19-7.43 (m, 6H), 7.51 (s, 1H), 10.83 (s, 1H). | 403 | 401 | Optically active substance Optical isomer of Example 96 |
| 6 | 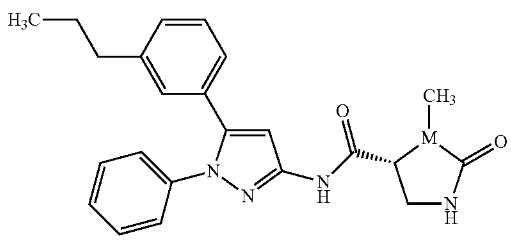 | 1H-NMR (DMSO-D6) δ: 0.77 (t, 3H, J = 7.3 Hz), 1.44 (tq, 2H, J = 7.5, 7.3 Hz), 2.46 (t, 3H, J = 7.5 Hz), 2.64 (s, 3H), 3.21 (dd, 1H, J = 8.8, 6.3 Hz), 3.54 (dd, 1H, J = 9.4, 8.8 Hz), 4.28 (dd, 1H, J = 9.4, 6.3 Hz), 6.44 (s, 1H), 6.92 (s, 1H), 7.01 (s, 1H), 7.08 (d, 1H, J = 7.0 Hz), 7.17 (d, 1H, J = 7.0 Hz), 7.20-7.44 (m, 6H), 11.02 (s, 1H). | 404 | 402 | R-form |
| 7 | 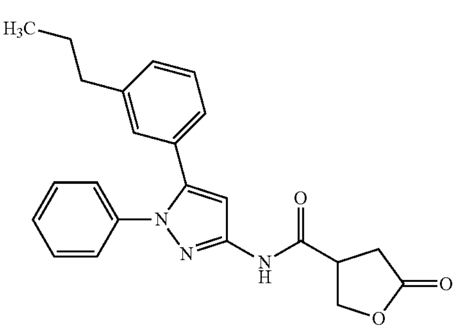 [SMILES: CCCc1cccc(-c2cc(NC(=O)C3COC(=O)C3)nn2-c2ccccc2)c1] | 1H-NMR (DMSO-D6) δ: 0.77 (t, 3H, J = 7.3 Hz), 1.38-1.50 (m, 2H), 2.46 (t, 2H, J = 7.5 Hz), 2.69 (dd, 1H, J = 17.4, 5.9 Hz), 2.81 (dd, 1H, J = 17.4, 9.0 Hz), 3.56-3.65 (m, 1H), 4.34 (dd, 1H, J = 8.8, 5.0 Hz), 4.47-4.55 (m, 1H), 6.89 (s, 1H), 7.00 (s, 1H), 7.07 (d, 1H, J = 7.5 Hz), 7.17 (d, 1H, J = 7.1 Hz), 7.20-7.30 (3H, m), 7.31-7.43 (3H, m), 11.00 (s, 1H). | 390 | 388 | Racemate |

TABLE 1-continued

| Ex. No. | Molecular Structure | NMR | MS (M + H) | MS (M − H) | Comments |
|---|---|---|---|---|---|
| 8 | 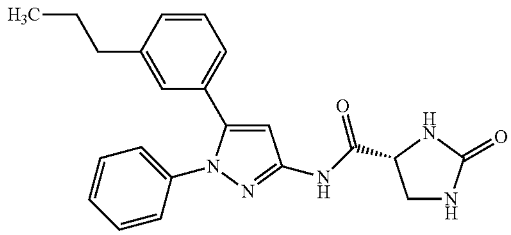 [SMILES: CCCc1cccc(-c2cc(NC(=O)[C@H]3CNC(=O)N3)nn2-c2ccccc2)c1] | 1H-NMR (DMSO-D6) δ: 0.77 (t, 3H, J = 7.3 Hz), 1.44 (tq, 2H, J = 7.5, 7.3 Hz), 2.46 (t, 2H, J = 7.5 Hz), 3.35 (dd, 1H, J = 8.8, 6.2 Hz), 3.59 (dd, 1H, J = 9.4, 8.8 Hz), 4.32 (dd, 1H, J = 9.4, 6.2 Hz), 6.34 (s, 1H), 6.61 (s, 1H), 6.90 (s, 1H), 7.00 (s, 1H), 7.08 (d, 1H, J = 7.7 Hz), 7.15-7.43 (m, 7H), 10.71 (s, 1H). | 390 | 388 | R-form |
| 9 | 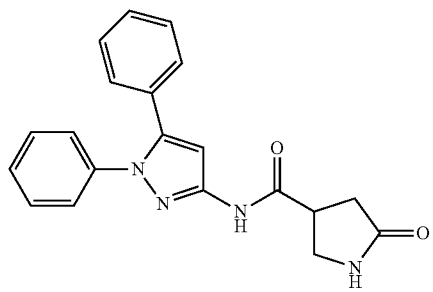 [SMILES: O=C1CC(C(=O)Nc2cc(-c3ccccc3)n(-c3ccccc3)n2)CN1] | 1H-NMR (DMSO-D6) δ: 2.36-2.42 (m, 2H), 3.30-3.36 (m, 1H), 3.37-3.47 (m, 1H), 3.47-3.54 (m, 1H), 6.90 (s, 1H), 7.20-7.26 (m, 4H), 7.31-7.42 (m, 6H), 7.64 (s, 1H), 10.86 (s, 1H). | 347 | 345 | Racemate |
| 10 | 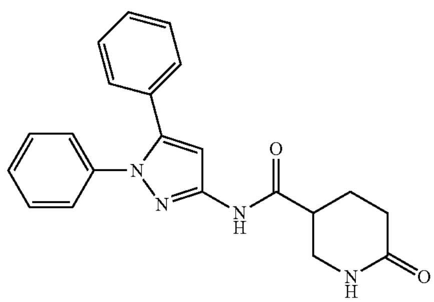 [SMILES: O=C1CCC(C(=O)Nc2cc(-c3ccccc3)n(-c3ccccc3)n2)CN1] | 1H-NMR (DMSO-D6) δ: 1.83-2.03 (m, 2H), 2.12-2.29 (m, 2H), 2.79-2.90 (m, 1H), 3.25-3.37 (m, 2H), 6.89 (s, 1H), 7.20-7.26 (m, 4H), 7.31-7.42 (m, 6H), 7.50 (s, 1H), 10.84 (s, 1H). | 361 | 359 | Racemate |
| 11 | 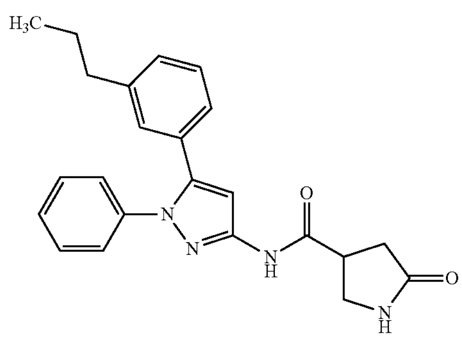 | 1H-NMR (DMSO-D6) δ: 0.77 (t, 3H, J = 7.3 Hz), 1.44 (tq, 2H, J = 7.3, 7.5 Hz), 2.37-2.42 (m, 2H), 2.46 (t, 2H, J = 7.5 Hz), 3.30-3.37 (m, 1H), 3.38-3.47 (m, 1H), 3.47-3.54 (m, 1H), 6.90 (s, 1H), 7.00 (s, 1H), 7.07 (d, 1H, J = 7.7 Hz), 7.17 (d, 1H, J = 7.7 Hz), 7.20-7.24 (m, 2H), 7.27 (dd, 1H, J = 7.7, 7.7 Hz), 7.31-7.42 (m, 3H), 7.63 (s, 1H), 10.85 (s, 1H). | 389 | 387 | Racemate |
| 12 | 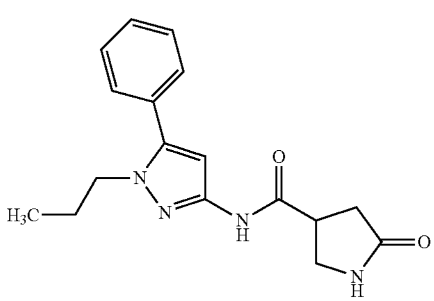 [SMILES: CCCn1nc(NC(=O)C2CNC(=O)C2)cc1-c1ccccc1] | 1H-NMR (DMSO-D6) δ: 0.73 (t, 3H, J = 7.5 Hz), 1.70 (tq, 2H, J = 7.1, 7.5 Hz), 2.33-2.38 (m, 2H), 3.27-3.33 (m, 1H), 3.34-3.43 (m, 1H), 3.44-3.50 (m, 1H), 3.95 (t, 2H, J = 7.1 Hz), 6.59 (s, 1H), 7.43-7.54 (m, 5H), 7.60 (s, 1H), 10.65 (s, 1H). | 313 | 311 | Racemate |

TABLE 1-continued

| Ex. No. | Molecular Structure | NMR | MS (M + H) | MS (M − H) | Comments |
|---|---|---|---|---|---|
| 13 | 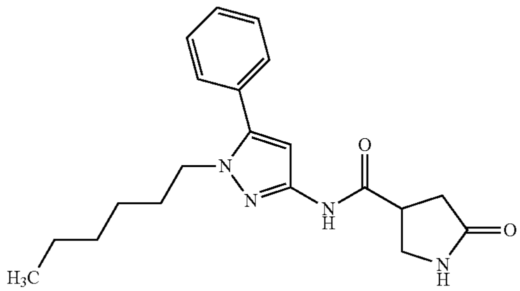 [SMILES: CCCCCCn1nc(NC(=O)C2CNC(=O)C2)cc1-c1ccccc1] | 1H-NMR (DMSO-D6) δ: 0.78 (t, 3H, J = 7.1 Hz), 1.06-1.20 (m, 6H), 1.62-1.71 (m, 2H), 2.33-2.38 (m, 2H), 3.27-3.33 (m, 1H), 3.34-3.43 (m, 1H), 3.44-3.50 (m, 1H), 3.99 (t, 2H, J = 7.1 Hz), 6.58 (s, 1H), 7.43-7.53 (m, 5H), 7.60 (s, 1H), 10.65 (s, 1H). | 355 | 353 | Racemate |
| 14 | 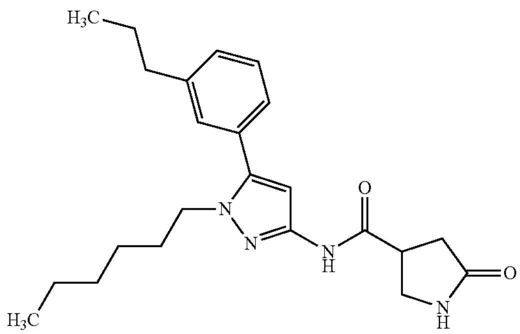 [SMILES: CCCCCCn1nc(NC(=O)C2CNC(=O)C2)cc1-c1cccc(CCC)c1] | 1H-NMR (DMSO-D6) δ: 0.77 (t, 3H, J = 7.1 Hz), 0.90 (t, 3H, J = 7.5 Hz), 1.07-1.20 (m, 6H), 1.62 (tq, 2H, J = 7.1, 7.7 Hz), 1.64-1.70 (m, 2H), 2.32-2.38 (m, 2H), 2.62 (t, 2H, J = 7.7 Hz), 3.27-3.33 (m, 1H), 3.33-3.43 (m, 1H), 3.44-3.50 (m, 1H), 3.98 (t, 2H, J = 7.1 Hz), 6.57 (s, 1H), 7.23-7.29 (m, 3H), 7.40 (dd, 1H, J = 7.7, 7.7 Hz), 7.60 (s, 1H), 10.64 (s, 1H). | 397 | 395 | Racemate |
| 15 | 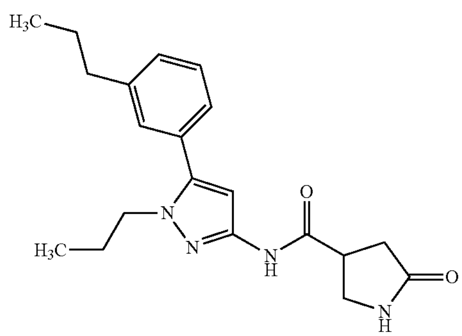 [SMILES: CCCc1cccc(-c2cc(NC(=O)C3CNC(=O)C3)nn2CCC)c1] | 1H-NMR (DMSO-D6) δ: 0.73 (t, 3H, J = 7.5 Hz), 0.90 (t, 3H, J = 7.3 Hz), 1.63 (tq, 2H, J = 7.5, 7.5 Hz), 1.70 (tq, 2H, J = 7.3, 7.5 Hz), 2.34-2.38 (m, 2H), 2.62 (t, 2H, J = 7.5 Hz), 3.27-3.33 (m, 1H), 3.34-3.43 (m, 1H), 3.44-3.50 (m, 1H), 3.95 (t, 2H, J = 7.1 Hz), 6.57 (s, 1H), 7.23-7.29 (m, 3H), 7.41 (dd, 1H, J = 7.7, 7.7 Hz), 7.60 (s, 1H), 10.64 (s, 1H). | 355 | 353 | Racemate |
| 16 | 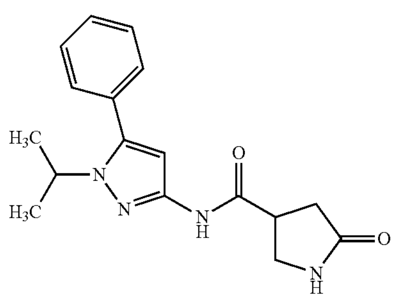 [SMILES: CC(C)n1nc(NC(=O)C2CNC(=O)C2)cc1-c1ccccc1] | 1H-NMR (DMSO-D6) δ: 1.35 (d, 6H, J = 6.4 Hz), 2.29-2.42 (m, 2H), 3.27-3.33 (m, 1H), 3.34-3.43 (m, 1H), 3.44-3.50 (m, 1H), 4.46 (sep, 1H, J = 6.4 Hz), 6.55 (s, 1H), 7.40-7.54 (m, 5H), 7.60 (s, 1H), 10.71 (s, 1H). | 313 | 311 | Racemate |
| 17 | 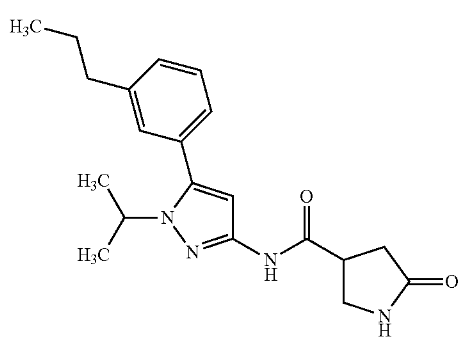 [SMILES: CCCc1cccc(-c2cc(NC(=O)C3CNC(=O)C3)nn2C(C)C)c1] | 1H-NMR (DMSO-D6) δ: 0.91 (t, 3H, J = 7.5 Hz), 1.34 (d, 6H, J = 6.4 Hz), 1.63 (tq, 2H, J = 7.5, 7.7 Hz), 2.30-2.41 (m, 2H), 2.62 (t, 2H, J = 7.7 Hz), 3.27-3.33 (m, 1H), 3.34-3.43 (m, 1H), 3.44-3.50 (m, 1H), 4.46 (sep, 1H, J = 6.4 Hz), 6.53 (s, 1H), 7.20-7.25 (m, 2H), 7.29 (d, 1H, J = 7.7 Hz), 7.41 (dd, 1H, J = 7.7, 7.7 Hz), 7.60 (s, 1H), 10.70 (s, 1H). | 355 | 353 | Racemate |

| Ex. No. | Molecular Structure | NMR | MS (M + H) | MS (M − H) | Comments |
|---|---|---|---|---|---|
| 18 | 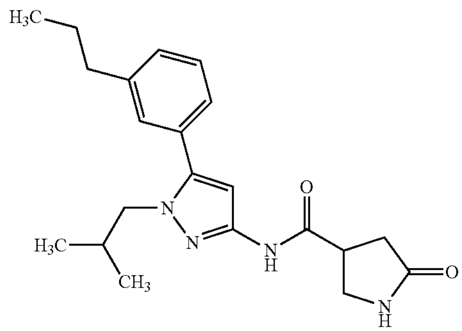 [SMILES: CCCc1cccc(-c2cc(NC(=O)C3CNC(=O)C3)nn2CC(C)C)c1] | 1H-NMR (DMSO-D6) δ: 0.71 (d, 6H, J = 6.6 Hz), 0.89 (t, 3H, J = 7.4 Hz), 1.62 (tq, 2H, J = 7.4, 7.4 Hz), 1.94-2.08 (m, 1H), 2.28-2.42 (m, 2H), 2.62 (t, 2H, J = 7.5 Hz), 3.23-3.51 (m, 3H), 3.82 (d, 2H, J = 7.3 Hz), 6.58 (s, 1H), 7.22-7.30 (m, 3H), 7.37-7.43 (m, 1H), 7.61 (s, 1H), 10.64 (s, 1H) | 369 | 367 | Racemate |
| 19 | 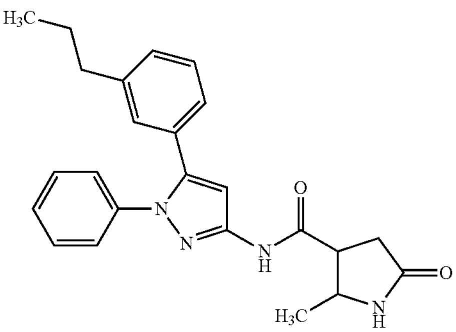 [SMILES: CCCc1cccc(-c2cc(NC(=O)C3CC(=O)NC3C)nn2-c2ccccc2)c1] | 1H-NMR (CDCl3) δ: 0.83 (t, 3H, J = 7.3 Hz), 1.11 (d, 3H, J = 6.0 Hz), 1.50 (tq, 2H, J = 7.5, 7.3 Hz), 2.45-2.63 (m, 3H), 2.68-2.81 (m, 2H), 3.96-4.06 (m, 1H), 6.66 (s, 1H), 7.02-7.08 (m, 3H), 7.12 (d, 1H, J = 7.4 Hz), 7.19 (d, 1H, J = 7.9 Hz), 7.22-7.26 (m, 3H), 7.28-7.38 (m, 3H), 9.55 (s, 1H). | 403 | 401 | Single diastereomer (Racemate) cis-trans isomer of Example 20 |
| 20 | 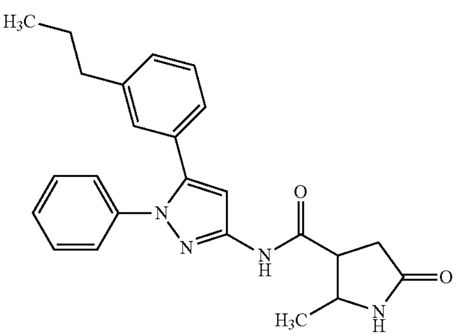 [SMILES: CCCc1cccc(-c2cc(NC(=O)C3CC(=O)NC3C)nn2-c2ccccc2)c1] | 1H-NMR (CDCl3) δ: 0.83 (t, 3H, J = 7.3 Hz), 1.09 (d, 3H, J = 6.5 Hz), 1.44-1.56 (tq, 2H, J = 7.5, 7.3 Hz), 2.32 (dd, 1H, J = 17.0, 8.8 Hz), 2.49 (t, 2H, J = 7.5 Hz), 2.95 (dd, 1H, J = 17.0, 8.7 Hz), 3.21 (q, 1H, J = 8.6 Hz), 3.83-3.92 (m, 1H), 6.30 (s, 1H), 7.02-7.07 (m, 3H), 7.12 (d, 1H, J = 7.7 Hz), 7.17-7.26 (m, 3H), 7.29-7.37 (m, 3H), 9.32 (s, 1H). | 403 | 401 | Single diastereomer (Racemate) cis-trans isomer of Example 19 |
| 21 | 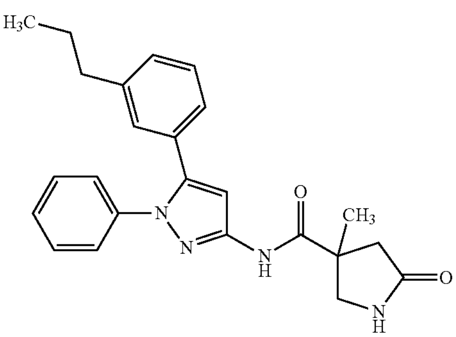 [SMILES: CCCc1cccc(-c2cc(NC(=O)C3(C)CNC(=O)C3)nn2-c2ccccc2)c1] | 1H-NMR (DMSO-D6) δ: 0.77 (t, 3H, J = 7.3 Hz), 1.38-1.49 (m, 5H), 2.15 (d, 1H, J = 16.5 Hz), 2.46 (t, 2H, J = 7.5 Hz), 2.74 (d, 1H, J = 16.5 Hz), 3.14 (d, 1H, J = 10.0 Hz), 3.65 (d, 1H, J = 10.0 Hz), 6.90 (s, 1H), 7.00 (s, 1H), 7.07 (dt, 1H, J = 7.7, 1.4 Hz), 7.17 (d, 1H, J = 7.7 Hz), 7.21-7.30 (m, 3H), 7.31-7.43 (m, 3H), 7.62 (s, 1H), 10.58 (s, 1H). | 403 | 401 | Racemate |
| 22 | 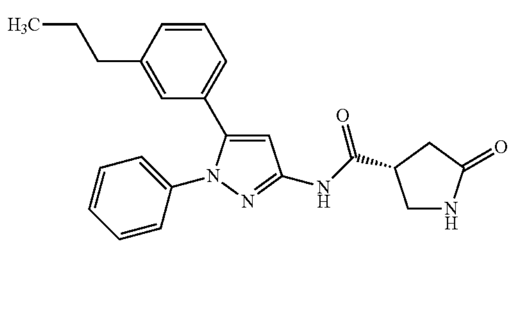 [SMILES: CCCc1cccc(-c2cc(NC(=O)[C@H]3CNC(=O)C3)nn2-c2ccccc2)c1] | 1H-NMR (DMSO-D6) δ: 0.77 (t, 3H, J = 7.3 Hz), 1.38-1.50 (tq, 2H, J = 7.5, 7.3 Hz), 2.36-2.49 (m, 4H), 3.33-3.54 (m, 3H), 6.90 (s, 1H), 7.00 (s, 1H), 7.07 (d, 1H, J = 7.9 Hz), 7.17 (d, 1H, J = 7.9 Hz), 7.19-7.43 (m, 6H), 7.64 (s, 1H), 10.85 (s, 1H). | 389 | 387 | R-form |

TABLE 1-continued

| Ex. No. | Molecular Structure | NMR | MS (M + H) | MS (M − H) | Comments |
|---|---|---|---|---|---|
| 23 | 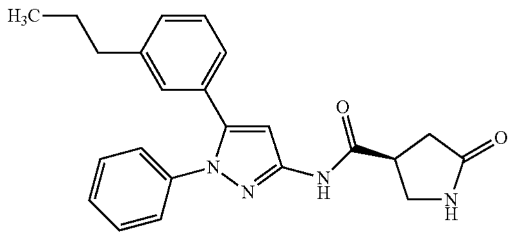 [SMILES: CCCc1cccc(-c2cc(NC(=O)[C@@H]3CNC(=O)C3)nn2-c2ccccc2)c1] | 1H-NMR (DMSO-D6) δ: 0.77 (t, 3H, J = 7.3 Hz), 1.38-1.50 (tq, 2H, J = 7.5, 7.3 Hz), 2.36-2.49 (m, 4H), 3.33-3.54 (m, 3H), 6.90 (s, 1H), 7.00 (s, 1H), 7.07 (d, 1H, J = 7.9 Hz), 7.17 (d, 1H, J = 7.9 Hz), 7.19-7.43 (m, 6H), 7.64 (s, 1H), 10.85 (s, 1H). | 389 | 387 | S-form |
| 24 | 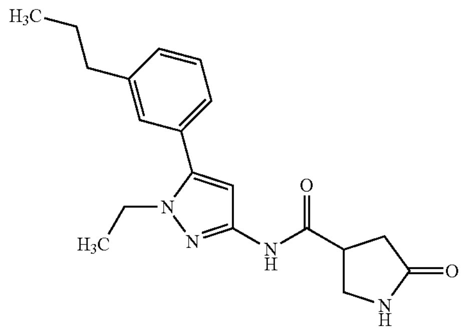 [SMILES: CCCc1cccc(-c2cc(NC(=O)C3CNC(=O)C3)nn2CC)c1] | 1H-NMR (DMSO-D6) δ: 0.90 (t, 3H, J = 7.3 Hz), 1.29 (t, 3H, J = 7.2 Hz), 1.62 (tq, 2H, J = 7.3, 7.3 Hz), 2.31-2.39 (m, 2H), 2.62 (t, 2H, J = 7.5 Hz), 3.24-3.52 (m, 3H), 4.01 (q, 2H, J = 7.1 Hz), 6.57 (s, 1H), 7.23-7.30 (m, 3H), 7.37-7.43 (m, 1H), 7.60 (s, 1H), 10.64 (s, 1H) | 341 | 339 | Racemate |
| 25 | 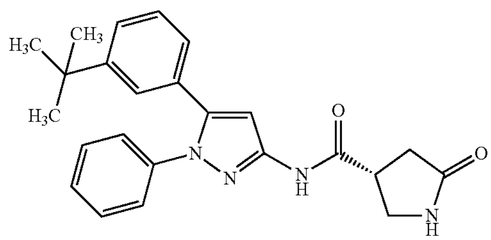 [SMILES: CC(C)(C)c1cccc(-c2cc(NC(=O)[C@H]3CNC(=O)C3)nn2-c2ccccc2)c1] | 1H-NMR (DMSO-D6) δ: 1.09 (s, 9H), 2.35-2.42 (m, 2H), 3.32-3.55 (m, 3H), 6.92 (s, 1H), 7.06 (s, 1H), 7.18 (d, 1H, J = 7.3 Hz), 7.21-7.26 (m, 2H), 7.28-7.44 (m, 5H), 7.63 (s, 1H), 10.84 (s, 1H). | 403 | 401 | R-form |
| 26 | 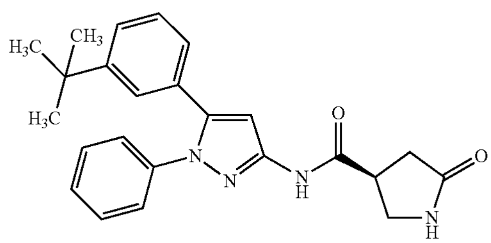 [SMILES: CC(C)(C)c1cccc(-c2cc(NC(=O)[C@@H]3CNC(=O)C3)nn2-c2ccccc2)c1] | 1H-NMR (DMSO-D6) δ: 1.09 (s, 9H), 2.35-2.42 (m, 2H), 3.32-3.55 (m, 3H), 6.92 (s, 1H), 7.06 (s, 1H), 7.18 (d, 1H, J = 7.3 Hz), 7.21-7.26 (m, 2H), 7.28-7.44 (m, 5H), 7.63 (s, 1H), 10.84 (s, 1H). | 403 | 401 | S-form |
| 27 | 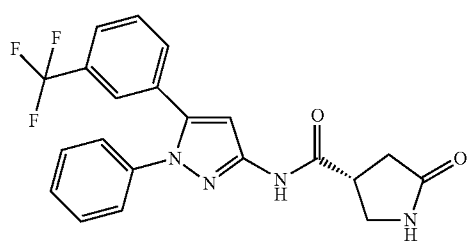 [SMILES: O=C1C[C@@H](C(=O)Nc2cc(-c3cccc(C(F)(F)F)c3)n(-c3ccccc3)n2)CN1] | 1H-NMR (DMSO-D6) δ: 2.35-2.43 (m, 2H), 3.32-3.54 (m, 3H), 7.05 (s, 1H), 7.23-7.29 (m, 2H), 7.34-7.75 (m, 8H), 10.91 (s, 1H). | 415 | 413 | R-form |
| 28 | 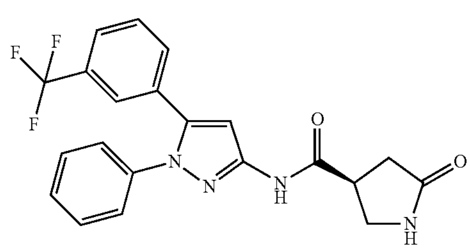 [SMILES: O=C1C[C@H](C(=O)Nc2cc(-c3cccc(C(F)(F)F)c3)n(-c3ccccc3)n2)CN1] | 1H-NMR (DMSO-D6) δ: 2.35-2.43 (m, 2H), 3.32-3.54 (m, 3H), 7.05 (s, 1H), 7.23-7.29 (m, 2H), 7.34-7.75 (m, 8H), 10.91 (s, 1H). | 415 | 413 | S-form |

TABLE 1-continued

| Ex. No. | Molecular Structure | NMR | MS (M + H) | MS (M − H) | Comments |
|---|---|---|---|---|---|
| 29 | 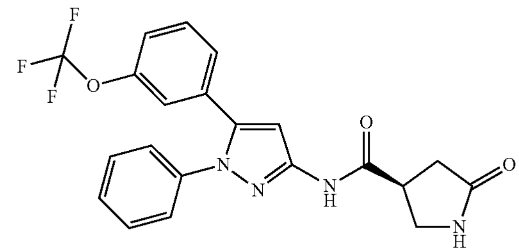 [SMILES: O=C1C[C@H](C(=O)Nc2cc(-c3cccc(OC(F)(F)F)c3)n(-c3ccccc3)n2)CN1] | 1H-NMR (DMSO-D6) δ: 2.35-2.42 (m, 2H), 3.31-3.54 (m, 3H), 7.01 (s, 1H), 7.08 (s, 1H), 7.22-7.28 (m, 2H), 7.32-7.46 (m, 5H), 7.52 (t, 1H, J = 8.0 Hz), 7.64 (s, 1H), 10.90 (s, 1H). | 431 | 429 | S-form |
| 30 | 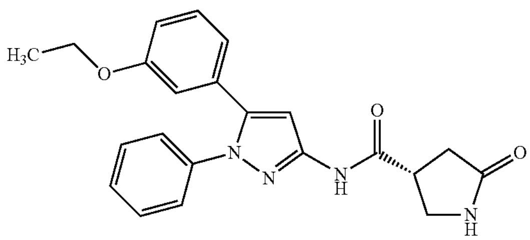 [SMILES: CCOc1cccc(-c2cc(NC(=O)[C@H]3CNC(=O)C3)nn2-c2ccccc2)c1] | 1H-NMR (DMSO-D6) δ: 1.24 (t, 3H, J = 7.0 Hz), 2.35-2.42 (m, 2H), 3.34-3.54 (m, 3H), 3.91 (q, 2H, J = 7.0 Hz), 6.72-6.80 (m, 2H), 6.88-6.93 (m, 2H), 7.22-7.28 (m, 3H), 7.31-7.44 (m, 3H), 7.64 (s, 1H), 10.86 (s, 1H). | 391 | 389 | R-form |
| 31 | 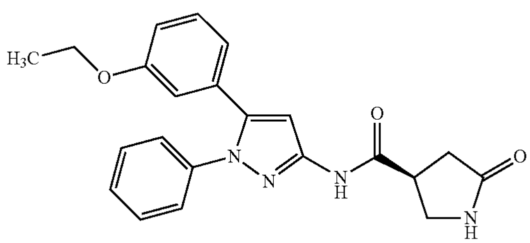 [SMILES: CCOc1cccc(-c2cc(NC(=O)[C@@H]3CNC(=O)C3)nn2-c2ccccc2)c1] | 1H-NMR (DMSO-D6) δ: 1.24 (t, 3H, J = 7.0 Hz), 2.35-2.42 (m, 2H), 3.34-3.54 (m, 3H), 3.91 (q, 2H, J = 7.0 Hz), 6.72-6.80 (m, 2H), 6.88-6.93 (m, 2H), 7.22-7.28 (m, 3H), 7.31-7.44 (m, 3H), 7.64 (s, 1H), 10.86 (s, 1H). | 391 | 389 | R-form |
| 32 | 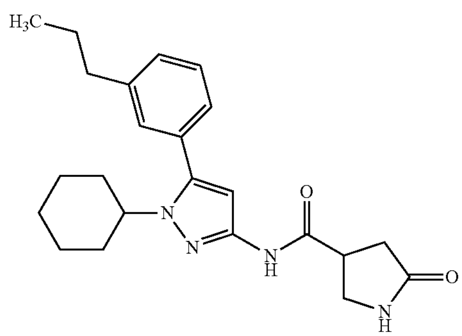 [SMILES: CCCc1cccc(-c2cc(NC(=O)C3CNC(=O)C3)nn2C2CCCCC2)c1] | 1H-NMR (DMSO-D6) δ: 0.90 (t, 3H, J = 7.4 Hz), 1.03-1.27 (m, 3H), 1.54-1.69 (m, 3H), 1.71-1.89 (m, 6H), 2.28-2.37 (m, 2H), 2.62 (t, 2H, J = 7.42 Hz), 3.22-3.53 (m, 3H), 3.94-4.08 (m, 1H), 6.52 (s, 1H), 7.18-7.24 (m, 2H), 7.25-7.31 (m, 1H), 7.37-7.44 (m, 1H), 7.60 (s, 1H), 10.68 (s, 1H) | 395 | 393 | Racemate |
| 33 | 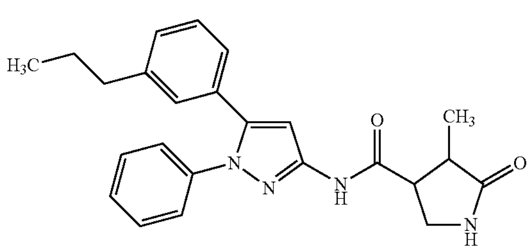 [SMILES: CCCc1cccc(-c2cc(NC(=O)C3CNC(=O)C3C)nn2-c2ccccc2)c1] | 1H-NMR (DMSO-D6) δ: 0.77 (t, 3H, J = 7.3 Hz), 1.08 (d, 3H, J = 7.2 Hz), 1.38-1.50 (tq, 2H, J = 7.5, 7.3 Hz), 2.46 (t, 2H, J = 7.5 Hz), 2.52-2.58 (m, 1H), 3.30 (ddd, 1H, J = 9.2, 8.8, 8.7 Hz), 3.23 (dd, 1H, J = 9.2, 8.8 Hz), 3.44 (dd, 1H, J = 9.2, 8.7 Hz), 6.92 (s, 1H), 7.01 (s, 1H), 7.07 (d, 1H, J = 7.9 Hz), 7.17 (d, 1H, J = 7.9 Hz), 7.20-7.43 (m, 6H), 7.67 (s, 1H), 10.94 (s, 1H) | 403 | 401 | trans-form (Racemate) |

TABLE 1-continued

| Ex. No. | Molecular Structure | NMR | MS (M + H) | MS (M − H) | Comments |
|---|---|---|---|---|---|
| 34 | 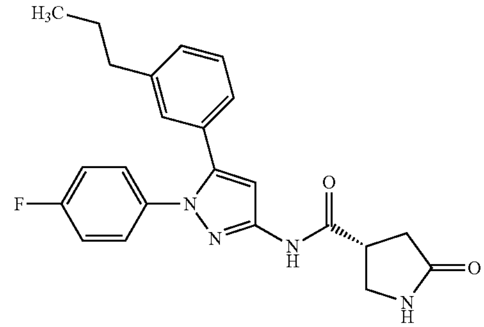 [SMILES: CCCc1cccc(-c2cc(NC(=O)[C@H]3CNC(=O)C3)nn2-c2ccc(F)cc2)c1] | 1H-NMR (DMSO-D6) δ: 0.78 (t, 3H, J = 7.5 Hz), 1.46 (tq, 2H, J = 7.3, 7.5 Hz), 2.37-2.41 (m, 2H), 2.47 (t, 2H, J = 7.3 Hz), 3.30-3.35 (m, 1H), 3.37-3.46 (m, 1H), 3.47-3.53 (m, 1H), 6.89 (s, 1H), 7.00 (s, 1H), 7.07 (d, 1H, J = 7.7 Hz), 7.18 (d, 1H, J = 7.7 Hz), 7.22-7.30 (m, 5H), 7.64 (s, 1H), 10.84 (s, 1H). | 407 | 405 | R-form |
| 35 | 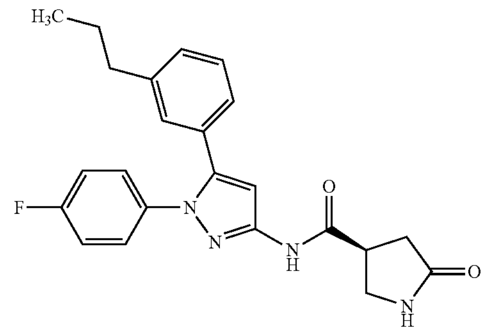 [SMILES: CCCc1cccc(-c2cc(NC(=O)[C@@H]3CNC(=O)C3)nn2-c2ccc(F)cc2)c1] | 1H-NMR (DMSO-D6) δ: 0.78 (t, 3H, J = 7.3 Hz), 1.46 (tq, 2H, J = 7.3, 7.3 Hz), 2.37-2.41 (m, 2H), 2.47 (t, 2H, J = 7.3 Hz), 3.30-3.36 (m, 1H), 3.37-3.46 (m, 1H), 3.47-3.53 (m, 1H), 6.89 (s, 1H), 7.00 (s, 1H), 7.07 (d, 1H, J = 7.7 Hz), 7.18 (d, 1H, J = 7.7 Hz), 7.21-7.30 (m, 5H), 7.64 (s, 1H), 10.84 (s, 1H). | 407 | 405 | S-form |
| 36 | 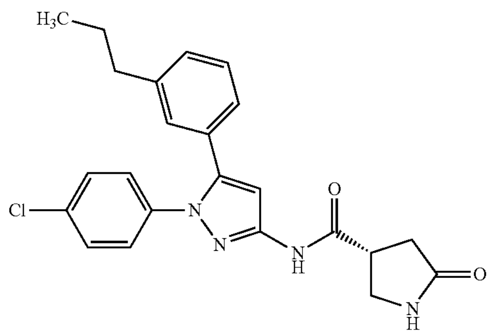 [SMILES: CCCc1cccc(-c2cc(NC(=O)[C@H]3CNC(=O)C3)nn2-c2ccc(Cl)cc2)c1] | 1H-NMR (DMSO-D6) δ: 0.78 (t, 3H, J = 7.3 Hz), 1.47 (tq, 2H, J = 7.3, 7.3 Hz), 2.36-2.41 (m, 2H), 2.48 (t, 2H, J = 7.3 Hz), 3.28-3.37 (m, 1H), 3.37-3.47 (m, 1H), 3.47-3.55 (m, 1H), 6.91 (s, 1H), 7.02 (s, 1H), 7.08 (d, 1H, J = 8.1 Hz), 7.19 (d, 1H, J = 7.7 Hz), 7.24 (d, 2H, J = 8.9 Hz), 7.30 (dd, 1H, J = 7.7, 8.1 Hz), 7.46 (d, 2H, J = 8.9 Hz), 7.64 (s, 1H), 10.88 (s, 1H). | 423 | 421 | R-form |
| 37 | 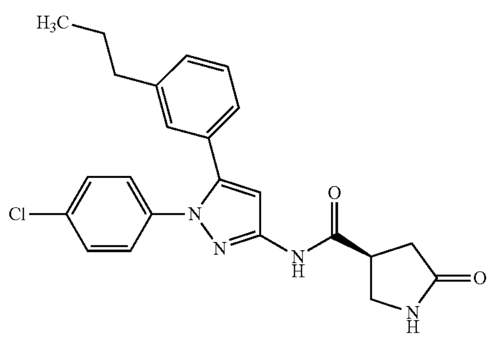 [SMILES: CCCc1cccc(-c2cc(NC(=O)[C@@H]3CNC(=O)C3)nn2-c2ccc(Cl)cc2)c1] | 1H-NMR (DMSO-D6) δ: 0.78 (t, 3H, J = 7.3 Hz), 1.47 (tq, 2H, J = 7.3, 7.3 Hz), 2.37-2.41 (m, 2H), 2.48 (t, 2H, J = 7.3 Hz), 3.31-3.36 (m, 1H), 3.38-3.46 (m, 1H), 3.47-3.53 (m, 1H), 6.91 (s, 1H), 7.02 (s, 1H), 7.08 (d, 1H, J = 8.1 Hz), 7.19 (d, 1H, J = 7.7 Hz), 7.24 (d, 2H, J = 8.9 Hz), 7.30 (dd, 1H, J = 7.7, 8.1 Hz), 7.46 (d, 2H, J = 8.9 Hz), 7.64 (s, 1H), 10.88 (s, 1H). | 423 | 421 | S-form |
| 38 | 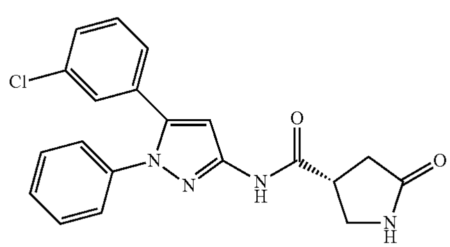 [SMILES: O=C1C[C@@H](C(=O)Nc2cc(-c3cccc(Cl)c3)n(-c3ccccc3)n2)CN1] | 1H-NMR (DMSO-D6) δ: 2.35-2.42 (m, 2H), 3.32-3.54 (m, 3H), 6.97 (s, 1H), 7.17 (d, 1H, J = 7.5 Hz), 7.23-7.31 (m, 3H), 7.34-7.46 (m, 5H), 7.64 (s, 1H), 10.89 (s, 1H). | 381 | 379 | R-form |

TABLE 1-continued

| Ex. No. | Molecular Structure | NMR | MS (M + H) | MS (M − H) | Comments |
|---|---|---|---|---|---|
| 39 | (3-chlorophenyl)-phenyl-pyrazole carboxamide pyrrolidinone | 1H-NMR (DMSO-D6) δ: 2.35-2.42 (m, 2H), 3.32-3.54 (m, 3H), 6.97 (s, 1H), 7.17 (d, 1H, J = 7.5 Hz), 7.23-7.31 (m, 3H), 7.34-7.46 (m, 5H), 7.64 (s, 1H), 10.89 (s, 1H). | 381 | 379 | S-form |
| 40 | cyclohexyl-phenyl-pyrazole carboxamide pyrrolidinone | 1H-NMR (DMSO-D6) δ: 1.09-1.37 (m, 5H), 1.55-1.83 (m, 5H), 2.31-2.40 (m, 2H), 2.60-2.70 (m, 1H), 3.27-3.50 (m, 3H), 6.59 (s, 1H), 7.40-7.56 (m, 5H), 7.62 (s, 1H), 10.67 (s, 1H). | 353 | 351 | R-form |
| 41 | cyclohexyl-phenyl-pyrazole carboxamide pyrrolidinone | 1H-NMR (DMSO-D6) δ: 1.09-1.37 (m, 5H), 1.55-1.83 (m, 5H), 2.31-2.40 (m, 2H), 2.60-2.70 (m, 1H), 3.27-3.50 (m, 3H), 6.59 (s, 1H), 7.40-7.56 (m, 5H), 7.62 (s, 1H), 10.67 (s, 1H). | 353 | 351 | S-form |
| 42 | (3-ethylphenyl)-tert-butyl-pyrazole carboxamide pyrrolidinone | 1H-NMR (DMSO-D6) δ: 0.88 (t, 3H, J = 7.3 Hz), 1.55-1.67 (m, 2H), 2.29-2.37 (m, 2H), 2.60 (t, 2H, J = 7.5 Hz), 3.24-3.51 (m, 3H), 6.38 (s, 1H), 7.14-7.22 (m, 2H), 7.23-7.29 (m, 1H), 7.30-7.38 (m, 1H), 7.59 (s, 1H), 10.57 (s, 1H) | 369 | 367 | Racemate |
| 43 | (3-ethylphenyl)-phenyl-pyrazole carboxamide pyrrolidinone | 1H-NMR (DMSO-D6) δ: 1.05 (t, 3H, J = 7.5 Hz), 2.36-2.41 (m, 2H), 2.52 (q, 2H, J = 7.5 Hz), 3.32-3.54 (m, 3H), 6.90 (s, 1H), 7.01-7.07 (m, 2H), 7.16-7.29 (m, 4H), 7.31-7.43 (m, 3H), 7.63 (s, 1H), 10.85 (s, 1H). | 375 | 373 | R-form |

TABLE 1-continued

| Ex. No. | Molecular Structure | NMR | MS (M + H) | MS (M − H) | Comments |
|---|---|---|---|---|---|
| 44 | 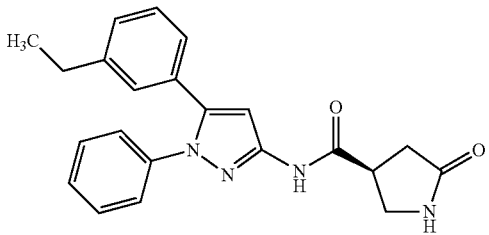 [SMILES: CCc1cccc(-c2cc(NC(=O)[C@@H]3CNC(=O)C3)nn2-c2ccccc2)c1] | 1H-NMR (DMSO-D6) δ: 1.05 (t, 3H, J = 7.5 Hz), 2.36-2.41 (m, 2H), 2.52 (q, 2H, J = 7.5 Hz), 3.32-3.54 (m, 3H), 6.90 (s, 1H), 7.01-7.07 (m, 2H), 7.16-7.29 (m, 4H), 7.31-7.43 (m, 3H), 7.63 (s, 1H), 10.85 (s, 1H). | 375 | 373 | S-form |
| 45 | 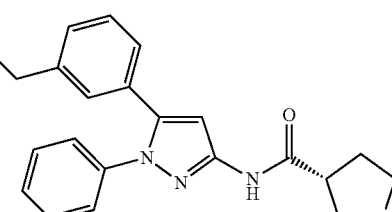 | 1H-NMR (DMSO-D6) δ: 0.82 (t, 3H, J = 7.3 Hz), 1.15 (tq, 2H, J = 7.5, 7.3 Hz), 1.39 (tt, 2H, J = 7.6, 7.5 Hz), 2.36-2.49 (m, 4H), 3.31-3.54 (m, 3H), 6.89 (s, 1H), 6.98 (s, 1H), 7.08 (d, 1H, J = 7.7 Hz), 7.17 (d, 1H, J = 7.7 Hz), 7.20-7.42 (m, 6H), 7.63 (s, 1H), 10.85 (s, 1H). | 403 | 401 | R-form |
| 46 | 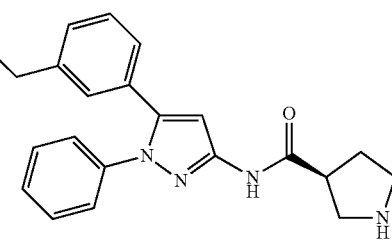 | 1H-NMR (DMSO-D6) δ: 0.82 (t, 3H, J = 7.3 Hz), 1.15 (tq, 2H, J = 7.5, 7.3 Hz), 1.39 (tt, 2H, J = 7.6, 7.5 Hz), 2.36-2.49 (m, 4H), 3.31-3.54 (m, 3H), 6.89 (s, 1H), 6.98 (s, 1H), 7.08 (d, 1H, J = 7.7 Hz), 7.17 (d, 1H, J = 7.7 Hz), 7.20-7.42 (m, 6H), 7.63 (s, 1H), 10.85 (s, 1H). | 403 | 401 | S-form |
| 47 | 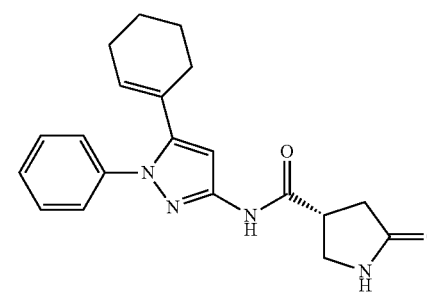 | 1H-NMR (DMSO-D6) δ: 1.49-1.61 (m, 4H), 1.92-2.10 (m, 4H), 2.33-2.38 (m, 2H), 3.25-3.51 (m, 3H), 5.75-5.81 (m, 1H), 6.63 (s, 1H), 7.33-7.51 (m, 5H), 7.62 (s, 1H), 10.74 (s, 1H). | 351 | 349 | R-form |
| 48 | 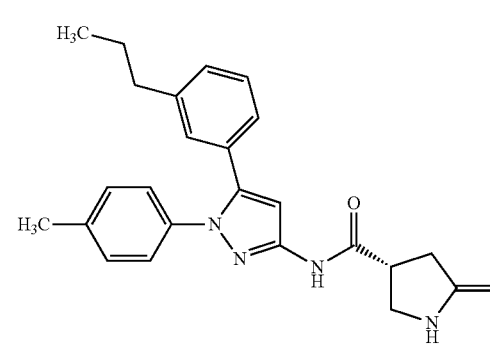 | 1H-NMR (DMSO-D6) δ: 0.77 (t, 3H, J = 7.3 Hz), 1.45 (tq, 2H, J = 7.3, 7.3 Hz), 2.31 (s, 3H), 2.36-2.41 (m, 2H), 2.47 (t, 2H, J = 7.3 Hz), 3.30-3.35 (m, 1H), 3.37-3.46 (m, 1H), 3.47-3.53 (m, 1H), 6.87 (s, 1H), 7.01 (s, 1H), 7.04 (d, 1H, J = 7.7 Hz), 7.10 (d, 2H, J = 8.5 Hz), 7.16 (d, 1H, J = 8.1 Hz), 7.19 (d, 2H, J = 8.5 Hz), 7.26 (dd, 1H, J = 7.7, 8.1 Hz), 7.63 (s, 1H), 10.83 (s, 1H). | 403 | 401 | R-form |

TABLE 1-continued

| Ex. No. | Molecular Structure | NMR | MS (M + H) | MS (M − H) | Comments |
|---|---|---|---|---|---|
| 49 | 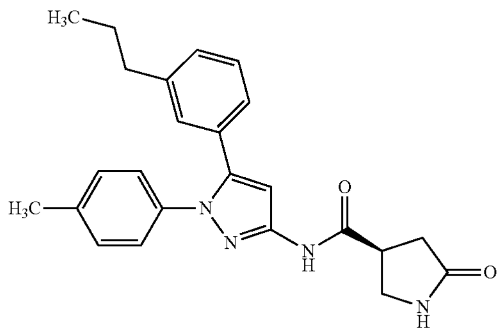 [SMILES: CCCc1cccc(-c2cc(NC(=O)[C@@H]3CNC(=O)C3)nn2-c2ccc(C)cc2)c1] | 1H-NMR (DMSO-D6) δ: 0.77 (t, 3H, J = 7.3 Hz), 1.45 (tq, 2H, J = 7.3, 7.3 Hz), 2.31 (s, 3H), 2.36-2.41 (m, 2H), 2.47 (t, 2H, J = 7.3 Hz), 3.30-3.35 (m, 1H), 3.37-3.46 (m, 1H), 3.47-3.53 (m, 1H), 6.87 (s, 1H), 7.01 (s, 1H), 7.04 (d, 1H, J = 7.3 Hz), 7.10 (d, 2H, J = 8.5 Hz), 7.16 (d, 1H, J = 7.7 Hz), 7.19 (d, 2H, J = 8.5 Hz), 7.26 (dd, 1H, J = 7.7, 7.3 Hz), 7.63 (s, 1H), 10.83 (s, 1H). | 403 | 401 | S-form |
| 50 | 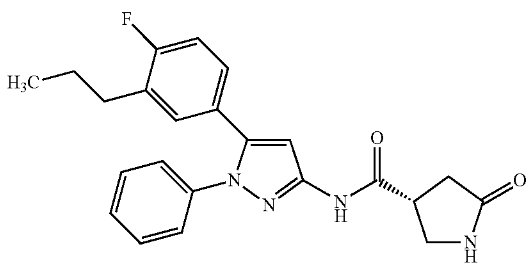 [SMILES: CCCc1cc(-c2cc(NC(=O)[C@H]3CNC(=O)C3)nn2-c2ccccc2)ccc1F] | 1H-NMR (DMSO-D6) δ: 0.77 (t, 3H, J = 7.3 Hz), 1.43 (tq, 2H, J = 7.5, 7.3 Hz), 2.35-2.41 (m, 2H), 2.50 (t, 2H, J = 7.5 Hz), 3.33-3.53 (m, 3H), 6.90 (s, 1H), 7.08-7.44 (m, 8H), 7.63 (s, 1H), 10.85 (s, 1H). | 407 | 405 | R-form |
| 51 | 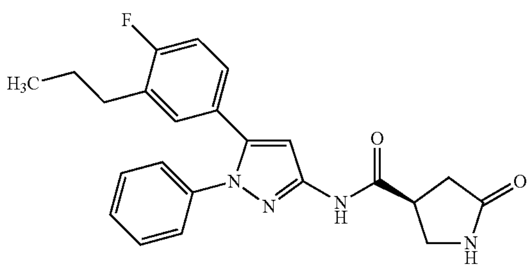 [SMILES: CCCc1cc(-c2cc(NC(=O)[C@@H]3CNC(=O)C3)nn2-c2ccccc2)ccc1F] | 1H-NMR (DMSO-D6) δ: 0.77 (t, 3H, J = 7.3 Hz), 1.43 (tq, 2H, J = 7.5, 7.3 Hz), 2.35-2.41 (m, 2H), 2.50 (t, 2H, J = 7.5 Hz), 3.33-3.53 (m, 3H), 6.90 (s, 1H), 7.08-7.44 (m, 8H), 7.63 (s, 1H), 10.85 (s, 1H). | 407 | 405 | S-form |
| 52 | 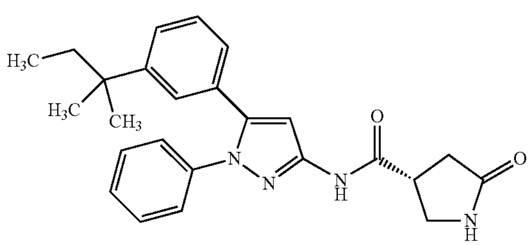 [SMILES: CCC(C)(C)c1cccc(-c2cc(NC(=O)[C@H]3CNC(=O)C3)nn2-c2ccccc2)c1] | 1H-NMR (DMSO-D6) δ: 0.46 (t, 3H, J = 7.4 Hz), 1.05 (s, 6H), 1.41 (q, 2H, J = 7.4 Hz), 2.34-2.43 (m, 2H), 3.32-3.55 (m, 3H), 6.91 (s, 1H), 6.96 (s, 1H), 7.19-7.44 (m, 8H), 7.63 (s, 1H), 10.84 (s, 1H). | 417 | 415 | R-form |
| 53 | 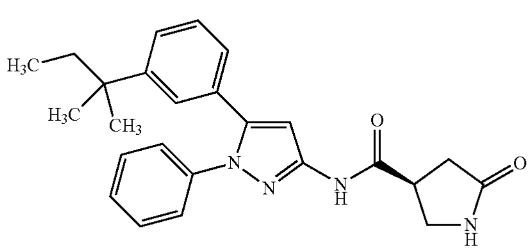 [SMILES: CCC(C)(C)c1cccc(-c2cc(NC(=O)[C@@H]3CNC(=O)C3)nn2-c2ccccc2)c1] | 1H-NMR (DMSO-D6) δ: 0.46 (t, 3H, J = 7.4 Hz), 1.05 (s, 6H), 1.41 (q, 2H, J = 7.4 Hz), 2.34-2.43 (m, 2H), 3.32-3.55 (m, 3H), 6.91 (s, 1H), 6.96 (s, 1H), 7.19-7.44 (m, 8H), 7.63 (s, 1H), 10.84 (s, 1H). | 417 | 415 | S-form |

TABLE 1-continued

| Ex. No. | Molecular Structure | NMR | MS (M + H) | MS (M − H) | Comments |
|---|---|---|---|---|---|
| 54 | 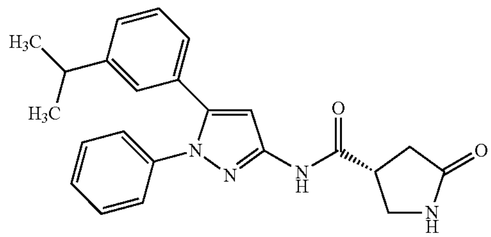 [SMILES: CC(C)c1cccc(-c2cc(NC(=O)[C@H]3CNC(=O)C3)nn2-c2ccccc2)c1] | 1H-NMR (DMSO-D6) δ: 1.04 (d, 6H, J = 7.1 Hz), 2.36-2.42 (m, 2H), 2.77-2.79 (m, 1H), 3.32-3.54 (m, 3H), 6.91 (s, 1H), 6.99 (s, 1H), 7.11 (d, 1H, J = 7.7 Hz), 7.18-7.44 (m, 7H), 7.63 (s, 1H), 10.84 (s, 1H). | 389 | 387 | R-form |
| 55 | 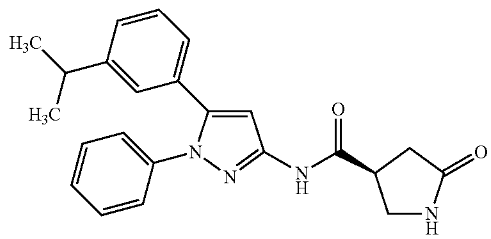 [SMILES: CC(C)c1cccc(-c2cc(NC(=O)[C@@H]3CNC(=O)C3)nn2-c2ccccc2)c1] | 1H-NMR (DMSO-D6) δ: 1.04 (d, 6H, J = 7.1 Hz), 2.36-2.42 (m, 2H), 2.77-2.79 (m, 1H), 3.32-3.54 (m, 3H), 6.91 (s, 1H), 6.99 (s, 1H), 7.11 (d, 1H, J = 7.7 Hz), 7.18-7.44 (m, 7H), 7.63 (s, 1H), 10.84 (s, 1H). | 389 | 387 | S-form |
| 56 | 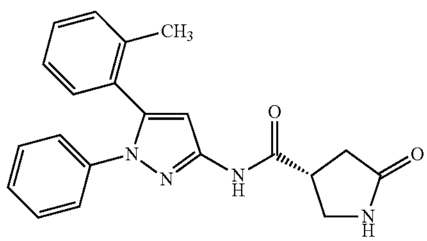 [SMILES: Cc1ccccc1-c1cc(NC(=O)[C@H]2CNC(=O)C2)nn1-c1ccccc1] | 1H-NMR (DMSO-D6) δ: 1.95 (s, 3H), 2.38-2.40 (m, 2H), 3.33-3.36 (m, 1H), 3.40-3.45 (m, 1H), 3.47-3.52 (m, 1H), 6.77 (s, 1H), 7.13-7.15 (m, 2H), 7.22-7.35 (m, 7H), 7.63 (s, 1H), 10.90 (s, 1H). | 361 | 359 | R-form |
| 57 | 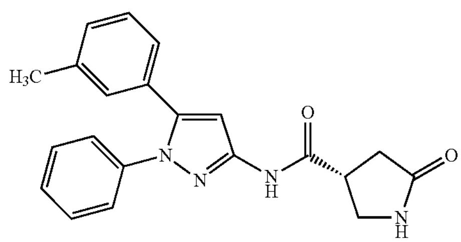 [SMILES: Cc1cccc(-c2cc(NC(=O)[C@H]3CNC(=O)C3)nn2-c2ccccc2)c1] | 1H-NMR (DMSO-D6) δ: 2.25 (s, 3H), 2.38-2.39 (m, 2H), 3.32-3.35 (m, 1H), 3.39-3.46 (m, 1H), 3.48-3.52 (m, 1H), 6.89 (s, 1H), 6.94 (d, 1H, J = 7.7 Hz), 7.13 (s, 1H), 7.16-7.24 (m, 4H), 7.32-7.41 (m, 3H), 7.63 (s, 1H), 10.85 (s, 1H). | 361 | 359 | R-form |
| 58 | 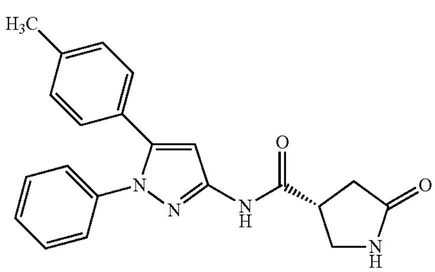 [SMILES: Cc1ccc(-c2cc(NC(=O)[C@H]3CNC(=O)C3)nn2-c2ccccc2)cc1] | 1H-NMR (DMSO-D6) δ: 2.30 (s, 3H), 2.38-2.39 (m, 2H), 3.32-3.35 (m, 1H), 3.39-3.46 (m, 1H), 3.48-3.52 (m, 1H), 6.86 (s, 1H), 7.11 (d, 2H, J = 8.2 Hz), 7.17 (d, 2H, J = 8.2 Hz), 7.22-7.23 (m, 2H), 7.31-7.41 (m, 3H), 7.63 (s, 1H), 10.84 (s, 1H). | 361 | 359 | R-form |
| 59 | 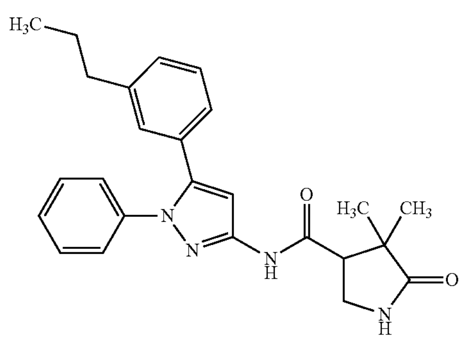 [SMILES: CCCc1cccc(-c2cc(NC(=O)C3CNC(=O)C3(C)C)nn2-c2ccccc2)c1] | 1H-NMR (DMSO-D6) δ: 0.78 (t, 3H, J = 7.3 Hz), 0.95 (s, 3H), 1.17 (s, 3H), 1.39-1.50 (tq, 2H, J = 7.5, 7.3 Hz), 2.46 (t, 2H, J = 7.5 Hz), 3.13 (dd, 1H, J = 7.3, 6.8 Hz), 3.29-3.35 (m, 1H), 3.43 (dd, 1H, J = 9.6, 6.8 Hz), 6.91 (s, 1H), 7.02 (s, 1H), 7.07 (d, 1H, J = 7.9 Hz), 7.17 (d, 1H, J = 7.9 Hz), 7.20-7.29 (m, 3H), 7.31-7.43 (m, 3H), 7.64 (s, 1H), 10.79 (s, 1H). | 417 | 415 | Racemate |

TABLE 1-continued

| Ex. No. | Molecular Structure | NMR | MS (M + H) | MS (M − H) | Comments |
|---|---|---|---|---|---|
| 60 | 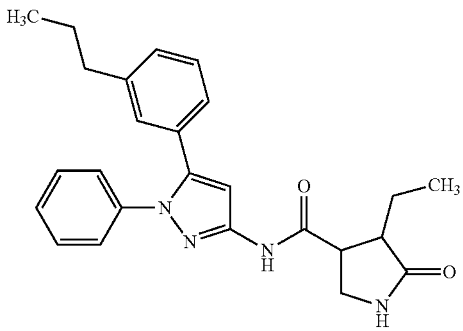 [SMILES: CCCc1cccc(-c2cc(NC(=O)C3CNC(=O)C3CC)nn2-c2ccccc2)c1] | 1H-NMR (DMSO-D6) δ: 0.77 (t, 3H, J = 7.3 Hz), 0.90 (t, 3H, J = 7.4 Hz), 1.42-1.46 (m, 3H), 1.63-1.76 (m, 1H), 2.46 (t, 2H, J = 7.5 Hz), 2.52-2.57 (m, 1H), 3.11-3.22 (m, 2H), 3.39-3.48 (m, 1H), 6.92 (s, 1H), 7.01 (s, 1H), 7.07 (d, 1H, J = 7.7 Hz), 7.17 (d, 1H, J = 7.7 Hz), 7.20-7.30 (m, 3H), 7.31-7.43 (m, 3H), 7.68 (s, 1H), 10.98 (s, 1H). | 417 | 415 | trans-form (Racemate) |
| 61 | 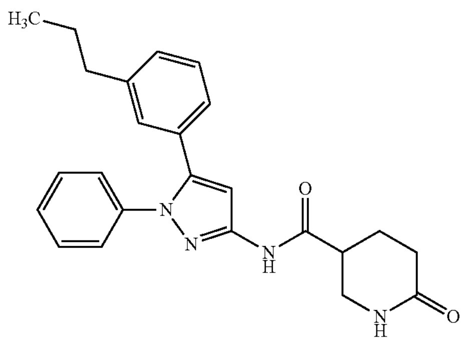 [SMILES: CCCc1cccc(-c2cc(NC(=O)C3CCC(=O)NC3)nn2-c2ccccc2)c1] | 1H-NMR (DMSO-D6) δ: 0.77 (t, 3H, J = 7.3 Hz), 1.44 (tq, 2H, J = 7.5, 7.3 Hz), 1.83-2.03 (m, 2H), 2.12-2.30 (m, 2H), 2.46 (t, 2H, J = 7.5 Hz), 2.84 (tt, 1H, J = 10.7, 3.6 Hz), 3.24-3.31 (m, 2H), 6.89 (s, 1H), 7.00 (s, 1H), 7.06 (d, 1H, J = 7.7 Hz), 7.17 (d, 1H, J = 7.7 Hz), 7.19-7.43 (m, 6H), 7.51 (s, 1H), 10.83 (s, 1H). | 403 | 401 | Racemate |
| 62 | 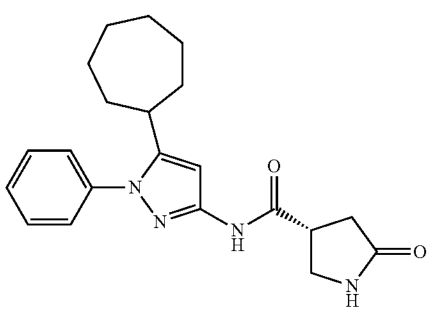 [SMILES: O=C1C[C@@H](C(=O)Nc2cc(C3CCCCCC3)n(-c3ccccc3)n2)CN1] | 1H-NMR (DMSO-D6) δ: 1.25-1.87 (m, 12H), 2.31-2.38 (m, 2H), 2.81-2.90 (m, 1H), 3.26-3.50 (m, 3H), 6.60 (s, 1H), 7.38-7.56 (m, 5H), 7.62 (s, 1H), 10.67 (s, 1H). | 367 | 365 | R-form |
| 63 | 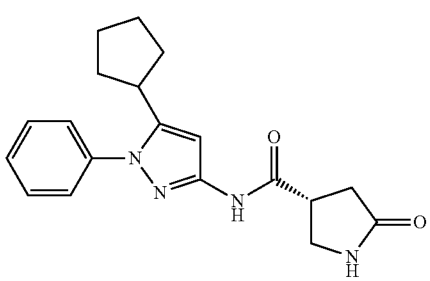 [SMILES: O=C1C[C@@H](C(=O)Nc2cc(C3CCCC3)n(-c3ccccc3)n2)CN1] | 1H-NMR (DMSO-D6) δ: 1.44-1.59 (m, 4H), 1.63-1.76 (m, 2H), 1.81-1.96 (m, 2H), 2.31-2.38 (m, 2H), 2.99-3.11 (m, 1H), 3.26-3.51 (m, 3H), 6.60 (s, 1H), 7.40-7.55 (m, 5H), 7.62 (s, 1H), 10.68 (s, 1H). | 339 | — | R-form |

TABLE 1-continued

| Ex. No. | Molecular Structure | NMR | MS (M + H) | MS (M − H) | Comments |
|---|---|---|---|---|---|
| 64 | 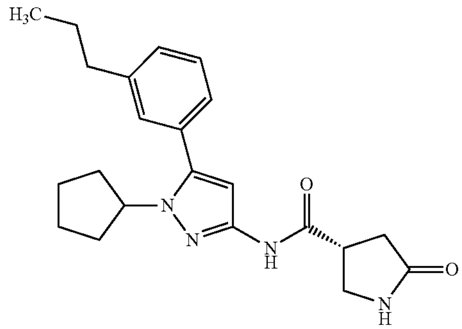 [SMILES: CCCc1cccc(-c2cc(NC(=O)[C@H]3CNC(=O)C3)nn2C2CCCC2)c1] | 1H-NMR (DMSO-D6) δ: 0.90 (t, 3H, J = 7.3 Hz), 1.48-1.68 (m, 4H), 1.74-2.03 (m, 6H), 2.27-2.43 (2H, m), 2.62 (2H, t, J = 7.5 Hz), 3.25-3.50 (3H, m), 4.61 (1H, quin, J = 7.4 Hz), 6.53 (1H, s), 7.20-7.30 (3H, m), 7.38-7.44 (1H, m), 7.61 (1H, s), 10.66 (1H, s) | 381 | 379 | R-form |
| 65 | 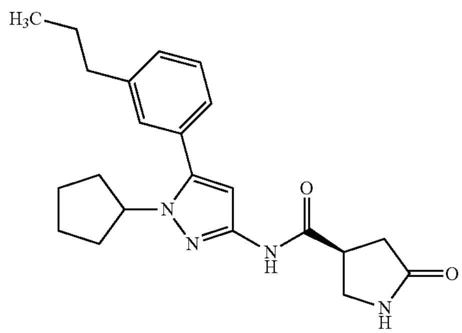 [SMILES: CCCc1cccc(-c2cc(NC(=O)[C@@H]3CNC(=O)C3)nn2C2CCCC2)c1] | 1H-NMR (DMSO-D6) δ: 0.90 (t, 3H, J = 7.3 Hz), 1.48-1.68 (m, 4H), 1.74-2.03 (m, 6H), 2.27-2.41 (2H, m), 2.62 (2H, t, J = 7.5 Hz), 3.25-3.50 (3H, m), 4.61 (1H, quin, J = 7.5 Hz), 6.53 (1H, s), 7.20-7.30 (3H, m), 7.37-7.44 (1H, m), 7.60 (1H, s), 10.66 (1H, s) | 381 | 379 | S-form |
| 66 | 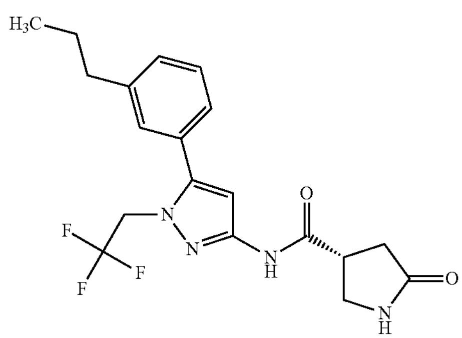 [SMILES: CCCc1cccc(-c2cc(NC(=O)[C@H]3CNC(=O)C3)nn2CC(F)(F)F)c1] | 1H-NMR (DMSO-D6) δ: 0.89 (3H, t, J = 7.3 Hz), 1.62 (2H, tq, J = 7.5, 7.6 Hz), 2.37 (2H, d, J = 8.4 Hz), 2.63 (2H, t, J = 7.5 Hz), 3.27-3.53 (3H, m), 4.88 (2H, q, J = 8.8 Hz), 6.73 (1H, s), 7.25-7.34 (3H, m), 7.40-7.46 (1H, m), 7.62 (1H, s), 10.83 (1H, s) | 395 | 393 | R-form |
| 67 | 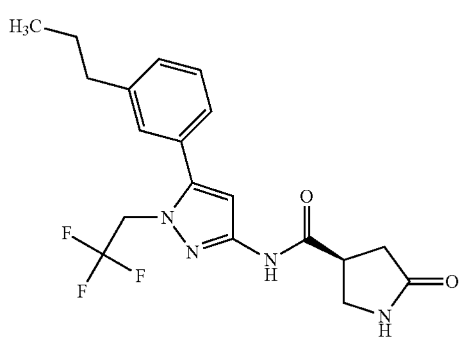 [SMILES: CCCc1cccc(-c2cc(NC(=O)[C@@H]3CNC(=O)C3)nn2CC(F)(F)F)c1] | 1H-NMR (DMSO-D6) δ: 0.89 (3H, t, J = 7.4 Hz), 1.62 (2H, tq, J = 7.5, 7.6 Hz), 2.37 (2H, d, J = 8.2 Hz), 2.63 (2H, t, J = 7.5 Hz), 3.28-.52 (3H, m), 4.88 (2H, q, J = 8.8 Hz), 6.73 (1H, s), 7.25-7.34 (3H, m), 7.40-7.46 (1H, m), 7.62 (1H, s), 10.83 (1H, s) | 395 | 393 | S-form |

TABLE 1-continued

| Ex. No. | Molecular Structure | NMR | MS (M + H) | MS (M − H) | Comments |
|---|---|---|---|---|---|
| 68 | 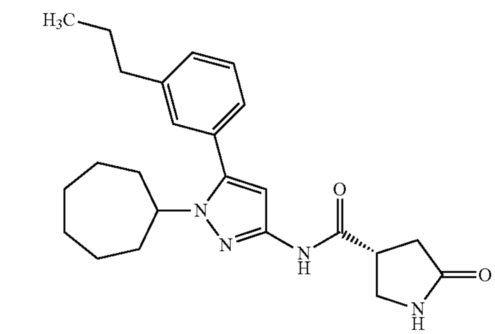 [SMILES: CCCc1cccc(-c2cc(NC(=O)[C@H]3CNC(=O)C3)nn2C2CCCCCC2)c1] | 1H-NMR (DMSO-D6) δ: 0.91 (3H, t, J = 7.4 Hz), 1.28-1.42 (2H, m), 1.46-1.80 (8H, m), 1.82-2.06 (4H, m), 2.28-2.42 (2H, m), 2.63 (2H, t, J = 7.5 Hz), 3.26-3.52 (3H, m), 4.19-4.29 (1H, m), 6.53 (1H, s), 7.18-7.24 (2H, m), 7.26-7.32 (1H, m), 7.39-7.45 (1H, m), 7.60 (1H, s), 10.68 (1H, s) | 409 | 407 | R-form |
| 69 | 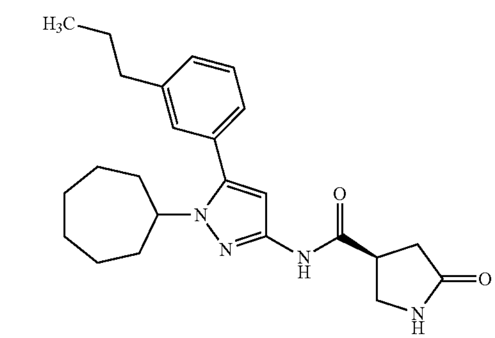 [SMILES: CCCc1cccc(-c2cc(NC(=O)[C@@H]3CNC(=O)C3)nn2C2CCCCCC2)c1] | 1H-NMR (DMSO-D6) δ: 0.91 (3H, t, J = 7.3 Hz), 1.28-1.42 (2H, m), 1.46-1.80 (8H, m), 1.82-2.06 (4H, m), 2.28-2.42 (2H, m), 2.63 (2H, t, J = 7.5 Hz), 3.26-3.52 (3H, m), 4.19-4.29 (1H, m), 6.53 (1H, s), 7.18-7.24 (2H, m), 7.26-7.32 (1H, m), 7.39-7.45 (1H, m), 7.60 (1H, s), 10.68 (1H, s) | 409 | 407 | S-form |
| 70 | 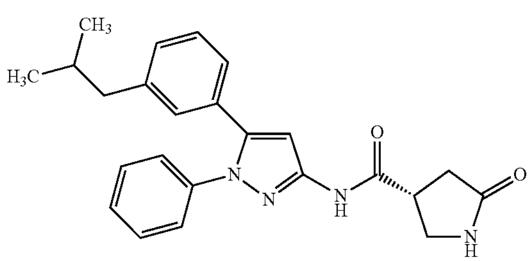 [SMILES: CC(C)Cc1cccc(-c2cc(NC(=O)[C@H]3CNC(=O)C3)nn2-c2ccccc2)c1] | 1H-NMR (DMSO-D6) δ: 0.74 (d, 6H, J = 6.6 Hz), 1.64 (tsep, 1H, J = 6.6, 7.1 Hz), 2.34 (d, 2H, J = 7.1 Hz), 2.39-2.41 (m, 2H), 3.34-3.36 (m, 2H), 3.39-3.44 (m, 1H), 3.47-3.51 (m, 1H), 6.89 (s, 1H), 6.93 (s, 1H), 7.10-7.40 (m, 8H), 7.63 (s, 1H), 10.84 (s, 1H). | 403 | 401 | R-form |
| 71 | 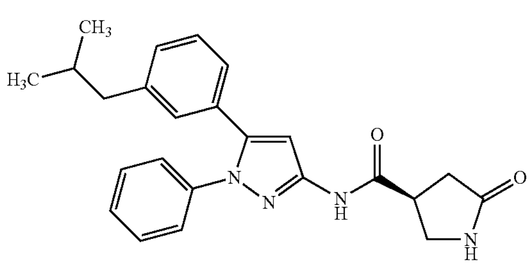 [SMILES: CC(C)Cc1cccc(-c2cc(NC(=O)[C@@H]3CNC(=O)C3)nn2-c2ccccc2)c1] | 1H-NMR (DMSO-D6) δ: 0.74 (d, 6H, J = 6.6 Hz), 1.64 (tsep, 1H, J = 6.6, 7.1 Hz), 2.34 (d, 2H, J = 7.1 Hz), 2.39-2.41 (m, 2H), 3.34-3.36 (m, 2H), 3.39-3.44 (m, 1H), 3.47-3.51 (m, 1H), 6.89 (s, 1H), 6.93 (s, 1H), 7.10-7.40 (m, 8H), 7.63 (s, 1H), 10.84 (s, 1H). | 403 | 401 | S-form |
| 72 | 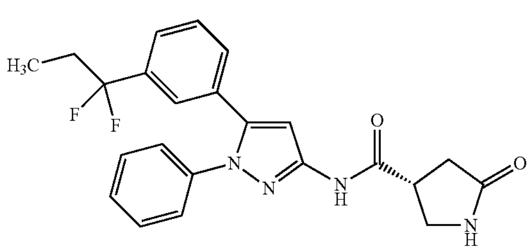 [SMILES: CCC(F)(F)c1cccc(-c2cc(NC(=O)[C@H]3CNC(=O)C3)nn2-c2ccccc2)c1] | 1H-NMR (DMSO-D6) δ: 0.76 (t, 3H, J = 7.6 Hz), 2.06 (tq, 2H, J = 16.5, 7.6 Hz), 2.38-2.40 (m, 2H), 3.33-3.37 (m, 1H), 3.39-3.48 (m, 1H), 3.49-3.53 (m, 1H), 6.99 (s, 1H), 7.22-7.25 (m, 3H), 7.34-7.52 (m, 6H), 7.64 (s, 1H), 10.89 (s, 1H). | 425 | 423 | R-form |

TABLE 1-continued

| Ex. No. | Molecular Structure | NMR | MS (M + H) | MS (M − H) | Comments |
|---|---|---|---|---|---|
| 73 | 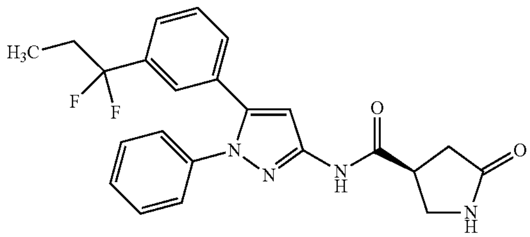 [SMILES: CCC(F)(F)c1cccc(-c2cc(NC(=O)[C@@H]3CNC(=O)C3)nn2-c2ccccc2)c1] | 1H-NMR (DMSO-D6) δ: 0.76 (t, 3H, J = 7.6 Hz), 2.06 (tq, 2H, J = 16.5, 7.6 Hz), 2.38-2.40 (m, 2H), 3.33-3.37 (m, 1H), 3.39-3.48 (m, 1H), 3.49-3.53 (m, 1H), 6.99 (s, 1H), 7.22-7.25 (m, 3H), 7.34-7.52 (m, 6H), 7.64 (s, 1H), 10.89 (s, 1H). | 425 | 423 | S-form |
| 74 | 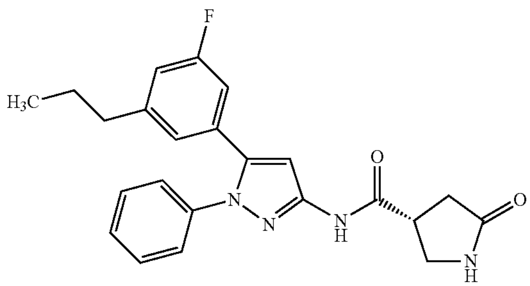 [SMILES: CCCc1cc(F)cc(-c2cc(NC(=O)[C@H]3CNC(=O)C3)nn2-c2ccccc2)c1] | 1H-NMR (DMSO-D6) δ: 0.76 (t, 3H, J = 7.4 Hz), 1.44 (tq, 2H, J = 7.7, 7.4 Hz), 2.38-2.40 (m, 2H), 2.46 (d, 2H, J = 7.7 Hz), 3.34-3.36 (m, 1H), 3.39-3.46 (m, 1H), 3.48-3.53 (m, 1H), 6.84 (s, 1H), 6.88 (d, 1H, J = 9.5 Hz), 6.96 (s, 1H), 7.04 (d, 1H, J = 9.9 Hz), 7.24-7.25 (m, 2H), 7.35-7.44 (m, 3H), 7.64 (s, 1H), 10.88 (s, 1H). | 407 | 405 | R-form |
| 75 | 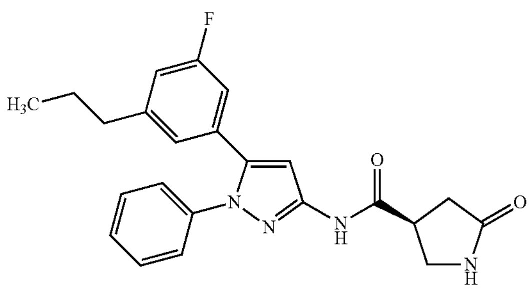 [SMILES: CCCc1cc(F)cc(-c2cc(NC(=O)[C@@H]3CNC(=O)C3)nn2-c2ccccc2)c1] | 1H-NMR (DMSO-D6) δ: 0.76 (t, 3H, J = 7.4 Hz), 1.44 (tq, 2H, J = 7.7, 7.4 Hz), 2.38-2.40 (m, 2H), 2.46 (d, 2H, J = 7.7 Hz), 3.34-3.36 (m, 1H), 3.39-3.46 (m, 1H), 3.48-3.53 (m, 1H), 6.84 (s, 1H), 6.88 (d, 1H, J = 9.5 Hz), 6.96 (s, 1H), 7.04 (d, 1H, J = 9.9 Hz), 7.24-7.25 (m, 2H), 7.35-7.44 (m, 3H), 7.64 (s, 1H), 10.88 (s, 1H). | 407 | 405 | S-form |
| 76 | 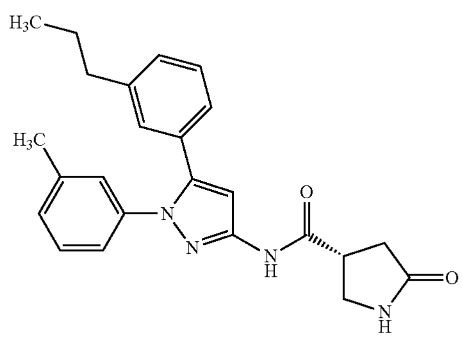 [SMILES: CCCc1cccc(-c2cc(NC(=O)[C@H]3CNC(=O)C3)nn2-c2cccc(C)c2)c1] | 1H-NMR (DMSO-D6) δ: 0.76 (3H, t, J = 7.3 Hz), 1.43 (2H, tq, J = 7.4, 7.4 Hz), 2.24 (3H, s), 2.35-2.41 (2H, m), 2.46 (2H, t, J = 7.4 Hz), 3.28-3.53 (3H, m), 6.88 (1H, s), 6.93-7.02 (2H, m), 7.04-7.10 (2H, m), 7.12-7.19 (2H, m), 7.21-7.30 (2H, m), 7.64 (1H, s), 10.84 (1H, s) | 403 | 401 | R-form |
| 77 | 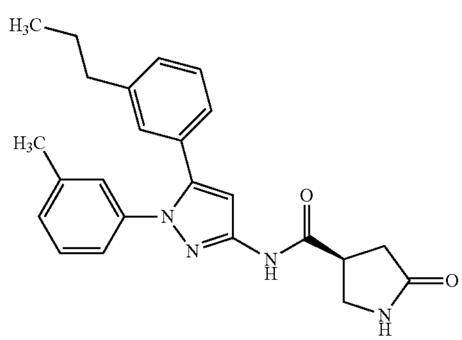 [SMILES: CCCc1cccc(-c2cc(NC(=O)[C@@H]3CNC(=O)C3)nn2-c2cccc(C)c2)c1] | 1H-NMR (DMSO-D6) δ: 0.76 (3H, t, J = 7.3 Hz), 1.43 (2H, tq, J = 7.4, 7.4 Hz), 2.24 (3H, s), 2.35-2.41 (2H, m), 2.46 (2H, t, J = 7.4 Hz), 3.28-3.53 (3H, m), 6.88 (1H, s), 6.93-7.02 (2H, m), 7.04-7.10 (2H, m), 7.12-7.19 (2H, m), 7.21-7.30 (2H, m), 7.64 (1H, s), 10.84 (1H, s) | 403 | 401 | S-form |

TABLE 1-continued

| Ex. No. | Molecular Structure | NMR | MS (M + H) | MS (M − H) | Comments |
|---|---|---|---|---|---|
| 78 | 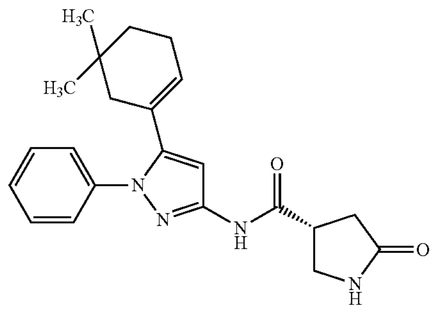 [SMILES: CC1(C)CCC=C(c2cc(NC(=O)[C@H]3CNC(=O)C3)nn2-c2ccccc2)C1] | 1H-NMR (DMSO-D6) δ: 0.82 (s, 6H), 1.29 (t, 2H, J = 6.4 Hz), 1.75-1.80 (m, 2H), 2.02-2.10 (m, 2H), 2.32-2.39 (m, 2H), 3.27-3.51 (m, 3H), 5.71-5.77 (m, 1H), 6.62 (s, 1H), 7.33-7.50 (m, 5H), 7.63 (s, 1H), 10.75 (s, 1H). | 379 | 377 | R-form |
| 79 | 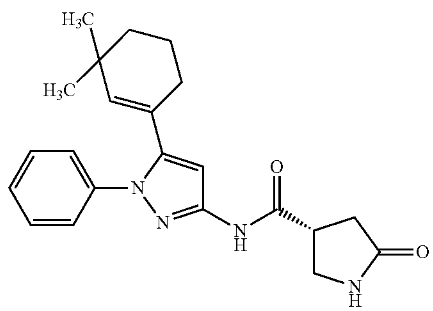 [SMILES: CC1(C)C=C(c2cc(NC(=O)[C@H]3CNC(=O)C3)nn2-c2ccccc2)CCC1] | 1H-NMR (DMSO-D6) δ: 0.86 (s, 6H), 1.34-1.42 (m, 2H), 1.55-1.65 (m, 2H), 1.98-2.06 (m, 2H), 2.31-2.39 (m, 2H), 3.27-3.51 (m, 3H), 5.34 (1H, s), 6.64 (s, 1H), 7.32-7.51 (m, 5H), 7.63 (s, 1H), 10.75 (s, 1H). | 379 | 377 | R-form |
| 80 | 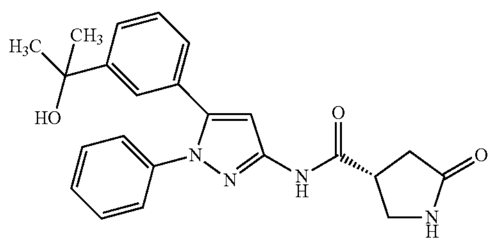 [SMILES: CC(C)(O)c1cccc(-c2cc(NC(=O)[C@H]3CNC(=O)C3)nn2-c2ccccc2)c1] | 1H-NMR (DMSO-D6) δ: 1.27 (s, 6H), 2.38-2.40 (m, 2H), 3.33-3.35 (m, 1H), 3.38-3.46 (m, 1H), 3.48-3.53 (m, 1H), 4.99 (s, 1H), 6.92 (s, 1H), 7.09 (d, 1H, J = 7.7 Hz), 7.21-7.46 (m, 8H), 7.64 (s, 1H), 10.86 (s, 1H). | 405 | 403 | R-form |
| 81 | 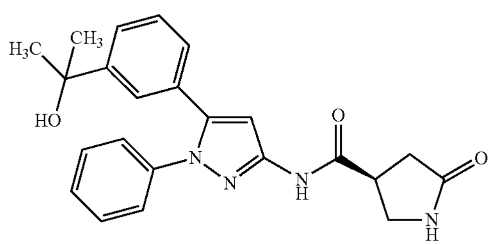 [SMILES: CC(C)(O)c1cccc(-c2cc(NC(=O)[C@@H]3CNC(=O)C3)nn2-c2ccccc2)c1] | 1H-NMR (DMSO-D6) δ: 1.27 (s, 6H), 2.38-2.40 (m, 2H), 3.33-3.35 (m, 1H), 3.38-3.46 (m, 1H), 3.48-3.53 (m, 1H), 4.99 (s, 1H), 6.92 (s, 1H), 7.09 (d, 1H, J = 7.7 Hz), 7.21-7.46 (m, 8H), 7.64 (s, 1H), 10.86 (s, 1H). | 405 | 403 | S-form |
| 82 | 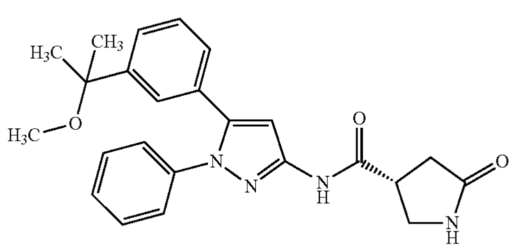 [SMILES: COC(C)(C)c1cccc(-c2cc(NC(=O)[C@H]3CNC(=O)C3)nn2-c2ccccc2)c1] | 1H-NMR (DMSO-D6) δ: 1.27 (s, 6H), 2.38-2.40 (m, 2H), 2.77 (s, 3H), 3.34-3.35 (m, 1H), 3.41-3.44 (m, 1H), 3.49-3.53 (m, 1H), 6.93 (s, 1H), 7.05 (s, 1H), 7.22-7.28 (m, 3H), 7.33-7.42 (m, 5H), 7.64 (s, 1H), 10.86 (s, 1H). | 419 | 417 | R-form |

TABLE 1-continued

| Ex. No. | Molecular Structure | NMR | MS (M + H) | MS (M − H) | Comments |
|---|---|---|---|---|---|
| 83 | 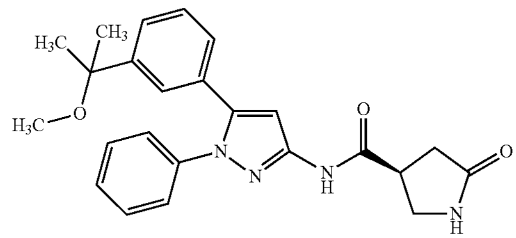 [SMILES: COC(C)(C)c1cccc(-c2cc(NC(=O)[C@@H]3CNC(=O)C3)nn2-c2ccccc2)c1] | 1H-NMR (DMSO-D6) δ: 1.27 (s, 6H), 2.38-2.40 (m, 2H), 2.77 (s, 3H), 3.34-3.35 (m, 1H), 3.41-3.44 (m, 1H), 3.49-3.53 (m, 1H), 6.93 (s, 1H), 7.05 (s, 1H), 7.22-7.28 (m, 3H), 7.33-7.42 (m, 5H), 7.64 (s, 1H), 10.86 (s, 1H). | 419 | 417 | S-form |
| 84 | 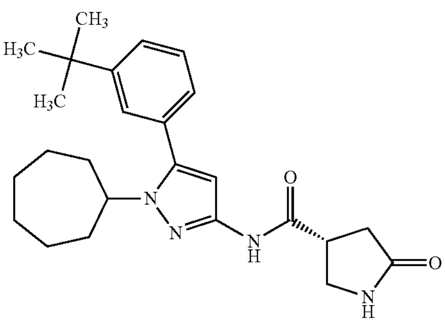 [SMILES: CC(C)(C)c1cccc(-c2cc(NC(=O)[C@H]3CNC(=O)C3)nn2C2CCCCCC2)c1] | 1H-NMR (DMSO-D6) δ: 1.28-1.42 (11H, m), 1.46-1.56 (4H, m), 1.65-1.80 (2H, m), 1.82-2.06 (4H, m), 2.28-2.41 (2H, m), 3.25-3.50 (3H, m), 4.18-4.29 (1H, m), 6.53 (1H, s), 7.21 (1H, d, J = 7.4 Hz), 7.36 (1H, s), 7.43 (1H, t, J = 7.7 Hz), 7.61 (1H, s), 10.70 (1H, s) | 423 | 421 | R-form |
| 85 | 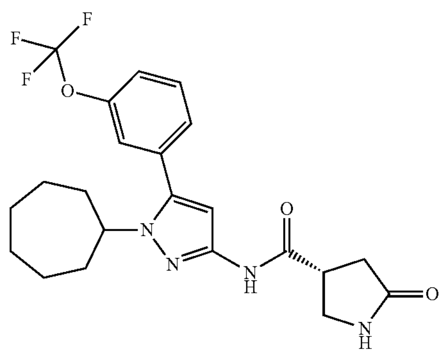 [SMILES: O=C1C[C@@H](C(=O)Nc2cc(-c3cccc(OC(F)(F)F)c3)n(C3CCCCCC3)n2)CN1] | 1H-NMR (DMSO-D6) δ: 1.28-1.42 (2H, m), 1.45-1.60 (4H, m), 1.65-1.79 (2H, m), 1.83-2.04 (4H, m), 2.28-2.41 (2H, m), 3.25-3.50 (3H, m), 4.15-4.25 (1H, m), 6.61 (1H, s), 7.39 (1H, s), 7.43-7.52 (1H, m), 7.68-7.71 (2H, m), 10.74 (1H, m) | 451 | 449 | R-form |
| 86 | 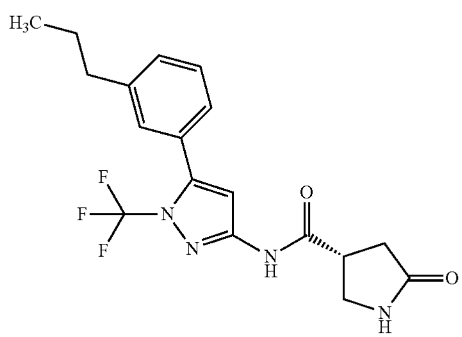 [SMILES: CCCc1cccc(-c2cc(NC(=O)[C@H]3CNC(=O)C3)nn2C(F)(F)F)c1] | 1H-NMR (DMSO-D6) δ: 0.89 (t, 3H, J = 7.3 Hz), 1.61 (tq, 2H, J = 7.3, 7.5 Hz), 2.37-2.40 (m, 2H), 2.62 (t, 2H, J = 7.5 Hz), 3.30-3.35 (m, 1H), 3.37-3.45 (m, 1H), 3.47-3.53 (m, 1H), 6.93 (s, 1H), 7.30 (d, 1H, J = 7.9 Hz), 7.31 (s, 1H), 7.36 (d, 1H, J = 7.7 Hz), 7.42 (dd, 1H, J = 7.7, 7.9 Hz), 7.65 (s, 1H), 11.17 (s, 1H). | 381 | 379 | R-form |
| 87 | 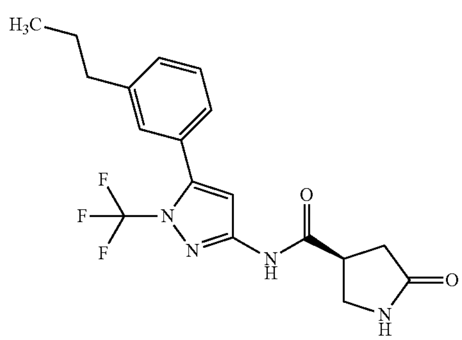 [SMILES: CCCc1cccc(-c2cc(NC(=O)[C@@H]3CNC(=O)C3)nn2C(F)(F)F)c1] | 1H-NMR (DMSO-D6) δ: 0.89 (t, 3H, J = 7.3 Hz), 1.61 (tq, 2H, J = 7.3, 7.5 Hz), 2.36-2.41 (m, 2H), 2.62 (t, 2H, J = 7.5 Hz), 3.30-3.35 (m, 1H), 3.37-3.45 (m, 1H), 3.47-3.53 (m, 1H), 6.93 (s, 1H), 7.30 (d, 1H, J = 8.1 Hz), 7.31 (s, 1H), 7.36 (d, 1H, J = 8.1 Hz), 7.42 (dd, 1H, J = 8.1, 8.1 Hz), 7.65 (s, 1H), 11.18 (s, 1H). | 381 | 379 | S-form |

TABLE 1-continued

| Ex. No. | Molecular Structure | NMR | MS (M + H) | MS (M − H) | Comments |
|---|---|---|---|---|---|
| 88 | 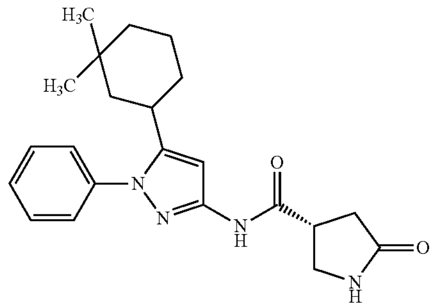 [SMILES: CC1(C)CCCC(c2cc(NC(=O)[C@H]3CNC(=O)C3)nn2-c2ccccc2)C1] | 1H-NMR (DMSO-D6) δ: 0.75 (s, 3H), 0.85 (s, 3H), 1.08-1.47 (m, 6H), 1.49-1.60 (m, 1H), 1.74-1.83 (m, 1H), 2.33 (dd, 1H, J = 16.5, 8.9 Hz), 2.38 (dd, 1H, J = 16.5, 7.7 Hz), 2.87 (tt, 1H, J = 12.1, 3.2 Hz), 3.30 (dd, 1H, J = 8.5, 6.0 Hz), 3.32-3.42 (m, 1H), 3.47 (dd, 1H, J = 8.5, 8.5 Hz), 6.58 (s, 1H), 7.41-7.47 (m, 3H), 7.49-7.56 (m, 2H), 7.62 (s, 1H), 10.68 (s, 1H). | 381 | 379 | Optically active substance Diastereomer of Example 89 Retention time under HPLC analysis condition 2 (17.02 minutes) |
| 89 | 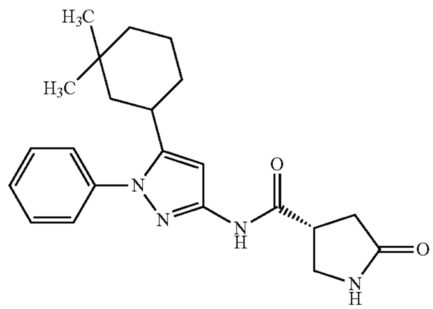 [SMILES: CC1(C)CCCC(c2cc(NC(=O)[C@H]3CNC(=O)C3)nn2-c2ccccc2)C1] | 1H-NMR (DMSO-D6) δ: 0.75 (s, 3H), 0.85 (s, 3H), 1.08-1.48 (m, 6H), 1.50-1.59 (m, 1H), 1.73-1.83 (m, 1H), 2.33 (dd, 1H, J =16.5, 8.9 Hz), 2.38 (dd, 1H, J = 16.5, 8.1 Hz), 2.87 (tt, 1H, J = 12.1, 3.0 Hz), 3.30 (dd, 1H, J = 8.7, 6.2 Hz), 3.32-3.43 (m, 1H), 3.47 (dd, 1H, J = 8.7, 8.3 Hz), 6.58 (s, 1H), 7.40-7.47 (m, 3H), 7.50-7.56 (m, 2H), 7.62 (s, 1H), 10.68 (s, 1H). | 381 | 379 | Optically active substance Diastereomer of Example 88 Retention time under HPLC analysis condition 2 (20.77 minutes) |
| 90 | 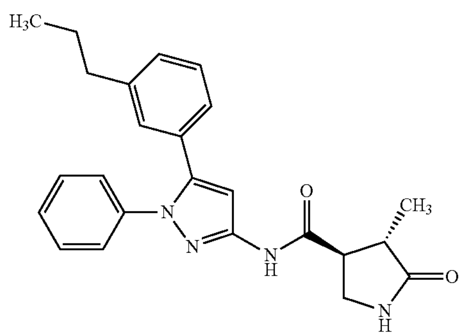 [SMILES: CCCc1cccc(-c2cc(NC(=O)[C@@H]3CNC(=O)[C@H]3C)nn2-c2ccccc2)c1] | 1H-NMR (DMSO-D6) δ: 0.77 (t, 3H, J = 7.5 Hz), 1.08 (d, 3H, J = 6.9 Hz), 1.44 (tq, 2H, J = 7.5, 7.5 Hz), 2.46 (t, 2H, J = 7.5 Hz), 2.54 (dq, 1H, J = 8.9, 6.9 Hz), 3.04 (ddd, 1H, J = 8.9, 8.9, 8.9 Hz), 3.23 (dd, 1H, J = 8.9, 8.9 Hz), 3.44 (dd, 1H, J = 8.9, 8.9 Hz), 6.92 (s, 1H), 7.01 (dd, 1H, J = 1.6, 1.6 Hz), 7.07 (ddd, 1H, J = 7.7, 1.6, 1.6 Hz), 7.17 (ddd, 1H, J = 7.7, 1.6, 1.6 Hz), 7.20-7.24 (m, 2H), 7.27 (dd, 1H, J = 7.7, 7.7 Hz), 7.31-7.42 (m, 3H), 7.68 (s, 1H), 10.94 (s, 1H). | 403 | 401 | (3S,4S)-form |
| 91 | 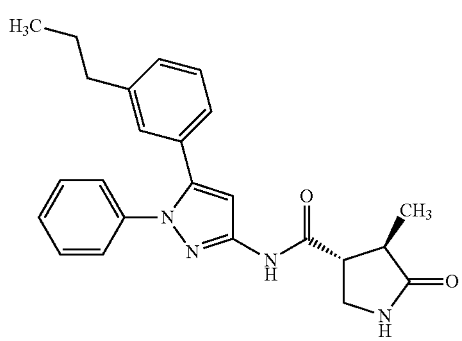 [SMILES: CCCc1cccc(-c2cc(NC(=O)[C@H]3CNC(=O)[C@@H]3C)nn2-c2ccccc2)c1] | 1H-NMR (DMSO-D6) δ: 0.77 (t, 3H, J = 7.5 Hz), 1.08 (d, 3H, J = 6.9 Hz), 1.44 (tq, 2H, J = 7.5, 7.5 Hz), 2.46 (t, 2H, J = 7.5 Hz), 2.54 (dq, 1H, J = 8.9, 6.9 Hz), 3.04 (ddd, 1H, J = 8.9, 8.9, 8.9 Hz), 3.23 (dd, 1H, J = 8.9, 8.9 Hz), 3.44 (dd, 1H, J = 8.9, 8.9 Hz), 6.92 (s, 1H), 7.01 (dd, 1H, J = 1.6, 1.6 Hz), 7.07 (ddd, 1H, J = 7.7, 1.6, 1.6 Hz), 7.17 (ddd, 1H, J = 7.7, 1.6, 1.6 Hz), 7.20-7.24 (m, 2H), 7.27 (dd, 1H, J = 7.7, 7.7 Hz), 7.31-7.42 (m, 3H), 7.68 (s, 1H), 10.94 (s, 1H). | 403 | 401 | (3R,4R)-form |

TABLE 1-continued

| Ex. No. | Molecular Structure | NMR | MS (M + H) | MS (M − H) | Comments |
|---|---|---|---|---|---|
| 92 | 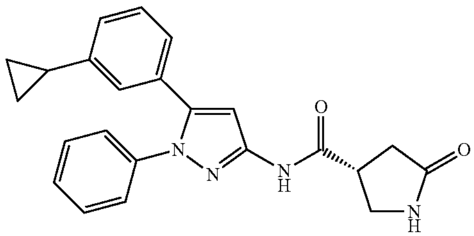 [SMILES: O=C1C[C@@H](C(=O)Nc2cc(-c3cccc(C4CC4)c3)n(-c3ccccc3)n2)CN1] | 1H-NMR (DMSO-D6) δ: 0.46-0.48 (m, 2H), 0.85-0.90 (m, 2H), 1.81-1.87 (m, 1H), 2.38-2.39 (m, 2H), 3.35-3.38 (m, 1H), 3.41-3.45 (m, 1H), 3.49-3.51 (m, 1H), 6.82 (s, 1H), 6.90 (s, 1H), 6.99 (d, 1H, J = 7.7 Hz), 7.09 (d, 1H, J = 7.7 Hz), 7.21-7.22 (m, 3H), 7.37-7.41 (m, 3H), 7.64 (s, 1H), 10.84 (s, 1H). | 387 | 385 | R-form |
| 93 | 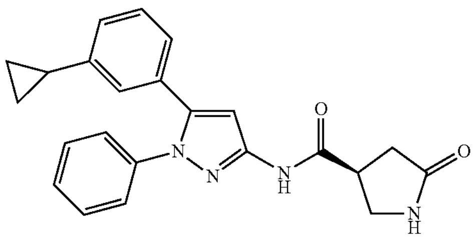 [SMILES: O=C1C[C@H](C(=O)Nc2cc(-c3cccc(C4CC4)c3)n(-c3ccccc3)n2)CN1] | 1H-NMR (DMSO-D6) δ: 0.46-0.48 (m, 2H), 0.85-0.90 (m, 2H), 1.81-1.87 (m, 1H), 2.38-2.39 (m, 2H), 3.35-3.38 (m, 1H), 3.41-3.45 (m, 1H), 3.49-3.51 (m, 1H), 6.82 (s, 1H), 6.90 (s, 1H), 6.99 (d, 1H, J = 7.7 Hz), 7.09 (d, 1H, J = 7.7 Hz), 7.21-7.22 (m, 3H), 7.37-7.41 (m, 3H), 7.64 (s, 1H), 10.84 (s, 1H). | 387 | 385 | S-form |
| 94 | 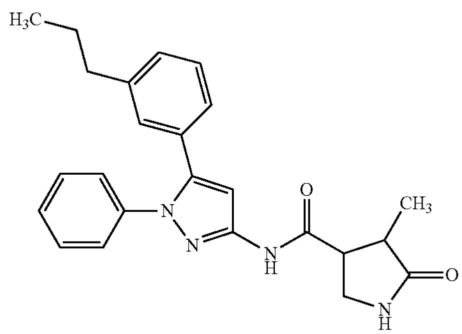 [SMILES: CCCc1cccc(-c2cc(NC(=O)C3CNC(=O)C3C)nn2-c2ccccc2)c1] | 1H-NMR (DMSO-D6) δ: 0.77 (t, 3H, J = 7.3 Hz), 0.98 (d, 3H, J = 7.4 Hz), 1.44 (tq, 2H, J = 7.5, 7.3 Hz), 2.46 (t, 2H, J = 7.5 Hz), 2.59-2.68 (m, 1H), 3.28-3.35 (m, 1H), 3.41-3.50 (m, 1H), 6.89 (s, 1H), 7.02 (s, 1H), 7.07 (d, 1H, J = 7.7 Hz), 7.17 (d, 1H, J = 7.7 Hz), 7.20-7.43 (6H, m), 7.63 (s, 1H), 10.81 (s, 1H). | 403 | 401 | cis-form (Racemate) |
| 95 | 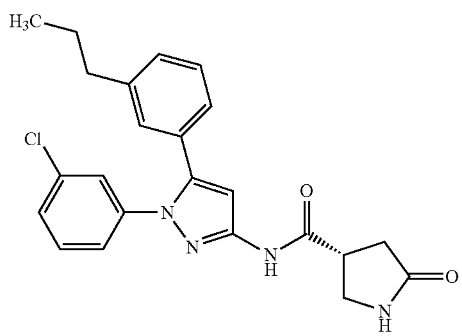 [SMILES: CCCc1cccc(-c2cc(NC(=O)[C@H]3CNC(=O)C3)nn2-c2cccc(Cl)c2)c1] | 1H-NMR (DMSO-D6) δ: 0.77 (3H, t, J = 7.3 Hz), 1.46 (2H, tq, J = 7.4, 7.4 Hz), 2.38 (2H, d, J = 8.1 Hz), 2.45-2.52 (2H, m), 3.29-3.53 (3H, m), 6.91 (1H, s), 7.03 (1H, s), 7.09-7.24 (3H, m), 7.27-7.35 (2H, s), 7.36-7.43 (2H, m), 7.65 (1H, s), 10.90 (1H, s) | 423 | 421 | R-form |
| 96 | 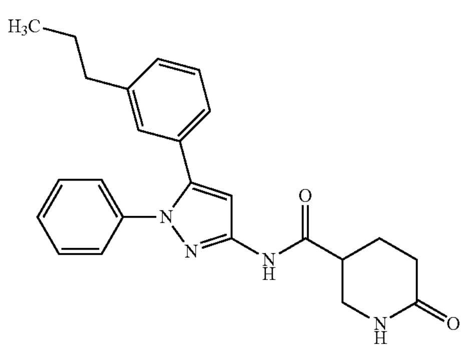 [SMILES: CCCc1cccc(-c2cc(NC(=O)C3CCC(=O)NC3)nn2-c2ccccc2)c1] | 1H-NMR (DMSO-D6) δ: 0.77 (t, 3H, J = 7.3 Hz), 1.44 (tq, 2H, J = 7.5, 7.3 Hz), 1.83-2.03 (m, 2H), 2.12-2.30 (m, 2H), 2.46 (t, 2H, J = 7.5 Hz), 2.84 (tt, 1H, J = 10.7, 3.6 Hz), 3.24-3.31 (m, 2H), 6.89 (s, 1H), 7.00 (s, 1H), 7.06 (d, 1H, J = 7.7 Hz), 7.17 (d, 1H, J = 7.7 Hz), 7.19-7.43 (m, 6H), 7.51 (s, 1H), 10.83 (s, 1H). | 403 | 401 | Optically active substance optical isomer of Example 5 |

TABLE 1-continued

| Ex. No. | Molecular Structure | NMR | MS (M + H) | MS (M − H) | Comments |
|---|---|---|---|---|---|
| 97 | 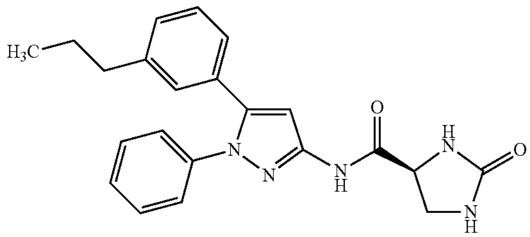 [SMILES: CCCc1cccc(-c2cc(NC(=O)[C@@H]3CNC(=O)N3)nn2-c2ccccc2)c1] | 1H-NMR (DMSO-D6) δ: 0.77 (t, 3H, J = 7.3 Hz), 1.44 (tq, 2H, J = 7.5, 7.3 Hz), 2.46 (t, 2H, J = 7.5 Hz), 3.35 (dd, 1H, J = 8.8, 6.2 Hz), 3.59 (dd, 1H, J = 9.4, 8.8 Hz), 4.32 (dd, 1H, J = 9.4, 6.2 Hz), 6.34 (s, 1H), 6.61 (s, 1H), 6.90 (s, 1H), 7.00 (s, 1H), 7.08 (d, 1H, J = 7.7 Hz), 7.15-7.43 (m, 7H), 10.71 (s, 1H). | 390 | 388 | S-form |
| 98 | 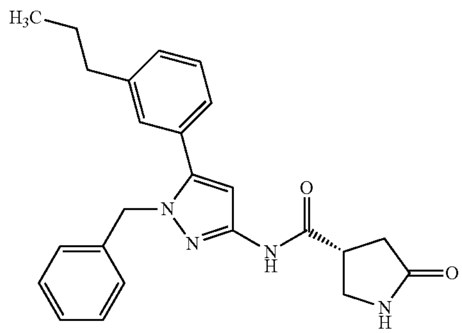 [SMILES: CCCc1cccc(-c2cc(NC(=O)[C@H]3CNC(=O)C3)nn2Cc2ccccc2)c1] | 1H-NMR (DMSO-D6) δ: 0.86 (t, 3H, J = 7.3 Hz), 1.56 (tq, 2H, J = 7.3, 7.5 Hz), 2.30-2.41 (m, 2H), 2.56 (t, 2H, J = 7.5 Hz), 3.27-3.34 (m, 1H), 3.34-3.41 (m, 1H), 3.44-3.49 (m, 1H), 5.25 (s, 2H), 6.69 (s, 1H), 6.99-7.04 (m, 2H), 7.21-7.32 (m, 6H), 7.37 (dd, 1H, J = 7.7, 7.7 Hz), 7.62 (s, 1H), 10.71 (s, 1H). | 403 | 401 | R-form |
| 99 | 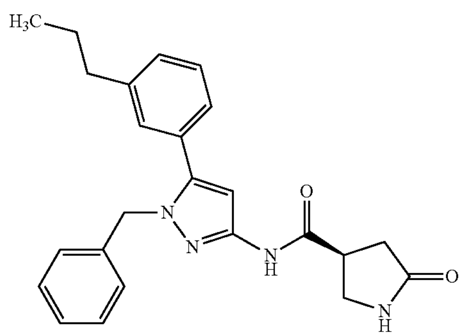 [SMILES: CCCc1cccc(-c2cc(NC(=O)[C@@H]3CNC(=O)C3)nn2Cc2ccccc2)c1] | 1H-NMR (DMSO-D6) δ: 0.86 (t, 3H, J = 7.3 Hz), 1.56 (tq, 2H, J = 7.3, 7.5 Hz), 2.30-2.41 (m, 2H), 2.56 (t, 2H, J = 7.5 Hz), 3.27-3.34 (m, 1H), 3.34-3.41 (m, 1H), 3.44-3.49 (m, 1H), 5.25 (s, 2H), 6.69 (s, 1H), 6.99-7.04 (m, 2H), 7.21-7.32 (m, 6H), 7.37 (dd, 1H, J = 7.9, 7.7 Hz), 7.62 (s, 1H), 10.71 (s, 1H). | 403 | 401 | S-form |
| 100 | 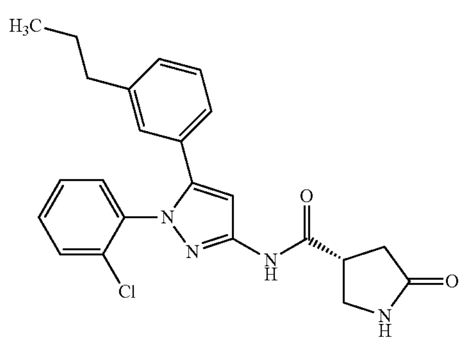 [SMILES: CCCc1cccc(-c2cc(NC(=O)[C@H]3CNC(=O)C3)nn2-c2ccccc2Cl)c1] | 1H-NMR (DMSO-D6) δ: 0.71 (3H, t, J = 7.4 Hz), 1.39 (2H, tq, J = 7.4, 7.5 Hz), 2.36-2.46 (4H, m), 3.31-3.54 (3H, m), 6.93-6.99 (2H, m), 7.04 (2H, d, J = 7.7 Hz), 7.11 (2H, d, J = 7.7 Hz), 7.22 (1H, t, J = 7.6 Hz), 7.43-7.62 (4H, m), 7.65 (1H, s), 10.82 (1H, s) | 423 | 421 | R-form |

TABLE 1-continued

| Ex. No. | Molecular Structure | NMR | MS (M + H) | MS (M − H) | Comments |
|---|---|---|---|---|---|
| 101 | 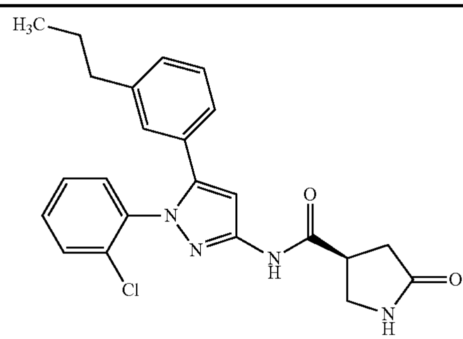 | 1H-NMR (DMSO-D6) δ: 0.71 (3H, t, J = 7.4 Hz), 1.39 (2H, tq, J = 7.4, 7.5 Hz), 2.36-2.46 (4H, m), 3.31-3.54 (3H, m), 6.93-6.99 (2H, m), 7.04 (2H, d, J = 7.7 Hz), 7.11 (2H, d, J = 7.7 Hz), 7.22 (1H, t, J = 7.7 Hz), 7.43-7.62 (4H, m), 7.65 (1H, s), 10.82 (1H, s) | 423 | 421 | S-form |
| 102 | 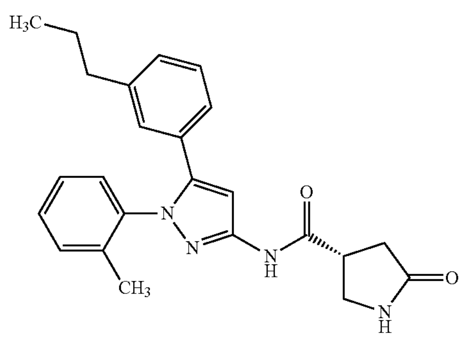 | 1H-NMR (DMSO-D6) δ: 0.71 (3H, t, J = 7.4 Hz), 1.38 (2H, tq, J = 7.2, 7.5 Hz), 1.89 (3H, s), 2.36-2.45 (4H, m), 3.31-3.54 (3H, m), 6.91-6.97 (2H, m), 7.01 (1H, d, J = 7.7 Hz), 7.10 (1H, d, J = 7.5 Hz), 7.20 (1H, t, J = 7.7 Hz), 7.65 (1H, s), 10.77 (1H, s) | 403 | 401 | R-form |
| 103 | 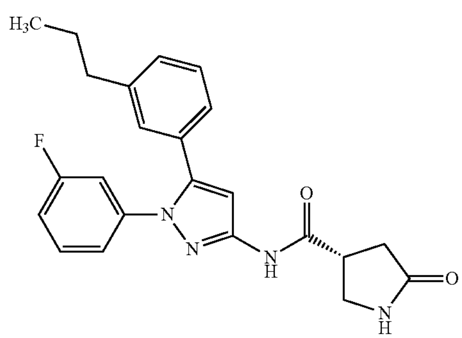 | 1H-NMR (DMSO-D6) δ: 0.78 (3H, t, J = 7.3 Hz), 1.46 (2H, tq, J = 7.1, 7.4 Hz), 2.39 (2H, d, J = 8.4 Hz), 2.45-2.53 (3H, m), 3.30-3.55 (3H, m), 6.91 (1H, s), 7.00-7.15 (4H, m), 7.16-7.24 (2H, m), 7.31 (1H, t, J = 7.6 Hz), 7.38-7.46 (1H, m), 7.65 (1H, s), 10.90 (1H, s) | 407 | 405 | R-form |
| 104 | 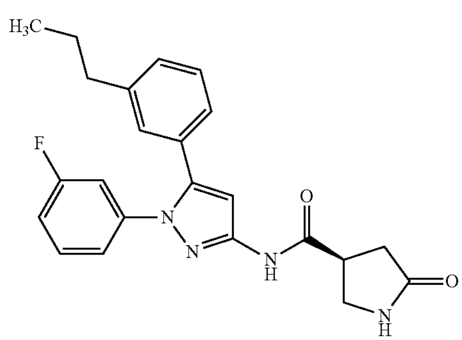 [SMILES: CCCc1cccc(-c2cc(NC(=O)[C@@H]3CNC(=O)C3)nn2-c2cccc(F)c2)c1] | 1H-NMR (DMSO-D6) δ: 0.78 (3H, t, J = 7.4 Hz), 1.46 (2H, tq, J = 7.1, 7.4 Hz), 2.39 (2H, d, J = 8.4 Hz), 2.45-2.53 (3H, m), 3.30-3.55 (3H, m), 6.91 (1H, s), 7.00-7.15 (4H, m), 7.16-7.24 (2H, m), 7.31 (1H, t, J = 7.6 Hz), 7.38-7.46 (1H, m), 7.65 (1H, s), 10.90 (1H, s) | 407 | 405 | S-form |

TABLE 1-continued

| Ex. No. | Molecular Structure | NMR | MS (M + H) | MS (M − H) | Comments |
|---|---|---|---|---|---|
| 105 | 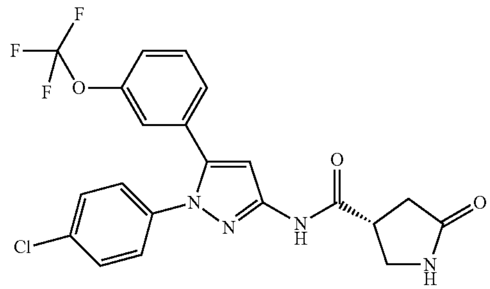 [SMILES: O=C1C[C@@H](C(=O)Nc2cc(-c3cccc(OC(F)(F)F)c3)n(-c3ccc(Cl)cc3)n2)CN1] | 1H-NMR (DMSO-D6) δ: 2.36-2.42 (m, 2H), 3.30-3.54 (m, 3H), 7.01 (s, 1H), 7.15 (s, 1H), 7.27 (dt, 2H, J = 9.3, 2.6 Hz), 7.35 (d, 1H, J = 8.0 Hz), 7.39 (d, 1H, J = 8.0 Hz), 7.49 (dt, 2H, J = 9.3, 2.6 Hz), 7.55 (t, 1H, J = 8.0 Hz), 7.65 (s, 1H), 10.94 (s, 1H). | 465 | 463 | R-form |
| 106 | 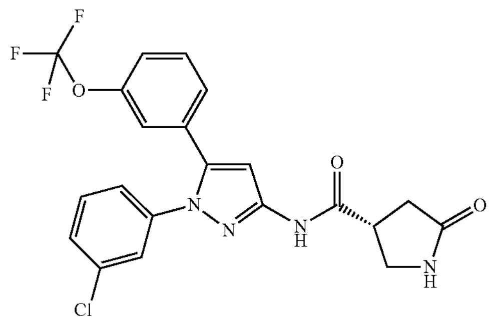 [SMILES: O=C1C[C@@H](C(=O)Nc2cc(-c3cccc(OC(F)(F)F)c3)n(-c3cccc(Cl)c3)n2)CN1] | 1H-NMR (DMSO-D6) δ: 2.35-2.43 (m, 2H), 3.33-3.54 (m, 3H), 7.02 (s, 1H), 7.13-7.21 (m, 2H), 7.34-7.47 (m, 5H), 7.56 (t, 1H, J = 8.0 Hz), 7.65 (s, 1H), 10.94 (s, 1H). | 465 | 463 | R-form |
| 107 | 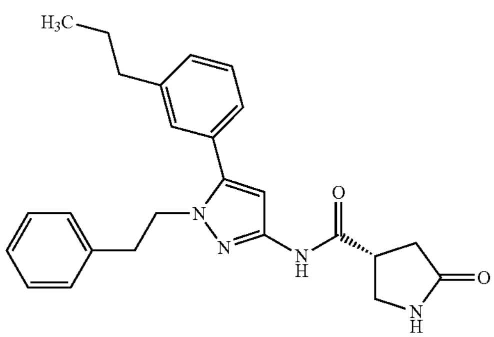 [SMILES: CCCc1cccc(-c2cc(NC(=O)[C@H]3CNC(=O)C3)nn2CCc2ccccc2)c1] | 1H-NMR (DMSO-D6) δ: 0.88 (t, 3H, J = 7.3 Hz), 1.55 (tq, 2H, J = 6.9, 7.3 Hz), 2.34-2.40 (m, 2H), 2.51 (t, 2H, J = 6.9 Hz), 3.06 (t, 2H, J = 7.1 Hz), 3.29-3.34 (m, 1H), 3.36-3.44 (m, 1H), 3.46-3.52 (m, 1H), 4.15 (t, 2H, J = 7.1 Hz), 6.53 (s, 1H), 6.80 (s, 1H), 6.95-7.00 (m, 2H), 7.00 (d, 1H, J = 7.7 Hz), 7.17-7.26 (m, 4H), 7.31 (dd, 1H, J = 7.7, 7.7 Hz), 7.63 (s, 1H), 10.74 (s, 1H). | 417 | 415 | R-form |
| 108 | 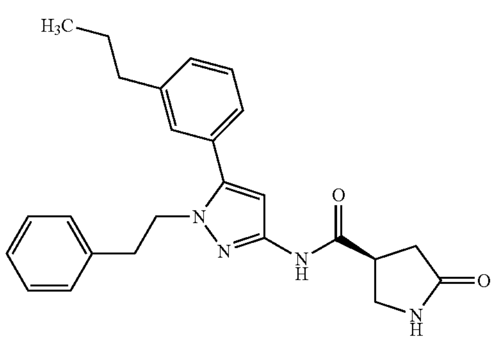 [SMILES: CCCc1cccc(-c2cc(NC(=O)[C@@H]3CNC(=O)C3)nn2CCc2ccccc2)c1] | 1H-NMR (DMSO-D6) δ: 0.88 (t, 3H, J = 7.3 Hz), 1.55 (tq, 2H, J = 6.9, 7.3 Hz), 2.34-2.40 (m, 2H), 2.51 (t, 2H, J = 6.9 Hz), 3.06 (t, 2H, J = 7.1 Hz), 3.29-3.34 (m, 1H), 3.36-3.44 (m, 1H), 3.46-3.52 (m, 1H), 4.15 (t, 2H, J = 7.1 Hz), 6.53 (s, 1H), 6.80 (s, 1H), 6.95-7.00 (m, 2H), 7.00 (d, 1H, J = 7.7 Hz), 7.17-7.26 (m, 4H), 7.31 (dd, 1H, J = 7.7, 7.7 Hz), 7.63 (s, 1H), 10.74 (s, 1H). | 417 | 415 | S-form |

TABLE 1-continued

| Ex. No. | Molecular Structure | NMR | MS (M + H) | MS (M − H) | Comments |
|---|---|---|---|---|---|
| 109 | 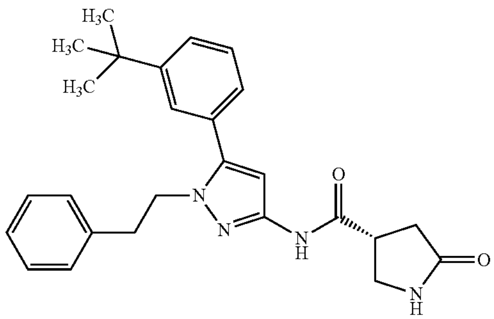 [SMILES: CC(C)(C)c1cccc(-c2cc(NC(=O)[C@H]3CNC(=O)C3)nn2CCc2ccccc2)c1] | 1H-NMR (DMSO-D6) δ: 1.26 (s, 9H), 2.35-2.39 (m, 2H), 3.06 (t, 2H, J = 7.1 Hz), 3.29-3.34 (m, 1H), 3.36-3.45 (m, 1H), 3.46-3.52 (m, 1H), 4.17 (t, 2H, J = 7.1 Hz), 6.54 (s, 1H), 6.94-6.99 (m, 2H), 6.99 (d, 1H, J = 7.7 Hz), 7.14-7.24 (m, 4H), 7.34 (dd, 1H, J = 7.7, 8.1 Hz), 7.44 (d, 1H, J = 8.1 Hz), 7.63 (s, 1H), 10.74 (s, 1H). | 431 | 429 | R-form |
| 110 | 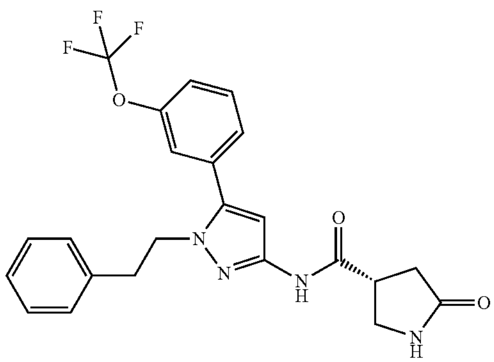 [SMILES: O=C1C[C@@H](C(=O)Nc2cc(-c3cccc(OC(F)(F)F)c3)n(CCc3ccccc3)n2)CN1] | 1H-NMR (DMSO-D6) δ: 2.35-2.40 (m, 2H), 3.03 (t, 2H, J = 6.9 Hz), 3.29-3.35 (m, 1H), 3.36-3.45 (m, 1H), 3.46-3.52 (m, 1H), 4.19 (t, 2H, J = 6.9 Hz), 6.59 (s, 1H), 6.90-6.95 (m, 2H), 6.98 (s, 1H), 7.14-7.23 (m, 4H), 7.40 (d, 1H, J = 8.1 Hz), 7.53 (dd, 1H, J = 7.7, 8.1 Hz), 7.64 (s, 1H), 10.79 (s, 1H). | 459 | 457 | R-form |
| 111 | 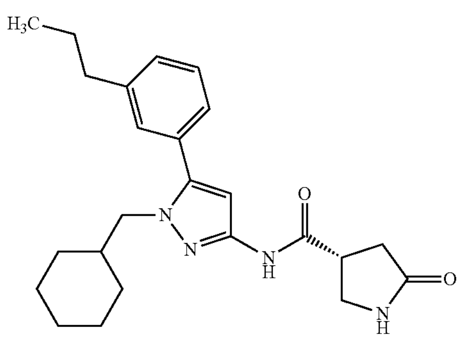 [SMILES: CCCc1cccc(-c2cc(NC(=O)[C@H]3CNC(=O)C3)nn2CC2CCCCC2)c1] | 1H-NMR (DMSO-D6) δ: 0.67-0.81 (m, 2H), 0.89 (t, 3H, J = 7.3 Hz), 0.99-1.14 (m, 3H), 1.37-1.46 (m, 2H), 1.48-1.67 (m, 3H), 1.62 (tq, 2H, J = 7.3, 7.3 Hz), 1.69-1.80 (m, 1H), 2.30-2.41 (m, 2H), 2.62 (t, 2H, J = 7.3 Hz), 3.27-3.35 (m, 1H), 3.35-3.43 (m, 1H), 3.44-3.50 (m, 1H), 3.84 (d, 2H, J = 7.3 Hz), 6.57 (s, 1H), 7.22-7.29 (m, 3H), 7.40 (dd, 1H, J = 8.1, 7.7 Hz), 7.62 (s, 1H), 10.65 (s, 1H). | 409 | 407 | R-form |
| 112 | 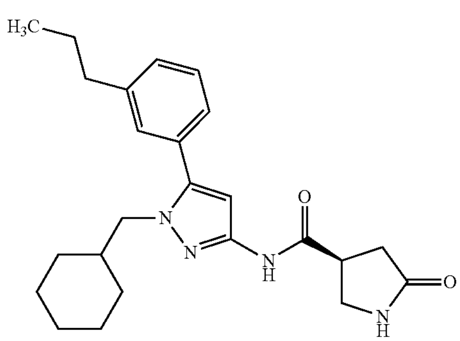 [SMILES: CCCc1cccc(-c2cc(NC(=O)[C@@H]3CNC(=O)C3)nn2CC2CCCCC2)c1] | 1H-NMR (DMSO-D6) δ: 0.67-0.80 (m, 2H), 0.89 (t, 3H, J = 7.3 Hz), 0.99-1.13 (m, 3H), 1.37-1.46 (m, 2H), 1.48-1.67 (m, 3H), 1.62 (tq, 2H, J = 7.3, 7.5 Hz), 1.69-1.79 (m, 1H), 2.30-2.41 (m, 2H), 2.62 (t, 2H, J = 7.5 Hz), 3.27-3.35 (m, 1H), 3.35-3.43 (m, 1H), 3.43-3.50 (m, 1H), 3.84 (d, 2H, J = 7.3 Hz), 6.57 (s, 1H), 7.22-7.29 (m, 3H), 7.40 (dd, 1H, J = 7.7, 8.1 Hz), 7.62 (s, 1H), 10.65 (s, 1H). | 409 | 407 | S-form |

TABLE 1-continued

| Ex. No. | Molecular Structure | NMR | MS (M + H) | MS (M − H) | Comments |
|---|---|---|---|---|---|
| 113 | 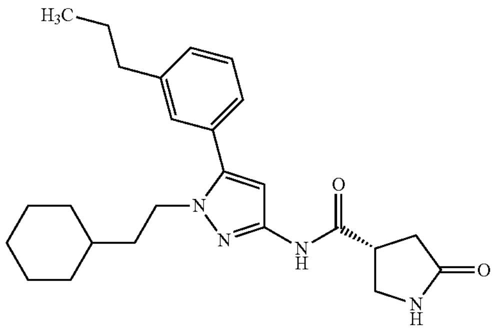 [SMILES: CCCc1cccc(-c2cc(NC(=O)[C@H]3CNC(=O)C3)nn2CCC2CCCCC2)c1] | 1H-NMR (DMSO-D6) δ: 0.71-0.83 (m, 2H), 0.90 (t, 3H, J = 7.3 Hz), 0.97-1.13 (m, 4H), 1.41-1.48 (m, 2H), 1.49-1.67 (m, 5H), 1.63 (tq, 2H, J = 7.3, 7.5 Hz), 2.30-2.41 (m, 2H), 2.62 (t, 2H, J = 7.5 Hz), 3.26-3.34 (m, 1H), 3.35-3.42 (m, 1H), 3.44-3.50 (m, 1H), 4.01 (t, 2H, J = 7.3 Hz), 6.56 (s, 1H), 7.23-7.30 (m, 3H), 7.41 (dd, 1H, J = 7.7, 8.1 Hz), 7.62 (s, 1H), 10.66 (s, 1H). | 423 | 421 | R-form |
| 114 | 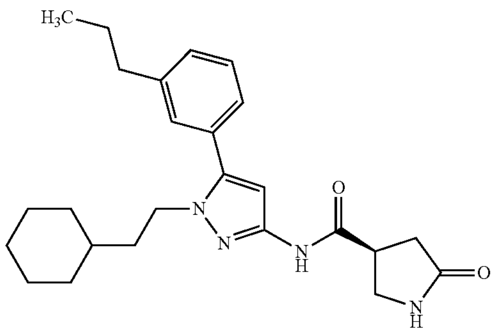 [SMILES: CCCc1cccc(-c2cc(NC(=O)[C@@H]3CNC(=O)C3)nn2CCC2CCCCC2)c1] | 1H-NMR (DMSO-D6) δ: 0.71-0.84 (m, 2H), 0.90 (t, 3H, J = 7.3 Hz), 0.99-1.11 (m, 4H), 1.41-1.49 (m, 2H), 1.50-1.68 (m, 5H), 1.63 (tq, 2H, J = 7.3, 7.7 Hz), 2.30-2.41 (m, 2H), 2.62 (t, 2H, J = 7.7 Hz), 3.26-3.35 (m, 1H), 3.35-3.42 (m, 1H), 3.44-3.50 (m, 1H), 4.01 (t, 2H, J = 7.3 Hz), 6.56 (s, 1H), 7.23-7.30 (m, 3H), 7.41 (dd, 1H, J = 7.7, 8.1 Hz), 7.62 (s, 1H), 10.66 (s, 1H). | 423 | 421 | S-form |
| 115 | 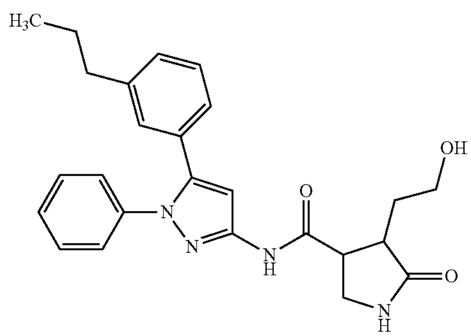 [SMILES: CCCc1cccc(-c2cc(NC(=O)C3CNC(=O)C3CCO)nn2-c2ccccc2)c1] | 1H-NMR (DMSO-D6) δ: 0.77 (t, 3H, J = 7.3 Hz), 1.38-1.59 (m, 1H), 1.80-1.93 (m, 1H), 2.46 (t, 3H, J = 7.5 Hz), 2.58-2.70 (m, 1H), 3.12-3.24 (m, 2H), 3.41-3.53 (m, 3H), 4.57 (t, 1H, J = 5.0 Hz), 6.92 (s, 1H), 7.01 (s, 1H), 7.07 (d, 1H, J = 7.7 Hz), 7.17 (d, 1H, J = 7.5 Hz), 7.20-7.43 (m, 6H), 7.72 (s, 1H), 10.93 (s, 1H). | 433 | 431 | trans-form (Racemate) |
| 116 | 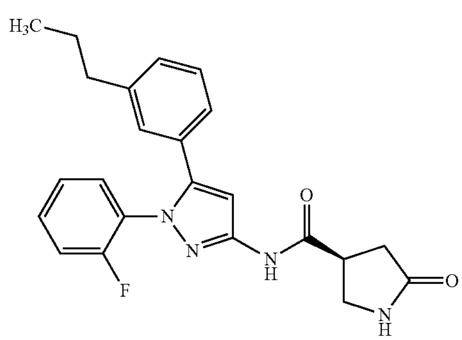 [SMILES: CCCc1cccc(-c2cc(NC(=O)[C@@H]3CNC(=O)C3)nn2-c2ccccc2F)c1] | 1H-NMR (DMSO-D6) δ: 0.73 (3H, t, J = 7.4 Hz), 1.41 (2H, tq, J = 7.3, 7.4 Hz), 2.36-2.47 (4H, m), 3.30-3.55 (3H, m), 6.93-7.01 (2H, m), 7.06 (1H, d, J = 7.7 Hz), 7.14 (1H, d, J = 7.7 Hz), 7.24 (1H, t, J = 7.6 Hz), 7.28-7.37 (2H, m), 7.45-7.57 (2H, m), 7.65 (1H, s), 10.84 (1H, s) | 407 | 405 | S-form |

TABLE 1-continued

| Ex. No. | Molecular Structure | NMR | MS (M + H) | MS (M − H) | Comments |
|---|---|---|---|---|---|
| 117 | 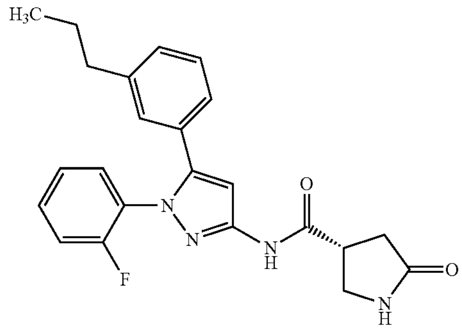 | 1H-NMR (DMSO-D6) δ: 0.74 (3H, t, J = 7.4 Hz), 1.41 (2H, tq, J = 7.3, 7.4 Hz), 2.35-2.48 (4H, m), 3.30-3.55 (3H, m), 6.93-7.01 (2H, m), 7.06 (1H, d, J = 7.5 Hz), 7.14 (1H, d, J = 7.5 Hz), 7.24 (1H, t, J = 7.6 Hz), 7.28-7.37 (2H, m), 7.45-7.58 (2H, m), 7.65 (1H, s), 10.84 (1H, s) | 407 | 405 | R-form |
| 118 | 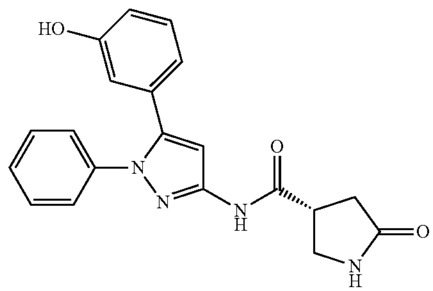 [SMILES: O=C1C[C@@H](C(=O)Nc2cc(-c3cccc(O)c3)n(-c3ccccc3)n2)CN1] | 1H-NMR (DMSO-D6) δ: 2.31-2.41 (m, 2H), 3.30-3.53 (m, 3H), 6.60-6.66 (m, 2H), 6.72-6.77 (m, 1H), 6.83 (s, 1H), 7.14 (t, 1H, J = 8.2 Hz), 7.23 (d, 2H, J = 7.1 Hz), 7.29-7.44 (m, 3H), 7.64 (s, 1H), 9.58 (s, 1H), 10.85 (s, 1H). | 363 | 361 | R-form |
| 119 | 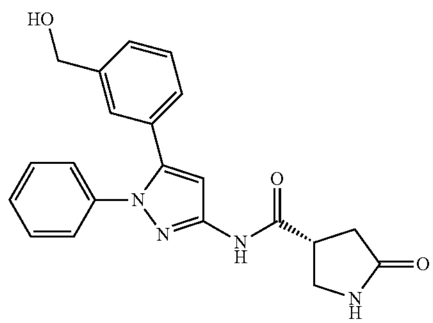 [SMILES: O=C1C[C@@H](C(=O)Nc2cc(-c3cccc(CO)c3)n(-c3ccccc3)n2)CN1] | 1H-NMR (DMSO-D6) δ: 2.36-2.42 (m, 2H), 3.33-3.54 (m, 3H), 4.45 (d, 2H, J = 5.7 Hz), 5.21 (t, 1H, J = 5.7 Hz), 6.90 (s, 1H), 6.99 (d, 1H, J = 6.6 Hz), 7.20-7.44 (m, 8H), 7.64 (s, 1H), 10.86 (s, 1H). | 377 | 375 | R-form |
| 120 | 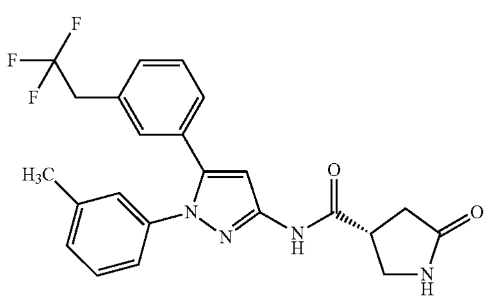 [SMILES: Cc1cccc(-n2nc(NC(=O)[C@H]3CNC(=O)C3)cc2-c2cccc(CC(F)(F)F)c2)c1] | 1H-NMR (DMSO-D6) δ: 2.26 (s, 3H), 2.36-2.41 (m, 2H), 3.33-3.54 (m, 3H), 6.97-7.03 (m, 2H), 7.08 (s, 1H), 7.10 (s, 1H), 7.19 (d, 1H, J = 7.5 Hz), 7.29 (t, 1H, J = 7.7 Hz), 7.34-7.40 (m, 2H), 7.53 (t, 1H, J = 8.0 Hz), 7.65 (s, 1H), 10.89 (s, 1H). | 445 | 443 | R-form |
| 121 | 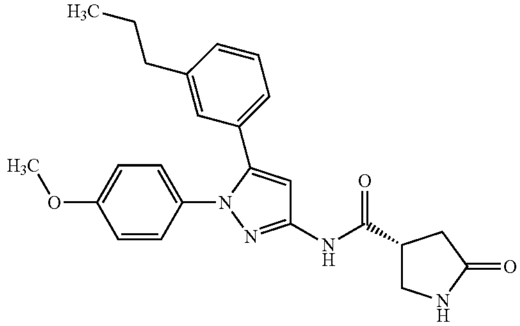 [SMILES: CCCc1cccc(-c2cc(NC(=O)[C@H]3CNC(=O)C3)nn2-c2ccc(OC)cc2)c1] | 1H-NMR (DMSO-D6) δ: 0.77 (3H, t, J = 7.3 Hz), 1.45 (2H, tq, J = 7.3, 7.6 Hz), 2.36-2.41 (2H, m), 2.42-2.50 (2H, t, J = 7.5 Hz), 3.29-3.54 (3H, m), 3.76 (3H, s), 6.86 (1H, s), 6.91-6.98 (2H, m), 7.00 (1H, s), 7.05 (1H, d, J = 7.6 Hz), 7.12-7.19 (3H, m), 7.25 (1H, t, J = 7.6 Hz), 7.64 (1H, s), 10.8 (1H, m) | 419 | 417 | R-form |

TABLE 1-continued

| Ex. No. | Molecular Structure | NMR | MS (M + H) | MS (M − H) | Comments |
|---|---|---|---|---|---|
| 122 | 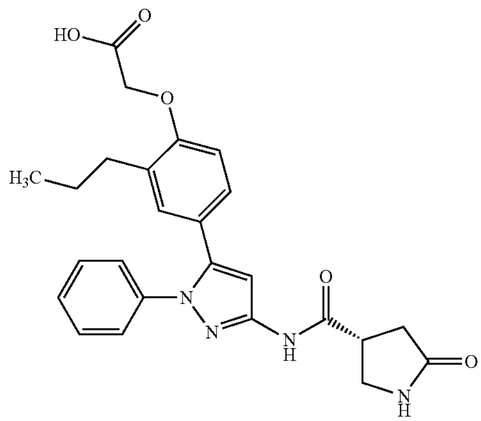 [SMILES: CCCc1cc(-c2cc(NC(=O)[C@H]3CNC(=O)C3)nn2-c2ccccc2)ccc1OCC(=O)O] | 1H-NMR (DMSO-D6) δ: 0.76 (t, 3H, J = 7.3 Hz), 1.41 (tq, 2H, J = 7.5, 7.3 Hz), 2.31-2.46 (m, 4H), 3.36-3.54 (m, 3H), 4.64 (s, 2H), 6.77-6.92 (m, 3H), 7.06 (dd, 1H, J = 8.6, 2.2 Hz), 7.20-7.44 (m, 5H), 7.64 (s, 1H), 10.82 (s, 1H). | 463 | 461 | R-form |
| 123 | 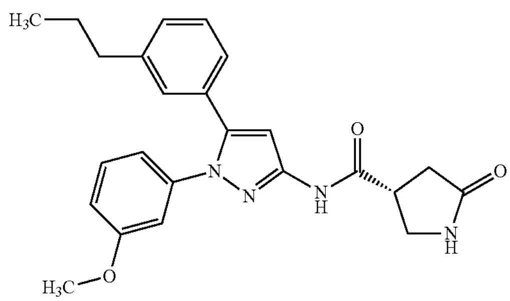 [SMILES: CCCc1cccc(-c2cc(NC(=O)[C@H]3CNC(=O)C3)nn2-c2cccc(OC)c2)c1] | 1H-NMR (DMSO-D6) δ: 0.78 (3H, t, J = 7.4 Hz), 1.35-1.55 (2H, m), 2.35-2.55 (4H, m), 3.25-3.6 (3H, m), 3.65 (3H, s), 6.7-6.83 (2H, m), 6.85-6.95 (2H, m), 7.03 (1H, s), 7.09 (1H, d, J = 8.0 Hz), 7.19 (1H, d, J = 8.0 Hz), 7.22-7.38 (2H, m), 7.64 (1H, s), 10.87 (1H, s) | 419 | 417 | R-form |
| 124 | 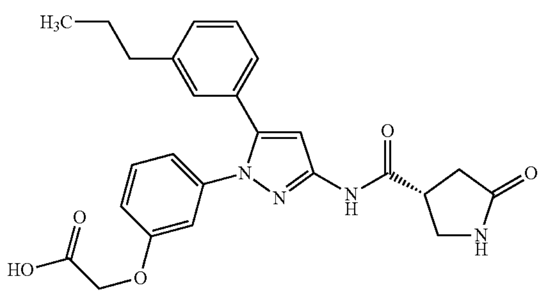 [SMILES: CCCc1cccc(-c2cc(NC(=O)[C@H]3CNC(=O)C3)nn2-c2cccc(OCC(=O)O)c2)c1] | 1H-NMR (DMSO-D6) δ: 0.79 (3H, t, J = 7.3 Hz), 1.47 (2H, tq, J = 7.3, 7.4 Hz), 2.36-2.42 (2H, m), 2.45-2.52 (2H, m), 2.99-3.55 (3H, m), 4.59 (2H, s), 6.75 (1H, dd, J = 8.0, 1.1 Hz), 6.80 (1H, t, J = 2.2 Hz), 6.86-6.92 (2H, m), 7.03 (1H, s), 7.07 (1H, d, J = 7.7 Hz), 7.18 (1H, d, J = 7.7 Hz), 7.23-7.32 (2H, m), 7.64 (1H, s), 10.88 (1H, s), 13.01 (1H, s) | 463 | 461 | R-form |
| 125 | 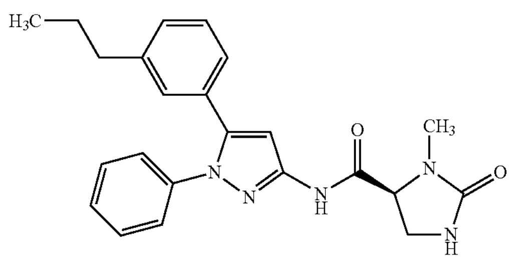 [SMILES: CCCc1cccc(-c2cc(NC(=O)[C@@H]3CNC(=O)N3C)nn2-c2ccccc2)c1] | 1H-NMR (DMSO-D6) δ: 0.77 (t, 3H, J = 7.3 Hz), 1.44 (tq, 2H, J = 7.5, 7.3 Hz), 2.46 (t, 3H, J = 7.5 Hz), 2.64 (s, 3H), 3.21 (dd, 1H, J = 8.8, 6.3 Hz), 3.54 (dd, 1H, J = 9.4, 8.8 Hz), 4.28 (dd, 1H, J = 9.4, 6.3 Hz), 6.44 (s, 1H), 6.92 (s, 1H), 7.01 (s, 1H), 7.08 (d, 1H, J = 7.0 Hz), 7.17 (d, 1H, J = 7.0 Hz), 7.20-7.44 (m, 6H), 11.02 (s, 1H). | 404 | 402 | S-form |

TABLE 1-continued

| Ex. No. | Molecular Structure | NMR | MS (M + H) | MS (M − H) | Comments |
|---|---|---|---|---|---|
| 126 | 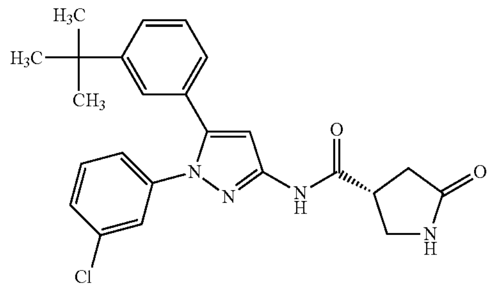 [SMILES: CC(C)(C)c1cccc(-c2cc(NC(=O)[C@H]3CNC(=O)C3)nn2-c2cccc(Cl)c2)c1] | 1H-NMR (DMSO-D6) δ: 1.13 (9H, s), 2.39 (2H, d, J = 7.9 Hz), 3.30-3.55 (3H, m), 6.94 (1H, s), 7.09 (1H, s), 7.17-7.26 (2H, m), 7.28 (1H, s), 7.33-7.48 (4H, m), 7.65 (1H, s), 10.90 (1H, s) | 437 | 435 | R-form |
| 127 | 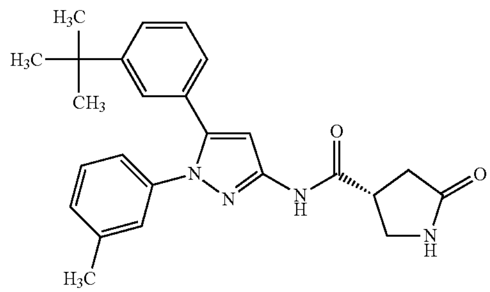 [SMILES: Cc1cccc(-n2nc(NC(=O)[C@H]3CNC(=O)C3)cc2-c2cccc(C(C)(C)C)c2)c1] | 1H-NMR (DMSO-D6) δ: 1.10 (9H, s), 2.25 (3H, s), 2.36-2.42 (2H, m), 3.3-3.55 (3H, m), 6.91 (1H, s), 7.00 (1H, d, J = 7.9 Hz), 7.04-7.10 (2H, m), 7.14-7.23 (2H, m), 7.24-7.41 (3H, m), 7.65 (1H, s), 10.84 (1H, s) | 417 | 415 | R-form |
| 128 | 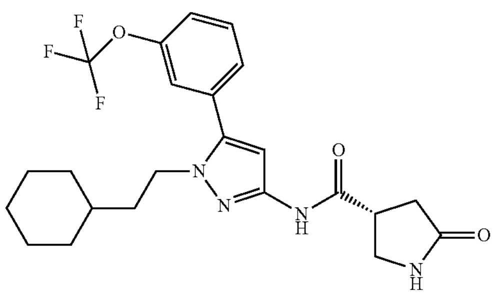 [SMILES: O=C1C[C@@H](C(=O)Nc2cc(-c3cccc(OC(F)(F)F)c3)n(CCC3CCCCC3)n2)CN1] | 1H-NMR (DMSO-D6) δ: 0.69-0.85 (m, 2H), 0.94-1.14 (m, 4H), 1.38-1.61 (m, 7H), 2.31-2.40 (m, 2H), 3.26-3.51 (m, 3H), 4.04 (t, 2H, J = 7.2 Hz), 6.66 (s, 1H), 7.45-7.69 (m, 5H), 10.71 (s, 1H). | 465 | 463 | R-form |
| 129 | 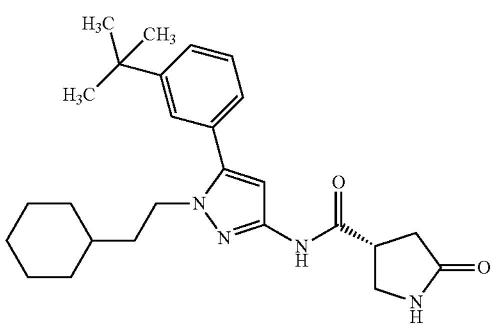 [SMILES: CC(C)(C)c1cccc(-c2cc(NC(=O)[C@H]3CNC(=O)C3)nn2CCC2CCCCC2)c1] | 1H-NMR (DMSO-D6) δ: 0.69-0.84 (m, 2H), 0.95-1.13 (m, 4H), 1.32 (s, 9H), 1.40-1.64 (m, 7H), 2.32-2.39 (m, 2H), 3.26-3.51 (m, 3H), 4.01 (t, 2H, J = 7.3 Hz), 6.57 (s, 1H), 7.25 (d, 1H, J = 7.3 Hz), 7.38-7.52 (m, 3H), 7.62 (s, 1H), 10.67 (s, 1H). | 437 | 435 | R-form |
| 130 | 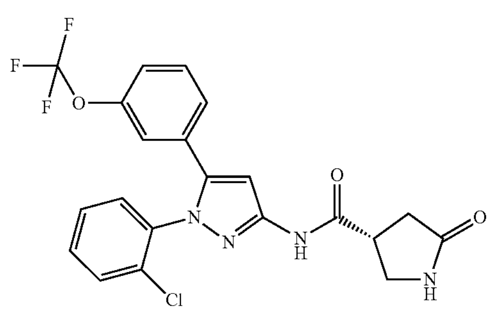 | 1H-NMR (DMSO-D6) δ: 2.40 (d, 2H, J = 8.5 Hz), 2.40 (d, 2H, J = 8.4 Hz), 3.34 (dd, 1H, J = 8.5, 8.6 Hz), 3.42 (dddd, 1H, J = 8.4, 8.5, 8.5, 8.6 Hz), 3.51 (dd, 1H, J = 8.5, 8.5 Hz), 7.01 (s, 1H), 7.09 (s, 1H), 7.31-7.35 (m, 2H), 7.47-7.56 (m, 3H), 7.60-7.66 (m, 3H), 10.88 (s, 1H). | 465 | 463 | R-form |

| Ex. No. | Molecular Structure | NMR | MS (M + H) | MS (M − H) | Comments |
|---|---|---|---|---|---|
| 131 | 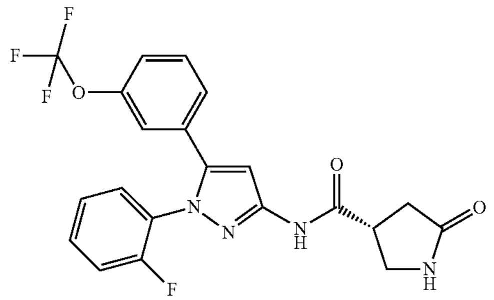 [SMILES: O=C1C[C@@H](C(=O)Nc2cc(-c3cccc(OC(F)(F)F)c3)n(-c3ccccc3F)n2)CN1] | 1H-NMR (DMSO-D6) δ: 2.40 (2H, d, J = 7.9 Hz), 3.30-3.55 (3H, m), 7.07 (2H, s), 7.29-7.40 (4H, m), 7.47-7.56 (2H, m), 7.60 (1H, dt, J = 7.8, 1.5 Hz), 7.65 (1H, s), 10.90 (1H, s) | 449 | 447 | R-form |
| 132 | 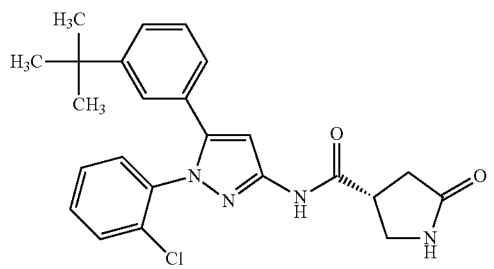 [SMILES: CC(C)(C)c1cccc(-c2cc(NC(=O)[C@H]3CNC(=O)C3)nn2-c2ccccc2Cl)c1] | 1H-NMR (DMSO-D6) δ: 1.06 (9H, s), 2.36-2.43 (2H, m), 3.30-3.55 (3H, m), 6.96-7.03 (2H, m), 7.16-7.23 (1H, m), 7.25-7.36 (2H, m), 7.43-7.58 (3H, m), 7.59-7.69 (2H, m), 10.82 (1H, s) | 437 | 435 | R-form |
| 133 | 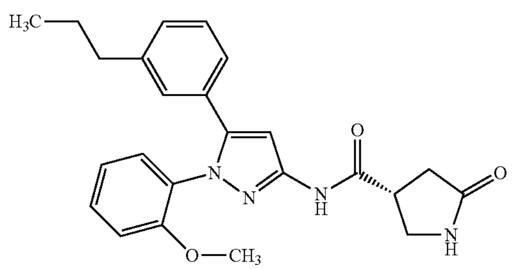 [SMILES: CCCc1cccc(-c2cc(NC(=O)[C@H]3CNC(=O)C3)nn2-c2ccccc2OC)c1] | 1H-NMR (DMSO-D6) δ: 0.72 (3H, t, J = 7.2 Hz), 1.38 (2H, tq, J = 7.2, 7.4 Hz), 2.30-2.45 (4H, m), 3.29-3.53 (6H, m), 6.85 (1H, s), 6.93 (1H, s), 6.96-7.11 (4H, m), 7.18 (1H, t, J = 7.6 Hz), 7.33 (1H, d, J = 7.7 Hz), 7.40 (1H, t, d = 7.9 Hz), 7.63 (1H, s), 10.72 (1H, s) | 419 | 417 | R-form |
| 134 | 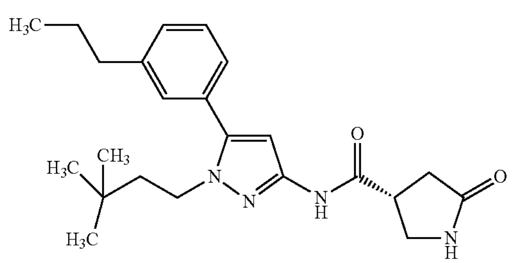 [SMILES: CCCc1cccc(-c2cc(NC(=O)[C@H]3CNC(=O)C3)nn2CCC(C)(C)C)c1] | 1H-NMR (DMSO-D6) δ: 0.82 (s, 9H), 0.89 (t, 3H, J = 7.3 Hz), 1.57-1.69 (m, 4H), 2.32-2.39 (m, 2H), 2.62 (t, 2H, J = 7.5 Hz), 3.26-3.40 (m, 2H), 3.47 (t, 1H, J = 8.5 Hz), 3.96-4.05 (m, 2H), 6.57 (s, 1H), 7.24-7.31 (m, 3H), 7.41 (t, 1H, J = 7.8 Hz), 7.62 (s, 1H), 10.66 (s, 1H). | 397 | 395 | R-form |
| 135 | 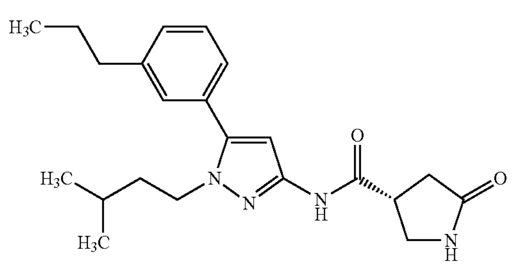 [SMILES: CCCc1cccc(-c2cc(NC(=O)[C@H]3CNC(=O)C3)nn2CCC(C)C)c1] | 1H-NMR (DMSO-D6) δ: 0.75 (d, 6H, J = 6.6 Hz), 0.89 (t, 3H, J = 7.4 Hz), 1.36-1.43 (m, 1H), 1.52-1.69 (m, 4H), 2.32-2.39 (m, 2H), 2.62 (t, 2H, J = 7.4 Hz), 3.26-3.50 (m, 3H), 4.01 (t, 2H, J = 7.3 Hz), 6.57 (s, 1H), 7.24-7.30 (m, 3H), 7.41 (t, 1H, J = 7.8 Hz), 7.62 (s, 1H), 10.65 (s, 1H). | 383 | 381 | R-form |

TABLE 1-continued

| Ex. No. | Molecular Structure | NMR | MS (M + H) | MS (M − H) | Comments |
|---|---|---|---|---|---|
| 136 | 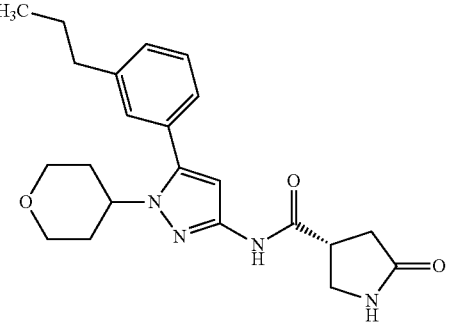 | 1H-NMR (DMSO-D6) δ: 0.91 (t, 3H, J = 7.5 Hz), 1.63 (tq, 2H, J = 7.5, 7.7 Hz), 1.75-1.82 (m, 2H), 2.00-2.12 (m, 2H), 2.30-2.41 (m, 2H), 2.63 (t, 2H, J = 7.7 Hz), 3.25-3.34 (m, 3H), 3.35-3.43 (m, 1H), 3.44-3.50 (m, 1H), 3.88-3.95 (m, 2H), 4.24-4.33 (m, 1H), 6.57 (s, 1H), 7.23-7.27 (m, 2H), 7.30 (d, 1H, J = 7.7 Hz), 7.42 (dd, 1H, J = 7.7, 8.1 Hz), 7.62 (s, 1H), 10.72 (s, 1H). | 397 | 395 | R-form |
| 137 | 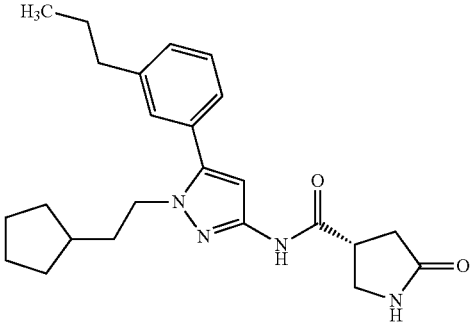 [SMILES: CCCc1cccc(-c2cc(NC(=O)[C@H]3CNC(=O)C3)nn2CCC2CCCC2)c1] | 1H-NMR (DMSO-D6) δ: 0.87-0.98 (m, 2H), 0.89 (t, 3H, J = 7.3 Hz), 1.32-1.43 (m, 2H), 1.43-1.72 (m, 7H), 1.62 (tq, 2H, J = 7.3, 7.5 Hz), 2.30-2.41 (m, 2H), 2.62 (t, 2H, J = 7.5 Hz), 3.27-3.33 (m, 1H), 3.33-3.42 (m, 1H), 3.44-3.50 (m, 1H), 4.00 (t, 2H, J = 7.1 Hz), 6.57 (s, 1H), 7.23-7.30 (m, 3H), 7.41 (dd, 1H, J = 7.7, 8.1 Hz), 7.62 (s, 1H), 10.65 (s, 1H). | 409 | 407 | R-form |
| 138 | 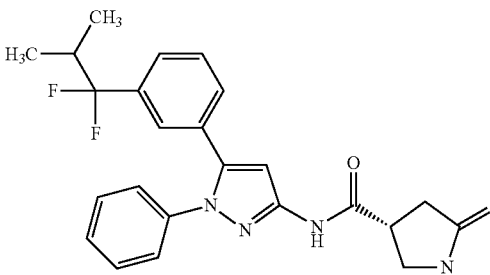 | 1H-NMR (DMSO-D6) δ: 0.78 (d, 6H, J = 6.7 Hz), 2.15-2.30 (m, 1H), 2.36-2.42 (m, 2H), 3.32-3.54 (m, 3H), 6.98 (s, 1H), 7.13 (s, 1H), 7.24 (d, 2H, J = 7.2 Hz), 7.32-7.55 (m, 6H), 7.64 (s, 1H), 10.89 (s, 1H). | 439 | 437 | R-form |
| 139 | 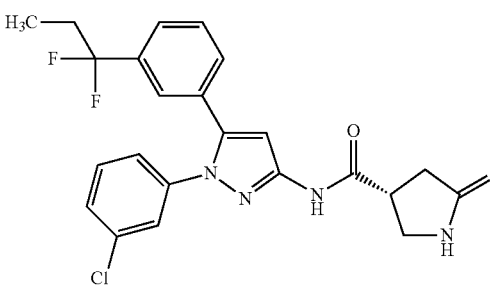 | 1H-NMR (DMSO-D6) δ: 0.78 (t, 3H, J = 7.3 Hz), 2.10 (tq, 2H, J = 16.5, 7.3 Hz), 2.36-2.42 (m, 2H), 3.32-3.55 (m, 3H), 7.01 (s, 1H), 7.15-7.21 (m, 1H), 7.28 (s, 1H), 7.33 (s, 1H), 7.39-7.58 (m, 5H), 7.64 (s, 1H), 10.92 (s, 1H). | 459 | 457 | R-form |
| 140 | 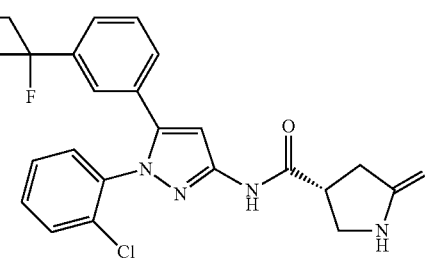 | 1H-NMR (DMSO-D6) δ: 0.69 (t, 3H, J = 7.4 Hz), 2.02 (tq, 2H, J = 16.0, 7.4 Hz), 2.38-2.41 (m, 2H), 3.33-3.37 (m, 1H), 3.38-3.46 (m, 1H), 3.49-3.54 (m, 1H), 7.06 (s, 1H), 7.16 (s, 1H), 7.41-7.65 (m, 8H), 10.86 (s, 1H). | 459 | 457 | R-form |

TABLE 1-continued

| Ex. No. | Molecular Structure | NMR | MS (M + H) | MS (M − H) | Comments |
|---|---|---|---|---|---|
| 141 | 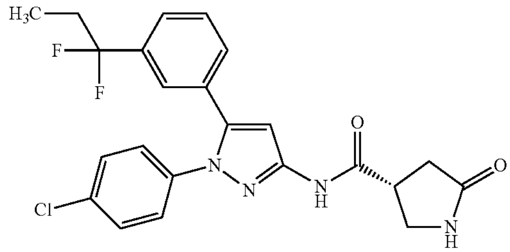 [SMILES: CCC(F)(F)c1cccc(-c2cc(NC(=O)[C@H]3CNC(=O)C3)nn2-c2ccc(Cl)cc2)c1] | 1H-NMR (DMSO-D6) δ: 0.78 (t, 3H, J = 7.4 Hz), 2.10 (tq, 2H, J = 16.2, 7.4 Hz), 2.38-2.40 (m, 2H), 3.33-3.35 (m, 1H), 3.39-3.44 (m, 1H), 3.49-3.52 (m, 1H), 7.00 (s, 1H), 7.24-7.28 (m, 3H), 7.42-7.54 (m, 5H), 7.64 (s, 1H), 10.92 (s, 1H). | 459 | 457 | R-form |
| 142 | 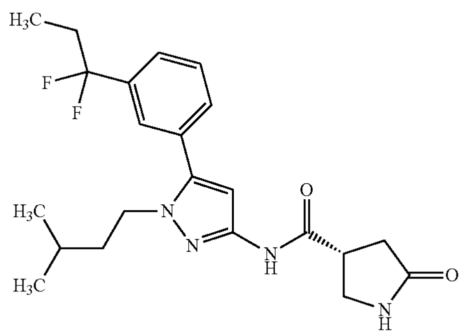 [SMILES: CCC(F)(F)c1cccc(-c2cc(NC(=O)[C@H]3CNC(=O)C3)nn2CCC(C)C)c1] | 1H-NMR (DMSO-D6) δ: 0.74 (d, 6H, J = 6.4 Hz), 0.92 (t, 3H, J = 7.5 Hz), 1.39 (tsep, 1H, J = 6.4, 7.0 Hz), 1.57 (dt, 2H, J = 7.0, 7.5 Hz), 2.27 (tq, 2H, J = 16.5, 7.5 Hz), 2.33-2.41 (m, 2H), 3.27-3.33 (m, 1H), 3.34-3.43 (m, 1H), 3.44-3.50 (m, 1H), 4.02 (t, 2H, J = 7.5 Hz), 6.65 (s, 1H), 7.55 (s, 1H), 7.58-7.67 (m, 4H), 10.70 (s, 1H). | 419 | 417 | R-form |
| 143 | 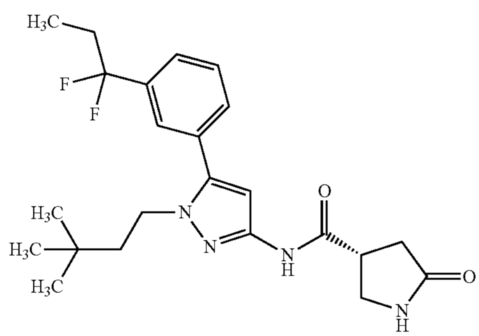 [SMILES: CCC(F)(F)c1cccc(-c2cc(NC(=O)[C@H]3CNC(=O)C3)nn2CCC(C)(C)C)c1] | 1H-NMR (DMSO-D6) δ: 0.82 (s, 9H), 0.92 (t, 3H, J = 7.5 Hz), 1.58-1.66 (m, 2H), 2.27 (tq, 2H, J = 16.5, 7.5 Hz), 2.33-2.39 (m, 2H), 3.27-3.34 (m, 1H), 3.34-3.42 (m, 1H), 3.44-3.51 (m, 1H), 3.97-4.05 (m, 2H), 6.66 (s, 1H), 7.56 (s, 1H), 7.58-7.67 (m, 4H), 10.70 (s, 1H). | 433 | 431 | R-form |
| 144 | 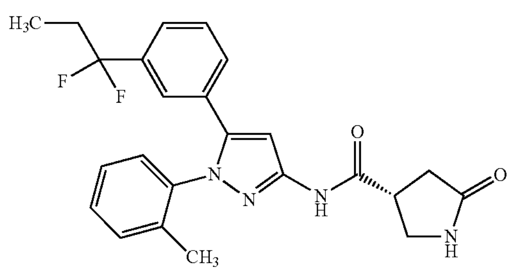 [SMILES: CCC(F)(F)c1cccc(-c2cc(NC(=O)[C@H]3CNC(=O)C3)nn2-c2ccccc2C)c1] | 1H-NMR (DMSO-D6) δ: 0.69 (3H, t, J = 7.5 Hz), 1.89 (3H, s), 1.92-2.08 (2H, m), 2.36-2.43 (2H, m), 3.3-3.55 (3H, m), 7.05 (1H, s), 7.13 (1H, s), 7.25-7.50 (7H, m), 7.65 (1H, s), 10.81 (1H, s) | 439 | 437 | R-form |
| 145 | 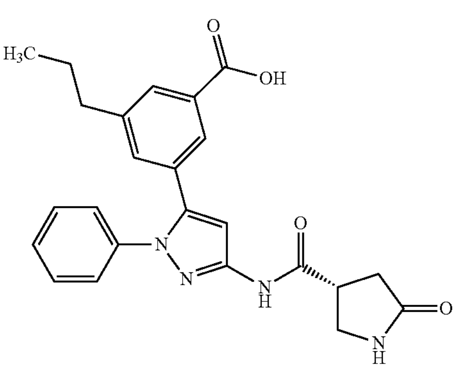 [SMILES: CCCc1cc(C(=O)O)cc(-c2cc(NC(=O)[C@H]3CNC(=O)C3)nn2-c2ccccc2)c1] | 1H-NMR (DMSO-D6) δ: 0.76 (t, 3H, J = 7.3 Hz), 1.44 (tq, 2H, J = 7.5, 7.3 Hz), 2.36-2.43 (m, 2H), 2.44-2.49 (m, 2H), 3.35-3.54 (m, 3H), 6.92 (s, 1H), 7.10 (s, 1H), 7.23 (d, 2H, J = 7.3 Hz), 7.30-7.44 (m, 3H), 7.59-7.72 (m, 3H), 10.87 (s, 1H). | 433 | 431 | R-form |

TABLE 1-continued

| Ex. No. | Molecular Structure | NMR | MS (M + H) | MS (M − H) | Comments |
|---|---|---|---|---|---|
| 146 | 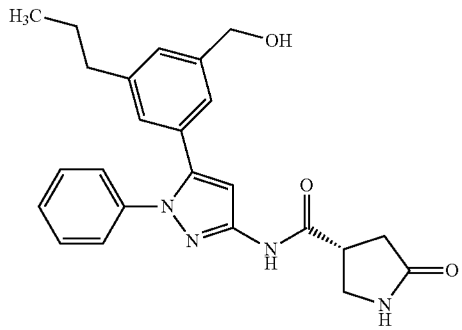 [SMILES: CCCc1cc(CO)cc(-c2cc(NC(=O)[C@H]3CNC(=O)C3)nn2-c2ccccc2)c1] | 1H-NMR (DMSO-D6) δ: 0.74 (t, 3H, J = 7.3 Hz), 1.40 (tq, 2H, J = 7.5, 7.3 Hz), 2.35-2.45 (m, 4H), 3.33-3.54 (m, 3H), 4.43 (d, 2H, J = 5.7 Hz), 5.17 (t, 1H, J = 5.7 Hz), 6.76 (s, 1H), 6.89 (s, 1H), 7.12 (d, 2H, J = 5.3 Hz), 7.23 (d, 2H, J = 7.3 Hz), 7.31-7.43 (m, 3H), 7.64 (s, 1H), 10.85 (s, 1H). | 419 | 417 | R-form |
| 147 | 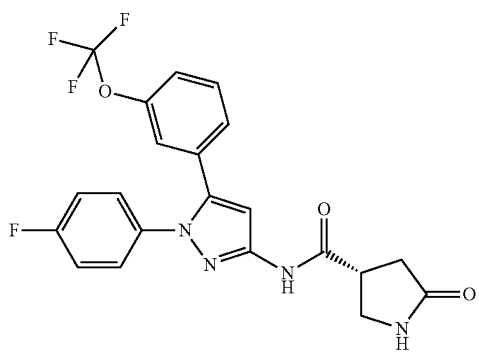 [SMILES: O=C1C[C@@H](C(=O)Nc2cc(-c3cccc(OC(F)(F)F)c3)n(-c3ccc(F)cc3)n2)CN1] | 1H-NMR (DMSO-D6) δ: 2.35-2.42 (m, 2H), 3.33-3.54 (m, 3H), 7.00 (s, 1H), 7.10 (s, 1H), 7.24-7.40 (m, 6H), 7.53 (t, 1H, J = 7.9 Hz), 7.64 (s, 1H), 10.90 (s, 1H). | 449 | 447 | R-form |
| 148 | 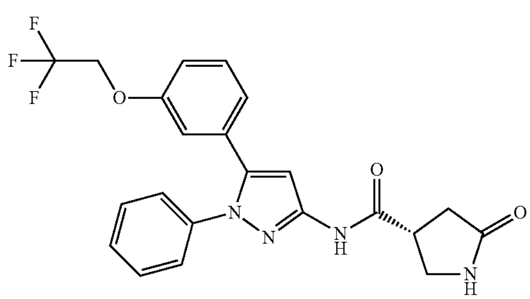 [SMILES: O=C1C[C@@H](C(=O)Nc2cc(-c3cccc(OCC(F)(F)F)c3)n(-c3ccccc3)n2)CN1] | 1H-NMR (DMSO-D6) δ: 2.39 (2H, d, J = 8.6 Hz), 3.30-3.55 (3H, m), 4.73 (2H, q, J = 8.9 Hz), 6.80 (1H, d, J = 7.9 Hz), 6.97 (1H, s), 6.98-7.08 (2H, m), 7.20-7.45 (6H, m), 7.64 (1H, s), 10.87 (1H, s) | 445 | 443 | R-form |
| 149 | 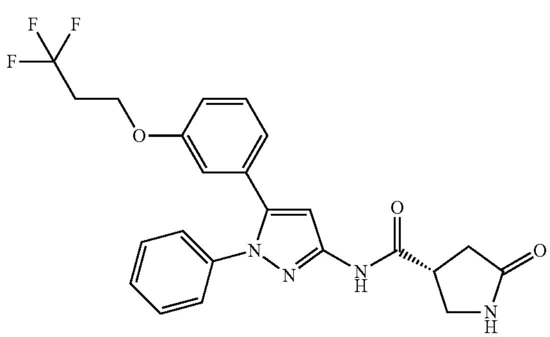 [SMILES: O=C1C[C@@H](C(=O)Nc2cc(-c3cccc(OCCC(F)(F)F)c3)n(-c3ccccc3)n2)CN1] | 1H-NMR (DMSO-D6) δ: 2.39 (2H, d, J = 8.4 Hz), 2.61-2.76 (2H, m), 3.30-3.55 (3H, m), 4.11 (2H, t, J = 5.7 Hz), 6.77-6.84 (2H, m), 6.91-6.98 (2H, m), 7.21-7.44 (6H, m), 7.64 (1H, s), 10.86 (1H, s) | 459 | 457 | R-form |

| Ex. No. | Molecular Structure | NMR | MS (M + H) | MS (M − H) | Comments |
|---|---|---|---|---|---|
| 150 | 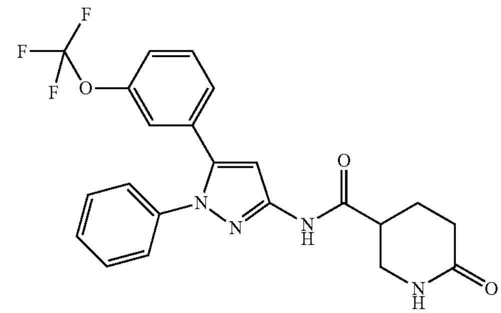 [SMILES: O=C1CCC(C(=O)Nc2cc(-c3cccc(OC(F)(F)F)c3)n(-c3ccccc3)n2)CN1] | 1H-NMR (DMSO-D6) δ: 1.84-1.98 (m, 2H), 2.14-2.29 (m, 2H), 2.81-2.88 (m, 1H), 3.27-3.33 (m, 2H), 6.99 (s, 1H), 7.08 (s, 1H), 7.24-7.26 (m, 2H), 7.34-7.54 (m, 7H), 10.88 (s, 1H). | 445 | 443 | Optically active substance (The same configuration as Example 5) |
| 151 | 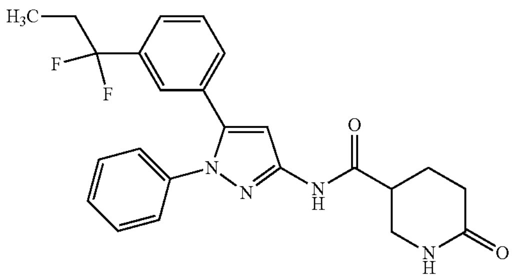 [SMILES: CCC(F)(F)c1cccc(-c2cc(NC(=O)C3CCC(=O)NC3)nn2-c2ccccc2)c1] | 1H-NMR (DMSO-D6) δ: 0.76 (t, 3H, J = 7.4 Hz), 1.88-2.28 (m, 6H), 2.82-2.87 (m, 1H), 3.30-3.32 (m, 2H), 6.98 (s, 1H), 7.22-7.25 (m, 3H), 7.34-7.52 (m, 7H), 10.87 (s, 1H). | 439 | 437 | Optically active substance (The same configuration as Example 5) |
| 152 | 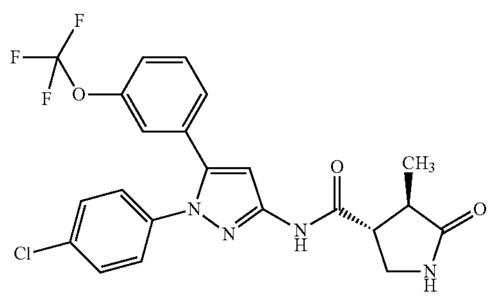 [SMILES: C[C@H]1C(=O)NC[C@@H]1C(=O)Nc1cc(-c2cccc(OC(F)(F)F)c2)n(-c2ccc(Cl)cc2)n1] | 1H-NMR (DMSO-D6) δ: 1.08 (d, 3H, J = 7.2 Hz), 2.54 (dq, 1H, J = 9.6, 7.2 Hz), 3.04 (ddd, 1H, J = 8.6, 9.0, 9.6 Hz), 3.23 (dd, 1H, J = 9.0, 8.4 Hz), 3.44 (dd, 1H, J = 8.6, 8.4 Hz), 7.03 (s, 1H), 7.15 (s, 1H), 7.26-7.29 (m, 2H), 7.34-7.40 (m, 2H), 7.48-7.56 (m, 3H), 7.68 (s, 1H), 11.02 (s, 1H). | 479 | 477 | (3R,4R)-form |
| 153 | 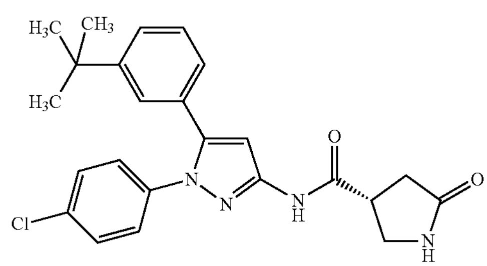 [SMILES: CC(C)(C)c1cccc(-c2cc(NC(=O)[C@H]3CNC(=O)C3)nn2-c2ccc(Cl)cc2)c1] | 1H-NMR (DMSO-D6) δ: 1.13 (s, 9H), 2.38-2.40 (m, 2H), 3.33-3.36 (m, 1H), 3.39-3.45 (m, 1H), 3.49-3.51 (m, 1H), 6.93 (s, 1H), 7.09 (s, 1H), 7.17 (d, 1H, J = 7.4 Hz), 7.25 (d, 2H, J = 8.8 Hz), 7.34 (dd, 1H, J = 7.4, 8.1 Hz), 7.39 (d, 1H, J = 8.1 Hz), 7.48 (d, 2H, J = 8.8 Hz), 7.64 (s, 1H), 10.88 (s, 1H). | 437 | 435 | R-form |
| 154 | 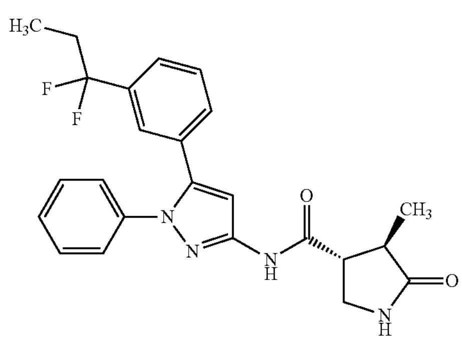 [SMILES: CCC(F)(F)c1cccc(-c2cc(NC(=O)[C@H]3CNC(=O)[C@@H]3C)nn2-c2ccccc2)c1] | 1H-NMR (DMSO-D6) δ: 0.76 (t, 3H, J = 7.5 Hz), 1.09 (d, 3H, J = 7.3 Hz), 2.06 (tq, 2H, J = 16.5, 7.5 Hz), 2.55 (dq, 1H, J = 9.7, 7.3 Hz), 3.04 (ddd, 1H, J = 8.5, 9.1, 9.7 Hz), 3.23 (dd, 1H, J = 8.5, 9.1 Hz), 3.45 (dd, 1H, J = 8.5, 8.5 Hz), 7.02 (s, 1H), 7.22-7.27 (m, 3H), 7.34-7.45 (m, 4H), 7.46-7.53 (m, 2H), 7.68 (s, 1H), 10.98 (s, 1H). | 439 | 437 | (3R,4R)-form |

TABLE 1-continued

| Ex. No. | Molecular Structure | NMR | MS (M + H) | MS (M − H) | Comments |
|---|---|---|---|---|---|
| 155 | 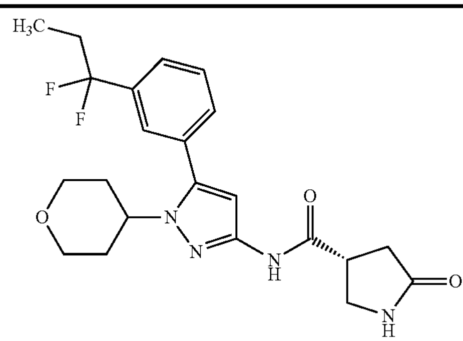 | 1H-NMR (DMSO-D6) δ: 0.94 (t, 3H, J = 7.5 Hz), 1.75-1.85 (m, 2H), 2.00-2.13 (m, 2H), 2.28 (tq, 2H, J = 16.5, 7.5 Hz), 2.33-2.39 (m, 2H), 3.26-3.34 (m, 3H), 3.35-3.44 (m, 1H), 3.45-3.51 (m, 1H), 3.88-3.95 (m, 2H), 4.21-4.31 (m, 1H), 6.65 (s, 1H), 7.53 (s, 1H), 7.57-7.68 (m, 4H), 10.76 (s, 1H). | 433 | 431 | R-form |
| 156 | 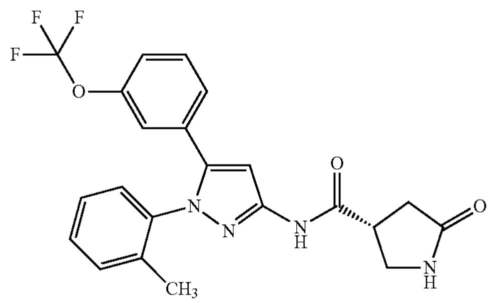 [SMILES: Cc1ccccc1-n1nc(NC(=O)[C@H]2CNC(=O)C2)cc1-c1cccc(OC(F)(F)F)c1] | 1H-NMR (DMSO-D6) δ: 1.91 (3H, s), 2.36-2.43 (2H, m), 3.30-3.55 (3H, m), 6.97 (1H, s), 7.07 (1H, s), 7.25-7.43 (6H, m), 7.47 (1H, t, J = 8.1 Hz), 7.64 (1H, s), 10.82 (1H, s) | 445 | 443 | R-form |
| 157 | 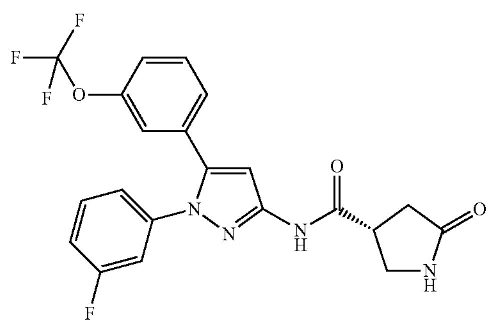 [SMILES: O=C1C[C@@H](C(=O)Nc2cc(-c3cccc(OC(F)(F)F)c3)n(-c3cccc(F)c3)n2)CN1] | 1H-NMR (DMSO-D6) δ: 2.38-2.40 (m, 2H), 3.32-3.35 (m, 1H), 3.38-3.45 (m, 1H), 3.49-3.53 (m, 1H), 7.02 (s, 1H), 7.05-7.07 (m, 1H), 7.13-7.26 (m, 3H), 7.38-7.48 (m, 3H), 7.56 (dd, 1H, J = 8.0, 8.0 Hz), 7.65 (s, 1H), 10.94 (s, 1H). | 449 | 447 | R-form |
| 158 | 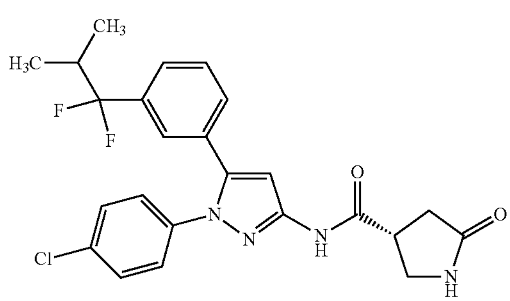 [SMILES: CC(C)C(F)(F)c1cccc(-c2cc(NC(=O)[C@H]3CNC(=O)C3)nn2-c2ccc(Cl)cc2)c1] | 1H-NMR (DMSO-D6) δ: 0.80 (d, 6H, J = 7.0 Hz), 2.23-2.40 (m, 3H), 3.34-3.36 (m, 1H), 3.39-3.45 (m, 1H), 3.48-3.53 (m, 1H), 6.99 (s, 1H), 7.14 (s, 1H), 7.26 (d, 2H, J = 8.6 Hz), 7.46-7.56 (m, 5H), 7.64 (s, 1H), 10.92 (s, 1H). | 473 | 471 | R-form |
| 159 | 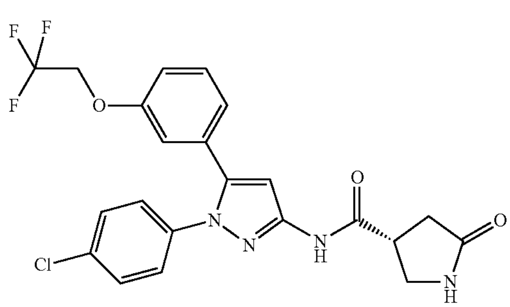 [SMILES: O=C1C[C@@H](C(=O)Nc2cc(-c3cccc(OCC(F)(F)F)c3)n(-c3ccc(Cl)cc3)n2)CN1] | 1H-NMR (DMSO-D6) δ: 2.38-2.40 (m, 2H), 3.33-3.36 (m, 1H), 3.39-3.46 (m, 1H), 3.48-3.52 (m, 1H), 4.76 (q, 2H, J = 8.8 Hz), 6.81 (d, 1H, J = 7.4 Hz), 6.98 (s, 1H), 7.05 (s, 1H), 7.07 (d, 1H, J = 8.0 Hz), 7.25 (d, 2H, J = 8.8 Hz), 7.32 (dd, 1H, J = 7.4, 8.0 Hz), 7.47 (d, 2H, J = 8.8 Hz), 7.64 (s, 1H), 10.90 (s, 1H). | 479 | 477 | R-form |

TABLE 1-continued

| Ex. No. | Molecular Structure | NMR | MS (M + H) | MS (M − H) | Comments |
|---|---|---|---|---|---|
| 160 | 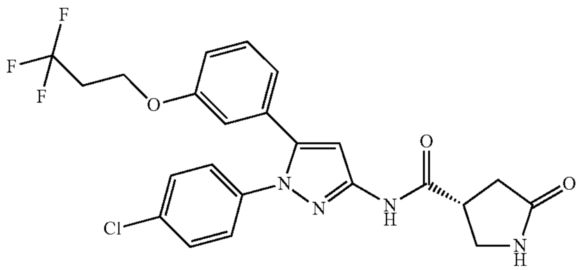 [SMILES: O=C1C[C@@H](C(=O)Nc2cc(-c3cccc(OCCC(F)(F)F)c3)n(-c3ccc(Cl)cc3)n2)CN1] | 1H-NMR (DMSO-D6) δ: 2.37-2.40 (m, 2H), 2.71 (tq, 2H, J = 5.9, 11.0 Hz), 3.32-3.35 (m, 1H), 3.38-3.46 (m, 1H), 3.48-3.52 (m, 1H), 4.15 (t, 2H, J = 5.9 Hz), 6.82 (d, 1H, J = 7.9 Hz), 6.84 (s, 1H), 6.94 (s, 1H), 6.97 (d, 1H, J = 8.4 Hz), 7.26 (d, 2H, J = 8.6 Hz), 7.30 (dd, 1H, J = 7.9, 8.4 Hz), 7.47 (d, 2H, J = 8.6 Hz), 7.64 (s, 1H), 10.89 (s, 1H). | 493 | 491 | R-form |
| 161 | 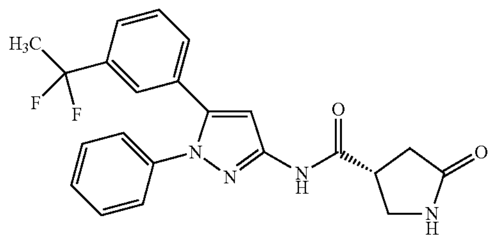 [SMILES: CC(F)(F)c1cccc(-c2cc(NC(=O)[C@H]3CNC(=O)C3)nn2-c2ccccc2)c1] | 1H-NMR (DMSO-D6) δ: 1.84 (t, 3H, J = 18.8 Hz), 2.38-2.40 (m, 2H), 3.33-3.35 (m, 1H), 3.39-3.46 (m, 1H), 3.47-3.53 (m, 1H), 7.00 (s, 1H), 7.23-7.26 (m, 2H), 7.33-7.54 (m, 7H), 7.64 (s, 1H), 10.89 (s, 1H). | 411 | 409 | R-form |
| 162 | 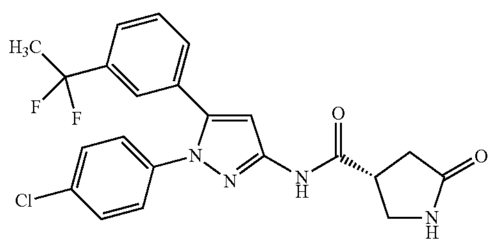 [SMILES: CC(F)(F)c1cccc(-c2cc(NC(=O)[C@H]3CNC(=O)C3)nn2-c2ccc(Cl)cc2)c1] | 1H-NMR (DMSO-D6) δ: 1.89 (t, 3H, J = 19.0 Hz), 2.39 (d, 2H, J = 8.1 Hz), 3.33 (dd, 1H, J = 8.6, 8.6 Hz), 3.42 (ddt, 1H, J = 8.1, 8.6, 8.6 Hz), 3.51 (dd, 1H, J = 8.6, 8.6 Hz), 7.01 (s, 1H), 7.27 (d, 2H, J = 8.6 Hz), 7.36 (d, 1H, J = 7.4 Hz), 7.40 (s, 1H), 7.49 (d, 2H, J = 8.6 Hz), 7.50 (dd, 1H, J = 7.4, 7.7 Hz), 7.56 (d, 1H, J = 7.7 Hz), 7.64 (s, 1H), 10.92 (s, 1H). | 445 | 443 | R-form |
| 163 | 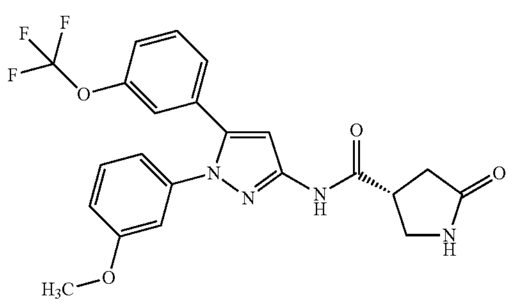 [SMILES: COc1cccc(-n2nc(NC(=O)[C@H]3CNC(=O)C3)cc2-c2cccc(OC(F)(F)F)c2)c1] | 1H-NMR (DMSO-D6) δ: 2.39 (2H, d, J = 8.2 Hz), 3.30-3.55 (3H, m), 3.67 (3H, s), 6.76 (1H, dd, J = 7.6, 1.4 Hz), 6.83 (1H, t, J = 2.2 Hz), 6.94 (1H, dd, J = 8.1, 2.2 Hz), 6.99 (1H, s), 7.13 (1H, s), 7.30 (1H, t, J = 8.1 Hz), 7.34-7.41 (2H, m), 7.54 (1H, t, J = 8.1 Hz), 7.64 (1H, s), 10.92 (1H, s) | 461 | 459 | R-form |
| 164 | 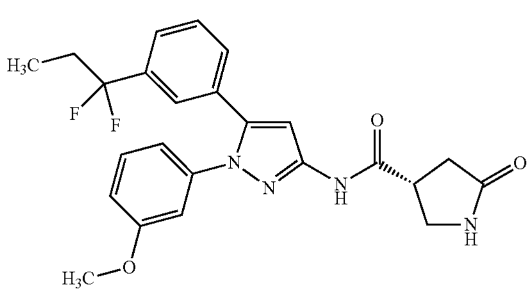 [SMILES: CCC(F)(F)c1cccc(-c2cc(NC(=O)[C@H]3CNC(=O)C3)nn2-c2cccc(OC)c2)c1] | 1H-NMR (DMSO-D6) δ: 0.77 (3H, t, J = 7.4 Hz), 2.08 (2H, m), 2.39 (2H, d, J = 8.4 Hz), 3.30-3.55 (3H, m), 3.66 (3H, s), 6.76 (1H, dd, J = 7.8, 1.2 Hz), 6.81 (1H, t, J = 2.2 Hz), 6.92 (1H, dd, J = 8.2, 2.2 Hz), 6.98 (1H, s), 7.24-7.32 (2H, m), 7.41-7.56 (3H, m), 7.64 (1H, s), 10.91 (1H, s) | 455 | 453 | R-form |

TABLE 1-continued

| Ex. No. | Molecular Structure | NMR | MS (M + H) | MS (M − H) | Comments |
|---|---|---|---|---|---|
| 165 | 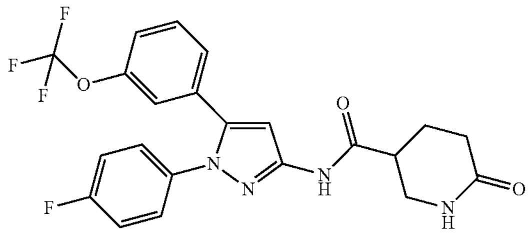 [SMILES: O=C1CCC(C(=O)Nc2cc(-c3cccc(OC(F)(F)F)c3)n(-c3ccc(F)cc3)n2)CN1] | 1H-NMR (DMSO-D6) δ: 1.86-1.99 (m, 2H), 2.13-2.28 (m, 2H), 2.80-2.88 (m, 1H), 3.28-3.31 (m, 2H), 6.99 (s, 1H), 7.10 (s, 1H), 7.25-7.37 (m, 6H), 7.51-7.54 (m, 2H), 10.87 (s, 1H). | 463 | 461 | Optically active substance (The same configuration as Example 5) |
| 166 | 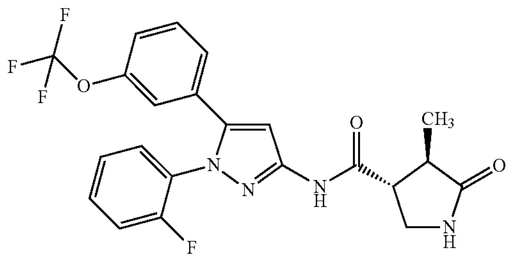 [SMILES: C[C@H]1C(=O)NC[C@@H]1C(=O)Nc1cc(-c2cccc(OC(F)(F)F)c2)n(-c2ccccc2F)n1] | 1H-NMR (DMSO-D6) δ: 1.09 (d, 3H, J = 7.0 Hz), 2.55 (dq, 1H, J = 9.3, 7.0 Hz), 3.03 (ddd, 1H, J = 9.1, 9.2, 9.3 Hz), 3.23 (dd, 1H, J = 9.2, 8.8 Hz), 3.45 (dd, 1H, J = 9.1, 8.8 Hz), 7.08 (s, 1H), 7.09 (s, 1H), 7.31-7.37 (m, 4H), 7.49-7.62 (m, 3H), 7.68 (s, 1H), 10.99 (s, 1H). | 463 | 461 | (3R,4R)-form |
| 167 | 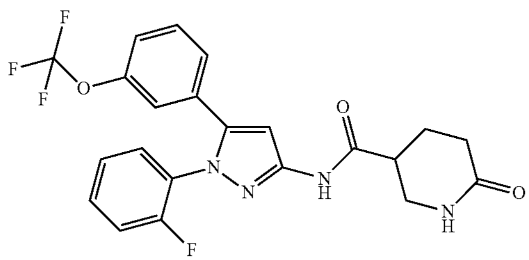 [SMILES: O=C1CCC(C(=O)Nc2cc(-c3cccc(OC(F)(F)F)c3)n(-c3ccccc3F)n2)CN1] | 1H-NMR (DMSO-D6) δ: 1.87-1.99 (m, 2H), 2.19-2.24 (m, 2H), 2.83-2.85 (m, 1H), 3.27-3.32 (m, 2H), 7.06-7.07 (m, 2H), 7.31-7.38 (m, 4H), 7.50-7.59 (m, 4H), 10.88 (s, 1H). | 463 | 461 | Optically active substance (The same configuration as Example 5) |
| 168 | 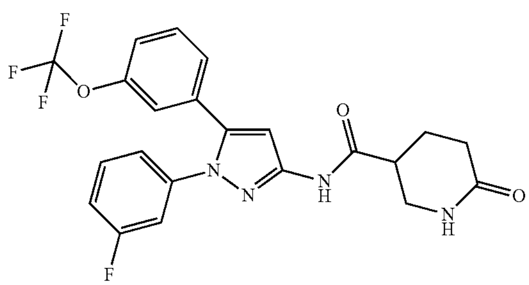 [SMILES: O=C1CCC(C(=O)Nc2cc(-c3cccc(OC(F)(F)F)c3)n(-c3cccc(F)c3)n2)CN1] | 1H-NMR (DMSO-D6) δ: 1.88-1.98 (m, 2H), 2.13-2.33 (m, 2H), 2.83-2.86 (m, 1H), 3.28-3.32 (m, 2H), 7.01 (s, 1H), 7.04-7.06 (m, 1H), 7.14-7.26 (m, 3H), 7.39-7.58 (m, 5H), 10.92 (s, 1H). | 463 | 461 | Optically active substance (The same configuration as Example 5) |
| 169 | 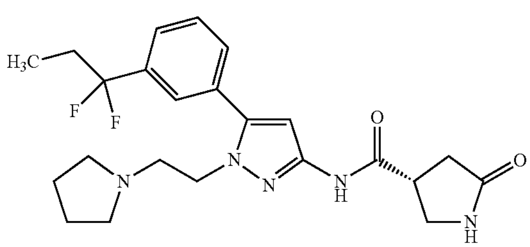 [SMILES: CCC(F)(F)c1cccc(-c2cc(NC(=O)[C@H]3CNC(=O)C3)nn2CCN2CCCC2)c1] | 1H-NMR (DMSO-D6) δ: 0.93 (t, 3H, J = 7.4 Hz), 1.55-1.57 (m, 4H), 2.23-2.36 (m, 8H), 2.77 (t, 2H, J = 6.4 Hz), 3.28-3.32 (m, 1H), 3.36-3.42 (m, 1H), 3.47-3.49 (m, 1H), 4.07 (t, 2H, J = 6.4 Hz), 6.65 (s, 1H), 7.61-7.66 (m, 5H), 10.71 (s, 1H). | 446 | 444 | R-form |
| 170 | 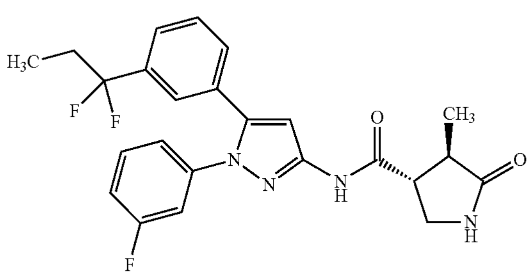 [SMILES: CCC(F)(F)c1cccc(-c2cc(NC(=O)[C@H]3CNC(=O)[C@@H]3C)nn2-c2cccc(F)c2)c1] | 1H-NMR (DMSO-D6) δ: 0.78 (t, 3H, J = 7.4 Hz), 1.09 (d, 3H, J = 7.3 Hz), 2.10 (tq, 2H, J = 16.4, 7.4 Hz), 2.54 (dq, 2H, J = 9.3, 7.3 Hz), 3.04 (ddd, 1H, J = 8.7, 8.8, 9.3 Hz), 3.23 (dd, 1H, J = 8.7, 8.8 Hz), 3.45 (dd, 1H, J = 8.7, 8.7 Hz), 7.03-7.28 (m, 5H), 7.41-7.53 (m, 4H), 7.68 (s, 1H), 11.01 (s, 1H). | 457 | 455 | (3R,4R)-form |

TABLE 1-continued

| Ex. No. | Molecular Structure | NMR | MS (M + H) | MS (M − H) | Comments |
|---|---|---|---|---|---|
| 171 | 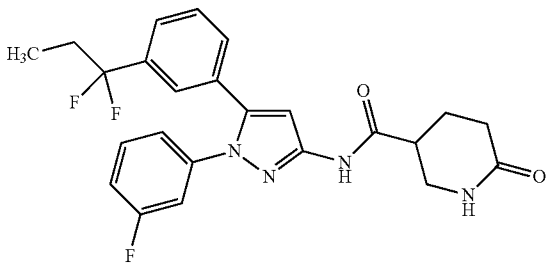 [SMILES: CCC(F)(F)c1cccc(-c2cc(NC(=O)C3CCC(=O)NC3)nn2-c2cccc(F)c2)c1] | 1H-NMR (DMSO-D6) δ: 0.77 (t, 3H, J = 7.4 Hz), 1.90-2.23 (m, 6H), 2.83-2.86 (m, 1H), 3.28-3.31 (m, 2H), 6.99 (s, 1H), 7.04-7.24 (m, 3H), 7.27 (s, 1H), 7.41-7.56 (m, 5H), 10.90 (s, 1H). | 457 | 455 | Optically active substance (The same configuration as Example 5) |
| 172 | 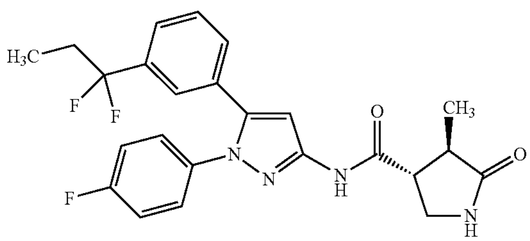 [SMILES: CCC(F)(F)c1cccc(-c2cc(NC(=O)[C@H]3CNC(=O)[C@@H]3C)nn2-c2ccc(F)cc2)c1] | 1H-NMR (DMSO-D6) δ: 0.77 (t, 3H, J = 7.4 Hz), 1.08 (d, 3H, J = 7.3 Hz), 2.09 (tq, 2H, J = 16.5, 7.4 Hz), 2.54 (dq, 1H, J = 9.3, 7.4 Hz), 3.04 (ddd, 1H, J = 9.3, 8.8, 8.4 Hz), 3.23 (dd, 1H, J = 8.8, 8.6 Hz), 3.45 (dd, 1H, J = 8.6, 8.4 Hz), 7.02 (s, 1H), 7.24-7.32 (m, 5H), 7.41-7.53 (m, 3H), 7.68 (s, 1H), 10.97 (s, 1H). | 457 | 455 | (3R,4R)-form |
| 173 | 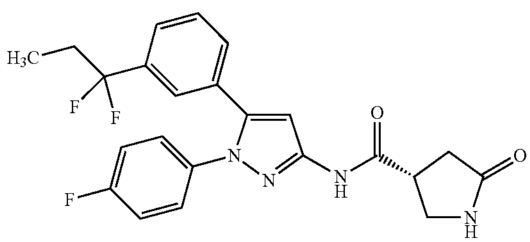 [SMILES: CCC(F)(F)c1cccc(-c2cc(NC(=O)[C@H]3CNC(=O)C3)nn2-c2ccc(F)cc2)c1] | 1H-NMR (DMSO-D6) δ: 0.77 (t, 3H, J = 7.5 Hz), 2.09 (tq, 2H, J = 16.5, 7.5 Hz), 2.38-2.40 (m, 2H), 3.34-3.35 (m, 1H), 3.38-3.46 (m, 1H), 3.50-3.52 (m, 1H), 6.99 (s, 1H), 7.23-7.32 (m, 5H), 7.42-7.54 (m, 3H), 7.65 (s, 1H), 10.89 (s, 1H). | 443 | 441 | R-form |
| 174 | 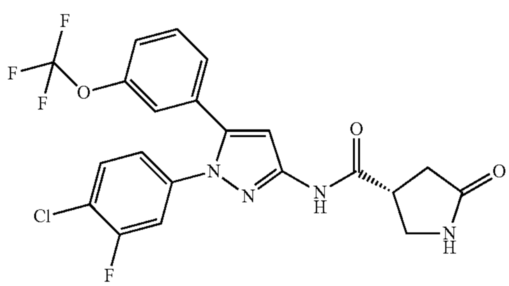 [SMILES: O=C1C[C@@H](C(=O)Nc2cc(-c3cccc(OC(F)(F)F)c3)n(-c3ccc(Cl)c(F)c3)n2)CN1] | 1H-NMR (DMSO-D6) δ: 2.31-2.33 (m, 2H), 3.23-3.28 (m, 1H), 3.36-3.38 (m, 1H), 3.43-3.45 (m, 1H), 6.56 (s, 1H), 7.18 (s, 1H), 7.25-7.30 (m, 2H), 7.39-7.41 (m, 1H), 7.48-7.55 (m, 2H), 7.60 (s, 1H), 7.82 (dd, 1H, J = 8.4, 8.4 Hz), 10.71 (s, 1H). | 483 | 481 | R-form |
| 175 | 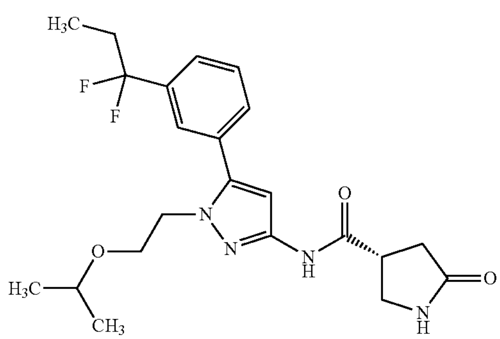 [SMILES: CCC(F)(F)c1cccc(-c2cc(NC(=O)[C@H]3CNC(=O)C3)nn2CCOC(C)C)c1] | 1H-NMR (DMSO-D6) δ: 0.93 (t, 3H, J = 7.5 Hz), 0.99 (d, 6H, J = 6.0 Hz), 2.26 (tq, 2H, J = 16.5, 7.5 Hz), 2.34-2.39 (m, 2H), 3.28-3.33 (m, 1H), 3.34-3.51 (m, 3H), 3.75 (t, 2H, J = 5.2 Hz), 4.07 (t, 2H, J = 5.2 Hz), 6.65 (s, 1H), 7.57-7.64 (m, 3H), 7.68 (d, 1H, J = 6.9 Hz), 7.77 (s, 1H), 10.72 (s, 1H). | 435 | 433 | R-form |

| Ex. No. | Molecular Structure | NMR | MS (M + H) | MS (M − H) | Comments |
|---|---|---|---|---|---|
| 176 | 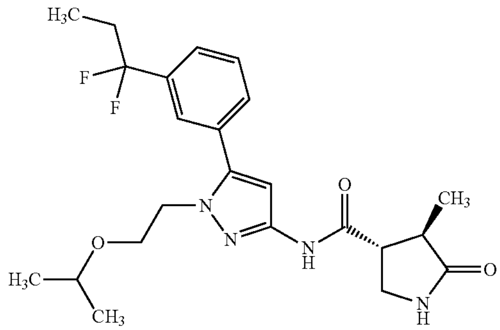 [SMILES: CCC(F)(F)c1cccc(-c2cc(NC(=O)[C@H]3CNC(=O)[C@@H]3C)nn2CCOC(C)C)c1] | 1H-NMR (DMSO-D6) δ: 0.93 (t, 3H, J = 7.5 Hz), 0.99 (d, 6H, J = 6.0 Hz), 1.07 (d, 3H, J = 6.9 Hz), 2.26 (tq, 2H, J = 16.5, 7.5 Hz), 2.51 (dq, 1H, J = 6.9, 9.7 Hz), 3.01 (ddd, 1H, J = 8.3, 8.9, 9.7 Hz), 3.20 (dd, 1H, J = 8.9, 8.9 Hz), 3.42 (dd, 1H, J = 8.3, 8.3 Hz), 3.44 (sep, 1H, J = 6.0 Hz), 3.75 (t, 2H, J = 5.2 Hz), 4.08 (t, 2H, J = 5.2 Hz), 6.68 (s, 1H), 7.57-7.71 (m, 4H), 7.77 (s, 1H), 10.80 (s, 1H). | 449 | 447 | (3R,4R)-form |
| 177 | 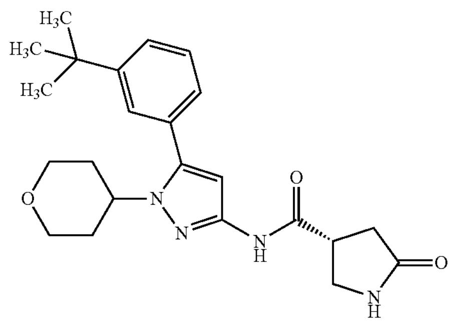 [SMILES: CC(C)(C)c1cccc(-c2cc(NC(=O)[C@H]3CNC(=O)C3)nn2C2CCOCC2)c1] | 1H-NMR (DMSO-D6) δ: 1.32 (s, 9H), 1.76-1.85 (m, 2H), 2.03-2.15 (m, 2H), 2.30-2.41 (m, 2H), 3.26-3.35 (m, 3H), 3.35-3.44 (m, 1H), 3.44-3.51 (m, 1H), 3.89-3.96 (m, 2H), 4.24-4.34 (m, 1H), 6.59 (s, 1H), 7.26 (ddd, 1H, J = 7.7, 1.3, 1.0 Hz), 7.40 (dd, 1H, J = 1.6, 1.3 Hz), 7.45 (dd, 1H, J = 7.7, 7.7 Hz), 7.51 (ddd, 1H, J = 7.7, 1.6, 1.0 Hz), 7.62 (s, 1H), 10.72 (s, 1H). | 411 | 409 | R-form |
| 178 | 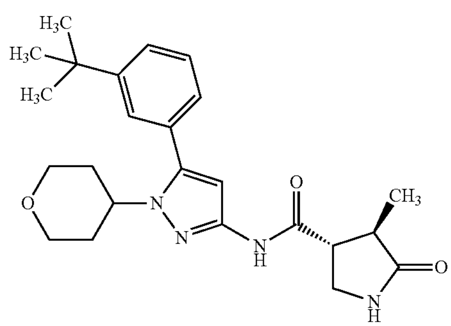 [SMILES: C[C@H]1C(=O)NC[C@@H]1C(=O)Nc1cc(-c2cccc(C(C)(C)C)c2)n(C2CCOCC2)n1] | 1H-NMR (DMSO-D6) δ: 1.06 (d, 3H, J = 6.9 Hz), 1.33 (s, 9H), 1.76-1.85 (m, 2H), 2.02-2.16 (m, 2H), 2.52 (dq, 1H, J = 9.7, 6.9 Hz), 3.01 (ddd, 1H, J = 8.5, 9.1, 9.7 Hz), 3.18 (dd, 1H, J = 9.1, 9.1 Hz), 3.26-3.35 (m, 2H), 3.41 (dd, 1H, J = 8.5, 8.5 Hz), 3.88-3.97 (m, 2H), 4.24-4.35 (m, 1H), 6.61 (s, 1H), 7.27 (ddd, 1H, J = 7.7, 1.6, 1.0 Hz), 7.40 (dd, 1H, J = 1.6, 1.6 Hz), 7.45 (dd, 1H, J = 7.7, 7.7 Hz), 7.51 (ddd, 1H, J = 7.7, 1.6, 1.0 Hz), 7.65 (s, 1H), 10.81 (s, 1H). | 425 | 423 | (3R,4R)-form |
| 179 | 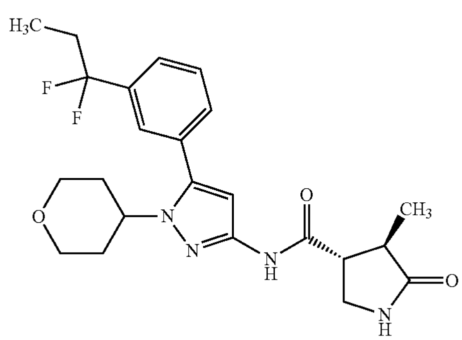 [SMILES: CCC(F)(F)c1cccc(-c2cc(NC(=O)[C@H]3CNC(=O)[C@@H]3C)nn2C2CCOCC2)c1] | 1H-NMR (DMSO-D6) δ: 0.94 (t, 3H, J = 7.5 Hz), 1.06 (d, 3H, J = 7.3 Hz), 1.75-1.85 (m, 2H), 2.01-2.14 (m, 2H), 2.28 (tq, 2H, J = 16.5, 7.5 Hz), 2.52 (dq, 1H, J = 9.7, 7.3 Hz), 3.02 (ddd, 1H, J = 8.5, 8.9, 9.7 Hz), 3.18 (dd, 1H, J = 8.9, 8.9 Hz), 3.25-3.35 (m, 2H), 3.42 (dd, 1H, J = 8.5, 8.5 Hz), 3.87-3.97 (m, 2H), 4.21-4.32 (m, 1H), 6.68 (s, 1H), 7.54 (s, 1H), 7.58-7.69 (m, 4H), 10.85 (s, 1H). | 447 | 445 | (3R,4R)-form |

TABLE 1-continued

| Ex. No. | Molecular Structure | NMR | MS (M + H) | MS (M − H) | Comments |
|---|---|---|---|---|---|
| 180 | 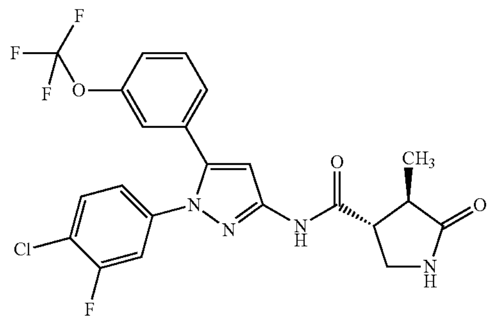 [SMILES: C[C@H]1C(=O)NC[C@@H]1C(=O)Nc1cc(-c2cccc(OC(F)(F)F)c2)n(-c2ccc(Cl)c(F)c2)n1] | 1H-NMR (DMSO-D6) δ: 1.03 (d, 3H, J = 7.0 Hz), 2.46 (dq, 1H, J = 9.3, 7.0 Hz), 2.97 (ddd, 1H, J = 9.7, 9.3, 8.7 Hz), 3.15 (dd, 1H, J = 8.3, 8.7 Hz), 3.38 (dd, 1H, J = 8.3, 9.7 Hz), 6.59 (s, 1H), 7.17 (s, 1H), 7.27-7.32 (m, 2H), 7.40 (d, 1H, J = 8.1 Hz), 7.49-7.57 (m, 2H), 7.64 (s, 1H), 7.83 (dd, 1H, J = 8.8, 8.1 Hz), 10.79 (s, 1H). | 497 | 495 | (3R,4R)-form |
| 181 | 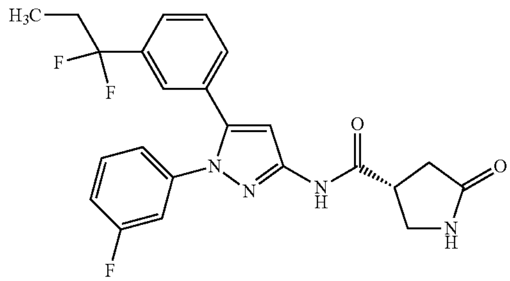 [SMILES: CCC(F)(F)c1cccc(-c2cc(NC(=O)[C@H]3CNC(=O)C3)nn2-c2cccc(F)c2)c1] | 1H-NMR (DMSO-D6) δ: 0.78 (t, 3H, J = 7.4 Hz), 2.10 (tq, 2H, J = 16.4, 7.4 Hz), 2.38-2.40 (m, 2H), 3.33-3.35 (m, 1H), 3.39-3.47 (m, 1H), 3.50-3.52 (m, 1H), 7.01 (s, 1H), 7.04-7.24 (m, 3H), 7.27 (s, 1H), 7.41-7.54 (m, 4H), 7.64 (s, 1H), 10.93 (s, 1H). | 443 | 441 | R-form |
| 182 | 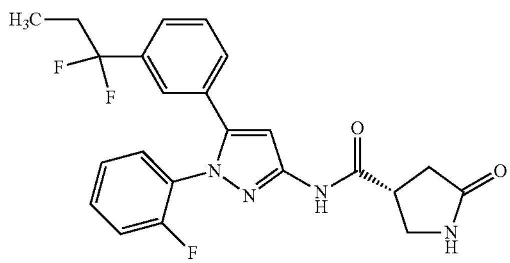 [SMILES: CCC(F)(F)c1cccc(-c2cc(NC(=O)[C@H]3CNC(=O)C3)nn2-c2ccccc2F)c1] | 1H-NMR (DMSO-D6) δ: 0.71 (t, 3H, J = 7.4 Hz), 2.02 (tq, 2H, J = 15.7, 7.4 Hz), 2.37-2.39 (m, 2H), 3.33-3.34 (m, 1H), 3.37-3.45 (m, 1H), 3.48-3.50 (m, 1H), 7.04 (s, 1H), 7.19 (s, 1H), 7.29-7.34 (m, 2H), 7.42-7.63 (m, 6H), 10.86 (s, 1H). | 443 | 441 | R-form |
| 183 | 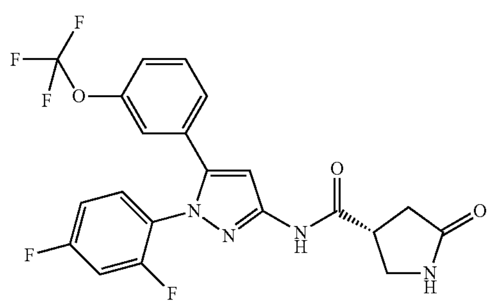 [SMILES: O=C1C[C@@H](C(=O)Nc2cc(-c3cccc(OC(F)(F)F)c3)n(-c3ccc(F)cc3F)n2)CN1] | 1H-NMR (DMSO-D6) δ: 2.37-2.39 (m, 2H), 3.33-3.36 (m, 1H), 3.40-3.44 (m, 1H), 3.47-3.51 (m, 1H), 6.84 (s, 1H), 7.41-7.43 (m, 1H), 7.51-7.53 (m, 1H), 7.60-7.63 (m, 3H), 7.69 (dd, 1H, J = 8.1, 8.1 Hz), 7.79-7.82 (m, 1H), 8.12-8.13 (m, 1H), 10.91 (s, 1H). | 467 | 465 | R-form |
| 184 | 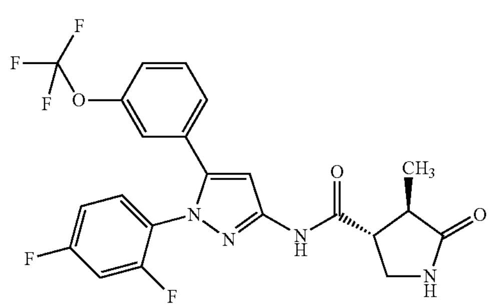 [SMILES: C[C@H]1C(=O)NC[C@@H]1C(=O)Nc1cc(-c2cccc(OC(F)(F)F)c2)n(-c2ccc(F)cc2F)n1] | 1H-NMR (DMSO-D6) δ: 1.08 (d, 3H, J = 7.2 Hz), 2.54 (dq, 1H, J = 9.3, 7.2 Hz), 3.03 (ddd, 1H, J = 8.5, 9.0, 9.3 Hz), 3.22 (dd, 1H, J = 8.5, 9.0 Hz), 3.44 (dd, 1H, J = 8.5, 9.0 Hz), 6.86 (s, 1H), 7.41-7.43 (m, 1H), 7.51-7.53 (m, 1H), 7.60-7.61 (m, 2H), 7.65-7.71 (m, 2H), 7.78-7.83 (m, 1H), 8.12-8.15 (m, 1H), 10.99 (s, 1H). | 481 | 479 | (3R,4R)-form |

TABLE 1-continued

| Ex. No. | Molecular Structure | NMR | MS (M + H) | MS (M − H) | Comments |
|---|---|---|---|---|---|
| 185 | 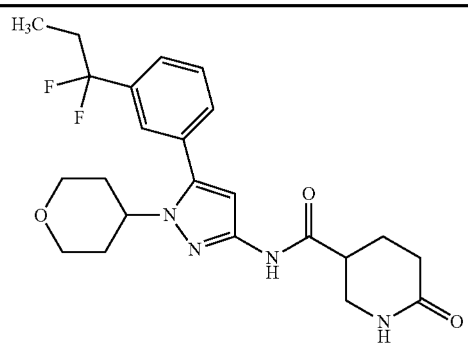 | 1H-NMR (DMSO-D6) δ: 0.94 (t, 3H, J = 7.5 Hz), 1.75-1.99 (m, 4H), 2.01-2.35 (m, 4H), 2.28 (tq, 2H, J = 16.5, 7.5 Hz), 2.76-2.86 (m, 1H), 3.23-3.35 (m, 4H), 3.87-3.96 (m, 2H), 4.21-4.31 (m, 1H), 6.64 (s, 1H), 7.48 (s, 1H), 7.53 (s, 1H), 7.57-7.68 (m, 3H), 10.74 (s, 1H). | 447 | 445 | Optically active substance (The same configuration as Example 5) |
| 186 | 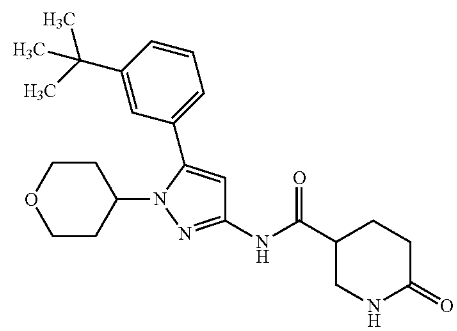 [SMILES: CC(C)(C)c1cccc(-c2cc(NC(=O)C3CCC(=O)NC3)nn2C2CCOCC2)c1] | 1H-NMR (DMSO-D6) δ: 1.32 (s, 9H), 1.75-1.99 (m, 4H), 2.02-2.28 (m, 4H), 2.76-2.85 (m, 1H), 3.22-3.36 (m, 4H), 3.89-3.97 (m, 2H), 4.24-4.33 (m, 1H), 6.57 (s, 1H), 7.26 (ddd, 1H, J = 7.7, 1.3, 1.4 Hz), 7.39 (dd, 1H, J = 1.5, 1.4 Hz), 7.45 (dd, 1H, J = 7.7, 7.7 Hz), 7.48 (s, 1H), 7.51 (ddd, 1H, J = 7.7, 1.5, 1.3 Hz), 10.71 (s, 1H). | 425 | 423 | Optically active substance (The same configuration as Example 5) |
| 187 | 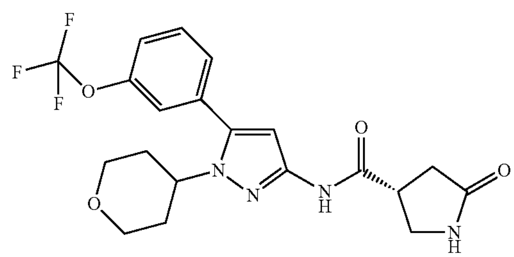 [SMILES: O=C1C[C@@H](C(=O)Nc2cc(-c3cccc(OC(F)(F)F)c3)n(C3CCOCC3)n2)CN1] | 1H-NMR (DMSO-D6) δ: 1.79-1.82 (m, 2H), 2.01-2.10 (m, 2H), 2.35 (d, 1H, J = 8.6 Hz), 2.36 (d, 1H, J = 7.9 Hz), 3.30-3.49 (m, 3H), 3.90-3.93 (m, 2H), 4.25-4.30 (m, 1H), 6.65 (s, 1H), 7.46 (s, 1H), 7.48-7.52 (m, 2H), 7.62 (s, 1H), 7.67 (dd, 1H, J = 8.0, 8.0 Hz), 10.77 (s, 1H). | 439 | 437 | R-form |
| 188 | 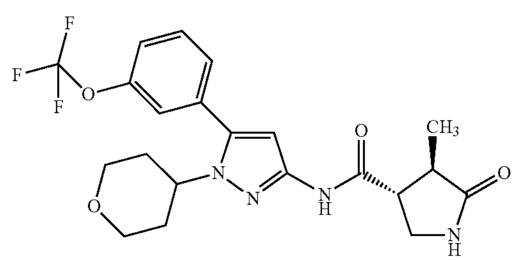 [SMILES: C[C@H]1C(=O)NC[C@@H]1C(=O)Nc1cc(-c2cccc(OC(F)(F)F)c2)n(C2CCOCC2)n1] | 1H-NMR (DMSO-D6) δ: 1.06 (d, 3H, J = 7.1 Hz), 1.78-1.84 (m, 2H), 2.01-2.10 (m, 2H), 2.53 (dq, 1H, J = 9.3, 7.1 Hz), 3.01 (ddd, 1H, J = 8.6, 9.3, 9.4 Hz), 3.18 (dd, 1H, J = 9.4, 8.5 Hz), 3.28-3.34 (m, 2H), 3.41 (dd, 1H, J = 8.6, 8.5 Hz), 3.90-3.93 (m, 2H), 4.25-4.30 (m, 1H), 6.68 (s, 1H), 7.46-7.53 (m, 3H), 7.65-7.69 (m, 2H), 10.85 (s, 1H). | 453 | 451 | (3R,4R)-form |
| 189 | 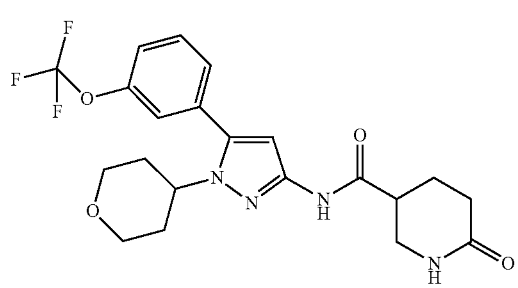 [SMILES: O=C1CCC(C(=O)Nc2cc(-c3cccc(OC(F)(F)F)c3)n(C3CCOCC3)n2)CN1] | 1H-NMR (DMSO-D6) δ: 1.79-2.27 (m, 8H), 2.79-2.83 (m, 1H), 3.23-3.36 (m, 4H), 3.90-3.93 (m, 2H), 4.26-4.29 (m, 1H), 6.64 (s, 1H), 7.45-7.52 (m, 4H), 7.66 (dd, 1H, J = 7.9, 7.9 Hz), 10.75 (s, 1H). | 453 | 451 | Optically active substance (The same configuration as Example 5) |

TABLE 1-continued

| Ex. No. | Molecular Structure | NMR | MS (M + H) | MS (M − H) | Comments |
|---|---|---|---|---|---|
| 190 | 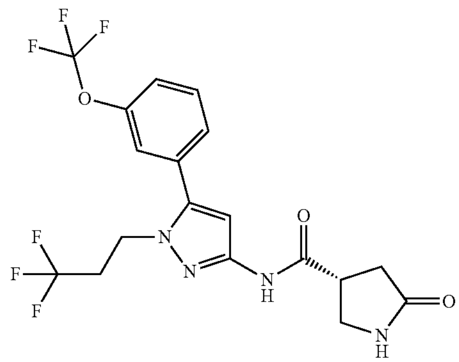 [SMILES: O=C1C[C@@H](C(=O)Nc2cc(-c3cccc(OC(F)(F)F)c3)n(CCC(F)(F)F)n2)CN1] | 1H-NMR (DMSO-D6) δ: 2.36 (d, 2H, J = 8.5 Hz), 2.82 (tq, 2H, J = 6.9, 11.3 Hz), 3.30 (dd, 1H, J = 8.5, 5.6 Hz), 3.39 (ddt, 1H, J = 8.5, 5.6, 8.5 Hz), 3.48 (dd, 1H, J = 8.5, 8.5 Hz), 4.25 (t, 2H, J = 6.9 Hz), 6.70 (s, 1H), 7.50 (ddd, 1H, J = 7.5, 1.3, 1.3 Hz), 7.51 (dd, 1H, J = 1.3, 1.3 Hz), 7.54 (ddd, 1H, J = 7.5, 1.3, 1.3 Hz), 7.63 (s, 1H), 7.67 (dd, 1H, J = 7.5, 7.5 Hz), 10.76 (s, 1H). | 451 | 449 | R-form |
| 191 | 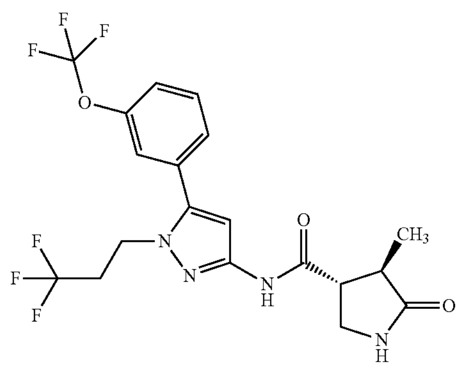 [SMILES: C[C@H]1C(=O)NC[C@@H]1C(=O)Nc1cc(-c2cccc(OC(F)(F)F)c2)n(CCC(F)(F)F)n1] | 1H-NMR (DMSO-D6) δ: 1.06 (d, 3H, J = 7.3 Hz), 2.52 (dq, 1H, J = 9.7, 7.3 Hz), 2.83 (tq, 2H, J = 6.9, 11.3 Hz), 3.01 (ddd, 1H, J = 8.3, 8.9, 9.7 Hz), 3.20 (dd, 1H, J = 8.9, 8.9 Hz), 3.42 (dd, 1H, J = 8.3, 8.3 Hz), 4.25 (t, 2H, J = 6.9 Hz), 6.72 (s, 1H), 7.51 (ddd, 1H, J = 7.7, 1.3, 1.3 Hz), 7.52 (dd, 1H, J = 1.3, 1.3 Hz), 7.54 (ddd, 1H, J = 7.7, 1.3, 1.3 Hz), 7.66 (s, 1H), 7.67 (dd, 1H, J = 7.7, 7.7 Hz), 10.84 (s, 1H). | 465 | 463 | (3R,4R)-form |
| 192 | 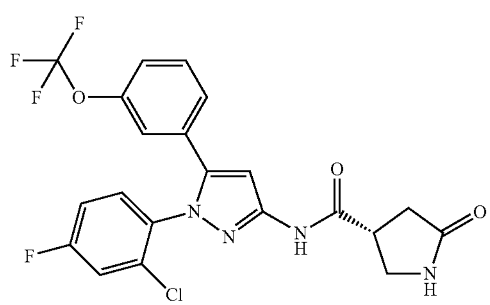 [SMILES: O=C1C[C@@H](C(=O)Nc2cc(-c3cccc(OC(F)(F)F)c3)n(-c3ccc(F)cc3Cl)n2)CN1] | 1H-NMR (DMSO-D6) δ: 2.37 (d, 1H, J = 8.6 Hz), 2.38 (d, 1H, J = 7.7 Hz), 3.32 (dd, 1H, J = 6.5, 8.5 Hz), 3.41 (dddd, 1H, J = 6.5, 7.7, 8.5, 8.6 Hz), 3.49 (dd, 1H, J = 8.5, 8.5 Hz), 6.80 (s, 1H), 7.47-7.57 (m, 4H), 7.63 (s, 1H), 7.66-7.71 (m, 2H), 8.01 (s, 1H), 10.82 (s, 1H). | 483 | 481 | R-form |
| 193 | 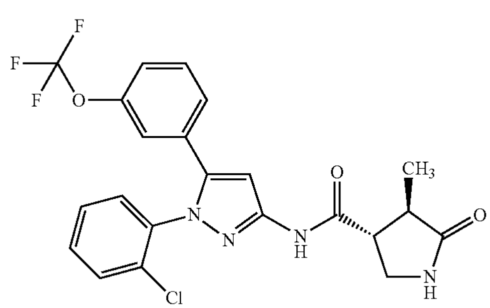 [SMILES: C[C@H]1C(=O)NC[C@@H]1C(=O)Nc1cc(-c2cccc(OC(F)(F)F)c2)n(-c2ccccc2Cl)n1] | 1H-NMR (DMSO-D6) δ: 1.09 (d, 3H, J = 7.2 Hz), 2.56 (dq, 1H, J = 9.3, 7.2 Hz), 3.03 (ddd, 1H, J = 9.0, 9.3, 9.3 Hz), 3.23 (dd, 1H, J = 8.4, 9.0 Hz), 3.45 (dd, 1H, J = 8.4, 9.3 Hz), 7.02 (s, 1H), 7.11 (s, 1H), 7.31-7.35 (m, 2H), 7.47-7.56 (m, 3H), 7.60-7.65 (m, 2H), 7.68 (s, 1H), 10.96 (s, 1H). | 479 | 477 | (3R,4R)-form |

| Ex. No. | Molecular Structure | NMR | MS (M + H) | MS (M − H) | Comments |
|---|---|---|---|---|---|
| 194 | 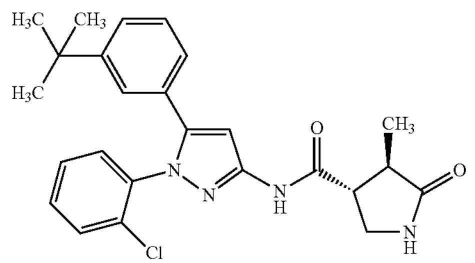 [SMILES: C[C@H]1C(=O)NC[C@@H]1C(=O)Nc1cc(-c2cccc(C(C)(C)C)c2)n(-c2ccccc2Cl)n1] | 1H-NMR (DMSO-D6) δ: 1.06 (s, 9H), 1.09 (d, 3H, J = 7.2 Hz), 2.56 (dq, 1H, J = 9.3, 7.2 Hz), 3.03 (ddd, 1H, J = 9.0, 9.2, 9.3 Hz), 3.23 (dd, 1H, J = 8.5, 9.2 Hz), 3.45 (dd, 1H, J = 8.5, 9.0 Hz), 7.01 (s, 1H), 7.01-7.02 (m, 1H), 7.19-7.21 (m, 1H), 7.27-7.33 (m, 2H), 7.45-7.56 (m, 3H), 7.61-7.63 (m, 1H), 7.67 (s, 1H), 10.90 (s, 1H). | 451 | 449 | (3R,4R)-form |
| 195 | 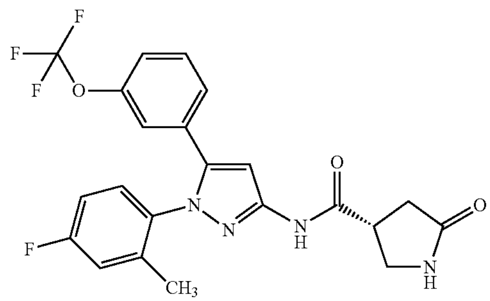 [SMILES: Cc1cc(F)ccc1-n1nc(NC(=O)[C@H]2CNC(=O)C2)cc1-c1cccc(OC(F)(F)F)c1] | 1H-NMR (DMSO-D6) δ: 1.91 (s, 3H), 2.39 (d, 1H, J = 8.6 Hz), 2.39 (d, 1H, J = 8.3 Hz), 3.34 (dd, 1H, J = 8.5, 6.5 Hz), 3.42 (dddd, 1H, J = 6.5, 8.3, 8.5, 8.6 Hz), 3.50 (dd, 1H, J = 8.5, 8.5 Hz), 7.00 (s, 1H), 7.06 (s, 1H), 7.14 (td, 1H, J = 8.5, 2.9 Hz), 7.24 (dd, 1H, J = 9.7, 2.9 Hz), 7.30-7.33 (m, 2H), 7.37 (dd, 1H, J = 8.7, 5.5 Hz), 7.49 (dd, 1H, J = 8.7, 8.0 Hz), 7.64 (s, 1H), 10.83 (s, 1H). | 463 | 461 | R-form |
| 196 | 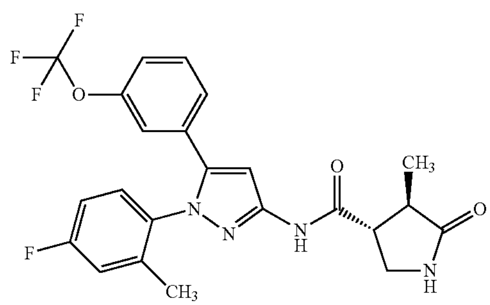 [SMILES: Cc1cc(F)ccc1-n1nc(NC(=O)[C@H]2CNC(=O)[C@@H]2C)cc1-c1cccc(OC(F)(F)F)c1] | 1H-NMR (DMSO-D6) δ: 1.08 (d, 3H, J = 7.2 Hz), 1.91 (s, 3H), 2.55 (dq, 1H, J = 9.2, 7.2 Hz), 3.03 (ddd, 1H, J = 8.5, 9.1, 9.2 Hz), 3.23 (dd, 1H, J = 8.7, 9.1 Hz), 3.45 (dd, 1H, J = 8.5, 8.7 Hz), 7.01 (s, 1H), 7.09 (s, 1H), 7.15 (dt, 1H, J = 2.8, 8.0 Hz), 7.24 (dd, 1H, J = 9.7, 2.8 Hz), 7.31-7.34 (m, 2H), 7.38 (dd, 1H, J = 8.0, 9.7 Hz), 7.49 (t, 1H, J = 8.0 Hz), 7.68 (s, 1H), 10.92 (s, 1H). | 477 | 475 | (3R,4R)-form |
| 197 | 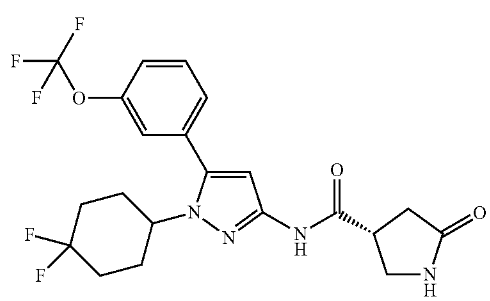 [SMILES: O=C1C[C@@H](C(=O)Nc2cc(-c3cccc(OC(F)(F)F)c3)n(C3CCC(F)(F)CC3)n2)CN1] | 1H-NMR (DMSO-D6) δ: 1.93-2.13 (m, 8H), 2.34-2.36 (m, 2H), 3.27-3.49 (m, 3H), 4.28-4.33 (m, 1H), 6.65 (s, 1H), 7.45 (s, 1H), 7.48-7.52 (m, 2H), 7.61 (s, 1H), 7.67 (dd, 1H, J = 7.9, 7.9 Hz), 10.77 (s, 1H). | 473 | 471 | R-form |
| 198 | 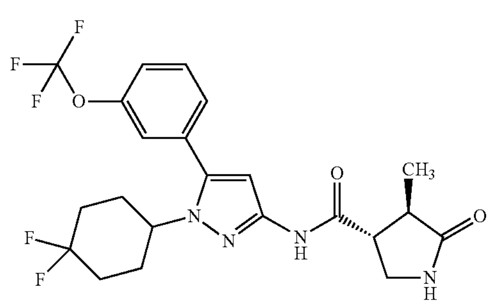 [SMILES: C[C@H]1C(=O)NC[C@@H]1C(=O)Nc1cc(-c2cccc(OC(F)(F)F)c2)n(C2CCC(F)(F)CC2)n1] | 1H-NMR (DMSO-D6) δ: 1.05 (d, 3H, J = 7.2 Hz), 1.92-2.13 (m, 8H), 2.53 (dq, 1H, J = 9.3, 7.2 Hz), 3.00 (ddd, 1H, J = 8.6, 9.0, 9.3 Hz), 3.18 (dd, 1H, J = 8.6, 9.0 Hz), 3.41 (dd, 1H, J = 8.4, 8.6 Hz), 4.28-4.33 (m, 1H), 6.67 (s, 1H), 7.46 (s, 1H), 7.49-7.52 (m, 2H), 7.65 (s, 1H), 7.67-7.69 (m, 1H), 10.86 (s, 1H). | 487 | 485 | (3R,4R)-form |

TABLE 1-continued

| Ex. No. | Molecular Structure | NMR | MS (M + H) | MS (M − H) | Comments |
|---|---|---|---|---|---|
| 199 | 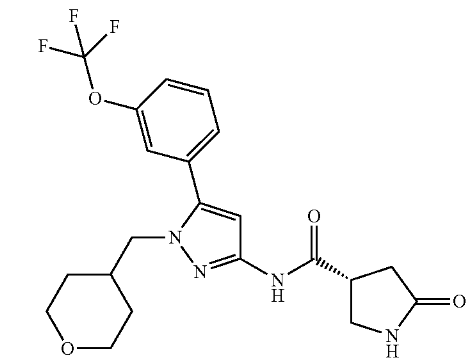 [SMILES: O=C1C[C@@H](C(=O)Nc2cc(-c3cccc(OC(F)(F)F)c3)n(CC3CCOCC3)n2)CN1] | 1H-NMR (DMSO-D6) δ: 0.96-1.10 (m, 2H), 1.27-1.35 (m, 2H), 1.90-2.03 (m, 1H), 2.36 (d, 2H, J = 8.5 Hz), 3.11-3.20 (m, 2H), 3.30 (dd, 1H, J = 8.3, 5.6 Hz), 3.38 (ddt, 1H, J = 8.5, 5.6, 8.3 Hz), 3.47 (dd, 1H, J = 8.3, 8.3 Hz), 3.69-3.77 (m, 2H), 3.92 (d, 2H, J = 7.3 Hz), 6.67 (s, 1H), 7.48 (dd, 1H, J = 1.2, 1.2 Hz), 7.48 (ddd, 1H, J = 8.9, 1.2, 1.2 Hz), 7.52 (ddd, 1H, J = 7.7, 1.2, 1.2 Hz), 7.62 (s, 1H), 7.65 (dd, 1H, J = 8.9, 7.7 Hz), 10.71 (s, 1H). | 453 | 451 | R-form |
| 200 | 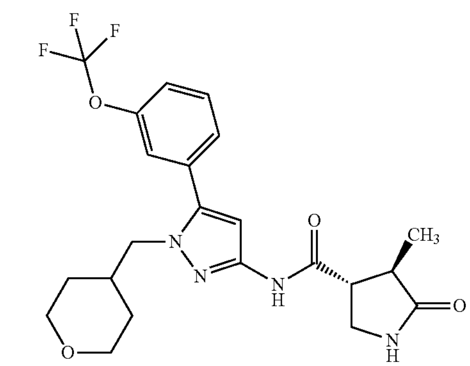 [SMILES: C[C@H]1C(=O)NC[C@@H]1C(=O)Nc1cc(-c2cccc(OC(F)(F)F)c2)n(CC2CCOCC2)n1] | 1H-NMR (DMSO-D6) δ: 0.98-1.10 (m, 2H), 1.06 (d, 3H, J = 6.9 Hz), 1.27-1.36 (m, 2H), 1.90-2.03 (m, 1H), 2.51 (dq, 1H, J = 9.7, 6.9 Hz), 3.00 (ddd, 1H, J = 8.5, 9.1, 9.7 Hz), 3.11-3.20 (m, 2H), 3.19 (dd, 1H, J = 9.1, 9.1 Hz), 3.41 (dd, 1H, J = 8.5, 8.5 Hz), 3.70-3.77 (m, 2H), 3.92 (d, 2H, J = 6.9 Hz), 6.70 (s, 1H), 7.47-7.51 (m, 2H), 7.52 (ddd, 1H, J = 7.7, 1.3, 1.3 Hz), 7.66 (dd, 1H, J = 8.9, 7.7 Hz), 7.66 (s, 1H), 10.80 (s, 1H). | 467 | 465 | (3R,4R)-form |
| 201 | 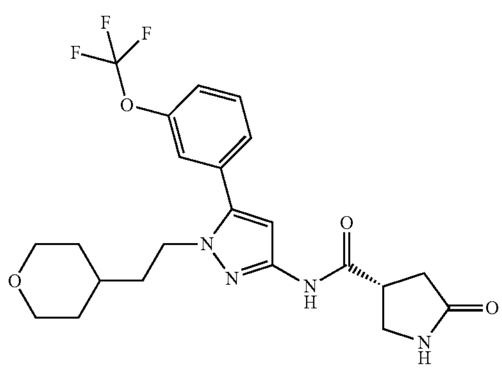 [SMILES: O=C1C[C@@H](C(=O)Nc2cc(-c3cccc(OC(F)(F)F)c3)n(CCC3CCOCC3)n2)CN1] | 1H-NMR (DMSO-D6) δ: 0.98-1.11 (m, 2H), 1.20-1.35 (m, 3H), 1.61 (dt, 2H, J = 7.1, 6.7 Hz), 2.36 (d, 2H, J = 8.5 Hz), 3.07-3.18 (m, 2H), 3.30 (dd, 1H, J = 8.7, 5.6 Hz), 3.38 (ddt, 1H, J = 8.5, 5.6, 8.7 Hz), 3.47 (dd, 1H, J = 8.7, 8.7 Hz), 3.67-3.75 (m, 2H), 4.06 (t, 2H, J = 7.1 Hz), 6.67 (s, 1H), 7.48 (ddd, 1H, J = 7.3, 1.2, 1.2 Hz), 7.49 (dd, 1H, J = 1.2, 1.2 Hz), 7.53 (ddd, 1H, J = 7.9, 1.2, 1.2 Hz), 7.62 (s, 1H), 7.66 (dd, 1H, J = 7.9, 7.3 Hz), 10.71 (s, 1H). | 467 | 465 | R-form |
| 202 | 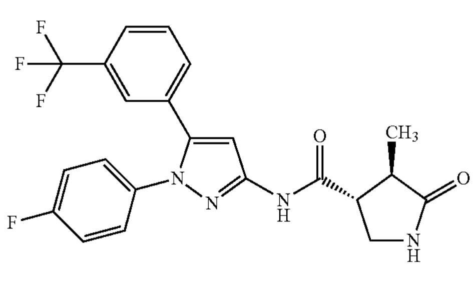 [SMILES: C[C@H]1C(=O)NC[C@@H]1C(=O)Nc1cc(-c2cccc(C(F)(F)F)c2)n(-c2ccc(F)cc2)n1] | 1H-NMR (DMSO-D6) δ: 1.08 (d, 3H, J = 7.0 Hz), 2.54-2.57 (m, 1H), 3.04 (ddd, 1H, J = 18.1, 8.4, 4.2 Hz), 3.23 (dd, 1H, J = 9.0, 4.5 Hz), 3.45 (dd, 1H, J = 8.5, 4.2 Hz), 7.07 (s, 1H), 7.26-7.34 (m, 4H), 7.53 (s, 1H), 7.55 (d, 1H, J = 7.9 Hz), 7.61 (dd, 1H, J = 7.7, 3.8 Hz), 7.68 (s, 1H), 7.73 (d, 1H, J = 7.7 Hz), 10.99 (s, 1H). | 447 | 445 | (3R,4R)-form |

TABLE 1-continued

| Ex. No. | Molecular Structure | NMR | MS (M + H) | MS (M − H) | Comments |
|---|---|---|---|---|---|
| 203 | 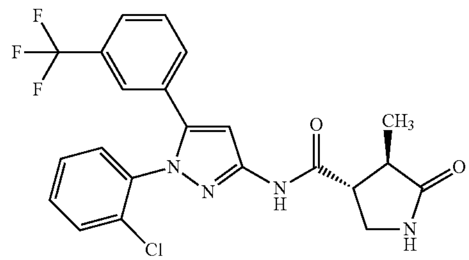 [SMILES: C[C@H]1C(=O)NC[C@@H]1C(=O)Nc1cc(-c2cccc(C(F)(F)F)c2)n(-c2ccccc2Cl)n1] | 1H-NMR (DMSO-D6) δ: 1.09 (d, 3H, J = 7.2 Hz), 2.54-2.60 (m, 1H), 3.04 (ddd, 1H, J = 18.1, 8.6, 4.3 Hz), 3.24 (dd, 1H, J = 8.8, 4.4 Hz), 3.46 (dd, 1H, J = 8.7, 4.4 Hz), 7.15 (s, 1H), 7.41 (s, 1H), 7.49-7.68 (m, 8H), 10.97 (s, 1H). | 463 | 461 | (3R,4R)-form |
| 204 | 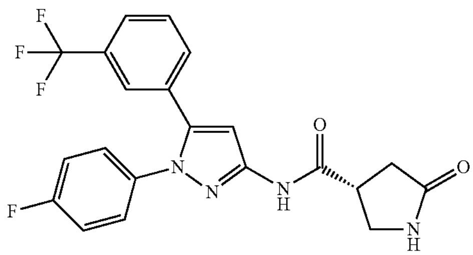 [SMILES: O=C1C[C@@H](C(=O)Nc2cc(-c3cccc(C(F)(F)F)c3)n(-c3ccc(F)cc3)n2)CN1] | 1H-NMR (DMSO-D6) δ: 2.39 (d, 2H, J = 8.4 Hz), 3.34-3.35 (m, 1H), 3.43-3.48 (m, 2H), 7.04 (s, 1H), 7.26-7.34 (m, 4H), 7.52 (s, 1H), 7.55 (d, 1H, J = 7.9 Hz), 7.60-7.64 (m, 2H), 7.73 (d, 1H, J = 7.7 Hz), 10.91 (s, 1H). | 433 | 431 | R-form |
| 205 | 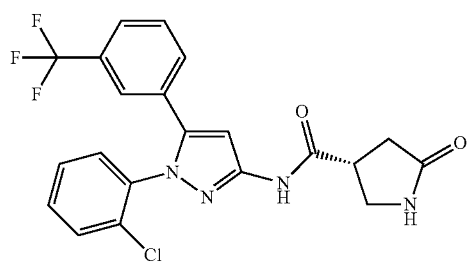 [SMILES: O=C1C[C@@H](C(=O)Nc2cc(-c3cccc(C(F)(F)F)c3)n(-c3ccccc3Cl)n2)CN1] | 1H-NMR (DMSO-D6) δ: 2.39-2.40 (m, 2H), 3.35-3.53 (m, 3H), 7.13 (s, 1H), 7.40 (s, 1H), 7.48-7.69 (m, 8H), 10.89 (s, 1H). | 449 | 447 | R-form |
| 206 | 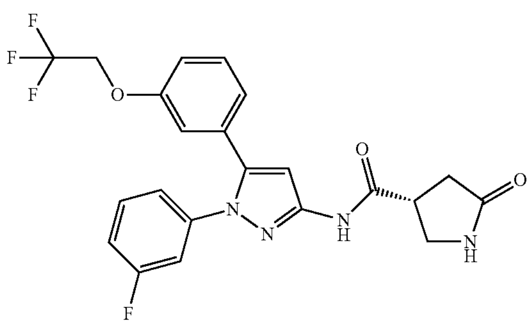 [SMILES: O=C1C[C@@H](C(=O)Nc2cc(-c3cccc(OCC(F)(F)F)c3)n(-c3cccc(F)c3)n2)CN1] | 1H-NMR (DMSO-D6) δ: 2.38-2.40 (m, 2H), 3.33-3.53 (m, 3H), 4.77 (q, 2H, J = 8.8 Hz), 6.84 (d, 1H, J = 7.9 Hz), 6.98 (s, 1H), 7.02-7.15 (m, 4H), 7.19-7.21 (m, 1H), 7.32-7.34 (m, 1H), 7.42-7.44 (m, 1H), 7.64 (s, 1H), 10.91 (s, 1H). | 463 | 461 | R-form |
| 207 | 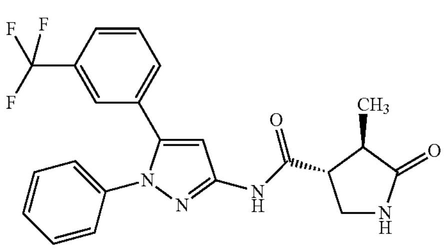 [SMILES: C[C@H]1C(=O)NC[C@@H]1C(=O)Nc1cc(-c2cccc(C(F)(F)F)c2)n(-c2ccccc2)n1] | 1H-NMR (DMSO-D6) δ: 1.09 (d, 3H, J = 7.0 Hz), 2.57 (dq, 1H, J = 9.3, 7.0 Hz), 3.04 (ddd, 1H, J = 9.3, 9.3, 9.3 Hz), 3.23 (dd, 1H, J = 8.5, 9.3 Hz), 3.45 (dd, 1H, J = 8.5, 9.3 Hz), 7.07 (s, 1H), 7.25-7.27 (m, 2H), 7.38-7.45 (m, 3H), 7.50 (s, 1H), 7.55-7.62 (m, 2H), 7.67-7.73 (m, 2H), 11.00 (s, 1H). | 429 | 427 | (3R,4R)-form |

TABLE 1-continued

| Ex. No. | Molecular Structure | NMR | MS (M + H) | MS (M − H) | Comments |
|---|---|---|---|---|---|
| 208 | 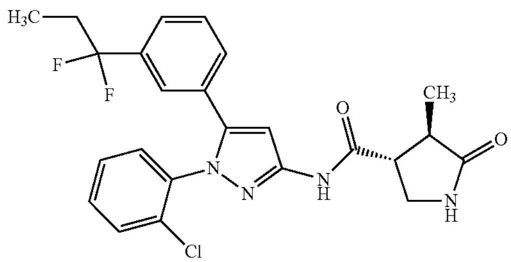 [SMILES: CCC(F)(F)c1cccc(-c2cc(NC(=O)[C@H]3CNC(=O)[C@@H]3C)nn2-c2ccccc2Cl)c1] | 1H-NMR (DMSO-D6) δ: 0.69 (t, 3H, J = 7.4 Hz), 1.09 (d, 3H, J = 7.2 Hz), 2.02 (tq, 2H, J = 16.2, 7.4 Hz), 2.56 (dq, 1H, J = 9.3, 7.2 Hz), 3.03 (ddd, 1H, J = 8.5, 9.1, 9.3 Hz), 3.24 (dd, 1H, J = 8.8, 9.1 Hz), 3.45 (dd, 1H, J = 8.5, 8.8 Hz), 7.09 (s, 1H), 7.17 (s, 1H), 7.41-7.54 (m, 5H), 7.58-7.63 (m, 2H), 7.68 (s, 1H), 10.94 (s, 1H). | 473 | 471 | (3R,4R)-form |
| 209 | 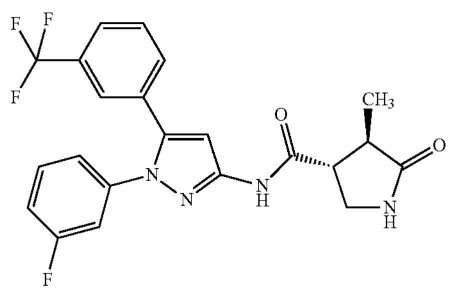 [SMILES: C[C@H]1C(=O)NC[C@@H]1C(=O)Nc1cc(-c2cccc(C(F)(F)F)c2)n(-c2cccc(F)c2)n1] | 1H-NMR (DMSO-D6) δ: 1.09 (d, 3H, J = 7.2 Hz), 2.56 (dq, 1H, J = 9.3, 7.2 Hz), 3.05 (ddd, 1H, J = 8.6, 9.2, 9.3 Hz), 3.23 (dd, 1H, J = 9.0, 9.2 Hz), 3.45 (dd, 1H, J = 8.6, 9.0 Hz), 7.04-7.06 (m, 1H), 7.08 (s, 1H), 7.18-7.27 (m, 2H), 7.42-7.47 (m, 1H), 7.56-7.65 (m, 3H), 7.68 (s, 1H), 7.75 (d, 1H, J = 7.7 Hz), 11.03 (s, 1H). | 447 | 445 | (3R,4R)-form |
| 210 | 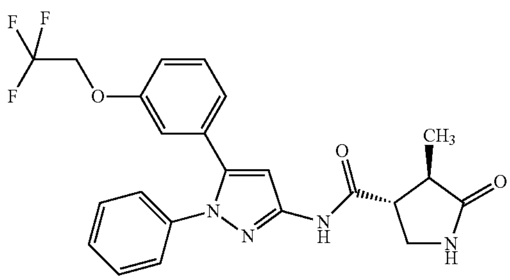 [SMILES: C[C@H]1C(=O)NC[C@@H]1C(=O)Nc1cc(-c2cccc(OCC(F)(F)F)c2)n(-c2ccccc2)n1] | 1H-NMR (DMSO-D6) δ: 1.08 (d, 3H, J = 7.2 Hz), 2.55 (dq, 1H, J = 9.3, 7.2 Hz), 3.04 (ddd, 1H, J = 8.6, 9.2, 9.3 Hz), 3.23 (dd, 1H, J = 8.6, 8.7 Hz), 3.44 (dd, 1H, J = 8.7, 9.2 Hz), 4.73 (q, 2H, J = 8.8 Hz), 6.80 (d, 1H, J = 8.1 Hz), 6.99 (s, 1H), 7.01-7.07 (m, 2H), 7.22-7.31 (m, 3H), 7.33-7.43 (m, 3H), 7.67 (s, 1H), 10.95 (s, 1H). | 459 | 457 | (3R,4R)-form |
| 211 | 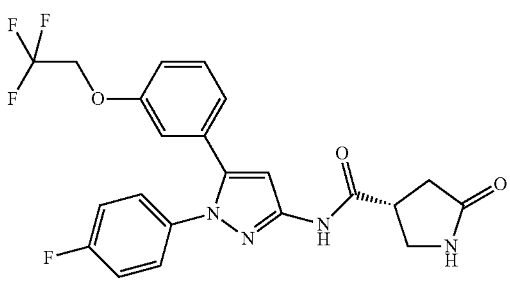 [SMILES: O=C1C[C@@H](C(=O)Nc2cc(-c3cccc(OCC(F)(F)F)c3)n(-c3ccc(F)cc3)n2)CN1] | 1H-NMR (DMSO-D6) δ: 2.39 (d, 2H, J = 8.4 Hz), 3.32-3.52 (m, 3H), 4.75 (q, 2H, J = 8.8 Hz), 6.80 (d, 1H, J = 7.9 Hz), 6.97 (s, 1H), 7.01-7.06 (m, 2H), 7.23-7.32 (m, 5H), 7.64 (s, 1H), 10.86 (s, 1H). | 463 | 461 | R-form |
| 212 | 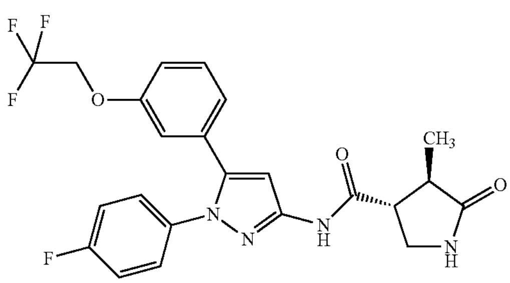 [SMILES: C[C@H]1C(=O)NC[C@@H]1C(=O)Nc1cc(-c2cccc(OCC(F)(F)F)c2)n(-c2ccc(F)cc2)n1] | 1H-NMR (DMSO-D6) δ: 1.08 (d, 3H, J = 7.2 Hz), 2.55 (dq, 1H, J = 9.3, 7.2 Hz), 3.03 (ddd, 1H, J = 8.6, 9.3, 9.3 Hz), 3.22 (dd, 1H, J = 8.8, 9.3 Hz), 3.44 (dd, 1H, J = 8.6, 8.8 Hz), 4.75 (q, 2H, J = 8.8 Hz), 6.79-6.81 (m, 1H), 6.99 (s, 1H), 7.03-7.06 (m, 2H), 7.24-7.32 (m, 5H), 7.67 (s, 1H), 10.95 (s, 1H). | 477 | 475 | (3R,4R)-form |

TABLE 1-continued

| Ex. No. | Molecular Structure | NMR | MS (M + H) | MS (M − H) | Comments |
|---|---|---|---|---|---|
| 213 | 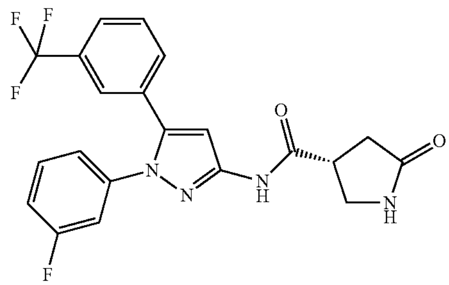 [SMILES: O=C1C[C@@H](C(=O)Nc2cc(-c3cccc(C(F)(F)F)c3)n(-c3cccc(F)c3)n2)CN1] | 1H-NMR (DMSO-D6) δ: 2.39 (d, 2H, J = 8.1 Hz), 3.33-3.35 (m, 1H), 3.39-3.53 (m, 2H), 7.04 (s, 1H), 7.06 (s, 1H), 7.19-7.26 (m, 2H), 7.41-7.47 (m, 1H), 7.56-7.66 (m, 4H), 7.75 (d, 1H, J = 7.7 Hz), 10.95 (s, 1H). | 433 | 431 | R-form |
| 214 | 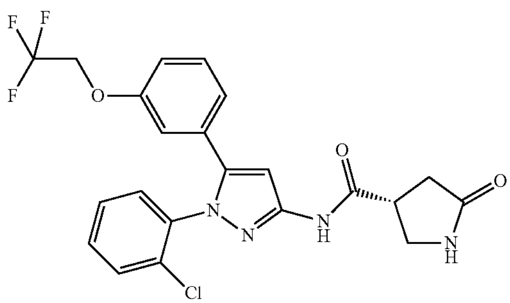 [SMILES: O=C1C[C@@H](C(=O)Nc2cc(-c3cccc(OCC(F)(F)F)c3)n(-c3ccccc3Cl)n2)CN1] | 1H-NMR (DMSO-D6) δ: 2.38-2.41 (m, 2H), 3.34-3.52 (m, 3H), 4.70 (q, 2H, J = 8.8 Hz), 6.76 (dd, 1H, J = 7.9, 2.0 Hz), 6.94 (dd, 1H, J = 2.0, 2.0 Hz), 7.00 (dd, 1H, J = 8.1, 2.1 Hz), 7.05 (s, 1H), 7.24 (dd, 1H, J = 7.9, 8.1 Hz), 7.46-7.54 (m, 2H), 7.57-7.61 (m, 2H), 7.64 (s, 1H), 10.83 (s, 1H). | 479 | 477 | R-form |
| 215 | 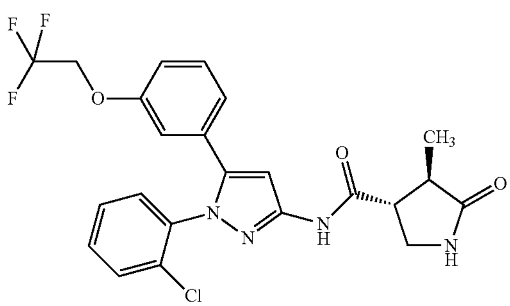 [SMILES: C[C@H]1C(=O)NC[C@@H]1C(=O)Nc1cc(-c2cccc(OCC(F)(F)F)c2)n(-c2ccccc2Cl)n1] | 1H-NMR (DMSO-D6) δ: 1.09 (d, 3H, J = 7.2 Hz), 2.57 (dq, 1H, J = 9.3, 7.2 Hz), 3.03 (ddd, 1H, J = 8.5, 8.8, 9.3 Hz), 3.23 (dd, 1H, J = 8.6, 8.8 Hz), 3.45 (dd, 1H, J = 8.5, 8.6 Hz), 4.71 (q, 2H, J = 8.8 Hz), 6.75-6.77 (m, 1H), 6.95-7.01 (m, 2H), 7.07 (s, 1H), 7.24 (dd, 1H, J = 8.3, 8.3 Hz), 7.46-7.54 (m, 2H), 7.57-7.62 (m, 2H), 7.68 (s, 1H), 10.92 (s, 1H). | 493 | 491 | (3R,4R)-form |
| 216 | 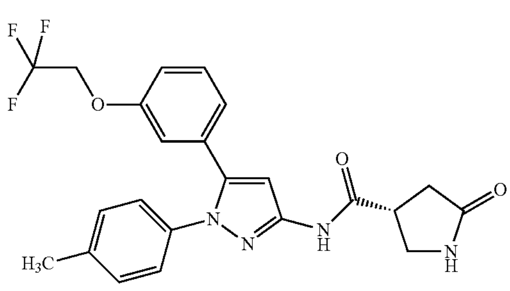 [SMILES: Cc1ccc(-n2nc(NC(=O)[C@H]3CNC(=O)C3)cc2-c2cccc(OCC(F)(F)F)c2)cc1] | 1H-NMR (DMSO-D6) δ: 2.31 (s, 3H), 2.38 (d, 2H, J = 8.6 Hz), 3.33 (dd, 1H, J = 8.4, 8.5 Hz), 3.41 (ddt, 1H, J = 8.4, 8.5, 8.6 Hz), 3.50 (dd, 1H, J = 8.4, 8.4 Hz), 4.73 (q, 2H, J = 8.9 Hz), 6.79 (d, 1H, J = 7.7 Hz), 6.95 (s, 1H), 7.00 (d, 1H, J = 2.4 Hz), 7.03 (dd, 1H, J = 8.0, 2.4 Hz), 7.12 (d, 2H, J = 8.4 Hz), 7.20 (d, 2H, J = 8.4 Hz), 7.28 (dd, 1H, J = 7.7, 8.0 Hz), 7.63 (s, 1H), 10.85 (s, 1H). | 459 | 457 | R-form |

TABLE 1-continued

| Ex. No. | Molecular Structure | NMR | MS (M + H) | MS (M − H) | Comments |
|---|---|---|---|---|---|
| 217 | 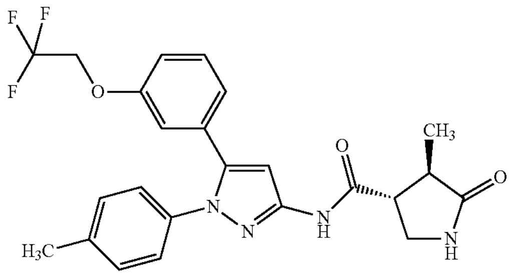 [SMILES: Cc1ccc(-n2nc(NC(=O)[C@H]3CNC(=O)[C@@H]3C)cc2-c2cccc(OCC(F)(F)F)c2)cc1] | 1H-NMR (DMSO-D6) δ: 1.08 (d, 3H, J = 7.7 Hz), 2.31 (s, 3H), 2.55 (dq, 1H, J = 9.3, 7.7 Hz), 3.03 (ddd, 1H, J = 9.3, 9.4, 9.5 Hz), 3.22 (dd, 1H, J = 8.7, 9.4 Hz), 3.44 (dd, 1H, J = 8.7, 9.5 Hz), 4.74 (q, 2H, J = 9.0 Hz), 6.78-6.80 (m, 1H), 6.97 (s, 1H), 7.02-7.05 (m, 2H), 7.12 (d, 2H, J = 8.4 Hz), 7.21 (d, 2H, J = 8.4 Hz), 7.28 (dd, 1H, J = 7.9, 7.9 Hz), 7.67 (s, 1H), 10.94 (s, 1H). | 473 | 471 | (3R,4R)-form |
| 218 | 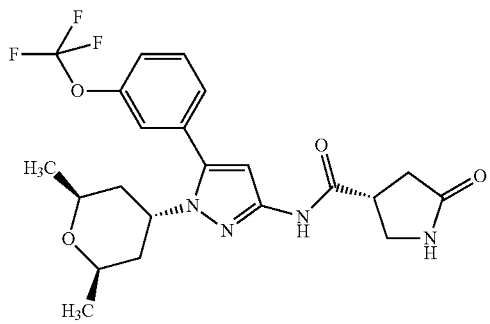 [SMILES: C[C@@H]1C[C@@H](n2nc(NC(=O)[C@H]3CNC(=O)C3)cc2-c2cccc(OC(F)(F)F)c2)C[C@H](C)O1] | 1H-NMR (DMSO-D6) δ: 1.08 (d, 6H, J = 6.0 Hz), 1.57-1.65 (m, 2H), 1.79-1.82 (m, 2H), 2.38-2.43 (m, 2H), 3.32-3.56 (m, 3H), 4.26-4.29 (m, 2H), 4.67-4.69 (m, 1H), 6.82 (s, 1H), 7.29 (d, 1H, J = 7.7 Hz), 7.55 (dd, 1H, J = 7.7, 7.7 Hz), 7.67 (s, 1H), 7.69 (s, 1H), 7.82 (d, 1H, J = 7.7 Hz), 10.04 (s, 1H). | 467 | 465 | Lactam ring: R-form Tetrahydro pyrane ring: (2R,4S,6S)-form |
| 219 | 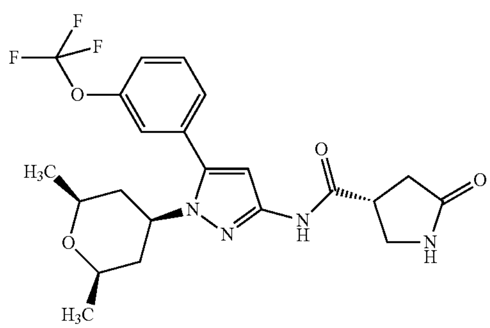 [SMILES: C[C@@H]1C[C@H](n2nc(NC(=O)[C@H]3CNC(=O)C3)cc2-c2cccc(OC(F)(F)F)c2)C[C@H](C)O1] | 1H-NMR (DMSO-D6) δ: 1.15 (d, 6H, J = 6.0 Hz), 1.63-1.72 (m, 2H), 1.82-1.85 (m, 2H), 2.39-2.44 (m, 2H), 3.35-3.37 (m, 1H), 3.42-3.49 (m, 1H), 3.53-3.57 (m, 3H), 4.36-4.41 (m, 1H), 6.75 (s, 1H), 7.27 (d, 1H, J = 8.1 Hz), 7.51 (dd, 1H, J = 7.7, 8.1 Hz), 7.67 (s, 1H), 7.68 (s, 1H), 7.79 (d, 1H, J = 7.7 Hz), 10.07 (s, 1H). | 467 | 465 | Lactam ring: R-form Tetrahydro pyrane ring: (2R,4S,6S)-form |
| 220 | 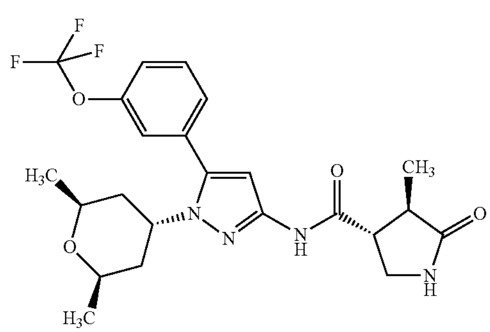 [SMILES: C[C@@H]1C[C@@H](n2nc(NC(=O)[C@H]3CNC(=O)[C@@H]3C)cc2-c2cccc(OC(F)(F)F)c2)C[C@H](C)O1] | 1H-NMR (DMSO-D6) δ: 1.07 (d, 6H, J = 6.0 Hz), 1.13 (d, 3H, J = 6.9 Hz), 1.58-1.66 (m, 2H), 1.80-1.83 (m, 2H), 2.53 (dq, 1H, J = 9.3, 6.9 Hz), 3.05 (ddd, 1H, J = 8.5, 9.1, 9.3 Hz), 3.26 (dd, 1H, J = 8.5, 8.9 Hz), 3.48 (dd, 1H, J = 8.9, 9.1 Hz), 4.24-4.30 (m, 2H), 4.66-4.69 (m, 1H), 6.84 (s, 1H), 7.29 (d, 1H, J = 8.1 Hz), 7.55 (dd, 1H, J = 8.1, 8.1 Hz), 7.70 (s, 1H), 7.71 (s, 1H), 7.83 (d, 1H, J = 8.1 Hz), 10.09 (s, 1H). | 481 | 479 | Lactam ring: (3R,4R)-form Tetrahydro pyrane ring: (2R,4S,6S)-form |

TABLE 1-continued

| Ex. No. | Molecular Structure | NMR | MS (M + H) | MS (M − H) | Comments |
|---|---|---|---|---|---|
| 221 | (structure) | 1H-NMR (DMSO-D6) δ: 1.14 (d, 3H, J = 7.3 Hz), 1.17 (d, 6H, J = 6.0 Hz), 1.64-1.74 (m, 2H), 1.82-1.88 (m, 2H), 2.55 (dq, 1H, J = 9.3, 7.3 Hz), 3.06 (ddd, 1H, J = 8.5, 8.9, 9.3 Hz), 3.27 (dd, 1H, J = 8.5, 9.3 Hz), 3.50 (dd, 1H, J = 8.9, 9.3 Hz), 3.54-3.60 (m, 2H), 4.35-4.40 (m, 1H), 6.79 (s, 1H), 7.29 (d, 1H, J = 7.7 Hz), 7.53 (dd, 1H, J = 7.7, 7.7 Hz), 7.71 (s, 1H), 7.72 (s, 1H), 7.81 (d, 1H, J = 7.7 Hz), 10.14 (s, 1H). | 481 | 479 | Lactam ring: (3R,4R)-form Tetrahydro pyrane ring: (2R,4S,6S)-form |
| 222 | (structure) | 1H-NMR (DMSO-D6) δ: 1.08 (d, 3H, J = 7.2 Hz), 2.55-2.57 (m, 1H), 3.04 (ddd, 1H, J = 8.8, 4.4, 2.2 Hz), 3.22 (dd, 1H, J = 9.0, 4.5 Hz), 3.45 (dd, 1H, J = 8.8, 4.4 Hz), 4.77 (q, 2H, J = 8.8 Hz), 6.84 (d, 1H, J = 7.7 Hz), 7.00 (s, 1H), 7.16-7.32 (m, 7H), 7.67 (s, 1H), 10.99 (s, 1H). | 477 | 475 | (3R,4R)-form |
| 223 | (structure) | 1H-NMR (DMSO-D6) δ: 1.07 (3H, d, J = 7.2 Hz), 1.90 (3H, s), 2.48-2.60 (1H, m), 3.02 (1H, ddd, J = 9.3, 9.0, 8.8 Hz), 3.22 (1H, dd, J = 9.0, 8.8 Hz), 3.44 (1H, dd, J = 9.0, 8.8 Hz), 6.97 (1H, s), 7.08 (1H, s), 7.24-7.42 (6H, m), 7.45 (1H, t, J = 8.0 Hz), 7.66 (1H, s), 10.90 (1H, s) | 459 | 457 | (3R,4R)-form |
| 224 | (structure) | 1H-NMR (DMSO-D6) δ: 1.90 (3H, s), 2.34-2.44 (2H, m), 3.30-3.55 (3H, m), 7.10 (1H, s), 7.24-7.42 (5H, m), 7.49-7.58 (2H, m), 7.59-7.68 (2H, m), 10.82 (1H, s) | 429 | 427 | R-form |
| 225 | (structure) | 1H-NMR (DMSO-D6) δ: 1.08 (3H, d, J = 7.2 Hz), 1.91 (3H, s), 2.48-2.60 (1H, m), 3.03 (1H, ddd, J = 8.8, 8.8, 8.8 Hz), 3.23 (1H, dd, J = 9.0, 8.6 Hz), 3.44 (1H, dd, J = 9.0, 8.6 Hz), 7.12 (1H, s), 7.26-7.42 (5H, m), 7.50-7.58 (2H, m), 7.60-7.69 (2H, m), 10.91 (1H, s) | 443 | 441 | (3R,4R)-form |

TABLE 1-continued

| Ex. No. | Molecular Structure | NMR | MS (M + H) | MS (M − H) | Comments |
|---|---|---|---|---|---|
| 226 | 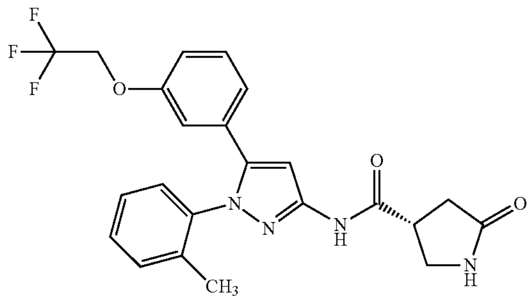 [SMILES: Cc1ccccc1-n1nc(NC(=O)[C@H]2CNC(=O)C2)cc1-c1cccc(OCC(F)(F)F)c1] | 1H-NMR (DMSO-D6) δ: 1.90 (s, 3H), 2.37-2.39 (br m, 2H), 3.32-3.51 (m, 3H), 4.65 (q, 2H, J = 8.9 Hz), 6.74 (d, 1H, J = 7.9 Hz), 6.88 (s, 1H), 6.96 (dd, 1H, J = 8.1, 2.6 Hz), 7.02 (s, 1H), 7.23-7.34 (m, 5H), 7.63 (s, 1H), 10.76 (s, 1H) | 459 | 457 | R-form |
| 227 | 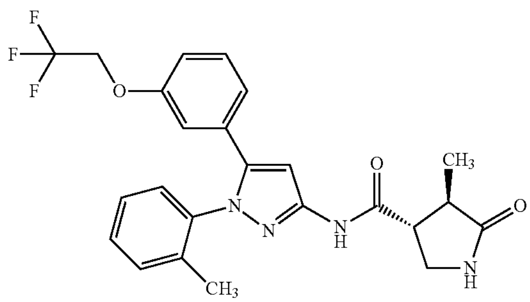 [SMILES: Cc1ccccc1-n1nc(NC(=O)[C@H]2CNC(=O)[C@@H]2C)cc1-c1cccc(OCC(F)(F)F)c1] | 1H-NMR (DMSO-D6) δ: 1.90 (s, 3H), 2.37-2.39 (m, 2H), 3.32-3.51 (m, 3H), 4.65 (q, 2H, J = 8.9 Hz), 6.74 (d, 1H, J = 7.9 Hz), 6.88 (s, 1H), 6.96 (dd, 1H, J = 8.1, 2.6 Hz), 7.02 (s, 1H), 7.23-7.34 (m, 5H), 7.63 (s, 1H), 10.76 (s, 1H) | 473 | 471 | (3R,4R)-form |
| 228 | 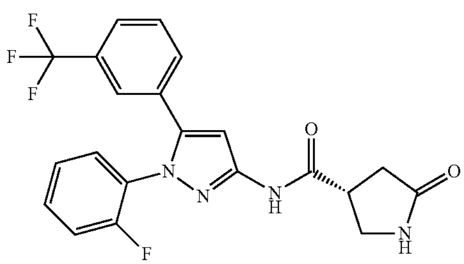 [SMILES: O=C1C[C@@H](C(=O)Nc2cc(-c3cccc(C(F)(F)F)c3)n(-c3ccccc3F)n2)CN1] | 1H-NMR (DMSO-D6) δ: 1.90 (s, 3H), 2.37-2.39 (m, 2H), 3.32-3.51 (m, 3H), 4.65 (q, 2H, J = 8.9 Hz), 6.74 (d, 1H, J = 7.9 Hz), 6.88 (s, 1H), 6.96 dd, 1H, J = 8.1, 2.6 Hz), 7.02 (s, 1H), 7.23-7.34 (m, 5H), 7.63 (s, 1H), 10.76 (s, 1H) | 433 | 431 | R-form |
| 229 | 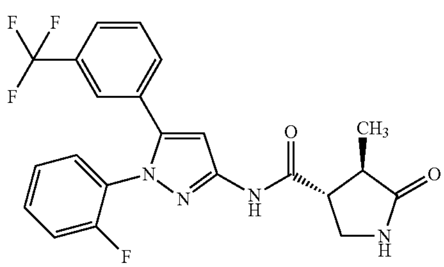 [SMILES: C[C@H]1C(=O)NC[C@@H]1C(=O)Nc1cc(-c2cccc(C(F)(F)F)c2)n(-c2ccccc2F)n1] | 1H-NMR (DMSO-D6) δ: 1.09 (d, 3H, J = 7.3 Hz), 2.52-2.59 (m, 1H), 3.04 (ddd, 1H, J = 8.5, 8.5, 8.5 Hz), 3.24 (dd, 1H, J = 8.9, 8.9 Hz), 3.45 (dd, 1H, J = 8.5, 8.5 Hz), 7.14 (s, 1H), 7.31-7.39 (m, 2H), 7.47 (s, 1H), 7.49-7.64 (m, 4H), 7.65-7.75 (m, 2H), 11.00 (s, 1H) | 447 | 445 | (3R,4R)-form |
| 230 | 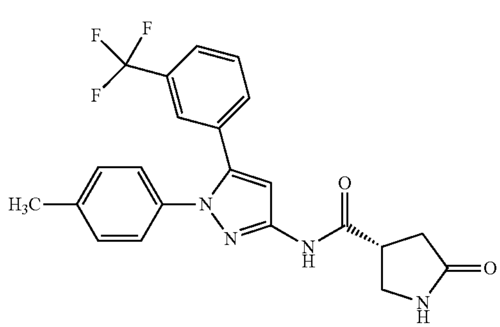 [SMILES: Cc1ccc(-n2nc(NC(=O)[C@H]3CNC(=O)C3)cc2-c2cccc(C(F)(F)F)c2)cc1] | 1H-NMR (DMSO-D6) δ: 2.31 (s, 3H), 2.37 (d, 2H, J = 8.4 Hz), 3.32 (dd, 5H, J = 8.5, 6.0 Hz), 3.36-3.45 (m, 1H), 3.49 (dd, 1H, J = 8.5, 8.5 Hz), 7.00 (s, 1H), 7.12 (dd, 2H, J = 6.5, 1.9 Hz), 7.21 (dd, 2H, J = 6.5, 2.1 Hz), 7.50 (d, 1H, J = 7.7 Hz), 7.51 (s, 1H), 7.58 (t, 1H, J = 7.7 Hz), 7.62 (s, 1H), 7.69 (d, 1H, J = 7.7 Hz), 10.88 (s, 1H). | 429 | 427 | R-form |

TABLE 1-continued

| Ex. No. | Molecular Structure | NMR | MS (M + H) | MS (M − H) | Comments |
|---|---|---|---|---|---|
| 231 | 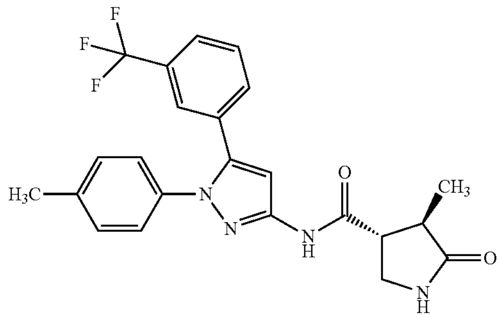 [SMILES: Cc1ccc(-n2nc(NC(=O)[C@H]3CNC(=O)[C@@H]3C)cc2-c2cccc(C(F)(F)F)c2)cc1] | 1H-NMR (DMSO-D6) δ: 1.07 (d, 3H, J = 7.2 Hz), 2.53 (dq, 1H, J = 9.5, 7.2 Hz), 3.02 (ddd, 1H, J = 9.5, 9.0, 9.0 Hz), 3.21 (dd, 1H, J = 9.0, 9.0 Hz), 3.43 (dd, 1H, J = 9.0, 9.0 Hz), 7.03 (s, 1H), 7.13 (dd, 2H, J = 6.4, 2.0 Hz), 7.21 (dd, 2H, J = 6.4, 1.9 Hz), 7.50 (d, 1H, J = 7.7 Hz), 7.52 (s, 1H), 7.58 (t, 1H, J = 7.7 Hz), 7.66 (s, 1H), 7.70 (d, 1H, J = 7.7 Hz), 10.97 (s, 1H). | 443 | 441 | (3R,4R)-form |
| 232 | 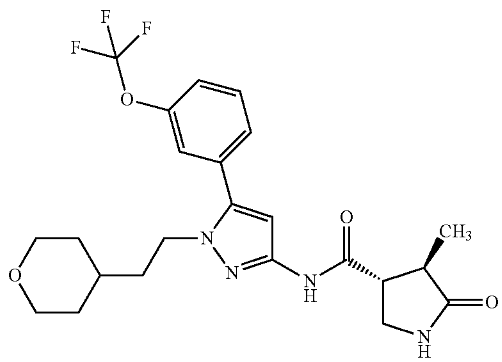 [SMILES: C[C@H]1C(=O)NC[C@@H]1C(=O)Nc1cc(-c2cccc(OC(F)(F)F)c2)n(CCC2CCOCC2)n1] | 1H-NMR (DMSO-D6) δ: 0.97-1.11 (m, 2H), 1.06 (d, 3H, J = 6.9 Hz), 1.20-1.35 (m, 3H), 1.61 (dt, 2H, J = 7.3, 6.5 Hz), 2.51 (dq, 1H, J = 9.7, 6.9 Hz), 3.00 (ddd, 1H, J = 8.5, 9.1, 9.7 Hz), 3.08-3.16 (m, 2H), 3.19 (dd, 1H, J = 9.1, 9.1 Hz), 3.41 (dd, 1H, J = 8.5, 8.5 Hz), 3.67-3.75 (m, 2H), 4.06 (t, 2H, J = 7.3 Hz), 6.69 (s, 1H), 7.48 (ddd, 1H, J = 7.1, 1.4, 1.4 Hz), 7.49 (dd, 1H, J = 1.4, 1.4 Hz), 7.54 (ddd, 1H, J = 7.9, 1.4, 1.4 Hz), 7.66 (dd, 1H, J = 7.9, 7.1 Hz), 7.66 (s, 1H), 10.80 (s, 1H). | 481 | 479 | (3R,4R)-form |
| 233 | 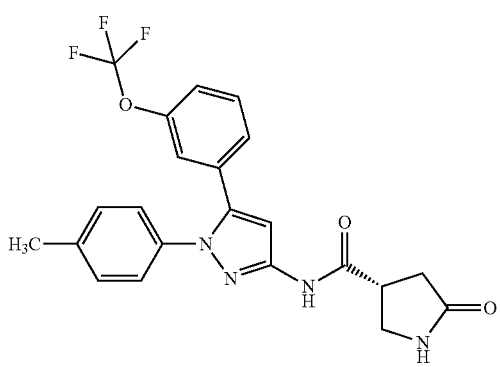 [SMILES: Cc1ccc(-n2nc(NC(=O)[C@H]3CNC(=O)C3)cc2-c2cccc(OC(F)(F)F)c2)cc1] | 1H-NMR (DMSO-D6) δ: 2.32 (s, 3H), 2.39 (d, 2H, J = 8.5 Hz), 3.33 (dd, 1H, J = 8.7, 5.6 Hz), 3.42 (ddt, 1H, J = 8.5, 5.6, 8.7 Hz), 3.50 (dd, 1H, J = 8.7, 8.7 Hz), 6.98 (s, 1H), 7.11 (dd, 1H, J = 1.2, 1.2 Hz), 7.13 (d, 2H, J = 8.1 Hz), 7.22 (d, 2H, J = 8.1 Hz), 7.32 (ddd, 1H, J = 8.1, 1.2, 1.2 Hz), 7.35 (ddd, 1H, J = 8.1, 1.2, 1.2 Hz), 7.51 (dd, 1H, J = 8.1, 8.1 Hz), 7.64 (s, 1H), 10.89 (s, 1H). | 445 | 443 | R-form |
| 234 | 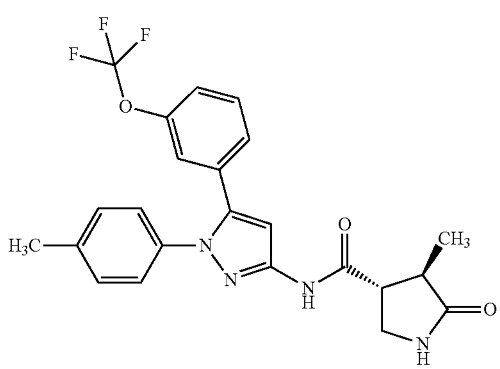 [SMILES: Cc1ccc(-n2nc(NC(=O)[C@H]3CNC(=O)[C@@H]3C)cc2-c2cccc(OC(F)(F)F)c2)cc1] | 1H-NMR (DMSO-D6) δ: 1.08 (d, 3H, J = 7.3 Hz), 2.32 (s, 3H), 2.54 (dq, 1H, J = 9.7, 7.3 Hz), 3.03 (ddd, 1H, J = 8.7, 9.1, 9.7 Hz), 3.23 (dd, 1H, J = 9.1, 9.1 Hz), 3.44 (dd, 1H, J = 8.7, 8.7 Hz), 7.01 (s, 1H), 7.11 (dd, 1H, J = 1.1, 1.3 Hz), 7.14 (d, 2H, J = 8.1 Hz), 7.22 (d, 2H, J = 8.1 Hz), 7.32 (ddd, 1H, J = 8.1, 1.1, 1.3 Hz), 7.35 (ddd, 1H, J = 8.1, 1.1, 1.3 Hz), 7.51 (dd, 1H, J = 8.1, 8.1 Hz), 7.68 (s, 1H), 10.98 (s, 1H). | 459 | 457 | (3R,4R)-form |

TABLE 2

| Example No. | Molecular Structure | NMR (400 MHz) | MS (M + H) | MS (M − H) | Comments |
|---|---|---|---|---|---|
| 235 | 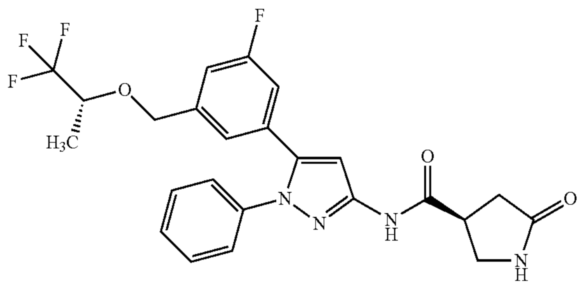 [SMILES: C[C@@H](OCc1cc(F)cc(-c2cc(NC(=O)[C@@H]3CNC(=O)C3)nn2-c2ccccc2)c1)C(F)(F)F] | ¹H-NMR (DMSO-D6) δ: 1.18 (d, 3H, J = 6.5 Hz), 2.36-2.38 (m, 2H), 3.32-3.33 (m, 1H), 3.37-3.41 (m, 1H), 3.46-3.49 (m, 1H), 4.10 (qq, 1H, J = 6.5, 9.4 Hz), 4.57 (d, 1H, J = 12.7 Hz), 4.61 (d, 1H, J = 12.7 Hz), 6.96-3.98 (m, 2H), 7.09 (s, 1H), 7.15-7.18 (m, 1H), 7.25-7.27 (m, 2H), 7.35-7.44 (m, 3H), 7.63 (s, 1H), 10.88 (s, 1H). | 491 | 489 | 2,2,2-trifluoromethyl-1-methyl-ethoxymethyl group: R-form Lactam ring: S-form |
| 236 | 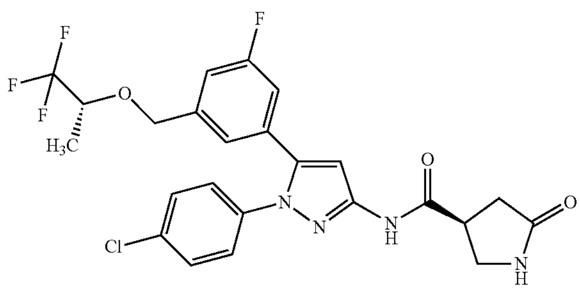 | ¹H-NMR (DMSO-D6) δ: 1.20 (d, 3H, J = 6.5 Hz), 2.38-2.40 (m, 2H), 3.33-3.35 (m, 1H), 3.40-3.44 (m, 1H), 3.48-3.51 (m, 1H), 4.10-4.15 (m, 1H), 4.63 (s, 2H), 6.99 (s, 1H), 7.06 (s, 1H), 7.08 (d, 1H, J = 9.3 Hz), 7.19 (d, 1H, J = 9.3 Hz), 7.27 (dd, 2H, J = 6.6, 2.0 Hz), 7.48 (dd, 2H, J = 6.6, 2.0 Hz), 7.63 (s, 1H), 10.91 (s, 1H). | 525 | 523 | 2,2,2-trifluoromethyl-1-methyl-ethoxymethyl group: R-form Lactam ring: S-form |
| 237 | 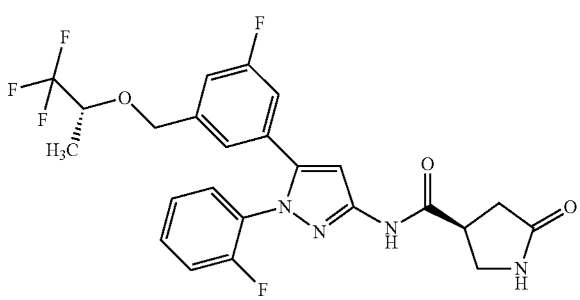 [SMILES: C[C@@H](OCc1cc(F)cc(-c2cc(NC(=O)[C@@H]3CNC(=O)C3)nn2-c2ccccc2F)c1)C(F)(F)F] | ¹H-NMR (CDCl₃) δ: 1.29 (d, 3H, J = 6.4 Hz), 2.59 (dd, 1H, J = 17.2, 9.6 Hz), 2.78 (dd, 1H, J = 17.2, 8.8 Hz), 3.29-3.40 (m, 1H), 3.60 (dd, 1H, J = 9.2 Hz), 3.67-3.80 (m, 2H), 4.52 (d, 1H, J = 12.0 Hz), 4.63 (d, 1H, J = 12.0 Hz), 6.08 (s, 1H), 6.85 (dt, 1H, J = 9.6, 2.0 Hz), 6.98-7.04 (m, 2H), 7.09-7.17 (m, 2H), 7.22 (t, 1H, J = 8.0 Hz), 7.34-7.22 (m, 2H), 8.69 (s, 1H). | 509 | 507 | 2,2,2-trifluoromethyl-1-methyl-ethoxymethyl group: R-form Lactam ring: S-form |
| 238 | 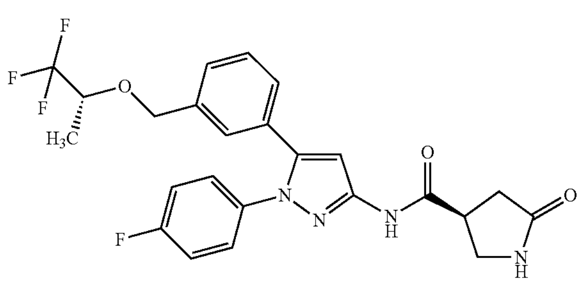 [SMILES: C[C@@H](OCc1cccc(-c2cc(NC(=O)[C@@H]3CNC(=O)C3)nn2-c2ccc(F)cc2)c1)C(F)(F)F] | ¹H-NMR (DMSO-D6) δ: 1.20 (d, 3H, J = 6.5 Hz), 2.38-2.39 (m, 2H), 3.33-3.34 (m, 1H), 3.39-3.43 (m, 1H), 3.49-3.51 (m, 1H), 4.09-4.11 (m, 1H), 4.59 (d, 1H, J = 12.1 Hz), 4.63 (d, 1H, J = 12.1 Hz), 6.92 (s, 1H), 7.18-7.39 (m, 8H), 7.63 (s, 1H), 10.85 (s, 1H). | 491 | 489 | 2,2,2-trifluoromethyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 239 | 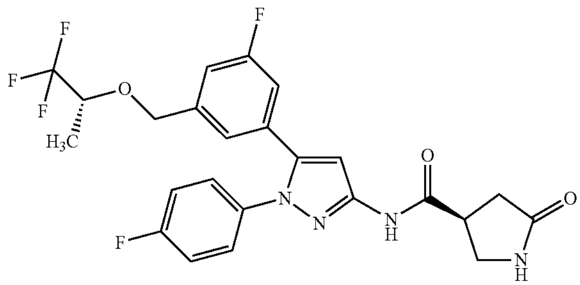 [SMILES: C[C@@H](OCc1cc(F)cc(-c2cc(NC(=O)[C@@H]3CNC(=O)C3)nn2-c2ccc(F)cc2)c1)C(F)(F)F] | $^1$H-NMR (CDCl$_3$) δ: 1.31 (d, 3H, J = 6.4 Hz), 2.61 (dd, 1H, J = 16.8, 9.6 Hz), 2.78 (dd, 1H, J = 16.8, 8.4 Hz), 3.31-3.42 (m, 1H), 3.61 (t, 1H, J = 8.8 Hz), 3.67-3.83 (m, 2H), 4.55 (d, 1H, J = 12.0 Hz), 4.65 (d, 1H, J = 12.0 Hz), 6.04 (s, 1H), 6.85 (d, 1H, J = 9.2 Hz), 6.98-7.10 (m, 5H), 7.19-7.25 (m, 2H), 8.48 (s, 1H). | 509 | 507 | 2,2,2-trifluoro methyl-1-methyl-ethoxy-methyl group: R-form Lactam ring: S-form |
| 240 | 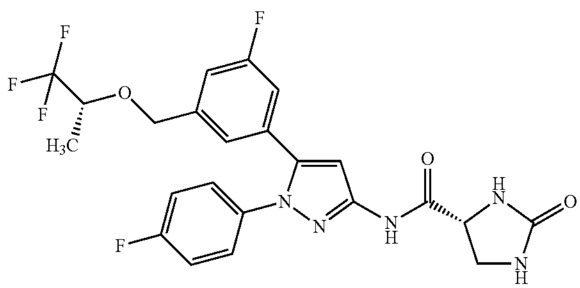 [SMILES: C[C@@H](OCc1cc(F)cc(-c2cc(NC(=O)[C@H]3CNC(=O)N3)nn2-c2ccc(F)cc2)c1)C(F)(F)F] | $^1$H-NMR (DMSO-D$_6$) δ: 1.20 (d, 3H, J = 6.0 Hz), 3.35 (dd, 1H, J = 8.6, 6.2 Hz), 3.58 (dd, 1H, J = 9.3, 8.6 Hz), 4.12 (tq, 1H, J = 9.7, 6.0 Hz), 4.31 (dd, 1H, J = 9.3, 6.2 Hz), 4.60 (d, 1H, J = 12.5 Hz), 4.63 (d, 1H, J = 12.5 Hz), 6.33 (s, 1H), 6.59 (s, 1H), 6.98 (s, 1H), 7.02-7.07 (m, 2H), 7.18 (d, 1H, J = 9.6 Hz), 7.23-7.35 (m, 4H), 10.72 (s, 1H). | 510 | 509 | 2,2,2-trifluoro methyl-1-methyl-ethoxy-methyl group: R-form Alpha position of carbonyl group (amide): R-form |
| 241 | 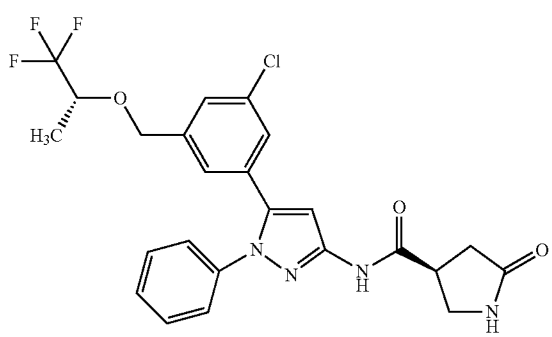 [SMILES: C[C@@H](OCc1cc(Cl)cc(-c2cc(NC(=O)[C@@H]3CNC(=O)C3)nn2-c2ccccc2)c1)C(F)(F)F] | 1H-NMR (DMSO-D6) δ: 1.18 (d, 3H, J = 6.5 Hz), 2.36-2.38 (m, 2H), 3.32-3.33 (m, 1H), 3.37-3.41 (m, 1H), 3.46-3.49 (m, 1H), 4.10 (qq, 1H, J = 6.5, 9.4 Hz), 4.57 (d, 1H, J = 12.7 Hz), 4.61 (d, 1H, J = 12.7 Hz), 6.98 (s, 1H), 7.19-7.20 (m, 2H), 7.25-7.27 (m, 2H), 7.35-7.45 (m, 4H), 7.63 (s, 1H), 10.88 (s, 1H). | 507 | 505 | 2,2,2-trifluoro methyl-1-methyl-ethoxy-methyl group: R-form Lactam ring: S-form |
| 242 | 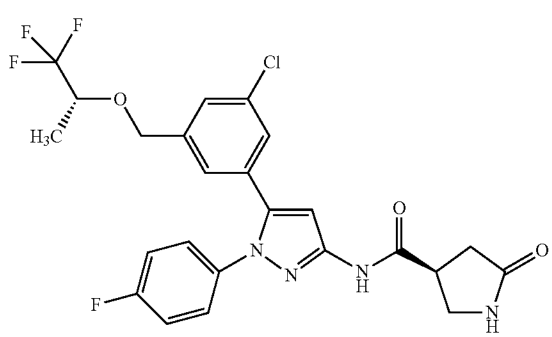 [SMILES: C[C@@H](OCc1cc(Cl)cc(-c2cc(NC(=O)[C@@H]3CNC(=O)C3)nn2-c2ccc(F)cc2)c1)C(F)(F)F] | 1H-NMR (DMSO-D6) : 1.18 (d, 3H, J = 6.5 Hz), 2.36-2.38 (m, 2H), 3.32-3.33 (m, 1H), 3.37-3.41 (m, 1H), 3.46-3.49 (m, 1H), 4.10 (qq, 1H, J = 6.5, 9.4 Hz), 4.57 (d, 1H, J = 12.7 Hz), 4.61 (d, 1H, J = 12.7 Hz), 6.97 (s, 1H), 7.13 (s, 1H), 7.23-7.32 (m, 5H), 7.37 (s, 1H), 7.61 (s, 1H), 10.86 (s, 1H). | 525 | 523 | 2,2,2-trifluoro methyl-1-methyl-ethoxy-methyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 243 | 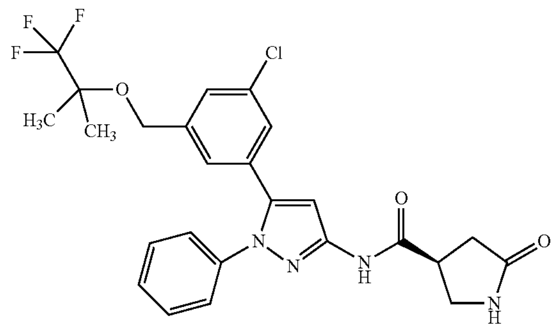 [SMILES: CC(C)(OCc1cc(Cl)cc(-c2cc(NC(=O)[C@@H]3CNC(=O)C3)nn2-c2ccccc2)c1)C(F)(F)F] | 1H-NMR (DMSO-D6) δ: 1.32 (s, 6H), 2.37-2.42 (m, 2H), 3.33-3.53 (m, 3H), 4.53 (s, 2H), 6.98 (s, 1H), 7.16 (s, 1H), 7.19 (s, 1H), 7.23-7.28 (m, 2H), 7.33-7.45 (m, 4H), 7.63 (s, 1H), 10.89 (s, 1H). | 521 | 519 | S-form |
| 244 | 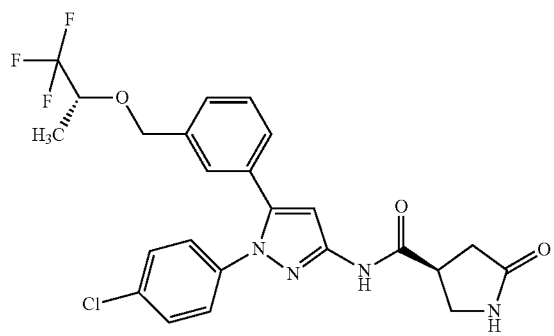 [SMILES: C[C@@H](OCc1cccc(-c2cc(NC(=O)[C@@H]3CNC(=O)C3)nn2-c2ccc(Cl)cc2)c1)C(F)(F)F] | $^1$H-NMR (CDCl$_3$) δ: 1.29 (d, 3H, J = 6.8 Hz), 2.61 (dd, 1H, J = 17.2, 9.6 Hz), 2.78 (dd, 1H, J = 17.2, 8.8 Hz), 3.30-3.40 (m, 1H), 3.61 (t, 1H, J = 8.8 Hz), 3.68-3.82 (m, 2H), 4.57 (d, 1H, J = 12.0 Hz), 4.68 (d, 1H, J = 12.0 Hz), 5.90 (s, 1H), 7.04 (s, 1H), 7.15-7.20 (m, 3H), 7.24 (br s, 1H), 7.28-7.35 (m, 4H), 8.38 (s, 1H). | 507 | 505 | 2,2,2-trifluoro methyl-1-methyl-ethoxy-methyl group: R-form Lactam ring: S-form |
| 245 | 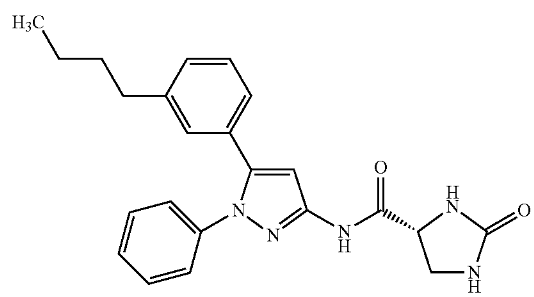 [SMILES: CCCCc1cccc(-c2cc(NC(=O)[C@H]3CNC(=O)N3)nn2-c2ccccc2)c1] | 1H-NMR (DMSO-D6) δ: 0.82 (t, 3H, J = 7.4 Hz), 1.15 (tq, 2H, J = 7.4 Hz, 7.4 Hz), 1.39 (tt, 2H, J = 7.4 Hz, 7.4 Hz), 2.48 (t, 2H, J = 7.4 Hz), 3.36 (dd, 1H, J = 9.2 Hz, 5.6 Hz), 3.59 (dd, 1H, J = 9.2 Hz, 9.2 Hz), 4.32 (dd, 1H, J = 9.2 Hz, 5.6 Hz), 6.33 (s, 1H), 6.60 (s, 1H), 6.90 (s, 1H), 6.98 (s, 1H), 7.09 (d, 1H, J = 7.6 Hz), 7.17 (d, 1H, J = 7.6 Hz), 7.20-7.30 (m, 3H), 7.32-7.43 (m, 3H), 10.70 (s, 1H). | 404 | 402 | R-form |
| 246 | 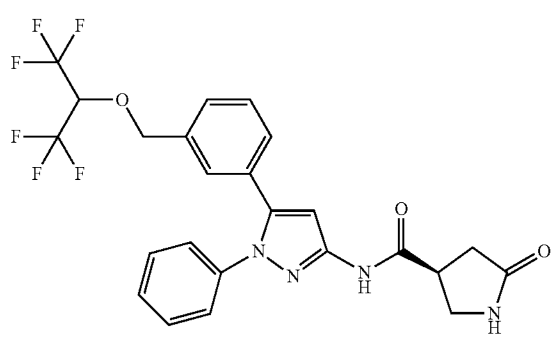 [SMILES: O=C1C[C@H](C(=O)Nc2cc(-c3cccc(COC(C(F)(F)F)C(F)(F)F)c3)n(-c3ccccc3)n2)CN1] | 1H-NMR (DMSO-D6) δ: 2.36-2.38 (m, 2H), 3.32-3.33 (m, 1H), 3.37-3.41 (m, 1H), 3.46-3.49 (m, 1H), 4.85 (m, 2H), 5.53-5.59 (m, 1H), 6.94 (s, 1H), 7.17-7.18 (m, 1H), 7.22-7.24 (m, 2H), 7.34-7.41 (m, 6H), 7.63 (s, 1H), 10.88 (s, 1H). | 527 | 525 | S-form |

TABLE 2-continued

| Example No. | Molecular Structure | NMR (400 MHz) | MS (M + H) | MS (M − H) | Comments |
|---|---|---|---|---|---|
| 247 | 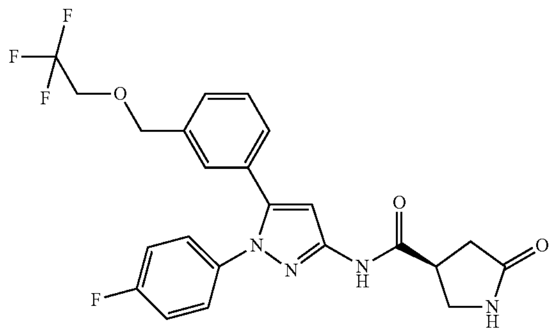 [SMILES: O=C1C[C@H](C(=O)Nc2cc(-c3cccc(COCC(F)(F)F)c3)n(-c3ccc(F)cc3)n2)CN1] | 1H-NMR (DMSO-D6): 2.38-2.40 (m, 2H), 3.32-3.35 (m, 1H), 3.40-3.45 (m, 1H), 3.48-3.52 (m, 1H), 3.98 (q, 2H, J = 9.3 Hz), 4.61 (s, 2H), 6.93 (s, 1H), 7.18-7.40 (m, 8H), 7.63 (s, 1H), 10.86 (s, 1H). | 477 | 475 | S-form |
| 248 | 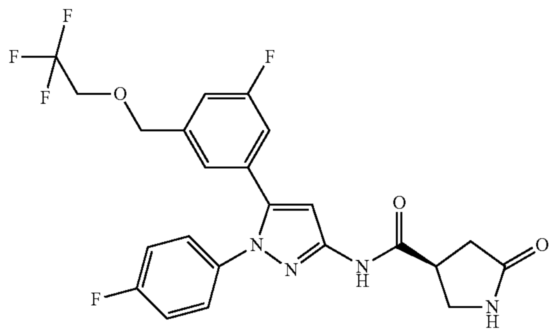 [SMILES: O=C1C[C@H](C(=O)Nc2cc(-c3cc(F)cc(COCC(F)(F)F)c3)n(-c3ccc(F)cc3)n2)CN1] | 1H-NMR (CDCl3) δ: 2.61 (dd, 1H, J = 17.2, 9.6 Hz), 2.78 (dd, 1H, J = 17.2, 8.8 Hz), 3.32-3.42 (m, 1H), 3.61 (t, 1H, J = 8.8 Hz) 3.71 (dd, 1H, J = 9.6, 7.2 Hz), 3.79 (q, 2H, J = 8.8 Hz), 4.59 (s, 2H), 6.04 (s, 1H), 6.89 (d, 1H, J = 9.2 Hz), 6.99-7.10 (m, 5H), 7.19-7.24 (m, 2H), 8.48 (s, 1H). | 495 | 493 | S-form |
| 249 | 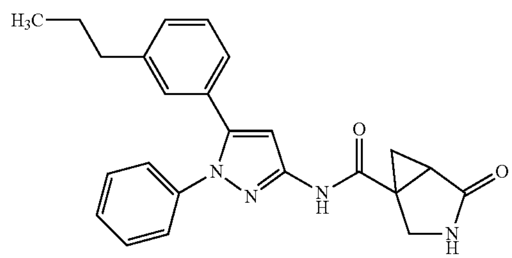 [SMILES: CCCc1cccc(-c2cc(NC(=O)C34CNC(=O)C3C4)nn2-c2ccccc2)c1] | 1H-NMR (CDCl3) δ: 0.83-0.88 (m, 4H), 1.22-1.28 (m, 3H), 1.95 (dd, 1H, J = 9.3, 4.8 Hz), 2.49 (t, 2H, J = 8.5 Hz), 3.60 (d, 1H, J = 10.1 Hz), 4.01 (d, 1H, J = 10.1 Hz), 5.14 (s, 1H), 6.99 (s, 1H), 7.04-7.34 (m, 9H), 7.83 (s, 1H). | 401 | 399 | Single Diastereoisomer (racemate) |
| 250 | 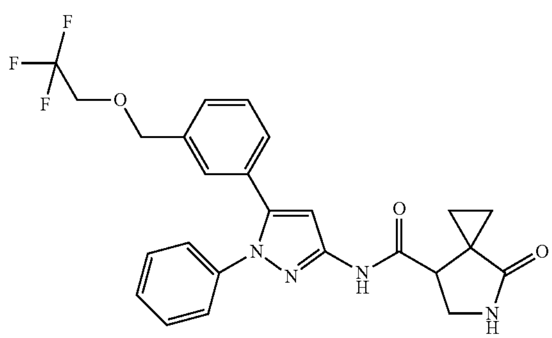 [SMILES: O=C(Nc1cc(-c2cccc(COCC(F)(F)F)c2)n(-c2ccccc2)n1)C1CNC(=O)C12CC2] | 1H-NMR (DMSO-D6) δ: 0.66-0.71 (m, 1H), 0.78-0.82 (m, 1H), 0.88-0.99 (m, 2H), 3.33-3.37 (m, 1H), 3.50-3.54 (m, 1H), 3.56-3.60 (m, 1H), 3.97 (q, 2H, J = 9.3 Hz), 4.61 (s, 2H), 6.93 (s, 1H), 7.15-7.17 (m, 1H), 7.22-7.26 (m, 3H), 7.31-7.41 (m, 5H), 7.72 (s, 1H), 10.73 (s, 1H). | 485 | 483 | Optically active substance |
| 251 | 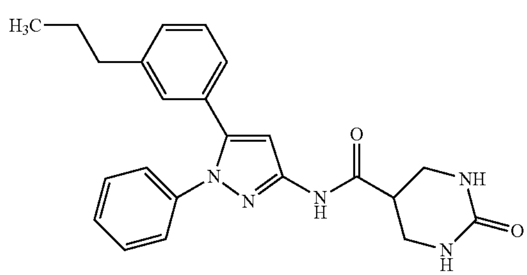 [SMILES: CCCc1cccc(-c2cc(NC(=O)C3CNC(=O)NC3)nn2-c2ccccc2)c1] | 1H-NMR (DMSO-D6) δ: 0.77 (t, 3H, J = 7.4 Hz), 1.44 (tq, 2H, J = 7.4, 7.4 Hz), 2.46 (t, 2H, J = 7.4 Hz), 2.87-2.92 (m, 1H), 3.27-3.30 (m, 4H), 6.23 (s, 2H), 6.88 (s, 1H), 6.99 (s, 1H), 7.05-7.07 (m, 1H), 7.17-7.27 (m, 4H), 7.33-7.41 (m, 3H), 10.91 (s, 1H). | 404 | 401 | None |

TABLE 2-continued

| Example No. | Molecular Structure | NMR (400 MHz) | MS (M + H) | MS (M − H) | Comments |
|---|---|---|---|---|---|
| 252 | 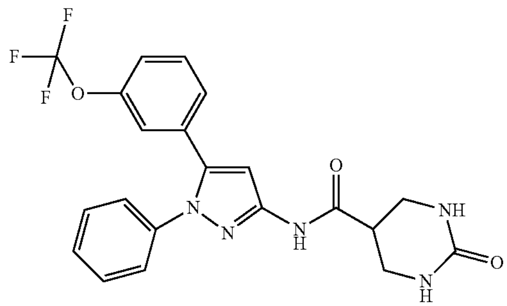 [SMILES: O=C1NCC(C(=O)Nc2cc(-c3cccc(OC(F)(F)F)c3)n(-c3ccccc3)n2)CN1] | 1H-NMR (DMSO-D6) δ: 2.88-2.91 (m, 1H), 3.27-3.31 (m, 4H), 6.23 (s, 2H), 6.99 (s, 1H), 7.08 (s, 1H), 7.24-7.26 (m, 2H), 7.33-7.54 (m, 6H), 10.96 (s, 1H). | 446 | 444 | None |
| 253 | 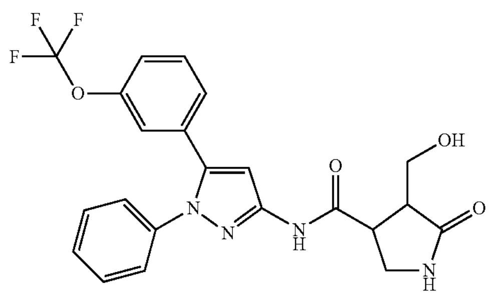 [SMILES: O=C1NCC(C(=O)Nc2cc(-c3cccc(OC(F)(F)F)c3)n(-c3ccccc3)n2)C1CO] | 1H-NMR (DMSO-D6) δ: 2.63-2.70 (m, 1H), 3.20-3.30 (m, 1H), 3.40-3.52 (m, 2H), 3.58-3.72 (m, 2H), 4.86 (t, 1H, J = 4.8 Hz), 7.02 (s, 1H), 7.08 (s, 1H), 7.23-7.28 (m, 2H), 7.33-7.45 (m, 5H), 7.52 (t, 1H, J = 8.0 Hz), 7.70 (s, 1H), 10.87 (s, 1H). | 461 | 459 | transform (racemate) |
| 254 | 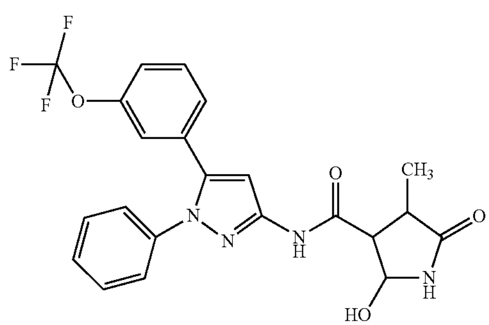 [SMILES: CC1C(=O)NC(O)C1C(=O)Nc1cc(-c2cccc(OC(F)(F)F)c2)n(-c2ccccc2)n1] | 1H-NMR (DMSO-D6) δ: 1.13 (d, 3H, J = 6.3 Hz), 2.52-2.55 (m, 1H), 2.71-2.77 (m, 1H), 3.69-3.73 (m, 1H), 4.21-4.23 (m, 1H), 4.33-4.36 (m, 1H), 6.99 (s, 1H), 7.09 (s, 1H), 7.25-7.27 (m, 2H), 7.34-7.44 (m, 6H), 7.51-7.53 (m, 1H), 11.16 (s, 1H). | 461 | 459 | Single Diastereo isomer (racemate) |
| 255 | 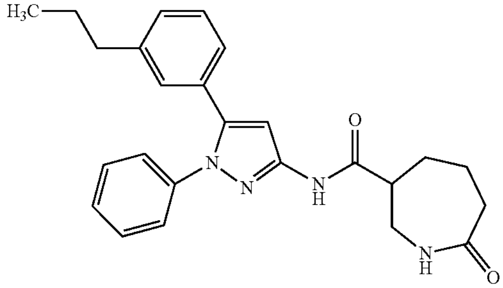 [SMILES: CCCc1cccc(-c2cc(NC(=O)C3CCCC(=O)NC3)nn2-c2ccccc2)c1] | 1H-NMR (DMSO-D6) δ: 0.77 (t, 3H, J = 7.4 Hz), 1.39-1.47 (m, 1H), 1.44 (tq, 2H, J = 7.4, 7.5 Hz), 1.76-2.06 (m, 3H), 2.19-2.22 (m, 1H), 2.45 (t, 2H, J = 7.5 Hz), 2.53-2.56 (m, 1H), 3.12-3.18 (m, 1H), 3.35-3.38 (m, 2H), 6.87 (s, 1H), 7.00 (s, 1H), 7.05-7.07 (m, 1H), 7.16-7.28 (m, 4H), 7.31-7.43 (m, 4H), 10.72 (s, 1H). | 417 | 415 | Optically active substance (Structure Information A) Optical isomer of Example 256 |

TABLE 2-continued

| Example No. | Molecular Structure | NMR (400 MHz) | MS (M + H) | MS (M − H) | Comments |
|---|---|---|---|---|---|
| 256 | 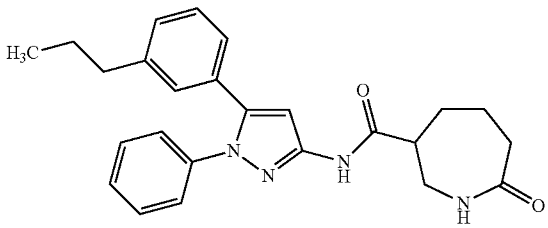 [SMILES: CCCc1cccc(-c2cc(NC(=O)C3CCCC(=O)NC3)nn2-c2ccccc2)c1] | 1H-NMR (DMSO-D6) δ: 0.77 (t, 3H, J = 7.4 Hz), 1.39-1.47 (m, 1H), 1.44 (tq, 2H, J = 7.4, 7.5 Hz), 1.76-2.06 (m, 3H), 2.19-2.22 (m, 1H), 2.45 (t, 2H, J = 7.5 Hz), 2.53-2.56 (m, 1H), 3.12-3.18 (m, 1H), 3.35-3.38 (m, 2H), 6.87 (s, 1H), 7.00 (s, 1H), 7.05-7.07 (m, 1H), 7.16-7.28 (m, 4H), 7.31-7.43 (m, 4H), 10.72 (s, 1H). | 417 | 415 | Optically active substance (Structure Information A) Optical isomer of Example 255 |
| 257 | 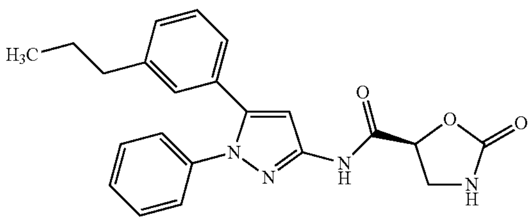 | 1H-NMR (DMSO-D6) δ: 0.77 (t, 3H, J = 7.3 Hz), 1.44 (tq, 2H, J = 7.3, 7.9 Hz), 2.45 (d, 2H, J = 7.9 Hz), 3.52 (dd, 1H, J = 9.0, 5.9 Hz), 3.75 (dd, 1H, J = 9.2, 9.0 Hz), 5.13 (dd, 1H, J = 9.2, 5.9 Hz), 6.89 (s, 1H), 7.01-7.10 (m, 2H), 7.19-7.41 (m, 7H), 7.75 (s, 1H), 11.04 (s, 1H). | 391 | 389 | S-form |
| 258 | 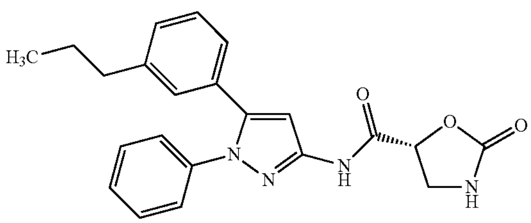 [SMILES: CCCc1cccc(-c2cc(NC(=O)[C@H]3CNC(=O)O3)nn2-c2ccccc2)c1] | 1H-NMR (DMSO-D6) δ: 0.77 (t, 3H, J = 7.3 Hz), 1.44 (tq, 2H, J = 7.3, 7.9 Hz), 2.45 (d, 2H, J = 7.9 Hz), 3.52 (dd, 1H, J = 9.0, 5.9 Hz), 3.75 (dd, 1H, J = 9.2, 9.0 Hz), 5.13 (dd, 1H, J = 9.2, 5.9 Hz), 6.89 (s, 1H), 7.01-7.10 (m, 2H), 7.19-7.41 (m, 7H), 7.75 (s, 1H), 11.04 (s, 1H). | 391 | 389 | R-form |
| 259 | 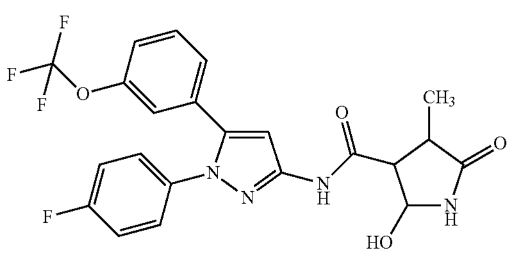 [SMILES: CC1C(=O)NC(O)C1C(=O)Nc1cc(-c2cccc(OC(F)(F)F)c2)n(-c2ccc(F)cc2)n1] | 1H-NMR (DMSO-D6) δ: 1.13 (d, 3H, J = 6.4 Hz), 2.74 (ddd, 1H, J = 9.6, 9.0, 4.0 Hz), 3.72 (dq, 1H, J = 12.8, 8.8 Hz), 4.22 (dd, 1H, J = 10.0, 10.0 Hz), 4.35 (dd, 1H, J = 10.8, 4.0 Hz), 6.99 (s, 1H), 7.10 (br s, 1H), 7.24-7.39 (m, 6H), 7.42 (br s, 1H), 7.53 (t, 1H, J = 8.4 Hz), 11.16 (s, 1H). | 479 | 477 | Single Diastereo isomer (racemate) |
| 260 | 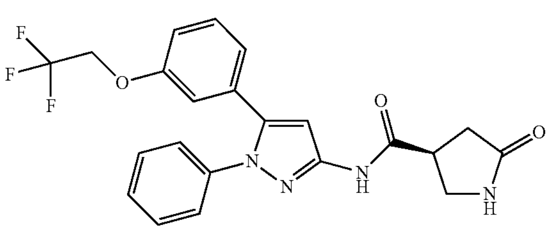 [SMILES: O=C1C[C@H](C(=O)Nc2cc(-c3cccc(OCC(F)(F)F)c3)n(-c3ccccc3)n2)CN1] | 1H-NMR (DMSO-D6) δ: 2.39 (d, 2H, J = 8.5 Hz), 3.30-3.54 (m, 3H), 4.73 (q, 2H, J = 8.9 Hz), 6.80 (d, 1H, J = 7.7 Hz), 6.97 (s, 1H), 6.99-7.07 (m, 2H), 7.22-7.44 (m, 6H), 7.64 (s, 1H), 10.87 (s, 1H). | 445 | 443 | S-form |

TABLE 2-continued

| Example No. | Molecular Structure | NMR (400 MHz) | MS (M + H) | MS (M − H) | Comments |
|---|---|---|---|---|---|
| 261 | 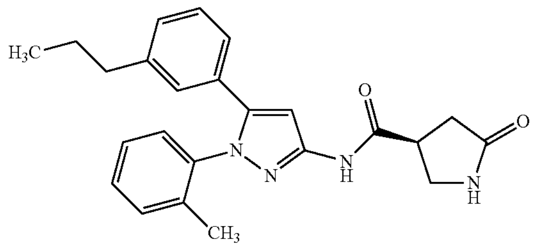 [SMILES: CCCc1cccc(-c2cc(NC(=O)[C@@H]3CNC(=O)C3)nn2-c2ccccc2C)c1] | 1H-NMR (DMSO-D6) δ: 0.71 (t, 3H, J = 7.5 Hz), 1.33-1.44 (m, 2H), 1.89 (s, 3H), 2.35-2.46 (m, 4H), 3.31-3.53 (m, 3H), 6.92-6.96 (m, 2H), 6.98-7.03 (m, 1H), 7.07-7.12 (m, 1H), 7.16-7.40 (m, 5H), 7.64 (s, 1H), 10.76 (s, 1H). | 403 | 401 | S-form |
| 262 | 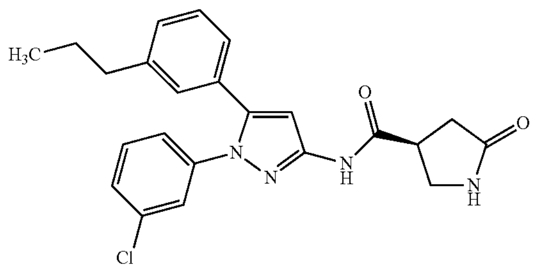 [SMILES: CCCc1cccc(-c2cc(NC(=O)[C@@H]3CNC(=O)C3)nn2-c2cccc(Cl)c2)c1] | 1H-NMR (DMSO-D6) δ: 0.78 (t, 3H, J = 7.5 Hz), 1.41-1.52 (m, 2H), 2.39 (d, 2H, J = 8.5 Hz), 6.91 (s, 1H), 7.02-7.05 (m, 1H), 7.10-7.24 (m, 3H), 7.28-7.34 (m, 2H), 7.38-7.42 (m, 2H), 7.64 (s, 1H), 10.89 (s, 1H). | 423 | 421 | S-form |
| 263 | 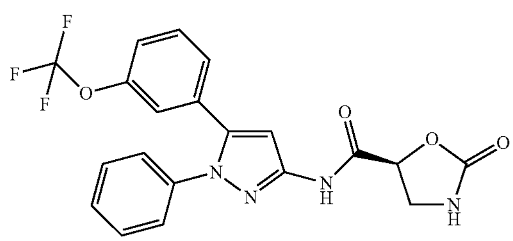 [SMILES: O=C1NC[C@@H](C(=O)Nc2cc(-c3cccc(OC(F)(F)F)c3)n(-c3ccccc3)n2)O1] | 1H-NMR (DMSO-D6) δ: 3.52 (dd, 1H, J = 9.1, 6.0 Hz), 3.76 (dd, 1H, J = 9.2, 9.1 Hz), 5.13 (dd, 1H, J = 9.2, 6.0 Hz), 7.01 (s, 1H), 7.09 (s, 1H), 7.25-7.28 (m, 2H), 7.36-7.45 (m, 5H), 7.53 (t, 1H, J = 8.0 Hz), 7.75 (s, 1H), 11.09 (s, 1H). | 433 | 431 | S-form |
| 264 | 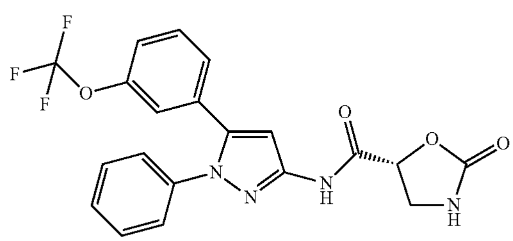 [SMILES: O=C1NC[C@H](C(=O)Nc2cc(-c3cccc(OC(F)(F)F)c3)n(-c3ccccc3)n2)O1] | 1H-NMR (DMSO-D6) δ: 3.52 (dd, 1H, J = 9.1, 6.0 Hz), 3.76 (dd, 1H, J = 9.2, 9.1 Hz), 5.13 (dd, 1H, J = 9.2, 6.0 Hz), 7.01 (s, 1H), 7.09 (s, 1H), 7.25-7.28 (m, 2H), 7.36-7.45 (m, 5H), 7.53 (t, 1H, J = 8.0 Hz), 7.75 (s, 1H), 11.09 (s, 1H). | 433 | 431 | R-form |
| 265 | 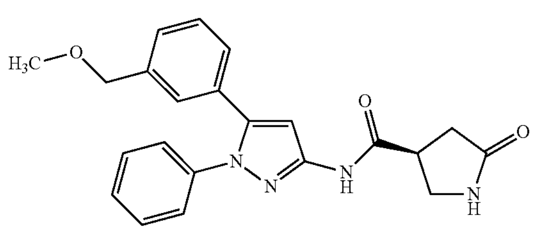 [SMILES: COCc1cccc(-c2cc(NC(=O)[C@@H]3CNC(=O)C3)nn2-c2ccccc2)c1] | 1H-NMR (DMSO-D6) δ: 2.37-2.40 (m, 2H), 3.18 (s, 3H), 3.34-3.36 (m, 1H), 3.40-3.44 (m, 1H), 3.48-3.52 (m, 1H), 4.35 (s, 2H), 6.91 (s, 1H), 7.11-7.13 (m, 1H), 7.20-7.25 (m, 3H), 7.28-7.41 (m, 5H), 7.63 (s, 1H), 10.86 (s, 1H). | 391 | 389 | S-form |

TABLE 2-continued

| Example No. | Molecular Structure | NMR (400 MHz) | MS (M + H) | MS (M − H) | Comments |
|---|---|---|---|---|---|
| 266 | 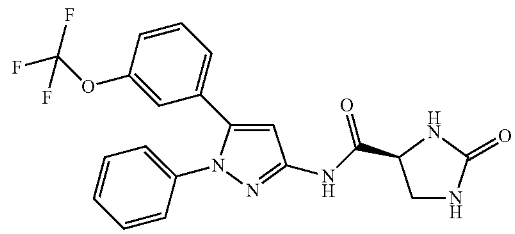 [SMILES: O=C1NC[C@@H](C(=O)Nc2cc(-c3cccc(OC(F)(F)F)c3)n(-c3ccccc3)n2)N1] | 1H-NMR (DMSO-D6) δ: 3.36 (dd, 1H, J = 9.0, 6.4 Hz), 3.60 (dd, 1H, J = 9.4, 9.0 Hz), 4.32 (dd, 1H, J = 9.4, 6.4 Hz), 6.33 (s, 1H), 6.60 (s, 1H), 7.01 (s, 1H), 7.09 (s, 1H), 7.24-7.28 (m, 2H), 7.35-7.46 (m, 5H), 7.53 (t, 1H, J = 7.9 Hz), 10.74 (s, 1H). | 432 | 430 | S-form |
| 267 | 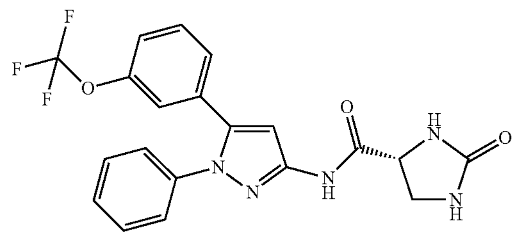 [SMILES: O=C1NC[C@H](C(=O)Nc2cc(-c3cccc(OC(F)(F)F)c3)n(-c3ccccc3)n2)N1] | 1H-NMR (DMSO-D6) δ: 3.36 (dd, 1H, J = 9.0, 6.4 Hz), 3.60 (dd, 1H, J = 9.4, 9.0 Hz), 4.32 (dd, 1H, J = 9.4, 6.4 Hz), 6.33 (s, 1H), 6.60 (s, 1H), 7.01 (s, 1H), 7.09 (s, 1H), 7.24-7.28 (m, 2H), 7.35-7.46 (m, 5H), 7.53 (t, 1H, J = 7.9 Hz), 10.74 (s, 1H). | 432 | 430 | R-form |
| 268 | 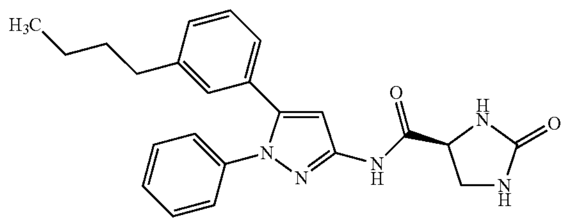 [SMILES: CCCCc1cccc(-c2cc(NC(=O)[C@@H]3CNC(=O)N3)nn2-c2ccccc2)c1] | 1H-NMR (DMSO-D6) δ: 0.82 (t, 3H, J = 7.4 Hz), 1.15 (tq, 2H, J = 7.4 Hz, 7.4 Hz), 1.39 (tt, 2H, J = 7.4 Hz, 7.4 Hz), 2.48 (t, 2H, J = 7.4 Hz), 3.36 (dd, 1H, J = 9.2 Hz, 5.6 Hz), 3.59 (dd, 1H, J = 9.2 Hz, 9.2 Hz), 4.32 (dd, 1H, J = 9.2 Hz, 5.6 Hz), 6.33 (s, 1H), 6.60 (s, 1H), 6.90 (s, 1H), 6.98 (s, 1H), 7.09 (d, 1H, J = 7.6 Hz), 7.17 (d, 1H, J = 7.6 Hz), 7.20-7.30 (m, 3H), 7.32-7.43 (m, 3H), 10.70 (s, 1H). | 404 | 402 | S-form |
| 269 | 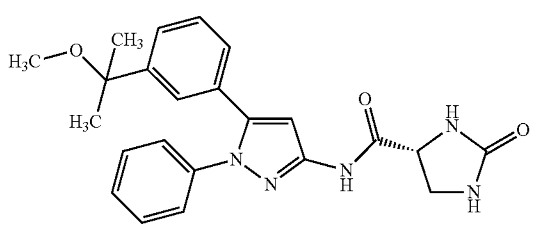 [SMILES: COC(C)(C)c1cccc(-c2cc(NC(=O)[C@H]3CNC(=O)N3)nn2-c2ccccc2)c1] | 1H-NMR (DMSO-D6) δ: 1.27 (s, 6H), 2.77 (s, 3H), 3.32-3.37 (br m, 1H), 3.60 (t, 1H, J = 9.3 Hz), 4.33 (dd, 1H, J = 9.3, 5.3 Hz), 6.33 (s, 1H), 6.60 (s, 1H), 6.93 (s, 1H), 7.05 (s, 1H), 7.22-7.42 (m, 8H), 10.69 (s, 1H). | 420 | 418 | R-form |
| 270 | 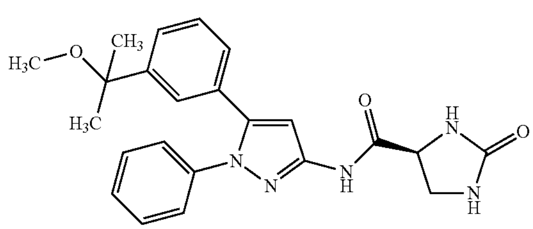 [SMILES: COC(C)(C)c1cccc(-c2cc(NC(=O)[C@@H]3CNC(=O)N3)nn2-c2ccccc2)c1] | 1H-NMR (DMSO-D6) δ: 1.27 (s, 6H), 2.77 (s, 3H), 3.32-3.37 (br m, 1H), 3.60 (t, 1H, J = 9.3 Hz), 4.33 (dd, 1H, J = 9.3, 5.3 Hz), 6.33 (br s, 1H), 6.60 (br s, 1H), 6.93 (s, 1H), 7.05 (br s, 1H), 7.22-7.42 (m, 8H), 10.69 (br s, 1H). | 420 | 418 | S-form |

TABLE 2-continued

| Example No. | Molecular Structure | NMR (400 MHz) | MS (M + H) | MS (M − H) | Comments |
|---|---|---|---|---|---|
| 271 | 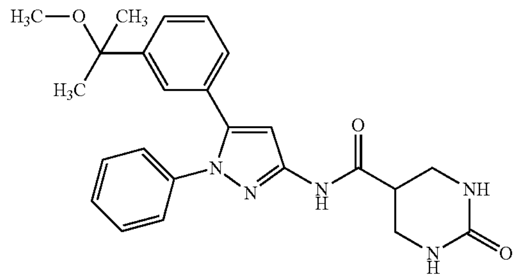 [SMILES: COC(C)(C)c1cccc(-c2cc(NC(=O)C3CNC(=O)NC3)nn2-c2ccccc2)c1] | 1H-NMR (DMSO-D6) δ: 1.27 (s, 6H), 2.77 (s, 3H), 2.85-2.94 (m, 1H), 3.23-3.34 (m, 4H), 6.25 (br s, 2H), 6.91 (s, 1H), 7.05 (br s, 1H), 7.22-7.27 (m, 3H), 7.32-7.43 (m, 5H), 10.92 (br s, 1H). | 434 | 432 | None |
| 272 | 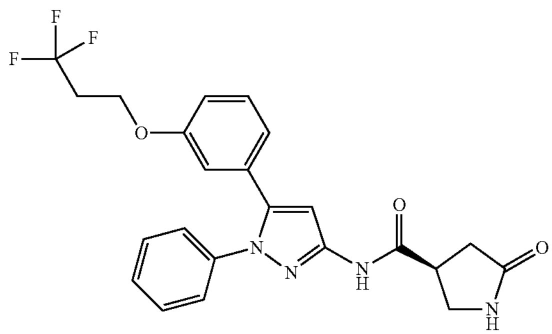 [SMILES: O=C1C[C@H](C(=O)Nc2cc(-c3cccc(OCCC(F)(F)F)c3)n(-c3ccccc3)n2)CN1] | 1H-NMR (DMSO-D6) δ: 2.39 (d, 2H, J = 8.4 Hz), 2.62-2.75 (m, 2H), 3.30-3.54 (m, 3H), 4.11 (t, 2H, J = 6.0 Hz), 6.78-6.83 (m, 2H), 6.92-6.97 (m, 2H), 7.22-7.43 (m, 6H), 7.64 (s, 1H), 10.86 (s, 1H). | 459 | 457 | S-form |
| 273 | 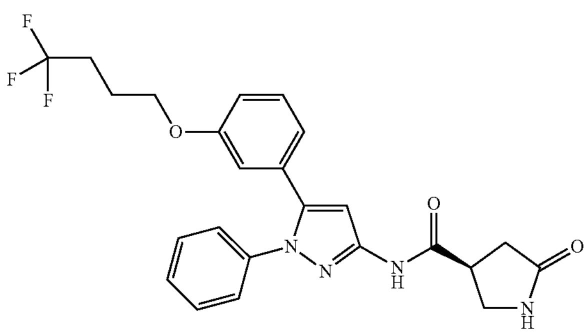 [SMILES: O=C1C[C@H](C(=O)Nc2cc(-c3cccc(OCCCC(F)(F)F)c3)n(-c3ccccc3)n2)CN1] | 1H-NMR (DMSO-D6) δ: 1.81-1.90 (m, 2H), 2.29-2.43 (m, 4H), 3.29-3.53 (m, 3H), 3.95 (t, 2H, J = 6.2 Hz), 6.75-6.82 (m, 2H), 6.90-6.96 (m, 2H), 7.22-7.29 (m, 3H), 7.31-7.44 (m, 3H), 7.64 (s, 1H), 10.86 (s, 1H). | 473 | 471 | S-form |
| 274 | 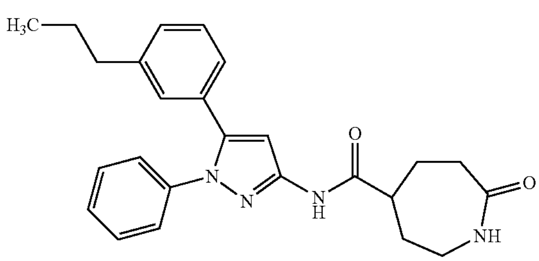 [SMILES: CCCc1cccc(-c2cc(NC(=O)C3CCNC(=O)CC3)nn2-c2ccccc2)c1] | 1H-NMR (DMSO-D6) δ: 0.77 (t, 3H, J = 7.3 Hz), 1.39-1.47 (m, 2H), 1.52-1.60 (m, 2H), 1.86-1.94 (m, 2H), 2.26-2.31 (m, 1H), 2.44-2.48 (m, 3H), 2.66-2.69 (m, 1H), 3.12-3.16 (m, 2H), 6.88 (s, 1H), 7.00 (s, 1H), 7.05-7.07 (m, 1H), 7.15-7.17 (m, 1H), 7.20-7.28 (m, 3H), 7.31-7.41 (m, 3H), 7.49-7.50 (m, 1H), 10.69 (s, 1H). | 417 | 415 | racemate |

TABLE 2-continued

| Example No. | Molecular Structure | NMR (400 MHz) | MS (M + H) | MS (M − H) | Comments |
|---|---|---|---|---|---|
| 275 | 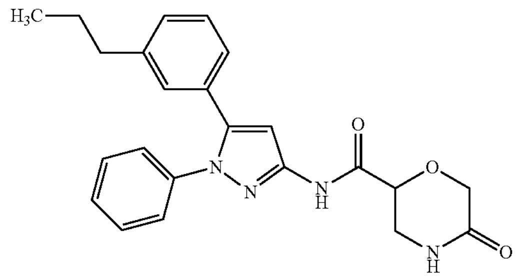 [SMILES: CCCc1cccc(-c2cc(NC(=O)C3CNC(=O)CO3)nn2-c2ccccc2)c1] | 1H-NMR (DMSO-D6) δ: 0.77 (t, 3H, J = 7.4 Hz), 1.44 (tq, 2H, J = 7.5, 7.4 Hz), 2.46 (t, 2H, J = 7.5 Hz), 3.43-3.47 (m, 2H), 4.13 (d, 1H, J = 16.1 Hz), 4.22 (d, 1H, J = 16.1 Hz), 4.46 (dd, 1H, J = 8.4, 4.4 Hz), 6.87 (s, 1H), 7.01 (s, 1H), 7.06-7.08 (m, 1H), 7.16-7.18 (m, 1H), 7.22-7.29 (m, 3H), 7.35-7.42 (m, 3H), 8.14 (s, 1H), 10.61 (s, 1H). | 405 | 403 | Optically active substance (Structure Information B) Optical isomer of Example 257 |
| 276 | 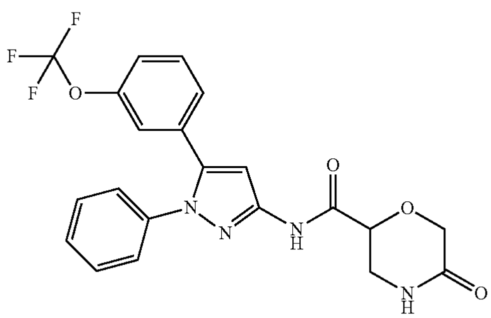 [SMILES: O=C1COC(C(=O)Nc2cc(-c3cccc(OC(F)(F)F)c3)n(-c3ccccc3)n2)CN1] | 1H-NMR (DMSO-D6) δ: 3.43-3.47 (m, 2H), 4.13 (d, 1H, J = 16.3 Hz), 4.22 (d, 1H, J =16.3 Hz), 4.47 (dd, 1H, J = 8.6, 4.4 Hz), 6.98 (s, 1H), 7.09 (s, 1H), 7.25-7.28 (m, 2H), 7.35-7.45 (m, 5H), 7.52 (t, 1H, J = 7.9 Hz), 8.14 (s, 1H), 10.68 (s, 1H). | 447 | 445 | Optically active substance (The same configuration as Example 275) Optical isomer of Example 278 |
| 277 | 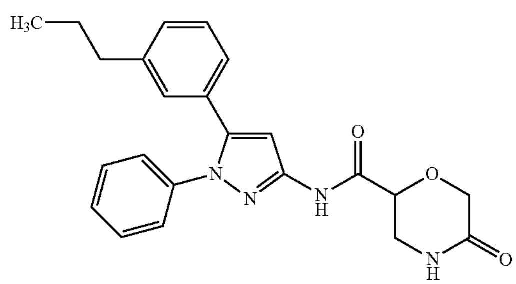 [SMILES: CCCc1cccc(-c2cc(NC(=O)C3CNC(=O)CO3)nn2-c2ccccc2)c1] | 1H-NMR (CDCl3) δ: 0.84 (t, 3H, J = 7.2 Hz), 1.51 (tq, 2H, J = 7.2, 8.0 Hz), 2.49 (t, 2H, J = 8.0 Hz), 3.61 (t, 1H, J = 12 Hz), 3.82-3.87 (m, 1H), 4.33 (d, 1H, J = 17.2 Hz), 4.42-4.48 (m, 2H), 6.13 (s, 1H), 7.00 (s, 1H), 7.04-7.08 (m, 2H), 7.13 (d, 1H, J = 7.6 Hz), 7.20 (d, 1H, J = 8.0 Hz), 7.23-7.26 (m, 2H), 7.28-7.36 (m, 3H), 8.90 (s, 1H). | 405 | 403 | Optically active substance (Structure Information B) Optical isomer of Example 275 |
| 278 | 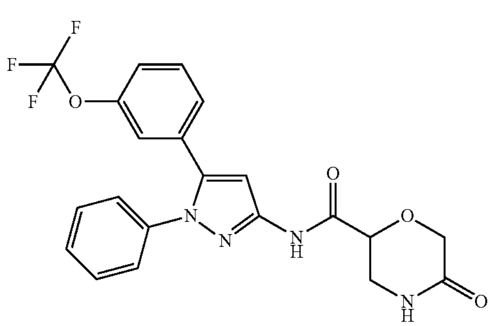 [SMILES: O=C1COC(C(=O)Nc2cc(-c3cccc(OC(F)(F)F)c3)n(-c3ccccc3)n2)CN1] | 1H-NMR (CDCl3) δ: 3.61 (t, 1H, J = 12 Hz), 3.85 (m, 1H), 4.33 (d, 1H, J = 17.2 Hz), 4.42-4.48 (m, 2H), 6.12 (s, 1H), 7.06 (m, 2H), 7.17 (d, 1H, J = 8.4 Hz), 7.21-7.25 (m, 3H), 7.33-7.40 (m, 4H), 8.91 (s, 1H). | 447 | 445 | Optically active substance (The same configuration as Example 277) Optical isomer of Example 276 |

| Example No. | Molecular Structure | NMR (400 MHz) | MS (M + H) | MS (M − H) | Comments |
|---|---|---|---|---|---|
| 279 | 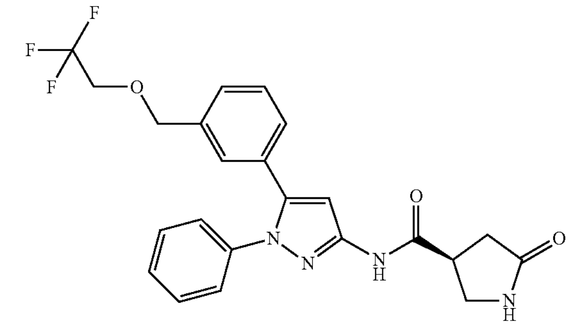 [SMILES: O=C1C[C@H](C(=O)Nc2cc(-c3cccc(COCC(F)(F)F)c3)n(-c3ccccc3)n2)CN1] | 1H-NMR (DMSO-D6) δ: 2.37-2.39 (m, 2H), 3.34-3.36 (m, 1H), 3.38-3.44 (m, 1H), 3.48-3.52 (m, 1H), 3.95 (d, 1H, J = 9.5 Hz), 4.00 (d, 1H, J = 9.5 Hz), 4.61 (s, 2H), 6.93 (s, 1H), 7.15-7.17 (m, 1H), 7.22-7.26 (m, 3H), 7.32-7.41 (m, 6H), 7.64 (s, 1H), 10.87 (s, 1H). | 459 | 457 | S-form |
| 280 | 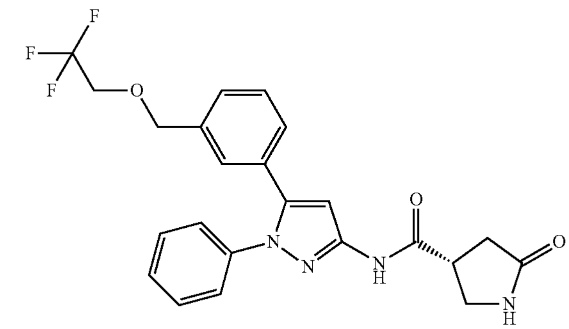 | 1H-NMR (DMSO-D6) δ: 2.37-2.39 (m, 2H), 3.34-3.36 (m, 1H), 3.38-3.44 (m, 1H), 3.48-3.52 (m, 1H), 3.95 (d, 1H, J = 9.5 Hz), 4.00 (d, 1H, J = 9.5 Hz), 4.61 (s, 2H), 6.93 (s, 1H), 7.15-7.17 (m, 1H), 7.22-7.26 (m, 3H), 7.32-7.41 (m, 6H), 7.64 (s, 1H), 10.87 (s, 1H). | 459 | 457 | R-form |
| 281 | 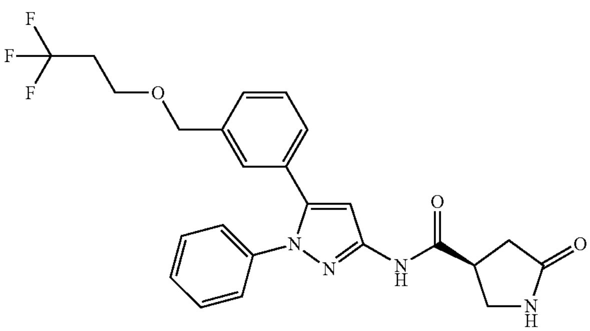 [SMILES: O=C1C[C@H](C(=O)Nc2cc(-c3cccc(COCCC(F)(F)F)c3)n(-c3ccccc3)n2)CN1] | 1H-NMR (DMSO-D6) δ: 2.39 (d, 2H, J = 8.4 Hz), 2.48-2.57 (m, 2H), 3.32-3.52 (m, 3H), 3.54 (t, 2H, J = 6.0 Hz), 4.45 (s, 2H), 6.91 (s, 1H), 7.12 (d, 1H, J = 7.6 Hz), 7.22-7.24 (m, 3H), 7.29-7.41 (m, 5H), 7.64 (s, 1H), 10.87 (s, 1H). | 473 | 471 | S-form |
| 282 | 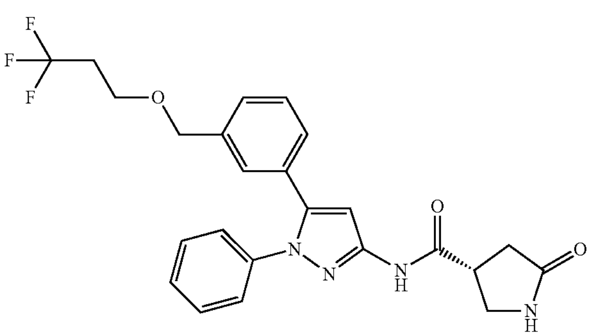 | 1H-NMR (DMSO-D6) δ: 2.39 (d, 2H, J = 8.4 Hz), 2.48-2.57 (m, 2H), 3.32-3.52 (m, 3H), 3.54 (t, 2H, J = 6.0 Hz), 4.45 (s, 2H), 6.91 (s, 1H), 7.12 (d, 1H, J = 7.6 Hz), 7.22-7.24 (m, 3H), 7.29-7.41 (m, 5H), 7.64 (s, 1H), 10.87 (s, 1H). | 473 | 471 | R-form |

TABLE 2-continued

| Example No. | Molecular Structure | NMR (400 MHz) | MS (M + H) | MS (M − H) | Comments |
|---|---|---|---|---|---|
| 283 | 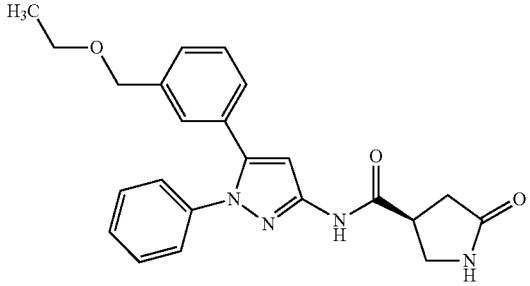 | 1H-NMR (DMSO-D6) δ: 1.07 (t, 3H, J = 6.8 Hz), 2.39 (d, 2H, J = 8.4 Hz), 3.31-3.37 (m, 3H), 3.38-3.53 (m, 2H), 4.39 (s, 2H), 6.91 (s, 1H), 7.13 (d, 1H, J = 7.6 Hz), 7.19 (s, 1H), 7.22-7.24 (m, 2H), 7.28-7.41 (m, 5H), 7.63 (s, 1H), 10.87 (s, 1H). | 405 | 403 | S-form |
| 284 | 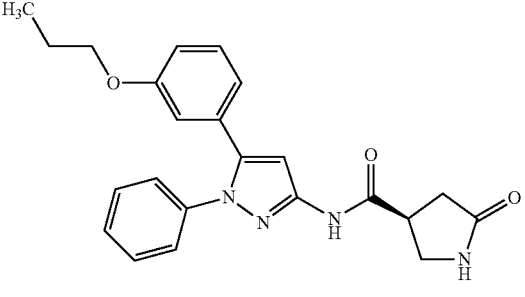 [SMILES: CCOCc1cccc(-c2cc(NC(=O)[C@@H]3CNC(=O)C3)nn2-c2ccccc2)c1] | 1H-NMR (CDCl3) δ: 0.98 (t, 3H, J = 7.6 Hz), 1.72 (tq, 2H, J = 7.6, 6.8 Hz), 2.43 (dd, 1H, J = 16.4, 9.2 Hz), 2.72 (dd, 1H, J = 16.4, 8.4 Hz), 3.10-3.20 (m, 1H), 3.43 (t, 1H, J = 8.8 Hz), 3.60 (dd, 1H, J = 9.6, 7.2 Hz), 3.78 (t, 2H, J = 6.8 Hz), 6.34 (s, 1H), 6.74-6.80 (m, 2H), 6.85 (dd, 1H, J = 8.0, 2.0 Hz), 7.05 (s, 1H), 7.18 (t, 1H, J = 8.0 Hz), 7.26-7.38 (m, 5H), 9.37 (s, 1H). | 405 | 403 | S-form |
| 285 | 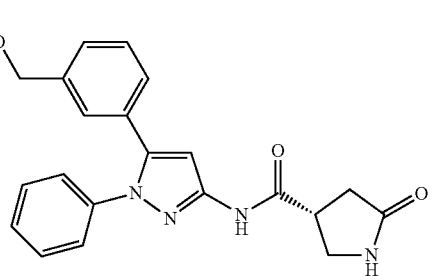 | 1H-NMR (CDCl3) δ: 0.98 (t, 3H, J = 7.6 Hz), 1.72 (tq, 2H, J = 7.6, 6.8 Hz), 2.43 (dd, 1H, J = 16.4, 9.2 Hz), 2.72 (dd, 1H, J = 16.4, 8.4 Hz), 3.10-3.20 (m, 1H), 3.43 (t, 1H, J = 8.8 Hz), 3.60 (dd, 1H, J = 9.6, 7.2 Hz), 3.78 (t, 2H, J = 6.8 Hz), 6.34 (s, 1H), 6.74-6.80 (m, 2H), 6.85 (dd, 1H, J = 8.0, 2.0 Hz), 7.05 (s, 1H), 7.18 (t, 1H, J = 8.0 Hz), 7.26-7.38 (m, 5H), 9.37 (s, 1H). | 405 | 403 | R-form |
| 286 | 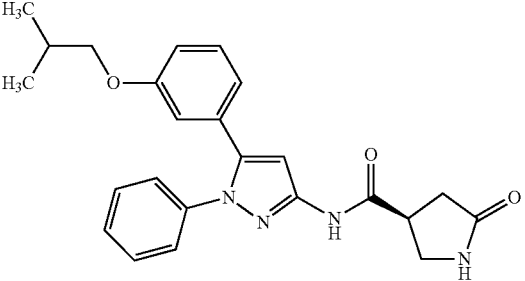 [SMILES: CC(C)COc1cccc(-c2cc(NC(=O)[C@@H]3CNC(=O)C3)nn2-c2ccccc2)c1] | 1H-NMR (CDCl3) δ: 0.97 (d, 6H, J = 6.4 Hz), 1.93-2.04 (m, 1H), 2.43 (dd, 1H, J = 16.8, 9.6 Hz), 2.72 (dd, 1H, J = 16.8, 8.4 Hz), 3.11-3.19 (m, 1H), 3.43 (t, 1H, J = 9.2 Hz), 3.54-3.64 (m, 3H), 6.35 (s, 1H), 6.72-6.89 (m, 3H), 7.05 (s, 1H), 7.17 (t, 1H, J = 8.0 Hz), 7.23-7.39 (m, 5H), 9.38 (s, 1H). | 419 | 417 | S-form |

TABLE 2-continued

| Example No. | Molecular Structure | NMR (400 MHz) | MS (M + H) | MS (M − H) | Comments |
|---|---|---|---|---|---|
| 287 | 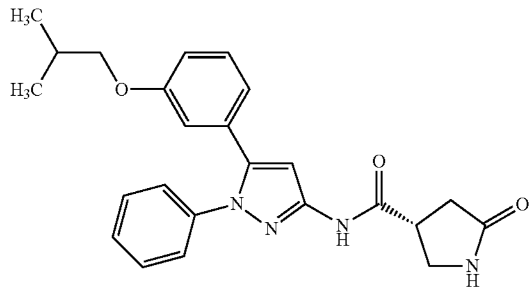 [SMILES: CC(C)COc1cccc(-c2cc(NC(=O)[C@H]3CNC(=O)C3)nn2-c2ccccc2)c1] | ¹H-NMR (CDCl₃) δ: 0.97 (d, 6H, J = 6.4 Hz), 1.93-2.04 (m, 1H), 2.43 (dd, 1H, J = 16.8, 9.6 Hz), 2.72 (dd, 1H, J = 16.8, 8.4 Hz), 3.11-3.19 (m, 1H), 3.43 (t, 1H, J = 9.2 Hz), 3.54-3.64 (m, 3H), 6.35 (s, 1H), 6.72-6.89 (m, 3H), 7.05 (s, 1H), 7.17 (t, 1H, J = 8.0 Hz), 7.23-7.39 (m, 5H), 9.38 (s, 1H). | 419 | 417 | R-form |
| 288 | 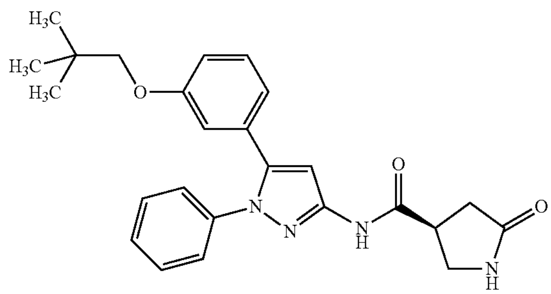 [SMILES: CC(C)(C)COc1cccc(-c2cc(NC(=O)[C@@H]3CNC(=O)C3)nn2-c2ccccc2)c1] | ¹H-NMR (CDCl₃) δ: 0.99 (s, 9H), 2.43 (dd, 1H, J = 16.8, 9.6 Hz), 2.72 (dd, 1H, J = 16.8, 8.4 Hz), 3.10-3.20 (m, 1H), 3.47-3.58 (m, 3H), 3.60 (dd, 1H, J = 9.6, 7.2 Hz), 6.34 (s, 1H), 6.71 (d, 1H, J = 7.6 Hz), 6.82-6.89 (m, 2H), 7.06 (s, 1H), 7.15 (t, 1H, J = 7.6 Hz), 7.24-7.39 (m, 5H), 9.39 (s, 1H). | 433 | 431 | S-form |
| 289 | 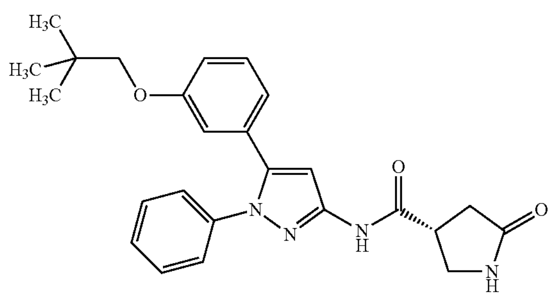 [SMILES: CC(C)(C)COc1cccc(-c2cc(NC(=O)[C@H]3CNC(=O)C3)nn2-c2ccccc2)c1] | ¹H-NMR (CDCl₃) δ: 0.99 (s, 9H), 2.43 (dd, 1H, J = 16.8, 9.6 Hz), 2.72 (dd, 1H, J = 16.8, 8.4 Hz), 3.10-3.20 (m, 1H), 3.47-3.58 (m, 3H), 3.60 (dd, 1H, J = 9.6, 7.2 Hz), 6.34 (s, 1H), 6.71 (d, 1H, J = 7.6 Hz), 6.82-6.89 (m, 2H), 7.06 (s, 1H), 7.15 (t, 1H, J = 7.6 Hz), 7.24-7.39 (m, 5H), 9.39 (s, 1H). | 433 | 431 | R-form |
| 290 | 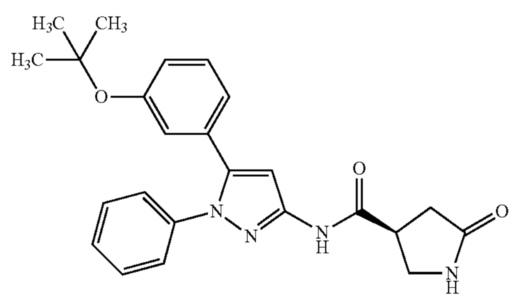 [SMILES: CC(C)(C)Oc1cccc(-c2cc(NC(=O)[C@@H]3CNC(=O)C3)nn2-c2ccccc2)c1] | 1H-NMR (DMSO-D6) δ: 1.11 (s, 9H), 2.36-2.41 (m, 2H), 3.30-3.53 (m, 3H), 6.67 (t, 1H, J = 1.8 Hz), 6.89 (s, 1H), 6.93-6.97 (m, 1H), 7.06-7.10 (m, 1H), 7.22-7.44 (m, 6H), 7.63 (s, 1H), 10.85 (s, 1H). | 419 | 417 | S-form |
| 291 | 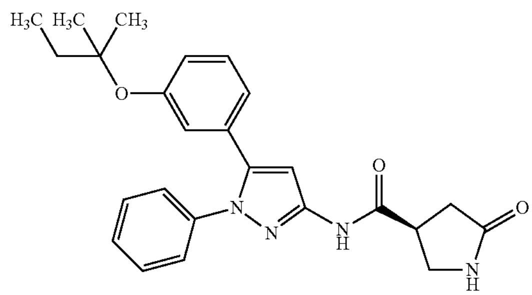 [SMILES: CCC(C)(C)Oc1cccc(-c2cc(NC(=O)[C@@H]3CNC(=O)C3)nn2-c2ccccc2)c1] | 1H-NMR (DMSO-D6) δ:0.81 (t, 3H, J = 7.5 Hz), 1.02 (s, 6H), 1.41 (q, 2H, J = 7.5 Hz), 2.37-2.41 (m, 2H), 3.30-3.53 (m, 3H), 6.63 (t, 1H, J = 2.0 Hz), 6.89 (s, 1H), 6.91-6.95 (m, 1H), 7.07-7.11 (m, 1H), 7.22-7.26 (m, 2H), 7.28-7.37 (m, 2H), 7.38-7.44 (m, 2H), 7.63 (s, 1H), 10.85 (s, 1H). | 433 | 431 | S-form |

TABLE 2-continued

| Example No. | Molecular Structure | NMR (400 MHz) | MS (M + H) | MS (M − H) | Comments |
|---|---|---|---|---|---|
| 292 | 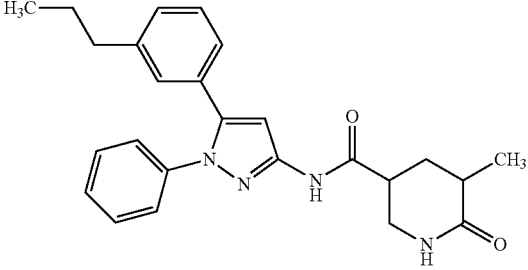 [SMILES: CCCc1cccc(-c2cc(NC(=O)C3CNC(=O)C(C)C3)nn2-c2ccccc2)c1] | 1H-NMR (DMSO-D6) δ: 0.77 (t, 3H, J = 7.5 Hz), 1.12 (d, 3H, J = 7.3 Hz), 1.39-1.50 (m, 2H), 1.66-1.74 (m, 1H), 2.08-2.17 (m, 1H), 2.36 (q, 1H, J = 6.9 Hz), 2.46 (t, 2H, J = 7.5 Hz), 2.93-3.01 (m, 1H), 3.26-3.39 (m, 2H), 6.89 (s, 1H), 6.99-7.01 (m, 1H), 7.04-7.09 (m, 1H), 7.14-7.19 (m, 1H), 7.20-7.45 (m, 7H), 10.84 (s, 1H). | 417 | 415 | Single Diastereo isomer (racemate) Geometrical isomer of Example 293 |
| 293 | 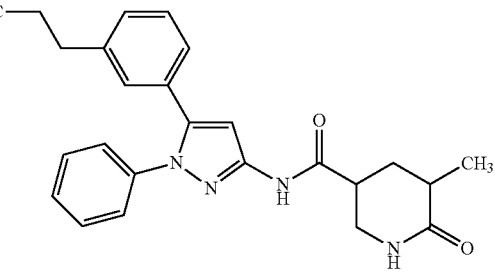 | 1H-NMR (DMSO-D6) δ: 0.77 (t, 3H, J = 7.5 Hz), 1.09 (d, 3H, J = 7.3 Hz), 1.39-1.49 (m, 2H), 1.62 (q, 1H, J = 12.4 Hz), 2.05-2.13 (m, 1H), 2.18-2.28 (m, 1H), 2.46 (t, 2H, J = 7.5 Hz), 2.88-2.98 (m, 1H), 3.24-3.37 (m, 2H), 6.88 (s, 1H), 6.98-7.01 (m, 1H), 7.05-7.09 (m, 1H), 7.15-7.19 (m, 1H), 7.20-7.29 (m, 3H), 7.31-7.44 (m, 4H), 10.81 (s, 1H). | 417 | 415 | Single Diastereo isomer (racemate) Geometrical isomer of Example 292 |
| 294 | 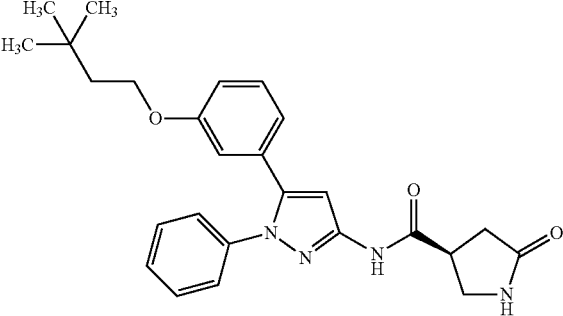 [SMILES: CC(C)(C)CCOc1cccc(-c2cc(NC(=O)[C@@H]3CNC(=O)C3)nn2-c2ccccc2)c1] | 1H-NMR (DMSO-D6) δ: 0.90 (s, 9H), 1.55 (t, 2H, J = 7.5 Hz), 2.37-2.42 (m, 2H), 3.30-3.54 (m, 3H), 3.85 (t, 2H, J = 7.5 Hz), 6.68-6.71 (m, 1H), 6.80-6.84 (m, 1H), 6.87-6.93 (m, 2H), 7.23-7.28 (m, 3H), 7.31-7.37 (m, 1H), 7.38-7.44 (m, 2H), 7.63 (s, 1H), 10.85 (s, 1H). | 447 | 445 | S-form |
| 295 | 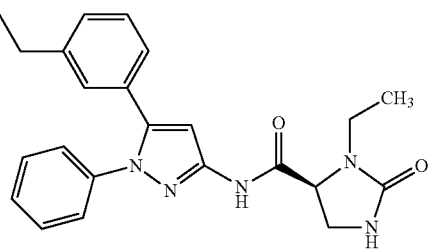 | 1H-NMR (DMSO-D6) δ: 0.77 (t, 3H, J = 7.3 Hz), 1.01 (t, 3H, J = 7.2 Hz), 1.44 (tq, 2H, J = 7.5, 7.3 Hz), 2.46 (t, 2H, J = 7.5 Hz), 2.87 (dq, 1H, J = 7.2, 14.0 Hz), 3.22 (dd, 1H, J = 9.2, 6.4 Hz), 3.36 (dq, 1H, J = 7.2, 14.0 Hz), 3.52 (dd, 1H, J = 9.5, 9.2 Hz), 4.41 (dd, 1H, J = 9.5, 6.4 Hz), 6.42 (s, 1H), 6.92 (s, 1H), 7.02 (s, 1H), 7.07-7.09 (m, 1H), 7.16-7.19 (m, 1H), 7.22-7.29 (m, 3H), 7.33-7.43 (m, 3H), 11.06 (s, 1H). | 418 | 416 | S-form |

TABLE 2-continued

| Example No. | Molecular Structure | NMR (400 MHz) | MS (M + H) | MS (M − H) | Comments |
|---|---|---|---|---|---|
| 296 | 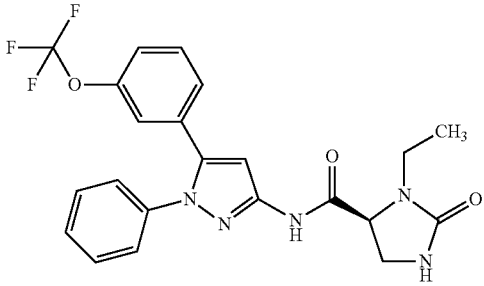 [SMILES: CCN1C(=O)NC[C@H]1C(=O)Nc1cc(-c2cccc(OC(F)(F)F)c2)n(-c2ccccc2)n1] | 1H-NMR (DMSO-D6) δ: 1.01 (t, 3H, J = 7.2 Hz), 2.87 (dq, 1H, J = 14.2, 7.2 Hz), 3.22 (dd, 1H, J = 8.9, 6.4 Hz), 3.36 (dq, 1H, J = 14.2, 7.2 Hz), 3.52 (dd, 1H, J = 9.6, 8.9 Hz), 4.41 (dd, 1H, J = 9.6, 6.4 Hz), 6.42 (s, 1H), 7.03 (s, 1H), 7.10 (s, 1H), 7.24-7.27 (m, 2H), 7.35-7.45 (m, 5H), 7.52 (t, 1H, J = 8.0 Hz), 11.12 (s, 1H). | 460 | 458 | S-form |
| 297 | 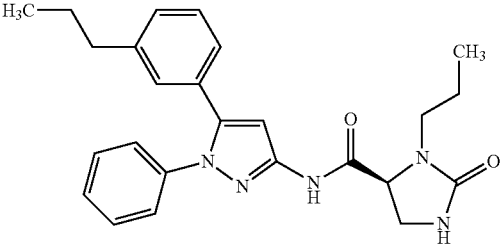 [SMILES: CCCc1cccc(-c2cc(NC(=O)[C@@H]3CNC(=O)N3CCC)nn2-c2ccccc2)c1] | 1H-NMR (DMSO-D6) δ: 0.77 (t, 3H, J = 7.4 Hz), 0.82 (t, 3H, J = 7.4 Hz), 1.35-1.52 (m, 4H), 2.46 (t, 2H, J = 7.4 Hz), 2.76-2.83 (m, 1H), 3.20-3.29 (m, 2H), 3.53 (dd, 1H, J = 9.5, 8.8 Hz), 4.39 (dd, 1H, J = 9.5, 6.0 Hz), 6.40 (s, 1H), 6.92 (s, 1H), 7.02 (s, 1H), 7.06-7.08 (m, 1H), 7.16-7.18 (m, 1H), 7.22-7.29 (m, 3H), 7.33-7.42 (m, 3H), 11.05 (s, 1H). | 432 | 430 | S-form |
| 298 | 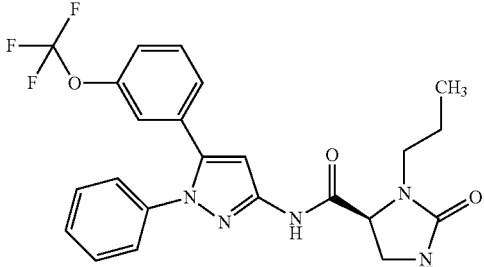 | 1H-NMR (DMSO-D6) δ: 0.82 (t, 3H, J = 7.4 Hz), 1.35-1.51 (m, 2H), 2.76-2.83 (m, 1H), 3.22-3.28 (m, 2H), 3.53 (dd, 1H, J = 9.5, 9.0 Hz), 4.39 (dd, 1H, J = 9.5, 6.0 Hz), 6.41 (s, 1H), 7.02 (s, 1H), 7.10 (s, 1H), 7.24-7.28 (m, 2H), 7.35-7.45 (m, 5H), 7.52 (t, 1H, J = 8.0 Hz), 11.10 (s, 1H). | 474 | 472 | S-form |
| 299 | 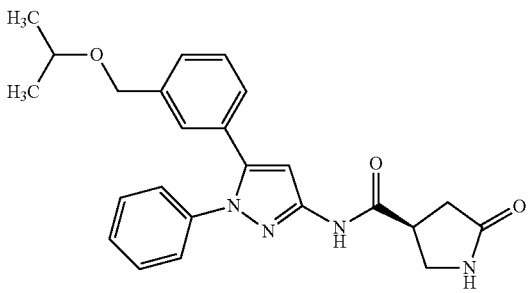 [SMILES: CC(C)OCc1cccc(-c2cc(NC(=O)[C@@H]3CNC(=O)C3)nn2-c2ccccc2)c1] | 1H-NMR (DMSO-D6) δ: 1.06 (d, 6H, J = 6.4 Hz), 2.39 (d, 2H, J = 8.4 Hz), 3.33-3.35 (m, 1H), 3.38-3.55 (m, 3H), 4.39 (s, 2H), 6.90 (s, 1H), 7.12 (d, 1H, J = 7.6 Hz), 7.20-7.24 (m, 3H), 7.27-7.41 (m, 5H), 7.63 (s, 1H), 10.86 (s, 1H). | 419 | 417 | S-form |

TABLE 2-continued

| Example No. | Molecular Structure | NMR (400 MHz) | MS (M + H) | MS (M − H) | Comments |
|---|---|---|---|---|---|
| 300 | 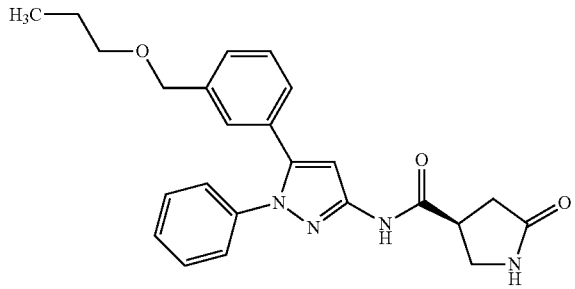 | 1H-NMR (DMSO-D6) δ: 0.84 (t, 3H, 7.2 Hz), 1.47 (tq, 2H, 6.4, 7.2 Hz), 2.39 (d, 2H, J = 8.4 Hz), 3.26 (t, 2H, J = 6.4 Hz), 3.32-3.52 (m, 3H), 4.39 (s, 2H), 6.91 (s, 1H), 7.14 (d, 1H, J = 7.6 Hz), 7.19 (s, 1H), 7.22-7.24 (m, 2H), 7.28-7.41 (m, 5H), 7.63 (s, 1H), 10.86 (s, 1H). | 419 | 417 | S-form |
| 301 | 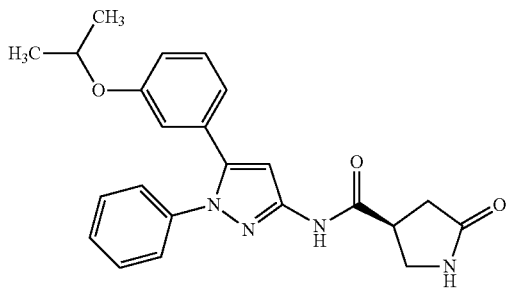 [SMILES: CC(C)Oc1cccc(-c2cc(NC(=O)[C@@H]3CNC(=O)C3)nn2-c2ccccc2)c1] | 1H-NMR (DMSO-D6) δ: 1.13 (d, 6H, J = 5.6 Hz), 2.36-2.42 (m, 2H), 3.30-3.36 (m, 1H), 3.37-3.46 (m, 1H), 3.47-3.54 (m, 1H), 4.43 (quint, 1H, J = 5.6 Hz), 6.67-6.69 (m, 1H), 6.79-6.82 (m, 1H), 6.86-6.90 (m, 1H), 6.90 (s, 1H), 7.21-7.28 (m, 3H), 7.32-7.37 (m, 1H), 7.38-7.43 (m, 2H), 7.63 (s, 1H), 10.84 (s, 1H). | 405 | 403 | S-form |
| 302 | 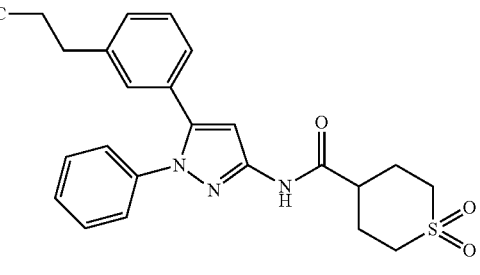 | 1H-NMR (DMSO-D6) δ: 0.77 (t, 3H, J = 7.5 Hz), 1.39-1.49 (m, 2H), 2.04-2.23 (m, 4H), 2.46 (t, 2H, J = 7.5 Hz), 2.72-2.80 (m, 1H), 3.13-3.20 (m, 4H), 6.89 (s, 1H), 6.99-7.02 (m, 1H), 7.04-7.08 (m, 1H), 7.15-7.19 (m, 1H), 7.20-7.29 (m, 3H), 7.31-7.42 (m, 3H), 10.83 (s, 1H). | 438 | 436 | None |
| 303 | 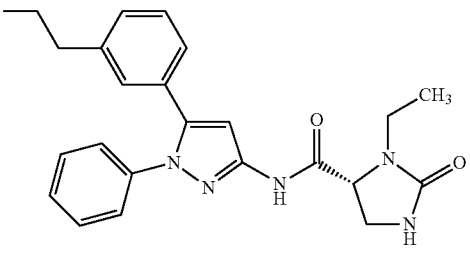 | 1H-NMR (DMSO-D6) δ: 0.77 (t, 3H, J = 7.3 Hz), 1.01 (t, 3H, J = 7.2 Hz), 1.44 (tq, 2H, J = 7.5, 7.3 Hz), 2.46 (t, 2H, J = 7.5 Hz), 2.87 (dq, 1H, J = 7.2, 14.0 Hz), 3.22 (dd, 1H, J = 9.2, 6.4 Hz), 3.36 (dq, 1H, J = 7.2, 14.0 Hz), 3.52 (dd, 1H, J = 9.5, 9.2 Hz), 4.41 (dd, 1H, J = 9.5, 6.4 Hz), 6.42 (s, 1H), 6.92 (s, 1H), 7.02 (s, 1H), 7.07-7.09 (m, 1H), 7.16-7.19 (m, 1H), 7.22-7.29 (m, 3H), 7.33-7.43 (m, 3H), 11.06 (s, 1H). | 418 | 416 | R-form |

TABLE 2-continued

| Example No. | Molecular Structure | NMR (400 MHz) | MS (M + H) | MS (M − H) | Comments |
|---|---|---|---|---|---|
| 304 | 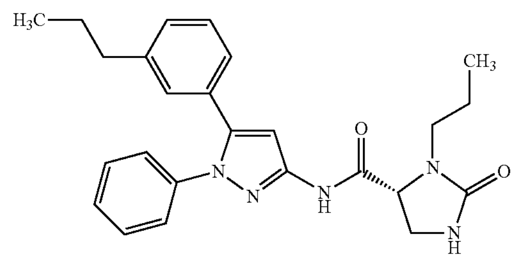 [SMILES: CCCc1cccc(-c2cc(NC(=O)[C@H]3CNC(=O)N3CCC)nn2-c2ccccc2)c1] | 1H-NMR (DMSO-D6) δ: 0.77 (t, 3H, J = 7.4 Hz), 0.82 (t, 3H, J = 7.4 Hz), 1.35-1.52 (m, 4H), 2.46 (t, 2H, J = 7.4 Hz), 2.76-2.83 (m, 1H), 3.20-3.29 (m, 2H), 3.53 (dd, 1H, J = 9.5, 8.8 Hz), 4.39 (dd, 1H, J = 9.5, 6.0 Hz), 6.40 (s, 1H), 6.92 (s, 1H), 7.02 (s, 1H), 7.06-7.08 (m, 1H), 7.16-7.18 (m, 1H), 7.22-7.29 (m, 3H), 7.33-7.42 (m, 3H), 11.05 (s, 1H). | 432 | 430 | R-form |
| 305 | 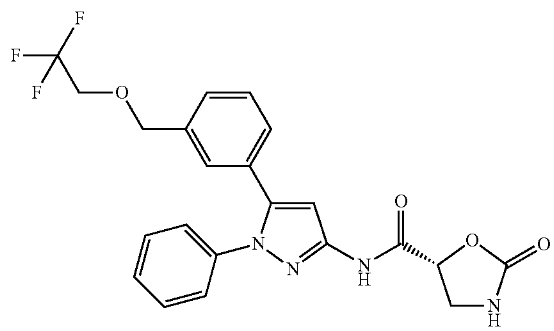 [SMILES: O=C1NC[C@H](C(=O)Nc2cc(-c3cccc(COCC(F)(F)F)c3)n(-c3ccccc3)n2)O1] | 1H-NMR (DMSO-D6) δ: 3.52 (dd, 1H, J = 8.7, 5.7 Hz), 3.75 (dd, 1H, J = 9.3, 8.7 Hz), 3.98 (q, 2H, J = 9.3 Hz), 4.61 (s, 2H), 5.13 (dd, 1H, J = 9.3, 5.7 Hz), 6.93 (s, 1H), 7.16-7.18 (m, 1H), 7.24-7.26 (m, 3H), 7.32-7.42 (m, 5H), 7.76 (s, 1H), 11.07 (s, 1H). | 461 | 459 | R-form |
| 306 | 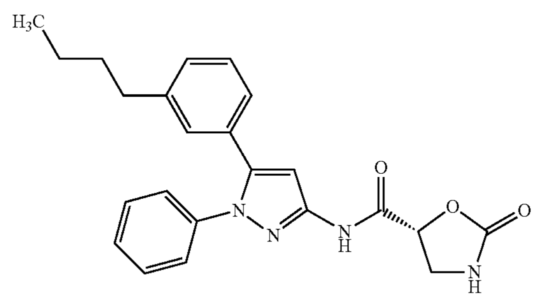 [SMILES: CCCCc1cccc(-c2cc(NC(=O)[C@H]3CNC(=O)O3)nn2-c2ccccc2)c1] | 1H-NMR (DMSO-D6) δ: 0.82 (t, 3H, J = 7.4 Hz), 1.15 (tq, 2H, J = 7.4 Hz, 7.4 Hz), 1.39 (tt, 2H, J = 7.4 Hz, 7.4 Hz), 2.49 (t, 2H, J = 7.4 Hz), 3.52 (dd, 1H, J = 9.2 Hz, 5.6 Hz), 3.75 (dd, 1H, J = 9.2 Hz, 9.2 Hz), 5.13 (dd, 1H, J = 9.2 Hz, 5.6 Hz), 6.90 (s, 1H), 6.99 (s, 1H), 7.09 (d, 1H, J = 7.6 Hz), 7.17 (d, 1H, J = 7.6 Hz), 7.22-7.30 (m, 3H), 7.32-7.43 (m, 3H), 7.75 (s, 1H), 11.04 (s, 1H). | 405 | 403 | R-form |
| 307 | 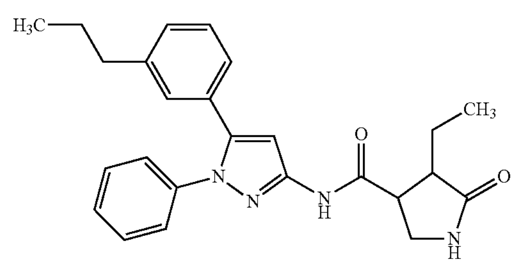 [SMILES: CCCc1cccc(-c2cc(NC(=O)C3CNC(=O)C3CC)nn2-c2ccccc2)c1] | 1H-NMR (DMSO-D6) δ: 0.77 (t, 3H, J = 7.4 Hz), 0.90 (t, 3H, J = 7.4 Hz), 1.39-1.50 (m, 4H), 1.65-1.75 (m, 1H), 2.46 (t, 2H, J = 7.4 Hz), 2.50-2.60 (m, 1H), 3.12-3.21 (m, 2H), 3.40-3.46 (m, 1H), 6.92 (s, 1H), 7.01 (s, 1H), 7.07 (d, 1H, J = 7.6 Hz), 7.17 (d, 1H, J = 7.6 Hz), 7.20-7.28 (m, 3H), 7.32-7.42 (m, 3H), 7.66 (s, 1H), 10.96 (s, 1H). | 417 | 415 | Optically active substance (transform, Structure Information C) Optical isomer of Example 309 |

TABLE 2-continued

| Example No. | Molecular Structure | NMR (400 MHz) | MS (M + H) | MS (M − H) | Comments |
|---|---|---|---|---|---|
| 308 | 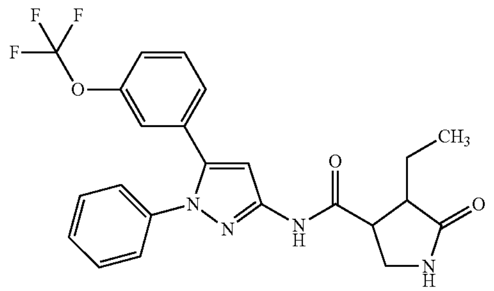 [SMILES: CCC1C(=O)NCC1C(=O)Nc1cc(-c2cccc(OC(F)(F)F)c2)n(-c2ccccc2)n1] | 1H-NMR (DMSO-D6) δ: 0.90 (t, 3H, J = 7.6 Hz), 1.39-1.49 (m, 1H), 1.65-1.75 (m, 1H), 2.50-2.60 (m, 1H), 3.12-3.21 (m, 2H), 3.40-3.48 (m, 1H), 7.02 (s, 1H), 7.09 (s, 1H), 7.26 (m, 2H), 7.33-7.45 (m, 5H), 7.52 (t, 1H, J = 8.0 Hz), 7.67 (s, 1H), 11.02 (s, 1H). | 459 | 457 | Optically active substance (transform, the same configuration as Example 307) Optical isomer of Example 310 |
| 309 | 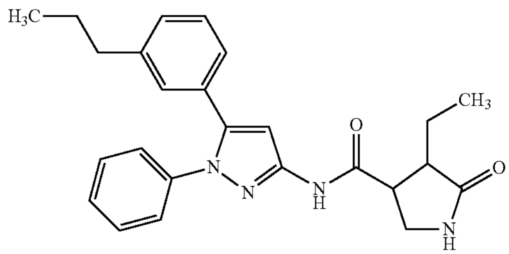 [SMILES: CCCc1cccc(-c2cc(NC(=O)C3CNC(=O)C3CC)nn2-c2ccccc2)c1] | 1H-NMR (DMSO-D6) δ: 0.77 (t, 3H, J = 7.4 Hz), 0.90 (t, 3H, J = 7.4 Hz), 1.39-1.50 (m, 4H), 1.65-1.75 (m, 1H), 2.46 (t, 2H, J = 7.4 Hz), 2.50-2.60 (m, 1H), 3.12-3.21 (m, 2H), 3.40-3.46 (m, 1H), 6.92 (s, 1H), 7.01 (s, 1H), 7.07 (d, 1H, J = 7.6 Hz), 7.17 (d, 1H, J = 7.6 Hz), 7.20-7.28 (m, 3H), 7.32-7.42 (m, 3H), 7.66 (s, 1H), 10.96 (s, 1H). | 417 | 415 | Optically active substance (transform, Structure Information C) Optical isomer of Example 307 |
| 310 | 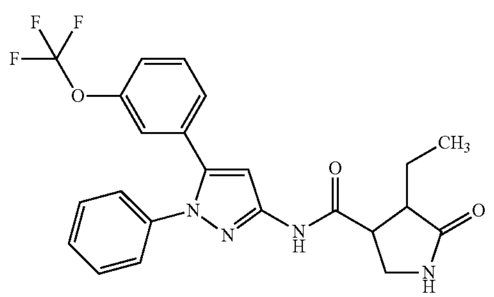 [SMILES: CCC1C(=O)NCC1C(=O)Nc1cc(-c2cccc(OC(F)(F)F)c2)n(-c2ccccc2)n1] | 1H-NMR (DMSO-D6) δ: 0.90 (t, 3H, J = 7.6 Hz), 1.39-1.49 (m, 1H), 1.65-1.75 (m, 1H), 2.50-2.60 (m, 1H), 3.12-3.21 (m, 2H), 3.40-3.48 (m, 1H), 7.02 (s, 1H), 7.09 (s, 1H), 7.26 (m, 2H), 7.33-7.45 (m, 5H), 7.52 (t, 1H, J = 8.0 Hz), 7.67 (s, 1H), 11.02 (s, 1H). | 459 | 457 | Optically active substance (transform, the same configuration as Example 309) Optical isomer of Example 308 |
| 311 | 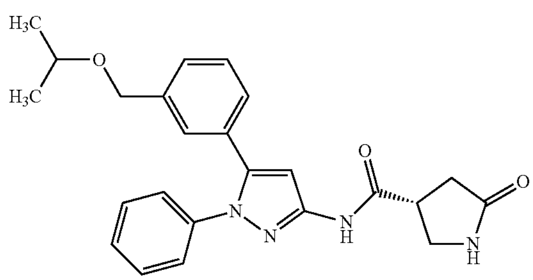 [SMILES: CC(C)OCc1cccc(-c2cc(NC(=O)[C@H]3CNC(=O)C3)nn2-c2ccccc2)c1] | 1H-NMR (DMSO-D6) δ: 1.06 (d, 6H, J = 6.4 Hz), 2.39 (d, 2H, J = 8.4 Hz), 3.33-3.35 (m, 1H), 3.38-3.55 (m, 3H), 4.39 (s, 2H), 6.90 (s, 1H), 7.12 (d, 1H, J = 7.6 Hz), 7.20-7.24 (m, 3H), 7.27-7.41 (m, 5H), 7.63 (s, 1H), 10.86 (s, 1H). | 419 | 417 | R-form |
| 312 | 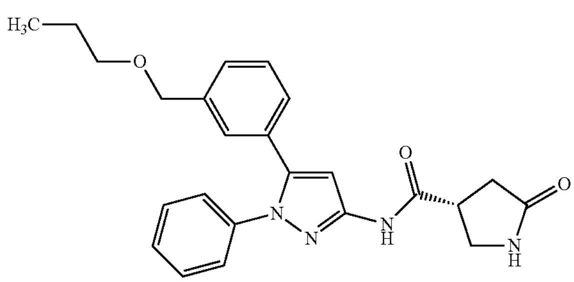 [SMILES: CCCOCc1cccc(-c2cc(NC(=O)[C@H]3CNC(=O)C3)nn2-c2ccccc2)c1] | 1H-NMR (DMSO-D6) δ: 0.84 (t, 3H, 7.2 Hz), 1.47 (tq, 2H, 6.4, 7.2 Hz), 2.39 (d, 2H, J = 8.4 Hz), 3.26 (t, 2H, J = 6.4 Hz), 3.32-3.52 (m, 3H), 4.39 (s, 2H), 6.91 (s, 1H), 7.14 (d, 1H, J = 7.6 Hz), 7.19 (s, 1H), 7.22-7.24 (m, 2H), 7.28-7.41 (m, 5H), 7.63 (s, 1H), 10.86 (s, 1H). | 419 | 417 | R-form |

TABLE 2-continued
| Example No. | Molecular Structure | NMR (400 MHz) | MS (M + H) | MS (M − H) | Comments |
|---|---|---|---|---|---|
| 313 | 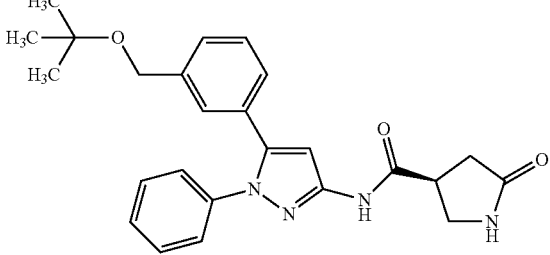 | 1H-NMR (DMSO-D6) δ: 1.14 (s, 9H), 2.39 (d, 2H, J = 8.4 Hz), 3.32-3.52 (m, 3H), 4.33 (s, 2H), 6.90 (s, 1H), 7.10 (d, 1H, J = 7.6 Hz), 7.20 (s, 1H), 7.23-7.42 (m, 7H), 7.64 (s, 1H), 10.86 (s, 1H). | 433 | 431 | S-form |
| 314 | 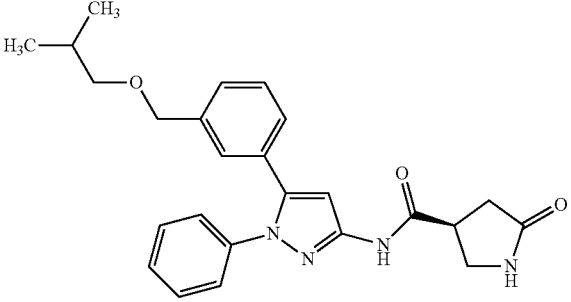 [SMILES: CC(C)COCc1cccc(-c2cc(NC(=O)[C@@H]3CNC(=O)C3)nn2-c2ccccc2)c1] | 1H-NMR (DMSO-D6) δ: 0.83 (d, 6H, J = 6.8 Hz), 1.70-1.81 (m, 1H), 2.39 (d, 2H, J = 8.4 Hz), 3.08 (d, 2H, J = 10. Hz), 3.32-3.52 (m, 3H), 4.39 (s, 2H), 6.90 (s, 1H), 7.14 (d, 1H, J = 7.6 Hz), 7.19 (s, 1H), 7.28-7.41 (m, 7H), 7.64 (s, 1H), 10.86 (s, 1H). | 433 | 431 | S-form |
| 315 | 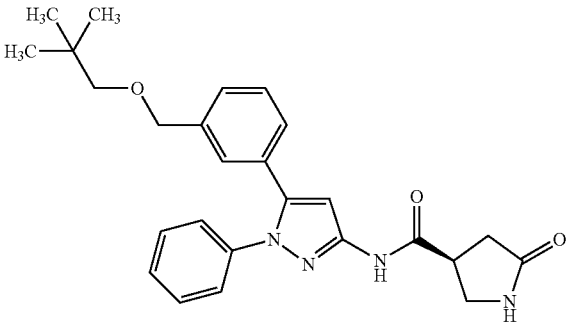 [SMILES: CC(C)(C)COCc1cccc(-c2cc(NC(=O)[C@@H]3CNC(=O)C3)nn2-c2ccccc2)c1] | 1H-NMR (DMSO-D6) δ: 0.83 (s, 9H), 2.39 (d, 2H, J = 8.4 Hz), 2.99 (s, 2H), 3.32-3.52 (m, 3H), 4.42 (s, 2H), 6.90 (s, 1H), 7.15 (d, 1H, J = 7.6 Hz), 7.19 (s, 1H), 7.28-7.41 (m, 7H), 7.64 (s, 1H), 10.86 (s, 1H). | 447 | 445 | S-form |
| 316 | 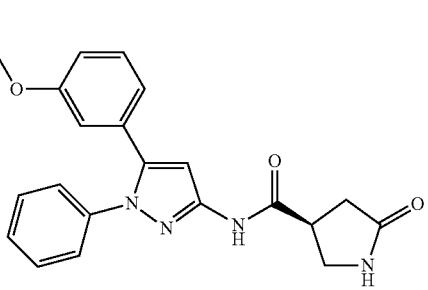 | 1H-NMR (DMSO-D6) δ: 0.89 (t, 3H, J = 7.3 Hz), 1.36 (sext, 2H, J = 7.3 Hz), 1.59 (quint, 2H, J = 7.3 Hz), 2.36-2.42 (m, 2H), 3.31-3.36 (m, 1H), 3.37-3.47 (m, 1H), 3.47-3.54 (m, 1H), 3.83 (t, 2H, J = 7.3 Hz), 6.71-6.75 (m, 1H), 6.75-6.81 (m, 1H), 6.87-6.93 (m, 1H), 6.91 (s, 1H), 7.21-7.29 (m, 3H), 7.31-7.38 (m, 1H), 7.38-7.45 (m, 2H), 7.63 (s, 1H), 10.84 (s, 1H). | 419 | 417 | S-form |

TABLE 2-continued

| Example No. | Molecular Structure | NMR (400 MHz) | MS (M + H) | MS (M − H) | Comments |
|---|---|---|---|---|---|
| 317 | 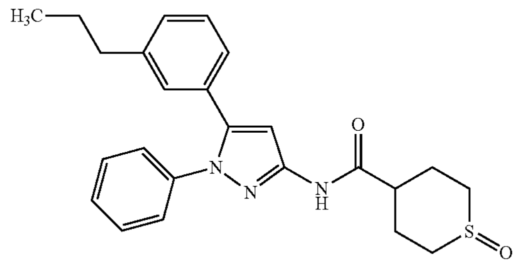 [SMILES: CCCc1cccc(-c2cc(NC(=O)C3CCS(=O)CC3)nn2-c2ccccc2)c1] | 1H-NMR (DMSO-D6) δ: 0.77 (t, 3H, J = 7.5 Hz), 1.38-1.49 (m, 2H), 1.75-1.86 (m, 2H), 2.16-2.25 (m, 2H), 2.46 (t, 2H, J = 7.5 Hz), 2.58-2.72 (m, 3H), 3.23-3.33 (m, 2H), 6.87 (s, 1H), 6.98-7.01 (m, 1H), 7.04-7.08 (m, 1H), 7.14-7.18 (m, 1H), 7.19-7.29 (m, 3H), 7.30-7.42 (m, 3H), 10.74 (s, 1H). | 422 | 420 | Single diastereo isomer Diastereo isomer of Example 318 |
| 318 | 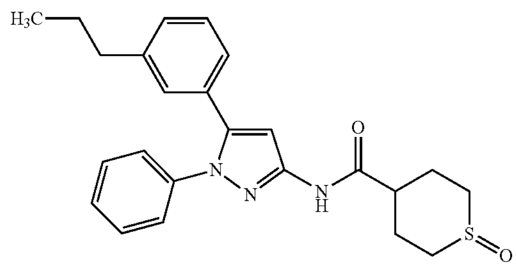 [SMILES: CCCc1cccc(-c2cc(NC(=O)C3CCS(=O)CC3)nn2-c2ccccc2)c1] | 1H-NMR (DMSO-D6) δ: 0.78 (t, 3H, J = 7.5 Hz), 1.39-1.49 (m, 2H), 1.73-1.83 (m, 2H), 2.22-2.35 (m, 2H), 2.46 (t, 2H, J = 7.5 Hz), 2.60-2.74 (m, 3H), 2.88-2.96 (m, 2H), 6.90 (s, 1H), 7.00-7.02 (m, 1H), 7.05-7.09 (m, 1H), 7.15-7.19 (m, 1H), 7.20-7.29 (m, 3H), 7.31-7.42 (m, 3H), 10.72 (s, 1H). | 422 | 420 | Principal component is a diastereo isomer of Example 317. |
| 319 | 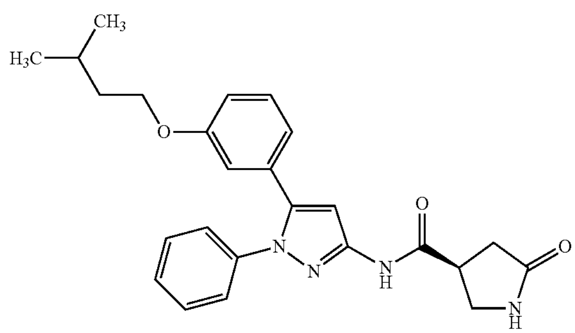 [SMILES: CC(C)CCOc1cccc(-c2cc(NC(=O)[C@@H]3CNC(=O)C3)nn2-c2ccccc2)c1] | 1H-NMR (DMSO-D6) δ: 0.88 (d, 6H, J = 6.9 Hz), 1.51 (q, 2H, J = 6.9 Hz), 1.62-1.75 (m, 1H), 2.36-2.42 (m, 2H), 3.31-3.36 (m, 1H), 3.36-3.47 (m, 1H), 3.47-3.53 (m, 1H), 3.84 (t, 2H, J = 6.9 Hz), 6.70-6.74 (m, 1H), 6.77-6.82 (m, 1H), 6.87-6.93 (m, 1H), 6.91 (s, 1H), 7.22-7.28 (m, 3H), 7.31-7.37 (m, 1H), 7.37-7.44 (m, 2H), 7.63 (s, 1H), 10.85 (s, 1H). | 433 | 431 | S-form |
| 320 | 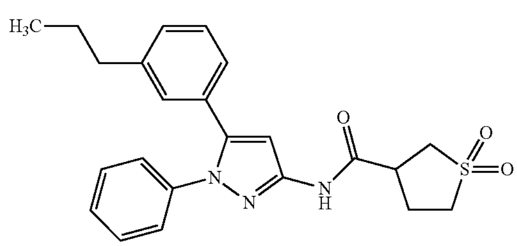 [SMILES: CCCc1cccc(-c2cc(NC(=O)C3CCS(=O)(=O)C3)nn2-c2ccccc2)c1] | 1H-NMR (DMSO-D6) δ: 0.77 (t, 3H, J = 7.5 Hz), 1.39-1.49 (m, 2H), 2.16-2.26 (m, 1H), 2.46 (t, 2H, J = 7.5 Hz), 3.08-3.32 (m, 3H), 3.38-3.52 (m, 2H), 6.89 (s, 1H), 6.99-7.01 (m, 1H), 7.05-7.09 (m, 1H), 7.15-7.19 (m, 1H), 7.21-7.29 (m, 3H), 7.32-7.42 (m, 3H), 10.99 (s, 1H). | 424 | 422 | racemate |

| Example No. | Molecular Structure | NMR (400 MHz) | MS (M + H) | MS (M − H) | Comments |
|---|---|---|---|---|---|
| 321 | 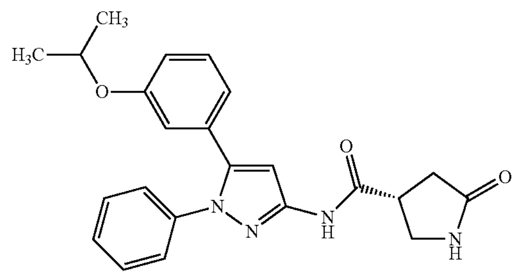 [SMILES: CC(C)Oc1cccc(-c2cc(NC(=O)[C@H]3CNC(=O)C3)nn2-c2ccccc2)c1] | 1H-NMR (DMSO-D6) δ: 1.13 (d, 6H, J = 5.6 Hz), 2.36-2.42 (m, 2H), 3.30-3.36 (m, 1H), 3.37-3.46 (m, 1H), 3.47-3.54 (m, 1H), 4.43 (quint, 1H, J = 5.6 Hz), 6.67-6.69 (m, 1H), 6.79-6.82 (m, 1H), 6.86-6.90 (m, 1H), 6.90 (s, 1H), 7.21-7.28 (m, 3H), 7.32-7.37 (m, 1H), 7.38-7.43 (m, 2H), 7.63 (s, 1H), 10.84 (s, 1H). | 405 | 403 | R-form |
| 322 | 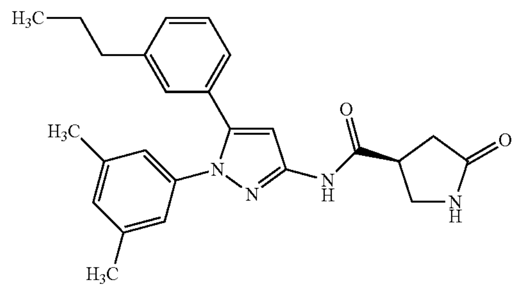 [SMILES: CCCc1cccc(-c2cc(NC(=O)[C@@H]3CNC(=O)C3)nn2-c2cc(C)cc(C)c2)c1] | $^1$H-NMR (CDCl$_3$) δ: 0.83 (t, 3H, J = 7.6 Hz), 1.45-1.56 (m, 2H), 2.24 (s, 6H), 2.38 (dd, 1H, J =16.8, 9.6 Hz), 2.50 (t, 2H, J = 7.6 Hz), 2.71 (dd, 1H, J = 16.8, 8.8 Hz), 3.05-3.15 (m, 1H), 3.40 (t, 1H, J = 8.8 Hz), 3.59 (dd, 1H, J = 9.6, 7.6 Hz), 6.29 (s, 1H), 6.85 (s, 2H), 6.94 (s, 1H), 7.01-7.14 (m, 4H), 7.20 (t, 1H, J = 7.6 Hz), 9.46 (s, 1H). | 417 | 415 | S-form |
| 323 | 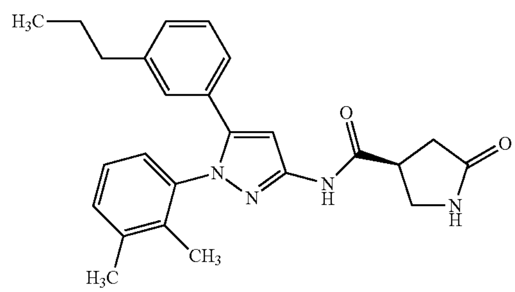 [SMILES: CCCc1cccc(-c2cc(NC(=O)[C@@H]3CNC(=O)C3)nn2-c2cccc(C)c2C)c1] | $^1$H-NMR (CDCl$_3$) δ: 0.77 (t, 3H, J = 7.2 Hz), 1.44 (tq, 2H, J = 7.2, 7.2 Hz), 1.79 (br s, 3H), 2.24 (s, 3H), 2.29-2.41 (m, 1H), 2.44 (t, 2H, J = 7.2 Hz), 2.71 (dd, 1H, J = 16.8, 8.8 Hz), 2.97-3.11 (m, 1H), 3.34-3.46 (m, 1H), 3.56-3.63 (m, 1H), 5.89 (s, 1H), 6.95-7.24 (m, 8H), 9.19 (br s, 1H). | 417 | 415 | S-form |
| 324 | 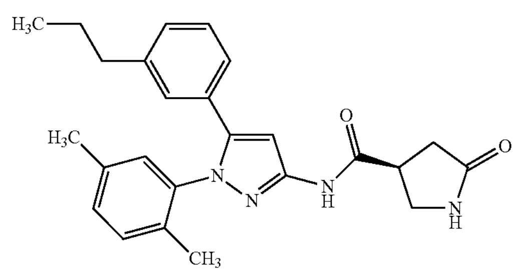 [SMILES: CCCc1cccc(-c2cc(NC(=O)[C@@H]3CNC(=O)C3)nn2-c2cc(C)ccc2C)c1] | $^1$H-NMR (CDCl$_3$) : 0.78 (t, 3H, J = 7.2 Hz), 1.46 (tq, 2H, J = 7.2, 7.2 Hz), 1.88 (s, 3H), 2.31 (s, 3H), 2.40-2.50 (m, 3H), 2.74 (dd, 1H, J = 16.8, 8.8 Hz), 3.10-3.21 (m, 1H), 3.50 (t, 1H, J = 9.2 Hz), 3.66 (dd, 1H, J = 9.2, 7.2 Hz), 5.72 (s, 1H), 6.98-7.17 (m, 8H), 8.70 (s, 1H). | 417 | 415 | S-form |

TABLE 2-continued

| Example No. | Molecular Structure | NMR (400 MHz) | MS (M + H) | MS (M − H) | Comments |
|---|---|---|---|---|---|
| 325 | 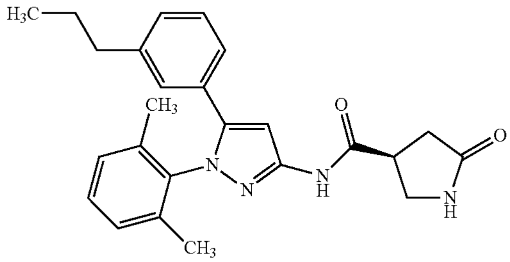 [SMILES: CCCc1cccc(-c2cc(NC(=O)[C@@H]3CNC(=O)C3)nn2-c2c(C)cccc2C)c1] | ¹H-NMR (CDCl₃) δ: 0.78 (t, 3H, J = 7.2 Hz), 1.45 (tq, 2H, J = 7.2, 7.2 Hz), 1.94 (s, 3H), 1.97 (s, 3H), 2.41-2.52 (m, 3H), 2.76 (dd, 1H, J = 17.2, 8.8 Hz), 3.11-3.21 (m, 1H), 3.51 (t, 1H, J = 9.2 Hz), 3.67 (dd, 1H, J = 9.2, 8.0 Hz), 5.73 (s, 1H), 6.93-7.26 (m, 8H), 8.70 (s, 1H). | 417 | 415 | S-form |
| 326 | 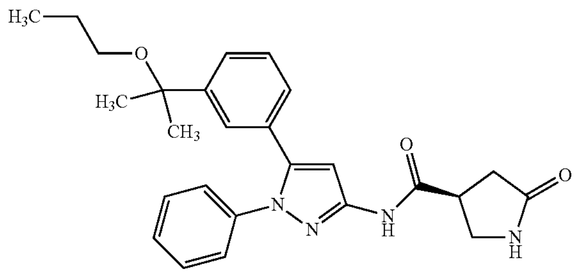 [SMILES: CCCOC(C)(C)c1cccc(-c2cc(NC(=O)[C@@H]3CNC(=O)C3)nn2-c2ccccc2)c1] | 1H-NMR (DMSO-D6) δ: 0.77 (t, 3H, J = 7.5 Hz), 1.28 (s, 6H), 1.33 (tq, 2H, J = 7.5, 6.6 Hz), 2.38-2.40 (m, 2H), 2.89 (t, 2H, J = 6.6 Hz), 3.32-3.53 (m, 3H), 6.92 (s, 1H), 7.08 (s, 1H), 7.21-7.27 (m, 3H), 7.32-7.41 (m, 5H), 7.63 (br s, 1H), 10.85 (br s, 1H). | 447 | 445 | S-form |
| 327 | 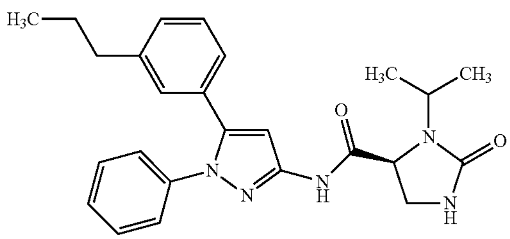 [SMILES: CCCc1cccc(-c2cc(NC(=O)[C@@H]3CNC(=O)N3C(C)C)nn2-c2ccccc2)c1] | 1H-NMR (DMSO-D6) δ: 0.77 (t, 3H, J = 7.4 Hz), 1.05 (d, 3H, J = 7.1 Hz), 1.12 (d, 3H, J = 7.1 Hz), 1.44 (tq, 2H, J = 7.4, 7.5 Hz), 2.46 (t, 2H, J = 7.5 Hz), 3.16 (dd, 1H, J = 9.0, 6.6 Hz), 3.50 (dd, 1H, J = 9.0, 9.7 Hz), 3.88 (tt, 1H, J = 7.1, 7.1 Hz), 4.42 (dd, 1H, J = 9.7, 6.6 Hz), 6.39 (s, 1H), 6.91 (s, 1H), 7.02 (s, 1H), 7.06-7.08 (m, 1H), 7.16-7.18 (m, 1H), 7.22-7.29 (m, 3H), 7.32-7.42 (m, 3H), 11.04 (s, 1H). | 432 | 430 | S-form |
| 328 | 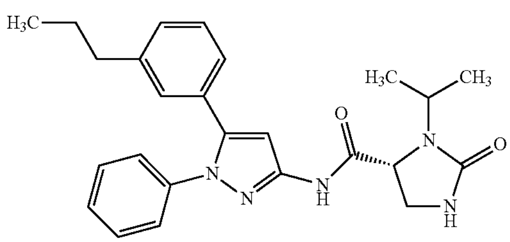 [SMILES: CCCc1cccc(-c2cc(NC(=O)[C@H]3CNC(=O)N3C(C)C)nn2-c2ccccc2)c1] | 1H-NMR (DMSO-D6) δ: 0.77 (t, 3H, J = 7.4 Hz), 1.05 (d, 3H, J = 7.1 Hz), 1.12 (d, 3H, J = 7.1 Hz), 1.44 (tq, 2H, J = 7.4, 7.5 Hz), 2.46 (t, 2H, J = 7.5 Hz), 3.16 (dd, 1H, J = 9.0, 6.6 Hz), 3.50 (dd, 1H, J = 9.0, 9.7 Hz), 3.88 (tt, 1H, J = 7.1, 7.1 Hz), 4.42 (dd, 1H, J = 9.7, 6.6 Hz), 6.39 (s, 1H), 6.91 (s, 1H), 7.02 (s, 1H), 7.06-7.08 (m, 1H), 7.16-7.18 (m, 1H), 7.22-7.29 (m, 3H), 7.32-7.42 (m, 3H), 11.04 (s, 1H). | 432 | 430 | S-form |

TABLE 2-continued

| Example No. | Molecular Structure | NMR (400 MHz) | MS (M + H) | MS (M − H) | Comments |
|---|---|---|---|---|---|
| 329 | 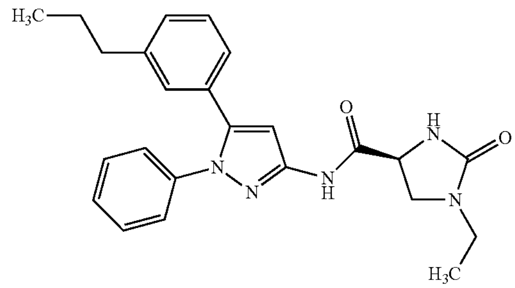 [SMILES: CCCc1cccc(-c2cc(NC(=O)[C@@H]3CN(CC)C(=O)N3)nn2-c2ccccc2)c1] | 1H-NMR (DMSO-D6) δ: 0.77 (t, 3H, J = 7.4 Hz), 1.00 (t, 3H, J = 7.4 Hz), 1.44 (tq, 2H, J = 7.5, 7.4 Hz), 2.46 (t, 2H, J = 7.5 Hz), 3.09 (q, 2H, J = 7.4 Hz), 3.39 (dd, 1H, J = 9.2, 6.0 Hz), 3.62 (dd, 1H, J = 9.6, 9.2 Hz), 4.26 (dd, 1H, J = 9.6, 6.0 Hz), 6.72 (s, 1H), 6.90 (s, 1H), 7.00 (s, 1H), 7.07-7.09 (m, 1H), 7.16-7.18 (m, 1H), 7.22-7.29 (m, 3H), 7.32-7.42 (m, 3H), 10.76 (s, 1H). | 418 | 416 | S-form |
| 330 | 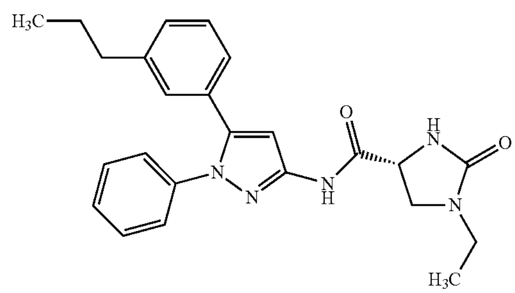 [SMILES: CCCc1cccc(-c2cc(NC(=O)[C@H]3CN(CC)C(=O)N3)nn2-c2ccccc2)c1] | 1H-NMR (DMSO-D6) δ: 0.77 (t, 3H, J = 7.4 Hz), 1.00 (t, 3H, J = 7.4 Hz), 1.44 (tq, 2H, J = 7.5, 7.4 Hz), 2.46 (t, 2H, J = 7.5 Hz), 3.09 (q, 2H, J = 7.4 Hz), 3.39 (dd, 1H, J = 9.2, 6.0 Hz), 3.62 (dd, 1H, J = 9.6, 9.2 Hz), 4.26 (dd, 1H, J = 9.6, 6.0 Hz), 6.72 (s, 1H), 6.90 (s, 1H), 7.00 (s, 1H), 7.07-7.09 (m, 1H), 7.16-7.18 (m, 1H), 7.22-7.29 (m, 3H), 7.32-7.42 (m, 3H), 10.76 (s, 1H). | 418 | 416 | R-form |
| 331 | 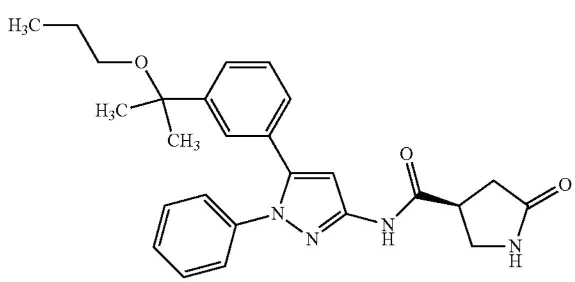 [SMILES: CCCOC(C)(C)c1cccc(-c2cc(NC(=O)[C@@H]3CNC(=O)C3)nn2-c2ccccc2)c1] | 1H-NMR (DMSO-D6) δ: 0.93 (t, 3H, J = 6.9 Hz), 1.27 (s, 6H), 2.38-2.40 (m, 2H), 2.97 (q, 2H, J = 7.0 Hz), 3.32-3.53 (m, 3H), 6.92 (s, 1H), 7.06 (br s, 1H), 7.21-7.27 (m, 3H), 7.32-7.41 (m, 5H), 7.63 (br s, 1H), 10.86 (br s, 1H). | 433 | 431 | S-form |
| 332 | 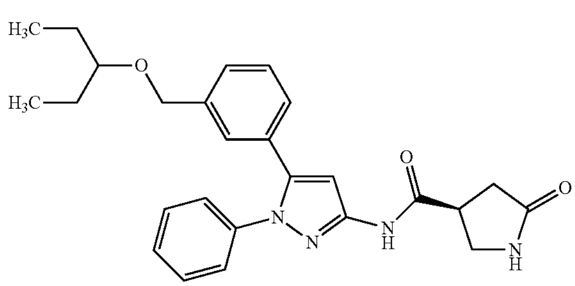 [SMILES: CCC(CC)OCc1cccc(-c2cc(NC(=O)[C@@H]3CNC(=O)C3)nn2-c2ccccc2)c1] | 1H-NMR (DMSO-D6) δ: 0.79 (t, 6H, J = 7.6 Hz), 1.39-1.46 (m, 4H), 2.39 (d, 2H, J = 8.4 Hz), 3.13-3.19 (m, 1H), 3.32-3.52 (m, 3H), 4.39 (s, 2H), 6.90 (s, 1H), 7.12 (d, 1H, J = 7.6 Hz), 7.22-7.24 (m, 3H), 7.31-7.41 (m, 5H), 7.64 (s, 1H), 10.86 (s, 1H). | 447 | 445 | S-form |

TABLE 2-continued

| Example No. | Molecular Structure | NMR (400 MHz) | MS (M + H) | MS (M − H) | Comments |
|---|---|---|---|---|---|
| 333 | 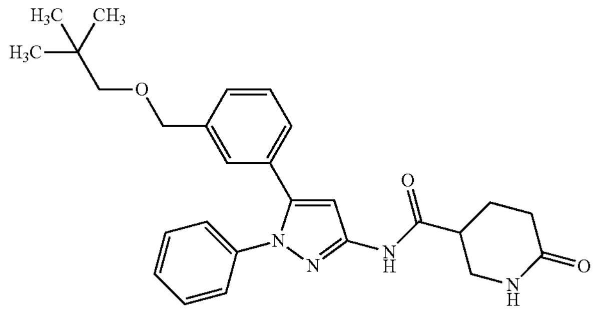 [SMILES: CC(C)(C)COCc1cccc(-c2cc(NC(=O)C3CCC(=O)NC3)nn2-c2ccccc2)c1] | 1H-NMR (DMSO-D6) δ: 0.83 (s, 9H), 1.86-1.98 (m, 2H), 2.13-2.26 (m, 2H), 2.83-2.85 (m, 1H), 2.99 (s, 2H), 3.29-3.35 (m, 2H), 4.41 (s, 2H), 6.89 (s, 1H), 7.15-7.18 (m, 2H), 7.22-7.24 (m, 2H), 7.28-7.40 (m, 5H), 7.50 (s, 1H), 10.84 (s, 1H). | 461 | 459 | Optically active substance (The same configuration as Example 5) |
| 334 | 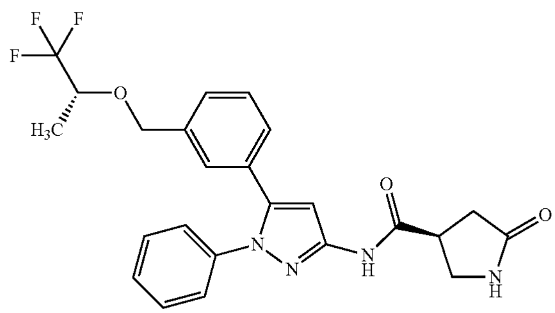 [SMILES: C[C@@H](OCc1cccc(-c2cc(NC(=O)[C@@H]3CNC(=O)C3)nn2-c2ccccc2)c1)C(F)(F)F] | 1H-NMR (DMSO-D6) δ: 1.19 (d, 3H, J = 6.4 Hz), 2.39 (d, 2H, J = 8.4 Hz), 3.32-3.52 (m, 3H), 4.06-4.13 (m, 1H), 4.61 (s, 2H), 6.92 (s, 1H), 7.15 (d, 1H, J = 6.8 Hz), 7.23-7.25 (m, 3H), 7.32-7.41 (m, 5H), 7.64 (s, 1H), 10.87 (s, 1H). | 473 | 471 | 2,2,2-trifluoro methyl-1-methyl-ethoxym ethyl group: R-form Lactam ring: S-form Diastereo isomer of Example 335 |
| 335 | 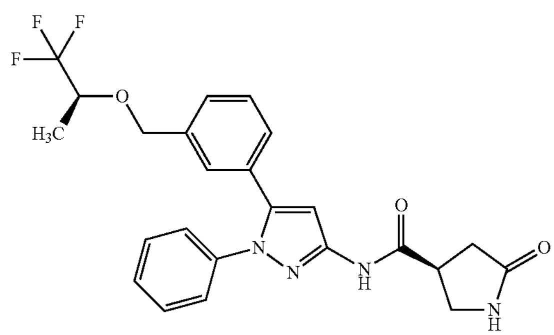 [SMILES: C[C@H](OCc1cccc(-c2cc(NC(=O)[C@@H]3CNC(=O)C3)nn2-c2ccccc2)c1)C(F)(F)F] | 1H-NMR (DMSO-D6) δ: 1.19 (d, 3H, J = 6.4 Hz), 2.39 (d, 2H, J = 8.4 Hz), 3.32-3.52 (m, 3H), 4.06-4.13 (m, 1H), 4.61 (s, 2H), 6.92 (s, 1H), 7.15 (d, 1H, J = 6.8 Hz), 7.23-7.25 (m, 3H), 7.32-7.41 (m, 5H), 7.64 (s, 1H), 10.87 (s, 1H). | 473 | 471 | 2,2,2-trifluoro methyl-1-methyl-ethoxym ethyl group: R-form Lactam ring: S-form Diastereo isomer of Example 334 |
| 336 | 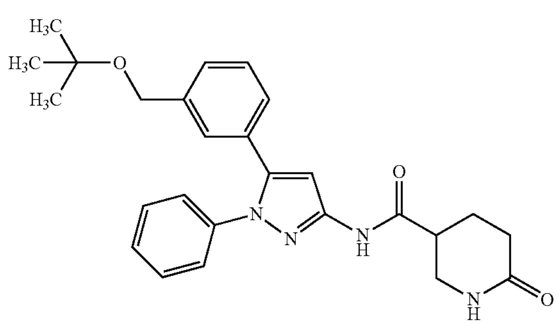 [SMILES: CC(C)(C)OCc1cccc(-c2cc(NC(=O)C3CCC(=O)NC3)nn2-c2ccccc2)c1] | 1H-NMR (DMSO-D6) δ: 0.94 (s, 9H), 1.85-2.30 (m, 2H), 2.13-2.28 (m, 2H), 2.50-2.58 (m, 1H), 2.80-2.90 (m, 1H), 3.29-3.38 (m, 1H), 3.49 (s, 2H), 6.72-6.78 (m, 2H), 6.88-6.92 (m, 2H), 7.20-7.27 (m, 3H), 7.33-7.43 (m, 3H), 7.49 (s, 1H), 10.82 (s, 1H). | 447 | 445 | Optically active substance (The same configuration as Example 5) |

TABLE 2-continued

| Example No. | Molecular Structure | NMR (400 MHz) | MS (M + H) | MS (M − H) | Comments |
|---|---|---|---|---|---|
| 337 | 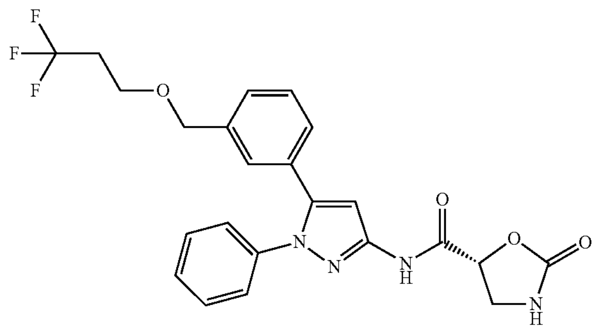 [SMILES: O=C1NC[C@H](C(=O)Nc2cc(-c3cccc(COCCC(F)(F)F)c3)n(-c3ccccc3)n2)O1] | 1H-NMR (DMSO-D6) δ: 2.50-2.60 (m, 2H), 3.49-3.56 (m, 3H), 3.75 (dd, 1H, J = 9.2 Hz, 9.2 Hz), 4.45 (s, 2H), 5.13 (dd, 1H, J = 9.2 Hz, 5.8 Hz), 6.91 (s, 1H), 7.12-7.15 (m, 1H), 7.22-7.27 (m, 3H), 7.29-7.43 (m, 5H), 7.75 (s, 1H), 11.06 (s, 1H). | 475 | 473 | R-form |
| 338 | 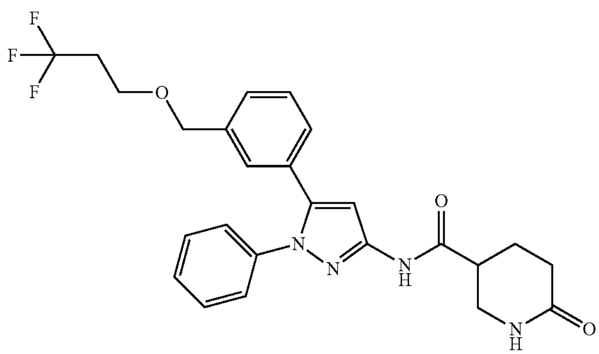 [SMILES: O=C1CCC(C(=O)Nc2cc(-c3cccc(COCCC(F)(F)F)c3)n(-c3ccccc3)n2)CN1] | 1H-NMR (DMSO-D6) δ: 1.85-2.30 (m, 2H), 2.13-2.28 (m, 2H), 2.50-2.58 (m, 3H), 2.80-2.90 (m, 1H), 3.29-3.38 (m, 1H), 3.54 (t, 2H, J = 6.0 Hz), 4.45 (s, 2H), 6.90 (s, 1H), 7.12 (d, 1H, J = 7.6 Hz), 7.20-7.23 (m, 3H), 7.28-7.42 (m, 5H), 7.49 (s, 1H), 10.83 (s, 1H). | 487 | 485 | Optically active substance (The same configuration as Example 5) |
| 339 | 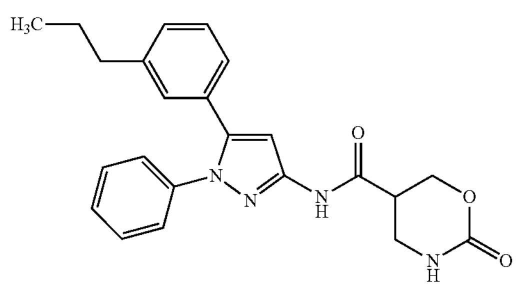 [SMILES: CCCc1cccc(-c2cc(NC(=O)C3CNC(=O)OC3)nn2-c2ccccc2)c1] | 1H-NMR (DMSO-D6) δ: 0.77 (t, 3H, J = 7.4 Hz), 1.43 (tq, 2H, J = 7.4 Hz, 7.4 Hz), 2.46 (t, 2H, J = 7.4 Hz), 3.07 (m, 1H), 3.35-3.46 (m, 2H), 4.28-4.41 (m, 2H), 6.87 (s, 1H), 7.00 (s, 1H), 7.07 (d, 1H, J = 8.0 Hz), 7.17 (d, 1H, J = 8.0 Hz), 7.20-7.42 (m, 7H), 11.01 (s, 1H). | 405 | 403 | racemate |
| 340 | 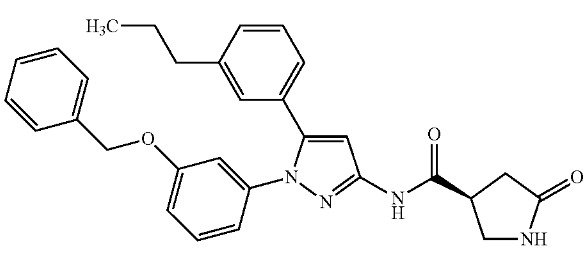 [SMILES: CCCc1cccc(-c2cc(NC(=O)[C@@H]3CNC(=O)C3)nn2-c2cccc(OCc3ccccc3)c2)c1] | 1H-NMR (DMSO-D6) δ: 0.78 (t, 3H, J = 7.3 Hz), 1.41-1.51 (m, 2H), 2.36-2.41 (m, 2H), 2.45-2.52 (m, 2H), 3.32-3.53 (m, 3H), 4.98 (s, 2H), 6.76-6.80 (m, 1H), 6.86 (t, 1H, J = 2.0 Hz), 6.88 (s, 1H), 6.98 (dd, 1H, J = 8.3, 2.0 Hz), 7.01-7.04 (m, 1H), 7.07-7.11 (m, 1H), 7.17-7.21 (m, 1H), 7.26-7.41 (m, 7H), 7.63 (s, 1H), 10.86 (s, 1H). | 495 | 493 | S-form |

TABLE 2-continued

| Example No. | Molecular Structure | NMR (400 MHz) | MS (M + H) | MS (M − H) | Comments |
|---|---|---|---|---|---|
| 341 | 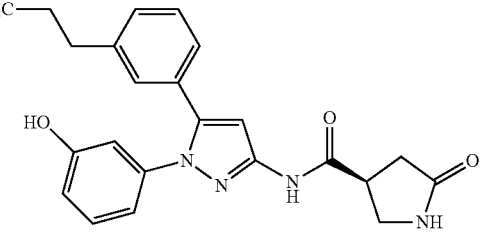 | 1H-NMR (DMSO-D6) δ: 0.79 (t, 3H, J = 7.5 Hz), 1.42-1.52 (m, 2H), 2.36-2.41 (m, 2H), 2.45-2.51 (m, 2H), 3.31-3.53 (m, 3H), 6.53-6.58 (m, 1H), 6.64 (t, 1H, J = 2.0 Hz), 6.68-6.73 (m, 1H), 6.86 (s, 1H), 7.01-7.04 (m, 1H), 7.06-7.18 (m, 3H), 7.27 (t, 1H, J = 7.7 Hz), 7.63 (s, 1H), 9.88 (br s, 1H), 10.82 (s, 1H). | 405 | 403 | S-form |
| 342 | 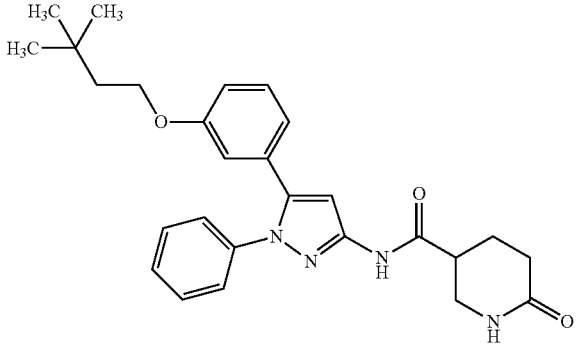 [SMILES: CC(C)(C)CCOc1cccc(-c2cc(NC(=O)C3CCC(=O)NC3)nn2-c2ccccc2)c1] | 1H-NMR (DMSO-D6) δ: 0.90 (s, 9H), 1.54 (t, 2H, J = 7.3 Hz), 1.83-2.03 (m, 2H), 2.12-2.30 (m, 2H), 2.79-2.87 (m, 1H), 3.25-3.35 (m, 2H), 3.85 (t, 2H, J = 7.3 Hz), 6.70 (t, 1H, J = 2.0 Hz), 6.80-6.84 (m, 1H), 6.87-6.92 (m, 2H), 7.23-7.28 (m, 3H), 7.32-7.44 (m, 3H), 7.50 (br s, 1H), 10.82 (s, 1H). | 461 | 459 | Optically active substance (The same configuration as Example 5) |
| 343 | 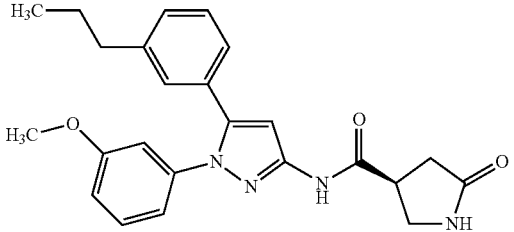 [SMILES: CCCc1cccc(-c2cc(NC(=O)[C@@H]3CNC(=O)C3)nn2-c2cccc(OC)c2)c1] | 1H-NMR (DMSO-D6) δ: 0.78 (t, 3H, J = 7.5 Hz), 1.41-1.52 (m, 2H), 2.36-2.41 (m, 2H), 2.45-2.53 (m, 2H), 3.31-3.53 (m, 3H), 3.65 (s, 3H), 6.73-6.77 (m, 1H), 6.79 (t, 1H, J = 2.2 Hz), 6.87-6.92 (m, 2H), 7.02-7.04 (m, 1H), 7.07-7.11 (m, 1H), 7.16-7.20 (m, 1H), 7.24-7.31 (m, 2H), 7.64 (s, 1H), 10.87 (s, 1H). | 419 | 417 | S-form |
| 344 | 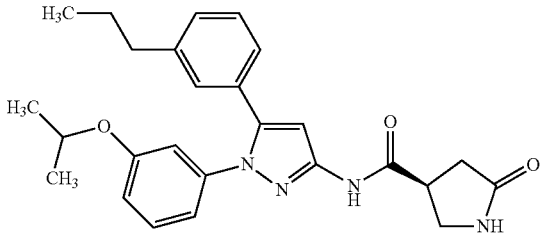 [SMILES: CCCc1cccc(-c2cc(NC(=O)[C@@H]3CNC(=O)C3)nn2-c2cccc(OC(C)C)c2)c1] | 1H-NMR (DMSO-D6) δ: 0.78 (t, 3H, J = 7.3 Hz), 1.13 (d, 6H, J = 6.0 Hz), 1.40-1.50 (m, 2H), 2.36-2.41 (m, 2H), 2.44-2.53 (m, 2H), 3.31-3.53 (m, 3H), 4.38-4.46 (m, 1H), 6.68 (t, 1H, J = 2.2 Hz), 6.78-6.82 (m, 1H), 6.84-6.88 (m, 2H), 7.01-7.03 (m, 1H), 7.07-7.11 (m, 1H), 7.15-7.20 (m, 1H), 7.24-7.31 (m, 2H), 7.63 (s, 1H), 10.84 (s, 1H). | 447 | 445 | S-form |

TABLE 2-continued

| Example No. | Molecular Structure | NMR (400 MHz) | MS (M + H) | MS (M − H) | Comments |
|---|---|---|---|---|---|
| 345 | 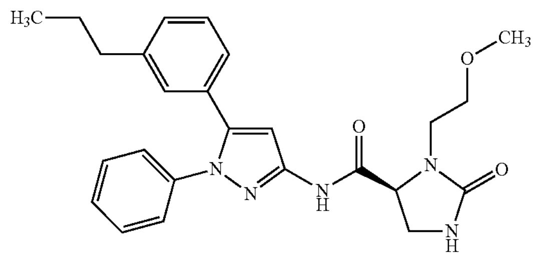 [SMILES: CCCc1cccc(-c2cc(NC(=O)[C@@H]3CNC(=O)N3CCOC)nn2-c2ccccc2)c1] | 1H-NMR (CDCl3) δ: 0.84 (t, 3H, J = 7.3 Hz), 1.50 (tq, 2H, J = 7.3, 7.5 Hz), 2.49 (t, 2H, J = 7.5 Hz), 3.27-3.33 (m, 1H), 3.52 (s, 3H), 3.54-3.65 (m, 3H), 3.85-3.94 (m, 2H), 4.37 (dd, 1H, J = 10.3, 7.4 Hz), 4.51 (s, 1H), 7.03-7.14 (m, 5H), 7.19-7.33 (m, 5H), 10.07 (s, 1H). | 448 | 446 | S-form |
| 346 | 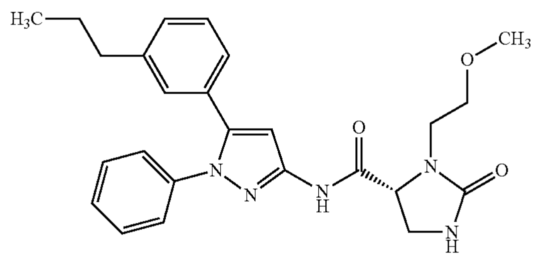 [SMILES: CCCc1cccc(-c2cc(NC(=O)[C@H]3CNC(=O)N3CCOC)nn2-c2ccccc2)c1] | 1H-NMR (CDCl3) δ: 0.84 (t, 3H, J = 7.3 Hz), 1.50 (tq, 2H, J = 7.3, 7.5 Hz), 2.49 (t, 2H, J = 7.5 Hz), 3.27-3.33 (m, 1H), 3.52 (s, 3H), 3.54-3.65 (m, 3H), 3.85-3.94 (m, 2H), 4.37 (dd, 1H, J = 10.3, 7.4 Hz), 4.51 (s, 1H), 7.03-7.14 (m, 5H), 7.19-7.33 (m, 5H), 10.07 (s, 1H). | 448 | 446 | R-form |
| 347 | 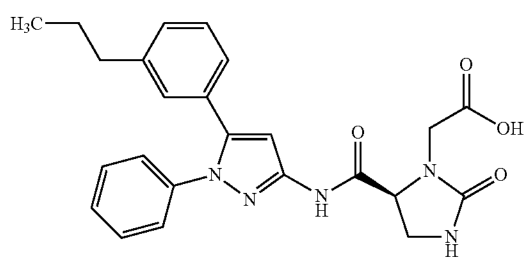 [SMILES: CCCc1cccc(-c2cc(NC(=O)[C@@H]3CNC(=O)N3CC(=O)O)nn2-c2ccccc2)c1] | 1H-NMR (DMSO-D6) δ: 0.77 (t, 3H, J = 7.3 Hz), 1.44 (tq, 2H, J = 7.3, 7.3 Hz), 2.45 (t, 2H, J = 7.3 Hz), 3.23-3.27 (m, 1H), 3.50-3.55 (m, 1H), 3.60-3.63 (m, 1H), 3.90-3.96 (m, 1H), 4.48-4.53 (m, 1H), 6.58 (s, 1H), 6.89 (s, 1H), 6.99-7.02 (m, 1H), 7.06-7.08 (m, 1H), 7.16-7.18 (m, 1H), 7.21-7.29 (m, 3H), 7.33-7.42 (m, 3H), 12.77 (br s, 1H). | 448 | 446 | S-form |
| 348 | 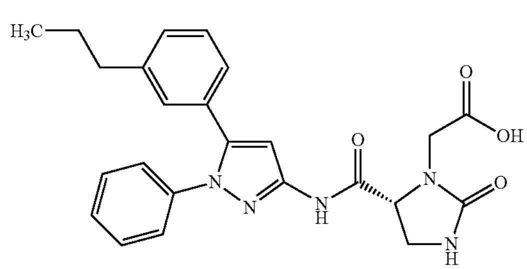 [SMILES: CCCc1cccc(-c2cc(NC(=O)[C@H]3CNC(=O)N3CC(=O)O)nn2-c2ccccc2)c1] | 1H-NMR (DMSO-D6) δ: 0.77 (t, 3H, J = 7.3 Hz), 1.44 (tq, 2H, J = 7.3, 7.3 Hz), 2.45 (t, 2H, J = 7.3 Hz), 3.23-3.27 (m, 1H), 3.50-3.55 (m, 1H), 3.60-3.63 (m, 1H), 3.90-3.96 (m, 1H), 4.48-4.53 (m, 1H), 6.58 (s, 1H), 6.89 (s, 1H), 6.99-7.02 (m, 1H), 7.06-7.08 (m, 1H), 7.16-7.18 (m, 1H), 7.21-7.29 (m, 3H), 7.33-7.42 (m, 3H), 12.77 (br s, 1H). | 448 | 446 | R-form |

TABLE 2-continued

| Example No. | Molecular Structure | NMR (400 MHz) | MS (M + H) | MS (M − H) | Comments |
|---|---|---|---|---|---|
| 349 | 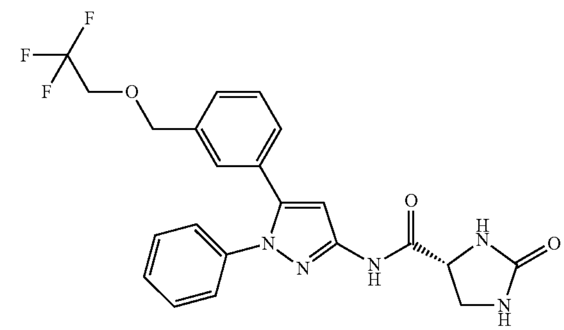 [SMILES: O=C1NC[C@H](C(=O)Nc2cc(-c3cccc(COCC(F)(F)F)c3)n(-c3ccccc3)n2)N1] | 1H-NMR (DMSO-D6) δ: 3.33-3.38 (m, 1H), 3.60 (dd, 1H, J = 10.1, 8.3 Hz), 3.97 (q, 2H, J = 9.2 Hz), 4.32 (dd, 1H, J = 8.8, 5.6 Hz), 4.61 (s, 2H), 6.33 (s, 1H), 6.59 (s, 1H), 6.93 (s, 1H), 7.16-7.17 (m, 1H), 7.22-7.26 (m, 3H), 7.34-7.40 (m, 5H), 10.71 (s, 1H). | 460 | 458 | R-form |
| 350 | 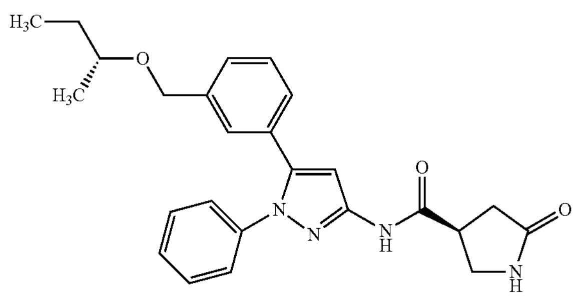 [SMILES: CC[C@@H](C)OCc1cccc(-c2cc(NC(=O)[C@@H]3CNC(=O)C3)nn2-c2ccccc2)c1] | 1H-NMR (DMSO-D6) δ: 0.80 (t, 3H, J = 7.6 Hz), 1.03 (d, 3H, J = 6.4 Hz), 1.32-1.50 (m, 2H), 2.39 (d, 2H, J = 8.4 Hz), 3.32-3.52 (m, 3H), 4.35 (d, 1H, J = 12.8 Hz), 4.44 (d, 1H, J = 12.8 Hz), 6.90 (s, 1H), 7.11 (d, 1H, J = 6.8 Hz), 7.21-7.24 (m, 3H), 7.28-7.41 (m, 5H), 7.63 (s, 1H), 10.86 (s, 1H). | 433 | 431 | sec-butoxymethyl group: R-form Lactam ring: S-form Diastereo isomer of Example 351 |
| 351 | 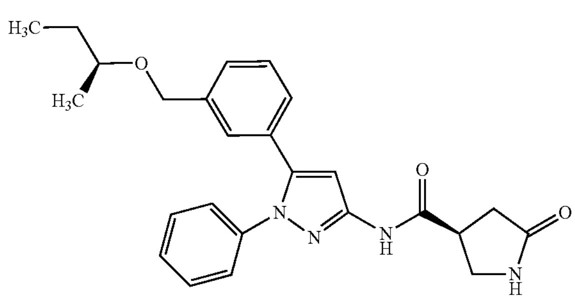 [SMILES: CC[C@H](C)OCc1cccc(-c2cc(NC(=O)[C@@H]3CNC(=O)C3)nn2-c2ccccc2)c1] | 1H-NMR (DMSO-D6) δ: 0.80 (t, 3H, J = 7.6 Hz), 1.03 (d, 3H, J = 6.4 Hz), 1.32-1.50 (m, 2H), 2.39 (d, 2H, J = 8.4 Hz), 3.32-3.52 (m, 3H), 4.35 (d, 1H, J = 12.8 Hz), 4.44 (d, 1H, J = 12.8 Hz), 6.90 (s, 1H), 7.11 (d, 1H, J = 6.8 Hz), 7.21-7.24 (m, 3H), 7.28-7.41 (m, 5H), 7.63 (s, 1H), 10.86 (s, 1H). | 433 | 431 | sec-butoxymethyl group: R-form Lactam ring: S-form Diastereo isomer of Example 350 |
| 352 | 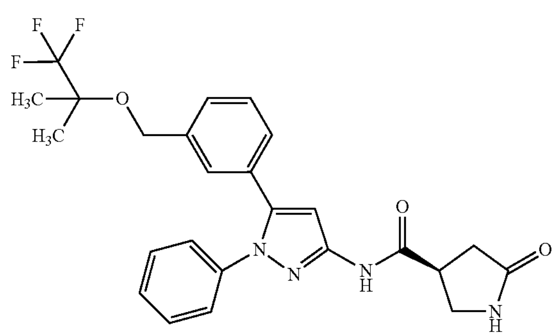 [SMILES: CC(C)(OCc1cccc(-c2cc(NC(=O)[C@@H]3CNC(=O)C3)nn2-c2ccccc2)c1)C(F)(F)F] | 1H-NMR (DMSO-D6) : 1.34 (s, 6H), 2.39 (d, 2H, J = 8.4 Hz), 3.32-3.52 (m, 3H), 4.53 (s, 2H), 6.91 (s, 1H), 7.13 (d, 1H, J = 7.6 Hz), 7.22-7.25 (m, 3H), 7.28-7.42 (m, 5H), 7.63 (s, 1H), 10.86 (s, 1H). | 487 | 485 | S-form |

TABLE 2-continued

| Example No. | Molecular Structure | NMR (400 MHz) | MS (M + H) | MS (M − H) | Comments |
|---|---|---|---|---|---|
| 353 | 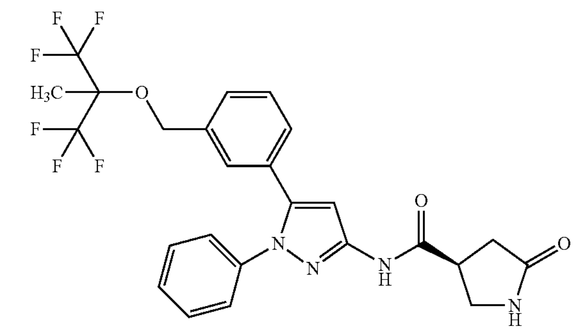 [SMILES: CC(OCc1cccc(-c2cc(NC(=O)[C@@H]3CNC(=O)C3)nn2-c2ccccc2)c1)(C(F)(F)F)C(F)(F)F] | 1H-NMR (DMSO-D6) : 1.72 (s, 3H), 2.39 (d, 2H, J = 8.4 Hz), 3.32-3.52 (m, 3H), 4.78 (s, 2H), 6.92 (s, 1H), 7.17 (d, 1H, J = 7.6 Hz), 7.22-7.26 (m, 3H), 7.31-7.41 (m, 5H), 7.63 (s, 1H), 10.87 (s, 1H). | 541 | 539 | S-form |
| 354 | 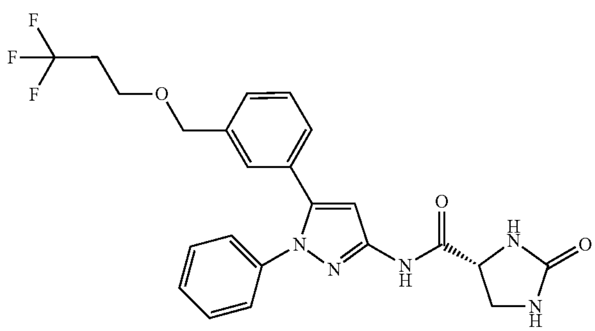 [SMILES: O=C1NC[C@H](C(=O)Nc2cc(-c3cccc(COCCC(F)(F)F)c3)n(-c3ccccc3)n2)N1] | 1H-NMR (DMSO-D6) δ: 2.47-2.57 (m, 2H), 3.34-3.38 (m, 1H), 3.54 (t, 2H, J = 6.0 Hz), 3.59 (t, 1H, 9.2 Hz), 4.30-4.34 (m, 1H), 4.45 (s, 2H), 6.33 (s, 1H), 6.60 (s, 1H), 6.92 (s, 1H), 7.12 (d, 1H, J = 7.6 Hz), 7.22-7.25 (m, 3H), 7.29-7.41 (m, 5H), 10.71 (s, 1H). | 474 | 472 | R-form |
| 355 | 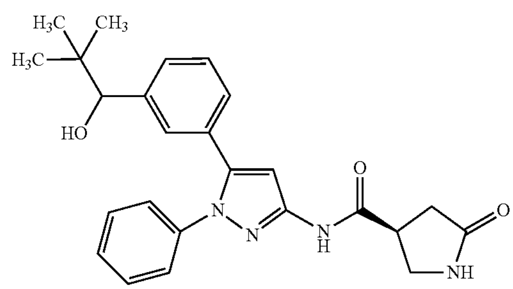 [SMILES: CC(C)(C)C(O)c1cccc(-c2cc(NC(=O)[C@@H]3CNC(=O)C3)nn2-c2ccccc2)c1] | 1H-NMR (DMSO-D6) δ: 0.67 (s, 9H), 2.37-2.41 (m, 2H), 3.30-3.52 (m, 3H), 4.12 (d, 1H, J = 4.0 Hz), 5.13 (d, 1H, J = 4.0 Hz), 6.86 (s, 1H), 7.07-7.10 (m, 1H), 7.14-7.18 (m, 1H), 7.20-7.40 (m, 7H), 7.63 (s, 1H), 10.85 (s, 1H). | 433 | 431 | 1-hydroxy-2,2-dimethyl-propyl group: racemate Lactam ring: S-form |
| 356 | 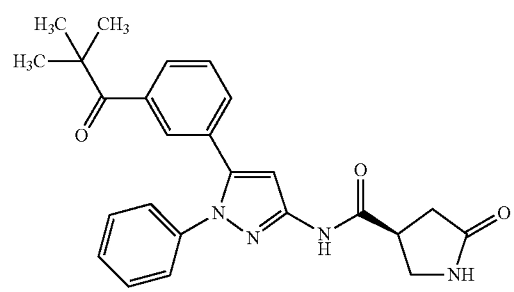 [SMILES: CC(C)(C)C(=O)c1cccc(-c2cc(NC(=O)[C@@H]3CNC(=O)C3)nn2-c2ccccc2)c1] | 1H-NMR (DMSO-D6) δ: 1.07 (s, 9H), 2.38-2.41 (m, 2H), 3.31-3.54 (m, 3H), 6.97 (s, 1H), 7.24-7.28 (m, 2H), 7.32-7.66 (m, 8H), 10.88 (s, 1H). | 431 | 429 | S-form |
| 357 | 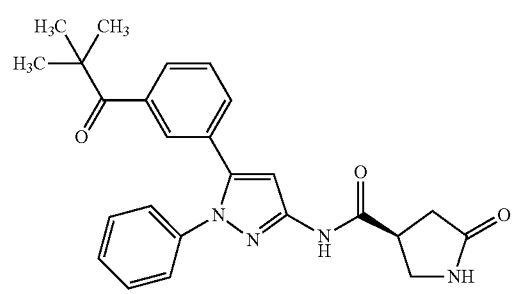 [SMILES: CC(C)(C)C(=O)c1cccc(-c2cc(NC(=O)[C@@H]3CNC(=O)C3)nn2-c2ccccc2)c1] | 1H-NMR (DMSO-D6) δ: 1.06 (s, 6H), 2.37-2.42 (m, 2H), 3.13 (s, 3H), 3.16 (s, 2H), 3.31-3.54 (m, 3H), 6.92 (s, 1H), 7.04-7.06 (m, 1H), 7.17-7.25 (m, 3H), 7.28-7.44 (m, 5H), 7.63 (s, 1H), 10.84 (s, 1H). | 433 | 431 | S-form |

TABLE 2-continued

| Example No. | Molecular Structure | NMR (400 MHz) | MS (M + H) | MS (M − H) | Comments |
|---|---|---|---|---|---|
| 358 | 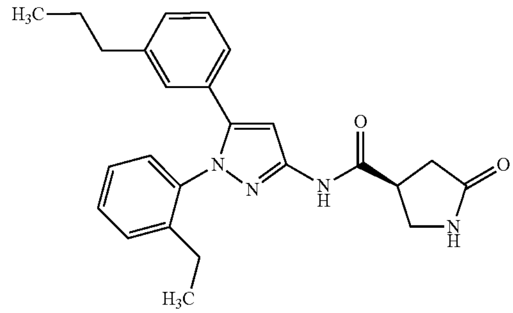 [SMILES: CCCc1cccc(-c2cc(NC(=O)[C@@H]3CNC(=O)C3)nn2-c2ccccc2CC)c1] | ¹H-NMR (CDCl₃) δ: 0.78 (t, 3H, J = 7.2 Hz), 0.97 (t, 3H, J = 7.6 Hz), 1.44 (tq, 2H, J = 7.2, 7.2 Hz), 2.33 (q, 2H, J = 7.6 Hz), 2.41-2.53(m, 3H), 2.75 (dd, 1H, J = 16.8, 8.4 Hz), 3.16-3.26 (m, 1H), 3.53 (t, 1H, J = 9.2 Hz), 3.68 (dd, 1H, J = 9.6, 7.6 Hz), 5.69 (s, 1H), 6.97-7.40 (m, 9H), 8.54 (s, 1H). | 417 | 415 | S-form |
| 359 | 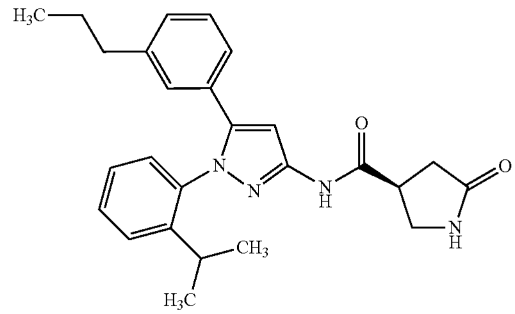 [SMILES: CCCc1cccc(-c2cc(NC(=O)[C@@H]3CNC(=O)C3)nn2-c2ccccc2C(C)C)c1] | ¹H-NMR (CDCl₃) δ: 0.65-1.20 (m, 9H), 1.43 (tq, 2H, J = 7.2, 7.2 Hz), 2.35-2.54 (m, 3H), 2.60-2.69(m, 1H), 2.74 (dd, 1H, J = 17.2, 8.8 Hz), 3.12-3.25 (m, 1H), 3.44-3.54 (m, 1H), 3.61-3.70 (m, 1H), 5.80 (s, 1H), 6.95-7.44 (m, 9H), 8.76 (br s, 1H). | 431 | 429 | S-form |
| 360 | 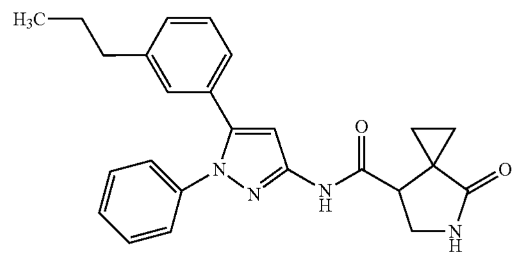 [SMILES: CCCc1cccc(-c2cc(NC(=O)C3CNC(=O)C34CC4)nn2-c2ccccc2)c1] | ¹H-NMR (CDCl₃) δ: 0.76-0.87 (m, 4H), 0.92-1.00 (m, 1H), 1.12-1.27 (m, 2H), 1.51 (tq, 2H, J = 7.6, 7.6 Hz), 2.49 (t, 2H, J = 7.6 Hz), 3.03 (dd, 1H, J = 8.4, 5.2 Hz), 3.46 (dd, 1H, J = 9.6, 8.4 Hz), 3.80 (dd, 1H, J = 9.6, 5.2 Hz), 6.46 (s, 1H), 7.03-7.37 (m, 10H), 9.29 (s, 1H). | 415 | 413 | Optically active substance Optical isomer of Example 361 (The same configuration as Example 250) |
| 361 | 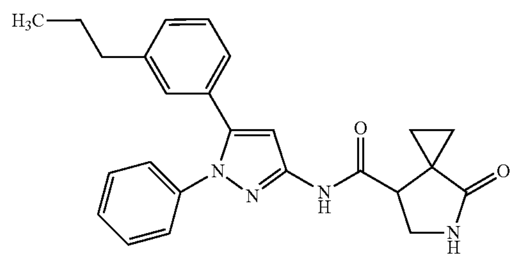 [SMILES: CCCc1cccc(-c2cc(NC(=O)C3CNC(=O)C34CC4)nn2-c2ccccc2)c1] | ¹H-NMR (CDCl₃) δ: 0.76-0.87 (m, 4H), 0.92-1.00 (m, 1H), 1.12-1.27 (m, 2H), 1.51 (tq, 2H, J = 7.6, 7.6 Hz), 2.49 (t, 2H, J = 7.6 Hz), 3.03 (dd, 1H, J = 8.4, 5.2 Hz), 3.46 (dd, 1H, J = 9.6, 8.4 Hz), 3.80 (dd, 1H, J = 9.6, 5.2 Hz), 6.46 (s, 1H), 7.03-7.37 (m, 10H), 9.29 (s, 1H). | 415 | 413 | Optically active substance Optical isomer of Example 360 |
| 362 | 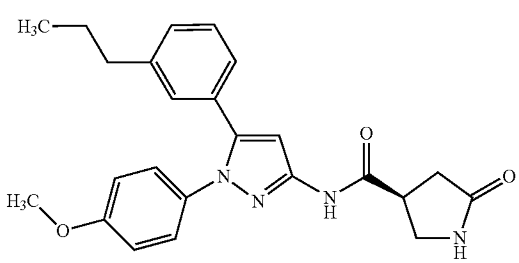 [SMILES: CCCc1cccc(-c2cc(NC(=O)[C@@H]3CNC(=O)C3)nn2-c2ccc(OC)cc2)c1] | 1H-NMR (DMSO-D6) δ: 0.77 (t, 3H, J = 7.4 Hz), 1.45 (tq, 2H, J = 7.4 Hz, 7.4 Hz), 2.35-2.40 (m, 2H), 2.46 (t, 2H, J = 7.4 Hz), 3.30-3.53 (m, 3H), 3.76 (s, 3H), 6.86 (s, 1H), 6.92-6.96 (m, 2H), 7.00 (s, 1H), 7.05 (d, 1H, J = 7.6 Hz), 7.12-7.18 (m, 3H), 7.25 (dd, 1H, J = 7.6 Hz, 7.6 Hz), 7.63 (s, 1H), 10.80 (s, 1H). | 419 | 417 | S-form |

TABLE 2-continued

| Example No. | Molecular Structure | NMR (400 MHz) | MS (M + H) | MS (M − H) | Comments |
|---|---|---|---|---|---|
| 363 | 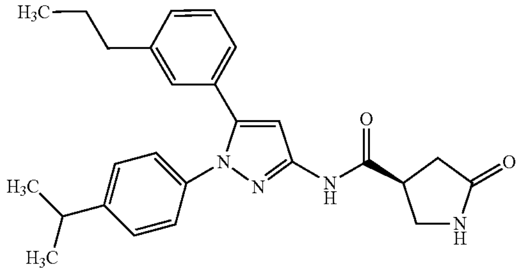 [SMILES: CCCc1cccc(-c2cc(NC(=O)[C@@H]3CNC(=O)C3)nn2-c2ccc(C(C)C)cc2)c1] | 1H-NMR (DMSO-D6) δ: 0.74 (t, 3H, J = 7.4 Hz), 1.19 (d, 6H, J = 6.8 Hz), 1.37 (tq, 2H, J = 7.4 Hz, 7.4 Hz), 2.36-2.44 (m, 4H), 2.91 (sep, 1H, J = 6.8 Hz), 3.30-3.53 (m, 3H), 6.88 (s, 2H), 7.10-7.18 (m, 4H), 7.23-7.31 (m, 3H), 7.62 (s, 1H), 10.81 (s, 1H). | 431 | 429 | S-form |
| 364 | 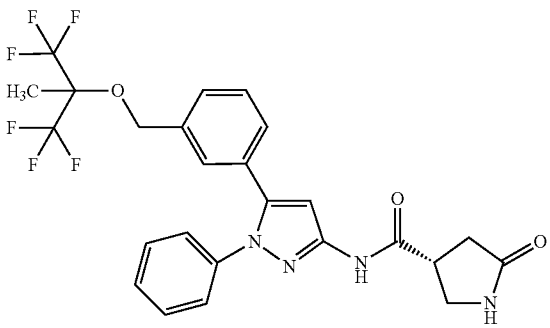 [SMILES: CC(OCc1cccc(-c2cc(NC(=O)[C@H]3CNC(=O)C3)nn2-c2ccccc2)c1)(C(F)(F)F)C(F)(F)F] | 1H-NMR (DMSO-D6) δ: 1.72 (s, 3H), 2.39 (d, 2H, J = 8.4 Hz), 3.32-3.52 (m, 3H), 4.78 (s, 2H), 6.92 (s, 1H), 7.17 (d, 1H, J = 7.6 Hz), 7.22-7.26 (m, 3H), 7.31-7.41 (m, 5H), 7.63 (s, 1H), 10.87 (s, 1H). | 541 | 539 | R-form |
| 365 | 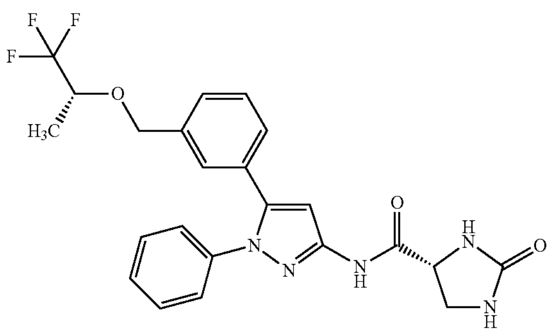 [SMILES: C[C@@H](OCc1cccc(-c2cc(NC(=O)[C@H]3CNC(=O)N3)nn2-c2ccccc2)c1)C(F)(F)F] | 1H-NMR (DMSO-D6) : 1.19 (d, 3H, J = 6.4 Hz), 3.34-3.38 (m, 1H), 3.60 (t, 1H, 9.2 Hz), 4.05-4.13 (m, 1H), 4.31-4.34 (m, 1H), 4.62 (s, 2H), 6.34 (s, 1H), 6.60 (s, 1H), 6.93 (s, 1H), 7.15 (d, 1H, J = 6.8 Hz), 7.23-7.25 (m, 3H), 7.32-7.42 (m, 5H), 10.72 (s, 1H). | 474 | 472 | 2,2,2-trifluoro methyl-1-methyl-ethoxym ethyl group: R-form Alpha position of carbonyl group (amide): R-form |
| 366 | 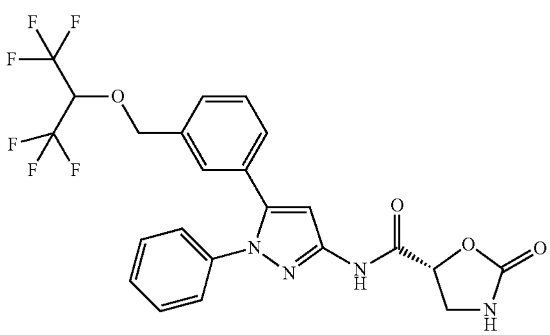 [SMILES: O=C1NC[C@H](C(=O)Nc2cc(-c3cccc(COC(C(F)(F)F)C(F)(F)F)c3)n(-c3ccccc3)n2)O1] | 1H-NMR (DMSO-D6) δ: 3.50-3.54 (m, 1H), 3.76 (t, 1H, J = 9.2 Hz), 4.86 (s, 2H), 5.11-5.15 (m, 1H), 5.52-5.59 (m, 1H), 6.93 (s, 1H), 7.16-7.18 (m, 1H), 7.24-7.26 (m, 2H), 7.34-7.42 (m, 6H), 7.76 (s, 1H), 11.08 (s, 1H). | 529 | 527 | R-form |

TABLE 2-continued

| Example No. | Molecular Structure | NMR (400 MHz) | MS (M + H) | MS (M − H) | Comments |
|---|---|---|---|---|---|
| 367 | 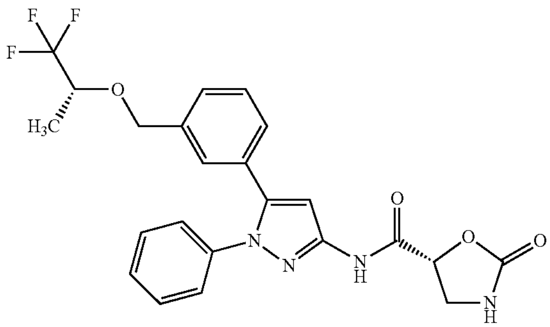 | 1H-NMR (DMSO-D6) δ: 1.19 (d, 3H, J = 6.4 Hz), 3.50-3.54 (m, 1H), 3.75 (t, 1H, J = 9.2 Hz), 4.06-4.13 (m, 1H), 4.62 (s, 2H), 5.11-5.15 (m, 1H), 6.92 (s, 1H), 7.15 (d, 1H, J = 7.6 Hz), 7.24-7.26 (m, 3H), 7.32-7.42 (m, 5H), 7.75 (s, 1H), 11.06 (s, 1H). | 475 | 473 | 2,2,2-trifluoromethyl-1-methyl-ethoxymethyl group: R-form Alpha position of carbonyl group (amide): R-form |
| 368 | 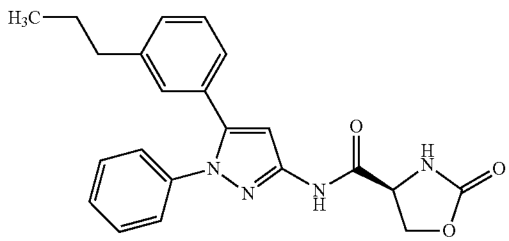 [SMILES: CCCc1cccc(-c2cc(NC(=O)[C@@H]3COC(=O)N3)nn2-c2ccccc2)c1] | 1H-NMR (DMSO-D6) δ: 0.77 (t, 3H, J = 7.3 Hz), 1.44 (tq, 2H, J = 7.4, 7.3 Hz), 2.46 (t, 2H, J = 7.4 Hz), 4.27-4.35 (m, 1H), 4.47-4.54 (m, 2H), 6.91 (s, 1H), 7.00 (s, 1H), 7.08 (d, 1H, J = 7.7 Hz), 7.18 (d, 1H, J = 7.7 Hz), 7.22-7.29 (m, 3H), 7.34-7.42 (m, 3H), 8.04 (br s, 1H), 10.98 (br s, 1H). | 391 | 389 | S-form |
| 369 | 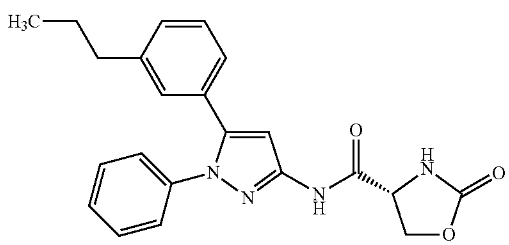 [SMILES: CCCc1cccc(-c2cc(NC(=O)[C@H]3COC(=O)N3)nn2-c2ccccc2)c1] | 1H-NMR (DMSO-D6) δ: 0.77 (t, 3H, J = 7.3 Hz), 1.44 (tq, 2H, J = 7.4, 7.3 Hz), 2.46 (t, 2H, J = 7.4 Hz), 4.27-4.34 (m, 1H), 4.47-4.54 (m, 2H), 6.91 (s, 1H), 7.00 (s, 1H), 7.08 (d, 1H, J = 7.9 Hz), 7.18 (d, 1H, J = 7.7 Hz), 7.22-7.29 (m, 3H), 7.33-7.42 (m, 3H), 8.04 (br s, 1H), 10.99 (br s, 1H). | 391 | 389 | R-form |
| 370 | 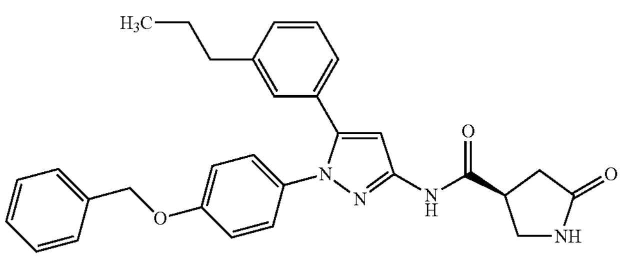 [SMILES: CCCc1cccc(-c2cc(NC(=O)[C@@H]3CNC(=O)C3)nn2-c2ccc(OCc3ccccc3)cc2)c1] | 1H-NMR (DMSO-D6) δ: 0.76 (t, 3H, J = 7.3 Hz), 1.43 (tq, 2H, J = 7.3, 7.3 Hz), 2.35-2.39 (m, 2H), 2.44 (t, 2H, J = 7.3 Hz), 3.32-3.35 (m, 1H), 3.39-3.42 (m, 1H), 3.46-3.50 (m, 1H), 5.08 (s, 2H), 6.85 (s, 1H), 6.98-7.05 (m, 4H), 7.13-7.15 (m, 3H), 7.22-7.26 (m, 1H), 7.30-7.44 (m, 5H), 7.61 (s, 1H), 10.77 (s, 1H). | 495 | 493 | S-form |

TABLE 2-continued

| Example No. | Molecular Structure | NMR (400 MHz) | MS (M + H) | MS (M − H) | Comments |
|---|---|---|---|---|---|
| 371 | 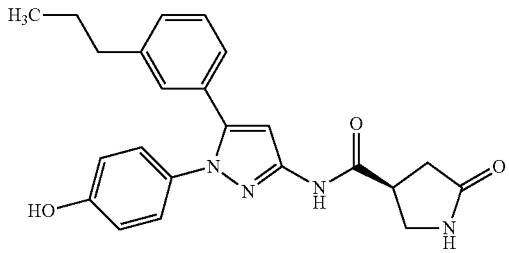 [SMILES: CCCc1cccc(-c2cc(NC(=O)[C@@H]3CNC(=O)C3)nn2-c2ccc(O)cc2)c1] | 1H-NMR (DMSO-D6) δ: 0.77 (t, 3H, J = 7.3 Hz), 1.45 (tq, 2H, J = 7.3, 7.4 Hz), 2.35-2.37 (m, 2H), 2.45 (t, 2H, J = 7.4 Hz), 3.33-3.35 (m, 1H), 3.37-3.43 (m, 1H), 3.46-3.50 (m, 1H), 6.71-6.73 (m, 2H), 6.83 (s, 1H), 6.98-7.04 (m, 4H), 7.11-7.13 (m, 1H), 7.23 (t, 1H, J = 7.7 Hz), 7.61 (s, 1H), 9.72 (br s, 1H), 10.74 (s, 1H). | 405 | 403 | S-form |
| 372 | 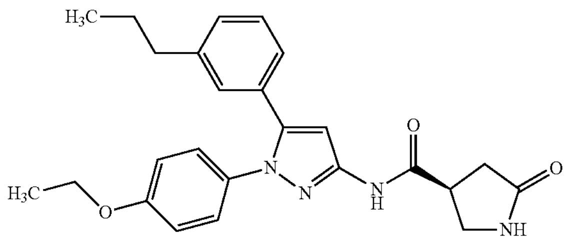 [SMILES: CCCc1cccc(-c2cc(NC(=O)[C@@H]3CNC(=O)C3)nn2-c2ccc(OCC)cc2)c1] | 1H-NMR (DMSO-D6) δ: 0.78 (t, 3H, J = 7.3 Hz), 1.32 (t, 3H, J = 6.9 Hz), 1.45 (tq, 2H, J = 14.9, 7.3 Hz), 2.38-2.40 (m, 2H), 2.46 (t, 2H, J = 7.7 Hz), 3.33-3.36 (m, 1H), 3.38-3.44 (m, 1H), 3.48-3.52 (m, 1H), 4.02 (q, 2H, J = 6.9 Hz), 6.86 (s, 1H), 6.91-6.93 (m, 2H), 6.99-7.01 (m, 1H), 7.04-7.06 (m, 1H), 7.12-7.16 (m, 3H), 7.24-7.26 (m, 1H), 7.62 (s, 1H), 10.79 (s, 1H). | 433 | 431 | S-form |
| 373 | 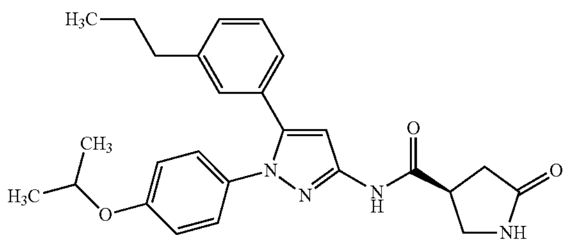 [SMILES: CCCc1cccc(-c2cc(NC(=O)[C@@H]3CNC(=O)C3)nn2-c2ccc(OC(C)C)cc2)c1] | 1H-NMR (DMSO-D6) δ: 0.77 (t, 3H, J = 7.3 Hz), 1.26 (d, 6H, J = 6.0 Hz), 1.42 (tq, 2H, J = 7.4, 7.3 Hz), 2.37-2.40 (m, 2H), 2.45 (t, 2H, J = 7.4 Hz), 3.32-3.35 (m, 1H), 3.40-3.44 (m, 1H), 3.48-3.52 (m, 1H), 4.60 (sep, 1H, J = 6.0 Hz), 6.85-6.97 (m, 4H), 7.08-7.15 (m, 4H), 7.27 (t, 1H, J = 7.6 Hz), 7.63 (s, 1H), 10.78 (s, 1H). | 447 | 445 | S-form |
| 374 | 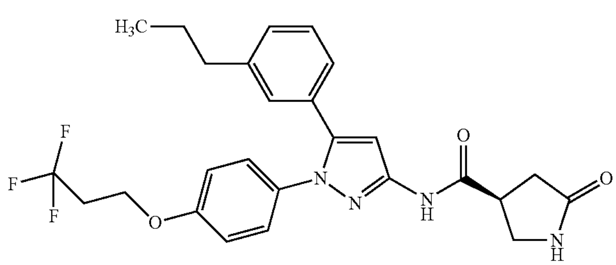 [SMILES: CCCc1cccc(-c2cc(NC(=O)[C@@H]3CNC(=O)C3)nn2-c2ccc(OCCC(F)(F)F)cc2)c1] | 1H-NMR (DMSO-D6) δ: 0.77 (t, 3H, J = 7.3 Hz), 1.44 (tq, 2H, J = 7.3, 7.2 Hz), 2.38-2.40 (m, 2H), 2.46 (t, 2H, J = 7.2 Hz), 2.74-2.82 (m, 2H), 3.32-3.35 (m, 1H), 3.39-3.42 (m, 1H), 3.48-3.51 (m, 1H), 4.20 (t, 2H, J = 5.8 Hz), 6.87 (s, 1H), 6.96-6.99 (m, 3H), 7.06-7.08 (m, 1H), 7.14-7.17 (m, 3H), 7.26 (t, 1H, J = 7.6 Hz), 7.63 (s, 1H), 10.80 (s, 1H). | 501 | 499 | S-form |

TABLE 2-continued

| Example No. | Molecular Structure | NMR (400 MHz) | MS (M + H) | MS (M − H) | Comments |
|---|---|---|---|---|---|
| 375 | 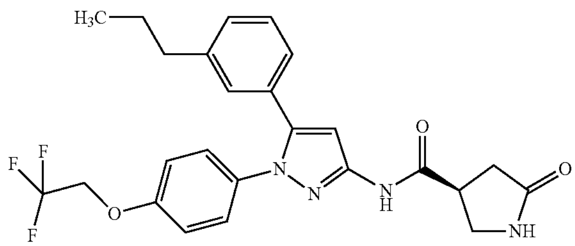 [SMILES: CCCc1cccc(-c2cc(NC(=O)[C@@H]3CNC(=O)C3)nn2-c2ccc(OCC(F)(F)F)cc2)c1] | 1H-NMR (DMSO-D6) δ: 0.78 (t, 3H, J = 7.3 Hz), 1.46 (tq, 2H, J = 7.7, 7.3 Hz), 2.37-2.39 (m, 2H), 2.46 (t, 2H, J = 7.7 Hz), 3.32-3.34 (m, 1H), 3.39-3.43 (m, 1H), 3.49-3.52 (m, 1H), 4.78 (q, 2H, J = 8.9 Hz), 6.87 (s, 1H), 7.00-7.09 (m, 4H), 7.15-7.28 (m, 4H), 7.63 (s, 1H), 10.81 (s, 1H). | 487 | 485 | S-form |
| 376 | 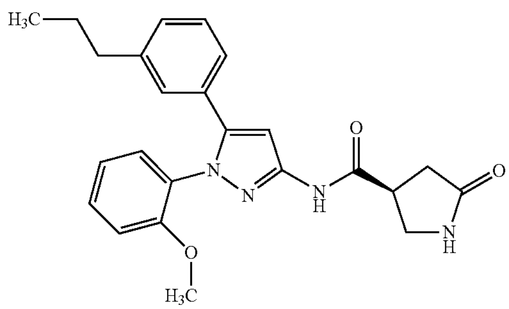 [SMILES: CCCc1cccc(-c2cc(NC(=O)[C@@H]3CNC(=O)C3)nn2-c2ccccc2OC)c1] | $^1$H-NMR (CDCl$_3$) δ: 0.80 (t, 3H, J = 7.2 Hz), 1.46 (tq, 2H, J = 7.2, 7.2 Hz), 2.15-2.33 (m, 1H), 2.46 (t, 2H, J = 7.2 Hz), 2.67 (dd, 1H, J = 16.8, 8.8 Hz), 2.90-3.04 (m, 1H), 3.31 (t, 1H, J = 8.8 Hz), 3.40 (s, 3H), 3.52 (t, 1H, J = 8.8 Hz), 6.03 (s, 1H), 6.87 (d, 1H, J = 8.4 Hz), 6.99-7.08 (m, 5H), 7.11-7.17 (m, 1H), 7.33-7.44 (m, 2H), 9.76 (s, 1H). | 419 | 417 | S-form |
| 377 | 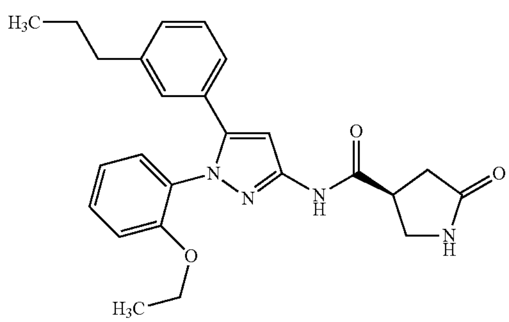 [SMILES: CCCc1cccc(-c2cc(NC(=O)[C@@H]3CNC(=O)C3)nn2-c2ccccc2OCC)c1] | $^1$H-NMR (CDCl$_3$) δ: 0.80 (t, 3H, J = 7.6 Hz), 0.93 (t, 3H, J = 6.8 Hz), 1.46 (tq, 2H, J = 7.6, 7.6 Hz), 2.01-2.33 (m, 1H), 2.45 (t, 2H, J = 7.6 Hz), 2.65 (dd, 1H, J = 16.8, 8.8 Hz), 2.85-3.01 (m, 1H), 3.13-3.87 (m, 4H), 6.00 (s, 1H), 6.83 (d, 1H, J = 8.4 Hz), 6.99-7.16 (m, 6H), 7.34 (t, 1H, J = 7.2 Hz), 7.47 (d, 1H, J = 7.6 Hz), 9.99 (br s, 1H). | 433 | 431 | S-form |
| 378 | 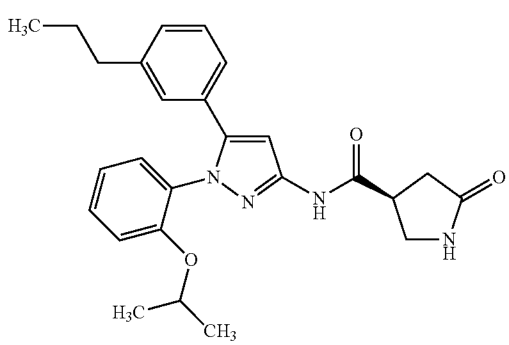 [SMILES: CCCc1cccc(-c2cc(NC(=O)[C@@H]3CNC(=O)C3)nn2-c2ccccc2OC(C)C)c1] | $^1$H-NMR (CDCl$_3$) δ: 0.38-1.18 (m, 9H), 1.46 (tq, 2H, J = 7.6, 7.6 Hz), 2.45 (t, 2H, J = 7.6 Hz), 2.66 (dd, 1H, J = 16.4, 8.8 Hz), 2.81-3.41 (m, 2H), 3.50 (t, 1H, J = 9.2 Hz), 4.20-4.31 (m, 1H), 6.11 (s, 1H), 6.80 (d, 1H, J = 8.0 Hz), 6.98-7.16 (m, 6H), 7.28-7.55 (m, 1H), 10.16 (br s, 1H). | 447 | 445 | S-form |

TABLE 2-continued

| Example No. | Molecular Structure | NMR (400 MHz) | MS (M + H) | MS (M − H) | Comments |
|---|---|---|---|---|---|
| 379 | 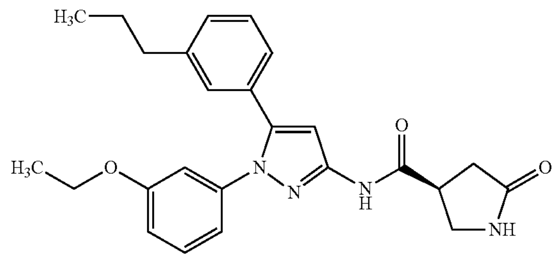 [SMILES: CCCc1cccc(-c2cc(NC(=O)[C@@H]3CNC(=O)C3)nn2-c2cccc(OCC)c2)c1] | 1H-NMR (DMSO-D6) δ: 0.78 (t, 3H, J = 7.3 Hz), 1.23 (t, 3H, J = 7.1 Hz), 1.40-1.51 (m, 2H), 2.37-2.41 (m, 2H), 2.44-2.51 (m, 2H), 3.31-3.53 (m, 3H), 3.89 (q, 2H, J = 7.1 Hz), 6.72-6.79 (m, 2H), 6.85-6.90 (m, 2H), 7.01-7.04 (m, 1H), 7.07-7.11 (m, 1H), 7.16-7.20 (m, 1H), 7.24-7.31 (m, 2H), 7.63 (s, 1H), 10.86 (s, 1H). | 433 | 431 | S-form |
| 380 | 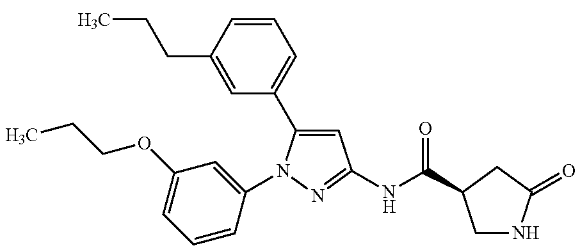 [SMILES: CCCOc1cccc(-n2nc(NC(=O)[C@@H]3CNC(=O)C3)cc2-c2cccc(CCC)c2)c1] | 1H-NMR (DMSO-D6) δ: 0.78 (t, 3H, J = 7.5 Hz), 0.90 (t, 3H, J = 7.5 Hz), 1.41-1.51 (m, 2H), 1.56-1.67 (m, 2H), 2.37-2.42 (m, 2H), 2.45-2.51 (m, 2H), 3.31-3.53 (m, 3H), 3.78 (t, 2H, J = 6.4 Hz), 6.73 (t, 1H, J = 2.2 Hz), 6.76-6.80 (m, 1H), 6.85-6.90 (m, 2H), 7.02-7.04 (m, 1H), 7.07-7.11 (m, 1H), 7.16-7.20 (m, 1H), 7.24-7.31 (m, 2H), 7.63 (s, 1H), 10.86 (s, 1H). | 447 | 445 | S-form |
| 381 | 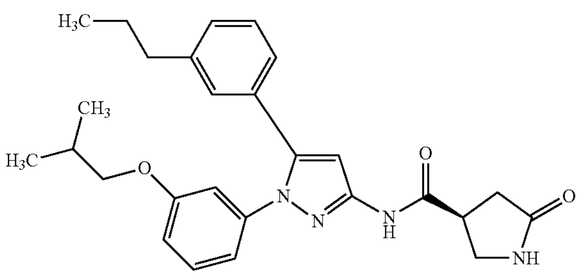 [SMILES: CCCc1cccc(-c2cc(NC(=O)[C@@H]3CNC(=O)C3)nn2-c2cccc(OCC(C)C)c2)c1] | 1H-NMR (DMSO-D6) δ: 0.78 (t, 3H, J = 7.3 Hz), 0.89 (d, 6H, J = 6.9 Hz), 1.41-1.51 (m, 2H), 1.83-1.94 (m, 1H), 2.37-2.41 (m, 2H), 2.45-2.52 (m, 2H), 3.31-3.54 (m, 3H), 3.58 (d, 2H, J = 6.9 Hz), 6.72 (t, 1H, J = 2.0 Hz), 6.76-6.81 (m, 1H), 6.85-6.90 (m, 2H), 7.02-7.04 (m, 1H), 7.07-7.12 (m, 1H), 7.17-7.21 (m, 1H), 7.24-7.31 (m, 2H), 7.63 (s, 1H), 10.86 (s, 1H). | 461 | 459 | S-form |
| 382 | 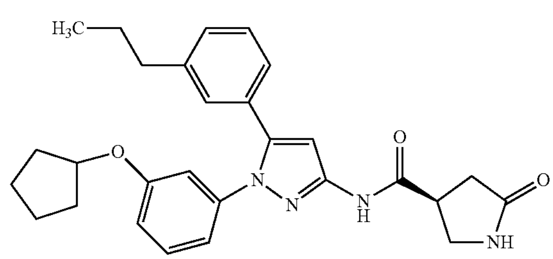 [SMILES: CCCc1cccc(-c2cc(NC(=O)[C@@H]3CNC(=O)C3)nn2-c2cccc(OC3CCCC3)c2)c1] | 1H-NMR (DMSO-D6) δ: 0.79 (t, 3H, J = 7.3 Hz), 1.40-1.76 (m, 10H), 2.36-2.41 (m, 2H), 2.44-2.52 (m, 2H), 3.29-3.53 (m, 3H), 4.57-4.63 (m, 1H), 6.64 (t, 1H, J = 2.2 Hz), 6.81-6.86 (m, 2H), 6.88 (s, 1H), 7.01-7.03 (m, 1H), 7.07-7.11 (m, 1H), 7.16-7.20 (m, 1H), 7.24-7.31 (m, 2H), 7.63 (s, 1H), 10.84 (s, 1H). | 473 | 471 | S-form |

TABLE 2-continued

| Example No. | Molecular Structure | NMR (400 MHz) | MS (M + H) | MS (M − H) | Comments |
|---|---|---|---|---|---|
| 383 | 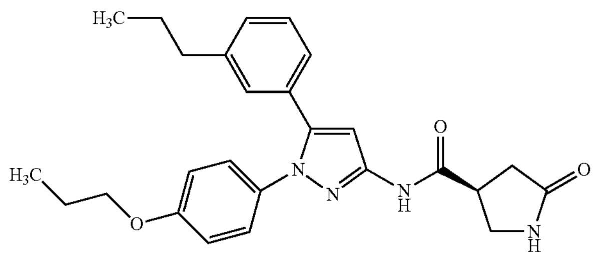 [SMILES: CCCOc1ccc(-n2nc(NC(=O)[C@@H]3CNC(=O)C3)cc2-c2cccc(CCC)c2)cc1] | 1H-NMR (DMSO-D6) δ: 0.77 (t, 3H, J = 7.3 Hz), 0.97 (t, 3H, J = 7.3 Hz), 1.45 (tq, 2H, J = 7.3, 7.2 Hz), 1.72 (tq, 2H, J = 6.9, 7.3 Hz), 2.38-2.39 (m, 2H), 2.45-2.46 (m, 5H), 3.32-3.35 (m, 1H), 3.39-3.39 (m, 1H), 3.48-3.50 (m, 1H), 3.92 (t, 2H, J = 6.5 Hz), 6.86 (s, 1H), 6.92-6.94 (m, 2H), 6.99-7.00 (m, 1H), 7.05-7.07 (m, 1H), 7.12-7.17 (m, 3H), 7.25 (t, 1H, J = 7.6 Hz), 7.62 (s, 1H), 10.79 (s, 1H). | 447 | 445 | S-form |
| 384 | 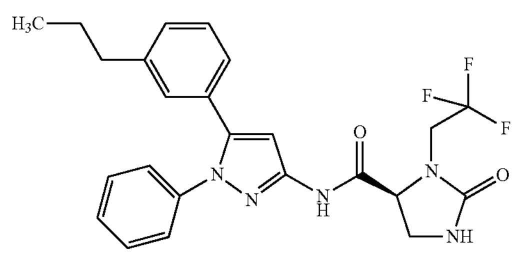 [SMILES: CCCc1cccc(-c2cc(NC(=O)[C@@H]3CNC(=O)N3CC(F)(F)F)nn2-c2ccccc2)c1] | 1H-NMR (DMSO-D6) δ: 0.77 (t, 3H, J = 7.3 Hz), 1.44 (tq, 2H, J = 7.3, 7.2 Hz), 2.47 (t, 2H, J = 7.2 Hz), 3.32-3.34 (m, 1H), 3.55-3.67 (m, 2H), 4.15-4.23 (m, 1H), 4.51-4.55 (m, 1H), 6.90 (s, 1H), 6.99-7.01 (m, 2H), 7.06-7.08 (m, 1H), 7.16-7.18 (m, 1H), 7.21-7.29 (m, 3H), 7.34-7.42 (m, 3H), 11.10 (s, 1H). | 472 | 470 | S-form |
| 385 | 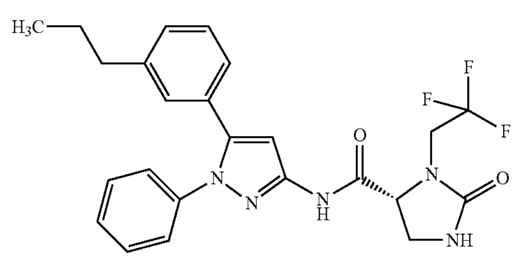 [SMILES: CCCc1cccc(-c2cc(NC(=O)[C@H]3CNC(=O)N3CC(F)(F)F)nn2-c2ccccc2)c1] | 1H-NMR (DMSO-D6) δ: 0.77 (t, 3H, J = 7.3 Hz), 1.44 (tq, 2H, J = 7.3, 7.2 Hz), 2.47 (t, 2H, J = 7.2 Hz), 3.32-3.34 (m, 1H), 3.55-3.67 (m, 2H), 4.15-4.23 (m, 1H), 4.51-4.55 (m, 1H), 6.90 (s, 1H), 6.99-7.01 (m, 2H), 7.06-7.08 (m, 1H), 7.16-7.18 (m, 1H), 7.21-7.29 (m, 3H), 7.34-7.42 (m, 3H), 11.10 (s, 1H). | 472 | 470 | R-form |
| 386 | 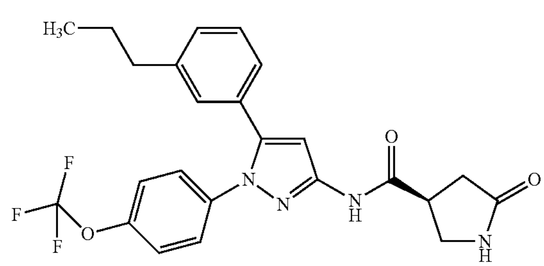 [SMILES: CCCc1cccc(-c2cc(NC(=O)[C@@H]3CNC(=O)C3)nn2-c2ccc(OC(F)(F)F)cc2)c1] | 1H-NMR (DMSO-D6) δ: 0.75 (t, 3H, J = 7.3 Hz), 1.41 (tq, 2H, J = 7.3, 7.7 Hz), 2.38-2.40 (m, 2H), 2.45 (t, 2H, J = 7.7 Hz), 3.33-3.35 (m, 1H), 3.40-3.45 (m, 1H), 3.49-3.52 (m, 1H), 6.92-6.94 (m, 2H), 7.15-7.20 (m, 2H), 7.30-7.36 (m, 3H), 7.40-7.42 (m, 2H), 7.63 (s, 1H), 10.87 (s, 1H). | 473 | 471 | S-form |

TABLE 2-continued

| Example No. | Molecular Structure | NMR (400 MHz) | MS (M + H) | MS (M − H) | Comments |
|---|---|---|---|---|---|
| 387 | 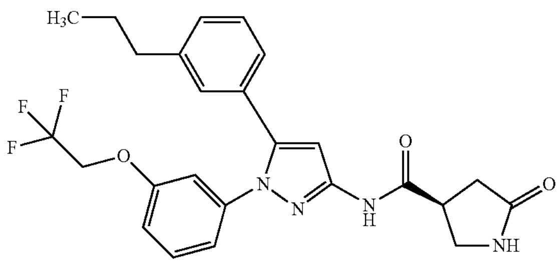 [SMILES: CCCc1cccc(-c2cc(NC(=O)[C@@H]3CNC(=O)C3)nn2-c2cccc(OCC(F)(F)F)c2)c1] | 1H-NMR (DMSO-D6) δ: 0.78 (t, 3H, J = 7.5 Hz), 1.41-1.51 (m, 2H), 2.37-2.41 (m, 2H), 2.45-2.52 (m, 2H), 3.30-3.53 (m, 3H), 4.68 (q, 2H, J = 8.9 Hz), 6.83-6.87 (m, 1H), 6.90 (s, 1H), 6.96 (t, 1H, J = 2.0 Hz), 7.02-7.06 (m, 2H), 7.07-7.11 (m, 1H), 7.17-7.21 (m, 1H), 7.26-7.36 (m, 2H), 7.63 (s, 1H), 10.86 (s, 1H). | 487 | 485 | S-form |
| 388 | 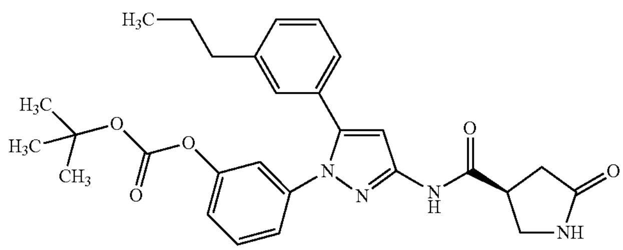 [SMILES: CCCc1cccc(-c2cc(NC(=O)[C@@H]3CNC(=O)C3)nn2-c2cccc(OC(=O)OC(C)(C)C)c2)c1] | 1H-NMR (DMSO-D6) δ: 0.79 (t, 3H, J = 7.5 Hz), 1.43-1.51 (m, 11H), 2.37-2.41 (m, 2H), 2.45-2.52 (m, 2H), 3.31-3.54 (m, 3H), 6.90 (s, 1H), 7.02-7.12 (m, 4H), 7.15-7.21 (m, 2H), 7.29 (t, 1H, J = 7.7 Hz), 7.40 (t, 1H, J = 8.1 Hz), 7.64 (s, 1H), 10.89 (s, 1H). | 505 | 503 | S-form |
| 389 | 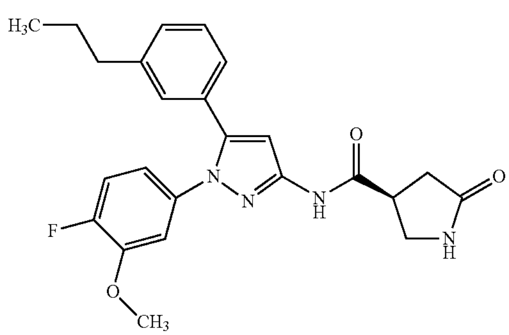 [SMILES: CCCc1cccc(-c2cc(NC(=O)[C@@H]3CNC(=O)C3)nn2-c2ccc(F)c(OC)c2)c1] | $^1$H-NMR (CDCl$_3$) δ: 0.86 (t, 3H, J = 7.6 Hz), 1.54 (tq, 2H, J = 7.6, 7.6 Hz), 2.52 (t, 2H, J = 7.6 Hz), 2.60 (dd, 1H, J = 17.2, 9.6 Hz), 2.78 (dd, 1H, J = 17.2, 8.4 Hz), 3.30-3.40 (m, 1H), 3.59 (t, 1H, J = 9.2 Hz), 3.67-3.75 (m, 4H), 6.00 (s, 1H), 6.73-6.85 (m, 2H), 6.98-7.08 (m, 4H), 7.12-7.25 (m, 2H), 8.48 (s, 1H). | 437 | 435 | S-form |
| 390 | 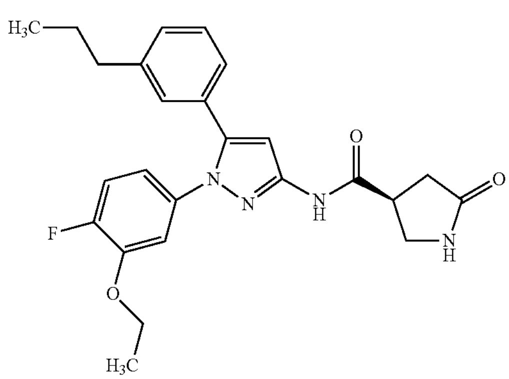 [SMILES: CCCc1cccc(-c2cc(NC(=O)[C@@H]3CNC(=O)C3)nn2-c2ccc(F)c(OCC)c2)c1] | $^1$H-NMR (CDCl$_3$) δ: 0.86 (t, 3H, J = 7.2 Hz), 1.34 (t, 3H, J = 7.2 Hz), 1.54 (tq, 2H, J = 7.2, 7.2 Hz), 2.52 (t, 2H, J = 7.2 Hz), 2.59 (dd, 1H, J = 17.2, 9.6 Hz), 2.78 (dd, 1H, J = 17.2, 8.4 Hz), 3.29-3.41 (m, 1H), 3.62 (t, 1H, J = 8.8 Hz), 3.74 (dd, 1H, J = 9.6, 7.6 Hz), 3.89 (q, 2H, J = 7.2 Hz), 5.71 (s, 1H), 6.73-6.83 (m, 2H), 6.98-7.08 (m, 4H), 7.12-7.25 (m, 2H), 8.17 (s, 1H). | 451 | 449 | S-form |

TABLE 2-continued

| Example No. | Molecular Structure | NMR (400 MHz) | MS (M + H) | MS (M − H) | Comments |
|---|---|---|---|---|---|
| 391 | 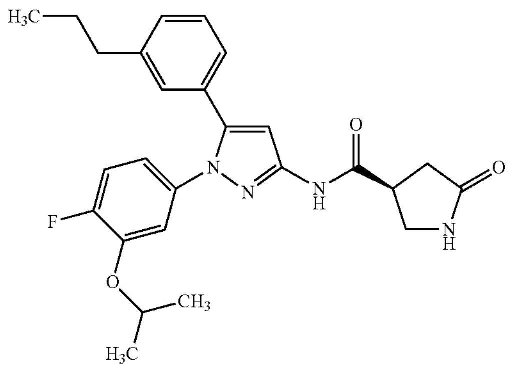 [SMILES: CCCc1cccc(-c2cc(NC(=O)[C@@H]3CNC(=O)C3)nn2-c2ccc(F)c(OC(C)C)c2)c1] | ¹H-NMR (CDCl₃) δ: 0.86 (t, 3H, J = 7.6 Hz), 1.18 (d, 3H, J = 6.0 Hz), 1.20 (d, 3H, J = 6.0 Hz), 1.54 (tq, 2H, J = 7.6, 7.6 Hz), 2.51 (t, 2H, J = 7.6 Hz), 2.59 (dd, 1H, J = 17.2, 10.0 Hz), 2.77 (dd, 1H, J = 17.2, 8.8 Hz), 3.28-3.38 (m, 1H), 3.57 (t, 1H, J = 8.8 Hz), 3.70 (dd, 1H, J = 9.6, 7.2 Hz), 4.22-4.32 (m, 1H), 6.13 (s, 1H), 6.73-6.86 (m, 2H), 6.99-7.09 (m, 4H), 7.13 (d, 1H, J = 7.6 Hz), 7.22 (t, 1H, J = 7.6 Hz), 8.67 (s, 1H). | 465 | 463 | S-form |
| 392 | 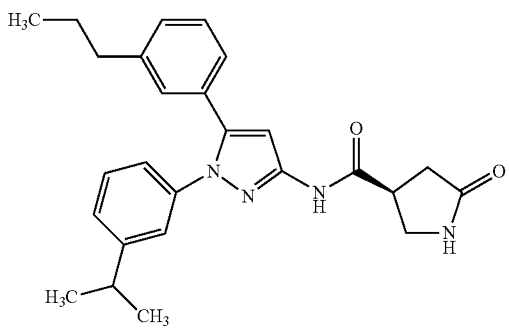 [SMILES: CCCc1cccc(-c2cc(NC(=O)[C@@H]3CNC(=O)C3)nn2-c2cccc(C(C)C)c2)c1] | ¹H-NMR (CDCl₃) δ: 0.84 (t, 3H, J = 7.6 Hz), 1.10 (d, 6H, J = 7.2 Hz), 1.50 (tq, 2H, J = 7.6, 7.6 Hz), 2.38-2.52 (m, 3H), 2.67-2.87 (m, 2H), 3.07-3.19 (m, 1H), 3.44 (t, 1H, J = 8.8 Hz), 3.62 (dd, 1H, J = 9.6, 7.6 Hz), 4.22-4.32 (m, 1H), 6.07 (s, 1H), 7.00-7.30 (m, 9H), 9.19 (s, 1H). | 431 | 429 | S-form |
| 393 | 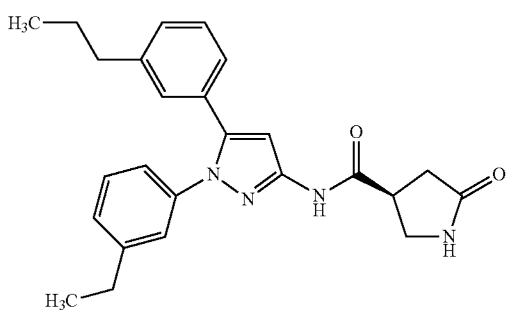 [SMILES: CCCc1cccc(-c2cc(NC(=O)[C@@H]3CNC(=O)C3)nn2-c2cccc(CC)c2)c1] | ¹H-NMR (CDCl₃) δ: 0.83 (t, 3H, J = 7.2 Hz), 1.11 (t, 3H, J = 7.6 Hz), 1.50 (tq, 2H, J = 7.2, 7.2 Hz), 2.36-2.76 (m, 6H), 3.07-3.17 (m, 1H), 3.38-3.66 (m, 2H), 6.18 (s, 1H), 7.01-7.25 (m, 9H), 9.33 (s, 1H). | 417 | 415 | S-form |
| 394 | 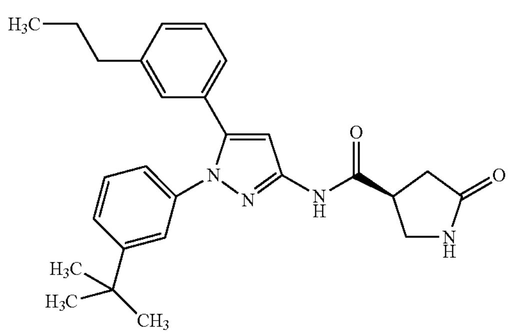 [SMILES: CCCc1cccc(-c2cc(NC(=O)[C@@H]3CNC(=O)C3)nn2-c2cccc(C(C)(C)C)c2)c1] | ¹H-NMR (CDCl₃) δ: 0.84 (t, 3H, J = 7.6 Hz), 1.15 (s, 9H), 1.51 (tq, 2H, J = 7.6, 7.6 Hz), 2.42-2.53 (m, 3H), 2.73 (dd, 1H, J = 17.2, 8.4 Hz), 3.13-3.24 (m, 1H), 3.50 (t, 1H, J = 8.8 Hz), 3.65 (dd, 1H, J = 9.6, 7.6 Hz), 5.88 (s, 1H), 7.00-7.33 (m, 9H), 8.89 (s, 1H). | 445 | 443 | S-form |

TABLE 2-continued

| Example No. | Molecular Structure | NMR (400 MHz) | MS (M + H) | MS (M − H) | Comments |
|---|---|---|---|---|---|
| 395 | (structure) | 1H-NMR (DMSO-D6) δ: 0.78 (t, 3H, 7.2 Hz), 1.17 (d, 3H, 6.4 Hz), 1.32-1.41 (m, 2H), 2.39 (d, 2H, J = 8.4 Hz), 2.95-3.00 (m, 1H), 3.06-3.11 (m, 1H), 3.32-3.52 (m, 3H), 4.29 (q, 1H, J = 6.4 Hz), 6.92 (s, 1H), 7.04 (s, 1H), 7.21-7.41 (m, 8H), 7.64 (s, 1H), 10.86 (s, 1H). | 433 | 431 | 1-propoxy-ethyl group: R-form Lactam ring: S-form Diastereo isomer of Example 396 |
| 396 | (structure) | 1H-NMR (DMSO-D6) δ: 0.78 (t, 3H, 7.2 Hz), 1.17 (d, 3H, 6.4 Hz), 1.32-1.41 (m, 2H), 2.39 (d, 2H, J = 8.4 Hz), 2.95-3.00 (m, 1H), 3.06-3.11 (m, 1H), 3.32-3.52 (m, 3H), 4.29 (q, 1H, J = 6.4 Hz), 6.92 (s, 1H), 7.04 (s, 1H), 7.21-7.41 (m, 8H), 7.64 (s, 1H), 10.86 (s, 1H). | 433 | 431 | 1-propoxy-ethyl group: R-form Lactam ring: S-form Diastereo isomer of Example 395 |
| 397 | (structure) | 1H-NMR (CDCl3) δ: 0.78 (t, 3H, J = 7.2 Hz), 0.95 (s,3H), 1.17 (s, 3H), 1.44 (tq, 2H, J = 7.2, 7.6 Hz), 2.46 (t, 2H, J = 7.6 Hz), 3.13 (t, 1H, J = 7.2 Hz), 3.30-3.37 (m, 1H), 3.41-3.45 (m, 1H), 6.91 (s, 1H), 7.02 (s, 1H), 7.06 (d, 1H, J = 7.6 Hz), 7.16 (d, 1H, J = 8.0 Hz), 7.22-7.28 (m, 3H), 7.32-7.41 (m, 3H), 7.64 (s, 1H), 10.79 (s, 1H). | 417 | 415 | Optically active substance (Structure 1nformation D) Optical isomer of Example 398 |
| 398 | (structure) | 1H-NMR (CDCl3) δ: 0.78 (t, 3H, J = 7.2 Hz), 0.95 (s,3H), 1.17 (s, 3H), 1.44 (tq,2H, J = 7.2, 7.6 Hz), 2.46 (t, 2H, J = 7.6 Hz), 3.13 (t, 1H, J = 7.2 Hz), 3.30-3.37 (m, 1H), 3.41-3.45 (m, 1H), 6.91 (s, 1H), 7.02 (s, 1H), 7.06 (d, 1H, J = 7.6 Hz), 7.16 (d, 1H, J = 8.0 Hz), 7.22-7.28 (m, 3H), 7.32-7.41 (m, 3H), 7.64 (s, 1H), 10.79 (s, 1H). | 417 | 415 | Optically active substance (Structure 1nformation D) Optical isomer of Example 397 |
| 399 | (structure) | 1H-NMR (DMSO-D6) δ: 2.39 (d, 2H, J = 8.4 Hz), 3.32-3.52 (m, 3H), 5.12 (s, 2H), 6.95 (s, 1H), 7.19-7.25 (m, 3H), 7.33-7.42 (m, 6H), 7.64 (s, 1H), 10.88 (s, 1H). | 445 | 444 | S-form |

TABLE 2-continued

| Example No. | Molecular Structure | NMR (400 MHz) | MS (M + H) | MS (M − H) | Comments |
|---|---|---|---|---|---|
| 400 | 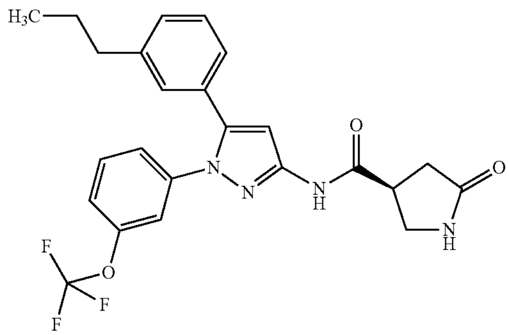 [SMILES: CCCc1cccc(-c2cc(NC(=O)[C@@H]3CNC(=O)C3)nn2-c2cccc(OC(F)(F)F)c2)c1] | 1H-NMR (DMSO-D6) δ: 0.78 (t, 3H, J = 7.3 Hz), 1.46 (tq, 2H, J = 7.0, 7.3 Hz), 2.38-2.40 (m, 2H), 2.47 (t, 2H, J = 7.0 Hz), 3.33-3.35 (m, 1H), 3.41-3.45 (m, 1H), 3.49-3.53 (m, 1H), 6.92 (s, 1H), 7.02-7.05 (m, 1H), 7.10-7.12 (m, 1H), 7.18-7.26 (m, 3H), 7.30-7.34 (m, 2H), 7.51 (t, 1H, J = 8.3 Hz), 7.63 (s, 1H), 10.92 (s, 1H). | 473 | 471 | S-form |
| 401 | 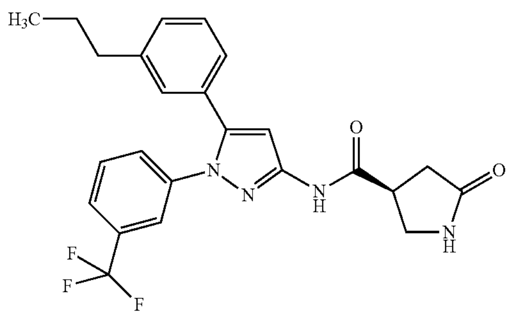 [SMILES: CCCc1cccc(-c2cc(NC(=O)[C@@H]3CNC(=O)C3)nn2-c2cccc(C(F)(F)F)c2)c1] | 1H-NMR (DMSO-D6) δ: 0.76 (t, 3H, J = 7.3 Hz), 1.45 (tq, 2H, J = 7.0, 7.3 Hz), 2.38-2.40 (m, 2H), 2.49 (t, 2H, J = 7.0 Hz), 3.33-3.36 (m, 1H), 3.39-3.47 (m, 1H), 3.49-3.53 (m, 1H), 6.93 (s, 1H), 7.05 (s, 1H), 7.12-7.14 (m, 1H), 7.22-7.23 (m, 1H), 7.30-7.34 (m, 1H), 7.49-7.55 (m, 2H), 7.59-7.69 (m, 3H), 10.93 (s, 1H). | 457 | 455 | S-form |
| 402 | 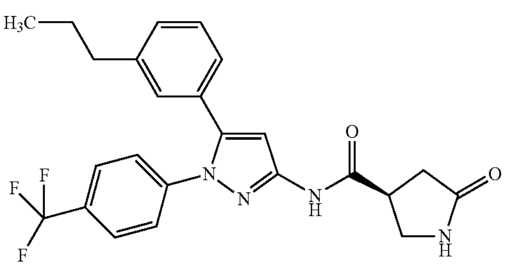 [SMILES: CCCc1cccc(-c2cc(NC(=O)[C@@H]3CNC(=O)C3)nn2-c2ccc(C(F)(F)F)cc2)c1] | 1H-NMR (DMSO-D6) δ: 0.73 (t, 3H, J = 7.3 Hz), 1.41 (tq, 2H, J = 7.0, 7.3 Hz), 2.37-2.39 (m, 2H), 2.46 (t, 2H, J = 7.0 Hz), 3.32-3.34 (m, 1H), 3.40-3.44 (m, 1H), 3.48-3.51 (m, 1H), 6.93 (s, 1H), 6.97 (s, 1H), 7.13 (d, 1H, J = 7.7 Hz), 7.20 (d, 1H, J = 7.7 Hz), 7.31 (dd, 1H, J = 7.7, 7.7 Hz), 7.40 (d, 2H, J = 8.6 Hz), 7.62 (s, 1H), 7.75 (d, 2H, J = 8.6 Hz), 10.92 (s, 1H). | 457 | 455 | S-form |
| 403 | 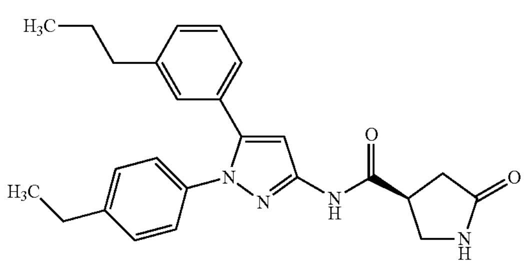 [SMILES: CCCc1cccc(-c2cc(NC(=O)[C@@H]3CNC(=O)C3)nn2-c2ccc(CC)cc2)c1] | 1H-NMR (DMSO-D6) δ: 0.76 (t, 3H, J = 7.4 Hz), 1.17 (t, 3H, J = 7.6 Hz), 1.41 (tq, 2H, J = 7.4 Hz, 7.4 Hz), 2.36-2.41 (m, 2H), 2.45 (t, 2H, J = 7.4 Hz), 2.61 (q, 2H, J = 7.6 Hz), 3.30-3.53 (m, 3H), 6.88 (s, 1H), 6.95 (s, 1H), 7.09 (d, 1H, J = 7.6 Hz), 7.12 (d, 2H, J = 8.4 Hz), 7.15 (d, 1H, J = 7.6 Hz), 7.22 (d, 2H, J = 8.4 Hz), 7.28 (dd, 1H, J = 7.6 Hz, 7.6 Hz), 7.62 (s, 1H), 10.82 (s, 1H). | 417 | 415 | S-form |

TABLE 2-continued

| Example No. | Molecular Structure | NMR (400 MHz) | MS (M + H) | MS (M − H) | Comments |
|---|---|---|---|---|---|
| 404 | 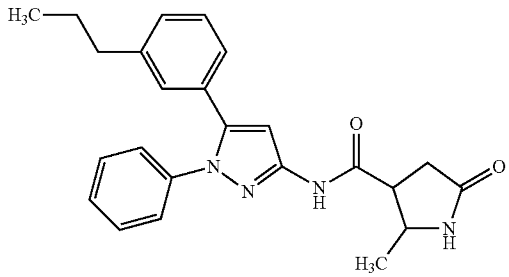 [SMILES: CCCc1cccc(-c2cc(NC(=O)C3CC(=O)NC3C)nn2-c2ccccc2)c1] | 1H-NMR (DMSO-D6) δ: 0.77 (t, 3H, J = 7.4 Hz), 1.20 (d, 3H, J = 6.4 Hz), 1.44 (tq, 2H, J = 7.4 Hz, 7.4 Hz), 2.37-2.50 (m, 4H), 2.91-2.98 (m, 1H), 3.73 (dq, 1H, J = 6.4 Hz), 6.91 (s, 1H), 7.00 (s, 1H), 7.07 (d, 1H, J = 7.6 Hz), 7.17 (d, 1H, J = 7.6 Hz), 7.20-7.30 (m, 3H), 7.31-7.42 (m, 3H), 7.77 (s, 1H), 10.91 (s, 1H). | 403 | 401 | Optically active substance (trans-form, Structure 1nformation E) Optical isomer of Example 405 |
| 405 | 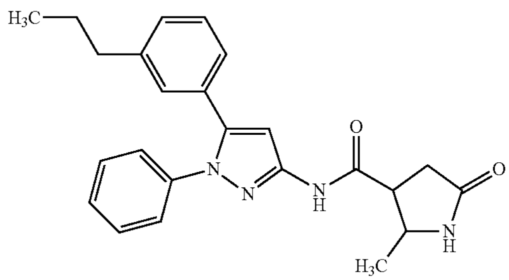 [SMILES: CCCc1cccc(-c2cc(NC(=O)C3CC(=O)NC3C)nn2-c2ccccc2)c1] | 1H-NMR (DMSO-D6) δ: 0.77 (t, 3H, J = 7.4 Hz), 1.20 (d, 3H, J = 6.4 Hz), 1.44 (tq, 2H, J = 7.4 Hz, 7.4 Hz), 2.37-2.50 (m, 4H), 2.91-2.98 (m, 1H), 3.73 (dq, 1H, J = 6.4 Hz), 6.91 (s, 1H), 7.00 (s, 1H), 7.07 (d, 1H, J = 7.6 Hz), 7.17 (d, 1H, J = 7.6 Hz), 7.20-7.30 (m, 3H), 7.31-7.42 (m, 3H), 7.77 (s, 1H), 10.91 (s, 1H). | 403 | 401 | Optically active substance (trans-form, Structure 1nformation E) Optical isomer of Example 404 |
| 406 | 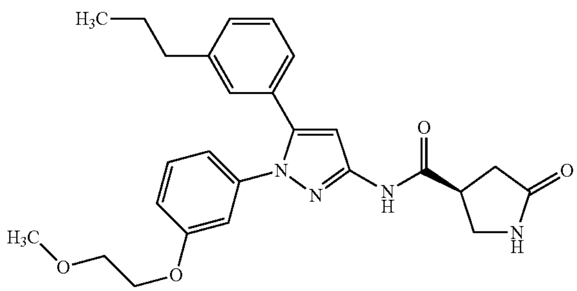 [SMILES: CCCc1cccc(-c2cc(NC(=O)[C@@H]3CNC(=O)C3)nn2-c2cccc(OCCOC)c2)c1] | 1H-NMR (DMSO-D6) δ: 0.78 (t, 3H, J = 7.3 Hz), 1.46 (tq, 2H, J = 7.3, 7.7 Hz), 2.38-2.40 (m, 2H), 2.48 (t, 2H, J = 7.7 Hz), 3.26 (s, 3H), 3.33-3.34 (m, 1H), 3.40-3.44 (m, 1H), 3.49-3.51 (m, 1H), 3.55-3.58 (m, 2H), 3.94-3.98 (m, 2H), 6.76-6.79 (m, 2H), 6.88-6.92 (m, 2H), 7.02-7.04 (m, 1H), 7.07-7.09 (m, 1H), 7.17-7.19 (m, 1H), 7.25-7.30 (m, 2H), 7.63 (s, 1H), 10.85 (s, 1H). | 463 | 461 | S-form |
| 407 | 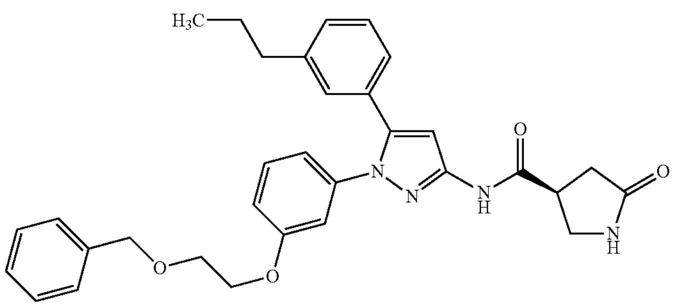 [SMILES: CCCc1cccc(-c2cc(NC(=O)[C@@H]3CNC(=O)C3)nn2-c2cccc(OCCOCc3ccccc3)c2)c1] | 1H-NMR (DMSO-D6) : 0.77 (t, 3H, J = 7.2 Hz), 1.45 (tq, 2H, J = 7.2, 7.2 Hz), 2.37-2.40 (m, 2H), 2.46 (t, 2H, J = 7.2 Hz), 3.34-3.36 (m, 1H), 3.38-3.43 (m, 1H), 3.49-3.51 (m, 1H), 3.68-3.70 (m, 2H), 4.00-4.03 (m, 2H), 4.51 (s, 2H), 6.76-6.80 (m, 2H), 6.88-6.93 (m, 2H), 7.02-7.09 (m, 2H), 7.16-7.18 (m, 1H), 7.25-7.36 (m, 7H), 7.63 (s, 1H), 10.85 (s, 1H). | 539 | 537 | S-form |

TABLE 2-continued

| Example No. | Molecular Structure | NMR (400 MHz) | MS (M + H) | MS (M − H) | Comments |
|---|---|---|---|---|---|
| 408 | 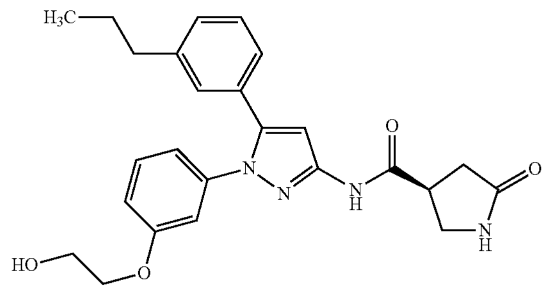 [SMILES: CCCc1cccc(-c2cc(NC(=O)[C@@H]3CNC(=O)C3)nn2-c2cccc(OCCO)c2)c1] | 1H-NMR (DMSO-D6) δ: 0.77 (t, 3H, J = 7.3 Hz), 1.45 (tq, 2H, J = 7.2, 7.3 Hz), 2.36-2.38 (m, 2H), 2.46 (t, 2H, J = 7.2 Hz), 3.32-3.35 (m, 1H), 3.39-3.43 (m, 1H), 3.48-3.50 (m, 1H), 3.62-3.64 (m, 2H), 3.84-3.86 (m, 2H), 4.81 (t, 1H, J = 5.6 Hz), 6.72-6.78 (m, 2H), 6.87-6.89 (m, 2H), 7.01-7.08 (m, 2H), 7.16-7.18 (m, 1H), 7.24-7.28 (m, 2H), 7.61 (s, 1H), 10.83 (s, 1H). | 449 | 447 | S-form |
| 409 | 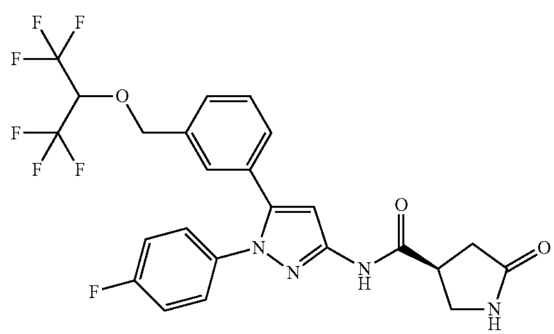 [SMILES: O=C1C[C@H](C(=O)Nc2cc(-c3cccc(COC(C(F)(F)F)C(F)(F)F)c3)n(-c3ccc(F)cc3)n2)CN1] | 1H-NMR (DMSO-D6) δ: 2.38-2.40 (m, 2H), 3.33-3.35 (m, 1H), 3.40-3.44 (m, 1H), 3.48-3.51 (m, 1H), 4.84 (s, 2H), 5.54 (sep, 1H, J = 6.6 Hz), 6.94 (s, 1H), 7.21-7.29 (m, 6H), 7.35-7.42 (m, 2H), 7.63 (s, 1H), 10.86 (s, 1H). | 545 | 543 | S-form |
| 410 | 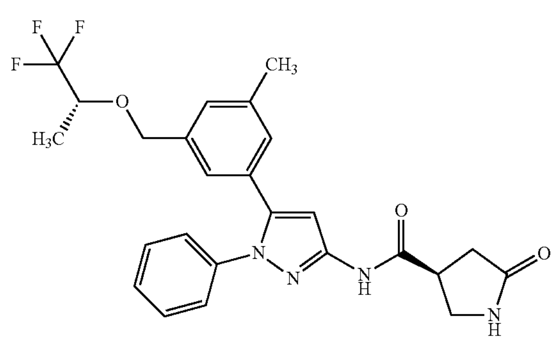 [SMILES: Cc1cc(CO[C@H](C)C(F)(F)F)cc(-c2cc(NC(=O)[C@@H]3CNC(=O)C3)nn2-c2ccccc2)c1] | 1H-NMR (DMSO-D6) δ: 1.17 (d, 3H, J = 6.4 Hz), 2.25 (s, 3H), 2.39 (d, 2H, J = 8.4 Hz), 3.32-3.52 (m, 3H), 4.02-4.08 (m, 1H), 4.54 (s, 2H), 6.90 (s, 1H), 6.97 (s, 1H), 7.04 (s, 1H), 7.14 (s, 1H), 7.22-7.25 (m, 2H), 7.32-7.41 (m, 3H), 7.63 (s, 1H), 10.85 (s, 1H). | 487 | 485 | 2,2,2-trifluoro methyl-1-methyl-ethoxym ethyl group: R-form Lactam ring: S-form |
| 411 | 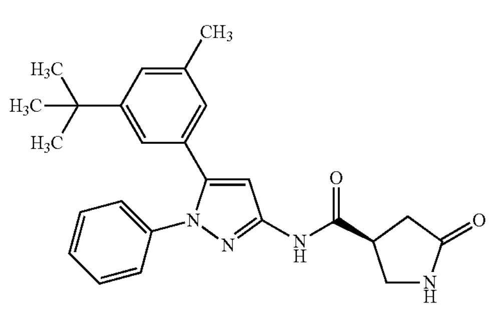 [SMILES: Cc1cc(-c2cc(NC(=O)[C@@H]3CNC(=O)C3)nn2-c2ccccc2)cc(C(C)(C)C)c1] | 1H-NMR (DMSO-D6) δ: 1.06 (s, 9H), 2.29 (s, 3H), 2.33-2.45 (m, 2H), 3.30-3.53 (m, 3H), 6.79 (s, 1H), 6.91 (s, 1H), 7.06 (s, 1H), 7.17 (s, 1H), 7.20-7.25 (m, 2H), 7.32-7.43 (m, 3H), 7.63 (s, 1H), 10.83 (s, 1H). | 417 | 415 | S-form |

TABLE 2-continued

| Example No. | Molecular Structure | NMR (400 MHz) | MS (M + H) | MS (M − H) | Comments |
|---|---|---|---|---|---|
| 412 | 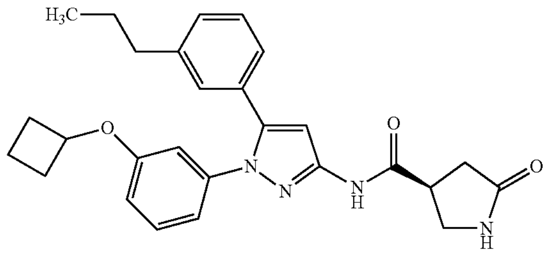 [SMILES: CCCc1cccc(-c2cc(NC(=O)[C@@H]3CNC(=O)C3)nn2-c2cccc(OC3CCC3)c2)c1] | 1H-NMR (DMSO-D6) δ: 0.79 (t, 3H, J = 7.3 Hz), 1.42-1.59 (m, 3H), 1.65-1.76 (m, 1H), 1.84-1.97 (m, 2H), 2.14-2.24 (m, 2H), 2.37-2.41 (m, 2H), 2.45-2.52 (m, 2H), 3.30-3.53 (m, 3H), 4.42-4.51 (m, 1H), 6.55 (t, 1H, J = 2.2 Hz), 6.77-6.89 (m, 3H), 7.03 (s, 1H), 7.06-7.10 (m, 1H), 7.17-7.20 (m, 1H), 7.26-7.31 (m, 2H), 7.63 (s, 1H), 10.85 (s, 1H). | 459 | 457 | S-form |
| 413 | 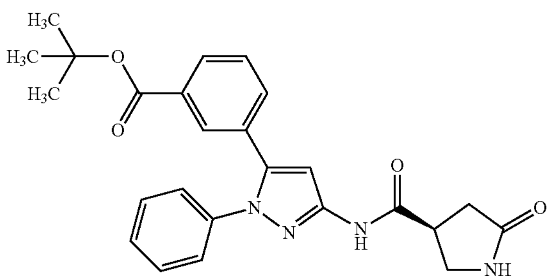 [SMILES: CC(C)(C)OC(=O)c1cccc(-c2cc(NC(=O)[C@@H]3CNC(=O)C3)nn2-c2ccccc2)c1] | 1H-NMR (DMSO-D6) δ: 1.47 (s, 9H), 2.38-2.41 (m, 2H), 3.31-3.54 (m, 3H), 6.99 (s, 1H), 7.24-7.28 (m, 2H), 7.35-7.54 (m, 5H), 7.64 (s, 1H), 7.67-7.70 (m, 1H), 7.84-7.88 (m, 1H), 10.89 (s, 1H). | 447 | 445 | S-form |
| 414 | 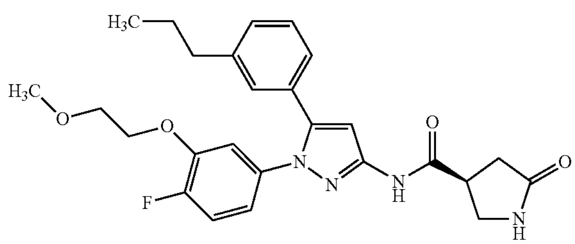 [SMILES: CCCc1cccc(-c2cc(NC(=O)[C@@H]3CNC(=O)C3)nn2-c2ccc(F)c(OCCOC)c2)c1] | $^1$H-NMR (CDCl$_3$) δ: 0.86 (t, 3H, J = 7.6 Hz), 1.54 (tq, 2H, J = 7.6, 7.6 Hz), 2.49-2.62 (m, 3H), 2.77 (dd, 1H, J = 17.2, 8.8 Hz), 3.28-3.38 (m, 1H), 3.40 (s, 3H), 3.56 (t, 1H, J = 8.8 Hz), 3.65-3.71 (m, 3H), 3.96-4.00 (m, 2H), 6.24 (s, 1H), 6.77 (ddd, 1H, J = 8.8, 4.0, 2.8 Hz), 6.86 (dd, 1H, J = 7.6, 2.8 Hz), 6.98-7.08 (m, 4H), 7.14 (d, 1H, J = 7.6 Hz), 7.22 (t, 1H, J = 7.6 Hz), 8.82 (s, 1H). | 481 | 479 | S-form |
| 415 | 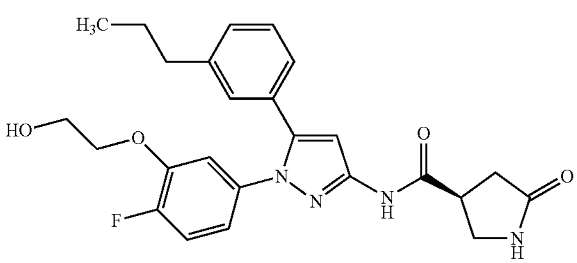 [SMILES: CCCc1cccc(-c2cc(NC(=O)[C@@H]3CNC(=O)C3)nn2-c2ccc(F)c(OCCO)c2)c1] | $^1$H-NMR (CDCl$_3$) δ: 0.86 (t, 3H, J = 7.6 Hz), 1.54 (tq, 2H, J = 7.6, 7.6 Hz), 2.48-2.58 (m, 3H), 2.76 (dd, 1H, J = 16.8, 8.4 Hz), 3.20-3.30 (m, 1H), 3.49 (t, 1H, J = 9.2 Hz), 3.65 (dd, 1H, J = 9.6, 7.6 Hz), 3.85-3.99 (m, 4H), 6.25 (s, 1H), 6.80 (ddd, 1H, J = 8.4, 4.0, 2.4 Hz), 6.86 (dd, 1H, J = 7.2, 2.4 Hz), 7.00-7.08 (m, 4H), 7.15 (d, 1H, J = 7.6 Hz), 7.23 (t, 1H, J = 7.6 Hz), 9.08 (s, 1H). | 467 | 465 | S-form |

TABLE 2-continued

| Example No. | Molecular Structure | NMR (400 MHz) | MS (M + H) | MS (M − H) | Comments |
|---|---|---|---|---|---|
| 416 | 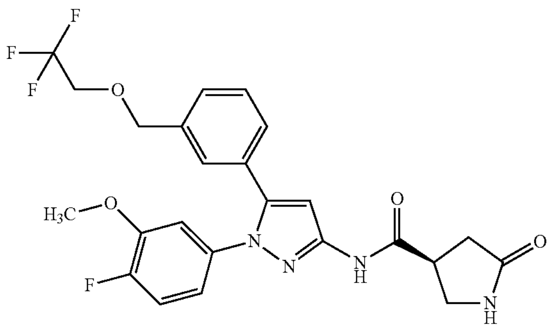 [SMILES: COc1cc(-n2nc(NC(=O)[C@@H]3CNC(=O)C3)cc2-c2cccc(COCC(F)(F)F)c2)ccc1F] | ¹H-NMR (CDCl₃) δ: 2.61 (dd, 1H, J = 16.8, 9.6 Hz), 2.78 (dd, 1H, J = 16.8, 8.8 Hz), 3.32-3.42 (m, 1H), 3.61 (t, 1H, J = 9.6 Hz), 3.69-3.81 (m, 6H), 4.61 (s, 2H), 6.00 (s, 1H), 6.72 (ddd, 1H, J = 8.8, 4.0, 2.8 Hz), 6.87 (dd, 1H, J = 7.6, 2.8 Hz), 6.98-7.05 (m, 2H), 7.18-7.36 (m, 4H), 8.49 (s, 1H). | 507 | 505 | S-form |
| 417 | 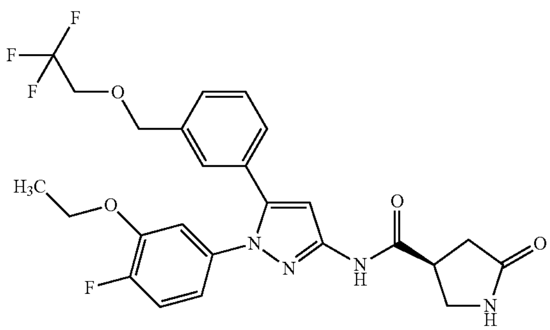 [SMILES: CCOc1cc(-n2nc(NC(=O)[C@@H]3CNC(=O)C3)cc2-c2cccc(COCC(F)(F)F)c2)ccc1F] | ¹H-NMR (CDCl₃) δ: 1.35 (t, 3H, J = 7.2 Hz), 2.61 (dd, 1H, J = 17.2, 9.6 Hz), 2.78 (dd, 1H, J = 17.2, 8.4 Hz), 3.30-3.40 (m, 1H), 3.61 (t, 1H, J = 8.8 Hz), 3.69-3.81 (m, 3H), 3.92 (q, 2H, J = 6.8 Hz), 4.61 (s, 2H), 5.93 (s, 1H), 6.72 (ddd, 1H, J = 9.2, 4.0, 2.8 Hz), 6.84 (dd, 1H, J = 7.6, 2.4 Hz), 6.98-7.05 (m, 2H), 7.17-7.36 (m, 4H), 8.41 (s, 1H). | 521 | 519 | S-form |
| 418 | 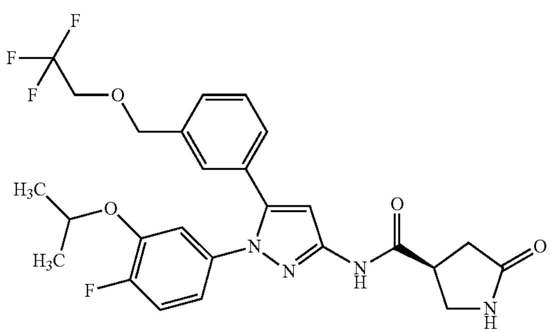 [SMILES: CC(C)Oc1cc(-n2nc(NC(=O)[C@@H]3CNC(=O)C3)cc2-c2cccc(COCC(F)(F)F)c2)ccc1F] | ¹H-NMR (CDCl₃) δ: 1.21 (d, 3H, J = 6.0 Hz), 1.22 (d, 1H, J = 6.0 Hz), 2.60 (dd, 1H, J = 17.2, 9.6 Hz), 2.78 (dd, 1H, J = 17.2, 8.4 Hz), 3.29-3.40 (m, 1H), 3.59 (t, 1H, J = 9.2 Hz), 3.68-3.81 (m, 3H), 4.27-4.37 (m, 1H), 4.61 (s, 2H), 6.14 (s, 1H), 6.76-6.83 (m, 2H), 7.01-7.07 (m, 2H), 7.17-7.36 (m, 4H), 8.65 (s, 1H). | 535 | 533 | S-form |
| 419 | 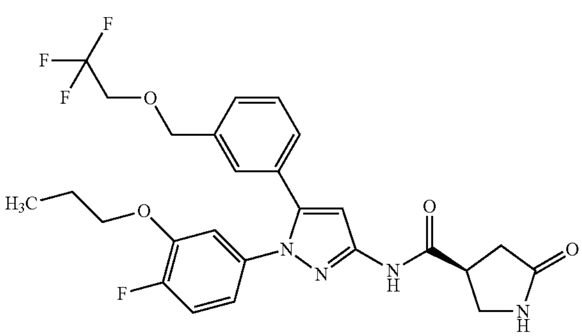 [SMILES: CCCOc1cc(-n2nc(NC(=O)[C@@H]3CNC(=O)C3)cc2-c2cccc(COCC(F)(F)F)c2)ccc1F] | ¹H-NMR (CDCl₃) δ: 0.97 (t, 3H, J = 7.6 Hz), 1.73 (tq, 2H, J = 7.6, 7.6 Hz), 2.61 (dd, 1H, J = 17.2, 9.6 Hz), 2.78 (dd, 1H, J = 17.2, 8.4 Hz), 3.31-3.40 (m, 1H), 3.61 (t, 1H, J = 8.8 Hz), 3.70-3.84 (m, 5H), 4.61 (s, 2H), 5.91 (s, 1H), 6.71 (ddd, 1H, J = 8.8, 4.0, 2.4 Hz), 6.84 (dd, 1H, J = 7.6, 2.4 Hz), 6.98-7.04 (m, 2H), 7.17-7.35 (m, 4H), 8.38 (s, 1H). | 535 | 533 | S-form |

TABLE 2-continued

| Example No. | Molecular Structure | NMR (400 MHz) | MS (M + H) | MS (M − H) | Comments |
|---|---|---|---|---|---|
| 420 | 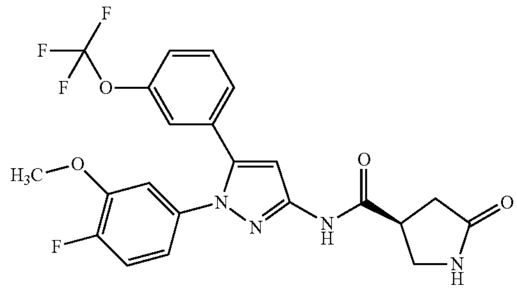 [SMILES: COc1cc(-n2nc(NC(=O)[C@@H]3CNC(=O)C3)cc2-c2cccc(OC(F)(F)F)c2)ccc1F] | ¹H-NMR (CDCl₃) δ: 2.62 (dd, 1H, J = 17.2, 9.6 Hz), 2.78 (dd, 1H, J = 17.2, 8.4 Hz), 3.32-3.42 (m, 1H), 3.60 (t, 1H, J = 9.2 Hz), 3.70-3.76 (m, 4H), 6.22 (s, 1H), 6.74 (ddd, 1H, J = 8.8, 4.0, 2.8 Hz), 6.83 (dd, 1H, J = 7.6, 2.4 Hz), 7.01-7.10 (m, 3H), 7.17-7.24 (m, 2H), 7.38 (t, 1H, J = 8.0 Hz), 8.68 (s, 1H). | 479 | 477 | S-form |
| 421 | 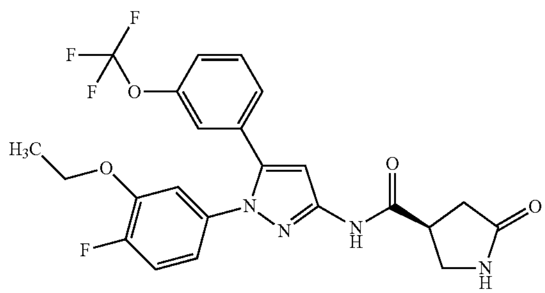 [SMILES: CCOc1cc(-n2nc(NC(=O)[C@@H]3CNC(=O)C3)cc2-c2cccc(OC(F)(F)F)c2)ccc1F] | ¹H-NMR (CDCl₃) δ: 1.35 (t, 3H, J = 7.2 Hz), 2.61 (dd, 1H, J = 17.2, 9.6 Hz), 2.77 (dd, 1H, J = 17.2, 8.4 Hz), 3.31-3.41 (m, 1H), 3.58 (t, 1H, J = 8.8 Hz), 3.69 (dd, 1H, J = 9.6, 7.2 Hz), 3.91 (q, 2H, 7.2 Hz), 6.25 (s, 1H), 6.72-6.81 (m, 2H), 7.02-7.09 (m, 3H), 7.17-7.22 (m, 2H), 7.37 (t, 1H, J = 8.0 Hz), 8.71 (s, 1H). | 493 | 491 | S-form |
| 422 | 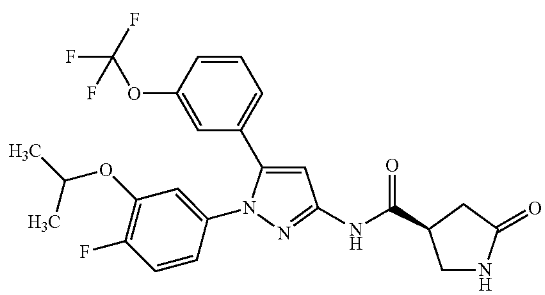 [SMILES: CC(C)Oc1cc(-n2nc(NC(=O)[C@@H]3CNC(=O)C3)cc2-c2cccc(OC(F)(F)F)c2)ccc1F] | ¹H-NMR (CDCl₃) δ: 1.20 (d, 3H, J = 6.0 Hz), 1.22 (d, 3H, J = 6.0 Hz), 2.61 (dd, 1H, J = 17.2, 9.6 Hz), 2.77 (dd, 1H, J = 17.2, 8.4 Hz), 3.31-3.41 (m, 1H), 3.58 (t, 1H, J = 9.2 Hz), 3.69 (dd, 1H, J = 9.6, 7.2 Hz), 4.25-4.36 (m, 1H), 6.40 (s, 1H), 6.73 (dd, 1H, J = 7.2, 2.4 Hz), 6.81 (ddd, 1H, J = 8.8, 4.0, 2.8 Hz), 7.04-7.11 (m, 3H), 7.16-7.23 (m, 2H), 7.37 (t, 1H, J = 8.4 Hz), 8.90 (s, 1H). | 507 | 505 | S-form |
| 423 | 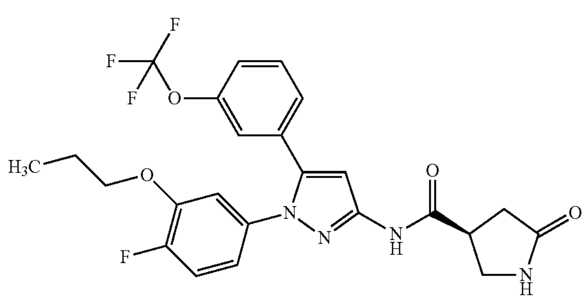 [SMILES: CCCOc1cc(-n2nc(NC(=O)[C@@H]3CNC(=O)C3)cc2-c2cccc(OC(F)(F)F)c2)ccc1F] | ¹H-NMR (CDCl₃) δ: 0.98 (t, 3H, J = 7.6 Hz), 1.74 (tq, 2H, J = 7.6, 7.6 Hz), 2.62 (dd, 1H, J = 17.2, 10.0 Hz), 2.77 (dd, 1H, J = 17.2, 8.8 Hz), 3.32-3.42 (m, 1H), 3.62 (t, 1H, J = 8.8 Hz), 3.73 (dd, 1H, J = 9.6, 7.2 Hz), 3.81 (t, 2H, J = 7.6 Hz), 5.90 (s, 1H), 6.73 (ddd, 1H, J = 8.8, 4.0, 2.8 Hz), 6.80 (dd, 1H, J = 7.6, 2.8 Hz), 7.01-7.10 (m, 3H), 7.17-7.23 (m, 2H), 7.37 (t, 1H, J = 8.0 Hz), 8.32 (s, 1H). | 507 | 505 | S-form |

TABLE 2-continued

| Example No. | Molecular Structure | NMR (400 MHz) | MS (M + H) | MS (M − H) | Comments |
|---|---|---|---|---|---|
| 424 | 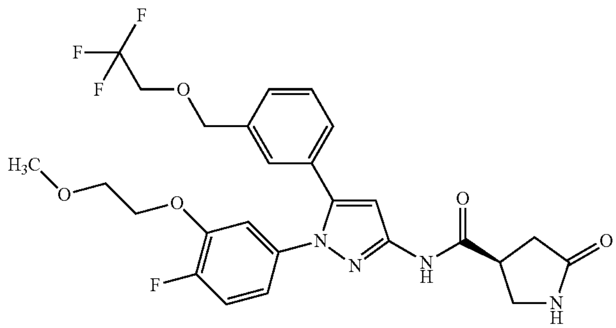 [SMILES: COCCOc1cc(-n2nc(NC(=O)[C@@H]3CNC(=O)C3)cc2-c2cccc(COCC(F)(F)F)c2)ccc1F] | ¹H-NMR (CDCl₃) δ: 2.57 (dd, 1H, J = 17.2, 9.6 Hz), 2.78 (dd, 1H, J = 17.2, 8.8 Hz), 3.30-3.42 (m, 4H), 3.53 (t, 1H, J = 9.2 Hz), 3.60-3.73 (m, 3H), 3.78 (q, 2H, J = 8.4 Hz), 3.95-4.03 (m, 2H), 4.60 (s, 2H), 6.72-6.90 (m, 3H), 6.98-7.08 (m, 2H), 7.15-7.26 (m, 2H), 7.28-7.36 (m, 2H), 9.39 (s, 1H). | 551 | 549 | S-form |
| 425 | | ¹H-NMR (CDCl₃) δ: 1.27-1.37 (m, 6H), 2.59 (dd, 1H, J = 17.2, 9.6 Hz), 2.77 (dd, 1H J = 17.2, 8.4 Hz), 3.29-3.40 (m, 1H), 3.56 (t, 1H, J = 8.8 Hz), 3.68 (dd, 1H, J = 9.6, 7.2 Hz), 3.72-3.82 (m, 1H), 3.90 (q, 2H, J = 7.2 Hz), 4.57 (d, 1H, J = 11.6 Hz), 4.66 (d, 1H, J = 11.6 Hz), 6.39 (s, 1H), 6.73-6.83 (m, 2H), 6.99-7.06 (m, 2H), 7.16-7.25 (m, 2H), 7.29-7.35 (m, 2H), 8.90 (s, 1H). | 535 | 533 | 2,2,2-trifluoro methyl-1-methyl-ethoxymethyl group: R-form Lactam ring: S-form |
| 426 | 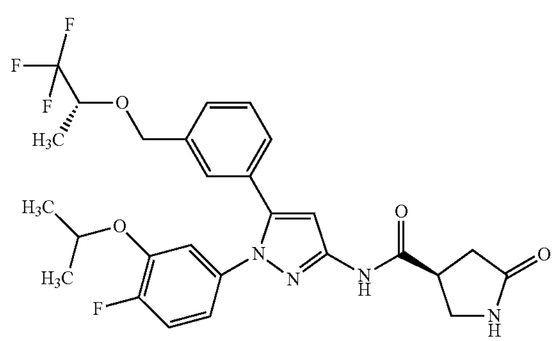 [SMILES: CC(C)Oc1cc(-n2nc(NC(=O)[C@@H]3CNC(=O)C3)cc2-c2cccc(CO[C@H](C)C(F)(F)F)c2)ccc1F] | ¹H-NMR (CDCl₃) δ: 1.27-1.37 (m, 6H), 2.59 (dd, 1H, J = 17.2, 9.6 Hz), 2.77 (dd, 1H, J = 17.2, 8.4 Hz), 3.29-3.40 (m, 1H), 3.56 (t, 1H, J = 8.8 Hz), 3.68 (dd, 1H, J = 9.6, 7.2 Hz), 3.72-3.82 (m, 1H), 3.90 (q, 2H, J = 7.2 Hz), 4.57 (d, 1H, J = 11.6 Hz), 4.66 (d, 1H, J = 11.6 Hz), 6.39 (s, 1H), 6.73-6.83 (m, 2H), 6.99-7.06 (m, 2H), 7.16-7.25 (m, 2H), 7.29-7.35 (m, 2H), 8.90 (s, 1H). | 549 | 547 | 2,2,2-trifluoro methyl-1-methyl-ethoxymethyl group: R-form Lactam ring: S-form |
| 427 | 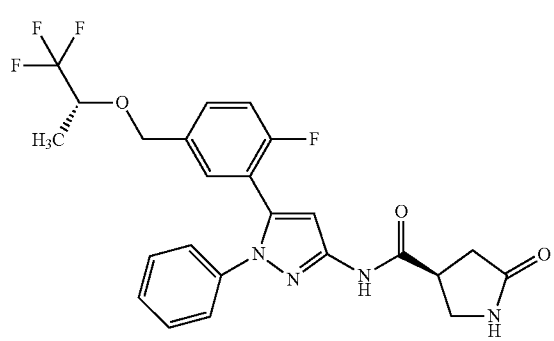 [SMILES: C[C@@H](OCc1ccc(F)c(-c2cc(NC(=O)[C@@H]3CNC(=O)C3)nn2-c2ccccc2)c1)C(F)(F)F] | 1H-NMR (DMSO-D6) δ: 1.21 (d, 3H, J = 6.4 Hz), 2.39 (d, 2H, J = 8.4 Hz), 3.32-3.52 (m, 3H), 4.10-4.17 (m, 1H), 4.63 (s, 2H), 6.93 (s, 1H), 7.20-7.25 (m, 3H), 7.28-7.38 (m, 4H), 7.42-7.46 (m, 1H), 7.63 (s, 1H), 10.92 (s, 1H). | 491 | 489 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 428 | 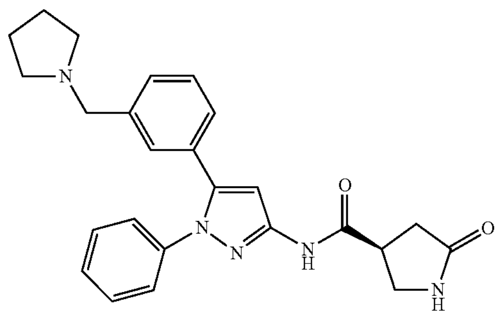 [SMILES: O=C1C[C@H](C(=O)Nc2cc(-c3cccc(CN4CCCC4)c3)n(-c3ccccc3)n2)CN1] | 1H-NMR (DMSO-D6) δ: 1.62 (brs, 4H), 2.27 (brs, 4H), 2.33-2.45 (m, 2H), 3.30-3.53 (m, 5H), 6.89 (s, 1H), 7.11 (s, 1H), 7.17 (d, 1H, J = 7.6 Hz), 7.20-7.29 (m, 3H), 7.30-7.42 (m, 4H), 7.32-7.43 (m, 3H), 7.63 (s, 1H), 10.85 (s, 1H). | 430 | 428 | S-form |
| 429 | 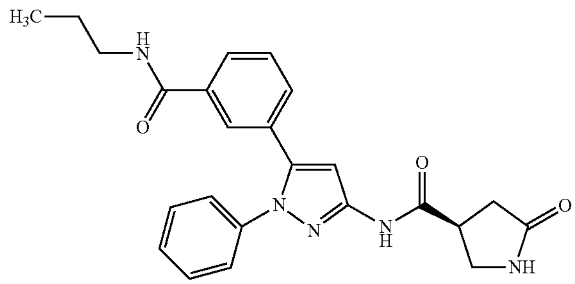 [SMILES: CCCNC(=O)c1cccc(-c2cc(NC(=O)[C@@H]3CNC(=O)C3)nn2-c2ccccc2)c1] | 1H-NMR (DMSO-D6) δ: 0.87 (t, 3H, J = 7.3 Hz), 1.47-1.57 (m, 2H), 2.37-2.42 (m, 2H), 3.20 (q, 2H, J = 6.6 Hz), 3.32-3.55 (m, 3H), 7.02 (s, 1H), 7.19-7.25 (m, 3H), 7.31-7.42 (m, 4H), 7.64 (s, 1H), 7.78-7.82 (m, 1H), 7.85-7.87 (m, 1H), 8.52 (t, 1H, J = 5.7 Hz), 10.88 (s, 1H). | 432 | 430 | S-form |
| 430 | 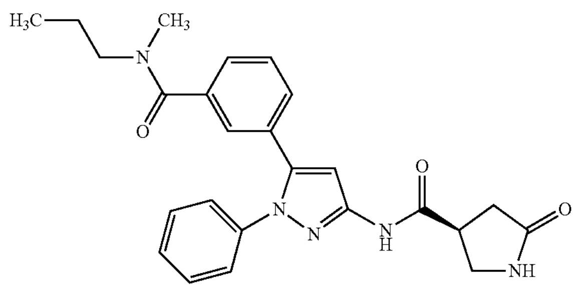 [SMILES: CCCN(C)C(=O)c1cccc(-c2cc(NC(=O)[C@@H]3CNC(=O)C3)nn2-c2ccccc2)c1] | 1H-NMR (DMSO-D6) δ: 0.55-0.90 (m, 3H), 1.30-1.57 (m, 2H), 2.37-2.42 (m, 2H), 2.60-2.65 (m, 1H), 2.82-2.98 (m, 2H), 3.30-3.54 (m, 5H), 6.95 (s, 1H), 7.09 (s, 1H), 7.22-7.28 (m, 2H), 7.31-7.48 (m, 6H), 7.63 (s, 1H), 10.87 (s, 1H). | 446 | 444 | S-form |
| 431 | 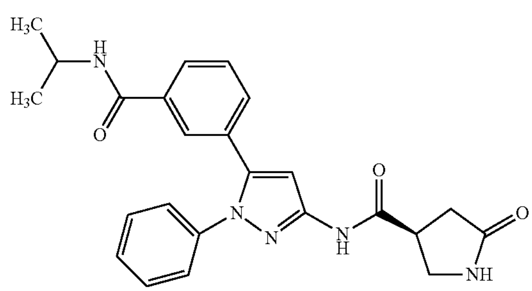 [SMILES: CC(C)NC(=O)c1cccc(-c2cc(NC(=O)[C@@H]3CNC(=O)C3)nn2-c2ccccc2)c1] | 1H-NMR (DMSO-D6) δ: 1.15 (d, 6H, J = 6.7 Hz), 2.38-2.42 (m, 2H), 3.30-3.54 (m, 3H), 4.03-4.12 (m, 1H), 7.02 (s, 1H), 7.17-7.26 (m, 3H), 7.32-7.42 (m, 4H), 7.64 (s, 1H), 7.78-7.83 (m, 1H), 7.87 (s, 1H), 8.28 (d, 1H, J = 7.7 Hz), 10.88 (s, 1H). | 432 | 430 | S-form |
| 432 | 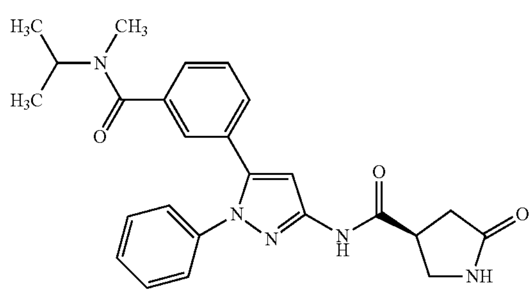 [SMILES: CC(C)N(C)C(=O)c1cccc(-c2cc(NC(=O)[C@@H]3CNC(=O)C3)nn2-c2ccccc2)c1] | 1H-NMR (DMSO-D6) δ: 0.90-1.15 (m, 6H), 2.37-2.42 (m, 2H), 2.69-2.81 (m, 1H), 3.28-3.53 (m, 6H), 6.94 (s, 1H), 7.00-7.15 (m, 1H), 7.21-7.27 (m, 2H), 7.31-7.50 (m, 6H), 7.63 (s, 1H), 10.88 (s, 1H). | 446 | 444 | S-form |

TABLE 2-continued

| Example No. | Molecular Structure | NMR (400 MHz) | MS (M + H) | MS (M − H) | Comments |
|---|---|---|---|---|---|
| 433 | 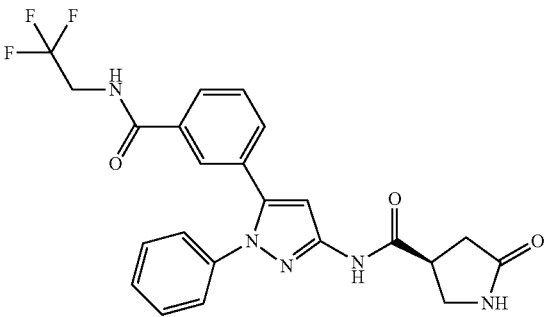 [SMILES: O=C1C[C@H](C(=O)Nc2cc(-c3cccc(C(=O)NCC(F)(F)F)c3)n(-c3ccccc3)n2)CN1] | 1H-NMR (DMSO-D6) δ: 2.38-2.42 (m, 2H), 3.30-3.55 (m, 3H), 4.03-4.15 (m, 2H), 7.05 (s, 1H), 7.22-7.27 (m, 3H), 7.32-7.45 (m, 4H), 7.64 (s, 1H), 7.85 (d, 1H, J = 7.9 Hz), 7.93 (s, 1H), 9.18 (t, 1H, J = 6.2 Hz), 10.89 (s, 1H). | 472 | 470 | S-form |
| 434 | 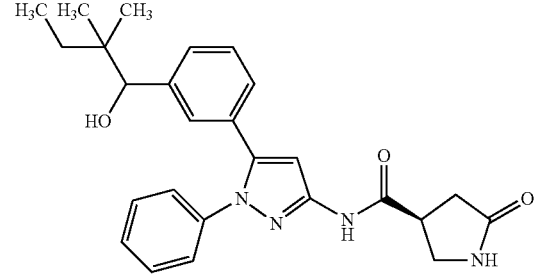 [SMILES: CCC(C)(C)C(O)c1cccc(-c2cc(NC(=O)[C@@H]3CNC(=O)C3)nn2-c2ccccc2)c1] | 1H-NMR (DMSO-D6) δ: 0.55 (s, 3H), 0.61 (s, 3H), 0.73 (t, 3H, J = 7.4 Hz), 0.94-1.05 (m, 1H), 1.11-1.22 (m, 1H), 2.36-2.42 (m, 2H), 3.31-3.53 (m, 3H), 4.18 (d, 1H, J = 4.2 Hz), 5.08 (d, 1H, J = 4.2 Hz), 6.86 (s, 1H), 7.07 (s, 1H), 7.15-7.40 (m, 8H), 7.63 (s, 1H), 10.84 (s, 1H). | 447 | 445 | 1-hydroxy-2,2-dimethyl-butyl group: racemate Lactam ring: S-form |
| 435 | 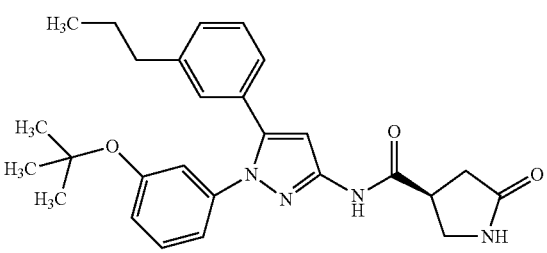 [SMILES: CCCc1cccc(-c2cc(NC(=O)[C@@H]3CNC(=O)C3)nn2-c2cccc(OC(C)(C)C)c2)c1] | 1H-NMR (DMSO-D6) δ: 0.80 (t, 3H, J = 7.3 Hz), 1.13 (s, 9H), 1.42-1.51 (m, 2H), 2.37-2.42 (m, 2H), 2.44-2.52 (m, 3H), 3.31-3.53 (m, 3H), 6.70-6.72 (m, 1H), 6.87 (s, 1H), 6.91-6.95 (m, 1H), 7.01-7.10 (m, 3H), 7.15-7.19 (m, 1H), 7.24-7.34 (m, 2H), 7.63 (s, 1H), 10.83 (s, 1H). | 461 | 459 | S-form |
| 436 | 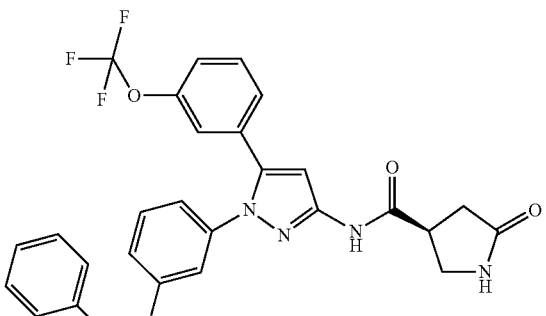 | 1H-NMR (DMSO-D6) δ: 2.38-2.40 (m, 2H), 3.33-3.36 (m, 1H), 3.40-3.44 (m, 1H), 3.48-3.51 (m, 1H), 5.01 (s, 2H), 6.78-6.81 (m, 1H), 6.90-6.92 (m, 1H), 6.99-7.03 (m, 2H), 7.11-7.13 (m, 1H), 7.28-7.40 (m, 8H), 7.53 (t, 1H, J = 7.9 Hz), 7.63 (s, 1H), 10.90 (s, 1H). | 537 | 535 | S-form |

TABLE 2-continued

| Example No. | Molecular Structure | NMR (400 MHz) | MS (M + H) | MS (M − H) | Comments |
|---|---|---|---|---|---|
| 437 | 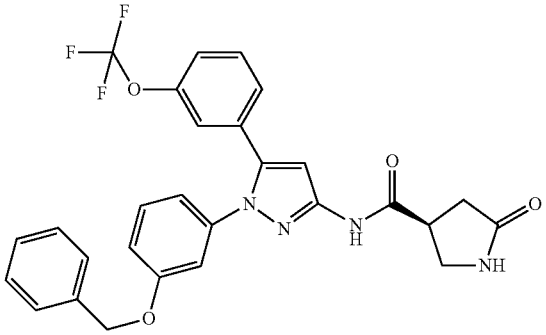 [SMILES: O=C1C[C@H](C(=O)Nc2cc(-c3cccc(OC(F)(F)F)c3)n(-c3cccc(OCc4ccccc4)c3)n2)CN1] | 1H-NMR (DMSO-D6) δ: 2.38-2.40 (m, 2H), 3.32-3.36 (m, 1H), 3.40-3.45 (m, 1H), 3.48-3.51 (m, 1H), 3.99 (q, 2H, J = 9.3 Hz), 4.63 (s, 2H), 5.00 (s, 2H), 6.76-6.78 (m, 1H), 6.89-6.92 (m, 2H), 6.97-6.99 (m, 1H), 7.16-7.18 (m, 1H), 7.25-7.40 (m, 9H), 7.63 (s, 1H), 10.87 (s, 1H). | 565 | 563 | S-form |
| 438 | 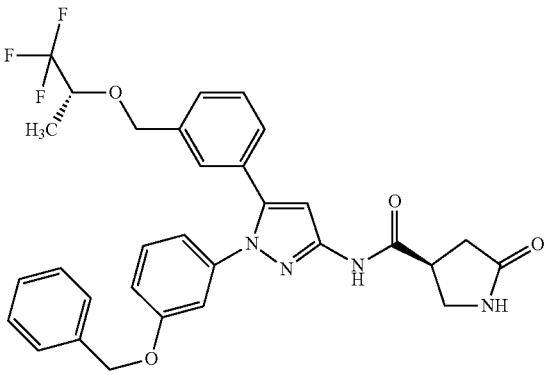 [SMILES: C[C@@H](OCc1cccc(-c2cc(NC(=O)[C@@H]3CNC(=O)C3)nn2-c2cccc(OCc3ccccc3)c2)c1)C(F)(F)F] | 1H-NMR (DMSO-D6) δ: 1.19 (d, 3H, J = 6.4 Hz), 2.37-2.41 (m, 2H), 3.33-3.35 (m, 1H), 3.39-3.45 (m, 1H), 3.46-3.52 (m, 1H), 4.05-4.16 (m, 1H), 4.63 (s, 2H), 4.99 (s, 2H), 6.77-6.79 (m, 1H), 6.89-6.92 (m, 2H), 6.97-6.99 (m, 1H), 7.15-7.17 (m, 1H), 7.25-7.48 (m, 9H), 7.63 (s, 1H) 10.87 (s, 1H). | 579 | 577 | 2,2,2-trifluoro methyl-1-methyl-ethoxymethyl group: R-form Lactam ring: S-form |
| 439 | 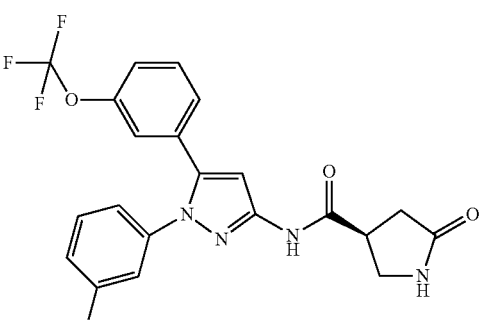 | 1H-NMR (DMSO-D6) δ: 2.38-2.40 (m, 2H), 3.33-3.36 (m, 1H), 3.41-3.45 (m, 1H), 3.48-3.52 (m, 1H), 6.60-6.62 (m, 1H), 6.66-6.67 (m, 1H), 6.75-6.77 (m, 1H), 6.97 (s, 1H), 7.10-7.12 (m, 1H), 7.16-7.20 (m, 1H), 7.34-7.36 (m, 2H), 7.53 (t, 1H, J = 8.2 Hz), 7.63 (s, 1H), 9.78 (br s, 1H), 10.87 (s, 1H). | 447 | 445 | S-form |
| 440 | 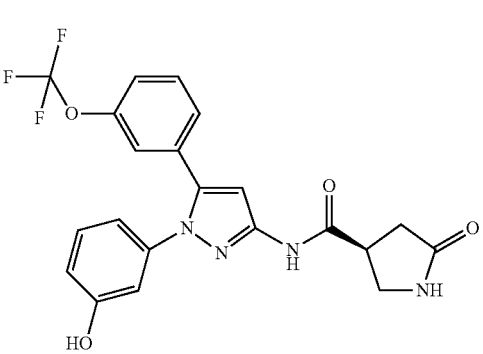 [SMILES: O=C1C[C@H](C(=O)Nc2cc(-c3cccc(OC(F)(F)F)c3)n(-c3cccc(O)c3)n2)CN1] | 1H-NMR (DMSO-D6) δ: 2.37-2.40 (m, 2H), 3.32-3.34 (m, 1H), 3.38-3.46 (m, 1H), 3.48-3.52 (m, 1H), 3.99 (q, 2H, J = 9.3 Hz), 4.62 (s, 2H), 6.57-6.60 (m, 1H), 6.65-6.67 (m, 1H), 6.71-6.73 (m, 1H), 6.89 (s, 1H), 7.12-7.18 (m, 2H), 7.26-7.28 (m, 1H), 7.32-7.39 (m, 2H), 7.63 (s, 1H), 9.78 (br s, 1H), 10.84 (s, 1H). | 475 | 473 | S-form |

TABLE 2-continued

| Example No. | Molecular Structure | NMR (400 MHz) | MS (M + H) | MS (M − H) | Comments |
|---|---|---|---|---|---|
| 441 | 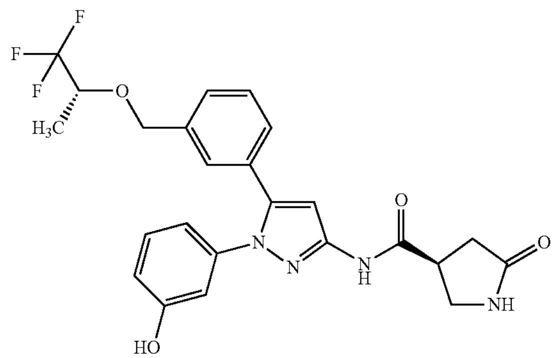 [SMILES: C[C@@H](OCc1cccc(-c2cc(NC(=O)[C@@H]3CNC(=O)C3)nn2-c2cccc(O)c2)c1)C(F)(F)F] | 1H-NMR (DMSO-D6) δ: 1.21 (d, 3H, J = 6.2 Hz), 2.37-2.40 (m, 2H), 3.33-3.35 (m, 1H), 3.38-3.46 (m, 1H), 3.48-3.52 (m, 1H), 4.08-4.15 (m, 1H), 4.63 (s, 2H), 6.57-6.60 (m, 1H), 6.66-6.68 (m, 1H), 6.70-6.74 (m, 1H), 6.89 (s, 1H), 7.12-7.17 (m, 2H), 7.26-7.28 (m, 1H), 7.32-7.38 (m, 2H), 7.63 (s, 1H), 9.79 (br s, 1H), 10.84 (s, 1H). | 489 | 487 | 2,2,2-trifluoro methyl-1-methyl-ethoxymethyl group: R-form Lactam ring: S-form |
| 442 | 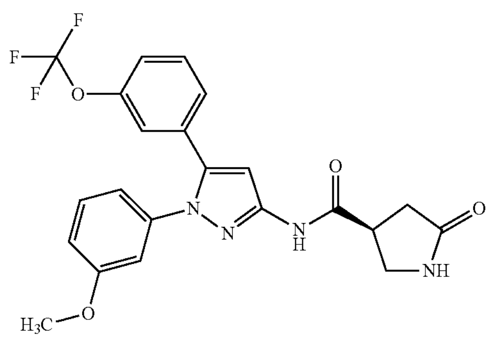 [SMILES: COc1cccc(-n2nc(NC(=O)[C@@H]3CNC(=O)C3)cc2-c2cccc(OC(F)(F)F)c2)c1] | 1H-NMR (DMSO-D6) δ: 2.38-2.40 (m, 2H), 3.32-3.35 (m, 1H), 3.40-3.45 (m, 1H), 3.48-3.51 (m, 1H), 3.67 (s, 3H), 6.76-6.78 (m, 1H), 6.83-6.84 (m, 1H), 6.92-6.95 (m, 1H), 6.99 (s, 1H), 7.12 (s, 1H), 7.30 (t, 1H, J = 8.0 Hz), 7.36-7.39 (m, 2H), 7.53 (t, 1H, J = 8.0 Hz), 7.63 (s, 1H), 10.91 (s, 1H). | 461 | 459 | S-form |
| 443 | 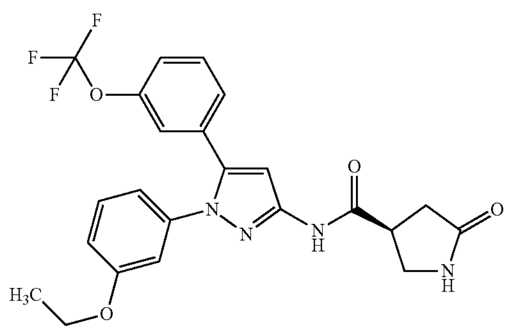 [SMILES: CCOc1cccc(-n2nc(NC(=O)[C@@H]3CNC(=O)C3)cc2-c2cccc(OC(F)(F)F)c2)c1] | 1H-NMR (DMSO-D6) : 1.24 (t, 3H, J = 7.0 Hz), 2.38-2.40 (m, 2H), 3.33-3.35 (m, 1H), 3.40-3.45 (m, 1H), 3.48-3.53 (m, 1H), 3.92 (q, 2H, J = 7.0 Hz), 6.75-6.79 (m, 2H), 6.91-6.93 (m, 1H), 6.99 (s, 1H), 7.11-7.13 (m, 1H), 7.27-7.30 (m, 1H), 7.35-7.38 (m, 2H), 7.53 (t, 1H, J = 8.0 Hz), 7.63 (s, 1H), 10.90 (s, 1H). | 475 | 473 | S-form |
| 444 | 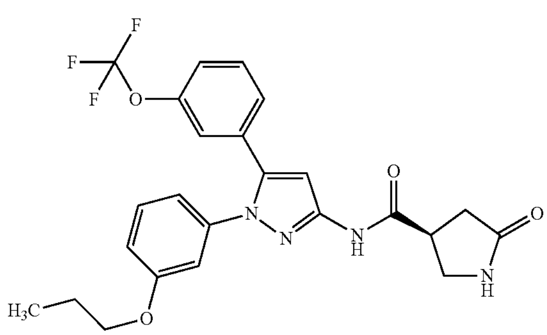 [SMILES: CCCOc1cccc(-n2nc(NC(=O)[C@@H]3CNC(=O)C3)cc2-c2cccc(OC(F)(F)F)c2)c1] | 1H-NMR (DMSO-D6) δ: 0.90 (t, 3H, J = 7.4 Hz), 1.62 (tq, 2H, J = 6.6, 7.4 Hz), 2.38-2.40 (m, 2H), 3.33-3.35 (m, 1H), 3.40-3.44 (m, 1H), 3.48-3.53 (m, 1H), 3.80 (t, 2H, J = 6.6 Hz), 6.76-6.80 (m, 2H), 6.91-6.94 (m, 1H), 6.98 (s, 1H), 7.11-7.13 (m, 1H), 7.29 (t, 1H, J = 8.3 Hz), 7.36-7.38 (m, 2H), 7.54 (t, 1H, J = 8.3 Hz), 7.63 (s, 1H), 10.89 (s, 1H). | 489 | 487 | S-form |

TABLE 2-continued

| Example No. | Molecular Structure | NMR (400 MHz) | MS (M + H) | MS (M − H) | Comments |
|---|---|---|---|---|---|
| 445 | 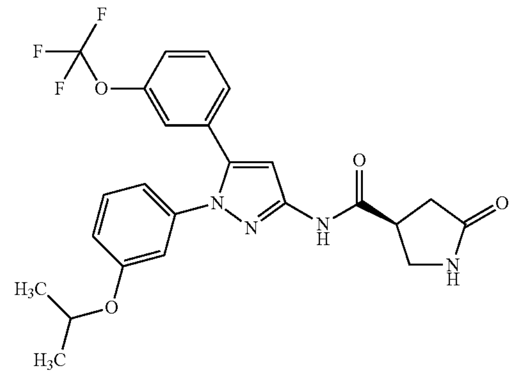 | 1H-NMR (DMSO-D6) δ: 1.13 (d, 6H, J = 6.0 Hz), 2.39 (d, 2H, J = 8.4 Hz), 3.33-3.35 (m, 1H), 3.39-3.44 (m, 1H), 3.48-3.52 (m, 1H), 4.45 (sep, 1H), 6.71-6.73 (m, 1H), 6.81-6.82 (m, 1H), 6.89-6.91 (m, 1H), 6.98 (s, 1H), 7.11 (s, 1H), 7.30 (t, 1H, J = 8.0 Hz), 7.34-7.38 (m, 2H), 7.53 (t, 1H, J = 8.0 Hz), 7.63 (s, 1H), 10.89 (s, 1H). | 489 | 487 | S-form |
| 446 | 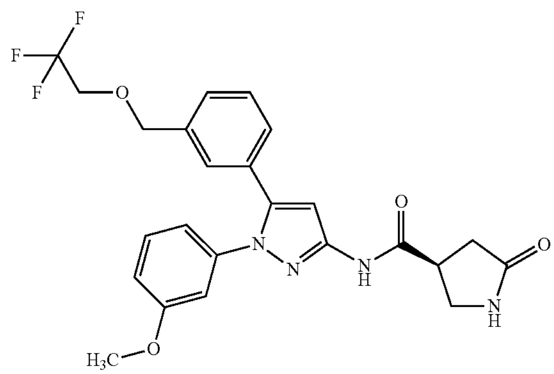 [SMILES: COc1cccc(-n2nc(NC(=O)[C@@H]3CNC(=O)C3)cc2-c2cccc(COCC(F)(F)F)c2)c1] | 1H-NMR (DMSO-D6) δ: 2.38-2.40 (m, 2H), 3.33-3.34 (m, 1H), 3.40-3.45 (m, 1H), 3.48-3.52 (m, 1H), 3.66 (s, 3H), 3.98 (q, 2H, J = 9.3 Hz), 4.62 (s, 2H), 6.73-6.75 (m, 1H), 6.81-6.84 (m, 1H), 6.88-6.91 (m, 2H), 7.18-7.20 (m, 1H), 7.25-7.28 (m, 2H), 7.33-7.40 (m, 2H), 7.63 (s, 1H), 10.88 (s, 1H). | 489 | 487 | S-form |
| 447 | 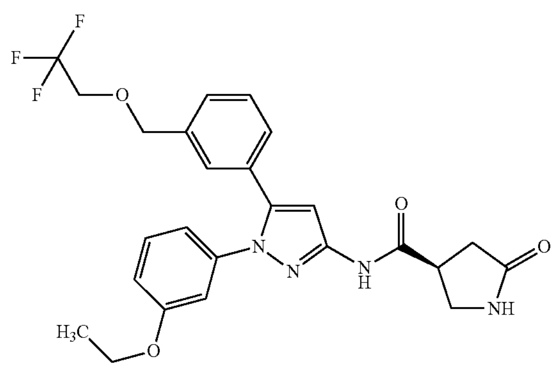 [SMILES: CCOc1cccc(-n2nc(NC(=O)[C@@H]3CNC(=O)C3)cc2-c2cccc(COCC(F)(F)F)c2)c1] | 1H-NMR (DMSO-D6) δ: 1.24 (t, 3H, J = 7.0 Hz), 2.38-2.40 (m, 2H), 3.33-3.35 (m, 1H), 3.39-3.44 (m, 1H), 3.49-3.52 (m, 1H), 3.90 (q, 2H, J = 7.0 Hz), 3.98 (q, 2H, J = 9.3 Hz), 4.62 (s, 2H), 6.74-6.79 (m, 2H), 6.86-6.88 (m, 1H), 6.91 (s, 1H), 7.17-7.19 (m, 1H), 7.23-7.29 (m, 2H), 7.33-7.40 (m, 2H), 7.63 (s, 1H), 10.87 (s, 1H). | 503 | 501 | S-form |
| 448 | 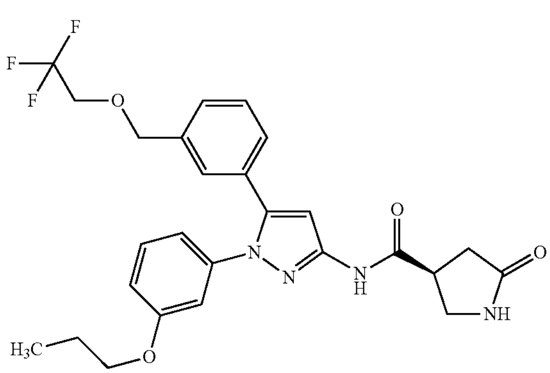 [SMILES: CCCOc1cccc(-n2nc(NC(=O)[C@@H]3CNC(=O)C3)cc2-c2cccc(COCC(F)(F)F)c2)c1] | 1H-NMR (DMSO-D6) : 0.90 (t, 3H, J = 7.3 Hz), 1.62 (tq, 2H, J = 6.6, 7.3 Hz), 2.37-2.41 (m, 2H), 3.34-3.36 (m, 1H), 3.39-3.43 (m, 1H), 3.48-3.52 (m, 1H), 3.80 (t, 2H, J = 6.6 Hz), 3.98 (q, 2H, J = 9.3 Hz), 4.62 (s, 2H), 6.74-6.79 (m, 2H), 6.86-6.89 (m, 1H), 6.91 (s, 1H), 7.18-7.20 (m, 1H), 7.23-7.28 (m, 2H), 7.33-7.40 (m, 2H), 7.63 (s, 1H), 10.87 (s, 1H). | 517 | 515 | S-form |

TABLE 2-continued

| Example No. | Molecular Structure | NMR (400 MHz) | MS (M + H) | MS (M − H) | Comments |
|---|---|---|---|---|---|
| 449 | 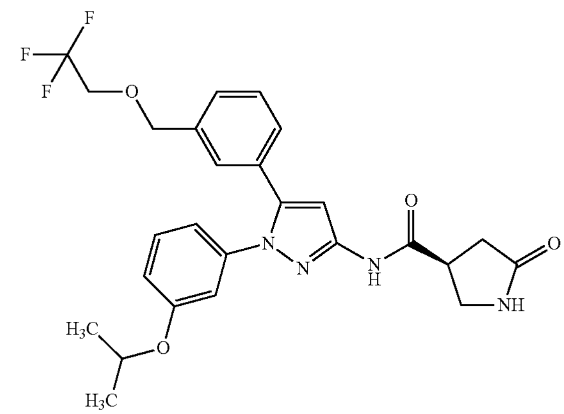 [SMILES: CC(C)Oc1cccc(-n2nc(NC(=O)[C@@H]3CNC(=O)C3)cc2-c2cccc(COCC(F)(F)F)c2)c1] | 1H-NMR (DMSO-D6) δ: 1.13 (d, 6H, J = 6.0 Hz), 2.37-2.39 (m, 2H), 3.33-3.35 (m, 1H), 3.41-3.45 (m, 1H), 3.48-3.52 (m, 1H), 3.98 (q, 2H, J = 9.3 Hz), 4.43 (sep, 1H, J = 6.0 Hz), 4.62 (s, 2H), 6.72-6.73 (m, 1H), 6.77-6.79 (m, 1H), 6.85-6.87 (m, 1H), 6.91 (s, 1H), 7.17-7.19 (m, 1H), 7.25-7.28 (m, 2H), 7.33-7.41 (m, 2H), 7.63 (s, 1H), 10.85 (s, 1H). | 517 | 515 | S-form |
| 450 | 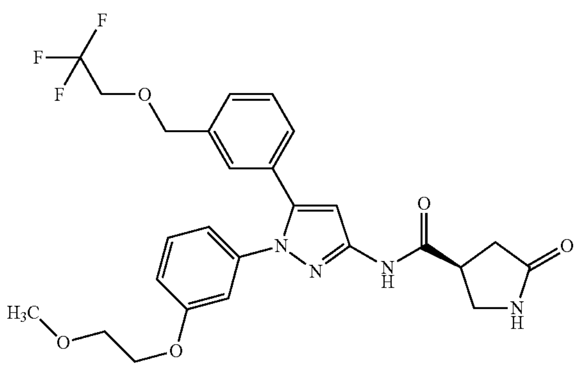 [SMILES: COCCOc1cccc(-n2nc(NC(=O)[C@@H]3CNC(=O)C3)cc2-c2cccc(COCC(F)(F)F)c2)c1] | 1H-NMR (DMSO-D6) δ: 2.38-2.40 (m, 2H), 3.26 (s, 3H), 3.34-3.36 (m, 1H), 3.40-3.44 (m, 1H), 3.48-3.52 (m, 1H), 3.55-3.58 (m, 2H), 3.96-4.02 (m, 4H), 4.62 (s, 2H), 6.76-6.81 (m, 2H), 6.89-6.91 (m, 2H), 7.17-7.18 (m, 1H), 7.24-7.29 (m, 2H), 7.33-7.40 (m, 2H), 7.62 (s, 1H), 10.86 (s, 1H). | 533 | 531 | S-form |
| 451 | 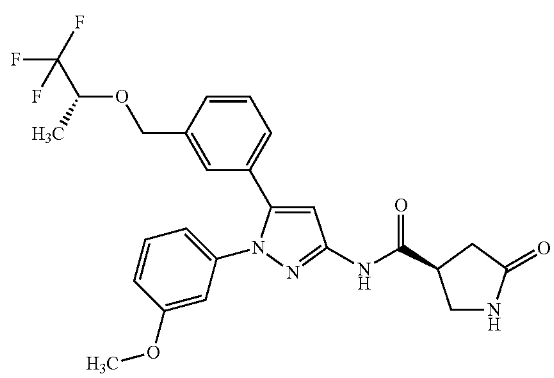 [SMILES: COc1cccc(-n2nc(NC(=O)[C@@H]3CNC(=O)C3)cc2-c2cccc(CO[C@H](C)C(F)(F)F)c2)c1] | 1H-NMR (DMSO-D6) δ: 1.20 (d, 3H, J = 6.5 Hz), 2.36-2.40 (m, 2H), 3.33-3.36 (m, 1H), 3.39-3.44 (m, 1H), 3.48-3.52 (m, 1H), 3.66 (s, 3H), 4.06-4.13 (m, 1H), 4.63 (s, 2H), 6.73-6.75 (m, 1H), 6.81-6.84 (m, 1H), 6.88-6.92 (m, 2H), 7.17-7.19 (m, 1H), 7.24-7.28 (m, 2H), 7.33-7.39 (m, 2H), 7.63 (s, 1H), 10.87 (s, 1H). | 503 | 501 | 2,2,2-trifluoromethyl-1-methyl-ethoxymethyl group: R-form Lactam ring: S-form |
| 452 | 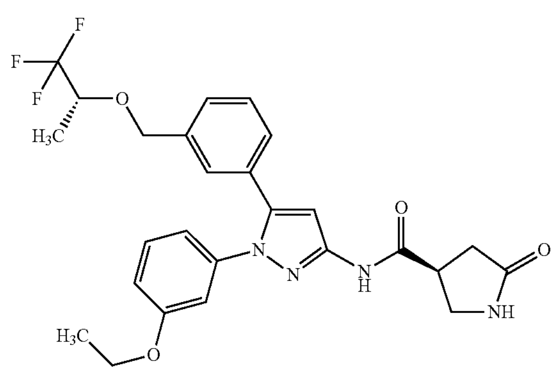 [SMILES: CCOc1cccc(-n2nc(NC(=O)[C@@H]3CNC(=O)C3)cc2-c2cccc(CO[C@H](C)C(F)(F)F)c2)c1] | 1H-NMR (DMSO-D6) δ: 1.20 (d, 3H, J = 6.3 Hz), 1.24 (t, 3H, J = 7.0 Hz), 2.38-2.40 (m, 2H), 3.33-3.36 (m, 1H), 3.40-3.44 (m, 1H), 3.47-3.53 (m, 1H), 3.91 (q, 2H, J = 7.0 Hz), 4.06-4.13 (m, 1H), 4.62 (s, 2H), 6.74-6.79 (m, 2H), 6.87-6.90 (m, 2H), 7.17-7.19 (m, 1H), 7.23-7.28 (m, 2H), 7.33-7.38 (m, 2H), 7.63 (s, 1H), 10.86 (s, 1H). | 517 | 515 | 2,2,2-trifluoromethyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 453 | 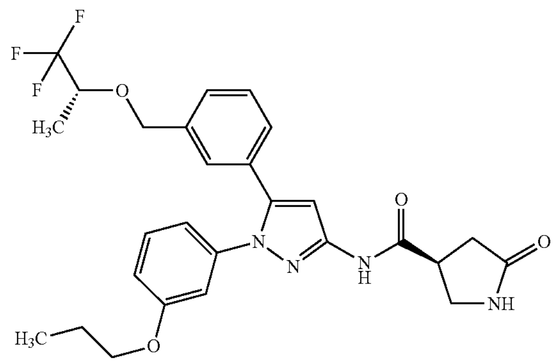 [SMILES: CCCOc1cccc(-n2nc(NC(=O)[C@@H]3CNC(=O)C3)cc2-c2cccc(CO[C@H](C)C(F)(F)F)c2)c1] | 1H-NMR (DMSO-D6) δ: 0.90 (t, 3H, J = 7.4 Hz), 1.20 (d, 3H, J = 0 6.5 Hz), 1.62 (tq, 2H, J = 7.0, 6.6 Hz), 2.38-2.40 (m, 2H), 3.33-3.36 (m, 1H), 3.40-3.45 (m, 1H), 3.48-3.52 (m, 1H), 3.80 (t, 2H, J = 6.6 Hz), 4.06-4.15 (m, 1H), 4.63 (s, 2H), 6.74-6.78 (m, 2H), 6.87-6.90 (m, 2H), 7.17-7.19 (m, 1H), 7.23-7.28 (m, 2H), 7.33-7.39 (m, 2H), 7.63 (s, 1H), 10.86 (s, 1H). | 531 | 529 | 2,2,2-trifluoro methyl-1-methyl-ethoxymethyl group: R-form Lactam ring: S-form |
| 454 | 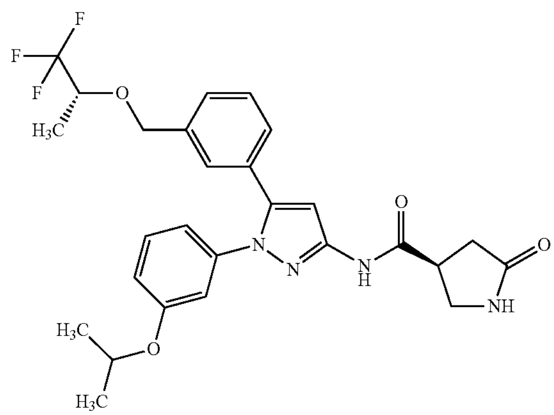 [SMILES: CC(C)Oc1cccc(-n2nc(NC(=O)[C@@H]3CNC(=O)C3)cc2-c2cccc(CO[C@H](C)C(F)(F)F)c2)c1] | 1H-NMR (DMSO-D6) : 1.14 (d, 6H, J = 6.0 Hz), 1.20 (d, 3H, J = 6.5 Hz), 2.37-2.40 (m, 2H), 3.33-3.35 (m, 1H), 3.40-3.44 (m, 1H), 3.48-3.52 (m, 1H), 4.07-4.14 (m, 1H), 4.43 (sep, 1H, J = 6.0 Hz), 4.62 (s, 2H), 6.71-6.73 (m, 1H), 6.76-6.79 (m, 1H), 6.85-6.87 (m, 1H), 6.90 (s, 1H), 7.17-7.19 (m, 1H), 7.24-7.28 (m, 2H), 7.32-7.39 (m, 2H), 7.63 (s, 1H), 10.85 (s, 1H). | 531 | 529 | 2,2,2-trifluoro methyl-1-methyl-ethoxymethyl group: R-form Lactam ring: S-form |
| 455 | 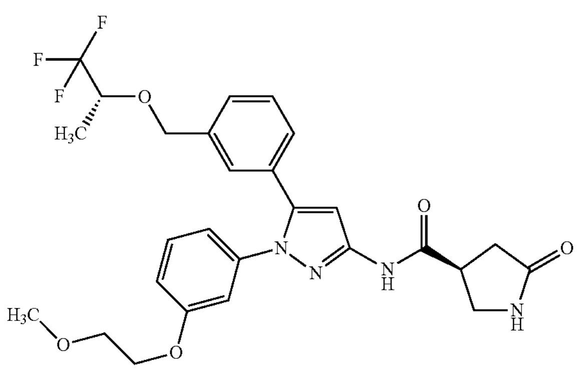 [SMILES: COCCOc1cccc(-n2nc(NC(=O)[C@@H]3CNC(=O)C3)cc2-c2cccc(CO[C@H](C)C(F)(F)F)c2)c1] | 1H-NMR (DMSO-D6) δ: 1.18 (d, 3H, J = 6.3 Hz), 2.36-2.38 (m, 2H), 3.24 (s, 3H), 3.32-3.33 (m, 1H), 3.40-3.44 (m, 1H), 3.47-3.49 (m, 1H), 3.53-3.57 (m, 2H), 3.94-3.97 (m, 2H), 4.06-4.13 (m, 1H), 4.61 (s, 2H), 6.74-6.76 (m, 1H), 6.79-6.81 (m, 1H), 6.88-6.91 (m, 2H), 7.14-7.16 (m, 1H), 7.23-7.28 (m, 2H), 7.33-7.37 (m, 2H), 7.61 (s, 1H), 10.85 (s, 1H). | 547 | 545 | 2,2,2-trifluoro methyl-1-methyl-ethoxymethyl group: R-form Lactam ring: S-form |
| 456 | 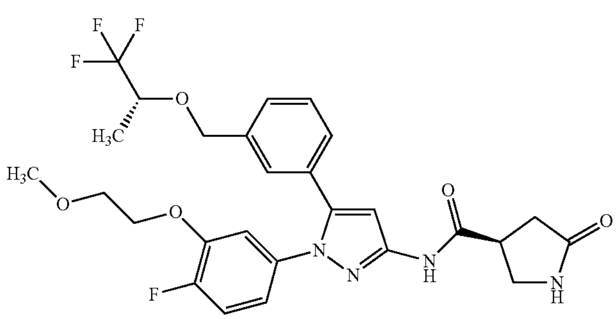 [SMILES: COCCOc1cc(-n2nc(NC(=O)[C@@H]3CNC(=O)C3)cc2-c2cccc(CO[C@H](C)C(F)(F)F)c2)ccc1F] | 1H-NMR (DMSO-D6) δ: 1.20 (d, 3H, J = 6.4 Hz), 2.33-2.45 (m, 2H), 2.46-2.58 (m, 4H), 3.30-3.53 (m, 3H), 3.70 (s, 3H), 4.10 (tt, 1H, J = 6.4 Hz, 6.4 Hz), 4.59-4.66 (m, 2H), 6.68-6.72 (m, 1H), 6.92 (s, 1H), 7.10 (dd, 1H, J = 7.8 Hz, 2.2 Hz), 7.16-7.26 (m, 3H), 7.32-7.42 (m, 2H), 7.63 (s, 1H), 10.89 (s, 1H). | 565 | 563 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 457 | 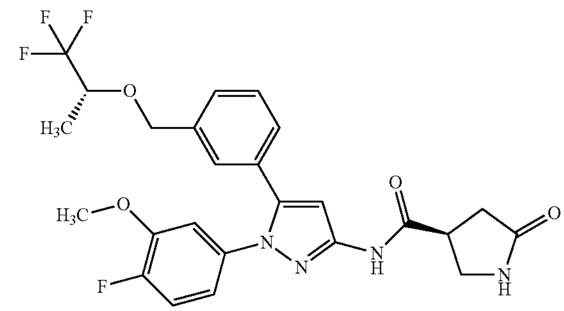 [SMILES: COc1cc(-n2nc(NC(=O)[C@@H]3CNC(=O)C3)cc2-c2cccc(CO[C@H](C)C(F)(F)F)c2)ccc1F] | 1H-NMR (DMSO-D6) δ: 1.20 (d, 3H, J = 6.4 Hz), 2.33-2.45 (m, 2H), 3.30-3.53 (m, 3H), 3.70 (s, 3H), 4.10 (tt, 1H, J = 6.4 Hz, 6.4 Hz), 4.59-4.66 (m, 2H), 6.68-6.72 (m, 1H), 6.92 (s, 1H), 7.10 (dd, 1H, J = 7.8 Hz, 2.6 Hz), 7.15-7.26 (m, 3H), 7.32-7.42 (m, 2H), 7.63 (s, 1H), 10.89 (s, 1H). | 521 | 519 | 2,2,2-trifluoro methyl-1-methyl-ethoxymethyl group: R-form Lactam ring: S-form |
| 458 | 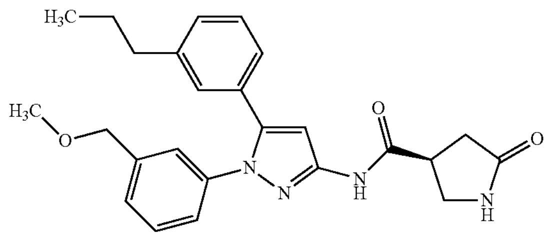 [SMILES: CCCc1cccc(-c2cc(NC(=O)[C@@H]3CNC(=O)C3)nn2-c2cccc(COC)c2)c1] | 1H-NMR (CDCl3) δ: 0.78 (t, 3H, J = 7.2 Hz), 1.45 (tq, 2H, J = 7.2, 7.6 Hz), 2.39 (d, 2H, J = 8.4 Hz), 2.47 (t, 2H, J = 7.6 Hz), 3.19 (s, 3H), 3.32-3.52 (m, 3H), 4.37 (s, 2H), 6.89 (s, 1H), 7.02 (s, 1H), 7.06-7.10 (m, 2H), 7.17 (d, 1H, J = 7.6 Hz), 7.22 (s, 1H), 7.25-7.29 (m, 2H), 7.34 (t, 1H, J = 8.0 Hz), 7.63 (s, 1H), 10.85 (s, 1H). | 433 | 431 | S-form |
| 459 | 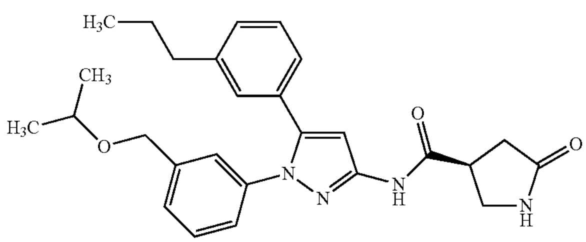 [SMILES: CCCc1cccc(-c2cc(NC(=O)[C@@H]3CNC(=O)C3)nn2-c2cccc(COC(C)C)c2)c1] | 1H-NMR (CDCl3) δ: 0.78 (t, 3H, J = 7.2 Hz), 1.06 (d, 6H, J = 6.0 Hz), 1.45 (tq, 2H, J = 7.2, 7.6 Hz), 2.39 (d, 2H, J = 8.4 Hz), 2.47 (t, 2H, J = 7.6 Hz), 3.32-3.52 (m, 4H), 4.41 (s, 2H), 6.89 (s, 1H), 7.02 (s, 1H), 7.06-7.10 (m, 2H), 7.16-7.20 (m, 2H), 7.25-7.29 (m, 2H), 7.33 (t, 1H, J = 8.0 Hz), 7.63 (s, 1H), 10.85 (s, 1H) | 461 | 459 | S-form |
| 460 | 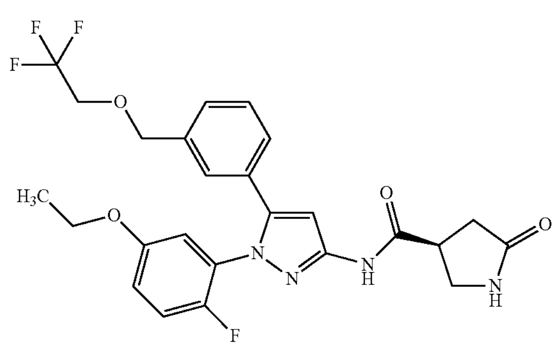 [SMILES: CCOc1ccc(F)c(-n2nc(NC(=O)[C@@H]3CNC(=O)C3)cc2-c2cccc(COCC(F)(F)F)c2)c1] | 1H-NMR (DMSO-D6) δ: 1.28 (t, 3H, J = 7.2 Hz), 2.39 (d, 2H, J = 8.4 Hz), 3.32-3.52 (m, 3H), 3.94-4.01 (m, 4H), 4.60 (s, 2H), 6.97-7.02 (m, 2H), 7.06-7.08 (m, 1H), 7.16-7.22 (m, 2H), 7.27 (s, 1H), 7.27-7.37 (m, 2H), 7.63 (s, 1H), 10.86 (s, 1H). | 521 | 519 | S-form |

TABLE 2-continued

| Example No. | Molecular Structure | NMR (400 MHz) | MS (M + H) | MS (M − H) | Comments |
|---|---|---|---|---|---|
| 461 | 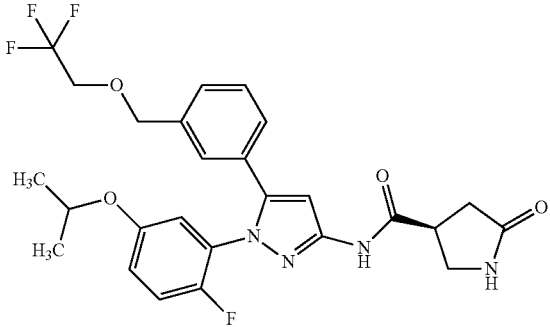 [SMILES: CC(C)Oc1ccc(F)c(-n2nc(NC(=O)[C@@H]3CNC(=O)C3)cc2-c2cccc(COCC(F)(F)F)c2)c1] | 1H-NMR (DMSO-D6) δ: 1.18 (d, 6H, J = 6.0 Hz), 2.39 (d, 2H, J = 8.4 Hz), 3.32-3.52 (m, 3H), 3.98 (q, 2H, J = 9.2 Hz), 4.53 (sep, 1H, J = 6.0 Hz), 4.60 (s, 2H), 6.95-7.00 (m, 2H), 7.02-7.04 (m, 1H), 7.17-7.22 (m, 2H), 7.26 (s, 1H), 7.30-7.37 (m, 2H), 7.64 (s, 1H), 10.86 (s, 1H). | 535 | 533 | S-form |
| 462 | 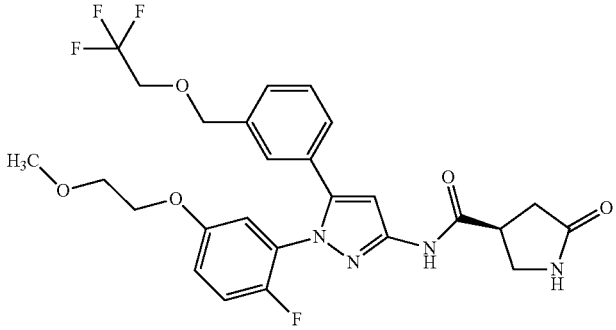 [SMILES: COCCOc1ccc(F)c(-n2nc(NC(=O)[C@@H]3CNC(=O)C3)cc2-c2cccc(COCC(F)(F)F)c2)c1] | 1H-NMR (DMSO-D6) δ: 2.39 (d, 2H, J = 8.4 Hz), 3.28 (s, 3H), 3.32-3.52 (m, 3H), 3.59-3.61 (m, 2H), 3.98 (q, 2H, J = 9.2 Hz), 4.04-4.07 (m, 2H), 4.61 (s, 2H), 6.97 (s, 1H), 7.01-7.05 (m, 1H), 7.10-7.12 (m, 1H), 7.15-7.23 (m, 2H), 7.28 (s, 1H), 7.30-7.37 (m, 2H), 7.64 (s, 1H), 10.86 (s, 1H). | 551 | 549 | S-form |
| 463 | 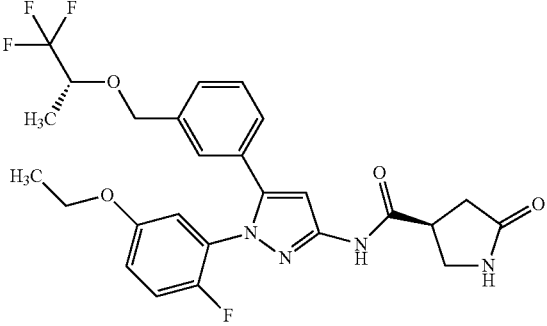 [SMILES: CCOc1ccc(F)c(-n2nc(NC(=O)[C@@H]3CNC(=O)C3)cc2-c2cccc(CO[C@H](C)C(F)(F)F)c2)c1] | 1H-NMR (DMSO-D6) δ: 1.19 (d, 3H, J = 6.4 Hz), 1.28 (t, 3H, J = 7.2 Hz), 2.39 (d, 2H, J = 8.4 Hz), 3.32-3.52 (m, 3H), 3.98 (q, 2H, 7.2 Hz), 4.06-4.12 (m, 1H), 4.61 (s, 2H), 6.96 (s, 1H), 6.98-7.02 (m, 1H), 7.06-7.09 (m, 1H), 7.16-7.22 (m, 2H), 7.26 (s, 1H), 7.29-7.36 (m, 2H), 7.64 (s, 1H), 10.86 (s, 1H). | 535 | 533 | 2,2,2-trifluoro methyl-1-methyl-ethoxymethyl group: R-form Lactam ring: S-form |
| 464 | 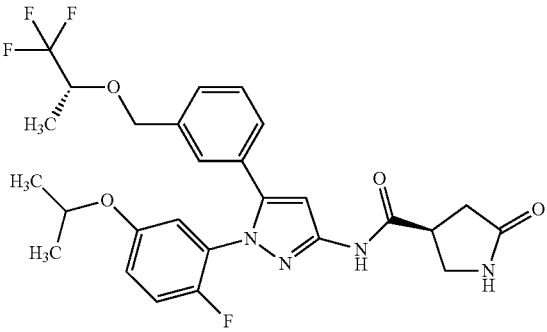 [SMILES: CC(C)Oc1ccc(F)c(-n2nc(NC(=O)[C@@H]3CNC(=O)C3)cc2-c2cccc(CO[C@H](C)C(F)(F)F)c2)c1] | 1H-NMR (DMSO-D6) δ: 1.14-1.20 (m, 9H), 2.39 (d, 2H, J = 8.4 Hz), 3.32-3.52 (m, 3H), 4.06-4.12 (m, 1H), 4.51-4.57 (m, 1H), 4.63 (s, 2H), 6.96 (s, 1H), 6.97-7.00 (m, 1H), 7.03-7.05 (m, 1H), 7.17-7.22 (m, 2H), 7.25 (s, 1H), 7.29-7.36 (m, 2H), 7.64 (s, 1H), 10.86 (s, 1H). | 549 | 547 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 465 | 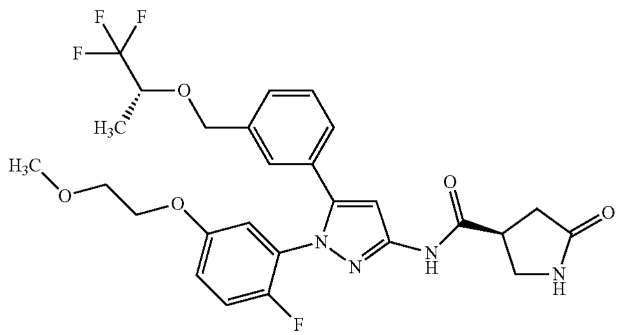 [SMILES: COCCOc1ccc(F)c(-n2nc(NC(=O)[C@@H]3CNC(=O)C3)cc2-c2cccc(CO[C@H](C)C(F)(F)F)c2)c1] | 1H-NMR (DMSO-D6) δ: 1.19 (d, 3H, J = 6.4 Hz), 2.39 (d, 2H, J = 8.4 Hz), 3.28 (s, 3H), 3.32-3.52 (m, 3H), 3.59-3.62 (m, 2H), 4.05-4.13 (m, 3H), 4.61 (s, 2H), 6.97 (s, 1H), 7.01-7.05 (m, 1H), 7.10-7.12 (m, 1H), 7.16-7.23 (m, 2H), 7.27 (s, 1H), 7.29-7.36 (m, 2H), 7.64 (s, 1H), 10.86 (s, 1H). | 565 | 563 | 2,2,2-trifluoro methyl-1-methyl-ethoxymethyl group: R-form Lactam ring: S-form |
| 466 | 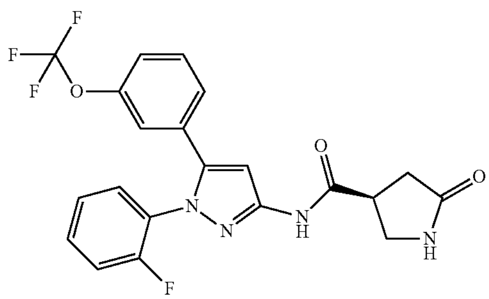 [SMILES: O=C1C[C@H](C(=O)Nc2cc(-c3cccc(OC(F)(F)F)c3)n(-c3ccccc3F)n2)CN1] | $^1$H-NMR (CDCl$_3$) δ: 2.56 (dd, 1H, J = 17.2, 9.6 Hz), 2.77 (dd, 1H, J = 17.2, 8.8 Hz), 3.28-3.39 (m, 1H), 3.58 (t, 1H, J = 8.8 Hz), 3.68 (dd, 1H, J = 9.2, 7.2 Hz), 6.29 (s, 1H), 7.01 (br s, 1H), 7.10-7.25 (m, 5H), 7.31-7.44 (m, 3H), 8.93 (s, 1H). | 449 | 447 | S-form |
| 467 | 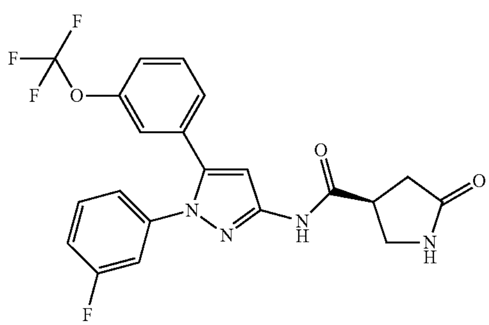 [SMILES: O=C1C[C@H](C(=O)Nc2cc(-c3cccc(OC(F)(F)F)c3)n(-c3cccc(F)c3)n2)CN1] | $^1$H-NMR (CDCl$_3$) δ: 2.54-2.87 (m, 2H), 3.33-3.75 (m, 3H), 6.39 (s, 1H), 6.93-7.11 (m, 5H), 7.19-7.42 (m, 4H), 8.90 (s, 1H). | 449 | 447 | S-form |
| 468 | 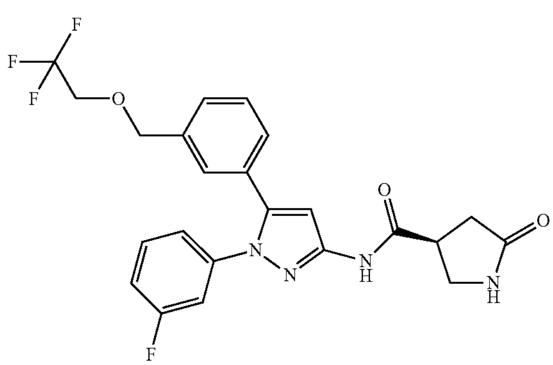 [SMILES: O=C1C[C@H](C(=O)Nc2cc(-c3cccc(COCC(F)(F)F)c3)n(-c3cccc(F)c3)n2)CN1] | $^1$H-NMR (CDCl$_3$) δ: 2.56-2.83 (m, 2H), 3.32-3.79 (m, 5H), 4.61 (s, 2H), 5.96 (s, 1H), 6.95-7.06 (m, 4H), 7.21-7.38 (m, 5H), 8.44 (s, 1H). | 477 | 475 | S-form |

TABLE 2-continued

| Example No. | Molecular Structure | NMR (400 MHz) | MS (M + H) | MS (M − H) | Comments |
|---|---|---|---|---|---|
| 469 | 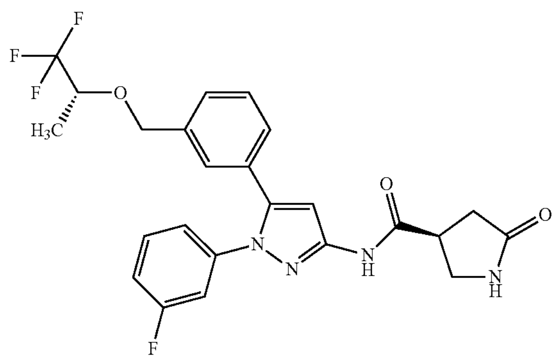 | ¹H-NMR (CDCl₃) δ: 1.28 (d, 3H, J = 6.4 Hz), 2.59 (dd, 1H, J = 17.2, 9.6 Hz), 2.76 (dd, 1H, J = 17.2, 8.4 Hz), 3.31-3.41 (m, 1H), 3.56-3.81 (m, 3H), 4.57 (d, 1H, J = 12.0 Hz), 4.68 (d, 1H, J = 12.0 Hz), 6.29 (s, 1H), 6.95-7.07 (m, 4H), 7.17-7.36 (m, 5H), 8.82 (s, 1H). | 491 | 489 | 2,2,2-trifluoro methyl-1-methyl-ethoxymethyl group: R-form Lactam ring: S-form |
| 470 | 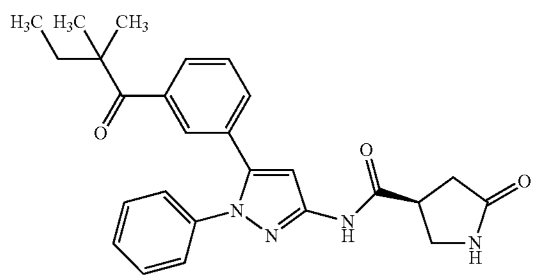 [SMILES: CCC(C)(C)C(=O)c1cccc(-c2cc(NC(=O)[C@@H]3CNC(=O)C3)nn2-c2ccccc2)c1] | 1H-NMR (DMSO-D6) δ: 0.62 (t, 3H, J = 7.5 Hz), 1.02 (s, 6H), 1.44 (q, 2H, J = 7.5 Hz), 2.37-2.41 (m, 2H), 3.31-3.54 (m, 3H), 6.97 (s, 1H), 7.24-7.29 (m, 3H), 7.33-7.44 (m, 3H), 7.48-7.59 (m, 3H), 7.63 (s, 1H), 10.88 (s, 1H). | 445 | 443 | S-form |
| 471 | 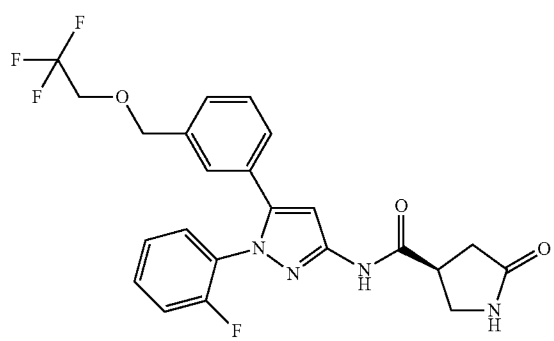 [SMILES: O=C1C[C@H](C(=O)Nc2cc(-c3cccc(COCC(F)(F)F)c3)n(-c3ccccc3F)n2)CN1] | ¹H-NMR (CDCl₃) δ: 2.57 (dd, 1H, J = 17.2, 9.6 Hz), 2.78 (dd, 1H, J = 17.2, 8.8 Hz), 3.29-3.39 (m, 1H), 3.58-3.75 (m, 4H), 4.57 (s, 2H), 5.88 (s, 1H), 7.07-7.42 (m, 9H), 8.46 (s, 1H). | 477 | 475 | S-form |
| 472 | 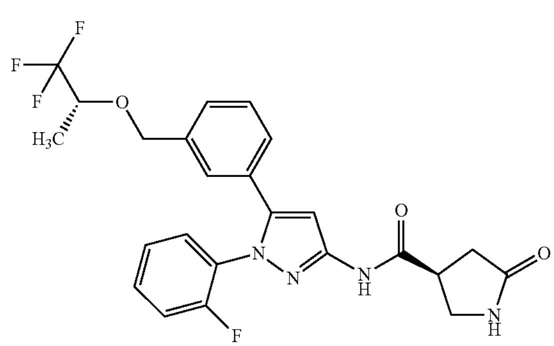 [SMILES: C[C@@H](OCc1cccc(-c2cc(NC(=O)[C@@H]3CNC(=O)C3)nn2-c2ccccc2F)c1)C(F)(F)F] | ¹H-NMR (CDCl₃) δ: 1.26 (d, 3H, J = 6.4 Hz), 2.55 (dd, 1H, J = 17.2, 9.6 Hz), 2.78 (dd, 1H, J = 17.2, 8.4 Hz), 3.26-3.37 (m, 1H), 3.55-3.76 (m, 3H), 4.52 (d, 1H, J = 12.4 Hz), 4.64 (d, 1H, J = 12.4 Hz), 6.05 (s, 1H), 7.07-7.42 (m, 9H), 8.68 (s, 1H). | 491 | 489 | 2,2,2-trifluoro methyl-1-methyl-ethoxymethyl group: R-form Lactam ring: S-form |

TABLE 2-continued
| Example No. | Molecular Structure | NMR (400 MHz) | MS (M + H) | MS (M − H) | Comments |
|---|---|---|---|---|---|
| 473 | 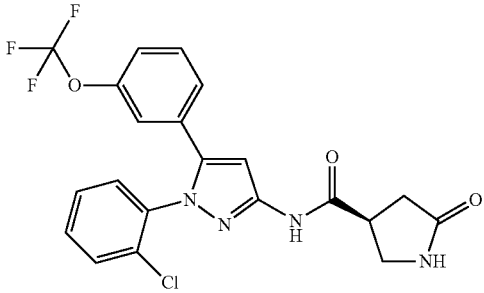 [SMILES: O=C1C[C@H](C(=O)Nc2cc(-c3cccc(OC(F)(F)F)c3)n(-c3ccccc3Cl)n2)CN1] | 1H-NMR (DMSO-D6) δ: 2.39-2.41 (m, 2H), 3.34-3.37 (m, 1H), 3.39-3.44 (m, 1H), 3.48-3.53 (m, 1H), 7.01 (s, 1H), 7.08 (s, 1H), 7.30-7.34 (m, 2H), 7.47-7.55 (m, 3H), 7.59-7.63 (m, 3H), 10.86 (s, 1H). | 465 | 463 | S-form |
| 474 | 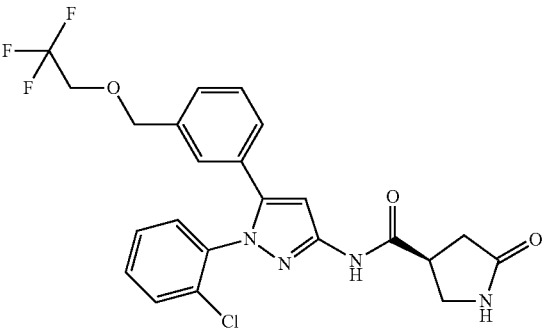 [SMILES: O=C1C[C@H](C(=O)Nc2cc(-c3cccc(COCC(F)(F)F)c3)n(-c3ccccc3Cl)n2)CN1] | 1H-NMR (DMSO-D6) δ: 2.37-2.40 (m, 2H), 3.32-3.34 (m, 1H), 3.38-3.42 (m, 1H), 3.46-3.51 (m, 1H), 3.94 (q, 2H, J = 9.3 Hz), 4.56 (s, 2H), 6.98 (s, 1H), 7.09-7.11 (m, 1H), 7.20-7.29 (m, 3H), 7.40-7.62 (m, 5H), 10.81 (s, 1H). | 493 | 491 | S-form |
| 475 | 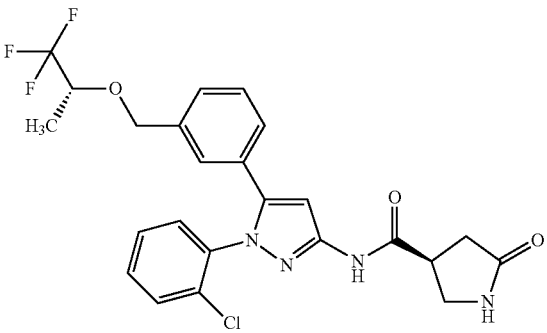 [SMILES: C[C@@H](OCc1cccc(-c2cc(NC(=O)[C@@H]3CNC(=O)C3)nn2-c2ccccc2Cl)c1)C(F)(F)F] | 1H-NMR (DMSO-D6) δ: 1.19 (d, 3H, J = 5.8 Hz), 2.38-2.40 (m, 2H), 3.35-3.37 (m, 1H), 3.40-3.44 (m, 1H), 3.48-3.52 (m, 1H), 4.05-4.10 (m, 1H), 4.57 (s, 2H), 6.99 (s, 1H), 7.11-7.12 (m, 1H), 7.21 (s, 1H), 7.26-7.32 (m, 2H), 7.46-7.60 (m, 4H), 7.63 (s, 1H), 10.82 (s, 1H). | 507 | 505 | 2,2,2-trifluoro methyl-1-methyl-ethoxymethyl group: R-form Lactam ring: S-form |
| 476 | 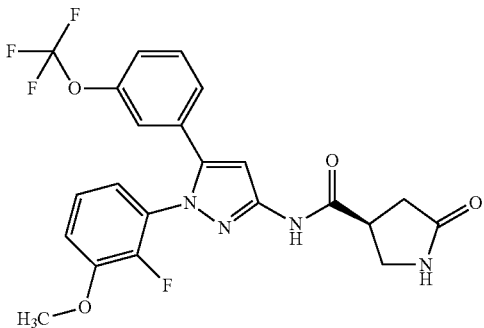 [SMILES: COc1cccc(-n2nc(NC(=O)[C@@H]3CNC(=O)C3)cc2-c2cccc(OC(F)(F)F)c2)c1F] | $^1$H-NMR (CDCl$_3$) δ: 2.51 (dd, 1H, J = 17.2, 9.6 Hz), 2.76 (dd, 1H, J = 17.2, 8.4 Hz), 3.23-3.34 (m, 1H), 3.55-3.72 (m, 2H), 3.87 (s, 3H), 5.97 (s, 1H), 6.91-7.37(m, 8H), 8.77 (s, 1H). | 479 | 477 | S-form |

TABLE 2-continued

| Example No. | Molecular Structure | NMR (400 MHz) | MS (M + H) | MS (M − H) | Comments |
|---|---|---|---|---|---|
| 477 | 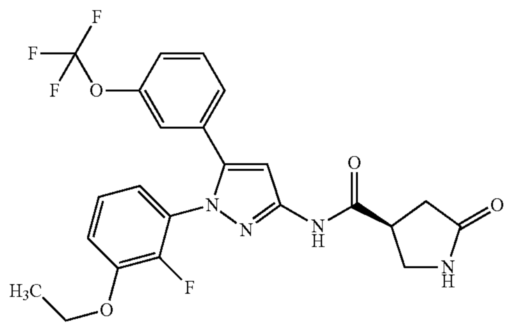 [SMILES: CCOc1cccc(-n2nc(NC(=O)[C@@H]3CNC(=O)C3)cc2-c2cccc(OC(F)(F)F)c2)c1F] | $^1$H-NMR (CDCl$_3$) δ: 1.40 (t, 3H, J = 6.8 Hz), 2.50 (dd, 1H, J = 17.2, 9.6 Hz), 2.76 (dd, 1H, J = 17.2, 8.4 Hz), 3.21-3.32 (m, 1H), 3.52-3.70 (m, 2H), 4.08 (q, 2H, J = 6.8 Hz), 6.16 (s, 1H), 6.89-7.38 (m, 8H), 8.99 (s, 1H). | 493 | 491 | S-form |
| 478 | 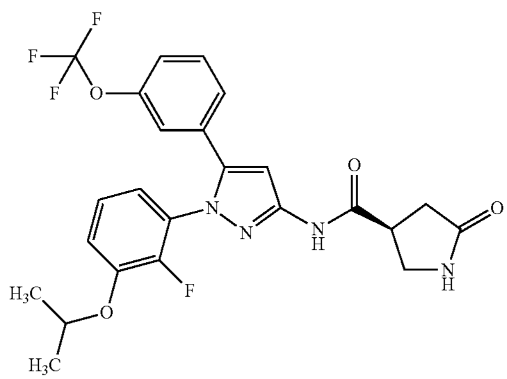 [SMILES: CC(C)Oc1cccc(-n2nc(NC(=O)[C@@H]3CNC(=O)C3)cc2-c2cccc(OC(F)(F)F)c2)c1F] | $^1$H-NMR (CDCl$_3$) δ: 1.29 (d, 6H, J = 6.0 Hz), 2.56 (dd, 1H, J = 17.2, 9.6 Hz), 2.77 (dd, 1H, J = 17.2, 8.4 Hz), 3.27-3.39 (m, 1H), 3.56-3.74 (m, 2H), 4.43-4.52 (m, 1H), 6.01 (s, 1H), 6.90-7.37 (m, 8H), 8.65 (s, 1H). | 507 | 505 | S-form |
| 479 | 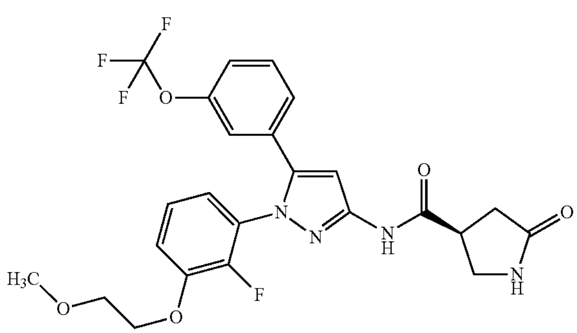 [SMILES: COCCOc1cccc(-n2nc(NC(=O)[C@@H]3CNC(=O)C3)cc2-c2cccc(OC(F)(F)F)c2)c1F] | $^1$H-NMR (CDCl$_3$) δ: 2.48 (dd, 1H, J = 17.2, 9.6 Hz), 2.76 (dd, 1H, J = 17.2, 8.4 Hz), 3.18-3.29 (m, 1H), 3.41 (s, 3H), 3.52-3.76 (m, 4H), 4.11-4.22 (m, 2H), 5.98 (s, 1H), 6.92-7.37 (m, 8H), 8.83 (s, 1H). | 523 | 521 | S-form |
| 480 | 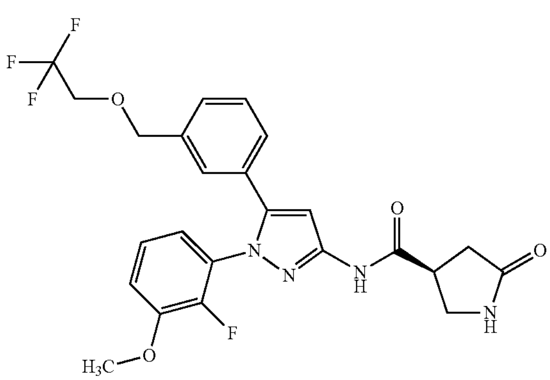 [SMILES: COc1cccc(-n2nc(NC(=O)[C@@H]3CNC(=O)C3)cc2-c2cccc(COCC(F)(F)F)c2)c1F] | $^1$H-NMR (CDCl$_3$) δ: 2.49 (dd, 1H, J = 17.2, 9.6 Hz), 2.76 (dd, 1H, J = 17.2, 8.4 Hz), 3.22-3.31 (m, 1H), 3.54-3.71 (m, 4H), 3.86 (s, 3H), 4.58 (s, 2H), 5.97 (s, 1H), 6.90-7.34 (m, 8H), 8.84 (s, 1H). | 507 | 505 | S-form |

TABLE 2-continued

| Example No. | Molecular Structure | NMR (400 MHz) | MS (M + H) | MS (M − H) | Comments |
| --- | --- | --- | --- | --- | --- |
| 481 | 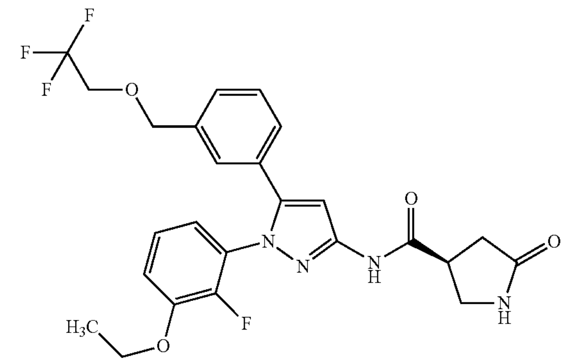 [SMILES: CCOc1cccc(-n2nc(NC(=O)[C@@H]3CNC(=O)C3)cc2-c2cccc(COCC(F)(F)F)c2)c1F] | ¹H-NMR (CDCl₃) δ: 1.39 (t, 3H, J = 6.8 Hz), 2.49 (dd, 1H, J = 17.2, 9.6 Hz), 2.76 (dd, 1H, J = 17.2, 8.4 Hz), 3.21-3.32 (m, 1H), 3.51-3.71 (m, 4H), 4.07 (q, 2H, J = 6.8 Hz), 4.58 (s, 2H), 6.11 (s, 1H), 6.88-7.12 (m, 4H), 7.20-7.34 (m, 4H), 9.01 (s, 1H). | 521 | 519 | S-form |
| 482 | 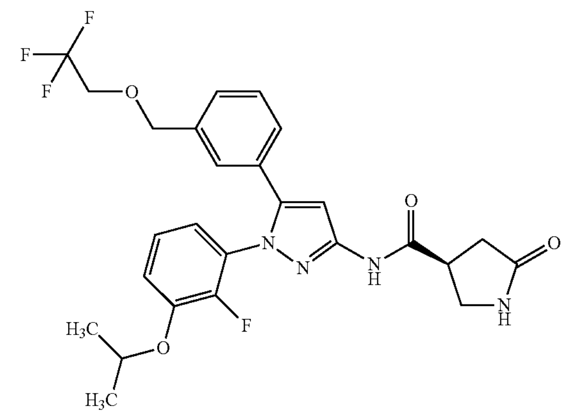 [SMILES: CC(C)Oc1cccc(-n2nc(NC(=O)[C@@H]3CNC(=O)C3)cc2-c2cccc(COCC(F)(F)F)c2)c1F] | ¹H-NMR (CDCl₃) δ: 1.29 (d, 6H, J = 6.4 Hz), 2.56 (dd, 1H, J = 17.2, 9.6 Hz), 2.78 (dd, 1H, J = 17.2, 8.4 Hz), 3.28-3.38 (m, 1H), 3.56-3.73 (m, 4H), 4.42-4.52 (m, 1H), 4.58 (s, 2H), 6.09 (s, 1H), 6.88-7.12 (m, 4H), 7.19-7.33 (m, 4H), 8.78 (s, 1H). | 535 | 533 | S-form |
| 483 | 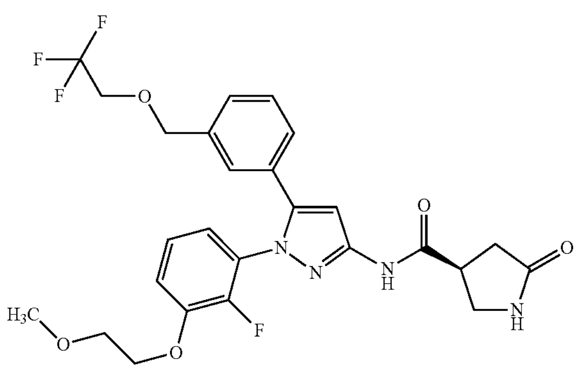 [SMILES: COCCOc1cccc(-n2nc(NC(=O)[C@@H]3CNC(=O)C3)cc2-c2cccc(COCC(F)(F)F)c2)c1F] | ¹H-NMR (CDCl₃) δ: 2.43 (dd, 1H, J = 17.2, 9.6 Hz), 2.75 (dd, 1H, J = 17.2, 8.4 Hz), 3.13-3.24 (m, 1H), 3.41 (s, 1H), 3.50-3.76 (m, 6H), 4.10-4.21 (m, 2H), 4.58 (s, 2H), 6.04 (s, 1H), 6.92-7.13 (m, 4H), 7.19-7.33 (m, 4H), 9.01 (s, 1H). | 551 | 549 | S-form |
| 484 | 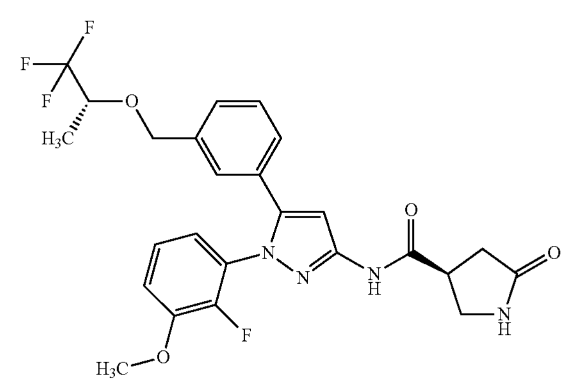 [SMILES: COc1cccc(-n2nc(NC(=O)[C@@H]3CNC(=O)C3)cc2-c2cccc(CO[C@H](C)C(F)(F)F)c2)c1F] | ¹H-NMR (CDCl₃) δ: 1.25 (d, 3H, J = 6.0 Hz), 2.48 (dd, 1H, J = 17.2, 9.6 Hz), 2.76 (dd, 1H, J = 17.2, 8.4 Hz), 3.20-3.30 (m, 1H), 3.52-3.76 (m, 3H), 3.86 (s, 1H), 4.53 (d, 1H, J = 12.0 Hz), 4.65 (d, 1H, J = 12.0 Hz), 6.05 (s, 1H), 6.88-7.31 (m, 8H), 8.95 (s, 1H). | 521 | 519 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 485 | 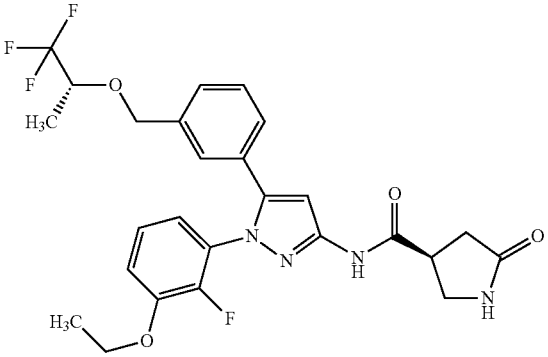 [SMILES: CCOc1cccc(-n2nc(NC(=O)[C@@H]3CNC(=O)C3)cc2-c2cccc(CO[C@H](C)C(F)(F)F)c2)c1F] | ¹H-NMR (CDCl₃) δ: 1.25 (d, 3H, J = 6.4 Hz), 1.39 (t, 3H, J = 7.2 Hz), 2.49 (dd, 1H, J = 17.2, 9.6 Hz), 2.76 (dd, 1H, J = 17.2, 8.4 Hz), 3.22-3.32 (m, 1H), 3.53-3.76 (m, 3H), 4.07 (q, 2H, J = 7.2 Hz), 4.53 (d, 1H, J = 12.0 Hz), 4.65 (d, 1H, J = 12.0 Hz), 6.04 (s, 1H), 6.87-7.11 (m, 4H), 7.17-7.31 (m, 4H), 8.92 (s, 1H). | 535 | 533 | 2,2,2-trifluoro methyl-1-methyl-ethoxymethyl group: R-form Lactam ring: S-form |
| 486 | 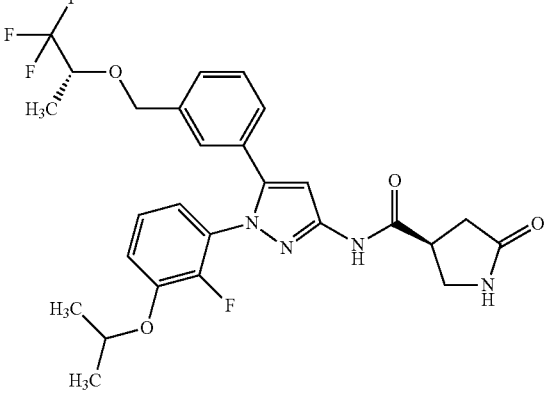 | ¹H-NMR (CDCl₃) δ: 1.24-1.31 (m, 9H), 2.56 (dd, 1H, J = 17.2, 9.6 Hz), 2.78 (dd, 1H, J = 17.2, 8.4 Hz), 3.28-3.38 (m, 1H), 3.56-3.77 (m, 3H), 4.42-4.68 (m, 3H), 6.01 (s, 1H), 6.88-7.10 (m, 4H), 7.16-7.31 (m, 4H), 8.65 (s, 1H). | 549 | 547 | 2,2,2-trifluoro methyl-1-methyl-ethoxymethyl group: R-form Lactam ring: S-form |
| 487 | 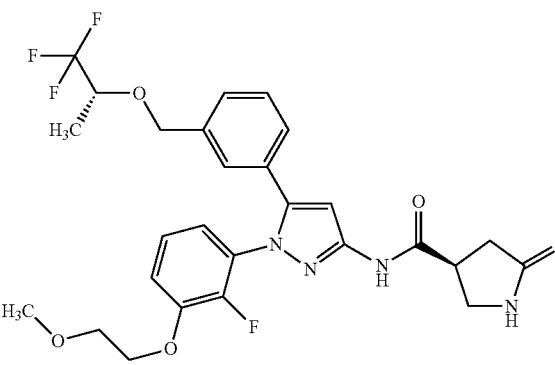 | ¹H-NMR (CDCl₃) δ: 1.26 (d, 3H, J = 6.8 Hz), 2.42 (dd, 1H, J = 17.2, 9.6 Hz), 2.75 (dd, 1H, J = 17.2, 8.4 Hz), 3.12-3.23 (m, 1H), 3.41 (s, 3H), 3.49-3.78 (m, 5H), 4.10-4.22 (m, 2H), 4.53 (d, 1H, J = 12.0 Hz), 4.66 (d, 1H, J = 12.0 Hz), 6.10 (s, 1H), 6.91-7.31 (m, 8H), 9.08 (s, 1H). | 565 | 563 | 2,2,2-trifluoro methyl-1-methyl-ethoxymethyl group: R-form Lactam ring: S-form |
| 488 | 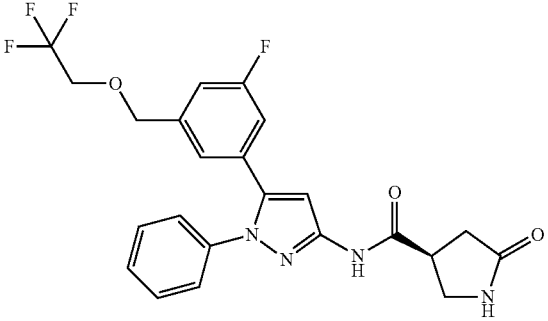 [SMILES: O=C1C[C@H](C(=O)Nc2cc(-c3cc(F)cc(COCC(F)(F)F)c3)n(-c3ccccc3)n2)CN1] | 1H-NMR (DMSO-D6) δ: 2.39 (d, 2H, J = 8.4 Hz), 3.32-3.52 (m, 3H), 3.99 (q, 2H, J = 9.2 Hz), 4.62 (s, 2H), 6.97-6.99 (m, 2H), 7.09 (s, 1H), 7.17 (d, 1H, J = 9.6 Hz), 7.25-7.27 (m, 2H), 7.35-7.44 (m, 3H), 7.64 (s, 1H), 10.89 (s, 1H). | 477 | 475 | S-form |

TABLE 2-continued

| Example No. | Molecular Structure | NMR (400 MHz) | MS (M + H) | MS (M − H) | Comments |
|---|---|---|---|---|---|
| 489 | 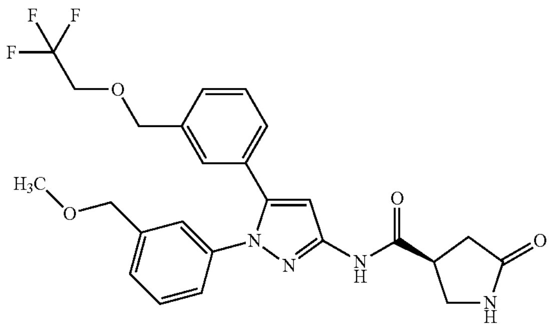 [SMILES: COCc1cccc(-n2nc(NC(=O)[C@@H]3CNC(=O)C3)cc2-c2cccc(COCC(F)(F)F)c2)c1] | 1H-NMR (DMSO-D6) δ: 2.39 (d, 2H, J = 8.4 Hz), 3.18 (s, 1H), 3.32-3.52 (m, 3H), 3.98 (q, 2H, J = 9.6 Hz), 4.37 (s, 2H), 4.61 (s, 2H), 6.92 (s, 1H), 7.10 (d, 1H, J = 8.4 Hz), 7.17 (d, 1H, J = 7.2 Hz), 7.23-7.26 (m, 3H), 7.32-7.39 (m, 3H), 7.63 (s, 1H), 10.87 (s, 1H). | 503 | 501 | S-form |
| 490 | 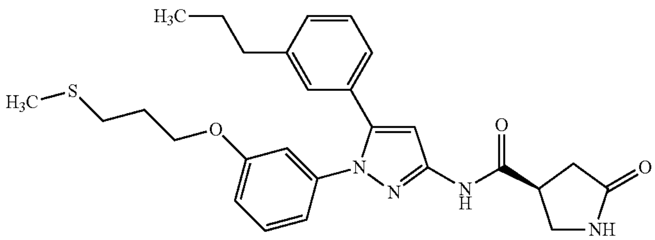 [SMILES: CCCc1cccc(-c2cc(NC(=O)[C@@H]3CNC(=O)C3)nn2-c2cccc(OCCCSC)c2)c1] | 1H-NMR (DMSO-D6) δ: 0.78 (t, 3H, J = 7.3 Hz), 1.42-1.51 (m, 2H), 1.84-1.92 (m, 2H), 2.04 (s, 3H), 2.36-2.41 (m, 2H), 2.46-2.56 (m, 4H), 3.31-3.53 (m, 3H), 3.92 (t, 2H, J = 6.2 Hz), 6.75-6.78 (m, 2H), 6.87-6.92 (m, 2H), 7.03 (s, 1H), 7.07-7.31 (m, 4H), 7.63 (s, 1H), 10.85 (s, 1H). | 493 | 491 | S-form |
| 491 | 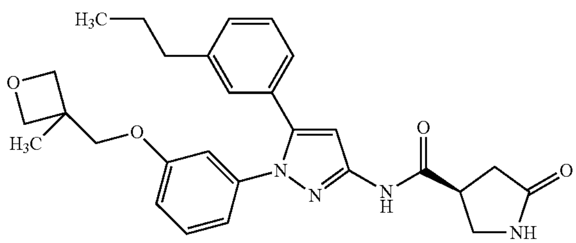 [SMILES: CCCc1cccc(-c2cc(NC(=O)[C@@H]3CNC(=O)C3)nn2-c2cccc(OCC3(C)COC3)c2)c1] | 1H-NMR (DMSO-D6) δ: 0.78 (t, 3H, J = 7.3 Hz), 1.30 (s, 3H), 1.40-1.51 (m, 2H), 2.37-2.42 (m, 2H), 2.45-2.55 (m, 2H), 3.31-3.53 (m, 3H), 3.91 (s, 2H), 4.27 (d, 2H, J = 5.8 Hz), 4.41 (d, 2H, J = 5.8 Hz), 6.76-6.96 (m, 4H), 7.03-7.05 (m, 1H), 7.09-7.13 (m, 1H), 7.17-7.21 (m, 1H), 7.25-7.32 (m, 2H), 7.63 (s, 1H), 10.85 (s, 1H). | 489 | 487 | S-form |
| 492 | 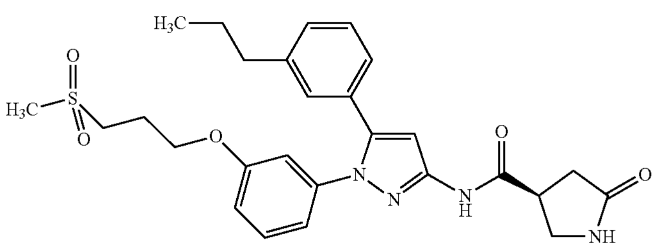 [SMILES: CCCc1cccc(-c2cc(NC(=O)[C@@H]3CNC(=O)C3)nn2-c2cccc(OCCCS(C)(=O)=O)c2)c1] | 1H-NMR (DMSO-D6) δ: 0.78 (t, 3H, J = 7.3 Hz), 1.42-1.51 (m, 2H), 2.04-2.13 (m, 2H), 2.36-2.42 (m, 2H), 2.44-2.54 (m, 2H), 3.00 (s, 3H), 3.18-3.24 (m, 2H), 3.30-3.53 (m, 3H), 3.99 (t, 2H, J = 6.2 Hz), 6.71-6.76 (m, 1H), 6.82-6.93 (m, 3H), 7.03 (s, 1H), 7.07-7.10 (m, 1H), 7.16-7.20 (m, 1H), 7.23-7.31 (m, 2H), 7.63 (s, 1H), 10.86 (s, 1H). | 525 | 523 | S-form |

TABLE 2-continued

| Example No. | Molecular Structure | NMR (400 MHz) | MS (M + H) | MS (M − H) | Comments |
|---|---|---|---|---|---|
| 493 | 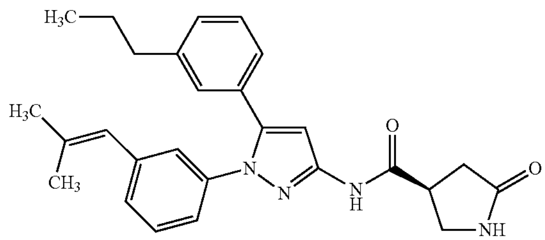 [SMILES: CCCc1cccc(-c2cc(NC(=O)[C@@H]3CNC(=O)C3)nn2-c2cccc(C=C(C)C)c2)c1] | 1H-NMR (DMSO-D6) δ: 0.77 (t, 3H, J = 7.3 Hz), 1.38-1.48 (m, 2H), 1.53 (s, 3H), 1.81 (s, 3H), 2.36-2.41 (m, 2H), 2.43-2.48 (m, 2H), 3.31-3.53 (m, 3H), 6.17 (s, 1H), 6.88 (s, 1H), 6.97-7.03 (m, 2H), 7.07-7.18 (m, 4H), 7.27 (t, 1H, J = 7.8 Hz), 7.36 (t, 1H, J = 7.8 Hz), 7.63 (s, 1H), 10.83 (s, 1H). | 443 | 441 | S-form |
| 494 | 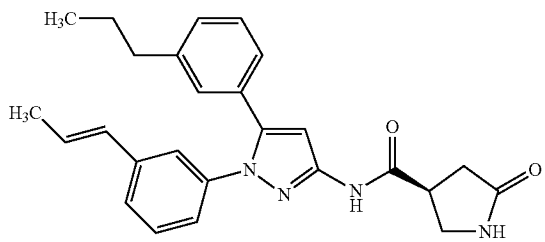 [SMILES: C/C=C/c1cccc(-n2nc(NC(=O)[C@@H]3CNC(=O)C3)cc2-c2cccc(CCC)c2)c1] | 1H-NMR (DMSO-D6) δ: 0.76 (t, 3H, J = 7.3 Hz), 1.39-1.49 (m, 2H), 1.80 (dd, 3H, J = 6.5, 1.2 Hz), 2.37-2.41 (m, 2H), 2.44-2.50 (m, 2H), 3.32-3.53 (m, 3H), 6.12-6.21 (m, 1H), 6.32-6.38 (m, 1H), 6.89 (s, 1H), 7.00-7.10 (m, 3H), 7.16-7.35 (m, 5H), 7.63 (s, 1H), 10.84 (s, 1H). | 429 | 427 | S-form |
| 495 | 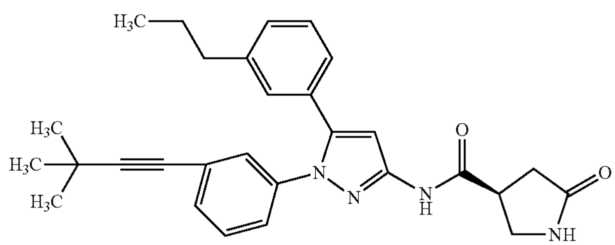 [SMILES: CCCc1cccc(-c2cc(NC(=O)[C@@H]3CNC(=O)C3)nn2-c2cccc(C#CC(C)(C)C)c2)c1] | 1H-NMR (DMSO-D6) δ: 0.79 (t, 3H, J = 7.3 Hz), 1.25 (s, 9H), 1.42-1.52 (m, 2H), 2.37-2.41 (m, 2H), 2.45-2.51 (m, 2H), 3.31-3.53 (m, 3H), 6.89 (s, 1H), 7.01-7.04 (m, 1H), 7.09-7.14 (m, 2H), 7.18-7.22 (m, 2H), 7.26-7.35 (m, 3H), 7.63 (s, 1H), 10.84 (s, 1H). | 469 | 467 | S-form |
| 496 | 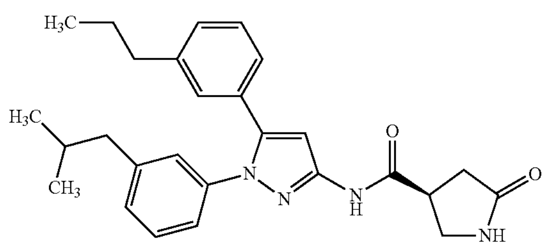 | 1H-NMR (DMSO-D6) δ: 0.72-0.81 (m, 9H), 1.39-1.50 (m, 2H), 1.60-1.71 (m, 1H), 2.35-2.41 (m, 4H), 2.45 (t, 2H, J = 7.4 Hz), 3.31-3.53 (m, 3H), 6.88 (s, 1H), 6.95-7.00 (m, 2H), 7.03-7.18 (m, 4H), 7.22-7.32 (m, 2H), 7.63 (s, 1H), 10.84 (s, 1H). | 445 | 443 | S-form |
| 497 | 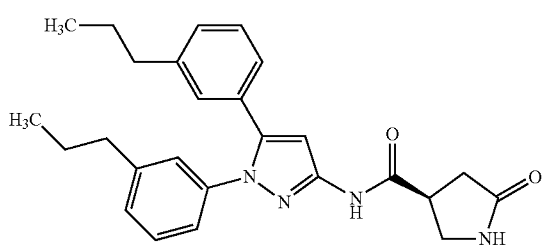 [SMILES: CCCc1cccc(-c2cc(NC(=O)[C@@H]3CNC(=O)C3)nn2-c2cccc(CCC)c2)c1] | 1H-NMR (DMSO-D6) δ: 0.78 (t, 6H, J = 7.2 Hz), 1.39-1.50 (m, 4H), 2.37-2.41 (m, 2H), 2.43-2.51 (m, 4H), 3.31-3.53 (m, 3H), 6.88 (s, 1H), 6.98-7.08 (m, 4H), 7.13-7.18 (m, 2H), 7.23-7.31 (m, 2H), 7.63 (s, 1H), 10.84 (s, 1H). | 431 | 429 | S-form |

TABLE 2-continued

| Example No. | Molecular Structure | NMR (400 MHz) | MS (M + H) | MS (M − H) | Comments |
|---|---|---|---|---|---|
| 498 | 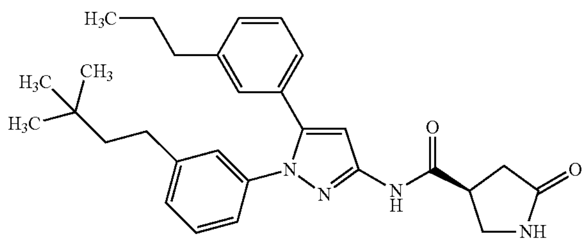 [SMILES: CCCc1cccc(-c2cc(NC(=O)[C@@H]3CNC(=O)C3)nn2-c2cccc(CCC(C)(C)C)c2)c1] | 1H-NMR (DMSO-D6) δ: 0.79 (t, 3H, J = 7.3 Hz), 0.87 (s, 9H), 1.21-1.28 (m, 2H), 1.40-1.51 (m, 2H), 2.36-2.50 (m, 6H), 3.31-3.53 (m, 3H), 6.88 (s, 1H), 6.95-7.10 (m, 4H), 7.12-7.20 (m, 2H), 7.25-7.31 (m, 2H), 7.63 (s, 1H), 10.84 (s, 1H). | 473 | 471 | S-form |
| 499 | 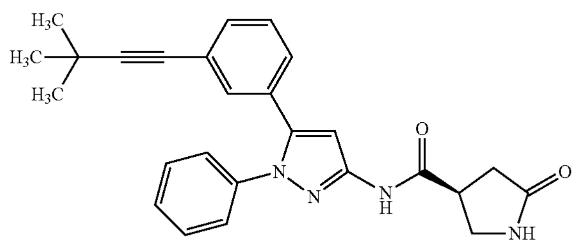 [SMILES: CC(C)(C)C#Cc1cccc(-c2cc(NC(=O)[C@@H]3CNC(=O)C3)nn2-c2ccccc2)c1] | 1H-NMR (DMSO-D6) : 1.26 (s, 9H), 2.37-2.41 (m, 2H), 3.31-3.52 (m, 3H), 6.92 (s, 1H), 7.06-7.10 (m, 1H), 7.22-7.44 (m, 8H), 7.63 (s, 1H), 10.86 (s, 1H). | 427 | 425 | S-form |
| 500 | 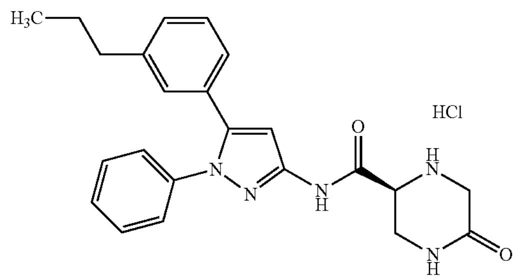 [SMILES: CCCc1cccc(-c2cc(NC(=O)[C@@H]3CNC(=O)CN3)nn2-c2ccccc2)c1 ; Cl] | 1H-NMR (DMSO-D6) δ: 0.77 (t, 3H, J = 7.4 Hz), 1.44 (sext, 2H, J = 7.4 Hz), 2.46 (t, 2H, J = 7.4 Hz), 3.61-3.91 (m, 4H), 4.41-4.51 (m, 1H), 6.89 (s, 1H), 6.99-7.02 (m, 1H), 7.07-7.12 (m, 1H), 7.16-7.21 (m, 1H), 7.21-7.26 (m, 2H), 7.26-7.31 (m, 1H), 7.34-7.45 (m, 3H), 8.45-8.50 (m, 1H), 9.85 (br s, 2H), 11.54 (s, 1H). | 440 | 438 | S-form |
| 501 | 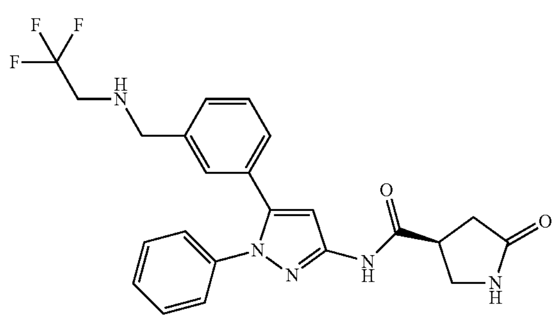 [SMILES: O=C1C[C@H](C(=O)Nc2cc(-c3cccc(CNCC(F)(F)F)c3)n(-c3ccccc3)n2)CN1] | 1H-NMR (DMSO-D6) δ: 0.92-1.02 (m, 2H), 2.33-2.45 (m, 2H), 2.85-2.95 (m, 1H), 2.98-3.10 (m, 2H), 3.30-3.53 (m, 3H), 3.72 (d, 2H, J = 5.6 Hz), 6.92 (s, 1H), 7.05-7.10 (m, 1H), 7.20-7.43 (m, 8H), 7.63 (s, 1H), 10.85 (s, 1H). | 458 | 456 | S-form |
| 502 | 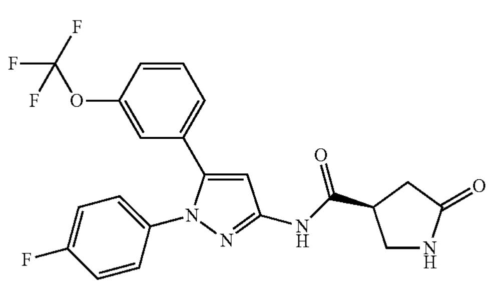 | 1H-NMR (DMSO-D6) δ: 2.38-2.40 (m, 2H), 3.32-3.35 (m, 1H), 3.40-3.46 (m, 1H), 3.48-3.52 (m, 1H), 7.00 (s, 1H), 7.10 (s, 1H), 7.25-7.39 (m, 6H), 7.53 (t, 1H, J = 8.0 Hz), 7.63 (s, 1H), 10.88 (s, 1H). | 449 | 447 | S-form |

TABLE 2-continued

| Example No. | Molecular Structure | NMR (400 MHz) | MS (M + H) | MS (M − H) | Comments |
|---|---|---|---|---|---|
| 503 | 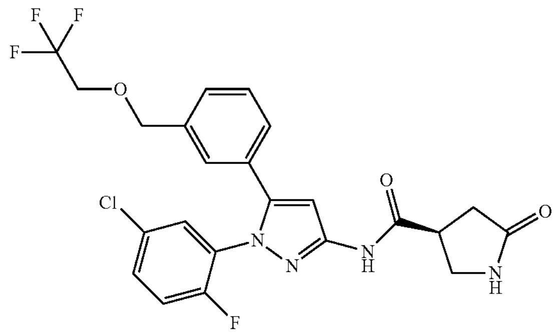 [SMILES: O=C1C[C@H](C(=O)Nc2cc(-c3cccc(COCC(F)(F)F)c3)n(-c3cc(Cl)ccc3F)n2)CN1] | 1H-NMR (DMSO-D6) δ: 2.28-2.35 (m, 2H), 3.20-3.45 (m, 3H), 3.90-4.00 (m, 2H), 4.58-4.63 (m, 2H), 6.48 (d, 1H, J = 2.4 Hz), 7.12-7.15 (m, 2H), 7.28-7.38 (m, 2H), 7.55-7.60 (m, 3H), 7.82 (dd, 1H, J = 9.0 Hz, 5.0 Hz), 10.63 (s, 1H). | 511 | 509 | S-form |
| 504 | 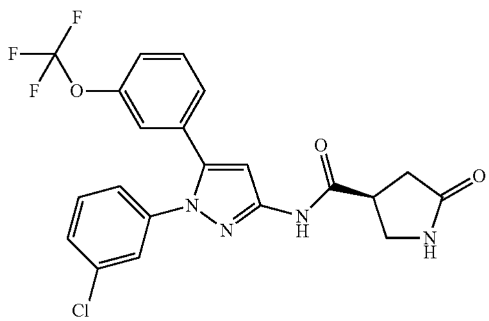 [SMILES: O=C1C[C@H](C(=O)Nc2cc(-c3cccc(OC(F)(F)F)c3)n(-c3cccc(Cl)c3)n2)CN1] | $^1$H-NMR (CDCl$_3$) δ: 2.62 (dd, 1H, J = 17.2, 9.6 Hz), 2.79 (dd, 1H, J = 17.2, 8.4 Hz), 3.35-3.45 (m, 1H), 3.58-3.74 (m, 2H), 6.37 (s, 1H), 6.99-7.11 (m, 3H), 7.19-7.42 (m, 6H), 8.90 (s, 1H). | 465 | 463 | S-form |
| 505 | 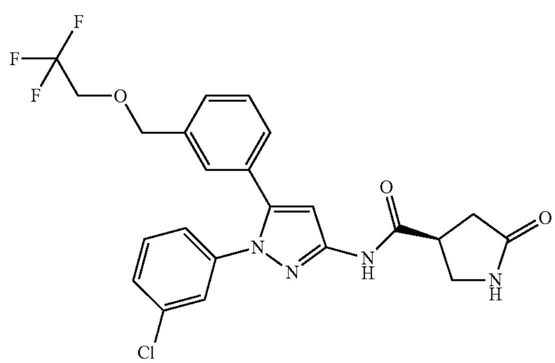 [SMILES: O=C1C[C@H](C(=O)Nc2cc(-c3cccc(COCC(F)(F)F)c3)n(-c3cccc(Cl)c3)n2)CN1] | $^1$H-NMR (CDCl$_3$) δ: 2.62 (dd, 1H, J = 17.2, 9.6 Hz), 2.79 (dd, 1H, J = 17.2, 8.4 Hz), 3.33-3.43 (m, 1H), 3.60-3.79 (m, 4H), 4.62 (s, 2H), 5.85 (s, 1H), 7.01-7.07 (m, 2H), 7.19-7.38 (m, 7H), 8.31 (s, 1H). | 493 | 491 | S-form |
| 506 | 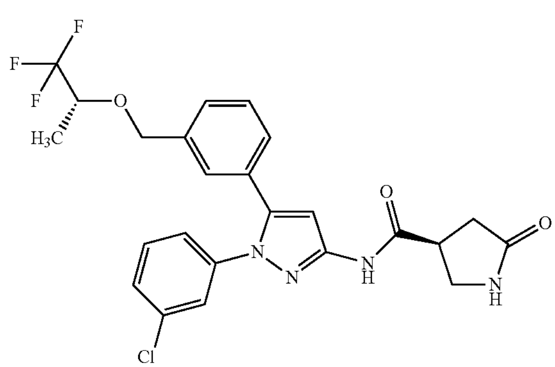 [SMILES: C[C@@H](OCc1cccc(-c2cc(NC(=O)[C@@H]3CNC(=O)C3)nn2-c2cccc(Cl)c2)c1)C(F)(F)F] | $^1$H-NMR (CDCl$_3$) δ: 1.29 (d, 3H, J = 6.4 Hz), 2.61 (dd, 1H, J = 17.2, 9.6 Hz), 2.79 (dd, 1H, J = 17.2, 8.4 Hz), 3.32-3.43 (m, 1H), 3.59-3.81 (m, 3H), 4.57 (d, 1H, J = 12.0 Hz), 4.69 (d, 1H, J = 12.0 Hz), 5.98 (s, 1H), 7.01-7.07 (m, 2H), 7.18-7.37 (m, 7H), 8.47 (s, 1H). | 507 | 505 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 507 | 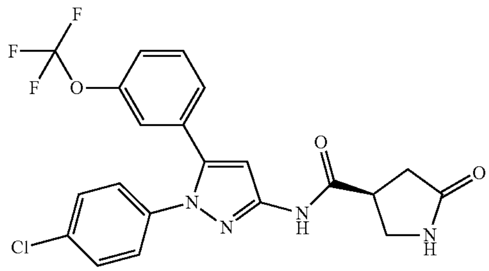 [SMILES: O=C1C[C@H](C(=O)Nc2cc(-c3cccc(OC(F)(F)F)c3)n(-c3ccc(Cl)cc3)n2)CN1] | ¹H-NMR (CDCl₃) δ: 2.61 (dd, 1H, J = 17.2, 9.6 Hz), 2.78 (dd, 1H, J = 17.2, 8.4 Hz), 3.32-3.42 (m, 1H), 3.56-3.74 (m, 2H), 6.26 (s, 1H), 7.05-7.10 (m, 2H), 7.13-7.23 (m, 4H), 7.31-7.47 (m, 3H), 8.76 (s, 1H). | 465 | 463 | S-form |
| 508 | 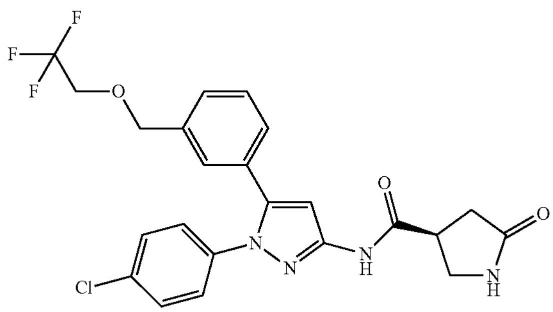 [SMILES: O=C1C[C@H](C(=O)Nc2cc(-c3cccc(COCC(F)(F)F)c3)n(-c3ccc(Cl)cc3)n2)CN1] | ¹H-NMR (CDCl₃) δ: 2.61 (dd, 1H, J = 17.2, 9.6 Hz), 2.78 (dd, 1H, J = 17.2, 8.4 Hz), 3.31-3.41 (m, 1H), 3.58-3.81 (m, 4H), 4.62 (s, 2H), 5.86 (s, 1H), 7.04 (s, 1H), 7.15-7.36 (m, 8H), 8.34 (s, 1H). | 493 | 491 | S-form |
| 509 | 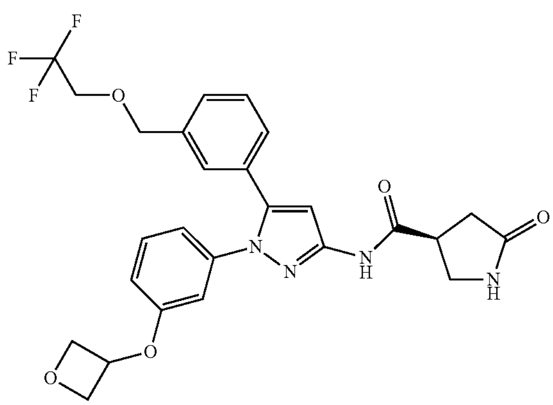 [SMILES: O=C1C[C@H](C(=O)Nc2cc(-c3cccc(COCC(F)(F)F)c3)n(-c3cccc(OC4COC4)c3)n2)CN1] | 1H-NMR (DMSO-D6) δ: 2.38-2.40 (m, 2H), 3.34-3.36 (m, 1H), 3.38-3.44 (m, 1H), 3.49-3.54 (m, 1H), 4.00 (q, 2H, J = 9.4 Hz), 4.38 (t, 2H, J = 5.8 Hz), 4.62 (s, 2H), 4.70 (t, 2H, J = 6.4 Hz), 5.12-5.14 (m, 1H), 6.50-6.53 (m, 1H), 6.79-6.81 (m, 1H), 6.88-6.92 (m, 2H), 7.16-7.19 (m, 1H), 7.25 (s, 1H), 7.30-7.41 (m, 3H), 7.63 (s, 1H), 10.87 (s, 1H). | 531 | 529 | S-form |
| 510 | 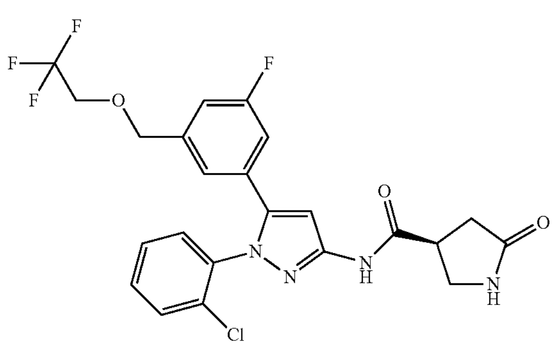 [SMILES: O=C1C[C@H](C(=O)Nc2cc(-c3cc(F)cc(COCC(F)(F)F)c3)n(-c3ccccc3Cl)n2)CN1] | 1H-NMR (DMSO-D6) : 2.39-2.41 (m, 2H), 3.35-3.36 (m, 1H), 3.40-3.44 (m, 1H), 3.48-3.52 (m, 1H), 3.99 (q, 2H, J = 9.3 Hz), 4.59 (s, 2H), 6.90 (d, 1H, J = 11.4 Hz), 7.06-7.08 (m, 2H), 7.13 (d, 1H, J = 11.4 Hz), 7.49-7.55 (m, 2H), 7.59-7.64 (m, 3H), 10.86 (s, 1H). | 511 | 509 | S-form |

TABLE 2-continued

| Example No. | Molecular Structure | NMR (400 MHz) | MS (M + H) | MS (M − H) | Comments |
|---|---|---|---|---|---|
| 511 | 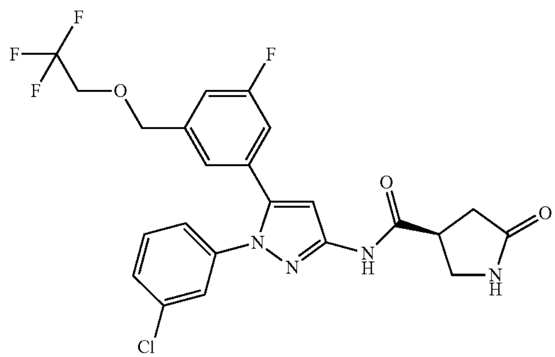 [SMILES: O=C1C[C@H](C(=O)Nc2cc(-c3cc(F)cc(COCC(F)(F)F)c3)n(-c3cccc(Cl)c3)n2)CN1] | 1H-NMR (DMSO-D6) δ: 2.38-2.40 (m, 2H), 3.32-3.35 (m, 1H), 3.39-3.46 (m, 1H), 3.49-3.53 (m, 1H), 4.01 (q, 2H, J = 9.2 Hz), 4.64 (s, 2H), 7.00 (s, 1H), 7.07-7.23 (m, 4H), 7.38-7.44 (m, 3H), 7.63 (s, 1H), 10.92 (s, 1H). | 511 | 509 | S-form |
| 512 | 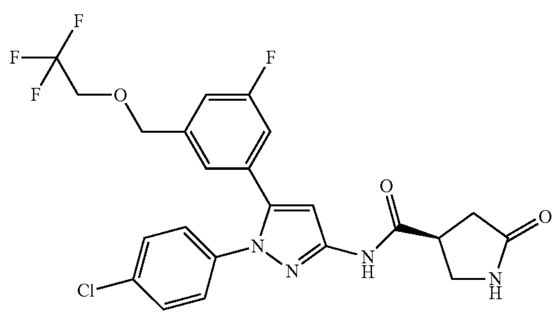 [SMILES: O=C1C[C@H](C(=O)Nc2cc(-c3cc(F)cc(COCC(F)(F)F)c3)n(-c3ccc(Cl)cc3)n2)CN1] | 1H-NMR (DMSO-D6) δ: 2.38-2.40 (m, 2H), 3.33-3.35 (m, 1H), 3.38-3.46 (m, 1H), 3.48-3.52 (m, 1H), 4.01 (q, 2H, J = 9.3 Hz), 4.63 (s, 2H), 6.99 (s, 1H), 7.07 (d, 1H, J = 8.8 Hz), 7.09 (s, 1H), 7.20 (d, 1H, J = 8.8 Hz), 7.26-7.29 (m, 2H), 7.47-7.49 (m, 2H), 7.63 (s, 1H), 10.92 (s, 1H). | 511 | 509 | S-form |
| 513 | 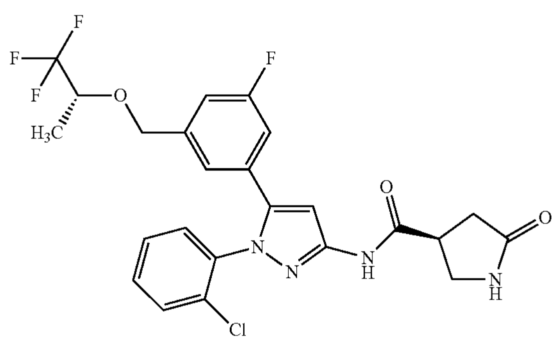 [SMILES: C[C@@H](OCc1cc(F)cc(-c2cc(NC(=O)[C@@H]3CNC(=O)C3)nn2-c2ccccc2Cl)c1)C(F)(F)F] | 1H-NMR (DMSO-D6) δ: 1.19 (d, 3H, J = 6.5 Hz), 2.39-2.41 (m, 2H), 3.35-3.37 (m, 1H), 3.39-3.45 (m, 1H), 3.48-3.52 (m, 1H), 4.08-4.15 (m, 1H), 4.59 (s, 2H), 6.92 (d, 1H, J = 9.1 Hz), 7.05-7.07 (m, 2H), 7.12 (d, 1H, J = 9.1 Hz), 7.47-7.56 (m, 2H), 7.59-7.65 (m, 3H), 10.86 (s, 1H). | 525 | 523 | 2,2,2-trifluoro methyl-1-methyl-ethoxymethyl group: R-form Lactam ring: S-form |
| 514 | 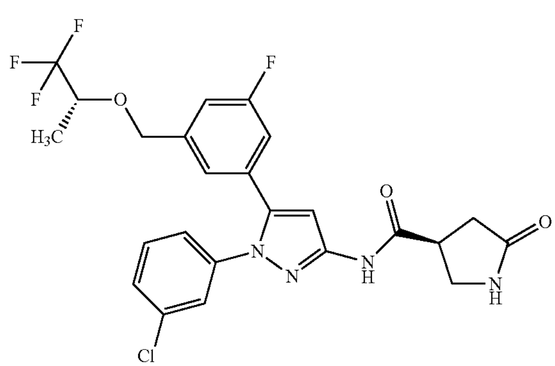 [SMILES: C[C@@H](OCc1cc(F)cc(-c2cc(NC(=O)[C@@H]3CNC(=O)C3)nn2-c2cccc(Cl)c2)c1)C(F)(F)F] | 1H-NMR (DMSO-D6) δ: 1.20 (d, 3H, J = 6.5 Hz), 2.38-2.40 (m, 2H), 3.33-3.35 (m, 1H), 3.41-3.44 (m, 1H), 3.48-3.52 (m, 1H), 4.10-4.16 (m, 1H), 4.64 (s, 2H), 6.99 (s, 1H), 7.07-7.10 (m, 2H), 7.14-7.22 (m, 2H), 7.38-7.43 (m, 3H), 7.63 (s, 1H), 10.92 (s, 1H). | 525 | 523 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 515 | 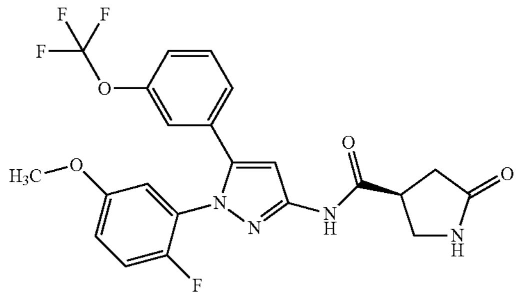 [SMILES: COc1ccc(F)c(-n2nc(NC(=O)[C@@H]3CNC(=O)C3)cc2-c2cccc(OC(F)(F)F)c2)c1] | 1H-NMR (DMSO-D6) δ: 2.39 (d, 2H, J = 8.4 Hz), 3.32-3.52 (m, 3H), 3.75 (s, 3H), 7.03-7.07 (m, 2H), 7.13 (s, 1H), 7.16-7.18 (m, 1H), 7.23 (t, 1H, J = 9.6 Hz), 7.35-7.37 (m, 2H), 7.52 (t, 1H, J = 8.0 Hz), 7.63 (s, 1H), 10.90 (s, 1H). | 479 | 477 | S-form |
| 516 | 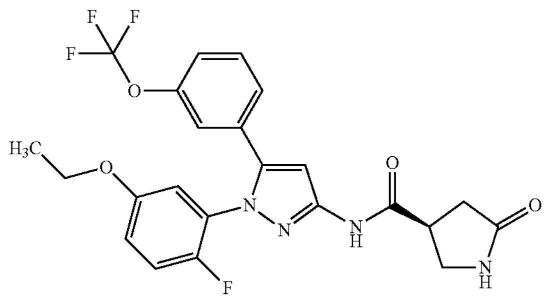 [SMILES: CCOc1ccc(F)c(-n2nc(NC(=O)[C@@H]3CNC(=O)C3)cc2-c2cccc(OC(F)(F)F)c2)c1] | 1H-NMR (DMSO-D6) δ: 1.28 (t, 3H, J = 6.8 Hz), 2.39 (d, 2H, J = 8.4 Hz), 3.32-3.52 (m, 3H), 4.00 (q, 2H, J = 6.8 Hz), 7.01-7.05 (m, 2H), 7.12-7.14 (m, 2H), 7.22 (t, 1H, J = 9.6 Hz), 7.35-7.37 (m, 2H), 7.52 (t, 1H, J = 8.0 Hz), 7.64 (s, 1H), 10.89 (s, 1H). | 493 | 491 | S-form |
| 517 | 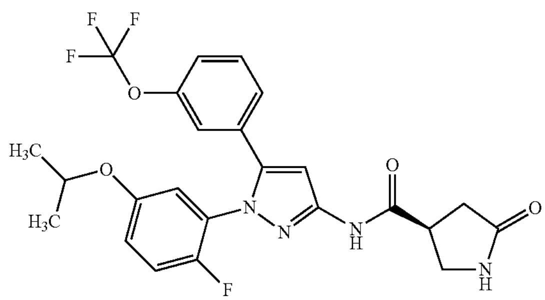 [SMILES: CC(C)Oc1ccc(F)c(-n2nc(NC(=O)[C@@H]3CNC(=O)C3)cc2-c2cccc(OC(F)(F)F)c2)c1] | 1H-NMR (DMSO-D6) δ: 1.19 (d, 6H, J = 6.0 Hz), 2.39 (d, 2H, J = 8.4 Hz), 3.32-3.52 (m, 3H), 4.55 (sep, 1H, 6.0 Hz), 7.01 (dt, 1H, J = 4.0, 8.8 Hz), 7.05 (s, 1H), 7.08-7.10 (m, 2H), 7.22 (t, 1H, J = 9.6 Hz), 7.34-7.39 (m, 2H), 7.52 (t, 1H, J = 8.0 Hz), 7.63 (s, 1H), 10.89 (s, 1H). | 507 | 505 | S-form |
| 518 | 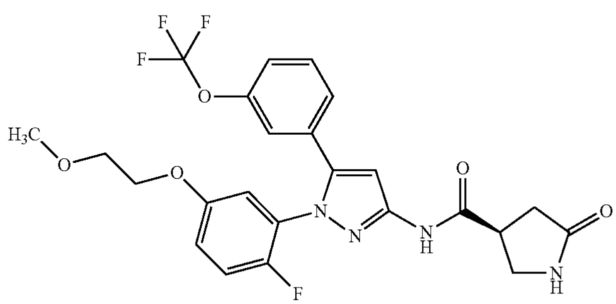 [SMILES: COCCOc1ccc(F)c(-n2nc(NC(=O)[C@@H]3CNC(=O)C3)cc2-c2cccc(OC(F)(F)F)c2)c1] | 1H-NMR (DMSO-D6) δ: 2.39 (d, 2H, J = 8.4 Hz), 3.28 (s, 3H), 3.32-3.52 (m, 3H), 3.60-3.63 (m, 2H), 4.06-4.09 (m, 2H), 7.04-7.08 (m, 2H), 7.13 (s, 1H), 7.16-7.18 (m, 1H), 7.23 (t, 1H, J = 9.6 Hz), 7.35-7.37 (m, 2H), 7.51 (t, 1H, J = 8.0 Hz), 7.63 (s, 1H), 10.89 (s, 1H). | 523 | 531 | S-form |
| 519 | 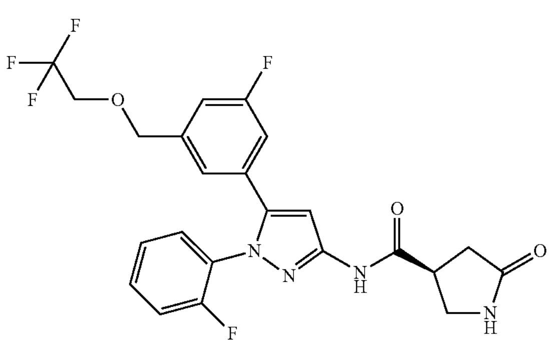 [SMILES: O=C1C[C@H](C(=O)Nc2cc(-c3cc(F)cc(COCC(F)(F)F)c3)n(-c3ccccc3F)n2)CN1] | ¹H-NMR (CDCl₃) δ: 2.60 (dd, 1H, J = 17.2, 9.6 Hz), 2.78 (dd, 1H, J = 17.2, 8.8 Hz), 3.30-3.40 (m, 1H), 3.59-3.76 (m, 4H), 4.56 (s, 2H), 5.78 (s, 1H), 6.88 (d, 1H, J = 9.2 Hz), 6.98-7.03 (m, 2H), 7.10-7.17 (m, 2H), 7.23 (t, 1H, J = 8.0 Hz), 7.34-7.44 (m, 2H), 8.29 (s, 1H). | 495 | 493 | S-form |

TABLE 2-continued

| Example No. | Molecular Structure | NMR (400 MHz) | MS (M + H) | MS (M − H) | Comments |
| --- | --- | --- | --- | --- | --- |
| 520 | 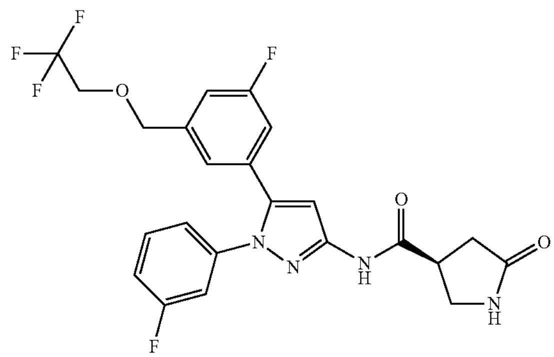 [SMILES: O=C1C[C@H](C(=O)Nc2cc(-c3cc(F)cc(COCC(F)(F)F)c3)n(-c3cccc(F)c3)n2)CN1] | ¹H-NMR (CDCl₃) δ: 2.62 (dd, 1H, J = 17.2, 9.6 Hz), 2.78 (dd, 1H, J = 17.2, 8.8 Hz), 3.29-3.43 (m, 1H), 3.60-3.82 (m, 4H), 4.60 (s, 2H), 5.92 (s, 1H), 6.88-7.09 (m, 7H), 7.27-7.34 (m, 1H), 8.37 (s, 1H). | 495 | 493 | S-form |
| 521 | 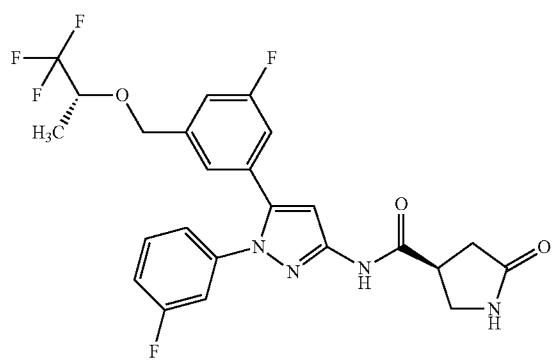 [SMILES: C[C@@H](OCc1cc(F)cc(-c2cc(NC(=O)[C@@H]3CNC(=O)C3)nn2-c2cccc(F)c2)c1)C(F)(F)F] | ¹H-NMR (CDCl₃) δ: 1.31 (d, 3H, J = 6.4 Hz), 2.62 (dd, 1H, J = 17.2, 9.6 Hz), 2.78 (dd, 1H, J = 17.2, 8.8 Hz), 3.33-3.43 (m, 1H), 3.61-3.82 (m, 3H), 4.56 (d, 1H, J = 12.8 Hz), 4.67 (d, 1H, J = 12.8 Hz), 5.81 (s, 1H), 6.86-7.10 (m, 7H), 7.27-7.34 (m, 1H), 8.26 (s, 1H). | 509 | 507 | 2,2,2-trifluoro methyl-1-methyl-ethoxymethyl group: R-form Lactam ring: S-form |
| 522 | 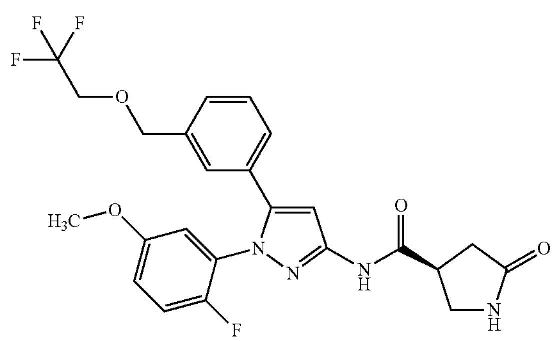 [SMILES: COc1ccc(F)c(-n2nc(NC(=O)[C@@H]3CNC(=O)C3)cc2-c2cccc(COCC(F)(F)F)c2)c1] | 1H-NMR (DMSO-D6) δ: 2.39 (d, 2H, J = 8.4 Hz), 3.32-3.52 (m, 3H), 3.74 (s, 3H), 3.98 (q, 2H, J = 9.2 Hz), 4.61 (s, 1H), 6.98 (s, 1H), 7.02 (dt, 1H, J = 4.0, 8.8 Hz), 7.10-7.13 (m, 1H), 7.16-7.23 (m, 2H), 7.27 (s, 1H), 7.30-7.37 (m, 2H), 7.64 (s, 1H), 10.87 (s, 1H). | 507 | 505 | S-form |
| 523 | 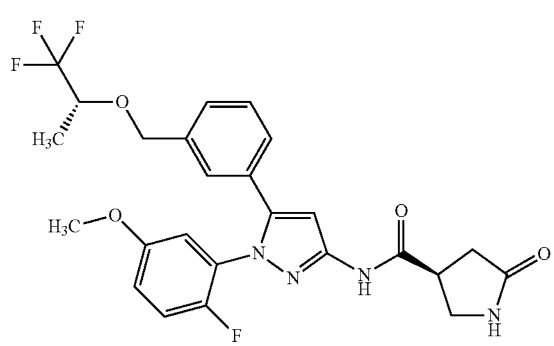 [SMILES: COc1ccc(F)c(-n2nc(NC(=O)[C@@H]3CNC(=O)C3)cc2-c2cccc(CO[C@H](C)C(F)(F)F)c2)c1] | 1H-NMR (DMSO-D6) δ: 1.19 (d, 3H, J = 6.8 Hz), 2.39 (d, 2H, J = 8.4 Hz), 3.32-3.52 (m, 3H), 3.74 (s, 3H), 4.02-4.12 (m, 1H), 4.61 (s, 2H), 6.97 (s, 1H), 7.00-7.04 (m, 1H), 7.11-7.13 (m, 1H), 7.17-7.23 (m, 2H), 7.27 (s, 1H), 7.29-7.36 (m, 2H), 7.63 (s, 1H), 10.86 (s, 1H). | 521 | 519 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 524 | 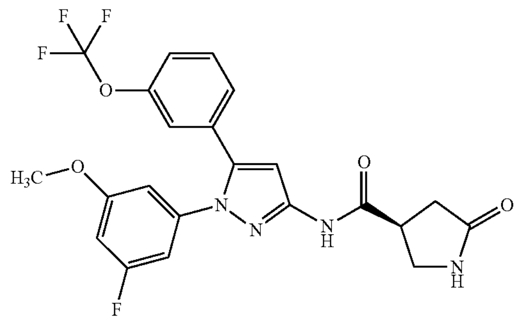 [SMILES: COc1cc(F)cc(-n2nc(NC(=O)[C@@H]3CNC(=O)C3)cc2-c2cccc(OC(F)(F)F)c2)c1] | 1H-NMR (DMSO-D6) δ: 2.35-2.45 (m, 2H), 3.28-3.53 (m, 3H), 3.68 (s, 3H), 6.62-6.68 (m, 2H), 6.84 (dt, 1H, J = 11.2 Hz, 2.4 Hz), 7.00 (s, 1H), 7.17 (s, 1H), 7.39-7.43 (m, 2H), 7.55-7.60 (m, 1H), 7.64 (s, 1H), 10.94 (s, 1H). | 479 | 477 | S-form |
| 525 | 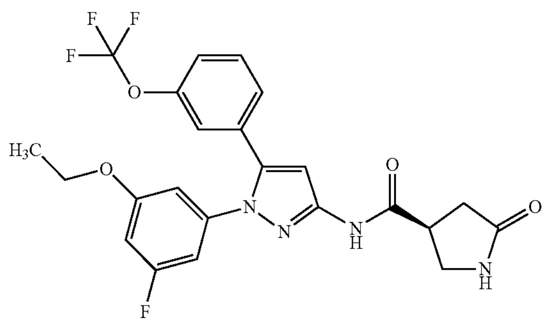 [SMILES: CCOc1cc(F)cc(-n2nc(NC(=O)[C@@H]3CNC(=O)C3)cc2-c2cccc(OC(F)(F)F)c2)c1] | 1H-NMR (DMSO-D6) δ: 1.22 (t, 3H, J = 7.0 Hz), 2.35-2.45 (m, 2H), 3.28-3.53 (m, 3H), 3.92 (q, 2H, J = 7.0 Hz), 6.59 (s, 1H), 6.67 (dt, 1H, J = 9.6 Hz, 2.0 Hz), 6.84 (dt, 1H, J = 10.8 Hz, 2.0 Hz), 7.00 (s, 1H), 7.17 (s, 1H), 7.39-7.43 (m, 2H), 7.55-7.59 (m, 1H), 7.64 (s, 1H), 10.93 (s, 1H). | 493 | 491 | S-form |
| 526 | 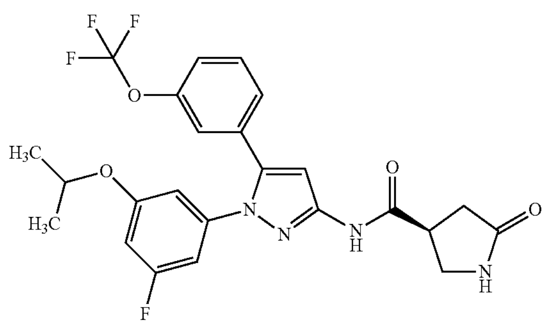 [SMILES: CC(C)Oc1cc(F)cc(-n2nc(NC(=O)[C@@H]3CNC(=O)C3)cc2-c2cccc(OC(F)(F)F)c2)c1] | 1H-NMR (DMSO-D6) δ: 1.12 (d, 6H, J = 6.0 Hz), 2.35-2.58 (m, 2H), 3.28-3.53 (m, 3H), 4.46 (sep, 1H, J = 6.0 Hz), 6.53 (s, 1H), 6.71 (dt, 1H, J = 9.2 Hz, 2.2 Hz), 6.81 (dt, 1H, J = 10.8 Hz, 2.2 Hz), 6.99 (s, 1H), 7.16 (s, 1H), 7.38-7.43 (m, 2H), 7.54-7.59 (m, 1H), 7.63 (s, 1H), 10.92 (s, 1H). | 507 | 505 | S-form |
| 527 | 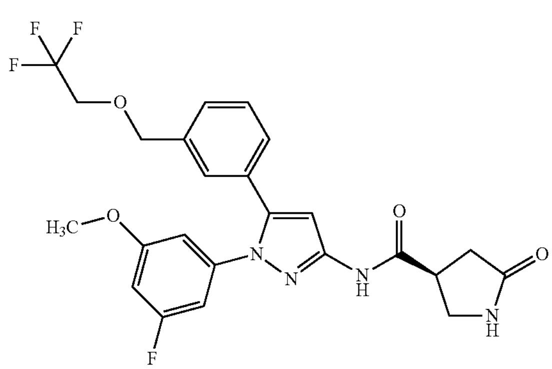 [SMILES: COc1cc(F)cc(-n2nc(NC(=O)[C@@H]3CNC(=O)C3)cc2-c2cccc(COCC(F)(F)F)c2)c1] | 1H-NMR (DMSO-D6) δ: 2.35-2.60 (m, 2H), 3.28-3.53 (m, 3H), 3.66 (s, 3H), 4.00 (q, 2H, J = 9.4 Hz), 4.64 (s, 1H), 6.62-6.65 (m, 2H), 6.81 (dt, 1H, J = 11.2 Hz, 2.4 Hz), 6.93 (s, 1H), 7.22-7.26 (m, 1H), 7.29 (s, 1H), 7.36-7.45 (m, 2H), 7.63 (s, 1H), 10.92 (s, 1H). | 507 | 505 | S-form |

TABLE 2-continued

| Example No. | Molecular Structure | NMR (400 MHz) | MS (M + H) | MS (M − H) | Comments |
|---|---|---|---|---|---|
| 528 | 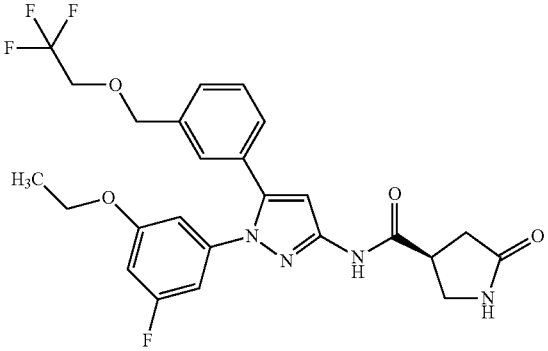 [SMILES: CCOc1cc(F)cc(-n2nc(NC(=O)[C@@H]3CNC(=O)C3)cc2-c2cccc(COCC(F)(F)F)c2)c1] | 1H-NMR (DMSO-D6) δ: 1.22 (t, 3H, J = 7.0 Hz), 2.35-2.63 (m, 2H), 3.28-3.53 (m, 3H), 3.90 (q, 2H, J = 7.0 Hz), 4.00 (q, 2H, J = 9.2 Hz), 4.64 (s, 2H), 6.58 (s, 1H), 6.64 (dt, 1H, J = 9.6 Hz, 2.0 Hz), 6.79 (dt, 1H, J = 11.2 Hz, 2.0 Hz), 6.92 (s, 1H), 7.22-7.25 (m, 1H), 7.29 (s, 1H), 7.36-7.45 (m, 2H), 7.63 (s, 1H), 10.91 (s, 1H). | 521 | 519 | S-form |
| 529 | 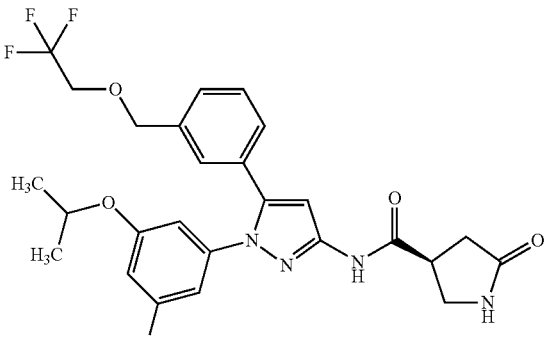 | 1H-NMR (DMSO-D6) δ: 1.12 (d, 6H, J = 6.0 Hz), 2.35-2.58 (m, 2H), 3.28-3.53 (m, 3H), 4.00 (q, 2H, J = 9.2 Hz), 4.44 (sep, 1H, J = 6.0 Hz), 4.64 (s, 2H), 6.52 (s, 1H), 6.67 (dt, 1H, J = 10.0 Hz, 2.0 Hz), 6.76 (dt, 1H, J = 11.0 Hz, 2.0 Hz), 6.92 (s, 1H), 7.24 (d, 1H, J = 7.6 Hz), 7.29 (s, 1H), 7.35-7.45 (m, 2H), 7.63 (s, 1H), 10.89 (s, 1H). | 535 | 533 | S-form |
| 530 | 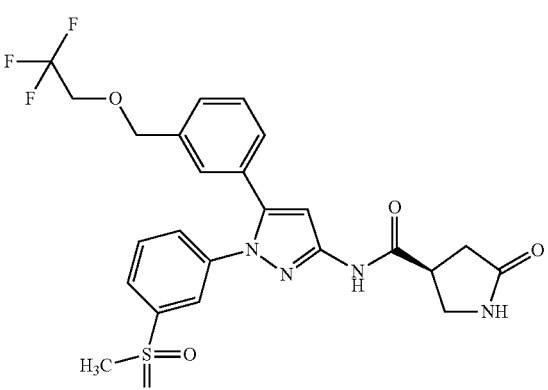 | 1H-NMR (DMSO-D6) δ: 2.39-2.41 (m, 3H), 3.15 (s, 3H), 3.32-3.35 (m, 1H), 3.37-3.45 (m, 1H), 3.49-3.53 (m, 1H), 4.02 (q, 2H, J = 9.4 Hz), 4.64 (s, 2H), 6.98 (s, 1H), 7.22-7.24 (m, 1H), 7.31 (s, 1H), 7.38-7.43 (m, 2H), 7.48-7.51 (m, 1H), 7.63 (t, 2H, J = 7.9 Hz), 7.81-7.86 (m, 2H), 10.97 (s, 1H). | 537 | 535 | S-form |
| 531 | 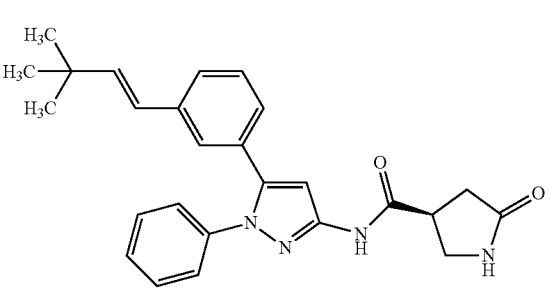 [SMILES: CC(C)(C)/C=C/c1cccc(-c2cc(NC(=O)[C@@H]3CNC(=O)C3)nn2-c2ccccc2)c1] | 1H-NMR (DMSO-D6) δ: 1.06 (s, 9H), 2.35-2.42 (m, 2H), 3.32-3.53 (m, 3H), 6.18 (d, 1H, J = 16.4 Hz), 6.27 (d, 1H, J = 16.4), 6.94 (s, 1H), 6.96-7.01 (m, 1H), 7.22-7.28 (m, 3H), 7.31-7.38 (m, 3H), 7.39-7.45 (m, 2H), 7.63 (s, 1H), 10.85 (s, 1H). | 429 | 427 | S-form |

TABLE 2-continued

| Example No. | Molecular Structure | NMR (400 MHz) | MS (M + H) | MS (M − H) | Comments |
|---|---|---|---|---|---|
| 532 | 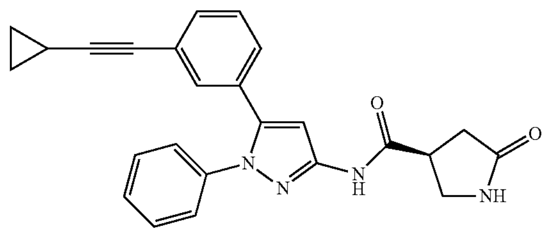 [SMILES: O=C1C[C@H](C(=O)Nc2cc(-c3cccc(C#CC4CC4)c3)n(-c3ccccc3)n2)CN1] | 1H-NMR (DMSO-D6) δ: 0.67-0.73 (m, 2H), 0.83-0.90 (m, 2H), 1.45-1.56 (m, 1H), 2.35-2.40 (m, 2H), 3.32-3.55 (m, 3H), 6.91 (s, 1H), 7.09-7.14 (m, 1H), 7.19-7.26 (m, 3H), 7.27-7.46 (m, 5H), 7.63 (s, 1H), 10.86 (s, 1H). | 411 | 409 | S-form |
| 533 | 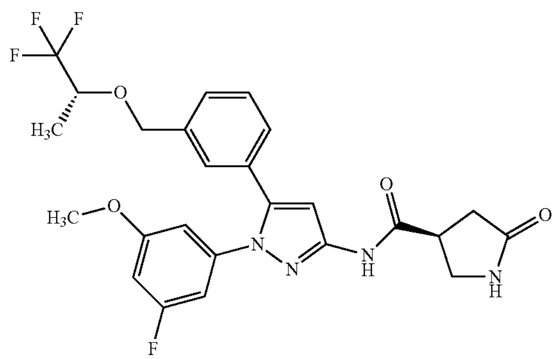 [SMILES: COc1cc(F)cc(-n2nc(NC(=O)[C@@H]3CNC(=O)C3)cc2-c2cccc(CO[C@H](C)C(F)(F)F)c2)c1] | 1H-NMR (DMSO-D6) : 1.20 (d, 3H, J = 6.4 Hz), 2.35-2.60 (m, 2H), 3.28-3.53 (m, 3H), 3.66 (s, 3H), 4.07-4.15 (m, 1H), 4.61-4.68 (m, 2H), 6.60-6.65 (m, 2H), 6.82 (dt, 1H, J = 10.8 Hz, 2.4 Hz), 6.92 (s, 1H), 7.24 (dt, 1H, J = 7.2 Hz, 1.6 Hz), 7.29 (s, 1H), 7.36-7.45 (m, 2H), 7.63 (s, 1H), 10.91 (s, 1H). | 521 | 519 | 2,2,2-trifluoro methyl-1-methyl-ethoxymethyl group: R-form Lactam ring: S-form |
| 534 | 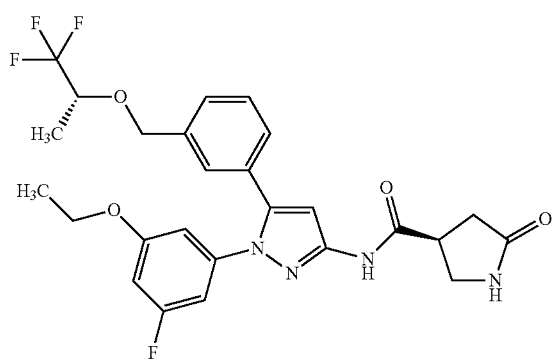 [SMILES: CCOc1cc(F)cc(-n2nc(NC(=O)[C@@H]3CNC(=O)C3)cc2-c2cccc(CO[C@H](C)C(F)(F)F)c2)c1] | 1H-NMR (DMSO-D6) δ: 1.19-1.24 (m, 6H), 2.35-2.58 (m, 2H), 3.28-3.53 (m, 3H), 3.90 (q, 2H, J = 7.0 Hz), 4.07-4.15 (m, 1H), 4.61-4.68 (m, 2H), 6.58 (s, 1H), 6.64 (dt, 1H, J = 9.2 Hz, 2.2 Hz), 6.79 (dt, 1H, J = 10.8 Hz, 2.2 Hz), 6.92 (s, 1H), 7.23 (d, 1H, J = 7.6 Hz), 7.29 (s, 1H), 7.36-7.45 (m, 2H), 7.63 (s, 1H), 10.90 (s, 1H). | 535 | 533 | 2,2,2-trifluoro methyl-1-methyl-ethoxymethyl group: R-form Lactam ring: S-form |
| 535 | 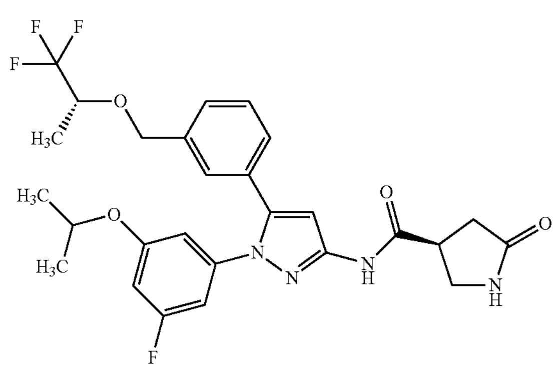 [SMILES: CC(C)Oc1cc(F)cc(-n2nc(NC(=O)[C@@H]3CNC(=O)C3)cc2-c2cccc(CO[C@H](C)C(F)(F)F)c2)c1] | 1H-NMR (DMSO-D6) δ: 1.12 (d, 6H, J = 6.0 Hz), 1.21(d, 3H, J = 6.4 Hz), 2.35-2.58 (m, 2H), 3.28-3.53 (m, 3H), 4.08-4.16 (m, 1H), 4.44 (sep, 1H, J = 6.0 Hz), 4.61-4.68 (m, 2H), 6.52 (s, 1H), 6.66 (dt, 1H, J = 9.4 Hz, 2.0 Hz), 6.77 (dt, 1H, J = 11.0 Hz, 2.0 Hz), 6.91 (s, 1H), 7.24 (d, 1H, J = 7.6 Hz), 7.28 (s, 1H), 7.35-7.45 (m, 2H), 7.63 (s, 1H), 10.89 (s, 1H). | 549 | 547 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 536 | 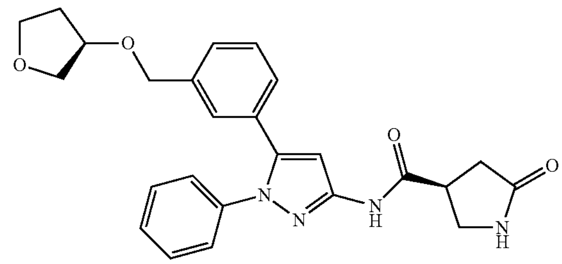 [SMILES: O=C1C[C@H](C(=O)Nc2cc(-c3cccc(CO[C@@H]4CCOC4)c3)n(-c3ccccc3)n2)CN1] | 1H-NMR (DMSO-D6) δ: 1.81-1.93 (m, 2H), 2.39 (d, 2H, J = 8.4 Hz), 3.32-3.52 (m, 3H), 3.58-3.73 (m, 4H), 4.05-4.09 (m, 1H), 4.41 (s, 2H), 6.91 (s, 1H), 7.14 (d, 1H, J = 7.2 Hz), 7.20-7.25 (m, 3H), 7.29-7.42 (m, 5H), 7.63 (s, 1H), 10.86 (s, 1H). | 447 | 445 | Tetrahydrofuran ring: R-form Lactam ring: S-form |
| 537 | 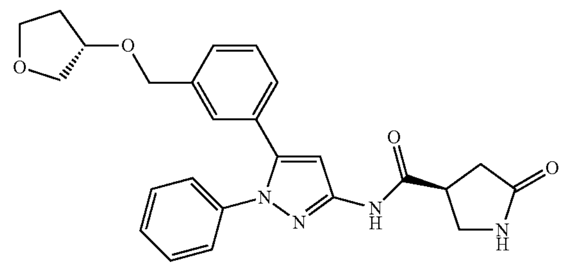 [SMILES: O=C1C[C@H](C(=O)Nc2cc(-c3cccc(CO[C@H]4CCOC4)c3)n(-c3ccccc3)n2)CN1] | 1H-NMR (DMSO-D6) δ: 1.81-1.93 (m, 2H), 2.39 (d, 2H, J = 8.4 Hz), 3.32-3.52 (m, 3H), 3.58-3.73 (m, 4H), 4.05-4.09 (m, 1H), 4.41 (s, 2H), 6.91 (s, 1H), 7.14 (d, 1H, J = 7.2 Hz), 7.20-7.25 (m, 3H), 7.29-7.42 (m, 5H), 7.63 (s, 1H), 10.86 (s, 1H). | 447 | 445 | Tetrahydrofuran ring: S-form Lactam ring: S-form |
| 538 | 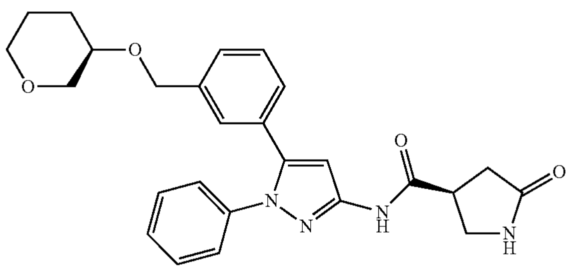 [SMILES: O=C1C[C@H](C(=O)Nc2cc(-c3cccc(CO[C@@H]4CCCOC4)c3)n(-c3ccccc3)n2)CN1] | 1H-NMR (DMSO-D6) δ: 1.44-1.53 (m, 1H), 1.72-1.90 (m, 3H), 2.39 (d, 2H, J = 8.4 Hz), 3.30-3.32 (m, 2H), 3.32-3.52 (m, 3H), 3.58-3.64 (m, 1H), 3.69-3.73 (m, 1H), 3.87-3.93 (m, 1H), 4.43 (s, 2H), 6.91 (s, 1H), 7.16 (d, 1H, J = 7.6 Hz), 7.22-7.24 (m, 3H), 7.28-7.41 (m, 5H), 7.63 (s, 1H), 10.86 (s, 1H). | 461 | 459 | Tetrahydropyran ring: R-form Lactam ring: S-form |
| 539 | 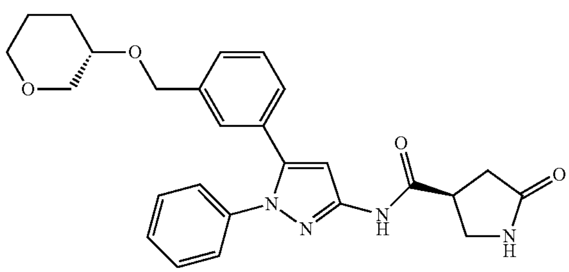 [SMILES: O=C1C[C@H](C(=O)Nc2cc(-c3cccc(CO[C@H]4CCCOC4)c3)n(-c3ccccc3)n2)CN1] | 1H-NMR (DMSO-D6) δ: 1.36-1.46 (m, 2H), 1.63-1.69 (m, 1H), 1.84-1.90 (m, 1H), 2.39 (d, 2H, J = 8.4 Hz), 3.16-3.21 (m, 1H), 3.25-3.31 (m, 1H), 3.32-3.52 (m, 4H), 3.56-3.61 (m, 1H), 3.66-3.70 (m, 1H), 4.46 (s, 2H), 6.91 (s, 1H), 7.12 (d, 1H, J = 7.6 Hz), 7.21-7.25 (m, 3H), 7.28-7.42 (m, 5H), 7.63 (s, 1H), 10.86 (s, 1H). | 461 | 459 | Tetrahydropyran ring: S-form Lactam ring: S-form |
| 540 | 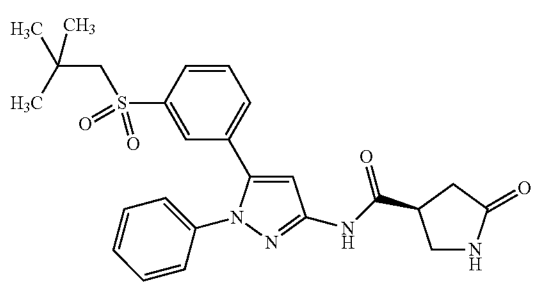 [SMILES: CC(C)(C)CS(=O)(=O)c1cccc(-c2cc(NC(=O)[C@@H]3CNC(=O)C3)nn2-c2ccccc2)c1] | $^1$H-NMR (CDCl$_3$) δ: 1.15 (s, 9H), 2.59 (dd, 1H, J = 16.8, 9.6 Hz), 2.79 (dd, 1H, J = 16.8, 8.4 Hz), 2.86 (s, 2H), 3.29-3.39 (m, 1H), 3.62 (t, 1H, J = 8.8 Hz), 3.72 (dd, 1H, J = 9.6, 7.6 Hz), 5.74 (s, 1H), 7.13 (s, 1H), 7.20-7.25 (m, 2H), 7.35-7.41 (m, 3H), 7.49-7.55 (m, 2H), 7.71-7.75 (m, 1H), 7.84-7.90 (m, 1H), 8.34 (s, 1H). | 481 | 479 | S-form |

TABLE 2-continued

| Example No. | Molecular Structure | NMR (400 MHz) | MS (M + H) | MS (M − H) | Comments |
|---|---|---|---|---|---|
| 541 | 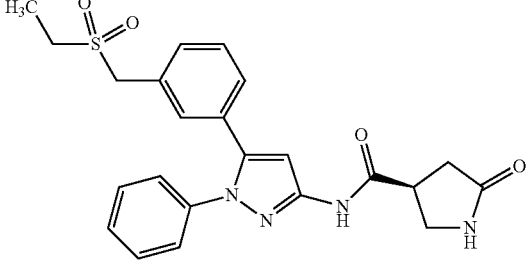 [SMILES: CCS(=O)(=O)Cc1cccc(-c2cc(NC(=O)[C@@H]3CNC(=O)C3)nn2-c2ccccc2)c1] | ¹H-NMR (CDCl₃) δ: 1.28 (t, 3H, J = 7.2 Hz), 2.54 (dd, 1H, J = 16.8, 9.6 Hz), 2.65-2.79 (m, 3H), 3.22-3.33 (m, 1H), 3.55 (t, 1H, J = 8.8 Hz), 3.68 (dd, 1H, J = 9.6, 7.6 Hz), 4.10 (s, 2H), 5.93 (s, 1H), 7.05 (s, 1H), 7.18-7.25 (m, 3H), 7.31-7.44 (m, 6H), 8.64 (s, 1H). | 453 | 451 | S-form |
| 542 | 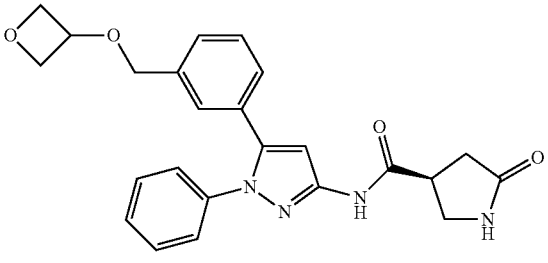 [SMILES: O=C1C[C@H](C(=O)Nc2cc(-c3cccc(COC4COC4)c3)n(-c3ccccc3)n2)CN1] | 1H-NMR (DMSO-D6) δ: 2.39 (d, 2H, J = 8.4 Hz), 3.32-3.52 (m, 3H), 4.33-4.37 (m, 4H), 4.47-4.52 (m, 1H), 4.55-4.59 (m, 2H), 6.92 (s, 1H), 7.13-7.16 (m, 1H), 7.23-7.25 (m, 3H), 7.30-7.43 (m, 5H), 7.63 (s, 1H), 10.86 (s, 1H). | 433 | 431 | S-form |
| 543 | 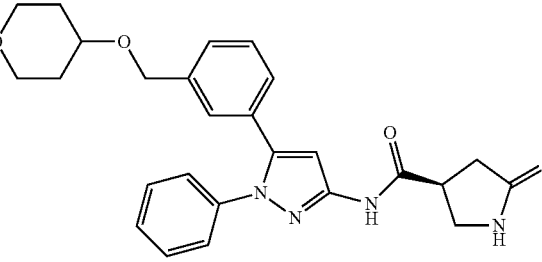 | 1H-NMR (DMSO-D6) δ: 1.32-1.41 (m, 2H), 1.76-1.80 (m, 2H), 2.39 (d, 2H, J = 8.4 Hz), 3.27-3.53 (m, 6H), 3.73-3.78 (m, 2H), 4.46 (s, 2H), 6.91 (s, 1H), 7.13-7.16 (m, 1H), 7.21-7.25 (m, 3H), 7.29-7.42 (m, 5H), 7.63 (s, 1H), 10.86 (s, 1H). | 461 | 459 | S-form |
| 544 | 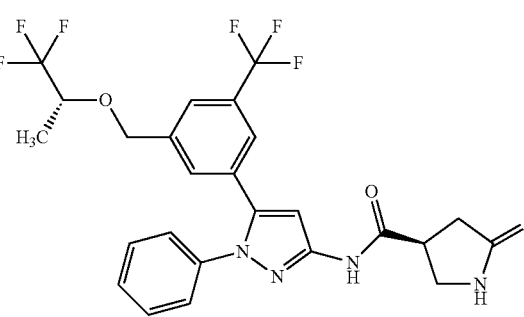 | 1H-NMR (DMSO-D6) δ: 1.22 (d, 3H, J = 6.4 Hz), 2.39 (d, 2H, J = 8.4 Hz), 3.32-3.52 (m, 3H), 4.15-4.21 (m, 1H), 4.71 (s, 2H), 7.07 (s, 1H), 7.26-7.28 (m, 2H), 7.36-7.45 (m, 4H), 7.57 (s, 1H), 7.64-7.66 (m, 2H), 10.91 (s, 1H). | 541 | 539 | 2,2,2-trifluoro methyl-1-methyl-ethoxymethyl group: R-form Lactam ring: S-form |
| 545 | 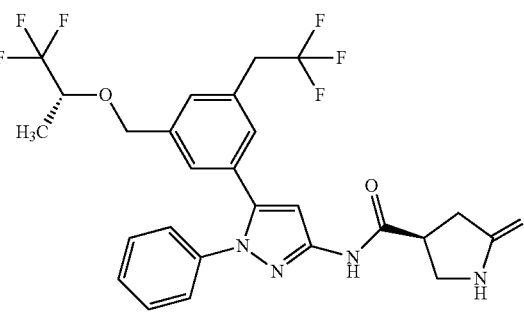 | 1H-NMR (DMSO-D6) δ: 1.22 (d, 3H, J = 6.4 Hz), 2.39 (d, 2H, J = 8.4 Hz), 3.32-3.52 (m, 3H), 4.13-4.23 (m, 1H), 4.69 (s, 2H), 6.98 (s, 1H), 7.02 (s, 1H), 7.25-7.27 (m, 2H), 7.31 (s, 1H), 7.36-7.47 (m, 4H), 7.64 (s, 1H), 10.90 (s, 1H). | 557 | 555 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 546 | 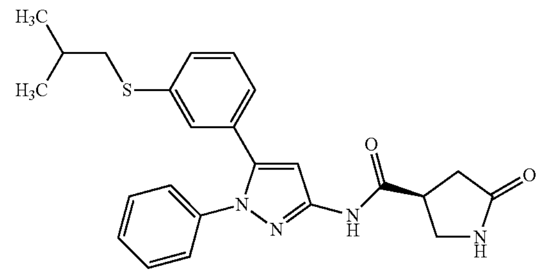 [SMILES: CC(C)CSc1cccc(-c2cc(NC(=O)[C@@H]3CNC(=O)C3)nn2-c2ccccc2)c1] | ¹H-NMR (CDCl₃) δ: 0.96 (d, 6H, J = 6.8 Hz), 1.66-1.77 (m, 1H), 2.52 (dd, 1H, J = 16.8, 9.6 Hz), 2.60 (d, 2H, J = 6.8 Hz), 2.75 (dd, 1H, J = 16.8, 8.4 Hz), 3.20-3.30 (m, 1H), 3.54 (t, 1H, J = 9.2 Hz), 3.68 (dd, 1H, J = 9.6, 7.2 Hz), 4.10 (s, 2H), 5.93 (s, 1H), 7.02-7.39 (m, 10H), 8.77 (s, 1H). | 435 | 433 | S-form |
| 547 | 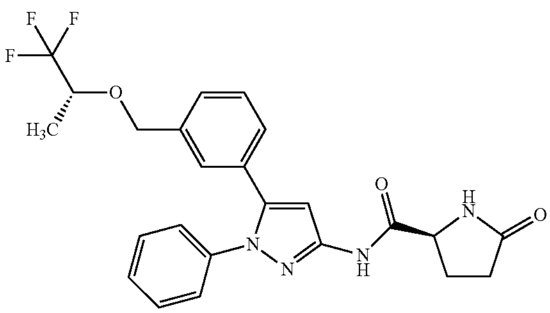 | 1H-NMR (DMSO-D6) δ: 1.19 (d, 3H, J = 6.4 Hz), 1.95-2.03 (m, 1H), 2.09-2.26 (m, 2H), 2.29-2.39 (m, 1H), 4.06-4.13 (m, 1H), 4.25-4.28 (m, 1H), 4.61 (s, 2H), 6.92 (s, 1H), 7.15 (d, 1H, J = 6.8 Hz), 7.23-7.25 (m, 3H), 7.32-7.41 (m, 5H), 7.88 (s, 1H), 10.86 (s, 1H). | 473 | 471 | 2,2,2-trifluoro methyl-1-methyl-ethoxymethyl group: R-form Lactam ring: S-form |
| 548 | 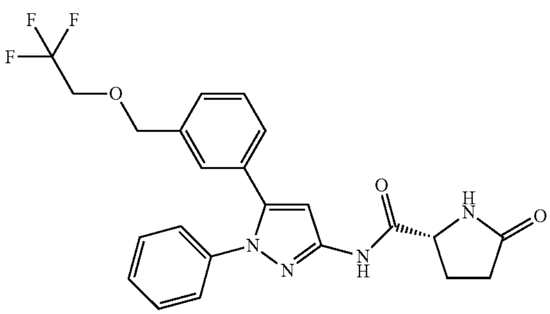 [SMILES: O=C1CC[C@H](C(=O)Nc2cc(-c3cccc(COCC(F)(F)F)c3)n(-c3ccccc3)n2)N1] | 1H-NMR (DMSO-D6) δ: 1.95-2.03 (m, 1H), 2.09-2.26 (m, 2H), 2.29-2.39 (m, 1H), 3.97 (q, 2H, J = 9.2 Hz), 4.25-4.28 (m, 1H), 4.61 (s, 2H), 6.92 (s, 1H), 7.15 (d, 1H, J = 6.8 Hz), 7.23-7.25 (m, 3H), 7.32-7.41 (m, 5H), 7.88 (s, 1H), 10.86 (s, 1H). | 459 | 457 | R-form |
| 549 | 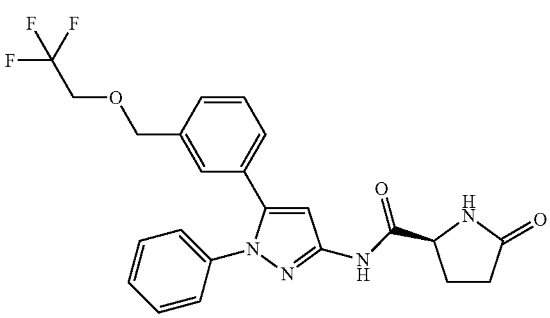 [SMILES: O=C1CC[C@@H](C(=O)Nc2cc(-c3cccc(COCC(F)(F)F)c3)n(-c3ccccc3)n2)N1] | 1H-NMR (DMSO-D6) δ: 1.95-2.03 (m, 1H), 2.09-2.26 (m, 2H), 2.29-2.39 (m, 1H), 3.97 (q, 2H, J = 9.2 Hz), 4.25-4.28 (m, 1H), 4.61 (s, 2H), 6.92 (s, 1H), 7.15 (d, 1H, J = 6.8 Hz), 7.23-7.25 (m, 3H), 7.32-7.41 (m, 5H), 7.88 (s, 1H), 10.86 (s, 1H). | 459 | 457 | S-form |
| 550 | 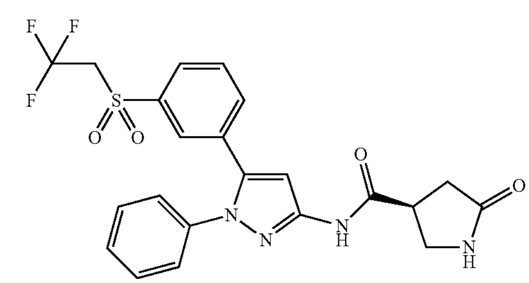 [SMILES: O=C1C[C@H](C(=O)Nc2cc(-c3cccc(S(=O)(=O)CC(F)(F)F)c3)n(-c3ccccc3)n2)CN1] | ¹H-NMR (DMS0-D6) δ: 2.40 (d, 2H, J = 8.4 Hz), 3.32-3.54 (m, 3H), 4.95 (q, 2H, J = 10.0 Hz), 7.11 (s, 1H), 7.23-7.28 (m, 2H), 7.35-7.45 (m, 3H), 7.54-7.69 (m, 3H), 7.85-7.94 (m, 2H), 10.93 (s, 1H). | 493 | 491 | S-form |

TABLE 2-continued

| Example No. | Molecular Structure | NMR (400 MHz) | MS (M + H) | MS (M − H) | Comments |
|---|---|---|---|---|---|
| 551 | 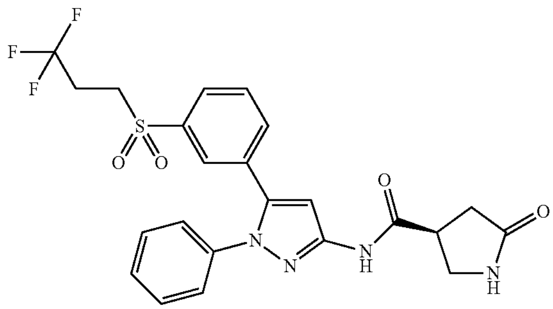 [SMILES: O=C1C[C@H](C(=O)Nc2cc(-c3cccc(S(=O)(=O)CCC(F)(F)F)c3)n(-c3ccccc3)n2)CN1] | ¹H-NMR (CDCl₃) δ: 2.33-2.83 (m, 4H), 3.08-3.15 (m, 2H), 3.30-3.41 (m, 1H), 3.60-3.78 (m, 2H), 5.68 (s, 1H), 7.15 (s, 1H), 7.19-7.25 (m, 2H), 7.36-7.42 (m, 3H), 7.57-7.70 (m, 3H), 7.87 (d, 1H, J = 8.0 Hz), 8.21 (s, 1H). | 507 | 505 | S-form |
| 552 | 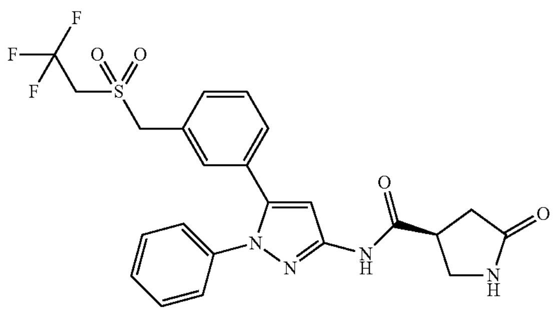 [SMILES: O=C1C[C@H](C(=O)Nc2cc(-c3cccc(CS(=O)(=O)CC(F)(F)F)c3)n(-c3ccccc3)n2)CN1] | ¹H-NMR (CDCl₃) δ: 2.56 (dd, 1H, J = 16.8, 9.6 Hz), 2.76 (dd, 1H, J = 16.8, 8.4 Hz), 3.25-3.35 (m, 1H), 3.44-3.74 (m, 4H), 4.29 (s, 2H), 5.84 (s, 1H), 7.06 (s, 1H), 7.20-7.26 (m, 3H), 7.30-7.45 (m, 6H), 8.51 (s, 1H). | 507 | 505 | S-form |
| 553 | 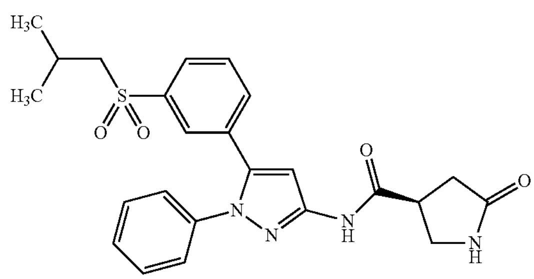 [SMILES: CC(C)CS(=O)(=O)c1cccc(-c2cc(NC(=O)[C@@H]3CNC(=O)C3)nn2-c2ccccc2)c1] | ¹H-NMR (CDCl₃) δ: 1.02 (d, 6H, J = 6.4 Hz), 2.08-2.19 (m, 1H), 2.58 (dd, 1H, J = 16.8, 9.6 Hz), 2.77 (dd, 1H, J = 16.8, 8.4 Hz), 2.84 (d, 2H, J = 6.8 Hz), 3.28-3.38 (m, 1H), 3.60 (t, 1H, J = 8.8 Hz), 3.72 (dd, 1H, J = 9.6, 7.6 Hz), 5.82 (s, 1H), 7.13 (s, 1H), 7.20-7.25 (m, 2H), 7.33-7.42 (m, 3H), 7.49-7.56 (m, 2H), 7.73 (br s, 1H), 7.87 (d, 1H, J = 6.4 Hz), 8.43 (s, 1H). | 467 | 465 | S-form |
| 554 | 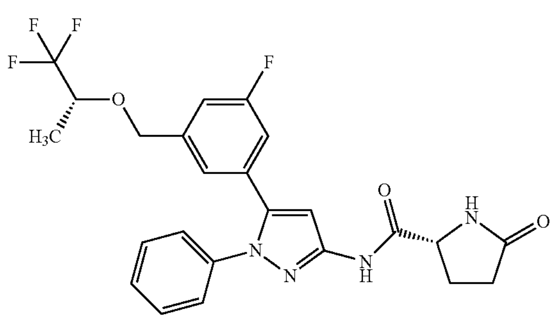 [SMILES: C[C@@H](OCc1cc(F)cc(-c2cc(NC(=O)[C@H]3CCC(=O)N3)nn2-c2ccccc2)c1)C(F)(F)F] | 1H-NMR (DMSO-D6) δ: 1.19 (d, 3H, J = 6.4 Hz), 1.95-2.03 (m, 1H), 2.09-2.26 (m, 2H), 2.29-2.39 (m, 1H), 4.07-4.17 (m, 1H), 4.25-4.28 (m, 1H), 4.62 (s, 2H), 6.97-6.98 (m, 2H), 7.10 (s, 1H), 7.17 (d, 1H, J = 6.8 Hz), 7.25-7.27 (m, 2H), 7.35-7.45 (m, 3H), 7.89 (s, 1H), 10.89 (s, 1H). | 491 | 489 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 555 | 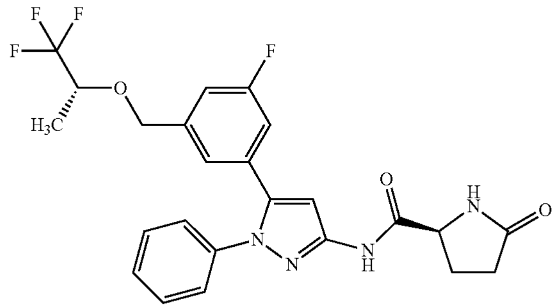 [SMILES: C[C@@H](OCc1cc(F)cc(-c2cc(NC(=O)[C@@H]3CCC(=O)N3)nn2-c2ccccc2)c1)C(F)(F)F] | 1H-NMR (DMSO-D6) δ: 1.19 (d, 3H, J = 6.4 Hz), 1.95-2.03 (m, 1H), 2.09-2.26 (m, 2H), 2.29-2.39 (m, 1H), 4.07-4.17 (m, 1H), 4.25-4.28 (m, 1H), 4.62 (s, 2H), 6.97-6.98 (m, 2H), 7.10 (s, 1H), 7.17 (d, 1H, J = 6.8 Hz), 7.25-7.27 (m, 2H), 7.35-7.45 (m, 3H), 7.89 (s, 1H), 10.89 (s, 1H). | 491 | 489 | 2,2,2-trifluoro methyl-1-methyl-ethoxymethyl group: R-form Lactam ring: S-form |
| 556 | 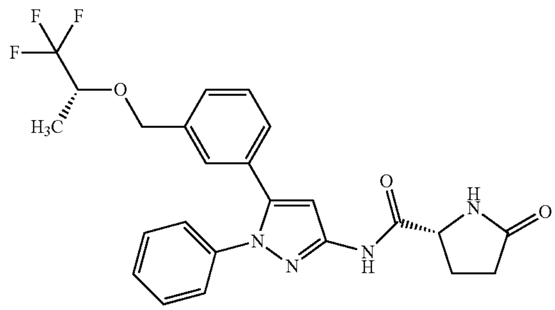 | 1H-NMR (DMSO-D6) δ: 1.19 (d, 3H, J = 6.4 Hz), 1.95-2.03 (m, 1H), 2.09-2.26 (m, 2H), 2.29-2.39 (m, 1H), 4.06-4.13 (m, 1H), 4.25-4.28 (m, 1H), 4.61 (s, 2H), 6.92 (s, 1H), 7.15 (d, 1H, J = 6.8 Hz), 7.23-7.25 (m, 3H), 7.32-7.41 (m, 5H), 7.88 (s, 1H), 10.86 (s, 1H). | 473 | 471 | 2,2,2-trifluoro methyl-1-methyl-ethoxymethyl group: R-form Lactam ring: S-form |
| 557 | 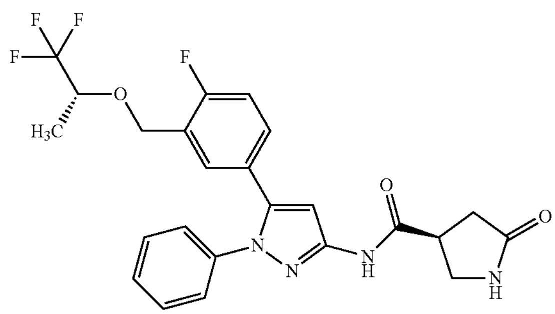 [SMILES: C[C@@H](OCc1cc(-c2cc(NC(=O)[C@@H]3CNC(=O)C3)nn2-c2ccccc2)ccc1F)C(F)(F)F] | 1H-NMR (DMSO-D6) δ: 1.18 (d, 3H, J = 6.4 Hz), 2.39 (d, 2H, J = 8.4 Hz), 3.32-3.52 (m, 3H), 4.09-4.16 (m, 1H), 4.66 (s, 2H), 6.90 (s, 1H), 7.22-7.25 (m, 4H), 7.33-7.42 (m, 4H), 7.63 (s, 1H), 10.87 (s, 1H). | 491 | 489 | 2,2,2-trifluoro methyl-1-methyl-ethoxymethyl group: R-form Lactam ring: S-form |
| 558 | 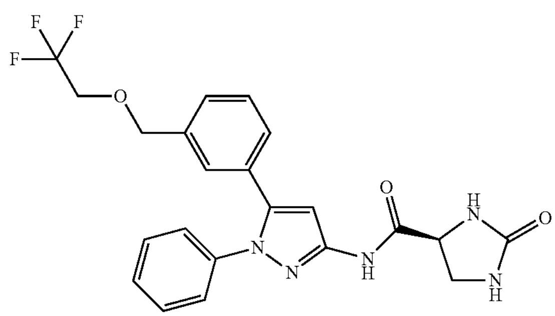 [SMILES: O=C1NC[C@@H](C(=O)Nc2cc(-c3cccc(COCC(F)(F)F)c3)n(-c3ccccc3)n2)N1] | 1H-NMR (DMSO-D6) δ: 3.33-3.38 (m, 1H), 3.60 (dd, 1H, J = 9.2 Hz, 9.2 Hz), 3.97 (q, 2H, J = 9.2 Hz), 4.30-4.35 (m, 1H), 4.61 (s, 2H), 6.32 (s, 1H), 6.59 (s, 1H), 6.93 (s, 1H), 7.16 (dd, 1H, 9.2 Hz, 2.0 Hz), 7.22-7.26 (m, 3H), 7.31-7.42 (m, 5H), 10.71 (s, 1H). | 460 | 458 | S-form |
| 559 | 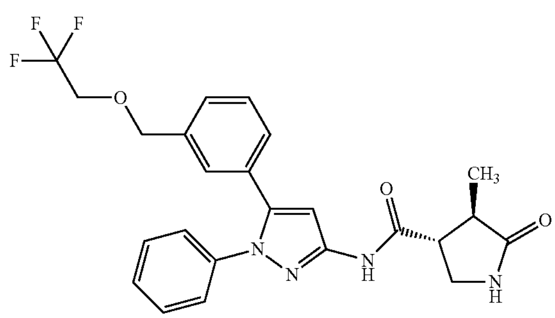 [SMILES: C[C@H]1C(=O)NC[C@@H]1C(=O)Nc1cc(-c2cccc(COCC(F)(F)F)c2)n(-c2ccccc2)n1] | 1H-NMR (DMSO-D6) δ: 1.08 (d, 3H, J = 7.6 Hz), 2.50-2.60 (m, 1H), 3.00-3.08 (m, 1H), 3.20-3.25 (m, 1H), 3.42-3.47 (m, 1H), 3.97 (q, 2H, J = 9.2 Hz), 4.61 (s, 2H), 6.93 (s, 1H), 7.16 (dd, 1H, 11.2 Hz, 2.0 Hz), 7.22-7.26 (m, 3H), 7.31-7.42 (m, 5H), 7.66 (s, 1H), 10.95 (s, 1H). | 473 | 471 | (3R, 4R) Body |

TABLE 2-continued

| Example No. | Molecular Structure | NMR (400 MHz) | MS (M + H) | MS (M − H) | Comments |
|---|---|---|---|---|---|
| 560 | 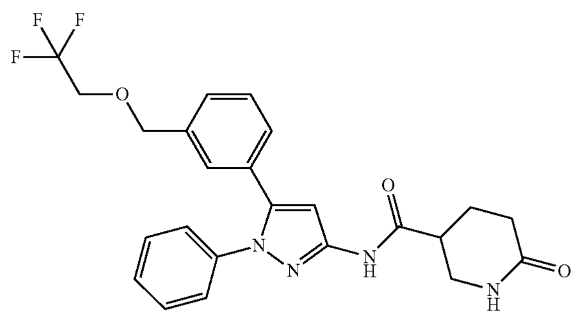 [SMILES: O=C1CCC(C(=O)Nc2cc(-c3cccc(COCC(F)(F)F)c3)n(-c3ccccc3)n2)CN1] | 1H-NMR (DMSO-D6) δ: 1.85-2.20 (m, 2H), 2.31-2.40 (m, 2H), 2.48-2.52 (m, 1H), 2.80-2.90 (m, 1H), 3.27-3.50 (m, 1H), 3.97 (q, 2H, J = 9.2 Hz), 4.60 (s, 2H), 6.92 (s, 1H), 7.15(dd, 1H, 7.2 Hz, 1.6 Hz), 7.22-7.26 (m, 3H), 7.31-7.42 (m, 5H), 7.49 (s, 1H), 10.83 (s, 1H). | 473 | 471 | Optically active substance (The same configuration as Example 5) |
| 561 | 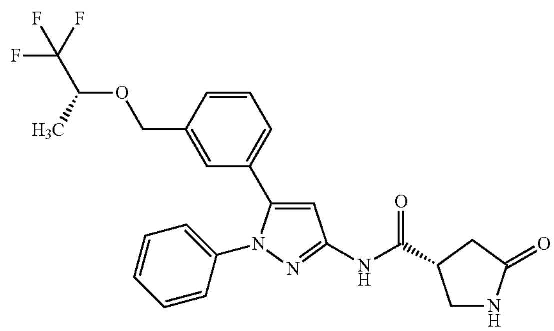 [SMILES: C[C@@H](OCc1cccc(-c2cc(NC(=O)[C@H]3CNC(=O)C3)nn2-c2ccccc2)c1)C(F)(F)F] | 1H-NMR (DMSO-D6) δ: 1.19(d, 3H, J = 6.0 Hz), 2.35-2.58 (m, 2H), 3.28-3.55 (m, 3H), 4.06-4.13 (m, 1H), 4.58-4.65 (m, 2H), 6.91 (s, 1H), 7.15 (dt, 1H, J = 6.8 Hz, 1.6 Hz), 7.22-7.26 (m, 3H), 7.31-7.42 (m, 5H), 7.62 (s, 1H), 10.86 (s, 1H). | 473 | 471 | 2,2,2-trifluoro methyl-1-methyl-ethoxymethyl group: R-form Lactam ring: R-form |
| 562 | 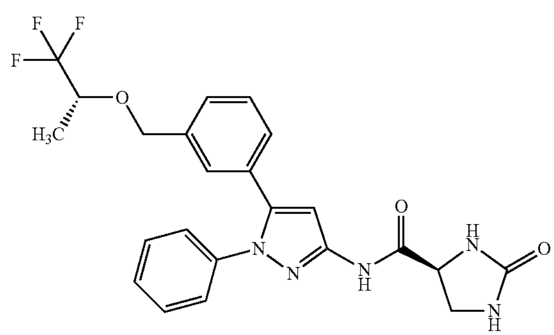 [SMILES: C[C@@H](OCc1cccc(-c2cc(NC(=O)[C@@H]3CNC(=O)N3)nn2-c2ccccc2)c1)C(F)(F)F] | 1H-NMR (DMSO-D6) δ: 1.19(4 3H, J = 6.0 Hz), 3.34-3.38 (m, 1H), 3.57-3.62 (m, 1H), 4.06-4.13 (m, 1H), 4.30-4.34 (m, 1H), 4.58-4.65 (m, 2H), 6.32 (s, 1H), 6.59 (s, 1H), 6.93 (s, 1H), 7.15 (dt, 1H, J = 8.0 Hz, 2.0 Hz), 7.22-7.26 (m, 3H), 7.31-7.42 (m, 5H), 10.71 (s, 1H). | 474 | 472 | 2,2,2-trifluoro methyl-1-methyl-ethoxymethyl group: R-form Alpha position of carbonyl group (amide): s-form |
| 563 | 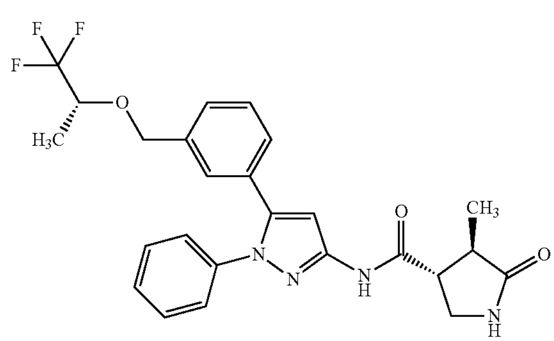 [SMILES: C[C@H]1C(=O)NC[C@@H]1C(=O)Nc1cc(-c2cccc(CO[C@H](C)C(F)(F)F)c2)n(-c2ccccc2)n1] | 1H-NMR (DMSO-D6) δ: 1.09 (d , 3H, J = 6.8 Hz), 1.19(d, 3H, J = 6.0 Hz), 2.50-2.60 (m, 1H), 3.00-3.08 (m, 1H), 3.20-3.25 (m, 1H), 3.42-3.47 (m, 1H), 4.06-4.13 (m, 1H), 4.58-4.65 (m, 2H), 6.95 (s, 1H), 7.15 (dt, 1H, J = 7.2 Hz, 1.8 Hz), 7.22-7.26 (m, 3H), 7.31-7.42 (m, 5H), 7.66 (s, 1H), 10.95 (s, 1H). | 487 | 485 | 2,2,2-trifluoro methyl-1-methyl-ethoxymethyl group: R-form Lactam ring: (3R, 4R) Body |

TABLE 2-continued

| Example No. | Molecular Structure | NMR (400 MHz) | MS (M + H) | MS (M − H) | Comments |
|---|---|---|---|---|---|
| 564 | 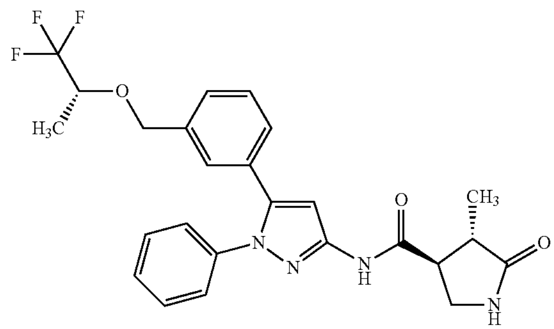 [SMILES: C[C@@H]1C(=O)NC[C@H]1C(=O)Nc1cc(-c2cccc(CO[C@H](C)C(F)(F)F)c2)n(-c2ccccc2)n1] | 1H-NMR (DMSO-D6) δ: 1.09 (d, 3H, J = 7.6 Hz), 1.19(d, 3H, J = 6.0 Hz), 2.50-2.60 (m, 1H), 3.00-3.08 (m, 1H), 3.20-3.25 (m, 1H), 3.42-3.47 (m, 1H), 4.06-4.13 (m, 1H), 4.58-4.65 (m, 2H), 6.95 (s, 1H), 7.15 (dt, 1H, J = 7.2 Hz, 1.8 Hz), 7.22-7.26 (m, 3H), 7.31-7.42 (m, 5H), 7.66 (s, 1H), 10.95 (s, 1H). | 487 | 485 | 2,2,2-trifluoro methyl-1-methyl-ethoxymethyl group: R-form Lactam ring: (3S, 4S) Body |
| 565 | 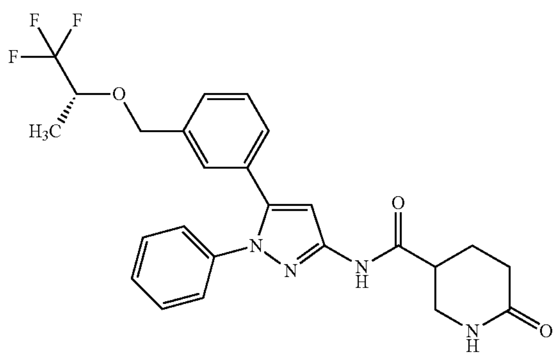 [SMILES: C[C@@H](OCc1cccc(-c2cc(NC(=O)C3CCC(=O)NC3)nn2-c2ccccc2)c1)C(F)(F)F] | 1H-NMR (DMSO-D6) δ: 1.19(d, 3H, J = 6.0 Hz), 1.85-2.05 (m, 2H), 2.15-2.30 (m, 2H), 2.48-2.52 (m, 1H), 2.80-2.90 (m, 1H), 3.27-3.50 (m, 1H), 4.06-4.13 (m, 1H), 4.58-4.65 (m, 2H), 6.91 (s, 1H), 7.15 (dd, 1H, 6.8 Hz, 2.0 Hz), 7.22-7.26 (m, 3H), 7.31-7.42 (m, 5H), 7.49 (s, 1H), 10.83 (s, 1H). | 487 | 485 | 2,2,2-trifluoro methyl-1-methyl-ethoxymethyl group: R-form Lactam ring: The same configuration as Example 5 |
| 566 | 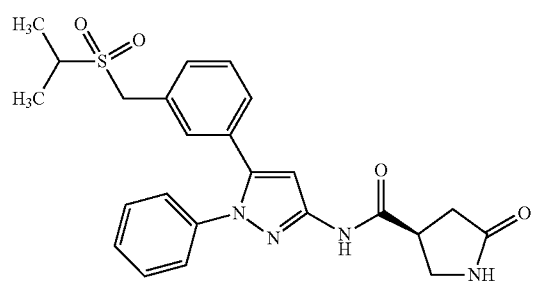 [SMILES: CC(C)S(=O)(=O)Cc1cccc(-c2cc(NC(=O)[C@@H]3CNC(=O)C3)nn2-c2ccccc2)c1] | 1H-NMR (DMSO-D6) δ: 1.18 (d, 6H, J = 6.8), 2.35-2.42 (m, 2H), 2.87-2.98 (m, 1H), 3.32-3.55 (m, 3H), 4.43 (s, 2H), 6.92 (s, 1H), 7.18-7.28 (m, 3H), 7.32-7.45 (m, 6H), 7.63 (s, 1H), 10.88 (s, 1H). | 467 | 465 | S-form |
| 567 | 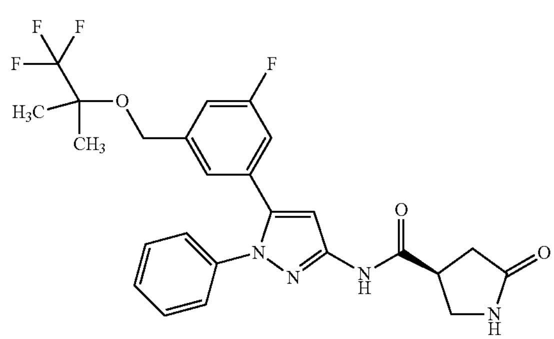 [SMILES: CC(C)(OCc1cc(F)cc(-c2cc(NC(=O)[C@@H]3CNC(=O)C3)nn2-c2ccccc2)c1)C(F)(F)F] | 1H-NMR (DMSO-D6) δ: 1.32(s, 6H), 2.35-2.58 (m, 2H), 3.28-3.55 (m, 3H), 4.54 (s, 2H), 6.95-6.97 (m, 2H), 7.06 (s, 1H), 7.12 (d, 1H, J = 9.6 Hz), 7.24-7.27 (m, 2H), 7.35-7.45 (m, 3H), 7.63 (s, 1H), 10.88 (s, 1H). | 505 | 503 | S-form |

TABLE 2-continued

| Example No. | Molecular Structure | NMR (400 MHz) | MS (M + H) | MS (M − H) | Comments |
|---|---|---|---|---|---|
| 568 | 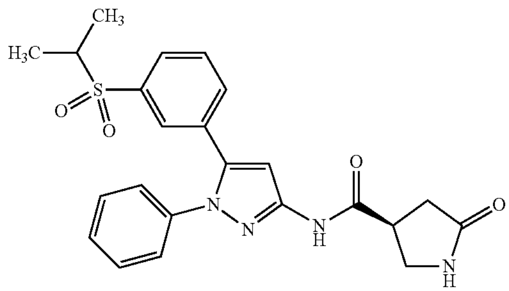 [SMILES: CC(C)S(=O)(=O)c1cccc(-c2cc(NC(=O)[C@@H]3CNC(=O)C3)nn2-c2ccccc2)c1] | ¹H-NMR (DMSO-D6) δ: 1.01 (d, 6H, J = 6.8 Hz), 2.40 (d, 2H, J = 8.4 Hz), 3.23-3.55 (m, 4H), 7.06 (s, 1H), 7.24-7.85 (m, 10H), 10.91 (s, 1H). | 453 | 451 | S-form |
| 569 | 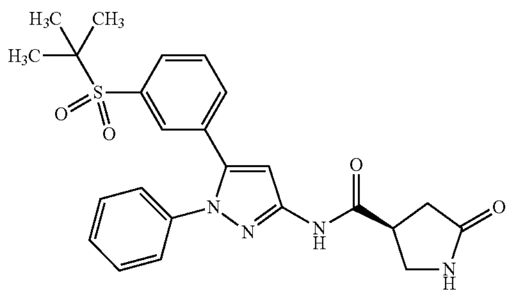 [SMILES: CC(C)(C)S(=O)(=O)c1cccc(-c2cc(NC(=O)[C@@H]3CNC(=O)C3)nn2-c2ccccc2)c1] | ¹H-NMR (DMSO-D6) δ: 1.07 (s, 9H), 2.39 (d, 2H, J = 8.4 Hz), 3.33-3.55 (m, 3H), 7.02 (s, 1H), 7.25-7.46 (m, 6H), 7.62-7.85 (m, 4H), 10.91 (s, 1H). | 467 | 465 | S-form |
| 570 | 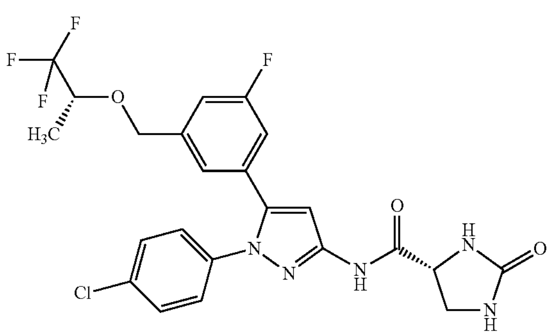 [SMILES: C[C@@H](OCc1cc(F)cc(-c2cc(NC(=O)[C@H]3CNC(=O)N3)nn2-c2ccc(Cl)cc2)c1)C(F)(F)F] | 1H-NMR (DMSO-D6) δ: 1.20 (d, 3H, J = 6.2 Hz), 3.36 (dd, 1H, J = 10.2, 5.0 Hz), 3.58 (dd, 1H, J = 10.2, 10.0 Hz), 4.09-4.16 (m, 1H), 4.32 (dd, 1H, J = 10.0, 5.0 Hz), 4.63 (s, 2H), 6.33 (s, 1H), 6.59 (s, 1H), 6.99 (s, 1H), 7.07 (s, 1H), 7.08 (d, 1H, J = 9.0 Hz), 7.20 (d, 1H, J = 9.0 Hz), 7.28 (dd, 2H, J = 6.2, 2.5 Hz), 7.48 (dd, 2H, J = 6.2, 2.5 Hz), 10.76 (s, 1H). | 526 | 524 | 2,2,2-trifluoro methyl-1-methyl-ethoxymethyl group: R-form Alpha position of carbonyl group (amide): R-form |
| 571 | 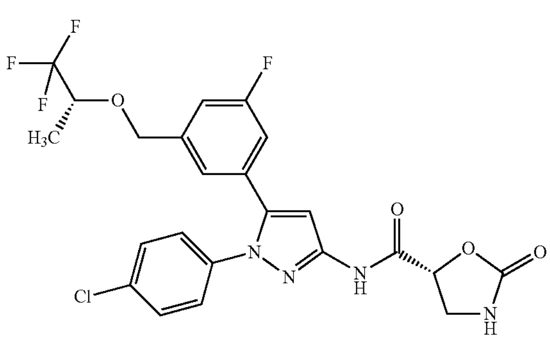 [SMILES: C[C@@H](OCc1cc(F)cc(-c2cc(NC(=O)[C@H]3CNC(=O)O3)nn2-c2ccc(Cl)cc2)c1)C(F)(F)F] | 1H-NMR (DMSO-D6) δ: 1.20 (d, 3H, J = 6.2 Hz), 3.51 (dd, 1H, J = 8.8, 5.5 Hz), 3.75 (dd, 1H, J = 9.2, 8.8 Hz), 4.09-4.17 (m, 1H), 4.63 (s, 2H), 5.13 (dd, 1H, J = 9.2, 5.5 Hz), 6.99 (s, 1H), 7.07 (s, 1H), 7.09 (d, 1H, J = 9.5 Hz), 7.20 (d, 1H, J = 9.5 Hz), 7.29 (dd, 2H, J = 6.7, 2.1 Hz), 7.49 (dd, 2H, J = 6.7, 2.1 Hz), 7.75 (s, 1H), 11.11 (s, 1H). | 527 | 525 | 2,2,2-trifluoro methyl-1-methyl-ethoxymethyl group: R-form Alpha position of carbonyl group (amide): R-form |

TABLE 2-continued

| Example No. | Molecular Structure | NMR (400 MHz) | MS (M + H) | MS (M − H) | Comments |
|---|---|---|---|---|---|
| 572 | 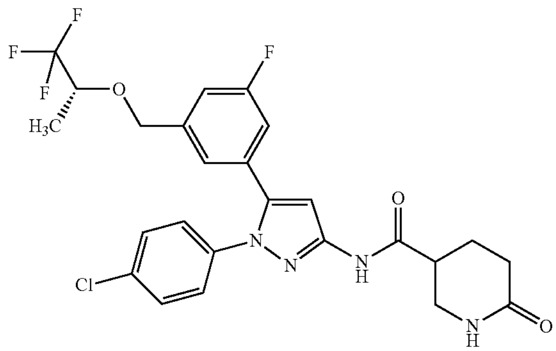 [SMILES: C[C@@H](OCc1cc(F)cc(-c2cc(NC(=O)C3CCC(=O)NC3)nn2-c2ccc(Cl)cc2)c1)C(F)(F)F] | 1H-NMR (DMSO-D6) δ: 1.20 (d, 3H, J = 6.2 Hz), 1.86-1.99 (m, 2H), 2.14-2.24 (m, 2H), 2.53-2.61 (m, 2H), 2.78-2.88 (m, 1H), 4.10-4.15 (m, 1H), 4.63 (s, 2H), 6.98 (s, 1H), 7.06 (s, 1H), 7.08 (d, 1H, J = 9.7 Hz), 7.19 (d, 1H, J = 9.7 Hz), 7.27 (dd, 2H, J = 6.7, 2.1 Hz), 7.47-7.49 (m, 3H), 10.89 (s, 1H). | 539 | 537 | 2,2,2-trifluoromethyl-1-methyl-ethoxymethyl group: R-form Lactam ring: The same configuration as Example 5 |
| 573 | 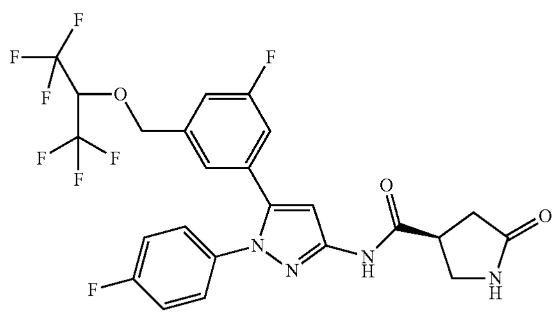 [SMILES: O=C1C[C@H](C(=O)Nc2cc(-c3cc(F)cc(COC(C(F)(F)F)C(F)(F)F)c3)n(-c3ccc(F)cc3)n2)CN1] | 1H-NMR (DMSO-D6) δ: 2.39 (d, 2H, J = 8.4), 3.33-3.55 (m, 3H), 4.85 (s, 2H), 5.50-5.64 (m, 1H), 7.00 (s, 1H), 7.05-7.13 (m, 2H), 7.18-7.41 (m, 5H), 7.63 (s, 1H), 10.89 (s, 1H). | 563 | 561 | S-form |
| 574 | 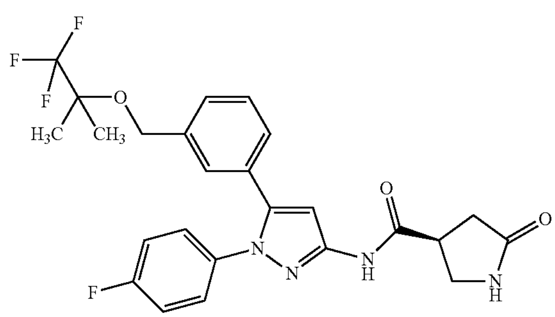 [SMILES: CC(C)(OCc1cccc(-c2cc(NC(=O)[C@@H]3CNC(=O)C3)nn2-c2ccc(F)cc2)c1)C(F)(F)F] | 1H-NMR (DMSO-D6) δ: 1.34 (s, 6H), 2.34-2.42 (m, 2H), 3.32-3.55 (m, 3H), 4.53 (s, 2H), 6.91 (s, 1H), 7.15-7.21 (m, 2H), 7.22-7.32 (m, 5H), 7.33-7.42 (m, 1H), 7.63 (s, 1H), 10.85 (s, 1H). | 505 | 503 | S-form |
| 575 | 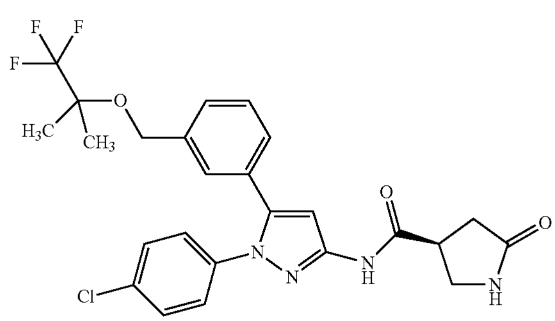 [SMILES: CC(C)(OCc1cccc(-c2cc(NC(=O)[C@@H]3CNC(=O)C3)nn2-c2ccc(Cl)cc2)c1)C(F)(F)F] | 1H-NMR (DMSO-D6) δ: 1.34 (s, 6H), 2.38-2.40 (m, 2H), 3.33-3.35 (m, 1H), 3.39-3.45 (m, 1H), 3.48-3.53 (m, 1H), 4.54 (s, 2H), 6.92 (s, 1H), 7.19-7.21 (m, 2H), 7.24-7.26 (m, 2H), 7.31 (d, 1H, J = 6.9 Hz), 7.36-7.40 (m, 1H), 7.44-7.47 (m, 2H), 7.63 (s, 1H), 10.89 (s, 1H). | 521 | 519 | S-form |

TABLE 2-continued

| Example No. | Molecular Structure | NMR (400 MHz) | MS (M + H) | MS (M − H) | Comments |
|---|---|---|---|---|---|
| 576 | 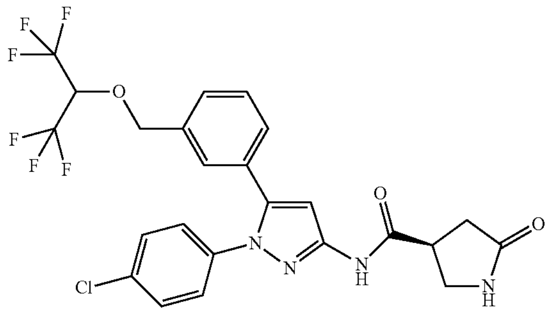 [SMILES: O=C1C[C@H](C(=O)Nc2cc(-c3cccc(COC(C(F)(F)F)C(F)(F)F)c3)n(-c3ccc(Cl)cc3)n2)CN1] | 1H-NMR (DMSO-D6) δ: 2.36-2.38 (m, 2H), 3.32-3.33 (m, 1H), 3.39-3.43 (m, 1H), 3.47-3.51 (m, 1H), 4.85 (s, 2H), 5.54 (sep, 1H, J = 6.5 Hz), 6.93 (s, 1H), 7.20-7.25 (m, 3H), 7.30 (s, 1H), 7.36-7.45 (m, 4H), 7.61 (s, 1H), 10.88 (s, 1H). | 561 | 559 | S-form |
| 577 | 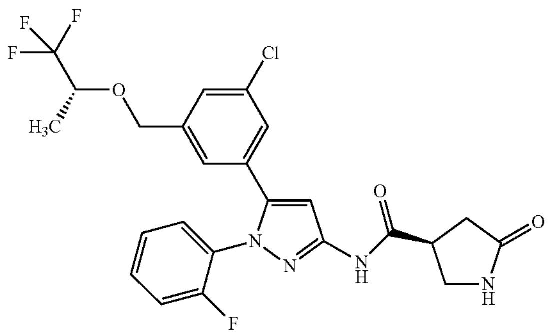 [SMILES: C[C@@H](OCc1cc(Cl)cc(-c2cc(NC(=O)[C@@H]3CNC(=O)C3)nn2-c2ccccc2F)c1)C(F)(F)F] | 1H-NMR (DMSO-D6) δ: 1.19 (d, 3H, J = 6.7 Hz), 2.38-2.41 (m, 2H), 3.33-3.36 (m, 1H), 3.41-3.45 (m, 1H), 3.49-3.53 (m, 1H), 4.10-4.14 (m, 1H), 4.59 (d, 1H, J = 12.7 Hz), 4.61 (d, 1H, J = 12.7 Hz), 7.05 (s, 1H), 7.18-7.19 (m, 2H), 7.32-7.36 (m, 3H), 7.50-7.58 (m, 2H), 7.63 (s, 1H), 10.88 (s, 1H). | 525 | 523 | 2,2,2-trifluoro methyl-1-methyl-ethoxymethyl group: R-form Lactam ring: S-form |
| 578 | 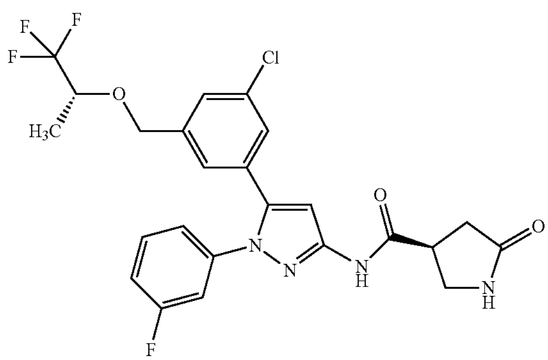 [SMILES: C[C@@H](OCc1cc(Cl)cc(-c2cc(NC(=O)[C@@H]3CNC(=O)C3)nn2-c2cccc(F)c2)c1)C(F)(F)F] | 1H-NMR (DMSO-D6) δ: 1.20 (d, 3H, J = 6.5 Hz), 2.38-2.40 (m, 2H), 3.33-3.36 (m, 1H), 3.40-3.44 (m, 1H), 3.49-3.52 (m, 1H), 4.10-4.16 (m, 1H), 4.61 (d, 1H, J = 12.5 Hz), 4.65 (d, 1H, J = 12.5 Hz), 7.00 (s, 1H), 7.04-7.06 (m, 1H), 7.16-7.29 (m, 4H), 7.42-7.47 (m, 2H), 7.63 (s, 1H), 10.92 (s, 1H). | 525 | 523 | 2,2,2-trifluoro methyl-1-methyl-ethoxymethyl group: R-form Lactam ring: S-form |
| 579 | 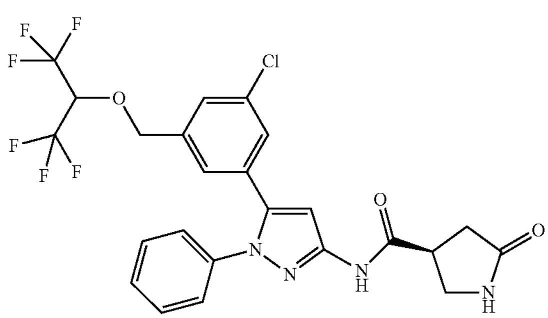 [SMILES: O=C1C[C@H](C(=O)Nc2cc(-c3cc(Cl)cc(COC(C(F)(F)F)C(F)(F)F)c3)n(-c3ccccc3)n2)CN1] | 1H-NMR (DMSO-D6) δ: 2.37-2.41 (m, 2H), 3.30-3.37 (m, 1H), 3.37-3.47 (m, 1H), 3.47-3.54 (m, 1H), 4.85 (s, 2H), 5.57 (t, 1H, J = 6.4 Hz), 7.00 (s, 1H), 7.20-7.22 (m, 1H), 7.23-7.30 (m, 3H), 7.34-7.46 (m, 4H), 7.63 (s, 1H), 10.89 (s, 1H). | 561 | 559 | S-form |

TABLE 2-continued

| Example No. | Molecular Structure | NMR (400 MHz) | MS (M + H) | MS (M − H) | Comments |
|---|---|---|---|---|---|
| 580 | 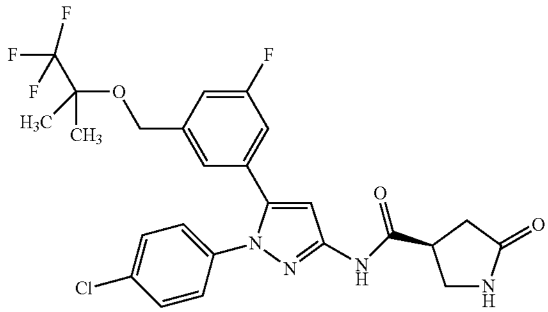 | ¹H-NMR (DMSO-D6) δ: 1.33 (s, 6H), 2.39 (d, 2H, J = 8.4 Hz), 3.31-3.53 (m, 3H), 4.55 (s, 2H), 6.98 (s, 1H), 7.02 (br s, 1H), 7.07 (d, 1H, J = 9.2 Hz), 7.15 (d, 1H, J = 9.2 Hz), 7.27 (dt, 2H, J = 9.2, 2.4 Hz), 7.48 (dt, 2H, J = 9.2, 2.4 Hz), 7.63 (br s, 1H), 10.91 (s, 1H). | 539 | 537 | S-form |
| 581 | 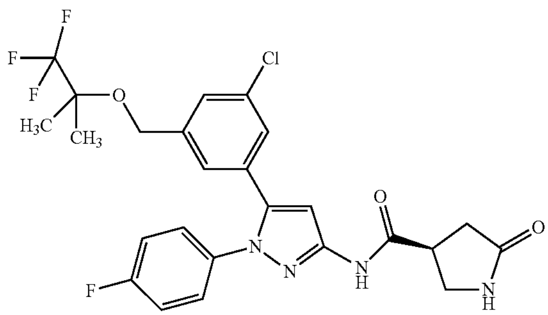 [SMILES: CC(C)(OCc1cc(Cl)cc(-c2cc(NC(=O)[C@@H]3CNC(=O)C3)nn2-c2ccc(F)cc2)c1)C(F)(F)F] | ¹H-NMR (DMSO-D6) δ: 1.32 (s, 6H), 2.39 (d, 2H, J = 8.4 Hz), 3.32-3.53 (m, 3H), 4.53 (s, 2H), 6.98 (s, 1H), 7.10 (br s, 1H), 7.23-7.37 (m, 6H), 7.63 (br s, 1H), 10.88 (s, 1H). | 539 | 537 | S-form |
| 582 | 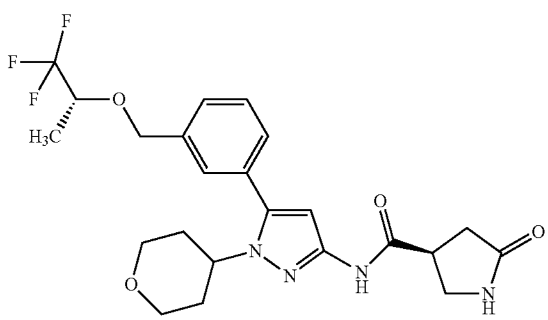 [SMILES: C[C@@H](OCc1cccc(-c2cc(NC(=O)[C@@H]3CNC(=O)C3)nn2C2CCOCC2)c1)C(F)(F)F] | 1H-NMR (DMSO-D6) δ: 1.30 (d, 3H, J = 6.4 Hz), 1.78 (d, 2H, J = 10.8 Hz), 2.08 (ddd, 2H, J = 24.1, 12.5, 4.6 Hz), 2.36 (dd, 2H, J = 8.3, 2.1 Hz), 3.20-3.54 (m, 5H), 3.92 (dd, 2H, J = 11.5, 4.0 Hz), 4.20-4.38 (m, 2H), 4.76 (dd, 2H, J = 20.4, 12.0 Hz), 6.59 (s, 1H), 7.39-7.45 (m, 3H), 7.49-7.56 (m, 1H), 7.60 (s, 1H), 10.72 (s, 1H). | 481 | 479 | 2,2,2-trifluoro methyl-1-methyl-ethoxymethyl group: R-form Lactam ring: S-form |
| 583 | 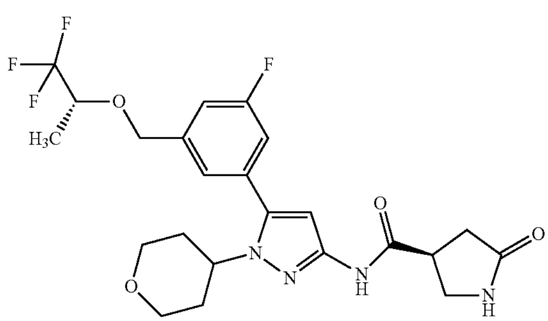 [SMILES: C[C@@H](OCc1cc(F)cc(-c2cc(NC(=O)[C@@H]3CNC(=O)C3)nn2C2CCOCC2)c1)C(F)(F)F] | 1H-NMR (DMSO-D6) δ: 1.31 (d, 3H, J = 6.6 Hz), 1.79 (d, 2H, J = 10.8 Hz), 2.06 (ddd, 2H, J = 4.6, 12.8, 24.8 Hz), 2.30-2.40 (m, 2H), 3.25-3.53 (m, 5H), 3.91 (dd, 2H, J = 3.9, 11.8 Hz), 4.23-4.36 (m, 2H), 4.77 (dd, 2H, J = 12.7, 20.0 Hz), 6.63 (s, 1H), 7.24-7.32 (m, 3H), 7.61 (s, 1H), 10.75 (s, 1H). | 499 | 497 | 2,2,2-trifluoro methyl-1-methyl-ethoxymethyl group: R-form Lactam ring: S-form |

TABLE 2-continued

| Example No. | Molecular Structure | NMR (400 MHz) | MS (M + H) | MS (M − H) | Comments |
|---|---|---|---|---|---|
| 584 | 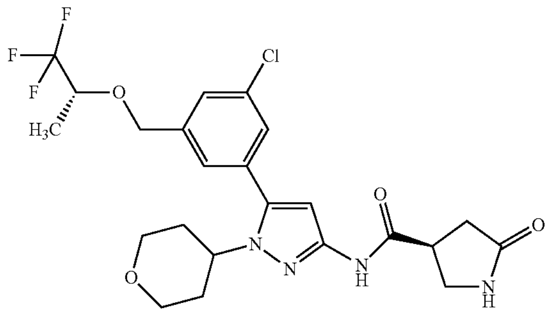 | 1H-NMR (DMSO-D6) δ: 1.30 (d, 3H, J = 6.4 Hz), 1.79 (d, 2H, J = 9.0 Hz), 1.99-2.13 (m, 2H), 2.29-2.40 (m, 2H), 3.26-3.53 (m, 5H), 3.87-3.3.95 (m, 2H), 4.20-4.34 (m, 2H), 4.77 (dd, 2H, J = 12.5, 21.3 Hz), 6.63 (s, 1H), 7.34-7.40 (m, 1H), 7.46-7.49 (m, 1H), 7.50-7.53 (m, 1H), 7.61 (s, 1H), 10.75 (s, 1H). | 515 | 513 | 2,2,2-trifluoromethyl-1-methyl-ethoxymethyl group: R-form Lactam ring: S-form |
| 585 | 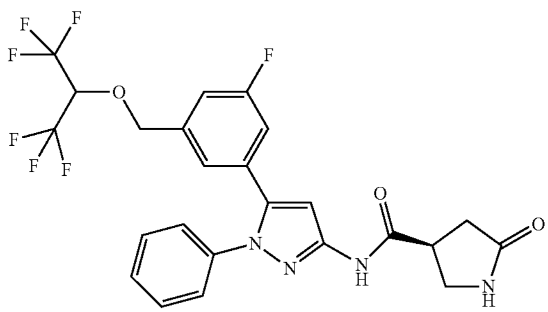 [SMILES: O=C1C[C@H](C(=O)Nc2cc(-c3cc(F)cc(COC(C(F)(F)F)C(F)(F)F)c3)n(-c3ccccc3)n2)CN1] | 1H-NMR (DMSO-D6) δ: 2.38-2.40 (m, 2H), 3.33-3.36 (m, 1H), 3.41-3.46 (m, 1H), 3.49-3.53 (m, 1H), 4.86 (s, 2H), 5.57 (sep, 1H, J = 6.4 Hz), 6.97-7.01 (m, 2H), 7.18-7.27 (m, 4H), 7.35-7.44 (m, 3H), 7.63 (s, 1H), 10.89 (s, 1H). | 545 | 543 | S-form |
| 586 | 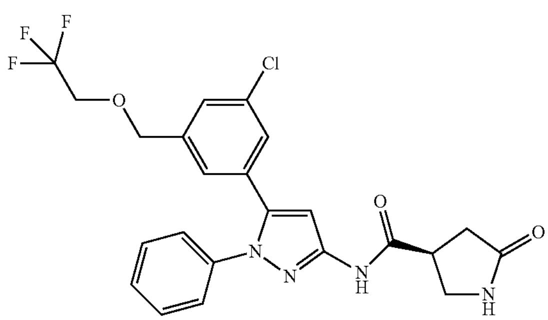 [SMILES: O=C1C[C@H](C(=O)Nc2cc(-c3cc(Cl)cc(COCC(F)(F)F)c3)n(-c3ccccc3)n2)CN1] | 1H-NMR (DMSO-D6) δ: 2.38-2.40 (m, 2H), 3.33-3.36 (m, 1H), 3.39-3.46 (m, 1H), 3.49-3.53 (m, 1H), 3.99 (q, 2H, J = 9.2 Hz), 4.61 (s, 2H), 7.00 (s, 1H), 7.20-7.27 (m, 4H), 7.35-7.44 (m, 4H), 7.63 (s, 1H), 10.89 (s, 1H). | 493 | 491 | S-form |
| 587 | 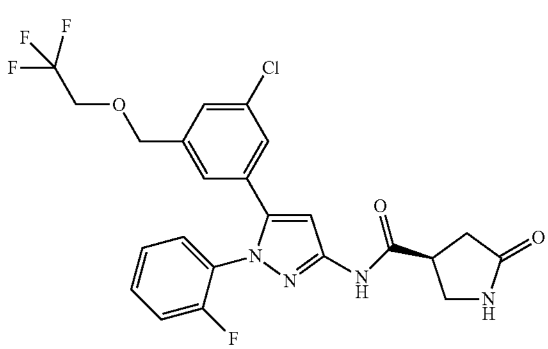 [SMILES: O=C1C[C@H](C(=O)Nc2cc(-c3cc(Cl)cc(COCC(F)(F)F)c3)n(-c3ccccc3F)n2)CN1] | 1H-NMR (DMSO-D6) δ: 2.38-2.40 (m, 2H), 3.34-3.36 (m, 1H), 3.40-3.44 (m, 1H), 3.48-3.52 (m, 1H), 3.99 (q, 2H, J = 9.2 Hz), 4.59 (s, 2H), 7.06 (s, 1H), 7.17-7.20 (m, 2H), 7.32-7.38 (m, 3H), 7.49-7.63 (m, 3H), 10.88 (s, 1H). | 511 | 509 | S-form |

TABLE 2-continued

| Example No. | Molecular Structure | NMR (400 MHz) | MS (M + H) | MS (M − H) | Comments |
|---|---|---|---|---|---|
| 588 | 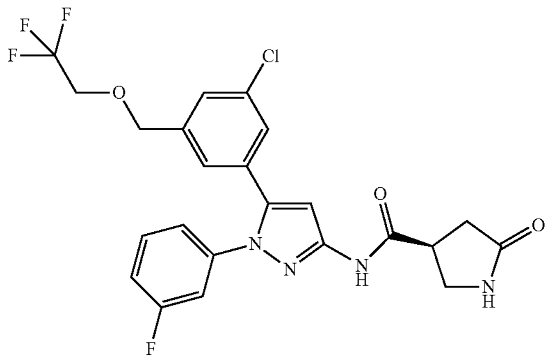 [SMILES: O=C1C[C@H](C(=O)Nc2cc(-c3cc(Cl)cc(COCC(F)(F)F)c3)n(-c3cccc(F)c3)n2)CN1] | 1H-NMR (DMSO-D6) δ: 2.38-2.40 (m, 2H), 3.33-3.36 (m, 1H), 3.41-3.46 (m, 1H), 3.48-3.53 (m, 1H), 4.01 (q, 2H, J = 9.3 Hz), 4.62 (s, 2H), 7.00-7.06 (m, 2H), 7.17-7.29 (m, 4H), 7.42-7.46 (m, 2H), 7.63 (s, 1H), 10.92 (s, 1H). | 511 | 509 | S-form |
| 589 | 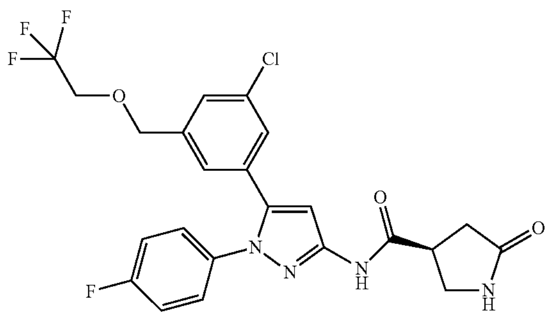 [SMILES: O=C1C[C@H](C(=O)Nc2cc(-c3cc(Cl)cc(COCC(F)(F)F)c3)n(-c3ccc(F)cc3)n2)CN1] | 1H-NMR (DMSO-D6) δ: 2.38-2.40 (m, 2H), 3.33-3.36 (m, 1H), 3.41-3.44 (m, 1H), 3.48-3.52 (m, 1H), 3.99 (q, 2H, J = 9.3 Hz), 4.60 (s, 2H), 6.99 (s, 1H), 7.15 (s, 1H), 7.24-7.33 (m, 5H), 7.40 (s, 1H), 7.63 (s, 1H), 10.88 (s, 1H). | 511 | 509 | S-form |
| 590 | 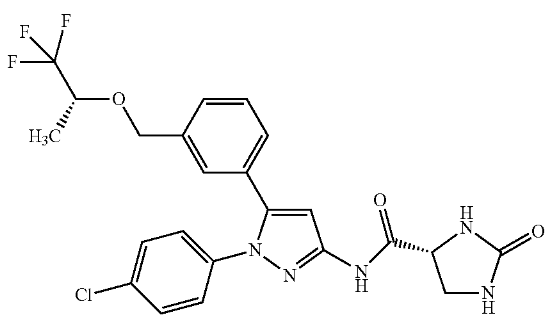 [SMILES: C[C@@H](OCc1cccc(-c2cc(NC(=O)[C@H]3CNC(=O)N3)nn2-c2ccc(Cl)cc2)c1)C(F)(F)F] | 1H-NMR (DMSO-D6) δ: 1.20 (d, 3H, J = 6.2 Hz), 3.35 (dd, 1H, J = 8.8, 5.3 Hz), 3.59 (dd, 1H, J = 9.0, 8.8 Hz), 4.07-4.14 (m, 1H), 4.32 (dd, 1H, J = 9.0, 5.3 Hz), 4.61 (d, 1H, J = 12.6 Hz), 4.65 (d, 1H, J = 12.6 Hz), 6.33 (s, 1H), 6.59 (s, 1H), 6.94 (s, 1H), 7.20-7.27 (m, 4H), 7.34-7.48 (m, 4H), 10.74 (s, 1H). | 508 | 506 | 2,2,2-trifluoro methyl-1-methyl-ethoxymethyl group: R-form Alpha position of carbonyl group (amide): R-form |
| 591 | 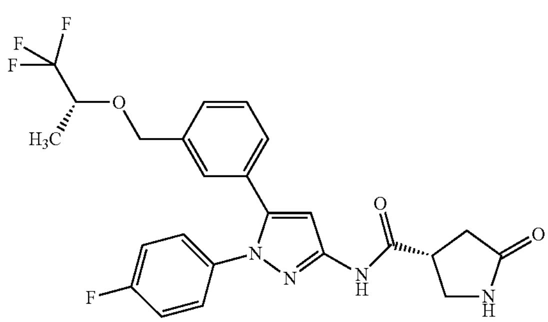 [SMILES: C[C@@H](OCc1cccc(-c2cc(NC(=O)[C@H]3CNC(=O)C3)nn2-c2ccc(F)cc2)c1)C(F)(F)F] | 1H-NMR (DMSO-D6) δ: 1.20 (d, 3H, J = 6.0 Hz), 3.36 (dd, 1H, J = 8.8, 5.2 Hz), 3.59 (dd, 1H, J = 8.9, 8.8 Hz), 4.07-4.13 (m, 1H), 4.32 (dd, 1H, J = 8.9, 5.2 Hz), 4.60 (d, 1H, J = 12.1 Hz), 4.63 (d, 1H, J = 12.1 Hz), 6.33 (s, 1H), 6.59 (s, 1H), 6.93 (s, 1H), 7.19-7.40 (m, 8H), 10.70 (s, 1H). | 492 | 490 | 2,2,2-trifluoro methyl-1-methyl-ethoxymethyl group: R-form Alpha position of carbonyl group (amide): R-form |

TABLE 2-continued

| Example No. | Molecular Structure | NMR (400 MHz) | MS (M + H) | MS (M − H) | Comments |
|---|---|---|---|---|---|
| 592 | 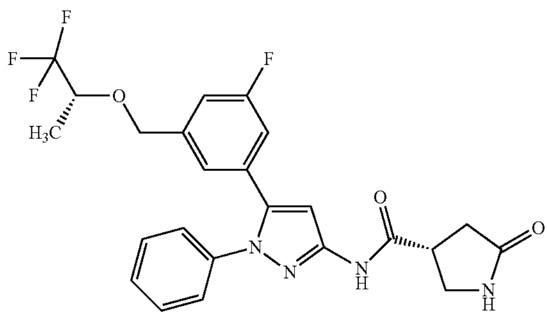 [SMILES: C[C@@H](OCc1cc(F)cc(-c2cc(NC(=O)[C@H]3CNC(=O)C3)nn2-c2ccccc2)c1)C(F)(F)F] | $^1$H-NMR (DMSO-D6) δ: 1.20 (d, 3H, J = 6.8 Hz), 3.36 (dd, 1H, J = 8.6, 6.2 Hz), 3.60 (dd, 1H, J = 9.3, 8.6 Hz), 4.12 (tq, 1H, J = 9.7, 6.0 Hz), 4.32 (dd, 1H, J = 9.3, 6.2 Hz), 4.62 (d, 1H, J = 12.5 Hz), 4.63 (d, 1H, J = 12.5 Hz), 6.33 (s, 1H), 6.59 (s, 1H), 6.95-7.00 (m, 2H), 7.10 (s, 1H), 7.17 (d, 1H, J = 9.2 Hz), 7.24-7.29 (m, 2H), 7.34-7.46 (m, 3H), 10.73 (s, 1H). | 492 | 490 | 2,2,2-trifluoro methyl-1-methyl-ethoxymethyl group: R-form Alpha position of carbonyl group (amide): R-form |
| 593 | 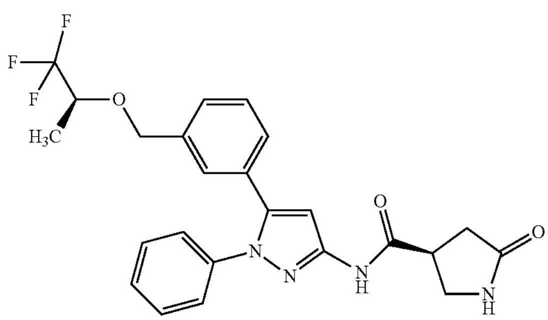 [SMILES: C[C@H](OCc1cccc(-c2cc(NC(=O)[C@@H]3CNC(=O)C3)nn2-c2ccccc2)c1)C(F)(F)F] | $^1$H-NMR (DMSO-D6) δ: 1.20 (d, 3H, J = 6.4 Hz), 2.39 (d, 2H, J = 8.4 Hz), 3.32-3.54 (m, 3H), 4.08-4.17 (m, 1H), 4.61 (d, 1H, J = 13.2 Hz), 4.63 (d, 1H, J = 13.2 Hz), 6.94-7.00 (m, 2H), 7.09 (s, 1H), 7.17 (d, 1H, J = 9.6 Hz), 7.23-7.29 (m, 2H), 7.34-7.45 (m, 3H), 7.63 (br s, 1H), 10.88 (s, 1H). | 491 | 489 | 2,2,2-trifluoro methyl-1-methyl-ethoxymethyl group: S-form Lactam ring: S-form |
| 594 | 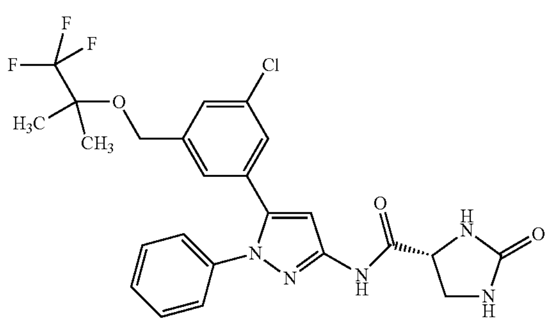 [SMILES: CC(C)(OCc1cc(Cl)cc(-c2cc(NC(=O)[C@H]3CNC(=O)N3)nn2-c2ccccc2)c1)C(F)(F)F] | $^1$H-NMR (DMSO-D6) δ: 1.32 (s, 6H), 3.36 (dd, 1H, J = 8.6, 6.2 Hz), 3.60 (dd, 1H, J = 9.3, 8.6 Hz), 4.32 (dd, 1H, J = 9.3, 6.2 Hz), 4.54 (s, 2H), 6.33 (s, 1H), 6.60 (s, 1H), 6.98 (s, 1H), 7.16 (s, 1H), 7.20 (t, 1H, J = 2.0 Hz), 7.24-7.29 (m, 2H), 7.33-7.46 (m, 4H), 10.74 (s, 1H). | 522 | 520 | R-form |
| 595 | 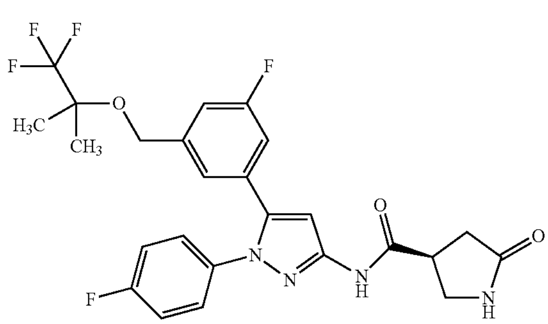 [SMILES: CC(C)(OCc1cc(F)cc(-c2cc(NC(=O)[C@@H]3CNC(=O)C3)nn2-c2ccc(F)cc2)c1)C(F)(F)F] | 1H-NMR (DMSO-D6) δ: 1.33 (s, 6H), 2.35-2.58 (m, 2H), 3.28-3.55 (m, 3H), 4.54 (s, 2H), 6.97 (s, 1H), 7.00 (s, 1H), 7.04 (d, 1H, J = 9.2 Hz), 7.13 (d, 1H, J = 9.2 Hz), 7.24-7.35 (m, 4H), 7.63 (s, 1H), 10.87 (s, 1H). | 523 | 521 | S-form |

TABLE 2-continued

| Example No. | Molecular Structure | NMR (400 MHz) | MS (M + H) | MS (M − H) | Comments |
|---|---|---|---|---|---|
| 596 | 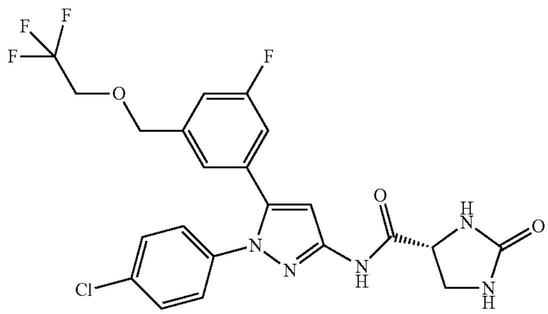 [SMILES: O=C1NC[C@H](C(=O)Nc2cc(-c3cc(F)cc(COCC(F)(F)F)c3)n(-c3ccc(Cl)cc3)n2)N1] | 1H-NMR (DMSO-D6) δ: 3.35 (dd, 1H, J = 9.1, 5.4 Hz), 3.59 (dd, 1H, J = 10.1, 9.1 Hz), 4.01 (q, 2H, J = 9.3 Hz), 4.32 (dd, 1H, J = 10.1, 5.4 Hz), 4.63 (s, 2H), 6.33 (s, 1H), 6.59 (s, 1H), 7.00 (s, 1H), 7.05-7.11 (m, 2H), 7.18-7.23 (m, 1H), 7.25-7.31 (m, 2H), 7.46-7.51 (m, 2H), 10.77 (s, 1H). | 512 | 510 | S-form |
| 597 | 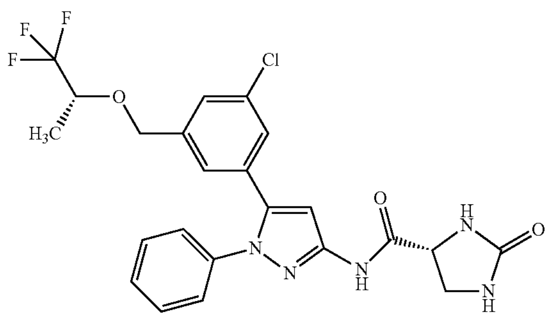 [SMILES: C[C@@H](OCc1cc(Cl)cc(-c2cc(NC(=O)[C@H]3CNC(=O)N3)nn2-c2ccccc2)c1)C(F)(F)F] | 1H-NMR (DMSO-D6) δ: 1.20 (d, 3H, J = 6.4 Hz), 3.36 (dd, 1H, J = 9.1, 5.4 Hz), 3.60 (dd, 1H, J = 9.7, 9.1 Hz), 4.07-4.18 (m, 1H), 4.33 (dd, 1H, J = 9.7, 5.4 Hz), 4.60 (d, 1H, J = 12.1 Hz), 4.63 (d, 1H, J = 12.1 Hz), 6.33 (s, 1H), 6.59 (s, 1H), 6.99 (s, 1H), 7.19-7.22 (m, 2H), 7.25-7.29 (m, 2H), 7.35-7.46 (m, 4H), 10.73 (s, 1H). | 508 | 506 | 2,2,2-trifluoromethyl-1-methyl-ethoxymethyl group: R-form Alpha position of carbonyl group (amide): R-form |
| 598 | 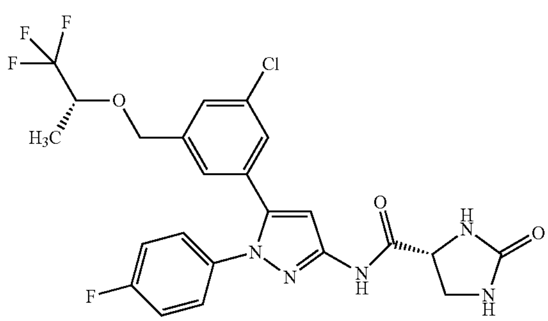 [SMILES: C[C@@H](OCc1cc(Cl)cc(-c2cc(NC(=O)[C@H]3CNC(=O)N3)nn2-c2ccc(F)cc2)c1)C(F)(F)F] | 1H-NMR (DMSO-D6) δ: 1.20 (d, 3H, J = 6.0 Hz), 3.35 (dd, 1H, J = 8.5, 6.0 Hz), 3.60 (dd, 1H, J = 9.3, 8.5 Hz), 4.06-4.17 (m, 1H), 4.32 (dd, 1H, J = 9.3, 6.0 Hz), 4.59 (d, 1H, J = 12.1 Hz), 4.63 (d, 1H, J = 12.1 Hz), 6.33 (s, 1H), 6.59 (s, 1H), 6.99 (s, 1H), 7.13-7.17 (m, 1H), 7.23-7.36 (m, 5H), 7.38-7.41 (m, 1H), 10.73 (s, 1H). | 526 | 524 | 2,2,2-trifluoromethyl-1-methyl-ethoxymethyl group: R-form Alpha position of carbonyl group (amide): R-form |
| 599 | 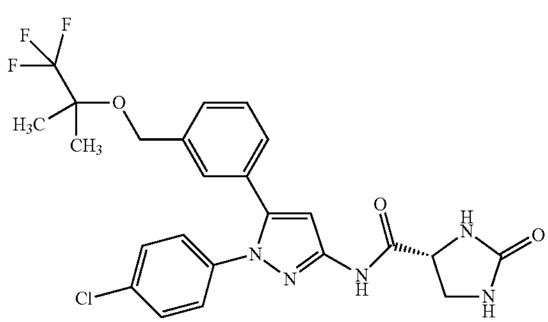 [SMILES: CC(C)(OCc1cccc(-c2cc(NC(=O)[C@H]3CNC(=O)N3)nn2-c2ccc(Cl)cc2)c1)C(F)(F)F] | 1H-NMR (DMSO-D6) δ: 1.34 (s, 6H), 3.35 (dd, 1H, J = 9.7, 6.0 Hz), 3.60 (dd, 1H, J = 9.7, 8.9 Hz), 4.32 (dd, 1H, J = 8.9, 6.0 Hz), 4.54 (s, 2H), 6.33 (s, 1H), 6.59 (s, 1H), 6.93 (s, 1H), 7.19-7.23 (m, 2H), 7.23-7.29 (m, 2H), 7.30-7.34 (m, 1H), 7.35-7.41 (m, 1H), 7.44-7.49 (m, 2H), 10.74 (s, 1H). | 522 | 520 | R-form |

| Example No. | Molecular Structure | NMR (400 MHz) | MS (M + H) | MS (M − H) | Comments |
|---|---|---|---|---|---|
| 600 | 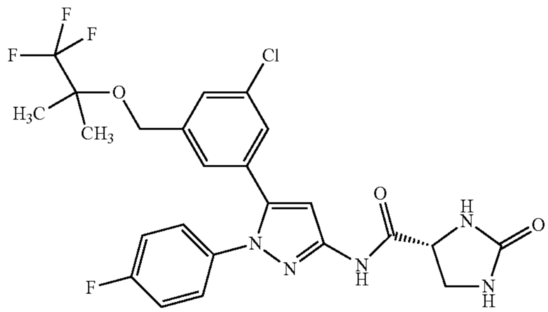 [SMILES: CC(C)(OCc1cc(Cl)cc(-c2cc(NC(=O)[C@H]3CNC(=O)N3)nn2-c2ccc(F)cc2)c1)C(F)(F)F] | ¹H-NMR (DMSO-D₆) δ: 1.32 (s, 6H), 3.35 (dd, 1H, J = 8.6, 6.2 Hz), 3.60 (dd, 1H, J = 9.3, 8.6 Hz), 4.32 (dd, 1H, J = 9.3, 6.2 Hz), 4.53 (s, 2H), 6.33 (s, 1H), 6.60 (s, 1H), 6.99 (s, 1H), 7.10 (s, 1H), 7.23-7.37 (m, 6H), 10.73 (s, 1H). | 540 | 538 | R-form |
| 601 | 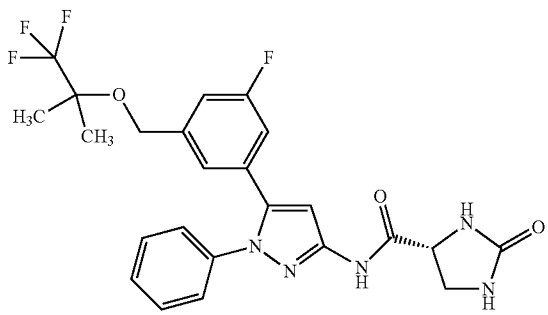 [SMILES: CC(C)(OCc1cc(F)cc(-c2cc(NC(=O)[C@H]3CNC(=O)N3)nn2-c2ccccc2)c1)C(F)(F)F] | 1H-NMR (DMSO-D6) δ: 1.33 (s, 6H), 3.36 (dd, 1H, J = 9.1, 5.8 Hz), 3.59 (dd, 1H, J = 9.1, 8.7 Hz), 4.32 (dd, 1H, J = 8.7, 5.8 Hz), 4.55 (s, 2H), 6.33 (s, 1H), 6.59 (s, 1H), 6.96-6.99 (m, 2H), 7.06 (s, 1H), 7.13 (d, 1H, J = 8.5 Hz), 7.25-7.28 (m, 2H), 7.37-7.45 (m, 3H), 10.73 (s, 1H). | 506 | 504 | R-form |
| 602 | 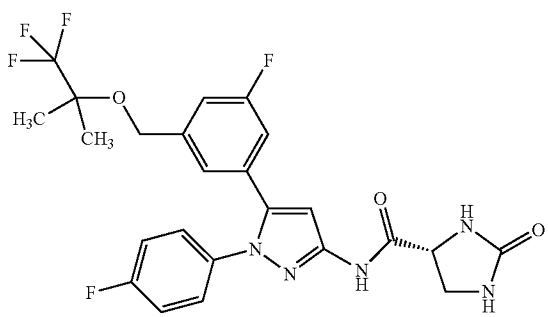 [SMILES: CC(C)(OCc1cc(F)cc(-c2cc(NC(=O)[C@H]3CNC(=O)N3)nn2-c2ccc(F)cc2)c1)C(F)(F)F] | 1H-NMR (DMSO-D6) δ: 1.33 (s, 6H), 3.36 (dd, 1H, J = 9.2, 5.5 Hz), 3.60 (dd, 1H, J = 9.2, 9.5 Hz), 4.32 (dd, 1H, J = 9.5, 5.5 Hz), 4.54 (s, 2H), 6.33 (s, 1H), 6.60 (s, 1H), 6.98 (s, 1H), 7.01 (s, 1H), 7.05 (d, 1H, J = 9.7 Hz), 7.14 (d, 1H, J = 9.7 Hz), 7.25-7.33 (m, 4H), 10.73 (s, 1H). | 524 | 522 | R-form |
| 603 | 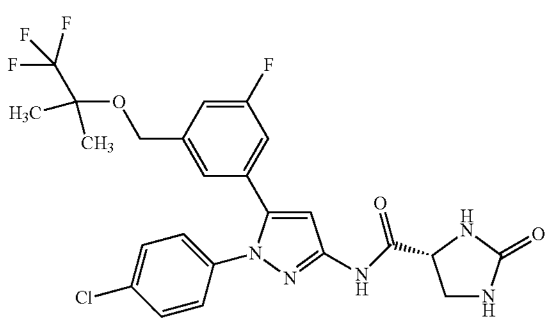 [SMILES: CC(C)(OCc1cc(F)cc(-c2cc(NC(=O)[C@H]3CNC(=O)N3)nn2-c2ccc(Cl)cc2)c1)C(F)(F)F] | 1H-NMR (DMSO-D6) δ: 1.32 (s, 6H), 3.35 (dd, 1H, J = 8.7, 5.8 Hz), 3.60 (dd, 1H, J = 9.5, 8.7 Hz), 4.32 (dd, 1H, J = 9.5, 5.8 Hz), 4.55 (s, 2H), 6.32 (s, 1H), 6.59 (s, 1H), 6.99 (s, 1H), 7.02 (s, 1H), 7.08 (d, 1H, J = 10.1 Hz), 7.15 (d, 1H, J = 10.1 Hz), 7.28 (dd, 2H, J = 6.6, 2.2 Hz), 7.48 (dd, 2H, J = 6.6, 2.2 Hz), 10.76 (s, 1H). | 540 | 538 | R-form |
| 604 | 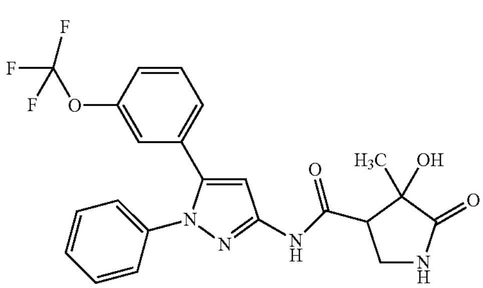 [SMILES: CC1(O)C(=O)NCC1C(=O)Nc1cc(-c2cccc(OC(F)(F)F)c2)n(-c2ccccc2)n1] | 1H-NMR (DMSO-D6) δ: 1.35 (s, 3H), 3.12-3.17 (m, 2H), 3.47-3.51 (m, 1H), 5.38 (s, 1H), 7.00 (s, 1H), 7.08 (s, 1H), 7.24-7.27 (m, 2H), 7.34-7.44 (m, 5H), 7.52 (t, 1H, J = 8.0 Hz), 7.78 (s, 1H), 10.62 (s, 1H). | 461 | 459 | Single Diastereo isomer (racemate) Geometrical isomer of Example 605 |

TABLE 2-continued

| Example No. | Molecular Structure | NMR (400 MHz) | MS (M + H) | MS (M − H) | Comments |
|---|---|---|---|---|---|
| 605 | 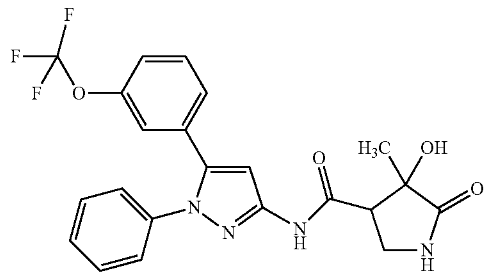 [SMILES: CC1(O)C(=O)NCC1C(=O)Nc1cc(-c2cccc(OC(F)(F)F)c2)n(-c2ccccc2)n1] | 1H-NMR (DMSO-D6) δ: 1.14 (s, 3H), 3.27-3.29 (m, 1H), 3.33-3.34 (m, 2H), 5.65 (s, 1H), 7.00 (s, 1H), 7.09 (s, 1H), 7.25-7.27 (m, 2H), 7.34-7.45 (m, 5H), 7.51-7.54 (m, 1H), 7.78 (s, 1H), 10.46 (s, 1H). | 461 | 459 | Single Diastereo isomer (racemate) Geometrical isomer of Example 604 |

In the table 2, Structure Information A, B, C, D and E (Examples 255, 256, 275, 277, 307, 309, 397, 398, 404 and 405) are the information on the enantiomer derived from an asymmetric carbon atom of the alphaposition of carbonyl group. Said enantiomer was isolated and purified according to the similar method as the Auxiliary step 2 of the Preparation Method 3-1 above.

Structure Information A

Examples 255 and 256

Example 255 was synthesized using a high-polarity component obtained by silicagel thin-layer chromatography (eluent: ethyl acetate) between the following Compound [60] or Compound [61]. Example 256 was synthesized using a low-polarity component.

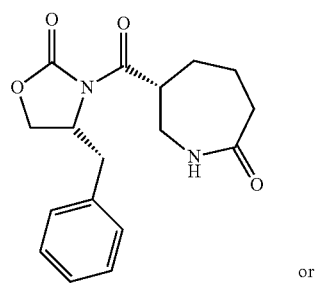

[60]

or

[61]

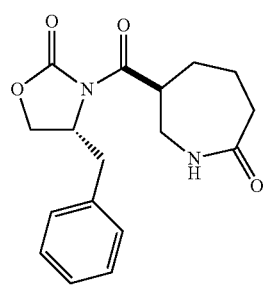

Structure Information B

Examples 275 and 277

Example 275 was synthesized using a low-polarity component obtained by silicagel thin-layer chromatography (eluent: n-hexane/ethyl acetate=1/3) between the following Compound [62] or Compound [63]. Example 277 was synthesized using a high-polarity component.

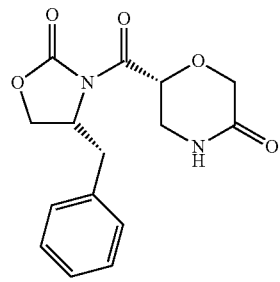

[62]

or

[63]

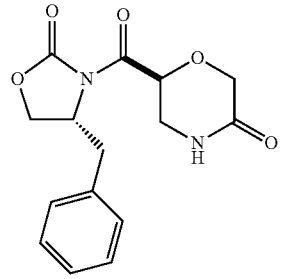

Structure Information C

Examples 307 and 309

Example 307 was synthesized using a low-polarity component obtained by silicagel thin-layer chromatography (eluent: n-hexane/ethyl acetate=1/1) between the following Compound [64] or Compound [65]. Example 309 was synthesized using a high-polarity component.

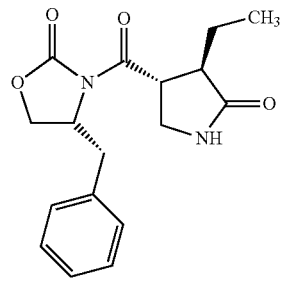

[64]

or

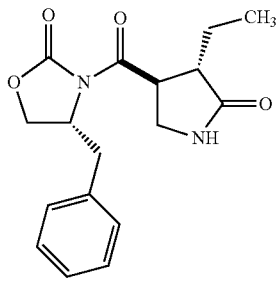

Structure Information D

Examples 397 and 398

Example 397 was synthesized using a low-polarity component obtained by silicagel thin-layer chromatography (eluent: n-hexane/ethyl acetate=3/7) between the following Compound [66] or Compound [67]. Example 398 was synthesized using a high-polarity component.

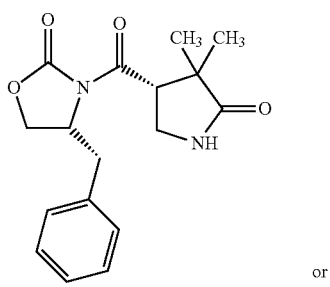

Structure Information E

Examples 404 and 405

Example 404 was synthesized using a low-polarity component obtained by silicagel thin-layer chromatography (eluent: chloroform/ethyl acetate=1/1) between the following Compound [68] or Compound [69]. Example 405 was synthesized using a high-polarity component.

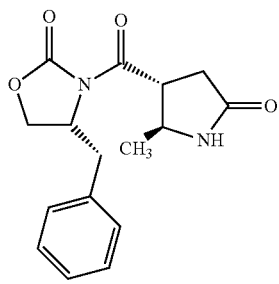

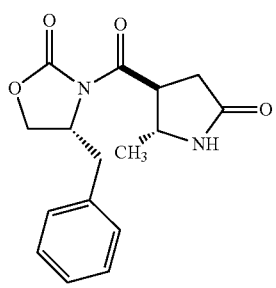

Test Example

SGLT1 inhibitory activity of a test compound ($IC_{50}$ value) was calculated based on an amount of intake into a cell of labeled α-methyl-D-glucopyranoside ($^{14}$C-AMG) which is transported by SGLT1.

1) Construction of Human SGLT1 Expression Plasmid

A DNA fragment containing human SGLT1, wherein NheI recognition and cleavage sequence was added upstream of a Kozac consensus sequence of the vector; and a stop codon (TAG) and a SalI recognition and cleavage sequence was added just downstream of a coding region of the human SGLT1, was amplified by PCR using pCMV6-hSGLT1 (OriGene) as a template. The purified DNA fragment was cleaved by restriction enzymes NheI and SalI, and the obtained fragment was ligated into pcDNA3.1 (+) which was cleaved by NheI and XhoI to construct human SGLT1 expression plasmid. The nucleic acid sequence of human SGLT1 inserted into the vector was completely identical to the coding region of human SGLT1 sequence (Accession number NM_000343) registered in GenBank. In addition, the sequence which connects the inserted nucleic acid sequence to the vector was those to be expected.

2) Establishment of Stable Cell Lines Expressing Human SGLT1

A human SGLT1 expression plasmid pcDNA-hSGLT1 was transfected into CHO-K1 cells by Lipofectamine-2000 (Invitrogen). The cells were cultured in the presence of G418 (Nakalai tesque) and drug-resistant cells were selected. A cell line having the highest S/B ratio of an amount of $^{14}$C-AMG uptake per cell treated by solvent to an amount of $^{14}$C-AMG uptake per cell treated by phlorizin (SGLT inhibitor) was selected from the drug-resistant cells as a stable cell lines expressing human SGLT1.

3) Evaluation of SGLT1 Inhibitory Activity

The stable cell line expressing human SGLT1 was seeded at $5\times10^4$ cells/well on BioCoat™ Poly-D-Lysine 96 well plate with Lid (Becton Dickinson and Company) and cultured at 37° C. under 5% $CO_2$ overnight. The medium was replaced with 100 μL/well of a Na (−) buffer (140 mM choline chloride, 2 mM KCl, 1 mM $MgCl_2$, 1 mM $CaCl_2$, 10 mM HEPES, 5 mM Tris, pH7.4) followed by incubation for 20 minutes at 37° C. under 5% $CO_2$. After removing the Na (−) buffer, a test compound solution which was prepared from Na (+) buffer (140 mM NaCl, 2 mM KCl, 1 mM $MgCl_2$, 1 mM $CaCl_2$, 10 mM HEPES, 5 mM Tris, pH7.4) containing BSA was added thereto at 40 μL/well. In addition, Na (+) buffer containing 8 kBq of $^{14}$C-AMG and 2 mM AMG was added thereto at 40 μL/well, and was mixed well. Na (−) buffer containing BSA was added to a blank well at 40 μL/well and additionally adding a Na (+) buffer containing 8 kBq of $^{14}$C-AMG and 2 mM AMG, and was mixed well. Cells were incubated for 1 hour at 37° C. under 5% $CO_2$. After the reaction, the cells were washed twice with 100 μL/well of iced wash buffer (100 mM AMG, 140 mM choline chloride, 2 mM KCl, 1 mM $MgCl_2$, 1 mM $CaCl_2$, 10 mM HEPES, 5 mM Tris, pH7.4), then lysed in 50 μL/well of a 0.2N aqueous solution of NaOH. The cell lysate was transferred to OptiPlate96 (Perkin-Elmer) and 100 μL/well of MicroScint-40 (Perkin-Elmer) was dispensed. The radioactivity was counted by TOPCOUNT NXT (Perkin-Elmer).

A data was obtained by deducting the average value (CPM) of blank wells from the average value (CPM) of each treated well. The inhibition ratio (%) was calculated by the following formula: inhibition rate (%)=[(A−B)/A]×100, where A is a data of the solvent control, and B is a data of a test compound. IC50 values (50% Inhibition Concentration) of a test compound was calculated based on two concentrations which have the inhibition rate before as well as after 50% and their inhibition rates. The each result of Examples 1 to 234 and Examples 249 to 605 is shown in the following tables 3 and 4.

TABLE 3

| Example No. | human SGLT1 $IC_{50}$ (uM) | % inhibition |
|---|---|---|
| 1 | 0.004 | |
| 2 | 0.0034 | |
| 3 | 0.0062 | |
| 4 | 0.0086 | |
| 5 | 0.0069 | |
| 6 | 0.0072 | |
| 7 | 0.033 | |
| 8 | 0.02 | |
| 9 | 1.6 | |
| 10 | 5.5 | |
| 11 | 0.0046 | |
| 12 | 4.4 | |
| 13 | 0.25 | |
| 14 | 0.012 | |
| 15 | 0.04 | |
| 16 | 11.7 | |
| 17 | 0.066 | |
| 18 | 0.031 | |
| 19 | 0.033 | |
| 20 | 0.15 | |
| 21 | 0.68 | |
| 22 | 0.0047 | |
| 23 | 0.0074 | |
| 24 | 0.13 | |
| 25 | 0.0018 | |
| 26 | 0.0035 | |
| 27 | 0.023 | |
| 28 | 0.052 | |
| 29 | 0.024 | |
| 30 | 0.095 | |
| 31 | 0.27 | |
| 32 | 0.012 | |
| 33 | 0.0061 | |
| 34 | 0.0068 | |
| 35 | 0.015 | |
| 36 | 0.0094 | |
| 37 | 0.016 | |

TABLE 3-continued

| Example No. | human SGLT1 $IC_{50}$ (uM) | % inhibition |
|---|---|---|
| 38 | 0.13 | |
| 39 | 0.35 | |
| 40 | 0.65 | |
| 41 | 1.9 | |
| 42 | 0.19 | |
| 43 | 0.011 | |
| 44 | 0.034 | |
| 45 | 0.0043 | |
| 46 | 0.0037 | |
| 47 | 0.42 | |
| 48 | 0.0035 | |
| 49 | 0.012 | |
| 50 | 0.022 | |
| 51 | 0.08 | |
| 52 | 0.0037 | |
| 53 | 0.0038 | |
| 54 | 0.01 | |
| 55 | 0.018 | |
| 56 | 14.3 | |
| 57 | 0.23 | |
| 58 | 3.5 | |
| 59 | 0.044 | |
| 60 | 0.017 | |
| 61 | 0.021 | |
| 62 | 0.47 | |
| 63 | 2.4 | |
| 64 | 0.012 | |
| 65 | 0.04 | |
| 66 | 0.21 | |
| 67 | | 29% (0.1 uM) |
| 68 | 0.0067 | |
| 69 | 0.018 | |
| 70 | 0.0016 | |
| 71 | 0.0035 | |
| 72 | 0.0047 | |
| 73 | 0.013 | |
| 74 | 0.0031 | |
| 75 | 0.0039 | |
| 76 | 0.0017 | |
| 77 | 0.002 | |
| 78 | 0.0077 | |
| 79 | 0.022 | |
| 80 | 0.22 | |
| 81 | | 43% (0.3 uM) |
| 82 | 0.012 | |
| 83 | 0.011 | |
| 84 | 0.0072 | |
| 85 | 0.05 | |
| 86 | 0.054 | |
| 87 | 0.11 | |
| 88 | 0.017 | |
| 89 | 0.14 | |
| 90 | 0.034 | |
| 91 | 0.0018 | |
| 92 | 0.025 | |
| 93 | 0.031 | |
| 94 | 0.01 | |
| 95 | 0.0024 | |
| 96 | 0.37 | |
| 97 | 0.01 | |
| 98 | 0.03 | |
| 99 | 0.073 | |
| 100 | 0.0019 | |
| 101 | 0.0024 | |
| 102 | 0.0022 | |
| 103 | 0.005 | |
| 104 | 0.0098 | |
| 105 | 0.037 | |
| 106 | 0.0068 | |
| 107 | 0.044 | |
| 108 | | 45% (0.1 uM) |
| 109 | 0.065 | |
| 110 | 0.085 | |

TABLE 3-continued

| Example No. | human SGLT1 IC$_{50}$ (uM) | % inhibition |
|---|---|---|
| 111 | 0.046 | |
| 112 | 0.083 | |
| 113 | 0.012 | |
| 114 | 0.027 | |
| 115 | 0.041 | |
| 116 | 0.0061 | |
| 117 | 0.0014 | |
| 118 | 9.3 | |
| 119 | 0.57 | |
| 120 | 0.0045 | |
| 121 | 0.011 | |
| 122 | | 9% (1 uM) |
| 123 | 0.005 | |
| 124 | 0.17 | |
| 125 | 0.017 | |
| 126 | 0.0012 | |
| 127 | 0.0014 | |
| 128 | 0.017 | |
| 129 | 0.028 | |
| 130 | 0.0013 | |
| 131 | 0.0063 | |
| 132 | 0.0009 | |
| 133 | 0.011 | |
| 134 | 0.0068 | |
| 135 | 0.011 | |
| 136 | 0.028 | |
| 137 | 0.014 | |
| 138 | 0.0015 | |
| 139 | 0.0017 | |
| 140 | 0.0011 | |
| 141 | 0.0055 | |
| 142 | 0.0092 | |
| 143 | 0.0065 | |
| 144 | 0.0013 | |
| 145 | | 43% (1 uM) |
| 146 | | 38% (0.1 uM) |
| 147 | 0.015 | |
| 148 | 0.01 | |
| 149 | 0.0095 | |
| 150 | 0.0077 | |
| 151 | 0.019 | |
| 152 | 0.0093 | |
| 153 | 0.0033 | |
| 154 | 0.0011 | |
| 155 | 0.019 | |
| 156 | 0.0027 | |
| 157 | 0.013 | |
| 158 | 0.0034 | |
| 159 | 0.017 | |
| 160 | 0.011 | |
| 161 | 0.022 | |
| 162 | 0.019 | |
| 163 | 0.0071 | |
| 164 | 0.0026 | |
| 165 | 0.022 | |
| 166 | 0.0029 | |
| 167 | 0.015 | |
| 168 | 0.036 | |
| 169 | | 4% (0.1 uM) |
| 170 | 0.003 | |
| 171 | 0.0083 | |
| 172 | 0.0055 | |
| 173 | 0.013 | |
| 174 | | 9% (1 uM) |
| 175 | | 40% (0.1 uM) |
| 176 | 0.055 | |
| 177 | 0.056 | |
| 178 | 0.014 | |
| 179 | 0.019 | |
| 180 | | −10% (0.3 uM) |
| 181 | 0.0043 | |
| 182 | 0.0038 | |
| 183 | 20.1 | |
| 184 | | 3% (0.03 uM) |
| 185 | 0.066 | |
| 186 | 0.075 | |
| 187 | 0.042 | |
| 188 | 0.023 | |
| 189 | 0.2 | |
| 190 | 0.13 | |
| 191 | 0.054 | |
| 192 | | 6% (0.3 uM) |
| 193 | 0.0013 | |
| 194 | 0.0007 | |
| 195 | 0.0083 | |
| 196 | 0.0048 | |
| 197 | 0.18 | |
| 198 | 0.067 | |
| 199 | | 40% (0.3 uM) |
| 200 | 0.12 | |
| 201 | 0.093 | |
| 202 | 0.012 | |
| 203 | 0.0014 | |
| 204 | 0.018 | |
| 205 | 0.0036 | |
| 206 | 0.0048 | |
| 207 | 0.0047 | |
| 208 | 0.0013 | |
| 209 | 0.0092 | |
| 210 | 0.0059 | |
| 211 | 0.017 | |
| 212 | 0.0058 | |
| 213 | 0.014 | |
| 214 | 0.0023 | |
| 215 | 0.0014 | |
| 216 | 0.0087 | |
| 217 | 0.0062 | |
| 218 | | 26% (0.1 uM) |
| 219 | | 20% (0.1 uM) |
| 220 | | 16% (0.1 uM) |
| 221 | | 15% (0.1 uM) |
| 222 | 0.0041 | |
| 223 | 0.0023 | |
| 224 | 0.0063 | |
| 225 | 0.0039 | |
| 226 | 0.0033 | |
| 227 | 0.0021 | |
| 228 | 0.0086 | |
| 229 | 0.0031 | |
| 230 | 0.012 | |
| 231 | 0.0067 | |
| 232 | 0.032 | |
| 233 | 0.02 | |
| 234 | 0.0074 | |

TABLE 4

| Example No. | human SGLT1 IC$_{50}$ (uM) | % Inhibition |
|---|---|---|
| 235 | 0.0034 | |
| 236 | 0.00535 | |
| 237 | 0.00385 | |
| 238 | 0.0079 | |
| 239 | 0.007 | |

TABLE 4-continued

| Example No. | human SGLT1 IC$_{50}$ (uM) | % Inhibition |
|---|---|---|
| 240 | 0.02 | |
| 241 | 0.00995 | |
| 242 | 0.009 | |
| 243 | 0.014 | |
| 244 | 0.008 | |
| 245 | 0.019 | |
| 246 | 0.0115 | |
| 247 | 0.022 | |
| 248 | 0.025 | |
| 249 | 0.039 | |
| 250 | 0.0034 | |
| 251 | | 41% (0.1 uM) |
| 252 | | 7% (0.03 uM) |
| 253 | 0.014 | |
| 254 | | 49% (0.3 uM) |
| 255 | | 7% (0.3 uM) |
| 256 | | 3% (0.3 uM) |
| 257 | 0.076 | |
| 258 | 0.023 | |
| 259 | | 20% (0.1 uM) |
| 260 | 0.023 | |
| 261 | 0.00377 | |
| 262 | 0.006 | |
| 263 | 0.37 | |
| 264 | 0.039 | |
| 265 | | 17% (0.1 uM) |
| 266 | 0.045 | |
| 267 | 0.081 | |
| 268 | 0.0085 | |
| 269 | 0.092 | |
| 270 | 0.045 | |
| 271 | 0.29 | |
| 272 | 0.037 | |
| 273 | 0.027 | |
| 274 | 0.18 | |
| 275 | | 48% (0.1 uM) |
| 276 | | 30% (0.1 uM) |
| 277 | | 48% (0.1 uM) |
| 278 | | 34% (0.1 uM) |
| 279 | 0.0175 | |
| 280 | 0.0098 | |
| 281 | 0.0215 | |
| 282 | 0.0099 | |
| 283 | 0.11 | |
| 284 | 0.075 | |
| 285 | 0.021 | |
| 286 | 0.03 | |
| 287 | 0.012 | |
| 288 | 0.0115 | |
| 289 | 0.0045 | |
| 290 | 0.0055 | |
| 291 | 0.0051 | |
| 292 | | 43% (0.1 uM) |
| 293 | | 27% (0.1 uM) |
| 294 | 0.0245 | |
| 295 | 0.029 | |
| 296 | | 48% (0.1 uM) |
| 297 | 0.071 | |
| 298 | | 38% (0.1 uM) |
| 299 | 0.033 | |
| 300 | 0.038 | |
| 301 | 0.063 | |
| 302 | 0.0015 | |
| 303 | 0.0047 | |
| 304 | 0.01 | |
| 305 | 0.029 | |
| 306 | 0.013 | |
| 307 | 0.006 | |
| 308 | 0.016 | |
| 309 | 0.049 | |
| 310 | | 42% (0.1 uM) |
| 311 | 0.0175 | |
| 312 | 0.022 | |
| 313 | 0.0195 | |
| 314 | 0.015 | |
| 315 | 0.0155 | |
| 316 | 0.039 | |
| 317 | | 40% (0.1 uM) |
| 318 | 0.0032 | |
| 319 | 0.028 | |
| 320 | 0.003 | |
| 321 | 0.022 | |
| 322 | 0.0047 | |
| 323 | 0.0048 | |
| 324 | 0.0022 | |
| 325 | 0.047 | |
| 326 | 0.015 | |
| 327 | | 15% (0.3 uM) |
| 328 | 0.029 | |
| 329 | | 35% (0.3 uM) |
| 330 | | 11% (0.3 uM) |
| 331 | 0.022 | |
| 332 | 0.022 | |
| 333 | 0.02 | |
| 334 | 0.0063 | |
| 335 | 0.016 | |
| 336 | 0.025 | |
| 337 | 0.032 | |
| 338 | 0.017 | |
| 339 | 0.057 | |
| 340 | 0.016 | |
| 341 | 0.06 | |
| 342 | 0.045 | |
| 343 | 0.0072 | |
| 344 | 0.00335 | |
| 345 | 0.0079 | |
| 346 | 0.0027 | |
| 347 | | 11% (0.3 uM) |
| 348 | | 26% (0.3 uM) |
| 349 | 0.072 | |
| 350 | 0.025 | |
| 351 | 0.032 | |
| 352 | 0.014 | |
| 353 | 0.016 | |
| 354 | 0.079 | |
| 355 | 0.0315 | |
| 356 | 0.011 | |
| 357 | 0.031 | |
| 358 | 0.017 | |
| 359 | 0.039 | |
| 360 | 0.0015 | |
| 361 | | 33% (0.1 uM) |
| 362 | 0.03 | |
| 363 | 0.013 | |
| 364 | 0.0083 | |
| 365 | 0.018 | |
| 366 | 0.02 | |
| 367 | 0.0115 | |
| 368 | 0.056 | |
| 369 | 0.015 | |
| 370 | 0.00635 | |
| 371 | 0.036 | |
| 372 | 0.014 | |
| 373 | 0.0053 | |
| 374 | 0.0088 | |
| 375 | 0.013 | |
| 376 | 0.031 | |
| 377 | 0.0097 | |
| 378 | 0.021 | |
| 379 | 0.00525 | |
| 380 | 0.00675 | |
| 381 | 0.0115 | |
| 382 | 0.012 | |
| 383 | 0.014 | |
| 384 | 0.048 | |
| 385 | 0.007 | |
| 386 | 0.035 | |
| 387 | 0.0125 | |
| 388 | 0.00535 | |
| 389 | 0.015 | |
| 390 | 0.0094 | |
| 391 | 0.00375 | |
| 392 | 0.0057 | |
| 393 | 0.00525 | |

TABLE 4-continued

| Example No. | human SGLT1 IC$_{50}$ (uM) | % Inhibition |
|---|---|---|
| 394 | 0.015 | |
| 395 | 0.013 | |
| 396 | 0.031 | |
| 397 | 0.016 | |
| 398 | | 7% (0.1 uM) |
| 399 | 0.019 | |
| 400 | 0.015 | |
| 401 | 0.013 | |
| 402 | 0.017 | |
| 403 | 0.012 | |
| 404 | 0.018 | |
| 405 | | 29% (0.1 uM) |
| 406 | 0.00785 | |
| 407 | 0.0076 | |
| 408 | 0.008 | |
| 409 | 0.012 | |
| 410 | 0.022 | |
| 411 | 0.0044 | |
| 412 | 0.01095 | |
| 413 | | 48% (0.1 uM) |
| 414 | 0.01145 | |
| 415 | 0.013 | |
| 416 | 0.015 | |
| 417 | 0.0043 | |
| 418 | 0.00235 | |
| 419 | 0.00475 | |
| 420 | 0.047 | |
| 421 | 0.02 | |
| 422 | 0.014 | |
| 423 | 0.016 | |
| 424 | 0.0071 | |
| 425 | 0.00185 | |
| 426 | 0.00205 | |
| 427 | | 49% (0.1 uM) |
| 428 | | 31% (0.1 uM) |
| 429 | | 40% (0.1 uM) |
| 430 | | 8% (0.1 uM) |
| 431 | | 21% (0.1 uM) |
| 432 | | 14% (0.1 uM) |
| 433 | | 8% (0.1 uM) |
| 434 | 0.021 | |
| 435 | 0.00345 | |
| 436 | 0.019 | |
| 437 | 0.0045 | |
| 438 | 0.0031 | |
| 439 | | 45% (0.1 uM) |
| 440 | 0.037 | |
| 441 | 0.009 | |
| 442 | 0.015 | |
| 443 | 0.011 | |
| 444 | 0.01 | |
| 445 | 0.0067 | |
| 446 | 0.0056 | |
| 447 | 0.0047 | |
| 448 | 0.0043 | |
| 449 | 0.0023 | |
| 450 | 0.0081 | |
| 451 | 0.0033 | |
| 452 | 0.0017 | |
| 453 | 0.0017 | |
| 454 | 0.002 | |
| 455 | 0.0031 | |
| 456 | 0.0034 | |
| 457 | 0.0037 | |
| 458 | 0.0059 | |
| 459 | 0.0048 | |
| 460 | 0.0021 | |
| 461 | 0.0014 | |
| 462 | 0.0034 | |
| 463 | 0.0011 | |
| 464 | 0.0014 | |
| 465 | 0.0017 | |
| 466 | 0.016 | |
| 467 | 0.026 | |
| 468 | 0.017 | |
| 469 | 0.0052 | |
| 470 | 0.007 | |
| 471 | 0.015 | |
| 472 | 0.0047 | |
| 473 | 0.0075 | |
| 474 | 0.0073 | |
| 475 | 0.0031 | |
| 476 | 0.021 | |
| 477 | 0.025 | |
| 478 | 0.036 | |
| 479 | | 46% (0.1 uM) |
| 480 | 0.0068 | |
| 481 | 0.0087 | |
| 482 | 0.012 | |
| 483 | 0.059 | |
| 484 | 0.0042 | |
| 485 | 0.0041 | |
| 486 | 0.0065 | |
| 487 | 0.023 | |
| 488 | 0.018 | |
| 489 | 0.011 | |
| 490 | 0.0076 | |
| 491 | 0.0065 | |
| 492 | 0.019 | |
| 493 | 0.0082 | |
| 494 | 0.0091 | |
| 495 | 0.022 | |
| 496 | 0.0069 | |
| 497 | 0.0033 | |
| 498 | 0.07 | |
| 499 | | 4% (0.1 uM) |
| 500 | | 19% (0.1 uM) |
| 501 | 0.069 | |
| 502 | 0.081 | |
| 503 | | −17% (0.1 uM) |
| 504 | 0.023 | |
| 505 | 0.011 | |
| 506 | 0.0047 | |
| 507 | | 50% (0.1 uM) |
| 508 | 0.02 | |
| 509 | 0.038 | |
| 510 | 0.0083 | |
| 511 | 0.0079 | |
| 512 | 0.016 | |
| 513 | 0.0032 | |
| 514 | 0.004 | |
| 515 | 0.012 | |
| 516 | 0.0083 | |
| 517 | 0.0038 | |
| 518 | 0.011 | |
| 519 | 0.013 | |
| 520 | 0.018 | |
| 521 | 0.00515 | |
| 522 | 0.0053 | |
| 523 | 0.00215 | |
| 524 | 0.027 | |
| 525 | 0.018 | |
| 526 | 0.0092 | |
| 527 | 0.0085 | |
| 528 | 0.0036 | |
| 529 | 0.0023 | |
| 530 | | 40% (0.1 uM) |
| 531 | 0.03 | |
| 532 | | 26% (0.1 uM) |
| 533 | 0.0021 | |
| 534 | 0.0018 | |
| 535 | 0.0028 | |
| 536 | | 15% (0.1 uM) |
| 537 | | 1% (0.1 uM) |
| 538 | | 33% (0.1 uM) |
| 539 | | 35% (0.1 uM) |
| 540 | 0.048 | |
| 541 | | 24% (0.1 uM) |
| 542 | | 18% (0.1 uM) |
| 543 | | 15% (0.1 uM) |
| 544 | | 21% (0.1 uM) |
| 545 | | 9% (0.1 uM) |
| 546 | 0.0057 | |
| 547 | 0.043 | |

TABLE 4-continued

| Example No. | human SGLT1 IC$_{50}$ (uM) | % Inhibition |
|---|---|---|
| 548 | | 3% (0.1 uM) |
| 549 | | 41% (0.1 uM) |
| 550 | | 29% (0.1 uM) |
| 551 | | 42% (0.1 uM) |
| 552 | | 8% (0.1 uM) |
| 553 | | 31% (0.1 uM) |
| 554 | | 32% (0.1 uM) |
| 555 | 0.024 | |
| 556 | | 23% (0.1 uM) |
| 557 | | 48% (0.1 uM) |
| 558 | 0.038 | |
| 559 | 0.0077 | |
| 560 | 0.024 | |
| 561 | 0.0055 | |
| 562 | 0.013 | |
| 563 | | 57% (0.00265 uM) |
| 564 | 0.045 | |
| 565 | 0.011 | |
| 566 | | 22% (0.3 uM) |
| 567 | 0.014 | |
| 568 | | 27% (0.3 uM) |
| 569 | | 29% (0.1 uM) |
| 570 | 0.0087 | |
| 571 | 0.0093 | |
| 572 | 0.0051 | |
| 573 | 0.013 | |
| 574 | 0.017 | |
| 575 | 0.012 | |
| 576 | 0.019 | |
| 577 | 0.0067 | |
| 578 | 0.0085 | |
| 579 | 0.023 | |
| 580 | 0.0076 | |
| 581 | 0.012 | |
| 582 | | 47% (0.1 uM) |
| 583 | | 48% (0.1 uM) |
| 584 | 0.084 | |
| 585 | 0.013 | |
| 586 | 0.046 | |
| 587 | 0.04 | |
| 588 | 0.04 | |
| 589 | 0.055 | |
| 590 | 0.013 | |
| 591 | 0.019 | |
| 592 | 0.015 | |
| 593 | 0.01 | |
| 594 | 0.066 | |
| 595 | 0.01 | |
| 596 | 0.035 | |
| 597 | 0.06 | |
| 598 | 0.047 | |
| 599 | 0.027 | |
| 600 | 0.041 | |
| 601 | 0.031 | |
| 602 | 0.028 | |
| 603 | 0.016 | |
| 604 | N.T | |
| 605 | N.T | |

[Formulations]

The formulation examples of the present invention include the following formulations. However, the present invention is not intended to be limited thereto.

Formulation 1 (Preparation of Capsule)

| 1) Compound 1 | 30 mg |
|---|---|
| 2) Microcrystalline cellulose | 10 mg |
| 3) Lactose | 19 mg |
| 4) Magnesium stearate | 1 mg |

1), 2), 3) and 4) are mixed to fill in a gelatin capsule.

Formulation 2 (Preparation of Tablet)

| 1) Compound 1 | 10 g |
|---|---|
| 2) Lactose | 50 g |
| 3) Cornstarch | 15 g |
| 4) Carmellose calcium | 44 g |
| 5) Magnesium stearate | 1 g |

The whole amount of 1), 2) and 3) and 30 g of 4) are combined with water, dried in vacuo, and then granulated. The resulting granules are mixed with 14 g of 4) and 1 g of 5), and pressed into tablets by a tableting machine. Then, 1000 tablets wherein Compound 1 (10 mg) is comprised in each tablet are obtained.

INDUSTRIAL APPLICABILITY

The compound or a pharmaceutically acceptable salt thereof in the present invention is useful for the treatment and/or prevention of various diseases or conditions which are expected to be improved by controlling SGLT1 activity because it has SGLT1 inhibitory activity. Such diseases or conditions include, for example, diabetes such as type II diabetes, obesity, diabetic complications (e.g., retinopathy, nephropathy and neuropathy which are known as microangiopathy, and cerebrovascular disease, ischemic heart disease and arteriosclerosis obliterans which are known as macroangiopathy), hypertrophic cardiomyopathy, ischemic heart disease, cancer and constipation.

The invention claimed is:

1. A compound or a pharmaceutically acceptable salt thereof represented by the general formula [Ib]:

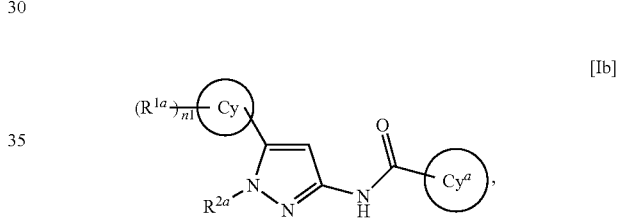

wherein
Ring Cy is
  (1) $C_{6-10}$ aryl,
  (2) $C_{3-8}$ cycloalkyl or
  (3) $C_{3-8}$ cycloalkenyl,
n1 is 0, 1, 2, 3 or 4,
$R^{1a}$ is
  (1) a halogen atom,
  (2) hydroxy,
  (3) carboxy,
  (4) a $C_{1-6}$ alkyl group,
  (5) a $C_{2-8}$ alkenyl group,
  (6) a $C_{2-8}$ alkynyl group,
  (7) a $C_{1-6}$ alkoxy group,
  (8) a $C_{3-6}$ cycloalkyl group,
  (9) a halo $C_{1-6}$ alkyl group,
  (10) a hydroxy $C_{1-6}$ alkyl group,
  (11) a $C_{1-6}$ alkoxy $C_{1-6}$ alkyl group,
  (12) a halo $C_{1-6}$ alkoxy $C_{1-6}$ alkyl group,
  (13) a $C_{1-6}$ alkylsulfonyl $C_{1-6}$ alkyl group,
  (14) a halo $C_{1-6}$ alkylsulfonyl $C_{1-6}$ alkyl group,
  (15) a halo $C_{1-6}$ alkylamino $C_{1-6}$ alkyl group,
  (16) a $C_{3-6}$ cycloalkyl $C_{2-6}$ alkynyl group,
  (17) a halo $C_{1-6}$ alkoxy group,
  (18) a carboxy $C_{1-6}$ alkoxy group,
  (19) a $C_{1-6}$ alkylsulfanyl group,
  (20) a $C_{1-6}$ alkylsulfonyl group,
  (21) a halo $C_{1-6}$ alkylsulfonyl group,

(22) a $C_{1-8}$ alkylcarbonyl group,
(23) a $C_{1-6}$ alkyloxycarbonyl group,
(24) a group represented by the Formula:

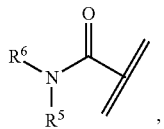

wherein
$R_5$ is
  (a) a hydrogen atom or
  (b) a $C_{1-6}$ alkyl group, and
$R_6$ is
  (a) a $C_{1-6}$ alkyl group, or
  (b) a halo $C_{1-6}$ alkyl group,
(25) a saturated heterocyclo $C_{1-6}$ alkyl group, wherein the saturated heterocycle is a 4-membered to 6-membered saturated heterocycle having 1 to 2 heteroatoms selected from nitrogen, oxygen, and sulfur, or
(26) a saturated heterocyclo oxy $C_{1-6}$ alkyl group, wherein the saturated heterocycle is a 4-membered to 6-membered saturated heterocycle having 1 to 2 heteroatoms selected from nitrogen, oxygen, and sulfur,
provided that when n1 is 2, 3 or 4, each $R^{1a}$ is the same or different,
$R^{2a}$ is
(1) a $C_{1-8}$ alkyl group,
(2) a $C_{3-8}$ cycloalkyl $C_{1-6}$ alkyl group,
(3) a $C_{6-10}$ aryl $C_{1-6}$ alkyl group,
(4) a saturated heterocyclo $C_{1-6}$ alkyl group, wherein the saturated heterocycle is a 4-membered to 6-membered saturated heterocycle having 1 to 2 heteroatoms selected from nitrogen, oxygen, and sulfur,
(5) a $C_{3-8}$ cycloalkyl group,
(6) a halo $C_{1-6}$ alkyl group,
(7) a $C_{1-6}$ alkoxy $C_{1-6}$ alkyl group,
(8) a halo $C_{3-8}$ cycloalkyl group,
(9) a $C_{6-10}$ aryl group, wherein the $C_{6-10}$ aryl group is optionally substituted by 1 to 4 substituents selected from the group consisting of:
  (a) a halogen atom,
  (b) hydroxy,
  (c) a $C_{1-6}$ alkyl group,
  (d) a $C_{2-8}$ alkenyl group,
  (e) a $C_{2-6}$ alkynyl group,
  (f) a $C_{1-6}$ alkoxy group,
  (g) a halo $C_{1-6}$ alkyl group,
  (h) a $C_{1-6}$ alkoxy $C_{1-6}$ alkyl group,
  (i) a halo $C_{1-6}$ alkoxy group,
  (j) a hydroxy $C_{1-6}$ alkoxy group,
  (k) a $C_{1-6}$ alkoxy $C_{1-6}$ alkoxy group,
  (l) a carboxy $C_{1-6}$ alkoxy group,
  (m) a $C_{6-10}$ aryl $C_{1-6}$ alkoxy group,
  (n) a $C_{1-6}$ alkylsulfanyl $C_{1-6}$ alkoxy group,
  (o) a $C_{1-6}$ alkylsulfonyl $C_{1-6}$ alkoxy group,
  (p) a $C_{6-10}$ aryl $C_{1-6}$ alkoxy $C_{1-6}$ alkoxy group,
  (q) a saturated heterocyclo $C_{1-6}$ alkoxy group, wherein the saturated heterocycle is a 4-membered to 6-membered saturated heterocycle having 1 to 2 heteroatoms selected from nitrogen, oxygen, and sulfur, and is optionally substituted by 1 to 2 $C_{1-6}$ alkyl groups,
  (r) a saturated heterocyclo oxy group, wherein the saturated heterocycle is a 4-membered to 6-membered saturated heterocycle having 1 to 2 heteroatoms selected from nitrogen, oxygen, and sulfur,
  (s) a $C_{3-8}$ cycloalkyloxy group,
  (t) a $C_{1-6}$ alkoxycarbonyloxy group and
  (u) a $C_{1-6}$ alkylsulfonyl group, or
(10) a saturated heterocycle group, wherein the saturated heterocycle is a 4-membered to 6-membered saturated heterocycle having 1 to 2 heteroatoms selected from nitrogen, oxygen, and sulfur, and is optionally substituted by 1 to 4 $C_{1-6}$ alkyl groups, and
Ring $Cy^a$ is a group selected from the group consisting of:
(1) a group represented by the Formula:

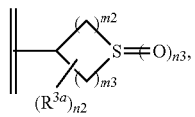

wherein
  m2 is 1, 2 or 3,
  m3 is 1, 2 or 3,
  n3 is 1 or 2,
(2) a group represented by the Formula:

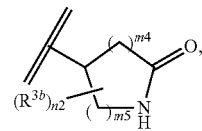

wherein
  m4 is 0, 1, 2 or 3,
  m5 is 0, 1 or 2,
  provided that the sum of m4 and m5 is 1 or more,
(3) a group represented by the Formula:

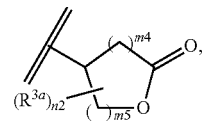

wherein
  m4 is 0, 1, 2 or 3,
  m5 is 0, 1 or 2,
  provided that the sum of m4 and m5 is 1 or more,
(4) a group represented by the Formula:

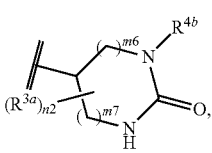

wherein
  m6 is 0, 1 or 2,
  m7 is 0, 1 or 2,
  provided that the sum of m6 and m7 is 1 or more, (5) a group represented by the Formula:

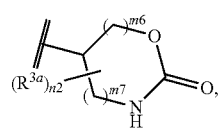

wherein
m6 is 0, 1 or 2,
m7 is 0, 1 or 2,
provided that the sum of m6 and m7 is 1 or more,
(6) a group represented by the Formula:

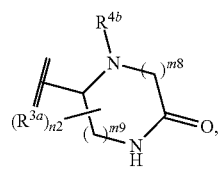

wherein
m8 is 1 or 2,
m9 is 1 or 2, and
(7) a group represented by the Formula:

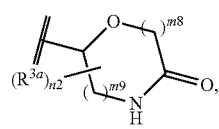

wherein
m8 is 1 or 2,
m9 is 1 or 2,
n2 is 0, 1, 2, 3 or 4,
$R^{3a}$ is
  (1) hydroxy,
  (2) a $C_{1-6}$ alkyl group or
  (3) a hydroxy $C_{1-6}$ alkyl group,
  provided that when n2 is 2, 3 or 4, each $R^{3a}$ is the same or different,
$R^{3b}$ is
  (1) hydroxy,
  (2) a $C_{1-6}$ alkyl group, which optionally forms a $C_{3-6}$ cycloalkyl group together with the carbon to which it is attached and the carbon adjacent thereto,
  (3) a hydroxy $C_{1-6}$ alkyl group, or
  (4) when two $R^{3b}$ are attached to the same carbon, they optionally form a $C_{3-6}$ cycloalkyl group together with the carbon to which they are attached,
  provided that when n2 is 2, 3 or 4, each $R^{3b}$ is the same or different, and
$R^{4b}$ is
  (1) a hydrogen atom,
  (2) a $C_{1-6}$ alkyl group,
  (3) a carboxy $C_{1-6}$ alkyl group,
  (4) a halo $C_{1-6}$ alkyl group or
  (5) a $C_{1-6}$ alkoxy $C_{1-6}$ alkyl group.

2. The compound or a pharmaceutically acceptable salt thereof according to claim 1, wherein Ring $Cy^a$ is selected from the group consisting of:
(1) a group represented by the Formula:

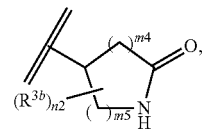

wherein
m4 is 0, 1, 2 or 3,
m5 is 0, 1 or 2,
provided that the sum of m4 and m5 is 1 or more,
(2) a group represented by the Formula:

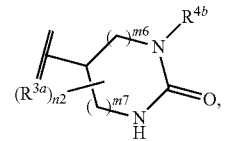

wherein
m6 is 0, 1 or 2,
m7 is 0, 1 or 2,
provided that the sum of m6 and m7 is 1 or more,
(3) a group represented by the Formula:

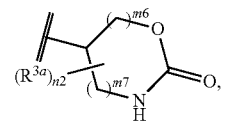

wherein
m6 is 0, 1 or 2,
m7 is 0, 1 or 2,
provided that the sum of m6 and m7 is 1 or more,
(4) a group represented by the Formula:

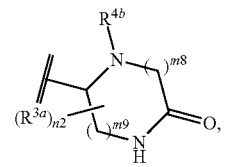

wherein
m8 is 1 or 2,
m9 is 1 or 2, and
(5) a group represented by the Formula:

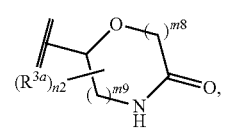

wherein
m8 is 1 or 2,
m9 is 1 or 2,
n2 is 0, 1, 2, 3 or 4, $R^{3a}$ is
 (1) hydroxy,
 (2) a $C_{1-6}$ alkyl group or
 (3) a hydroxy $C_{1-6}$ alkyl group,
 provided that when n2 is 2, 3 or 4, each $R^{3a}$ is the same or different,
$R^{3b}$ is
 (1) hydroxy,
 (2) a $C_{1-6}$ alkyl group, which optionally forms a $C_{3-6}$ cycloalkyl group together with the carbon to which it is attached and the carbon adjacent thereto,
 (3) a hydroxy $C_{1-6}$ alkyl group, or
 (4) when two $R^{3b}$ are attached to the same carbon, they optionally form a $C_{3-6}$ cycloalkyl group together with the carbon to which they are attached,
 provided that when n2 is 2, 3 or 4, each $R^{3b}$ is the same or different, and
$R^{4b}$ is
 (1) a hydrogen atom,
 (2) a $C_{1-6}$ alkyl group,
 (3) a carboxy $C_{1-6}$ alkyl group,
 (4) a halo $C_{1-6}$ alkyl group or
 (5) a $C_{1-6}$ alkoxy $C_{1-6}$ alkyl group.

3. The compound or a pharmaceutically acceptable salt thereof according to claim 1, wherein
Ring $Cy^a$ is selected from the group consisting of:
 (1) a group represented by the Formula:

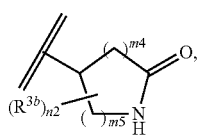

wherein,
 m4 is 0, 1, 2 or 3,
 m5 is 0, 1 or 2,
 provided that the sum of m4 and m5 is 1 or more, and
 (2) a group represented by the Formula:

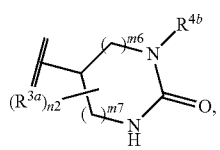

wherein
 m6 is 0, 1 or 2,
 m7 is 0, 1 or 2,
 provided that the sum of m6 and m7 is 1 or more,
n2 is 0, 1, 2, 3 or 4,
$R^{3a}$ is
 (1) hydroxy,
 (2) a $C_{1-6}$ alkyl group or
 (3) a hydroxy $C_{1-6}$ alkyl group,
 provided that when n2 is 2, 3 or 4, each $R^{3a}$ is the same or different,
$R^{3b}$ is
 (1) hydroxy,
 (2) a $C_{1-6}$ alkyl group, which optionally forms a $C_{3-6}$ cycloalkyl group together with the carbon to which it is attached and the carbon adjacent thereto,
 (3) a hydroxy $C_{1-6}$ alkyl group, or
 (4) when two $R^{3b}$ are attached to the same carbon, they optionally form a $C_{3-6}$ cycloalkyl group together with the carbon to which they are attached,
 provided that when n2 is 2, 3 or 4, each $R^{3b}$ is the same or different, and
$R^{4b}$ is
 (1) a hydrogen atom,
 (2) a $C_{1-6}$ alkyl group,
 (3) a carboxy $C_{1-6}$ alkyl group,
 (4) a halo $C_{1-6}$ alkyl group or
 (5) a $C_{1-6}$ alkoxy $C_{1-6}$ alkyl group.

4. The compound or a pharmaceutically acceptable salt thereof according to claim 1, wherein
Ring $Cy^a$ is selected from the group consisting of:
 (1) a group represented by the Formula:

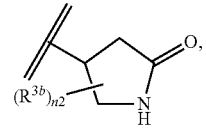

wherein
n2 is 0, 1, 2, 3 or 4, and
 (2) a group represented by the Formula:

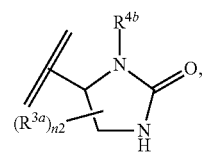

wherein
 n2 is 0 or 1,
$R^{3a}$ is
 (1) hydroxy,
 (2) a $C_{1-6}$ alkyl group or
 (3) a hydroxy $C_{1-6}$ alkyl group, and
$R^{3b}$ is
 (1) hydroxy,
 (2) a $C_{1-6}$ alkyl group, which optionally forms a $C_{3-6}$ cycloalkyl group together with the carbon to which it is attached and the carbon adjacent thereto) or,
 (3) a hydroxy $C_{1-6}$ alkyl group, or
 (4) when two $R^{3b}$ are attached to the same carbon, they optionally form a $C_{3-6}$ cycloalkyl group together with the carbon to which they are attached,
 provided that when n2 is 2, 3 or 4, each $R^{3b}$ is the same or different, and
$R^{4b}$ is
 (1) a hydrogen atom,
 (2) a $C_{1-6}$ alkyl group,
 (3) a carboxy $C_{1-6}$ alkyl group,
 (4) a halo $C_{1-6}$ alkyl group or
 (5) a $C_{1-6}$ alkoxy $C_{1-6}$ alkyl group.

5. The compound or a pharmaceutically acceptable salt thereof according to claim 1, wherein the ring Cy is $C_{6-10}$ aryl.

6. The compound or a pharmaceutically acceptable salt thereof according to claim 5, wherein the ring Cy is phenyl.

7. The compound or a pharmaceutically acceptable salt thereof according to claim 1 wherein $R^{1a}$ is
 (1) a halogen atom,
 (2) a $C_{1-6}$ alkyl group, (3) a $C_{1-6}$ alkoxy group,
(4) a halo $C_{1-6}$ alkyl group,
(5) a $C_{1-6}$ alkoxy $C_{1-6}$ alkyl group,
(6) a halo $C_{1-6}$ alkoxy $C_{1-6}$ alkyl group or
(7) a halo $C_{1-6}$ alkoxy group,
provided that when n1 is 2, 3, or 4, each $R^{1a}$ is the same or different.

8. The compound or a pharmaceutically acceptable salt thereof according to claim 1, wherein $R^{2a}$ is a $C_{6-10}$ aryl group and
wherein the $C_{6-10}$ aryl group is optionally substituted by 1 to 4 substituents selected from the group consisting of:
(a) a halogen atom,
(b) a $C_{1-6}$ alkyl group,
(c) a $C_{1-6}$ alkoxy group and
(d) a carboxy $C_{1-6}$ alkoxy group.

9. The compound or a pharmaceutically acceptable salt thereof according to claim 8, wherein $R^{2a}$ is a phenyl group and
wherein the phenyl group is optionally substituted by 1 to 4 substituents selected from the group consisting of:
(a) a halogen atom,
(b) a $C_{1-6}$ alkyl group,
(c) a $C_{1-6}$ alkoxy group and
(d) a carboxy $C_{1-6}$ alkoxy group.

10. The compound or pharmaceutically acceptable salt thereof of claim 1, wherein the compound is selected from the following Formulae:

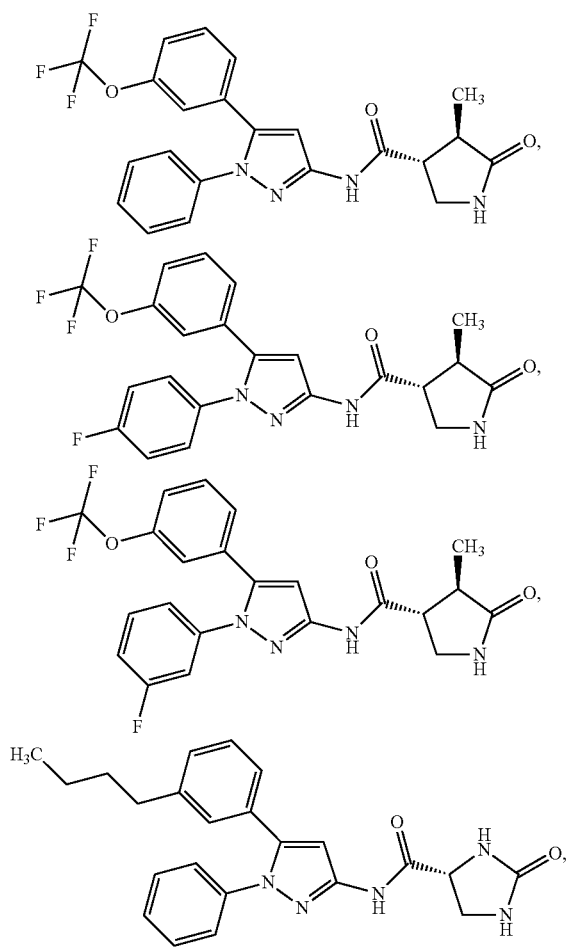

-continued

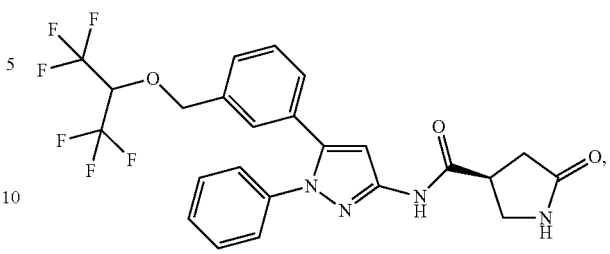

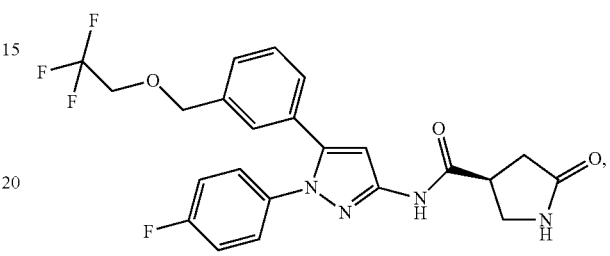

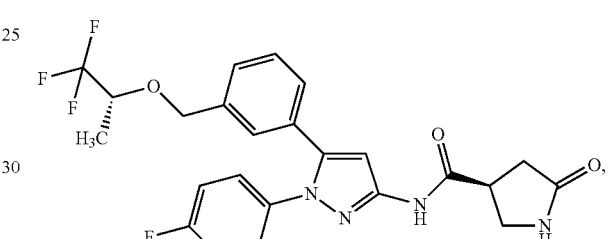

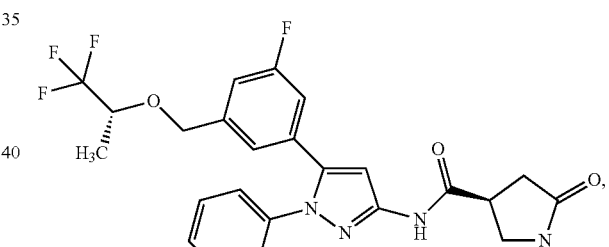

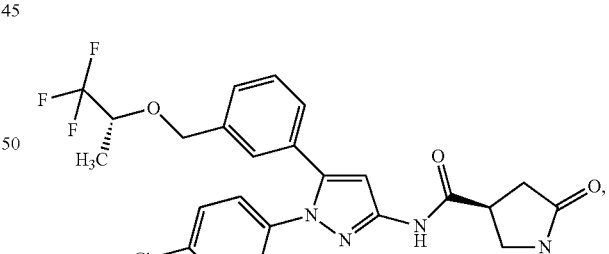

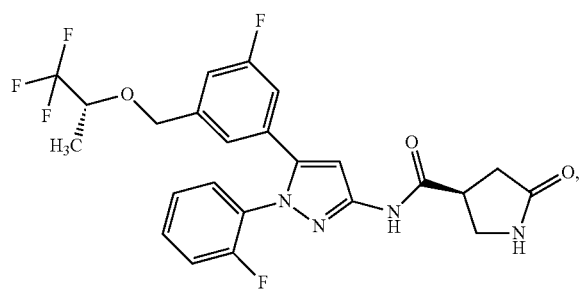

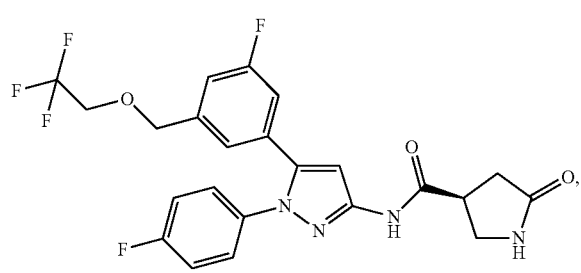

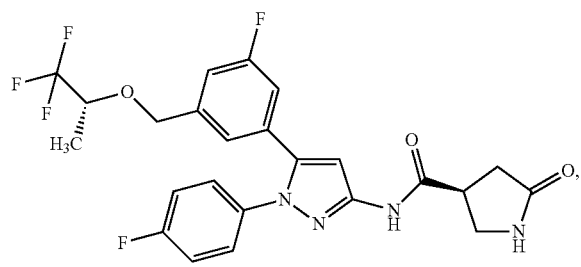

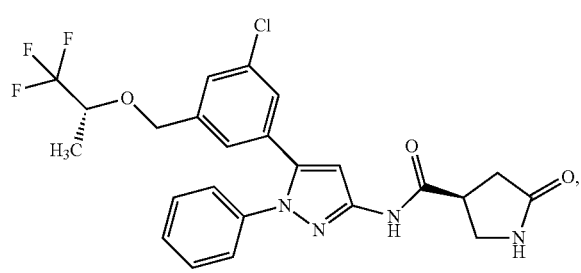

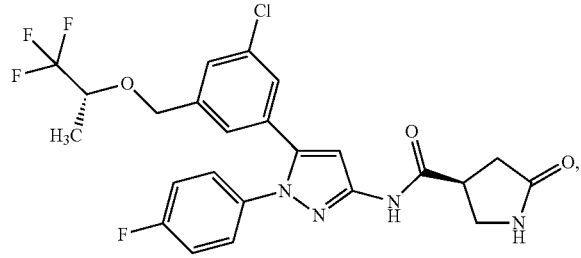

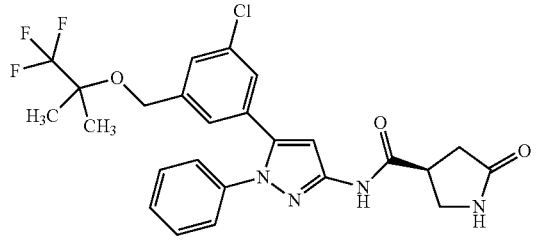

and

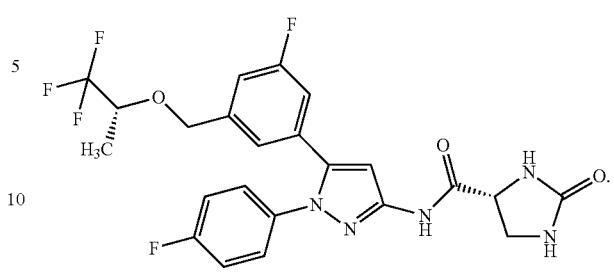

11. A pharmaceutical composition which comprises a compound or a pharmaceutically acceptable salt thereof according to claim 1 and a pharmaceutically acceptable carrier.

12. A SGLT1 inhibitor which comprises a compound or a pharmaceutically acceptable salt thereof according to claim 1.

13. A method for inhibiting SGLT1 comprising administering to a mammal a therapeutically effective amount of a compound or a pharmaceutically acceptable salt thereof according to claim 1.

14. A method for treating or preventing diabetes comprising administering to a mammal a therapeutically effective amount of a compound or a pharmaceutically acceptable salt thereof according to claim 1.

15. The method according to claim 14, wherein the diabetes is type II diabetes mellitus.

16. The compound or pharmaceutically acceptable salt thereof of claim 1 represented by the following Formula:

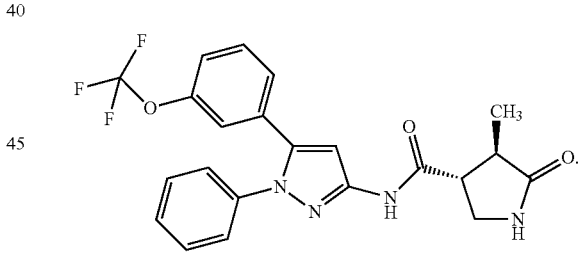

17. The compound or pharmaceutically acceptable salt thereof of claim 1 represented by the following Formula:

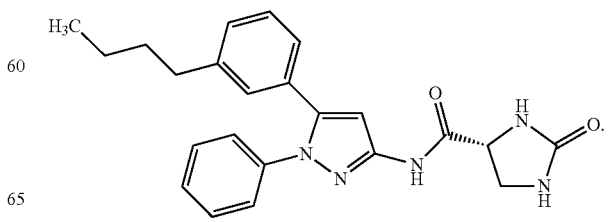

18. The compound or pharmaceutically acceptable salt thereof of claim 1 represented by the following Formula:

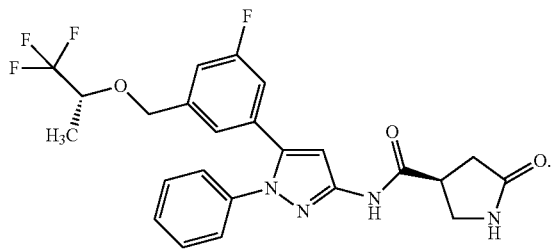 [SMILES: C[C@@H](OCc1cc(F)cc(-c2cc(NC(=O)[C@@H]3CNC(=O)C3)nn2-c2ccccc2)c1)C(F)(F)F]

19. The compound or pharmaceutically acceptable salt thereof of claim 1 represented by the following Formula:

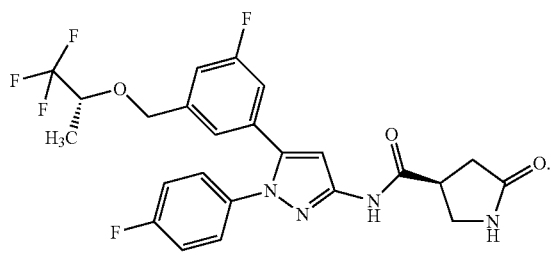 [SMILES: C[C@@H](OCc1cc(F)cc(-c2cc(NC(=O)[C@@H]3CNC(=O)C3)nn2-c2ccc(F)cc2)c1)C(F)(F)F]

20. The compound or pharmaceutically acceptable salt thereof of claim 1 represented by the following Formula:

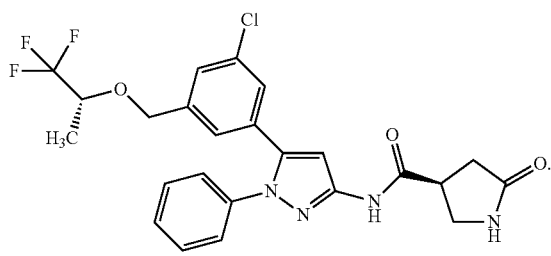 [SMILES: C[C@@H](OCc1cc(Cl)cc(-c2cc(NC(=O)[C@@H]3CNC(=O)C3)nn2-c2ccccc2)c1)C(F)(F)F]

21. The compound or pharmaceutically acceptable salt thereof of claim 1 represented by the following Formula:

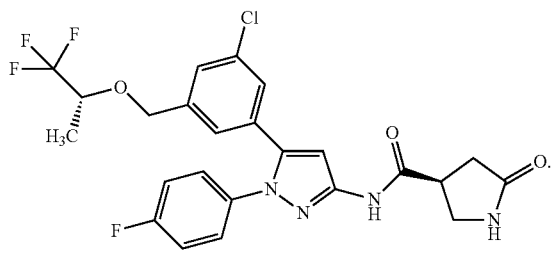 [SMILES: C[C@@H](OCc1cc(Cl)cc(-c2cc(NC(=O)[C@@H]3CNC(=O)C3)nn2-c2ccc(F)cc2)c1)C(F)(F)F]

22. The compound or pharmaceutically acceptable salt thereof of claim 1, represented by the following Formula:

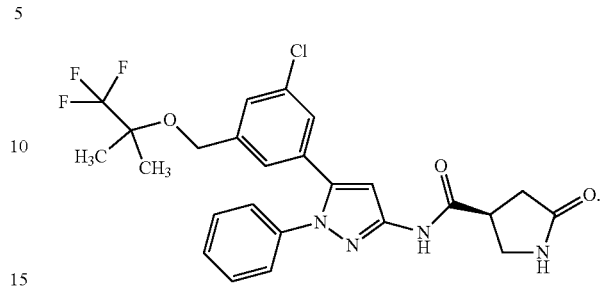

23. The compound of claim 1 represented by the following Formula:

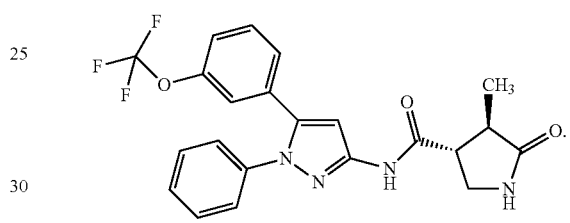

24. The compound of claim 1 represented by the following Formula:

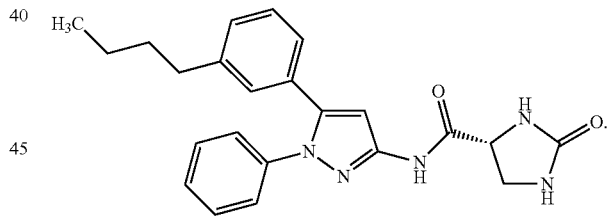

25. The compound of claim 1 represented by the following Formula:

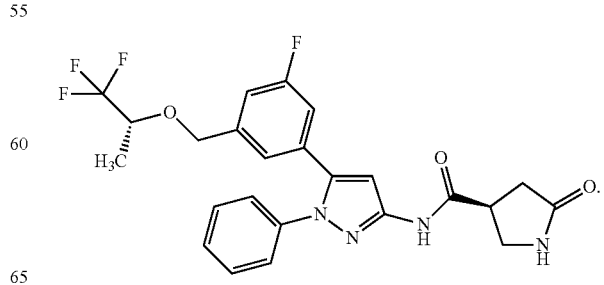

26. The compound of claim 1 represented by the following Formula:

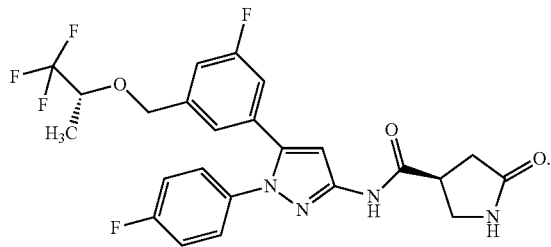 [SMILES: C[C@@H](OCc1cc(F)cc(-c2cc(NC(=O)[C@@H]3CNC(=O)C3)nn2-c2ccc(F)cc2)c1)C(F)(F)F]

27. The compound of claim 1 represented by the following Formula:

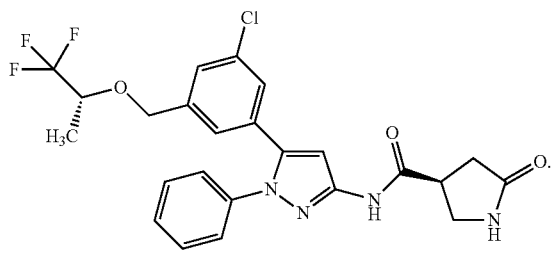 [SMILES: C[C@@H](OCc1cc(Cl)cc(-c2cc(NC(=O)[C@@H]3CNC(=O)C3)nn2-c2ccccc2)c1)C(F)(F)F]

28. The compound of claim 1 represented by the following Formula:

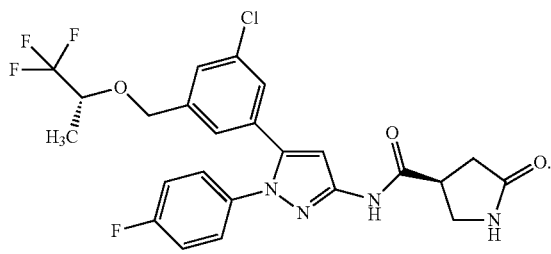 [SMILES: C[C@@H](OCc1cc(Cl)cc(-c2cc(NC(=O)[C@@H]3CNC(=O)C3)nn2-c2ccc(F)cc2)c1)C(F)(F)F]

29. The compound of claim 1 represented by the following Formula:

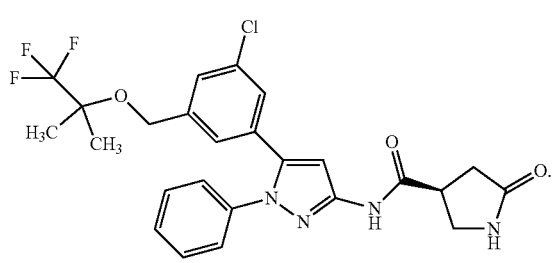 [SMILES: CC(C)(OCc1cc(Cl)cc(-c2cc(NC(=O)[C@@H]3CNC(=O)C3)nn2-c2ccccc2)c1)C(F)(F)F]

30. A pharmaceutical composition which comprises a compound or a pharmaceutically acceptable salt thereof according to any one of claims 16 to 29 and a pharmaceutically acceptable carrier.

31. A method for inhibiting SGLT1 comprising administering to a mammal a therapeutically effective amount of a compound or a pharmaceutically acceptable salt thereof according to any one of claims 16 to 29.

32. A method for treating or preventing diabetes comprising administering to a mammal a therapeutically effective amount of a compound or a pharmaceutically acceptable salt thereof according to any one of claims 16 to 29.

33. The method according to claim 32, wherein the mammal is a human.

34. The method according to claim 32, wherein the method is for treating diabetes.

35. The method according to claim 34, wherein the mammal is a human.

36. The method according to claim 14, wherein the mammal is a human.

37. The method according to claim 14, wherein the method is for treating diabetes.

38. The method according to claim 37, wherein the mammal is a human.

* * * * *

UNITED STATES PATENT AND TRADEMARK OFFICE
CERTIFICATE OF CORRECTION

PATENT NO. : 8,846,746 B2  
APPLICATION NO. : 13/599665  
DATED : September 30, 2014  
INVENTOR(S) : Tomoya Miura et al.

Page 1 of 1

It is certified that error appears in the above-identified patent and that said Letters Patent is hereby corrected as shown below:

In the Specification,

COLUMN 375:

Molecular Structure for Example No. 425, " 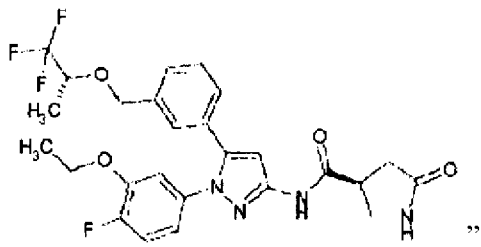 " should be added.

In the Claims,

COLUMN 480:

Line 47, ") or" should be deleted.

Signed and Sealed this  
Sixteenth Day of June, 2015

Michelle K. Lee  
*Director of the United States Patent and Trademark Office*